United States Patent
Apgar et al.

(10) Patent No.: US 9,290,517 B2
(45) Date of Patent: Mar. 22, 2016

(54) AZABENZIMIDAZOLE HEXAHYDROFURO[3,2-B]FURAN DERIVATIVES

(71) Applicant: Merck Sharp & Dohme Corp., Rahway, NJ (US)

(72) Inventors: James M. Apgar, Highland, NJ (US); Ashok Arasappan, Bridgewater, NJ (US); Tesfaye Biftu, Freehold, NJ (US); Ping Chen, Edison, NJ (US); Danqing Feng, Green Brook, NJ (US); Erin Guidry, Cranford, NJ (US); Jacqueline D. Hicks, Scotch Plains, NJ (US); Ahmet Kekec, Jersey City, NJ (US); Kenneth J. Leavitt, Mount Laurel, NJ (US); Bing Li, Towaco, NJ (US); Troy McCracken, Garwood, NJ (US); Iyassu Sebhat, Jersey City, NJ (US); Xiaoxia Qian, New York, NY (US); Lan Wei, Berkeley Heights, NJ (US); Robert R. Wilkening, Maplewood, NJ (US); Zhicai Wu, Montvale, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/419,774

(22) PCT Filed: Aug. 19, 2013

(86) PCT No.: PCT/US2013/055528
§ 371 (c)(1),
(2) Date: Feb. 5, 2015

(87) PCT Pub. No.: WO2014/031515
PCT Pub. Date: Feb. 27, 2014

(65) Prior Publication Data
US 2015/0284411 A1    Oct. 8, 2015

Related U.S. Application Data

(60) Provisional application No. 61/692,018, filed on Aug. 22, 2012.

(51) Int. Cl.
| | |
|---|---|
| *C07D 401/14* | (2006.01) |
| *A61K 31/437* | (2006.01) |
| *C07D 519/00* | (2006.01) |
| *A61K 31/438* | (2006.01) |
| *A61K 31/506* | (2006.01) |
| *A61K 31/501* | (2006.01) |
| *A61K 31/5377* | (2006.01) |
| *A61K 31/541* | (2006.01) |
| *A61K 45/06* | (2006.01) |

(52) U.S. Cl.
CPC ............ *C07D 519/00* (2013.01); *A61K 31/437* (2013.01); *A61K 31/438* (2013.01); *A61K 31/501* (2013.01); *A61K 31/506* (2013.01); *A61K 31/5377* (2013.01); *A61K 31/541* (2013.01); *A61K 45/06* (2013.01)

(58) Field of Classification Search
CPC ........................... C07D 401/14; A61K 31/437
USPC .......................................... 546/119; 514/303
See application file for complete search history.

(56) References Cited

U.S. PATENT DOCUMENTS

| | | | |
|---|---|---|---|
| 6,312,662 B1 | 11/2001 | Erion et al. | |
| 6,420,373 B1 * | 7/2002 | Borcherding | C07D 473/34 |
| | | | 514/263.1 |
| 6,489,476 B1 | 12/2002 | Dang et al. | |
| 2005/0038068 A1 | 2/2005 | Iyengar et al. | |
| 2005/0148643 A1 | 7/2005 | Rui et al. | |
| 2006/0287356 A1 | 12/2006 | Iyengar et al. | |
| 2007/0015665 A1 | 1/2007 | Potluri et al. | |
| 2007/0032529 A1 | 2/2007 | Takagi et al. | |

(Continued)

FOREIGN PATENT DOCUMENTS

| | | |
|---|---|---|
| CA | 2811025 A1 | 3/2012 |
| DE | 3316095 A1 | 5/1983 |
| EP | 0120403 A2 | 10/1984 |

(Continued)

OTHER PUBLICATIONS

Bergeron, R. et al., Effect of 5-Aminoimidazole-4-Caroboxamide-1-B-D-Ribofuranoside Infusion on In Vivo Glucose and Lipid Metabolism in Lean and Obese Zucker Rats, Diabetes, 2001, p. 1076-1082, vol. 50.

(Continued)

*Primary Examiner* — Niloofar Rahmani
(74) *Attorney, Agent, or Firm* — Baerbel R. Brown; Catherine D. Fitch

(57) ABSTRACT

Novel compounds of the structural formula (I) are activators of AMP-protein kinase and may be useful in the treatment, prevention and suppression of diseases mediated by the AMPK activated protein kinase. The compounds of the present invention may be useful in the treatment of Type 2 diabetes, hyperglycemia, metabolic syndrome, obesity, hypercholesterolemia, and hypertension.

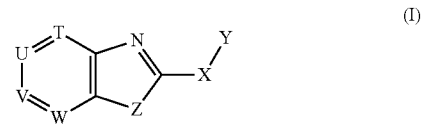

(I)

20 Claims, No Drawings

(56) References Cited

U.S. PATENT DOCUMENTS

| | | | |
|---|---|---|---|
| 2011/0195964 A1 | 8/2011 | Dang et al. | |
| 2011/0218174 A1 | 9/2011 | Bao et al. | |

FOREIGN PATENT DOCUMENTS

| | | |
|---|---|---|
| EP | 120403 A3 | 10/1984 |
| EP | 0126030 A2 | 11/1984 |
| EP | 126030 A3 | 11/1984 |
| EP | 0128862 A2 | 12/1984 |
| EP | 128862 A3 | 12/1984 |
| EP | 0129506 B1 | 12/1984 |
| JP | 6298731 | 10/1994 |
| WO | WO9307124 A1 | 4/1993 |
| WO | WO9529897 A1 | 11/1995 |
| WO | WO9839342 A1 | 9/1998 |
| WO | WO9839343 A1 | 9/1998 |
| WO | WO0003997 A1 | 1/2000 |
| WO | WO0014095 A1 | 3/2000 |
| WO | WO0153272 A1 | 7/2001 |
| WO | WO0153291 A1 | 7/2001 |
| WO | WO0240019 A1 | 5/2002 |
| WO | WO02092575 A1 | 11/2002 |
| WO | WO03018061 A1 | 3/2003 |
| WO | WO2005002520 A2 | 1/2005 |
| WO | WO2005002520 A3 | 1/2005 |
| WO | W02005020892 A2 | 3/2005 |
| WO | WO2005018672 A1 | 3/2005 |
| WO | WO2005020892 A3 | 3/2005 |
| WO | WO2005051298 A2 | 6/2005 |
| WO | WO2005051298 A3 | 6/2005 |
| WO | WO2006094209 A2 | 9/2006 |
| WO | WO2006094209 A3 | 9/2006 |
| WO | WO2008006432 A1 | 1/2008 |
| WO | WO2010036613 A1 | 4/2010 |
| WO | WO2010047982 A1 | 4/2010 |
| WO | WO2010051176 A1 | 5/2010 |
| WO | WO2010051206 A1 | 5/2010 |
| WO | WO2011106273 A1 | 9/2011 |
| WO | WO2012033149 A1 | 3/2012 |
| WO | WO2014031441 A1 | 2/2014 |
| WO | WO2014031445 A1 | 2/2014 |
| WO | WO2014031465 A1 | 2/2014 |
| WO | WO2014031468 A1 | 2/2014 |
| WO | WO2014031517 A1 | 2/2014 |

OTHER PUBLICATIONS

Blazquez, C. et al., The AMP-Activated Protein Kinase Is Involved in the Reulation of Ketone Body Production by Astrocytes, Journal of Neurochemistry, 1999, p. 1674-1682, vol. 73.

Buhl. E. S. et al. Long-Term AICAR Administration Reduces Metabolic Disturbances and Lowers Blood Pressure in Rats Displaying Features of the Insulin Resistance Syndrome, Diabetes, 2002, p. 2199-2206, vol. 51.

Carling, D. et al., A common bicyclic protein kinase cascade inactivates the regulatory enzymes of fatty acid and cholesterol biosynthesis, Feb. 1987, p. 217-222, vol. 223, No. 2.

Chen, Z, P. et al., AMP-activated protein kinase phosphorylation of endothelial NO synthase, FEBS Letters, 1999, p. 285-289, vol. 443.

Halseth, A. E. et al., Acute and chronic treatment of ob/ob and db/db mice with AICAR decreases blood glucose concentrations, Biochemical and Biophysical Research Communications, 2002, p. 798-805, vol. 294.

Hardie, D. G. et al., AMP-activated protein kinase: the energy charge hypothesis revisited, BioEssays, 2001, p. 1112-1119, vol. 23.

Ikehara, M. et al, Studies of Nuclieosides and Nucleotides-Liv Purine Cyclonucleosides-19. Further Investigations on the Cleavage of the 8,2-O-Anhydro Linkage. A New Synthesis of 9-B-D-Arabinofuranosyladenine, Tetrohedron, 1972, p. 3695-3704, vol. 28.

Kemp, B. E. et al., AMPK 2002—2nd Intternational Meeting on AMP-activated Protein kinase, Biochemical Society, 2003, p. 162-168, vol. 31.

Leclerc, I. et al., Hepatocyte Nuclear Factor-4a Involved in Type 1 Maturity-Onset Diabetes of the Young is a Novel Target of AMP-Activated Protein Kinase, Diabetes, 2001, p. 1515-1521, vol. 50.

Lochhead, P. A. et al., 5-Aminoimidazole-4-Carboxamide Riboside Mimics the Effects of Insulin on the Expression of the 2 Key Gluconeogenic Genes PEPCK and Glucose-6-Phosphatase, Diabetes, 2000, p. 896-903, vol. 49.

Minokoshi, Y. et al., Leptin stimulates fatty-acid oxidation by activating AMP-activated protein kinase, Nature, 2002, p. 339—, vol. 415.

Mu, J. et al., A Role for AMP-Activated Protein Kinase in Contraction- and Hypoxia-Regulated Glucose Transport in Skeletal Muscle, Molecular Cell, 2001, p. 1085-1094, vol. 7.

Muoio, D. M. et al., AMP-activated kinase reciprocally regulates triacylglycerol synthesis and fatty acid oxidation in liver and muscle: evidence that sn-glycerol-3-phosphate acyltransferase is a novel target, Biochem J., 1999, p. 783-791, vol. 338.

Musi, N. et al., Metofrmin Increases AMP-Activated Protein Kinase Activity in Skeletal Muscle of Subjects With Type 2 Diabetes, Diabetes, 2002, p. 2074-2081, vol. 51.

Musi, N. et al., Targeting the AMP-Activated Protein Kinase for the Treatment of Type 2 Diabetes, Current Drug Targets—Immune, Endocrine & Metabolic Disorders, 2002, p. 119-127, vol. 2.

Song, X. M. et al., 5-Aminoimidazole-4-carboxamide ribonucleoside treatment improve glucose homeostasis in insulin-resistant diabetic (ob/ob) mice, Diabetologia, 2002, p. 56-65, vol. 45.

Zhou, G. et al., Role of AMP-activated protein kinase in mechanism of metformin action, The Journal of Clinical Investigation, 2001, p. 1167-1174, vol. 108, No. 8.

Zhou, M. et al., UCP-3 expression in skeletal muscle: effects of exercise, hypoxia, and AMP-activated protein kinase, Am. J. Physiol Endocrinol Metab, 2000, p. E622-E629, vol. 279.

* cited by examiner

AZABENZIMIDAZOLE HEXAHYDROFURO[3,2-B]FURAN DERIVATIVES

CROSS-REFERENCE TO RELATED APPLICATIONS

This application is a U.S. National Phase application under 35 U.S.C. §371 of PCT Application No. PCT/US2013/055528, filed on Aug. 19, 2013, which claims priority from and the benefit of U.S. Provisional Application No. 61/692,018, filed Aug. 22, 2012.

BACKGROUND OF THE INVENTION

Diabetes is characterized by elevated levels of plasma glucose (hyperglycemia) in the fasting state or after administration of glucose during an oral glucose tolerance test. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced by islet cells in the pancreas. Patients with Type 2 diabetes have a resistance to the effects of insulin in stimulating glucose and lipid metabolism in the main insulin-sensitive tissues, including muscle, liver and adipose tissues. These patients often have normal levels of insulin, and may have hyperinsulinemia (elevated plasma insulin levels), as they compensate for the reduced effectiveness of insulin by secreting increased amounts of insulin (Polonsky, Int. J. Obes. Relat. Metab. Disord. 24 Suppl 2:S29-31, 2000). Insulin resistance is not primarily caused by a diminished number of insulin receptors but rather by a post-insulin receptor binding defect that is not yet completely understood. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver. Eventually, a patient may be become diabetic due to the inability to properly compensate for insulin resistance. In humans, the beta cells within the pancreatic islets initially compensate for insulin resistance by increasing insulin output. The onset of Type 2 diabetes due to insufficient increases (or actual declines) in beta cell mass is apparently due to increased beta cell apoptosis relative to non-diabetic insulin resistant individuals (Butler et al., Diabetes 52:102-110, 2003).

Persistent or uncontrolled hyperglycemia is associated with increased and premature morbidity and mortality. Often abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, effective therapeutic control of glucose homeostasis, lipid metabolism, obesity, and hypertension are critically important in the clinical management and treatment of diabetes mellitus.

Patients who have insulin resistance often exhibit several symptoms that together are referred to as Syndrome X or Metabolic Syndrome. According to one widely used definition, a patient having Metabolic Syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with Metabolic Syndrome, whether or not they have or develop overt diabetes mellitus, have an increased risk of developing the macrovascular and microvascular complications that occur with Type 2 diabetes, such as atherosclerosis and coronary heart disease.

There are several available treatments for Type 2 diabetes, each of which has its own limitations and potential risks. Physical exercise and a reduction in dietary intake of calories often dramatically improve the diabetic condition and are the usual recommended first-line treatment of Type 2 diabetes and of pre-diabetic conditions associated with insulin resistance. Compliance with this treatment is generally very poor because of well-entrenched sedentary lifestyles and excess food consumption, especially of foods containing high amounts of fat and carbohydrates. Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, MCC-555, netoglitazone, T-131, LY-300512, LY-818 and pioglitazone), (3) insulin secretion (sulfonylureas, such as tolbutamide, glipizide and glimipiride); (4) incretin hormone mimetics (GLP-1 derivatives and analogs, such as exenatide and liraglutide); and (5) inhibitors of incretin hormone degradation (DPP-4 inhibitors, such as sitagliptin).

Many of the current treatments for diabetes have unwanted side effects. Phenformin and metformin can induce lactic acidosis, nausea/vomiting, and diarrhea. Metformin has a lower risk of side effects than phenformin and is widely prescribed for the treatment of Type 2 diabetes. The currently marketed PPAR gamma agonists are modestly effective in reducing plasma glucose and hemoglobinA1C, and do not greatly improve lipid metabolism or the lipid profile. Sulfonylureas and related insulin secretagogues can cause insulin secretion even if the glucose level is low, resulting in hypoglycemia, which can be fatal in severe cases. The administration of insulin secretagogues must therefore be carefully controlled. There remains a need for treatments for diabetes that work by novel mechanisms of action and that exhibit fewer side effects.

AMP-activated protein kinase (AMPK) has been identified as a regulator of carbohydrate and fatty acid metabolism that helps maintain energy balance in response to environmental and nutritional stress. There is evidence that activation of AMPK results in a number of beneficial effects on lipid and glucose metabolism by reducing glucogenesis and de novo lipogenesis (fatty acid and cholesterol synthesis), and by increasing fatty acid oxidation and skeletal muscle glucose uptake. Inhibition of ACC, by phosphorylation by AMPK, leads to a decrease in fatty acid synthesis and to an increase in fatty acid oxidation, while inhibition of HMG-CoA reductase, by phosphorylation by AMPK, leads to a decrease in cholesterol synthesis (Carling, D. et. al., FEBS Letters 223: 217 (1987)).

In the liver, AMPK activation results in a decrease in fatty acid and cholesterol synthesis, inhibiting hepatic glucose production and increasing fatty acid oxidation. It has been shown that AMP-activated protein kinase regulates triacylglycerol synthesis and fatty acid oxidation in liver and muscle via glycerol-3-phosphate acyltransferase (Muoio, D. M. et. al., Biochem. J. 338:783 (1999)). Another substrace of AMPK, hepatocyte nuclear factor-4α, has been shown to be involved in type-1 maturity onset diabetes (Leclerc, I. et. al., Diabetes 50:1515 (2001)). Additional processes believed to be regulated through AMPK activation include the stimulation of glucose transport in skeletal muscle and the regulation of key genes in fatty acid and glucose metabolism in the liver (Hardie, D. G. and Hawley, S. A., Bioessays 23: 1112 (2001), Kemp, B. E. et. al., Biochem. Soc. Transactions 31:162 (2003), Musi, N. and Goodyear, L. J. Current Drug Targets-Immune, Endocrine and Metabolic Disorders 2:119 (2002); Lochhead, P. A. et. al., Diabetes 49:896 (2000); and Zhou, G. et. al., J. of Clin. Invest. 108: 1167 (2001).

In vivo studies have demonstrated the following beneficial effects of both acute and chronic administration of AICAR, an AMPK activator, in rodent models of obesity and type 2 diabetes: 1) an improvement in glucose homeostasis in insulin-resistant diabetic (ob/ob) mice; 2) a decrease in blood glucose concentrations in ob/ob and db/db mice and a blood glucose reduction of 35% following 8 weeks of administration; and 3) a reduction in metabolic disturbances and a reduction of blood pressure in rats displaying characteristics of insulin resistance syndrome (Bergeron, R. et. al., Diabetes 50:1076 (2001); Song, S. M. et. al., Diabetologia 45:56 (2002); Halseth, A. E. et. al., Biochem. and Biophys. Res. Comm. 294:798 (2002); and Buhl, E. S. et. al., Diabetes 51: 2199 (2002)). A further study of 7 week AICAR administration in obese Zucker (fa/fa) rats lead to a reduction in plasma triglycerides and free fatty acids; an increase in HDL cholesterol; and a normalization of glucose metabolism as assessed by an oral glucose tolerance test (Minokoshi, Y. et. al., Nature 415: 339 (2002)). Expression of dominant negative AMPK in skeletal muscle of transgenic mice has demonstrated that the AICAR effect on stimulation of glucose transport is dependent on AMPK activation (Mu, J. et. al., Molecular Cell 7: 1085 (2001)).

Recent data also suggest that AMPK activation is involved in the glucose and lipid-lowering effects of the anti-diabetic drug metformin. It has been shown that the diabetes drug metformin can activate AMPK in vivo at high concentrations (Zhou, G. et. al., J. of Clin. Invest. 108: 1167 (2001); Musi, N. et. al. Diabetes 51: 2074 (2002)).

Based on these studies, it is expected that the in vivo activation of AMPK in the liver may result in the reduction of hepatic glucose output, an improvement in overall glucose homeostasis, a decrease in fatty acid and cholesterol synthesis, and an increase in fatty acid oxidation. Stimulation of AMPK in skeletal muscle is expected to result in an increase in glucose uptake and fatty acid oxidation with resulting improvement of glucose homeostasis, and an improvement in insulin action. Finally, the resulting increase in energy expenditure may lead to a decrease in body weight. The lowering of blood pressure has also been reported to be a consequence of AMPK activation.

Increased fatty acid synthesis is a characteristic of many tumor cells, therefore decreasing the synthesis of fatty acids via AMPK activation may also be useful as a cancer therapy. Activation of AMPK may also be useful to treat ischemic events in the brain (Blazquez, C. et. al., J. Neurochem. 73: 1674 (1999)); to prevent damage from reactive oxygen species (Zhou, M. et. al., Am. J. Physiol. Endocrinol. Metab. 279: E622 (2000)); and to improve local circulatory systems (Chen, Z.-P., et. al. AMP-activated protein kinase phosphorylation of endothelial NO synthase. FEBS Letters 443: 285 (1999)).

Compounds that activate AMPK may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight. There is a need for potent AMPK activators that have pharmacokinetic and pharmacodynamic properties suitable for use as human pharmaceuticals.

Benzimidazole compounds are disclosed in WO 2010/051206; WO 2010/051176; WO 2010/047982; WO 2010/036613; WO 93/07124; WO 95/29897; WO 98/39342; WO 98/39343; WO 00/03997; WO 00/14095; WO 01/53272; WO 01/53291; WO 02/092575; WO 02/40019; WO 03/018061; WO 05/002520; WO 05/018672; WO 06/094209; U.S. Pat. No. 6,312,662; U.S. Pat. No. 6,489,476; US 2005/0148643; DE 3 316 095; JP 6 298 731; EP 0 126 030; EP 0 128 862; EP 0 129 506; and EP 0 120 403. AMPK activators are disclosed in WO 08/006432; WO 05/051298; WO 05/020892; US 2007/015665; US 2007/032529; US 2006/287356; and US 2005/038068. Azabenzimidazole compounds are disclosed in WO 2012/33149.

SUMMARY OF THE INVENTION

The present invention is concerned with novel benzimidazole derivatives of structural Formula I:

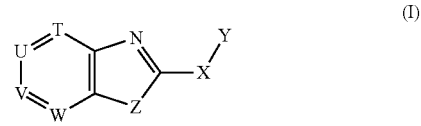

(I)

and pharmaceutically acceptable salts thereof. The compounds of structural formula I, and salts thereof, are activators of AMP-activated protein kinase (AMPK) and are useful in the treatment, prevention and suppression of diseases, disorders and conditions mediated by activation of AMP-activated protein kinase. As AMPK activators, the compounds of structural formula I may be useful to treat Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that are responsive to activation of AMP-activated protein kinase in a subject in need thereof by administering the compounds and pharmaceutical compositions of the present invention. The present invention also relates to the use of compounds of the present invention for manufacture of a medicament useful in treating diseases, disorders and conditions are responsive to the activation of AMP-activated protein kinase. The present invention is also concerned with treatment of these diseases, disorders and conditions by administering the compounds of the present invention in combination with a therapeutically effective amount of another agent useful to treat the disease, disorder and condition. The invention is further concerned with processes for preparing the compounds of this invention.

DETAILED DESCRIPTION OF THE INVENTION

The present invention is concerned with novel compounds of structural Formula I:

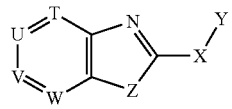

(I)

or a pharmaceutically acceptable salt thereof, wherein:
T is selected from the group consisting of: $CR^3$, N and N-oxide;
U is selected from the group consisting of: $CR^1$, N and N-oxide;
V is selected from the group consisting of: $CR^2$, N and N-oxide;
W is selected from the group consisting of: $CR^4$, N and N-oxide,
provided that at least one of T, U, V and W is N or N-oxide;
X is selected from:
 (1) —$CH_2$—,
 (2) —CHF—,
 (3) —$CF_2$—,
 (4) —S—,
 (5) —O—,
 (6) —O—$CH_2$—,
 (7) —O—$CH_2CH_2$—,
 (8) —NH—,
 (9) —C(O)—,
 (10) —NHC(O)—,
 (11) —C(O)NH—,
 (12) —$NHSO_2$—,
 (13) —$SO_2NH$—, and
 (14) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl;
Y is selected from:

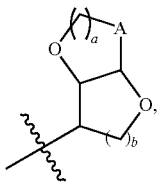

wherein A is selected from: $CH_2$, NH, $NC_{1-6}$alkyl, O and S, and wherein Y is unsubstituted or substituted with 1, 2, 3 or 4 substituents selected from $R^b$;
Z is selected from:
 (1) —$NR^5$,
 (2) —S—, and
 (3) —O—;
each $R^1$ and $R^2$ is independently selected from:
 (1) hydrogen,
 (2) halogen,
 (3) CN,
 (4) $CF_3$,
 (5) —$C_{1-6}$alkyl,
 (6) —$C_{2-6}$alkenyl,
 (7) —$C_{2-6}$alkynyl,
 (8) —$(CH_2)_pC_{3-10}$cycloalkyl,
 (9) —$(CH_2)_pC_{3-7}$cycloalkyl-aryl,
 (10) —$(CH_2)_pC_{3-7}$cycloalkyl-heteroaryl,
 (11) —$(CH_2)_pC_{4-10}$cycloalkenyl,
 (12) —$(CH_2)_pC_{4-7}$cycloalkenyl-aryl,
 (13) —$(CH_2)_pC_{4-7}$cycloalkenyl-heteroaryl,
 (14) —$(CH_2)_pC_{2-10}$cycloheteroalkyl,
 (15) —$(CH_2)_pC_{2-10}$cycloheteroalkenyl,
 (16) —$(CH_2)_p$aryl,
 (17) —$(CH_2)_p$aryl-$C_{1-8}$alkyl,
 (18) —$(CH_2)_p$aryl-$C_{2-8}$alkenyl,
 (19) —$(CH_2)_p$aryl-$C_{2-8}$alkynyl-$C_{1-8}$alkyl,
 (20) —$(CH_2)_p$aryl-$C_{2-8}$alkynyl-$C_{3-7}$cycloalkyl,
 (21) —$(CH_2)_p$aryl-$C_{2-8}$alkynyl-$C_{3-7}$cycloalkenyl,
 (22) —$(CH_2)_p$aryl-$C_{2-8}$alkynyl-$C_{2-10}$cycloheteroalkyl,
 (23) —$(CH_2)_p$aryl-$C_{2-8}$alkynyl-$C_{2-10}$cycloheteroalkenyl,
 (24) —$(CH_2)_p$aryl-$C_{2-8}$alkynyl-aryl,
 (25) —$(CH_2)_p$aryl-$C_{2-8}$alkynyl-heteroaryl,
 (26) —$(CH_2)_p$aryl-$C_{3-7}$cycloalkyl,
 (27) —$(CH_2)_p$aryl-$C_{3-7}$cycloalkenyl,
 (28) —$(CH_2)_p$aryl-$C_{2-10}$cycloheteroalkyl,
 (29) —$(CH_2)_p$aryl-$C_{2-10}$cycloheteroalkenyl,
 (30) —$(CH_2)_p$aryl-aryl,
 (31) —$(CH_2)_p$aryl-heteroaryl,
 (32) —$(CH_2)_p$heteroaryl,
 (33) —$(CH_2)_p$heteroaryl-$C_{3-7}$cycloalkyl,
 (34) —$(CH_2)_p$heteroaryl-$C_{2-10}$cycloheteroalkyl,
 (35) —$(CH_2)_p$heteroaryl-$C_{2-10}$cycloheteroalkenyl,
 (36) —$(CH_2)_p$heteroaryl-aryl,
 (37) —$(CH_2)_p$heteroaryl-heteroaryl,
 (38) —$C_{2-6}$alkenyl-alkyl,
 (39) —$C_{2-6}$alkenyl-aryl,
 (40) —$C_{2-6}$alkenyl-heteroaryl,
 (41) —$C_{2-6}$alkenyl-$C_{3-7}$cycloalkyl,
 (42) —$C_{2-6}$alkenyl-$C_{3-7}$cycloalkenyl,
 (43) —$C_{2-6}$alkenyl-$C_{2-7}$cycloheteroalkyl,
 (44) —$C_{2-6}$alkenyl-$C_{2-7}$cycloheteroalkenyl,
 (45) —$C_{2-6}$alkynyl-$(CH_2)_{1-3}$—O-aryl,
 (46) —$C_{2-6}$alkynyl-alkyl,
 (47) —$C_{2-6}$alkynyl-aryl,
 (48) —$C_{2-6}$alkynyl-heteroaryl,
 (49) —$C_{2-6}$alkynyl-$C_{3-7}$cycloalkyl,
 (50) —$C_{2-6}$alkynyl-$C_{3-7}$cycloalkenyl,
 (51) —$C_{2-6}$alkynyl-$C_{2-7}$cycloheteroalkyl,
 (52) —$C_{2-6}$alkynyl-$C_{2-7}$cycloheteroalkenyl, and
 (53) —$C(O)NH$—$(CH_2)_{0-3}$phenyl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$,
provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl;
$R^3$ and $R^4$ are each independently absent or selected from:
 (1) hydrogen,
 (2) halogen,
 (3) —$C_{1-6}$alkyl,
 (4) —$C_{2-6}$alkenyl,
 (5) —$C_{2-6}$alkynyl,
 (6) —$C_{3-10}$cycloalkyl, (7) —$C_{3-10}$cycloalkenyl,
(8) aryl,
(9) heteroaryl,
(10) —CN,
(11) —$CF_3$,
(12) —OH,
(13) —$OC_{1-6}$alkyl,
(14) —$NH_2$,
(15) —$NHC_{1-6}$alkyl,
(16) —$N(C_{1-6}alkyl)_2$,
(17) —$SC_{1-6}$alkyl,
(18) —$SOC_{1-6}$alkyl,
(19) —$SO_2C_{1-6}$alkyl,
(20) —$NHSO_2C_{1-6}$alkyl,
(21) —$NHC(O)C_{1-6}$alkyl,
(22) —$SO_2NHC_{1-6}$alkyl, and
(23) —$C(O)NHC_{1-6}$alkyl;

$R^5$ is selected from:
(1) hydrogen,
(2) —$C_{1-6}$alkyl,
(3) —$C_{1-6}$alkenyl,
(4) —$(CH_2)_uOH$,
(5) —$CH_2CO_2H$, and
(6) —$CH_2CO_2C_{1-6}$alkyl;

each $R^a$ is independently selected from the group consisting of:
(1) —$(CH_2)_m$-halogen,
(2) oxo,
(3) —$(CH_2)_mOH$,
(4) —$(CH_2)_mN(R^j)_2$,
(5) —$(CH_2)_mNO_2$,
(6) —$(CH_2)_mCN$,
(7) —$C_{1-6}$alkyl,
(8) —$(CH_2)_mCF_3$,
(9) —$(CH_2)_mOCF_3$,
(10) —O—$(CH_2)_m$—$OC_{1-6}$alkyl,
(11) —$(CH_2)_mN(R^j)C(O)R^f$,
(12) —$(CH_2)_mN(R^j)CO_2R^f$,
(13) —$(CH_2)_mC(=N-OH)N(R^j)_2$,
(14) —$(CH_2)_mOC_{1-6}$alkyl,
(15) —$(CH_2)_mO$—$(CH_2)_m$—$C_{3-7}$cycloalkyl,
(16) —$(CH_2)_mO$—$(CH_2)_m$—$C_{2-7}$cycloheteroalkyl,
(17) —$(CH_2)_mO$—$(CH_2)_m$-aryl,
(18) —$(CH_2)_mO$—$(CH_2)_m$-heteroaryl,
(19) —$(CH_2)_mSC_{1-6}$alkyl,
(20) —$(CH_2)_mS(O)C_{1-6}$alkyl,
(21) —$(CH_2)_mSO_2C_{1-6}$alkyl,
(22) —$(CH_2)_mO$—$SO_2C_{1-6}$alkyl,
(23) —$(CH_2)_mSO_2(CH_2)_m$—$C_{3-7}$cycloalkyl,
(24) —$(CH_2)_mSO_2(CH_2)_m$—$C_{2-7}$cycloheteroalkyl,
(25) —$(CH_2)_mSO_2(CH_2)_m$-aryl,
(26) —$(CH_2)_mSO_2(CH_2)_m$-heteroaryl,
(27) —$(CH_2)_mSO_2NH_2$,
(28) —$(CH_2)_mSO_2NHC_{1-6}$alkyl,
(29) —$(CH_2)_mSO_2NHC_{3-7}$cycloalkyl,
(30) —$(CH_2)_mSO_2NHC_{2-7}$cycloheteroalkyl,
(31) —$(CH_2)_mSO_2NH$-aryl,
(32) —$(CH_2)_mSO_2NH$-heteroaryl,
(33) —$(CH_2)_mNHSO_2$—$C_{1-6}$alkyl,
(34) —$(CH_2)_mNHSO_2$—$C_{3-7}$cycloalkyl,
(35) —$(CH_2)_mNHSO_2$—$C_{2-7}$cycloheteroalkyl,
(36) —$(CH_2)_mNHSO_2$-aryl,
(37) —$(CH_2)_mNHSO_2NH$-heteroaryl,
(38) —$(CH_2)_mN(R^j)$—$C_{1-6}$alkyl,
(39) —$(CH_2)_mN(R^j)$—$C_{3-7}$cycloalkyl,
(40) —$(CH_2)_mN(R^j)$—$(CH_2)_m$—$C_{3-7}$cycloalkyl,
(41) —$(CH_2)_mN(R^j)$—$C_{2-7}$cycloheteroalkyl,
(42) —$(CH_2)_mH(R^j)$—$(CH_2)_m$—$C_{2-7}$cycloheteroalkyl,
(43) —$(CH_2)_mN(R^j)$—$C_{2-7}$cycloheteroalkenyl,
(44) —$(CH_2)_mN(R^j)$—$(CH_2)_m$—$C_{2-7}$cycloheteroalkenyl,
(45) —$(CH_2)_mN(R^j)$-aryl,
(46) —$(CH_2)_mN(R^j)$—$(CH_2)_m$-aryl,
(47) —$(CH_2)_mN(R^j)$-heteroaryl,
(48) —$(CH_2)_mN(R^j)$—$(CH_2)_m$-heteroaryl,
(49) —$(CH_2)_mC(O)R^f$,
(50) —$(CH_2)_mC(O)N(R^j)_2$,
(51) —$(CH_2)_mN(R^j)C(O)N(R^j)_2$,
(52) —$(CH_2)_mCO_2H$,
(53) —$(CH_2)_mOCOH$,
(54) —$(CH_2)_mCO_2R^f$,
(55) —$(CH_2)_mOCOR^f$,
(56) —$(CH_2)_mC_{3-7}$cycloalkyl,
(57) —$(CH_2)_mC_{3-7}$cycloalkenyl,
(58) —$(CH_2)_mC_{2-6}$cycloheteroalkyl,
(59) —$(CH_2)_mC_{2-6}$cycloheteroalkenyl,
(60) —$(CH_2)_m$aryl, and
(61) —$(CH_2)_m$heteroaryl, wherein each $CH_2$ is unsubstituted or substituted with 1 or 2 substituents selected from: oxo, —OH, —$(CH_2)_{1-3}OH$, —CN, —$NH_2$, —$NH(C_{1-6}alkyl)$, —$N(C_{1-6}alkyl)_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}OH$, —CN, —$NH_2$, —$NH(C_{1-6}alkyl)$, —$N(C_{1-6}alkyl)_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$(CH_2)_{1-5}CF_3$ optionally substituted with 1, 2 or 3 —OH, —$CO_2H$, —$CO_2C_{1-6}$alkyl, —$SO_2C_{1-6}$alkyl, —$C_{3-7}$cycloalkyl, phenyl, $CH_2$phenyl, heteroaryl and $CH_2$heteroaryl;

each $R^b$ is independently selected from:
(1) hydrogen,
(2) —$C_{1-6}$alkyl,
(3) —$C_{1-6}$alkenyl,
(4) —$(CH_2)_nC_{3-10}$cycloalkyl,
(5) —$(CH_2)_nC_{3-10}$cycloalkenyl,
(6) —$(CH_2)_nC_{2-10}$cycloheteroalkyl,
(7) —$(CH_2)_nC_{2-10}$cycloheteroalkenyl,
(8) —$(CH_2)_n$aryl,
(9) —$(CH_2)_n$heteroaryl,
(10) oxo,
(11) —$(CH_2)_nCF_3$,
(12) —$(CH_2)_nCN$,
(13) —$(CH_2)t$-halogen,
(14) —$(CH_2)s$-OH,
(15) —$(CH_2)_nNO_2$,
(16) —$(CH_2)_nNH_2$,
(17) —$(CH_2)_nNH(C_{1-6}alkyl)$,
(18) —$(CH_2)_nN(C_{1-6}alkyl)_2$,
(19) —$(CH_2)_nNHCO_2H$,
(20) —$(CH_2)_nOC_{1-6}$alkyl,
(21) —$(CH_2)_nOC_{1-6}$alkenyl,
(22) $(CH_2)_nCOC_{1-6}$alkyl,
(23) $(CH_2)_nCO_2H$,
(24) $(CH_2)_nOCOH$,
(25) $(CH_2)_nCO_2R^i$,
(26) $(CH_2)_nOC(O)R^i$,
(27) —$(CH_2)_qC(O)N(R^e)_2$,
(28) —$(CH_2)_qCO_2N(R^e)_2$,
(29) $(CH_2)_nC(O)(CH_2)_nN(R^g)_2$,
(30) $(CH_2)_nOC(O)(CH_2)_nN(R^g)_2$,

(31) —(CH$_2$)$_n$N(R$^e$)C(O)C$_{1-6}$alkyl,
(32) (CH$_2$)$_n$N(R$^e$)SO$_2$R$^i$,
(33) (CH$_2$)$_n$SO$_2$C$_{1-6}$alkyl,
(34) (CH$_2$)$_n$SO$_2$N(R$^e$)R$^g$,
(35) (CH$_2$)$_n$SO$_2$N(R$^e$)C(O)R$^i$,
(36) (CH$_2$)$_n$SO$_2$N(R$^e$)CO$_2$R$^i$,
(37) (CH$_2$)$_n$SO$_2$N(R$^e$)CON(R$^g$)$_2$,
(38) (CH$_2$)$_n$C(O)N(R$^e$)SO$_2$R$^i$,
(39) (CH$_2$)$_n$N(R$^e$)C(O)N(R$^g$)$_2$,
(40) =N(OH), and
(41) =N(OC$_{1-6}$alkyl),
wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from R$^c$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^c$;

each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each R$^e$, R$^g$ and R$^h$ is independently selected from:
(1) hydrogen,
(2) —C$_{1-6}$alkyl, and
(3) —O—C$_{1-6}$alkyl,
wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^j$ is independently selected from:
(1) hydrogen,
(2) C$_{1-6}$alkyl,
(3) C$_{3-6}$cycloalkyl,
(4) —C(O)R$^i$,
(5) —CO$_2$R$^i$, and
(6) —SO$_2$R$^i$,
wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$;

each R$^f$ and R$^i$ is independently selected from:
(1) —C$_{1-6}$alkyl,
(2) —(CH$_2$)$_r$C$_{4-7}$cycloalkyl,
(1) —(CH$_2$)$_r$C$_{4-7}$cycloalkenyl,
(2) —(CH$_2$)$_r$C$_{3-7}$cycloheteroalkyl,
(3) —(CH$_2$)$_r$C$_{3-7}$cycloheteroalkenyl,
(4) —(CH$_2$)$_r$aryl, and
(5) —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl;

a is 1 or 2;
b is 1 or 2;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4;
t is 0, 1, 2, 3 or 4, and
u is 0, 1, 2, 3 or 4.

In one embodiment of the present invention, T is selected from the group consisting of: CR$^3$, N and N-oxide; U is selected from the group consisting of: CR$^1$, N and N-oxide; V is selected from the group consisting of: CR$^2$, N and N-oxide; and W is selected from the group consisting of: CR$^4$, N and N-oxide, provided that at least one of T, U, V and W is N or N-oxide.

In another embodiment of the present invention, T is selected from the group consisting of: —CR$^3$—, N, and N-oxide. In a class of this embodiment, T is —CR$^3$—. In another class of this embodiment, T is selected from the group consisting of: N, and N-oxide. In another class of this embodiment, T is N. In another class of this embodiment, T is N-oxide.

In another embodiment of the present invention, U is selected from the group consisting of: —CR$^1$—, N, and N-oxide. In a class of this embodiment, U is —CR$^1$—. In another class of this embodiment, U is selected from the group consisting of: N, and N-oxide. In another class of this embodiment, U is N. In another class of this embodiment, U is selected from the group consisting of: N-oxide.

In another embodiment of the present invention, V is selected from the group consisting of: —CR$^2$—, N, and N-oxide. In a class of this embodiment, V is —CR$^2$—. In another class of this embodiment, V is selected from the group consisting of: N, and N-oxide. In another class of this embodiment, V is N. In another class of this embodiment, V is N-oxide.

In another embodiment of the present invention, W is selected from the group consisting of: —CR$^4$—, N, and N-oxide. In a class of this embodiment, W is selected from the group consisting of: —CR$^4$—. In another class of this embodiment, W is selected from the group consisting of: N, and N-oxide. In another class of this embodiment, W is N. In another class of this embodiment, W is N-oxide.

In another embodiment of the present invention, one of T, V and W is N or N-oxide.

In another embodiment of the present invention, one of T, V and W is N or N-oxide, and U is —$CR^1$—; or a pharmaceutically acceptable salt thereof In another embodiment of the present invention, one of T and W is N or N-oxide, U is $CR^1$ and V is $CR^2$, provided that if W is N or N-oxide then $R^1$ is selected from hydrogen, halogen, —CN, —$CF_3$, —$C_{1-6}$alkyl, —$C_{2-6}$alkenyl and —$C_{2-6}$alkynyl, and if T is N or N-oxide then $R^2$ is selected from hydrogen, halogen, —CN, —$CF_3$, —$C_{1-6}$alkyl, —$C_{2-6}$alkenyl and —$C_{2-6}$alkynyl.

In another embodiment of the present invention, one of T and W is N or N-oxide, U is $CR^1$ and V is $CR^2$, provided that if W is N or N-oxide then $R^1$ is halogen, and if T is N or N-oxide then $R^2$ is halogen.

In another embodiment of the present invention, T is N or N-oxide; U is —$CR^1$—; V is —$CR^2$—; and W is —$CR^4$—. In a class of this embodiment, T is N or N-oxide; U is —$CR^1$—; V is —$CR^2$—, wherein $R^2$ is halogen; and W is —$CR^4$—. In another class of this embodiment, T is N; U is —CO—; V is —$CR^2$—, wherein $R^2$ is halogen; and W is —$CR^4$—. In another class of this embodiment, T is N; U is —$CR^1$—; V is —$CR^2$—, wherein $R^2$ is halogen; and W is —$CR^4$—.

In another class of this embodiment, T is N or N-oxide; U is —$CR^1$—; V is —$CR^2$—, wherein $R^2$ is hydrogen, —$C_{1-6}$alkyl, CN, or halogen; and W is —$CR^4$—. In another class of this embodiment, T is N; U is —$CR^1$—; V is —$CR^2$—, wherein $R^2$ is hydrogen, —$C_{1-6}$alkyl, CN, or halogen; and W is —$CR^4$—. In another class of this embodiment, T is N; U is —CO—; V is —$CR^2$—, wherein $R^2$ is hydrogen, —$CH_3$, CN, F, or Cl; and W is —$CR^4$—. In another class of this embodiment, T is N; U is —$CR^1$—; V is —$CR^2$—, wherein $R^2$ is hydrogen, —$CH_3$, CN, or Cl; and W is —$CR^4$—.

In another embodiment of the present invention, T and V are N or N-oxide; U is —CO—; and W is —$CR^4$—. In a class of this embodiment, T and V are N; U is —CO—; and W is —$CR^4$—.

In another embodiment of the present invention, T and W are N or N-oxide; U is —$CR^1$—; and V is —$CR^2$—. In a class of this embodiment, T and W are N; U is —$CR^1$—; and V is —$CR^2$—. In a class of this embodiment, T and W are N; U is —$CR^1$—; and V is —$CR^2$—, wherein $R^2$ is halogen.

In another embodiment of the present invention, X is selected from: —$CH_2$—, —CHF—, —$CF_2$—, —S—, —O—, —O—$CH_2$—, —O—$CH_2CH_2$—, —NH—, —C(O)—, —NHC(O)—, —C(O)NH—, —$NHSO_2$—, —$SO_2NH$—, and —$CO_2$—, wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl. In a class of this embodiment, X is selected from: —$CH_2$—, —S—, —O—, O—$CH_2CH_2$— and —NH—, wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl. In another class of this embodiment, X is selected from: —$CH_2$—, —S—, —O—, O—$CH_2CH_2$—, and —NH—.

In another embodiment of the present invention, X is selected from: —S—, —O—, and —NH—. In another embodiment of the present invention, X is —O—. In another embodiment of the present invention, X is —S—. In another embodiment of the present invention, X is —NH—. In a subclass of this class, X is —O—.

In another embodiment of the present invention, Y is selected from:

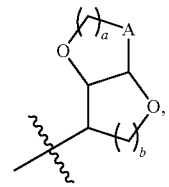

wherein A is selected from: $CH_2$, NH, $NC_{1-6}$alkyl, O and S, and wherein Y is unsubstituted or substituted with 1, 2, 3 or 4 substituents selected from $R^b$.

In another embodiment of the present invention, Y is selected from:

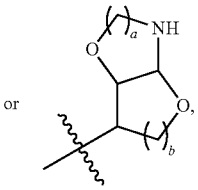 or 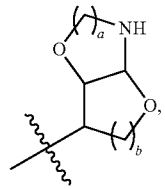

wherein Y is unsubstituted or substituted with 1, 2, 3 or 4 substituents selected from $R^b$.

In another embodiment of the present invention, Y is selected from:

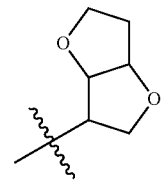

wherein Y is unsubstituted or substituted with 1, 2, 3 or 4 substituents selected from $R^b$. In a class of this embodiment, Y is:

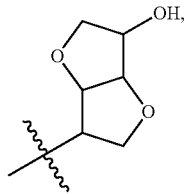

wherein Y is unsubstituted or substituted with 1, 2, 3 or 4 substituents selected from $R^b$. In another class of this embodiment, Y is:

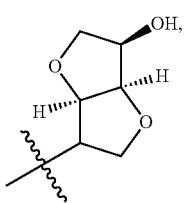

wherein Y is unsubstituted or substituted with 1, 2, 3 or 4 substituents selected from $R^b$.

In another embodiment of the present invention, Y is:

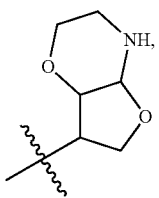

wherein Y is unsubstituted or substituted with 1, 2, 3 or 4 substituents selected from $R^b$. In a class of this embodiment, Y is:

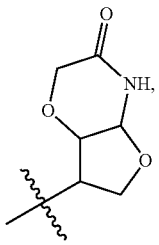

wherein Y is unsubstituted or substituted with 1, 2, 3 or 4 substituents selected from $R^b$. In another class of this embodiment, Y is:

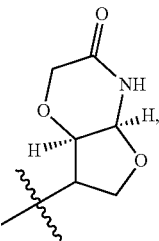

wherein Y is unsubstituted or substituted with 1, 2, 3 or 4 substituents selected from $R^b$.

In another embodiment of the present invention, Z is selected from: $NR^5$, —S—, and —O—. In a class of this embodiment, Z is $NR^5$. In another class of this embodiment, Z is —S—. In another class of this embodiment, Z is —O—.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_p$ $C_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl, —$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CF_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{4-10}$cycloalkenyl, —$(CH_2)_pC_{2-10}$cycloheteroalkyl, —$(CH_2)_pC_{2-10}$cycloheteroalkenyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_p$ $C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl-$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, at least one of and only one of $R^1$ and $R^2$ is selected from hydrogen, halogen, —CN, and —$C_{1-6}$alkyl. In another class of this embodiment, at least one of and only one of $R^1$ and $R^2$ is selected from halogen. In a subclass of this class, at least one of and only one of $R^1$ and $R^2$ is selected from: F and Cl. In a subclass of this class, at least one of and only one of $R^1$ and $R^2$ is Cl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl-$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, at least one of and only one of $R^1$ and $R^2$ is selected from hydrogen, halogen, —CN, and —$C_{1-6}$alkyl. In another class of this embodiment, at least one of and only one of $R^1$ and $R^2$ is selected from halogen. In a subclass of this class, at least one of and only one of $R^1$ and $R^2$ is selected from: F and Cl. In a subclass of this class, at least one of and only one of $R^1$ and $R^2$ is Cl.

In another embodiment of the present invention, each $R^1$ and $R^2$ is independently selected from: hydrogen, halogen, CN, $CF_3$, —$C_{1-6}$alkyl, —$C_{2-6}$alkenyl, —$C_{2-6}$alkynyl, —$(CH_2)_pC_{3-10}$cycloalkyl, —$(CH_2)_pC_{3-7}$cycloalkyl-aryl, —$(CH_2)_pC_{3-7}$cycloalkyl-heteroaryl, —$(CH_2)_pC_{4-10}$cycloalkenyl, —$(CH_2)_pC_{4-7}$cycloalkenyl-aryl, —$(CH_2)_pC_{4-7}$cycloalkenyl-heteroaryl, —$(CH_2)_pC_{2-10}$cycloheteroalkyl, —$(CH_2)_pC_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl-$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl. In a class of this embodiment, at least one of and only one of $R^1$ and $R^2$ is selected from halogen. In a subclass of this class, at least one of and only one of $R^1$ and $R^2$ is selected from: F and Cl.

In another class of this embodiment, each $R^1$ and $R^2$ is independently selected from: halogen, —$(CH_2)_pC_{2-10}$cycloheteroalkyl, —$(CH_2)_p$aryl-$C_{2-8}$alkynyl-$C_{2-10}$cycloheteroalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{2-10}$cycloheteroalkyl, —$(CH_2)_p$heteroaryl-aryl, and —$(CH_2)_p$heteroaryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from halogen. In a subclass of this class, at least one of and only one of $R^1$ and $R^2$ is selected from: F and Cl.

In another embodiment of the present invention, each $R^1$ and $R^2$ is independently selected from: hydrogen, halogen, —CN, —$C_{1-6}$alkyl, $C_{4-10}$cycloalkenyl, $C_{2-10}$cycloheteroalkyl, $C_{2-10}$cycloheteroalkenyl, aryl-$C_{2-8}$alkynyl-$C_{2-10}$cycloheteroalkyl, aryl, aryl-$C_{1-8}$alkyl, aryl-$C_{3-7}$cycloalkyl, aryl-$C_{3-7}$cycloalkenyl, aryl-$C_{2-10}$cycloheteroalkyl, aryl-$C_{2-10}$cycloheteroalkenyl, aryl-aryl, aryl-heteroaryl, heteroaryl, heteroaryl-$C_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from hydrogen, halogen, —CN, and —$C_{1-6}$alkyl. In a class of this embodiment, at least one of and only one of $R^1$ and $R^2$ is selected from halogen. In a subclass of this subclass, at least one of and only one of $R^1$ and $R^2$ is selected from: F and Cl. In another subclass of this subclass, at least one of and only one of $R^1$ and $R^2$ is selected from: Cl.

In another embodiment of the present invention, each $R^1$ and $R^2$ is independently selected from: hydrogen, halogen, —CN, —$C_{1-6}$alkyl, dihydropyrrolo-pyrazole, tetrahydroisoquinoline, cyclohexene, cyclopentene, pyrrolidine, piperidine, piperazine, azepane, 3,6-dihydrothiopyran, 2,5-dihydrothiophene, phenyl, phenyl-$(CH_2)_2$OH, phenyl-$(CH_2)_3$OH, phenyl-$(CH_2)_2$C$(CH_3)_2$OH, phenyl-cyclohexyl, phenyl-cyclopropyl, phenyl-cyclobutyl, phenyl-cyclohexene, phenyl-$C_2$alkynyl-piperidine, phenyl-dihydropyrrolopyrazole, phenyl-dihydroimidazole, phenyl-dihydrothiopyran, biphenyl, phenyl-tetrahydroisoquinoline, phenyl-oxetane, phenyl-thietane, phenyl-pyrazolidine, phenyl-morpholine, phenyl-azetidine, phenyl-pyrrolidine, phenyl-piperazine, phenyl-piperidine, phenyl-tetrahydropyran, phenyl-tetrahydrothiopyran phenyl-azepane, phenyl-thiomorpholine, phenyl-pyrazolidine, phenyl-oxazolidine, phenyl-cyclobutyldioxolane, phenyl-naphthalene, phenyl-isoquinoline, phenyl-pyrrole, phenyl-imidazole, phenyl-pyrazole, phenyl-tetrazole, phenyl-pyrimidine, phenyl-quinazoline, phenyl-6,7-dihydro-5H-pyrrolo[1,2-a]imidazole, pyridine, indole, azaindole, isoxazole, pyrazole, benzisoxazole, thiazolo[4,5-c]pyridine, benzodioxane, pyrrole, furan, pyrimidine, thiophene, quinazoline, 4,5,6,7-tetrahydropyrazolo[1,5-a]pyridine, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, pyridine-oxazolidine, pyridine-piperidine, and pyridine-piperazine, wherein each alkyl, alkynyl, cycloalkyl, cycloalkenyl, cycloheteroalkyl, cycloheteroalkenyl, aryl, phenyl and heteroaryl is unsubstituted or substituted with 1, 2, 3 or 4 substituents independently selected from $R^a$, provided that at least one of and only one of $R^1$ and $R^2$ is selected from hydrogen, halogen, —CN, and —$C_{1-6}$alkyl. In a class of this embodiment, at least one of and only one of $R^1$ and $R^2$ is selected from hydrogen, F, Cl, CN, and $CH_3$. In another class of this embodiment, at least one of and only one of $R^1$ and $R^2$ is selected from hydrogen, Cl, CN, and $CH_3$. In another class of this embodiment, at least one of and only one of $R^1$ and $R^2$ is selected from halogen. In a subclass of this subclass, at least one of and only one of $R^1$ and $R^2$ is selected from: F and Cl. In another subclass of this subclass, at least one of and only one of $R^1$ and $R^2$ is Cl.

In another subclass of this embodiment of the present invention, each $R^1$ and $R^2$ is independently selected from: halogen, $C_{2-10}$cycloheteroalkyl, aryl-$C_{2-8}$alkynyl-$C_{2-10}$cycloheteroalkyl, aryl-$C_{2-10}$cycloheteroalkyl, aryl-$C_{2-10}$cycloheteroalkenyl, aryl-aryl, aryl-heteroaryl, heteroaryl, heteroaryl-$C_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from halogen. In a subclass of this subclass, at least one of and only one of $R^1$ and $R^2$ is selected from: F and Cl. In another subclass of this embodiment of the present invention, each $R^1$ and $R^2$ is independently selected from: halogen, dihydropyrrolo-pyrazole, phenyl-$C_2$alkynyl-piperidine, phenyl-dihydropyrrolopyrazole, phenyl-dihydroimidazole, biphenyl, phenyl-naphthalene, phenyl-isoquinoline, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, and pyridine-pyrazole, wherein each alkynyl, cycloheteroalkyl, cycloheteroalkenyl, phenyl and heteroaryl is unsubstituted or substituted with 1, 2, 3 or 4 substituents independently selected from $R^a$, provided that at least one of and only one of $R^1$ and $R^2$ is selected from halogen. In a subclass of this subclass, at least one of and only one of $R^1$ and $R^2$ is selected from: F and Cl.

In another subclass of this embodiment of the present invention, each $R^1$ and $R^2$ is independently selected from: halogen, 4,6-dihydropyrrolo[3,4-c]pyrazole, phenyl-$C_2$alkynyl-piperidine, phenyl-4,6-dihydropyrrolo[3,4-c]pyrazole, phenyl-2,6-diazaspiro[3,3]heptane, phenyl 3,9-diazaspiro[5,5]undecane, phenyl-2,7diazaspiro[3,5]nonane, phenyl 4,5-dihydro-1H-imidazole, biphenyl, phenyl-naphthalene, phenyl-isoquinoline, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, wherein each alkynyl, cycloheteroalkyl, cycloheteroalkenyl, phenyl, and heteroaryl is unsubstituted or substituted with 1, 2, 3 or 4 substituents independently selected from $R^a$, provided that at least one of and only one of $R^1$ and $R^2$ is selected from halogen. In a subclass of this subclass, at least one of and only one of $R^1$ and $R^2$ is selected from: F and Cl.

In another class of this embodiment of the present invention, each $R^1$ and $R^2$ is independently selected from: halogen, aryl-$C_{2-8}$alkynyl-$C_{2-10}$cycloheteroalkyl, aryl-$C_{2-10}$cycloheteroalkyl, and aryl-aryl, wherein each alkynyl, cycloheteroalkyl and aryl is unsubstituted or substituted with 1, 2, 3 or 4 substituents independently selected from $R^a$, provided that at least one of and only one of $R^1$ and $R^2$ is Cl. In a subclass of this class, each $R^1$ and $R^2$ is independently selected from: halogen, aryl-$C_2$alkynyl-$C_{4-10}$cycloheteroalkyl, aryl-$C_{2-10}$cycloheteroalkyl, and aryl-aryl, wherein each alkynyl, cycloheteroalkyl and aryl is unsubstituted or substituted with 1, 2, 3 or 4 substituents independently selected from $R^a$, provided that at least one of and only one of $R^1$ and $R^2$ is Cl. In another subclass of this class, each $R^1$ and $R^2$ is independently selected from: halogen, phenyl-$C_2$alkynyl-piperidine, phenyl-dihydropyrrolopyrazole and biphenyl, wherein each alkynyl, cycloheteroalkyl and phenyl is unsubstituted or substituted with 1, 2, 3 or 4 substituents independently selected from $R^a$, provided that at least one of and only one of $R^1$ and $R^2$ is Cl.

In another embodiment of the present invention, each $R^1$ is independently selected from: —$(CH_2)_p C_{3-10}$cycloalkyl, —$(CH_2)_p C_{3-7}$cycloalkyl-aryl, —$(CH_2)_p C_{3-7}$cycloalkyl-heteroaryl, —$(CH_2)_p C_{4-10}$cycloalkenyl, —$(CH_2)_p C_{4-7}$cycloalkenyl-aryl, —$(CH_2)_p C_{4-7}$cycloalkenyl-heteroaryl, —$(CH_2)_p C_{2-10}$cycloheteroalkyl, —$(CH_2)_p C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl, —(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, and R$^2$ is selected from the group consisting of: hydrogen, halogen, —CN, —CF$_3$, —C$_{1-6}$alkyl, —C$_{2-6}$alkenyl and —C$_{2-6}$alkynyl.

In another embodiment of the present invention, each R$^1$ is independently selected from: —(CH$_2$)$_p$C$_{3-10}$cycloalkyl, —(CH$_2$)$_p$C$_{4-10}$cycloalkenyl, —(CH$_2$)$_p$C$_{2-10}$cycloheteroalkyl, —(CH$_2$)$_p$C$_{2-10}$cycloheteroalkenyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{1-8}$alkyl, —(CH$_2$)$_p$aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{3-7}$cycloalkenyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl-(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, and R$^2$ is selected from the group consisting of: hydrogen, halogen, —CN, —CF$_3$, —C$_{1-6}$alkyl, —C$_{2-6}$alkenyl and —C$_{2-6}$alkynyl. In a class of this embodiment, R$^2$ is selected from hydrogen, halogen, —CN, and —C$_{1-6}$alkyl. In another class of this embodiment, R$^2$ is selected from halogen. In a subclass of this class, R$^2$ is selected from: F and Cl. In another subclass of this class, R$^2$ is Cl.

In another embodiment of the present invention, each R$^1$ is independently selected from: —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{1-8}$alkyl, —(CH$_2$)$_p$aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{3-7}$cycloalkenyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl-(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, and R$^2$ is selected from the group consisting of: hydrogen, halogen, —CN, —CF$_3$, —C$_{1-6}$alkyl, —C$_{2-6}$alkenyl and —C$_{2-6}$alkynyl. In a class of this embodiment, R$^2$ is selected from hydrogen, halogen, —CN, and —C$_{1-6}$alkyl. In another class of this embodiment, R$^2$ is selected from halogen. In a subclass of this class, R$^2$ is selected from: F and Cl. In another subclass of this class, R$^2$ is Cl.

In another embodiment of the present invention, each R$^1$ is independently selected from: C$_{4-10}$cycloalkenyl, C$_{2-10}$cycloheteroalkyl, C$_{2-10}$cycloheteroalkenyl, aryl-C$_{2-8}$alkynyl-C$_{2-10}$cycloheteroalkyl, aryl, aryl-C$_{1-8}$alkyl, aryl-C$_{3-7}$cycloalkyl, aryl-C$_{3-7}$cycloalkenyl, aryl-C$_{2-10}$cycloheteroalkyl, aryl-C$_{2-10}$cycloheteroalkenyl, aryl-aryl, aryl-heteroaryl, heteroaryl, heteroaryl-C$_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from R$^a$, and R$^2$ is selected from hydrogen, halogen, —CN, and —C$_{1-6}$alkyl. In a class of this embodiment, R$^2$ is selected from halogen. In a subclass of this subclass, R$^2$ is selected from: F and Cl. In another subclass of this subclass, R$^2$ is Cl.

In another embodiment of the present invention, each R$^1$ is independently selected from: dihydropyrrolo-pyrazole, tetrahydroisoquinoline, cyclohexene, cyclopentene, pyrrolidine, piperidine, piperazine, azepane, 3,6-dihydrothiopyran, 2,5-dihydrothiophene, phenyl, phenyl-(CH$_2$)$_2$OH, phenyl-(CH$_2$)$_3$OH, phenyl-(CH$_2$)$_2$C(CH$_3$)$_2$OH, phenyl-cyclohexyl, phenyl-cyclopropyl, phenyl-cyclobutyl, phenyl-cyclohexene, phenyl-C$_2$alkynyl-piperidine, phenyl-dihydropyrrolopyrazole, phenyl-dihydroimidazole, phenyl-dihydrothiopyran, biphenyl, phenyl-tetrahydroisoquinoline, phenyl-oxetane, phenyl-thietane, phenyl-pyrazolidine, phenyl-morpholine, phenyl-azetidine, phenyl-pyrrolidine, phenyl-piperazine, phenyl-piperidine, phenyl-tetrahydropyran, phenyl-tetrahydrothiopyran phenyl-azepane, phenyl-thiomorpholine, phenyl-pyrazolidine, phenyl-oxazolidine, phenyl-cyclobutyldioxolane, phenyl-naphthalene, phenyl-isoquinoline, phenyl-pyrrole, phenyl-imidazole, phenyl-pyrazole, phenyl-tetrazole, phenyl-pyrimidine, phenyl-quinazoline, phenyl-6,7-dihydro-5H-pyrrolo[1,2-a]imidazole, pyridine, indole, azaindole, isoxazole, pyrazole, benzisoxazole, thiazolo[4,5-c]pyridine, benzodioxane, pyrrole, furan, pyrimidine, thiophene, quinazoline, 4,5,6,7-tetrahydropyrazolo[1,5-a]pyridine, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, pyridine-oxazolidine, pyridine-piperidine, and pyridine-piperazine, wherein each alkyl, alkynyl, cycloalkyl, cycloalkenyl, cycloheteroalkyl, cycloheteroalkenyl, aryl, phenyl and heteroaryl is unsubstituted or substituted with 1, 2, 3 or 4 substituents independently selected from $R^a$, and $R^2$ is selected from hydrogen, halogen, —CN, and —$C_{1-6}$alkyl. In a class of this embodiment, $R^2$ is selected from hydrogen, F, Cl, CN, and $CH_3$. In another class of this embodiment, $R^2$ is selected from hydrogen, Cl, CN, and $CH_3$. In another class of this embodiment, $R^2$ is selected from halogen. In a subclass of this subclass, $R^2$ is selected from: F and Cl. In another subclass of this subclass, $R^2$ is Cl.

In another embodiment of the present invention, each $R^1$ is independently selected from: hydrogen, halogen, CN, $CF_3$, —$C_{1-6}$alkyl, —$C_{2-6}$alkenyl, —$C_{2-6}$alkynyl, —$(CH_2)_p$$C_{3-10}$cycloalkyl, —$(CH_2)_p$$C_{3-7}$cycloalkyl-aryl, —$(CH_2)_p$$C_{3-7}$cycloalkyl-heteroaryl, —$(CH_2)_p$$C_{4-10}$cycloalkenyl, —$(CH_2)_p$$C_{4-7}$cycloalkenyl-aryl, —$(CH_2)_p$$C_{4-7}$cycloalkenyl-heteroaryl, —$(CH_2)_p$$C_{2-10}$cycloheteroalkyl, —$(CH_2)_p$$C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl-$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$.

In another embodiment of the present invention, each $R^1$ is independently selected from: —$(CH_2)_p$$C_{3-10}$cycloalkyl, —$(CH_2)_p$$C_{3-7}$cycloalkyl-aryl, —$(CH_2)_p$$C_{3-7}$cycloalkyl-heteroaryl, —$(CH_2)_p$$C_{4-10}$cycloalkenyl, —$(CH_2)_p$$C_{4-7}$cycloalkenyl-aryl, —$(CH_2)_p$$C_{4-7}$cycloalkenyl-heteroaryl, —$(CH_2)_p$$C_{2-10}$cycloheteroalkyl, —$(CH_2)_p$$C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl-$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$.

In another class of this embodiment of the present invention, each $R^1$ is independently selected from: —$(CH_2)_p$$C_{2-10}$cycloheteroalkyl, —$(CH_2)_p$aryl-$C_{2-8}$alkynyl-$C_{2-10}$cycloheteroalkyl, —$(CH_2)_p$aryl-$C_{2-10}$cycloheteroalkyl, —$(CH_2)_p$aryl-$C_{2-10}$cycloheteroalkyl, —$(CH_2)_p$aryl-aryl, —$(CH_2)_p$aryl-heteroaryl, —$(CH_2)_p$heteroaryl, —$(CH_2)_p$heteroaryl-$C_{2-10}$cycloheteroalkyl, —$(CH_2)_p$heteroaryl-aryl, and —$(CH_2)_p$heteroaryl-heteroaryl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkynyl, cycloheteroalkyl, cycloheteroalkenyl, aryl and heteroaryl is unsubstituted or substituted with 1, 2, 3 or 4 substituents independently selected from $R^a$.

In another subclass of this embodiment of the present invention, each $R^1$ is independently selected from: $C_{2-10}$cycloheteroalkyl, aryl-$C_{2-8}$alkynyl-$C_{2-10}$cycloheteroalkyl, aryl-$C_{2-10}$cycloheteroalkyl, aryl-$C_{2-10}$cycloheteroalkenyl, aryl-aryl, aryl-heteroaryl, heteroaryl, heteroaryl-$C_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from $R^a$. In another subclass of this embodiment of the present invention, each $R^1$ is independently selected from: dihydropyrrolo-pyrazole, phenyl-$C_2$alkynyl-piperidine, phenyl-dihydropyrrolopyrazole, phenyl-dihydroimidazole, biphenyl, phenyl-naphthalene, phenyl-isoquinoline, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, and pyridine-pyrazole, wherein each alkynyl, cycloheteroalkyl, cycloheteroalkenyl, phenyl and heteroaryl is unsubstituted or substituted with 1, 2, 3 or 4 substituents independently selected from $R^a$. In another subclass of this embodiment of the present invention, each $R^1$ is independently selected from: 4,6-dihydropyrrolo[3,4-c]pyrazole, phenyl-$C_2$alkynyl-piperidine, phenyl-4,6-dihydropyrrolo[3,4-c]pyrazole, phenyl 4,5-dihydro-1H-imidazole, biphenyl, phenyl-naphthalene, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, wherein each alkynyl, cycloheteroalkyl, cycloheteroalkenyl, phenyl, and heteroaryl is unsubstituted or substituted with 1, 2, 3 or 4 substituents independently selected from $R^a$. In another class of this embodiment of the present invention, each $R^1$ is independently selected from: aryl-$C_{2-8}$alkynyl-$C_{2-10}$cycloheteroalkyl, aryl-$C_{2-10}$cycloheteroalkyl and aryl-aryl, wherein each alkynyl, cycloheteroalkyl and aryl is unsubstituted or substituted with 1, 2, 3 or 4 substituents independently selected from $R^a$.

In another embodiment of the present invention, each $R^1$ is independently selected from: aryl-$C_2$alkynyl-$C_{2-10}$cycloheteroalkyl, aryl-$C_{2-10}$cycloheteroalkyl, and aryl-aryl, wherein each alkynyl, cycloheteroalkyl and aryl is unsubstituted or substituted with 1, 2, 3 or 4 substituents independently selected from $R^a$.

In another embodiment of the present invention, each $R^1$ is independently selected from: phenyl-$C_2$alkynyl-piperidine, phenyl-dihydropyrrolopyrazole, and biphenyl, wherein each alkynyl, cycloheteroalkyl and phenyl is unsubstituted or substituted with 1, 2, 3 or 4 substituents independently selected from $R^a$.

In another embodiment of the present invention, each $R^1$ is independently selected from: hydrogen, halogen, —CN, —$CF_3$, —$C_{1-6}$alkyl, —$C_{2-6}$alkenyl and —$C_{2-6}$alkynyl. In another embodiment of the present invention, each $R^1$ is independently selected from: halogen. In another embodiment of the present invention, each $R^1$ is independently selected from: Cl and F. In a class of this embodiment, $R^1$ is Cl. In another class of this embodiment, $R^1$ is F.

In another embodiment of the present invention, each $R^2$ is independently selected from: hydrogen, halogen, CN, $CF_3$, —$C_{1-6}$alkyl, —$C_{2-6}$alkenyl, —$C_{2-6}$alkynyl, —$(CH_2)_p$$C_{3-10}$cycloalkyl, —$(CH_2)_p$$C_{3-7}$cycloalkyl-aryl, —$(CH_2)_p$$C_{3-7}$cycloalkyl-heteroaryl, —$(CH_2)_p$$C_{4-10}$cycloalkenyl, —$(CH_2)_p$$C_{4-7}$cycloalkenyl-aryl, —$(CH_2)_p$$C_{4-7}$cycloalkenyl-heteroaryl, —$(CH_2)_p$$C_{2-10}$cycloheteroalkyl, —$(CH_2)_p$$C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —$(CH_2)_p$aryl-heteroaryl, —$(CH_2)_p$heteroaryl, —$(CH_2)_p$heteroaryl-$C_{3-7}$cycloalkyl, —$(CH_2)_p$heteroaryl-$C_{2-10}$cycloheteroalkyl, —$(CH_2)_p$heteroaryl-$C_{2-10}$cycloheteroalkenyl, —$(CH_2)_p$heteroaryl-aryl, —$(CH_2)_p$heteroaryl-heteroaryl, —$C_{2-6}$alkenyl-alkyl, —$C_{2-6}$alkenyl-aryl, —$C_{2-6}$alkenyl-heteroaryl, —$C_{2-6}$alkenyl-$C_{3-7}$cycloalkyl, —$C_{2-6}$alkenyl-$C_{3-7}$cycloalkenyl, —$C_{2-6}$alkenyl-$C_{2-7}$cycloheteroalkyl, —$C_{2-6}$alkenyl-$C_{2-7}$cycloheteroalkenyl, —$C_{2-6}$alkynyl-$(CH_2)_{1-3}$—O-aryl, —$C_{2-6}$alkynyl-alkyl, —$C_{2-6}$alkynyl-aryl, —$C_{2-6}$alkynyl-heteroaryl, —$C_{2-6}$alkynyl-$C_{3-7}$cycloalkyl, —$C_{2-6}$alkynyl-$C_{3-7}$cycloalkenyl, —$C_{2-6}$alkynyl-$C_{2-7}$cycloheteroalkyl, —$C_{2-6}$alkynyl-$C_{2-7}$cycloheteroalkenyl, and —C(O)NH—$(CH_2)_{0-3}$phenyl, wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}alkyl)_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$, and $R^1$ is selected from the group consisting of: hydrogen, halogen, —CN, —$CF_3$, —$C_{1-6}$alkyl, —$C_{2-6}$alkenyl and —$C_{2-6}$alkynyl.

In another embodiment of the present invention, each $R^2$ is independently selected from: hydrogen, halogen, CN, $CF_3$, —$C_{1-6}$alkyl, —$C_{2-6}$alkenyl, —$C_{2-6}$alkynyl, —$(CH_2)_p$$C_{3-10}$cycloalkyl, —$(CH_2)_p$$C_{4-10}$cycloalkenyl, —$(CH_2)_p$$C_{2-10}$cycloheteroalkyl, —$(CH_2)_p$$C_{2-10}$ cycloheteroalkenyl, —$(CH_2)_p$$C_{3-7}$cycloalkyl-aryl, —$(CH_2)_p$$C_{3-7}$cycloalkyl-heteroaryl, —$(CH_2)_p$$C_{4-10}$cycloalkenyl, —$(CH_2)_p$$C_{4-7}$cycloalkenyl-aryl, —$(CH_2)_p$$C_{4-7}$cycloalkenyl-heteroaryl, —$(CH_2)_p$$C_{2-10}$cycloheteroalkyl, —$(CH_2)_p$$C_{2-10}$cycloheteroalkenyl, —$(CH_2)_p$aryl, —$(CH_2)_p$aryl-$C_{1-8}$alkyl, —$(CH_2)_p$aryl-$C_{2-8}$alkenyl, —$(CH_2)_p$aryl-$C_{2-8}$alkynyl-$C_{1-8}$alkyl, —$(CH_2)_p$aryl-$C_{2-8}$ alkynyl-$C_{3-7}$cycloalkyl, —$(CH_2)_p$aryl-$C_{2-8}$alkynyl-$C_{3-7}$cycloalkenyl, —$(CH_2)_p$aryl-$C_{2-8}$alkynyl-$C_{2-10}$cycloheteroalkyl, —$(CH_2)_p$aryl-$C_{2-8}$alkynyl-$C_{2-10}$cycloheteroalkenyl, —$(CH_2)_p$aryl-$C_{2-8}$alkynyl-aryl, —$(CH_2)_p$aryl-$C_{2-8}$alkynyl-heteroaryl, —$(CH_2)_p$aryl-$C_{3-7}$cycloalkyl, —$(CH_2)_p$aryl-$C_{3-7}$cycloalkenyl, —$(CH_2)_p$aryl-$C_{2-10}$cycloheteroalkyl, —$(CH_2)_p$aryl-$C_{2-10}$cycloheteroalkenyl, —$(CH_2)_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl-(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$, and R$^1$ is selected from the group consisting of: hydrogen, halogen, —CN, —CF$_3$, —C$_{1-6}$alkyl, —C$_{2-6}$alkenyl and —C$_{2-6}$alkynyl. In a class of this embodiment, R$^1$ is selected from hydrogen, halogen, —CN, and —C$_{1-6}$alkyl. In another class of this embodiment, R$^1$ is selected from halogen. In a subclass of this class, R$^1$ is selected from: F and Cl. In a subclass of this class, R$^1$ is Cl.

In another embodiment of the present invention, each R$^2$ is independently selected from: hydrogen, halogen, —CN, —C$_{1-6}$alkyl, C$_{4-10}$cycloalkenyl, C$_{2-10}$cycloheteroalkyl, C$_{2-10}$cycloheteroalkenyl, aryl-C$_{2-8}$alkynyl-C$_{2-10}$cycloheteroalkyl, aryl, aryl-C$_{1-8}$alkyl, aryl-C$_{3-7}$cycloalkyl, aryl-C$_{3-7}$cycloalkenyl, aryl-C$_{2-10}$cycloheteroalkyl, aryl-C$_{2-10}$cycloheteroalkenyl, aryl-aryl, aryl-heteroaryl, heteroaryl, heteroaryl-C$_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from R$^a$, and R$^1$ is selected from hydrogen, halogen, —CN, and —C$_{1-6}$alkyl. In a class of this embodiment, R$^1$ is selected from halogen. In a subclass of this subclass, R$^1$ is selected from: F and Cl. In another subclass of this subclass, R$^1$ is Cl.

In another embodiment of the present invention, each R$^2$ is independently selected from: hydrogen, halogen, —CN, —C$_{1-6}$alkyl, dihydropyrrolo-pyrazole, tetrahydroisoquinoline, cyclohexene, cyclopentene, pyrrolidine, piperidine, piperazine, azepane, 3,6-dihydrothiopyran, 2,5-dihydrothiophene, phenyl, phenyl-(CH$_2$)$_2$OH, phenyl-(CH$_2$)$_3$OH, phenyl-(CH$_2$)$_2$C(CH$_3$)$_2$OH, phenyl-cyclohexyl, phenyl-cyclopropyl, phenyl-cyclobutyl, phenyl-cyclohexene, phenyl-C$_2$alkynyl-piperidine, phenyl-dihydropyrrolopyrazole, phenyl-dihydroimidazole, phenyl-dihydrothiopyran, biphenyl, phenyl-tetrahydroisoquinoline, phenyl-oxetane, phenyl-thietane, phenyl-pyrazolidine, phenyl-morpholine, phenyl-azetidine, phenyl-pyrrolidine, phenyl-piperazine, phenyl-piperidine, phenyl-tetrahydropyran, phenyl-tetrahydrothiopyran phenyl-azepane, phenyl-thiomorpholine, phenyl-pyrazolidine, phenyl-oxazolidine, phenyl-cyclobutyldioxolane, phenyl-naphthalene, phenyl-isoquinoline, phenyl-pyrrole, phenyl-imidazole, phenyl-pyrazole, phenyl-tetrazole, phenyl-pyrimidine, phenyl-quinazoline, phenyl-6,7-dihydro-5H-pyrrolo[1,2-a]imidazole, pyridine, indole, azaindole, isoxazole, pyrazole, benzisoxazole, thiazolo[4,5-c]pyridine, benzodioxane, pyrrole, furan, pyrimidine, thiophene, quinazoline, 4,5,6,7-tetrahydropyrazolo[1,5-a]pyridine, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, pyridine-oxazolidine, pyridine-piperidine, and pyridine-piperazine, wherein each alkyl, alkynyl, cycloalkyl, cycloalkenyl, cycloheteroalkyl, cycloheteroalkenyl, aryl, phenyl and heteroaryl is unsubstituted or substituted with 1, 2, 3 or 4 substituents independently selected from R$^a$, and R$^1$ is selected from hydrogen, halogen, —CN, and —C$_{1-6}$alkyl. In a class of this embodiment, R$^1$ is selected from hydrogen, F, Cl, CN, and CH$_3$. In another class of this embodiment, R$^1$ is selected from hydrogen, Cl, CN, and CH$_3$. In another class of this embodiment, R$^1$ is selected from halogen. In a subclass of this subclass, R$^1$ is selected from: F and Cl. In another subclass of this subclass, R$^1$ is Cl.

In another embodiment of the present invention, each R$^2$ is independently selected from: hydrogen, halogen, CN, CF$_3$, —C$_{1-6}$alkyl, —C$_{2-6}$alkenyl, —C$_{2-6}$alkynyl, —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, (CH$_2$)$_p$aryl-C$_{1-8}$alkyl, —(CH$_2$)$_p$aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl-(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$.

In another embodiment of the present invention, R$^2$ is independently selected from: —(CH$_2$)$_p$C$_{3-10}$cycloalkyl, —(CH$_2$)$_p$C$_{3-7}$cycloalkyl-aryl, —(CH$_2$)$_p$C$_{3-7}$cycloalkyl-heteroaryl, —(CH$_2$)$_p$C$_{4-10}$cycloalkenyl, —(CH$_2$)$_p$C$_{4-7}$cycloalkenyl-aryl, —(CH$_2$)$_p$C$_{4-7}$cycloalkenyl-heteroaryl, —(CH$_2$)$_p$C$_{2-10}$cycloheteroalkyl, —(CH$_2$)$_p$C$_{2-10}$cycloheteroalkenyl, —(CH$_2$)$_p$aryl, —(CH$_2$)$_p$aryl-C$_{1-8}$alkyl, —(CH$_2$)$_p$aryl-C$_{2-8}$alkenyl, —(CH$_2$)$_p$aryl-C$_{2-8}$alkynyl-C$_{1-8}$alkyl, —(CH$_2$)$_p$aryl-C$_{2-8}$alkynyl-C$_{3-7}$cycloalkyl, —(CH$_2$)$_p$aryl-C$_{2-8}$alkynyl-C$_{3-7}$cycloalkenyl, —(CH$_2$)$_p$aryl-C$_{2-8}$alkynyl-C$_{2-10}$cycloheteroalkyl, —(CH$_2$)$_p$aryl-C$_{2-8}$alkynyl-C$_{2-10}$cycloheteroalkenyl, —(CH$_2$)$_p$aryl-C$_{2-8}$alkynyl-aryl, —(CH$_2$)$_p$aryl-C$_{2-8}$alkynyl-heteroaryl, —(CH$_2$)$_p$aryl-C$_{3-7}$cycloalkyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{3-7}$cycloalkyl, —(CH$_2$)$_p$heteroaryl-C$_{2-10}$cycloheteroalkyl-(CH$_2$)$_p$heteroaryl-C$_{2-10}$cycloheteroalkenyl, —(CH$_2$)$_p$heteroaryl-aryl, —(CH$_2$)$_p$heteroaryl-heteroaryl, —C$_{2-6}$alkenyl-alkyl, —C$_{2-6}$alkenyl-aryl, —C$_{2-6}$alkenyl-heteroaryl, —C$_{2-6}$alkenyl-C$_{3-7}$cycloalkyl, —C$_{2-6}$alkenyl-C$_{3-7}$cycloalkenyl, —C$_{2-6}$alkenyl-C$_{2-7}$cycloheteroalkyl, —C$_{2-6}$alkenyl-C$_{2-7}$cycloheteroalkenyl, —C$_{2-6}$alkynyl-(CH$_2$)$_{1-3}$—O-aryl, —C$_{2-6}$alkynyl-alkyl, —C$_{2-6}$alkynyl-aryl, —C$_{2-6}$alkynyl-heteroaryl, —C$_{2-6}$alkynyl-C$_{3-7}$cycloalkyl, —C$_{2-6}$alkynyl-C$_{3-7}$cycloalkenyl, —C$_{2-6}$alkynyl-C$_{2-7}$cycloheteroalkyl, —C$_{2-6}$alkynyl-C$_{2-7}$cycloheteroalkenyl, and —C(O)NH—(CH$_2$)$_{0-3}$phenyl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$.

In another class of this embodiment of the present invention, R$^2$ is independently selected from: —(CH$_2$)$_p$C$_{2-10}$cycloheteroalkyl, —(CH$_2$)$_p$aryl-C$_{2-8}$alkynyl-C$_{2-10}$cycloheteroalkyl, —(CH$_2$)$_p$aryl-C$_{2-10}$cycloheteroalkyl, —(CH$_2$)$_p$aryl-C$_{2-10}$cycloheteroalkenyl, —(CH$_2$)$_p$aryl-aryl, —(CH$_2$)$_p$aryl-heteroaryl, —(CH$_2$)$_p$heteroaryl, —(CH$_2$)$_p$heteroaryl-C$_{2-10}$cycloheteroalkyl, —(CH$_2$)$_p$heteroaryl-aryl, and —(CH$_2$)$_p$heteroaryl-heteroaryl, wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$, and wherein each alkynyl, cycloheteroalkyl, cycloheteroalkenyl, aryl and heteroaryl is unsubstituted or substituted with 1, 2, 3 or 4 substituents independently selected from R$^a$. In a subclass of this embodiment, R$^2$ is independently selected from: C$_{2-10}$cycloheteroalkyl, aryl-C$_{2-8}$alkynyl-C$_{2-10}$cycloheteroalkyl, aryl-C$_{4-10}$cycloheteroalkyl, aryl-C$_{2-10}$cycloheteroalkyl, aryl-aryl, aryl-heteroaryl, heteroaryl, heteroaryl-C$_{2-10}$cycloheteroalkyl, heteroaryl-aryl, and heteroaryl-heteroaryl, wherein each alkynyl, cycloheteroalkyl, cycloheteroalkenyl, aryl and heteroaryl is unsubstituted or substituted with 1, 2, 3 or 4 substituents independently selected from R$^a$. In another subclass of this embodiment, R$^2$ is independently selected from: dihydropyrrolo-pyrazole, phenyl-C$_2$alkynyl-piperidine, phenyl-dihydropyrrolopyrazole, phenyl-dihydroimidazole, biphenyl, phenyl-naphthalene, phenyl-isoquinoline, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, and pyridine-pyrazole, wherein each alkynyl, cycloheteroalkyl, cycloheteroalkenyl, phenyl and heteroaryl is unsubstituted or substituted with 1, 2, 3 or 4 substituents independently selected from R$^a$. In another subclass of this embodiment of the present invention, R$^2$ is independently selected from: 4,6-dihydropyrrolo[3,4-c]pyrazole, phenyl-C$_2$alkynyl-piperidine, phenyl-4,6-dihydropyrrolo[3,4-c]pyrazole, phenyl-3,9-diazaspiro[5,5]undecane, phenyl-2,7-diazaspiro[3,5]nonane, phenyl 4,5-dihydro-1H-imidazole, biphenyl, phenyl-naphthalene, pyridine, indole, azaindole, isoxazole, pyrazole, benzisoxazole, pyridine-pyrrolidine, pyridine-morpholine, thiazole-phenyl, pyridine-phenyl, isoxazole-phenyl, pyrimidine-phenyl, furan-phenyl, pyrazole-phenyl, pyridine-pyrazole, wherein each alkynyl, cycloheteroalkyl, cycloheteroalkenyl, phenyl, and heteroaryl is unsubstituted or substituted with 1, 2, 3 or 4 substituents independently selected from R$^a$.

In another class of this embodiment of the present invention, R$^2$ is independently selected from: aryl-C$_{2-8}$alkynyl-C$_{2-10}$cycloheteroalkyl, aryl-C$_{2-10}$cycloheteroalkyl, and aryl-aryl, wherein each alkynyl, cycloheteroalkyl and aryl is unsubstituted or substituted with 1, 2, 3 or 4 substituents independently selected from R$^a$. In a subclass of this class, R$^2$ is independently selected from: aryl-C$_2$alkynyl-C$_{2-10}$cycloheteroalkyl, aryl-C$_{2-10}$cycloheteroalkyl, and aryl-aryl, wherein each alkynyl, cycloheteroalkyl and aryl is unsubstituted or substituted with 1, 2, 3 or 4 substituents independently selected from R$^a$. In another subclass of this class, R$^2$ is independently selected from: phenyl-C$_2$alkynyl-piperidine, phenyl-dihydropyrrolopyrazole and biphenyl, wherein each alkynyl, cycloheteroalkyl and phenyl is unsubstituted or substituted with 1, 2, 3 or 4 substituents independently selected from R$^a$.

In another embodiment of the present invention, each R$^2$ is independently selected from: hydrogen, halogen, —CN, —CF$_3$, —C$_{1-6}$alkyl, —C$_{2-6}$alkenyl and —C$_{2-6}$alkynyl. In another embodiment of the present invention, each R$^2$ is independently selected from: halogen. In another embodiment of the present invention, each R$^2$ is independently selected from: Cl and F. In a class of this embodiment, R$^2$ is Cl. In another class of this embodiment, R$^2$ is F.

In another embodiment of the present invention, R$^3$ and R$^4$ are each independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, each R$^3$ is independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, R$^3$ is selected from hydrogen, halogen, and —C$_{1-6}$alkyl. In a class of this embodiment, R$^3$ is hydrogen. In a class of this embodiment, R$^3$ is halogen. In another class of this embodiment of the present invention, R$^3$ is absent.

In another embodiment of the present invention, each R$^4$ is absent or independently selected from: hydrogen, halogen, —C$_{1-6}$alkyl, —C$_{2-6}$alkenyl, —C$_{2-6}$alkynyl, —C$_{3-10}$cycloalkyl, —C$_{3-10}$cycloalkenyl, aryl, heteroaryl, —CN, —CF$_3$, —OH, —OC$_{1-6}$alkyl, —NH$_2$, —NHC$_{1-6}$alkyl, —N(C$_{1-6}$alkyl)$_2$, —SC$_{1-6}$alkyl, —SOC$_{1-6}$alkyl, —SO$_2$C$_{1-6}$alkyl, —NHSO$_2$C$_{1-6}$alkyl, —NHC(O)C$_{1-6}$alkyl, —SO$_2$NHC$_{1-6}$alkyl, and —C(O)NHC$_{1-6}$alkyl.

In another embodiment of the present invention, R$^4$ is selected from hydrogen, halogen, and —C$_{1-6}$alkyl. In a class of this embodiment, R$^4$ is hydrogen. In another class of this embodiment, R$^4$ is halogen. In another class of this embodiment of the present invention, R$^4$ is absent.

In another embodiment of the present invention, R$^5$ is selected from: hydrogen, —C$_{1-6}$alkyl, —C$_{1-6}$alkenyl, —(CH$_2$)$_u$OH, —CH$_2$CO$_2$H, and —CH$_2$CO$_2$C$_{1-6}$alkyl. In a class of this embodiment, R$^5$ is selected from: hydrogen, —C$_{1-6}$alkyl and —(CH$_2$)$_u$OH. In a subclass of this class, R$^5$ is selected from: hydrogen, —CH(CH$_3$)$_2$ and —CH$_2$OH. In another subclass of this class, R$^5$ is hydrogen. In another subclass of this class, R$^5$ is selected from: —C$_{1-6}$alkyl. In another subclass of this class, R$^5$ is —CH(CH$_3$)$_2$. In another subclass of this class, R$^5$ is selected from: —(CH$_2$)$_u$OH. In another subclass of this class, R$^5$ is —CH$_2$OH.

In another embodiment of the present invention, each $R^a$ is independently selected from the group consisting of: —$(CH_2)_m$-halogen, oxo, —$(CH_2)_m$OH, —$(CH_2)_mN(R^j)_2$, —$(CH_2)_mNO_2$, —$(CH_2)_mCN$, —$C_{1-6}$alkyl, —$(CH_2)_mCF_3$, —$(CH_2)_mOCF_3$, —O—$(CH_2)_m$—OC$_{1-6}$alkyl, —$(CH_2)_mN(R^j)C(O)R^f$, —$(CH_2)_mN(R^j)CO_2R^f$, —$(CH_2)_mC(=N-OH)N(R^j)_2$, —$(CH_2)_mOC_{1-6}$alkyl, —$(CH_2)_mO-(CH_2)_m$—C$_{3-7}$cycloalkyl, —$(CH_2)_mO-(CH_2)_m$—C$_{2-7}$cycloheteroalkyl, —$(CH_2)_mO-(CH_2)_m$-aryl, —$(CH_2)_mO-(CH_2)_m$-heteroaryl, —$(CH_2)_mSC_{1-6}$alkyl, —$(CH_2)_mS(O)C_{1-6}$alkyl, —$(CH_2)_mSO_2C_{1-6}$alkyl, —$(CH_2)_mO-SO_2C_{1-6}$alkyl, —$(CH_2)_mSO_2(CH_2)_m$—C$_{3-7}$cycloalkyl, —$(CH_2)_mSO_2(CH_2)_m$—C$_{2-7}$cycloheteroalkyl, —$(CH_2)_mSO_2(CH_2)_m$-aryl, —$(CH_2)_mSO_2(CH_2)_m$-heteroaryl, —$(CH_2)_mSO_2NH_2$, —$(CH_2)_mSO_2NHC_{1-6}$alkyl, —$(CH_2)_mSO_2NHC_{3-7}$cycloalkyl, —$(CH_2)_mSO_2NHC_{2-7}$cycloheteroalkyl, —$(CH_2)_mSO_2NH$-aryl, —$(CH_2)_mSO_2NH$-heteroaryl, —$(CH_2)_mNHSO_2$—C$_{1-6}$alkyl, —$(CH_2)_mNHSO_2$—C$_{3-7}$cycloalkyl, —$(CH_2)_mNHSO_2$—C$_{2-7}$cycloheteroalkyl, —$(CH_2)_mNHSO_2$-aryl, —$(CH_2)_mNHSO_2NH$-heteroaryl, —$(CH_2)_mN(R^j)$—C$_{1-6}$alkyl, —$(CH_2)_mN(R^j)$—C$_{3-7}$cycloalkyl, —$(CH_2)_mN(R^j)$—$(CH_2)_m$—C$_{3-7}$cycloalkyl, —$(CH_2)_mN(R^j)$—C$_{2-7}$cycloheteroalkyl, —$(CH_2)_mN(R^j)$—$(CH_2)_m$—C$_{2-7}$cycloheteroalkyl, —$(CH_2)_mN(R^j)$—$(CH_2)_m$—C$_{2-7}$cycloheteroalkenyl, —$(CH_2)_mN(R^j)$—$(CH_2)_m$—C$_{2-7}$cycloheteroalkenyl, —$(CH_2)_mN(R^j)$-aryl, —$(CH_2)_mN(R^j)$-heteroaryl, —$(CH_2)_mN(R^j)$—$(CH_2)_m$-aryl, —$(CH_2)_mN(R^j)$-heteroaryl, —$(CH_2)_mN(R^j)$—$(CH_2)_m$-heteroaryl, —$(CH_2)_mC(O)R^f$, —$(CH_2)_mC(O)N(R^j)_2$, —$(CH_2)_mN(R^j)C(O)N(R^j)_2$, —$(CH_2)_mCO_2H$, —$(CH_2)_mO$-COH, —$(CH_2)_mCO_2R^f$, —$(CH_2)_mOCOR^f$, —$(CH_2)_mC_{3-7}$cycloalkyl, —$(CH_2)_mC_{3-7}$cycloalkenyl, —$(CH_2)_mC_{2-6}$cycloheteroalkyl, —$(CH_2)_mC_{2-6}$cycloheteroalkenyl, —$(CH_2)_m$aryl, and —$(CH_2)_m$heteroaryl, wherein each CH$_2$ is unsubstituted or substituted with 1 or 2 substituents selected from: oxo, —OH, —$(CH_2)_{1-3}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —$(CH_2)_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl.

In another embodiment of the present invention, each $R^a$ is independently selected from the group consisting of: —$(CH_2)_m$-halogen, oxo, —$(CH_2)_m$OH, —$(CH_2)_mN(R^j)_2$, —$(CH_2)_mNO_2$, —$(CH_2)_mCN$, —C$_{1-6}$alkyl, —$(CH_2)_mCF_3$, —$(CH_2)_mOCF_3$, —O—$(CH_2)_m$—OC$_{1-6}$alkyl, —$(CH_2)_mN(R^j)C(O)R^f$, —$(CH_2)_mN(R^j)CO_2R^f$, —$(CH_2)_mC(=N-OH)N(R^j)_2$, —$(CH_2)_mOC_{1-6}$alkyl, —$(CH_2)_mO-(CH_2)_m$—C$_{3-7}$cycloalkyl, —$(CH_2)_mO-(CH_2)_m$—C$_{2-7}$cycloheteroalkyl, —$(CH_2)_mO-(CH_2)_m$-aryl, —$(CH_2)_mO-(CH_2)_m$-heteroaryl, —$(CH_2)_mSC_{1-6}$alkyl, —$(CH_2)_mS(O)C_{1-6}$alkyl, —$(CH_2)_mSO_2C_{1-6}$alkyl, —$(CH_2)_mSO_2(CH_2)_m$—C$_{3-7}$cycloalkyl, —$(CH_2)_mSO_2(CH_2)_m$—C$_{2-7}$cycloheteroalkyl, —$(CH_2)_mSO_2(CH_2)_m$-aryl, —$(CH_2)_mSO_2(CH_2)_m$-heteroaryl, —$(CH_2)_mSO_2NH_2$, —$(CH_2)_mSO_2NHC_{1-6}$alkyl, —$(CH_2)_mSO_2NHC_{3-7}$cycloalkyl, —$(CH_2)_mSO_2NHC_{2-7}$cycloheteroalkyl, —$(CH_2)_mSO_2NH$-aryl, —$(CH_2)_mSO_2NH$-heteroaryl, —$(CH_2)_mNHSO_2$—C$_{1-6}$alkyl, —$(CH_2)_mNHSO_2$—C$_{3-7}$cycloalkyl, —$(CH_2)_mNHSO_2$—C$_{2-7}$cycloheteroalkyl, —$(CH_2)_mNHSO_2$-aryl, —$(CH_2)_mNHSO_2NH$-heteroaryl, —$(CH_2)_mN(R^j)$—C$_{1-6}$alkyl, —$(CH_2)_mN(R^j)$—$(CH_2)_m$—C$_{3-7}$cycloalkyl, —$(CH_2)_mN(R^j)$—C$_{2-7}$cycloheteroalkyl, —$(CH_2)_mN(R^j)$—$(CH_2)_m$—C$_{2-7}$cycloheteroalkyl, —$(CH_2)_mN(R^j)$—C$_{2-7}$cycloheteroalkenyl, —$(CH_2)_mN(R^j)$-aryl, —$(CH_2)_mN(R^j)$-heteroaryl, —$(CH_2)_mC(O)R^f$, —$(CH_2)_mC(O)N(R^j)_2$, —$(CH_2)_mN(R^j)C(O)N(R^j)_2$, —$(CH_2)_mCO_2H$, —$(CH_2)_mO$-COH, —$(CH_2)_mCO_2R^f$, —$(CH_2)_mOCOR^f$, —$(CH_2)_mC_{3-7}$cycloalkyl, —$(CH_2)_mC_{3-7}$cycloalkenyl, —$(CH_2)_mC_{2-6}$cycloheteroalkyl, —$(CH_2)_mC_{2-6}$cycloheteroalkenyl, —$(CH_2)_m$aryl, and —$(CH_2)_m$heteroaryl, wherein each CH$_2$ is unsubstituted or substituted with 1 or 2 substituents selected from: oxo, —OH, —$(CH_2)_{1-30}$H, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —$(CH_2)_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl. In a class of this embodiment, each CH$_2$ is unsubstituted, and alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —$(CH_2)_{1-5}$CF$_3$ optionally substituted with 1, 2 or 3 —OH, —CO$_2$H, —CO$_2$C$_{1-6}$alkyl, —SO$_2$C$_{1-6}$alkyl, and —C$_{3-7}$cycloalkyl.

In another embodiment of the present invention, each $R^a$ is independently selected from the group consisting of: —$(CH_2)_m$-halogen, oxo, —$(CH_2)_m$OH, —$(CH_2)_mN(R^j)_2$, —$(CH_2)_mCN$, —C$_{1-6}$alkyl, —$(CH_2)_mCF_3$, —$(CH_2)_mN(R^j)C(O)R^f$, —$(CH_2)_mN(R^j)CO_2R^f$, —$(CH_2)_mOC_{1-6}$alkyl, —$(CH_2)_mO-(CH_2)_m$—C$_{3-7}$cycloalkyl, —$(CH_2)_mO$—$(CH_2)_m$—C$_{2-7}$cycloheteroalkyl, —$(CH_2)_mO-(CH_2)_m$-aryl, —$(CH_2)_mO-(CH_2)_m$-heteroaryl, —$(CH_2)_mSO_2C_{1-6}$alkyl, —$(CH_2)_mSO_2(CH_2)_m$—C$_{3-7}$cycloalkyl, —$(CH_2)_mSO_2(CH_2)_m$—C$_{2-7}$cycloheteroalkyl, —$(CH_2)_mSO_2(CH_2)_m$-aryl, —$(CH_2)_mSO_2NH_2$, —$(CH_2)_mNHSO_2$—C$_{1-6}$alkyl, —$(CH_2)_mN(R^j)$—$(CH_2)_m$—C$_{2-7}$cycloheteroalkyl, —$(CH_2)_mN(R^j)C(O)N(R^j)_2$, —$(CH_2)_mC(O)R^f$, —$(CH_2)_mC(O)N(R^j)_2$, —$(CH_2)_mCO_2H$, —$(CH_2)_mCO_2R^f$, —$(CH_2)_mO$-COR$^f$, —$(CH_2)_mC_{3-7}$cycloalkyl, —$(CH_2)_mC_{2-6}$cycloheteroalkyl, —$(CH_2)_mC_{2-6}$cycloheteroalkenyl, —$(CH_2)_m$aryl, and —$(CH_2)_m$heteroaryl, wherein each CH$_2$ is unsubstituted or substituted with 1 or 2 substituents selected from: oxo, —OH, —$(CH_2)_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —$(CH_2)_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl.

In another embodiment of the present invention, each R$^a$ is independently selected from the group consisting of: —(CH$_2$)$_m$-halogen, oxo, —(CH$_2$)$_m$OH, —(CH$_2$)$_m$N(R$^j$)$_2$, —(CH$_2$)$_m$CN, —C$_{1-6}$alkyl, —(CH$_2$)$_m$CF$_3$, —(CH$_2$)$_m$N(R$^j$)C(O)R$^f$, —(CH$_2$)$_m$N(R$^j$)CO$_2$R$^f$, —(CH$_2$)$_m$OC$_{1-6}$alkyl, —(CH$_2$)$_m$SO$_2$C$_{1-6}$alkyl, —(CH$_2$)$_m$SO$_2$(CH$_2$)$_m$—C$_{3-7}$cycloalkyl, —(CH$_2$)$_m$SO$_2$(CH$_2$)$_m$—C$_{2-7}$cycloheteroalkyl, —(CH$_2$)$_m$SO$_2$(CH$_2$)$_m$-aryl, —(CH$_2$)$_m$SO$_2$NH$_2$, —(CH$_2$)$_m$C(O)R$^f$, —(CH$_2$)$_m$C(O)N(R$^j$)$_2$, —(CH$_2$)$_m$CO$_2$H, —(CH$_2$)$_m$CO$_2$R$^f$, —(CH$_2$)$_m$C$_{3-7}$cycloalkyl, —(CH$_2$)$_m$C$_{2-6}$cycloheteroalkyl, —(CH$_2$)$_m$C$_{2-6}$cycloheteroalkenyl and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl.

In another embodiment of the present invention, each R$^a$ is independently selected from the group consisting of: halogen, oxo, —(CH$_2$)$_m$OH, —(CH$_2$)$_m$N(O$_2$, —(CH$_2$)$_m$CN, —C$_{1-6}$alkyl, —(CH$_2$)$_m$CF$_3$, —(CH$_2$)$_m$OC$_{1-6}$alkyl, —O—(CH$_2$)$_m$—C$_{3-7}$cycloalkyl, —O—(CH$_2$)$_m$—C$_{2-7}$cycloheteroalkyl, —O—(CH$_2$)$_m$-aryl, —O—(CH$_2$)$_m$-heteroaryl, —(CH$_2$)$_m$NHSO$_2$—C$_{1-6}$alkyl, —N(R$^j$)—(CH$_2$)$_m$—C$_{2-7}$cycloheteroalkyl, —(CH$_2$)$_m$C(O)N(R$^j$)$_2$, —N(R$^j$)C(O)N(R$^j$)$_2$, —OCOR$^f$, —(CH$_2$)$_m$N(R$^j$)C(O)R$^f$, —N(R$^j$)CO$_2$R$^f$, —OC$_{1-6}$alkyl, —SO$_2$C$_{1-6}$alkyl, —SO$_2$—C$_{3-7}$cycloalkyl, —SO$_2$—C$_{2-7}$cycloheteroalkyl, —SO$_2$-aryl, —SO$_2$NH$_2$, —C(O)R$^f$, —C(O)N(R$^j$)$_2$, —(CH$_2$)$_m$CO$_2$H, —CO$_2$R$^f$, —C$_{3-7}$cycloalkyl, —C$_{2-6}$cycloheteroalkyl, —C$_{2-6}$cycloheteroalkenyl, aryl, and —(CH$_2$)$_m$heteroaryl, wherein R$^a$ is unsubstituted or substituted with 1, 2, 3 or 4 substituents selected from: oxo, —OH, (CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl. In another class of this embodiment, wherein each CH$_2$ is unsubstituted or substituted with 1 or 2 substituents selected from: oxo, —OH, (CH$_2$)$_{1-3}$OH, —CN, —N(C$_{1-6}$alkyl)$_2$, —C$_{1-6}$alkyl, —C$_{1-6}$alkyl substituted with 1-5 OH, —OC$_{1-6}$alkyl, halogen, —CF$_3$, —CO$_2$H, —CO$_2$C$_{1-6}$alkyl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —N(C$_{1-6}$alkyl)$_2$, —C$_{1-6}$alkyl, —C$_{1-6}$alkyl substituted with 1-5 OH, —OC$_{1-6}$alkyl, halogen, —CO$_2$H, and —CO$_2$C$_{1-6}$alkyl.

In another embodiment of the present invention, each R$^a$ is independently selected from the group consisting of: halogen, oxo, —(CH$_2$)$_m$OH, —N(R$^j$)$_2$, —(CH$_2$)$_m$CN, —C$_{1-6}$alkyl, —(CH$_2$)$_m$CF$_3$, —(CH$_2$)$_m$N(R$^j$)C(O)R$^f$, —N(R$^j$)CO$_2$R$^f$, —OC$_{1-6}$alkyl, —SO$_2$C$_{1-6}$alkyl, —SO$_2$—C$_{3-7}$cycloalkyl, —SO$_2$—C$_{2-7}$cycloheteroalkyl, —SO$_2$-aryl, —SO$_2$NH$_2$, —C(O)R$^f$, —C(O)N(R$^j$)$_2$, —(CH$_2$)$_m$CO$_2$H, —CO$_2$R$^f$, —C$_{3-7}$cycloalkyl, —C$_{2-6}$cycloheteroalkyl, —C$_{2-6}$cycloheteroalkenyl, and —(CH$_2$)$_m$heteroaryl, wherein alkyl, cycloalkyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: F, Cl, oxo, —CH$_2$OH, —OH, —N(CH$_2$CH$_3$)$_2$, —CN, —(CH$_2$)$_2$CN, —CH$_2$CN, —CH$_3$, —CH$_2$CH$_3$, —C(CH$_3$)$_3$, —CH$_2$C(OH)(CH$_3$)$_2$, —C(OH)(CH$_3$)$_2$, —C(CH$_2$OH)$_2$(CH$_3$), —C(OH)(CH$_3$)CH$_2$CH$_3$, —CF$_3$, —CH$_2$CF$_3$, —C(OH)(CF$_3$)$_2$, —(CH$_2$)$_2$OH, —(CH$_2$)$_3$OH, —C(CH$_3$)$_2$CH$_2$OH, —C(CH$_3$)$_2$OH, —CH$_2$C(CH$_3$)$_2$OH, —(CH$_2$)$_2$C(CH$_3$)$_2$OH, —C(OH)CH$_2$OH, —NH$_2$, —CH$_2$NH$_2$, —C(CH$_3$)F$_2$, —O—CH$_2$CH$_3$, —(CH$_2$)$_2$OCH$_3$, —OCH$_2$CF$_3$, —O-cyclopropyl, OCH$_2$-cyclopropyl, —O-azetidine, —OCH$_2$-piperidine, —O(CH$_2$)$_2$piperidine, —OCH$_2$-morpholine, —O(CH$_2$)$_2$morpholine, —O(CH$_2$)$_3$morpholine, —OCH$_2$-oxetane, —OCH$_2$-tetrahydropyran, —O— phenyl, —O—CH$_2$phenyl, —O(CH$_2$)$_2$pyridine, —O(CH$_2$)$_2$pyrazole, —O(CH$_2$)$_2$imidazole, —O(CH$_2$)$_2$triazole, —CH$_2$NHC(O)CH$_3$, —NHCO$_2$H, —OCH$_3$, —O(CH$_2$)$_2$N(CH$_3$)$_2$, —SO$_2$CH$_3$, —SO$_2$cyclopropyl, —SO$_2$-piperidine, —SO$_2$-phenyl, —SO$_2$NH$_2$, —CH$_2$NHSO$_2$CH$_3$, —NH(CH$_2$)$_2$-morpholine, —C(O)CH$_3$, —C(O)CH(NH$_2$)CH(CH$_3$)$_2$, —C(O)NH(CH$_3$), —(CH$_2$)$_2$C(O)NH(CH$_3$), —C(O)N(CH$_3$)$_2$, —C(O)NH$_2$, —(CH$_2$)$_3$CO$_2$H, —CO$_2$H, —CO$_2$CH$_2$CH$_3$, —CO$_2$CH$_3$, —CO$_2$CH(CH$_3$)$_2$, —CO$_2$CH$_2$CH(CH$_3$)$_2$, —CO$_2$C(CH$_3$)$_3$, cyclopropyl, cyclobutyl, phenyl, 4,6-dihydropyrrolo[3,4-c]pyrazole, piperidine, pyrrolidine, piperazine, morpholine, oxetane, pyrrolidinone, tetrahydropyran, pyrroline, pyridine, pyrimidine, imidazole, pyrazole, tetrazole, —CH$_2$-tetrazole, —CH$_2$-imidazole, oxadiazole, triazole, —CH$_2$-triazole, pyridazine, oxazole, 6,7-dihydro-5H-pyrrolo[1,2-a]imidazole, imidazo[1,2-a]pyridine, thiazole, —CH$_2$-thiazole, —CH$_2$C(O)NHCH$_3$, —NHC(O)N(H)CH$_2$CH$_3$, —OC(O)-piperidine, wherein R$^a$ is unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, (CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, R$^a$ is unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CO$_2$H, and —CO$_2$C$_{1-6}$alkyl. In another class of this embodiment, R$^a$ is unsubstituted.

In a class of this embodiment, each R$^a$ is independently selected from the group consisting of: F, Cl, oxo, —CH$_2$OH, —OH, —N(CH$_2$CH$_3$)$_2$, —CN, —(CH$_2$)$_2$CN, —CH$_2$CN, —CH$_3$, —CH$_2$CH$_3$, —C(CH$_3$)$_3$, —CH$_2$C(OH)(CH$_3$)$_2$, —C(OH)(CH$_3$)$_2$, —C(CH$_2$OH)$_2$(CH$_3$), —C(OH)(CH$_3$) CH$_2$CH$_3$, —CF$_3$, —CH$_2$CF$_3$, —C(OH)(CF$_3$)$_2$, —CH$_2$NHC (O)CH$_3$, —NHCO$_2$H, —OCH$_3$, —O(CH$_2$)$_2$N(CH$_3$)$_2$, —SO$_2$CH$_3$, —SO$_2$cyclopropyl, —SO$_2$-piperidine, —SO$_2$-phenyl, —SO$_2$NH$_2$, —C(O)CH$_3$, —C(O)CH(NH$_2$)CH (CH$_3$)$_2$, —C(O)NH(CH$_3$), —(CH$_2$)$_2$C(O)NH(CH$_3$), —C(O) N(CH$_3$)$_2$, —C(O)NH$_2$, —(CH$_2$)$_3$CO$_2$H, —CO$_2$H, —CO$_2$CH$_2$CH$_3$, cyclopropyl, 4,6-dihydropyrrolo[3,4-c] pyrazole, piperidine, pyrrolidine, piperazine, morpholine, oxetane, pyrrolidinone, tetrahydropyran, pyrroline, pyridine, pyrimidine, imidazole, pyrazole, tetrazole, —CH$_2$-tetrazole, —CH$_2$-imidazole, oxadiazole, triazole, pyridazine, oxazole, 6,7-dihydro-5H-pyrrolo[1,2-a]imidazole, imidazo[1,2-a]pyridine and thiazole, wherein alkyl, cycloalkyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, (CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, alkyl, cycloalkyl, cycloheteroalkyl, cycloheteroalkenyl, aryl and heteroaryl are unsubstituted.

In another embodiment of the present invention, each R$^a$ is independently selected from the group consisting of: halogen, —(CH$_2$)CN, —C$_{1-6}$alkyl, —(CH$_2$)$_m$CF$_3$, —(CH$_2$)$_m$OC$_{1-6}$alkyl, —(CH$_2$)$_m$C$_{3-7}$cycloalkyl, —(CH$_2$)$_m$C$_{2-6}$cycloheteroalkyl, and —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloheteroalkyl and heteroaryl are unsubstituted or substituted with 1, 2, 3 or 4 substituents selected from: oxo, —OH, —(CH$_2$)$_{1-5}$ OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$ CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl. In a class of this embodiment, each CH$_2$ is unsubstituted and alkyl, cycloalkyl, cycloheteroalkyl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: halogen, —CN, —C$_{1-6}$alkyl, —(CH$_2$)$_m$CF$_3$, —OC$_{1-6}$alkyl, —C$_{3-7}$cycloalkyl, —C$_{2-6}$cycloheteroalkyl, and -heteroaryl, wherein alkyl, cycloalkyl, cycloheteroalkyl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^a$ is independently selected from the group consisting of: F, —CN, —CH$_2$C(OH)(CH$_3$)$_2$, —C(OH)(CH$_3$)$_2$, —C(CH$_2$OH)$_2$(CH$_3$), —CH$_2$CF$_3$, —O(CH$_2$)$_2$N(CH$_3$)$_2$, cyclopropyl, morpholine, and imidazole, wherein alkyl, cycloalkyl, cycloheteroalkyl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl. In a class of this embodiment, each R$^a$ is independently selected from the group consisting of: F, —CN, —CH$_2$C(OH)(CH$_3$)$_2$, —C(OH)(CH$_3$)$_2$, —C(CH$_2$OH)$_2$(CH$_3$), —CH$_2$CF$_3$, —O(CH$_2$)$_2$N(CH$_3$)$_2$, cyclopropyl, morpholine and imidazole, wherein cycloalkyl, cycloheteroalkyl, and heteroaryl are unsubstituted or substituted with 1, 2, 3 or 4 substituents selected from: oxo, —OH, (CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, and —SO$_2$C$_{1-6}$alkyl.

In another embodiment of the present invention, each R$^b$ is independently selected from: hydrogen, —C$_{1-6}$alkyl, —C$_{1-6}$alkenyl, —(CH$_2$)nC$_{3-10}$cycloalkyl, —(CH$_2$)nC$_{3-10}$cycloalkenyl, —(CH$_2$)nC$_{2-10}$cycloheteroalkyl, —(CH$_2$) nC$_{2-10}$cycloheteroalkenyl, —(CH$_2$)naryl, —(CH$_2$)nheteroaryl, oxo, —(CH$_2$)nCF$_3$, —(CH$_2$)nCN, —(CH$_2$)t-halogen, —(CH$_2$)s-OH, —(CH$_2$)nNO$_2$, —(CH$_2$)nNH$_2$, —(CH$_2$) nNH(C$_{1-6}$alkyl), —(CH$_2$)nN(C$_{1-6}$alkyl)$_2$, —(CH$_2$) nNHCO$_2$H, —(CH$_2$)nOC$_{1-6}$alkyl, —(CH$_2$)nOC$_{1-6}$alkenyl, —(CH$_2$)$_n$COC$_{1-6}$alkyl, —(CH$_2$)$_n$CO$_2$H, —(CH$_2$)$_n$OCOH, —(CH$_2$)$_n$CO$_2$R$^i$, —(CH$_2$)$_n$OC(O)R$^i$, —(CH$_2$)$_q$C(O)N(R$^e$)$_2$, —(CH$_2$)$_q$CO$_2$N(R$^e$)$_2$, —(CH$_2$)$_n$C(O)(CH$_2$)$_n$N(R$^g$)$_2$, —(CH$_2$)$_n$OC(O)(CH$_2$)$_n$N(R$^g$)$_2$, —(CH$_2$)$_n$N(R$^e$)C(O) C$_{1-6}$alkyl, —(CH$_2$)$_n$N(R$^e$)SO$_2$R$^i$, —(CH$_2$)$_n$SO$_2$C$_{1-6}$alkyl, —(CH$_2$)$_n$SO$_2$N(R$^e$)R$^g$, —(CH$_2$)$_n$SO$_2$N(R$^e$)C(O)R$^i$, —(CH$_2$)$_n$SO$_2$N(R$^e$)CO$_2$R$^i$, —(CH$_2$)$_n$SO$_2$N(R$^e$)CON(R$^g$)$_2$, —(CH$_2$)$_n$C(O)N(R$^e$)SO$_2$R$^i$, —(CH$_2$)$_n$N(R$^e$)C(O)N(R$^g$)$_2$, =N(OH), and =N(OC$_{1-6}$alkyl), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from R$^e$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^e$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^e$.

In another embodiment of the present invention, each R$^b$ is independently selected from: —C$_{1-6}$alkyl, —C$_{1-6}$alkenyl, —(CH$_2$)nC$_{3-10}$cycloalkyl, —(CH$_2$)naryl, oxo, —(CH$_2$)s-

OH, —(CH$_2$)nNH$_2$, —(CH$_2$)nNHCO$_2$H, —(CH$_2$)nOC$_{1-6}$alkyl, —(CH$_2$)nOC$_{1-6}$alkenyl, —(CH$_2$)$_n$CO$_2$H, —(CH$_2$)$_n$CO$_2$R$^i$, —(CH$_2$)$_n$OC(O)R$^i$, —(CH$_2$)$_q$C(O)N(R$^e$)$_2$, and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^e$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^e$. In another class of this embodiment, each R$^b$ is independently selected from: —C$_{1-6}$alkyl, —C$_{1-6}$alkenyl, —(CH$_2$)nC$_{3-10}$cycloalkyl, —(CH$_2$)naryl, oxo, —(CH$_2$)s-OH, —(CH$_2$)nNH$_2$, —(CH$_2$)nNHCO$_2$H, —(CH$_2$)nOC$_{1-6}$alkyl, —(CH$_2$)nOC$_{1-6}$alkenyl, —(CH$_2$)$_n$CO$_2$H, —(CH$_2$)$_n$CO$_2$R$^i$, —(CH$_2$)$_n$OC(O)R$^i$, —(CH$_2$)$_q$C(O)N(R$^e$)$_2$ and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$.

In another embodiment of the present invention, each R$^b$ is independently selected from: —C$_{1-6}$alkyl, —C$_{1-6}$alkenyl, —C$_{3-10}$-cycloalkyl, -aryl, oxo, —(CH$_2$)s-OH, —NH$_2$, —NHCO$_2$H, —OC$_{1-6}$alkyl, —OC$_{1-6}$alkenyl, —(CH$_2$)$_n$CO$_2$H, —(CH$_2$)$_n$CO$_2$R$^i$, —OC(O)R$^i$, —(CH$_2$)$_q$C(O)N(R$^e$)$_2$, and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^e$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^e$. In another class of this embodiment, each R$^b$ is independently selected from: —C$_{1-6}$alkyl, —C$_{1-6}$alkenyl, —C$_{3-10}$cycloalkyl, -aryl, oxo, —(CH$_2$)s-OH, —NH$_2$, —NHCO$_2$H, —OC$_{1-6}$ alkyl, —OC$_{1-6}$alkenyl, —(CH$_2$)$_n$CO$_2$H, —(CH$_2$)$_n$CO$_2$R$^i$, —OC(O)R$^i$, —(CH$_2$)$_q$C(O)N(R$^e$)$_2$, and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$.

In another embodiment, each R$^b$ is independently selected from: —CH$_3$, —CH(CH$_3$)$_2$, —CH$_2$C(OH)(CH$_3$)$_2$, —(CH$_2$)$_2$OH, —CH(OH)CH$_2$OH, —CH$_2$CH(OH)CH$_2$OH, —CH=CH$_2$, —CH$_2$CH=CH$_2$, cyclopropyl, phenyl, oxo, —OH, —CH$_2$OH, —(CH$_2$)$_2$OH, —CH(OH)CH$_2$OH, —NH$_2$, —NHCO$_2$H, —OCH$_3$, OCH(CH$_3$)$_2$, —O(CH$_2$)$_2$OH, —OCH$_2$CH(OH)CH$_2$OH, —O(CH$_2$)$_2$OH, —OCH$_2$CO$_2$H, —OCH$_2$CH=CH$_2$, —CH$_2$CO$_2$H, —CH$_2$CO$_2$CH$_2$CH$_3$, —OC(O)CH$_3$, —CH$_2$CONH$_2$, and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^e$. In a class of this embodiment, two R$^b$ substituents and the carbon to which they are attached may form a 3-6 membered cycloheteroalkyl ring, wherein the ring is unsubstituted or substituted with 1, 2, 3 or 4 substituents selected from R$^e$. In another class of this embodiment, each R$^b$ is independently selected from: —CH$_3$, —CH(CH$_3$)$_2$, —CH$_2$C(OH)(CH$_3$)$_2$, —(CH$_2$)$_2$OH, —CH(OH)CH$_2$OH, —CH$_2$CH(OH)CH$_2$OH, —CH=CH$_2$, —CH$_2$CH=CH$_2$, cyclopropyl, phenyl, oxo, —OH, —CH$_2$OH, —(CH$_2$)$_2$OH, —CH(OH)CH$_2$OH, —NH$_2$, —NHCO$_2$H, —OCH$_3$, OCH(CH$_3$)$_2$, —O(CH$_2$)$_2$OH, —OCH$_2$CH(OH)CH$_2$OH, —O(CH$_2$)$_2$OH, —OCH$_2$CO$_2$H, —OCH$_2$CH=CH$_2$, —CH$_2$CO$_2$H, —CH$_2$CO$_2$CH$_2$CH$_3$, —OC(O)CH$_3$, —CH$_2$CONH$_2$, and =N(OH), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^e$, and wherein each alkyl, alkenyl, cycloalkyl and aryl is unsubstituted or substituted with 1, 2, 3 or 4 substituents selected from R$^e$. In another class of this embodiment of the present invention, each R$^b$ is independently selected from: —CH$_3$, —CH(CH$_3$)$_2$, —CH$_2$C(OH)(CH$_3$)$_2$, —(CH$_2$)$_2$OH, —CH(OH)CH$_2$OH, —CH$_2$CH(OH)CH$_2$OH, —CH=CH$_2$, —CH$_2$CH=CH$_2$, cyclopropyl, phenyl, oxo, —OH, —CH$_2$OH, —(CH$_2$)$_2$OH, —CH(OH)CH$_2$OH, —NH$_2$, —NHCO$_2$H, —OCH$_3$, OCH(CH$_3$)$_2$, —O(CH$_2$)$_2$OH, —OCH$_2$CH(OH)CH$_2$OH, —O(CH$_2$)$_2$OH, —OCH$_2$CO$_2$H, —OCH$_2$CH=CH$_2$, —CH$_2$CO$_2$H, —CH$_2$CO$_2$CH$_2$CH$_3$, —OC(O)CH$_3$, —CH$_2$CONH$_2$, and =N(OH).

In another embodiment of the present invention, R$^b$ is —(CH$_2$)s-OH. In a class of this embodiment, R$^b$ is OH.

In another embodiment of the present invention, each R$^e$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, —(CH$_2$)$_r$CO$_2$R$^f$, —(CH$_2$)$_r$C$_{3-7}$cycloalkyl, —(CH$_2$)$_r$C$_{2-6}$cycloheteroalkyl, —(CH$_2$)$_r$aryl, and —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In a class of this embodiment, each R$^e$ is independently selected from: oxo, —(CH$_2$)$_r$OH, —(CH$_2$)$_r$CO$_2$H, and —(CH$_2$)$_r$CO$_2$R$^f$, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl. In a subclass of this class, each R$^e$ is independently selected from: oxo, —OH, —CO$_2$H and —CO$_2$R$^f$.

In another embodiment of the present invention, each R$^e$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, —C$_{1-6}$alkyl-OH, —OCH$_2$OC$_{1-6}$alkyl, —(CH$_2$)$_r$OC$_{1-6}$alkyl, —OCH$_2$aryl, —(CH$_2$)$_r$SC$_{1-6}$alkyl, —(CH$_2$)$_r$C(O)R$^f$, —(CH$_2$)$_r$C(O)N(R$^e$)$_2$, —(CH$_2$)$_r$CO$_2$H, and —(CH$_2$)$_r$CO$_2$R$^f$, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, and —CO$_2$C$_{1-6}$alkyl.

In another embodiment of the present invention, each R$^e$ is independently selected from: halogen, oxo, —(CH$_2$)$_r$OH, —(CH$_2$)$_r$N(R$^e$)$_2$, —(CH$_2$)$_r$CN, —C$_{1-6}$alkyl, —CF$_3$, and —C$_{1-6}$alkyl-OH.

In another embodiment of the present invention, each R$^e$ is independently selected from: halogen, oxo, and —C$_{1-6}$alkyl.

In another embodiment of the present invention, each R$^e$, R$^g$ and R$^h$ is independently selected from: hydrogen, —C$_{1-6}$alkyl, and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^e$, R$^g$ and R$^h$ is hydrogen.

In another embodiment of the present invention, each R$^e$ is independently selected from: hydrogen, —C$_{1-6}$alkyl and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^e$ is hydrogen.

In another embodiment of the present invention, each R$^g$ is independently selected from: hydrogen, —C$_{1-6}$alkyl and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^g$ is hydrogen.

In another embodiment of the present invention, each R$^h$ is independently selected from: hydrogen, —C$_{1-6}$alkyl and —O—C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^h$ is hydrogen.

In another embodiment of the present invention, each R$^j$ is independently selected from: hydrogen, —C$_{1-6}$alkyl, —C$_{3-6}$cycloalkyl, —C(O)R$^i$, —CO$_2$R$^i$, and —SO$_2$R$^i$, wherein alkyl and cycloalkyl are unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a class of this embodiment, each R$^j$ is independently selected from: hydrogen and C$_{1-6}$alkyl, wherein alkyl is unsubstituted or substituted with 1, 2, 3 or 4 substituents selected from: —OH, oxo, halogen, C$_{1-6}$alkyl, —OC$_{1-6}$alkyl, —NH$_2$, —NH(C$_{1-6}$alkyl), and —N(C$_{1-6}$alkyl)$_2$. In a subclass of this class, each R$^j$ is independently selected from: hydrogen, —CH$_3$, and —CH$_2$CH$_3$.

In another embodiment of the present invention, each R$^f$ and R$^i$ is independently selected from: —C$_{1-6}$alkyl, —(CH$_2$)$_r$C$_{4-7}$cycloalkyl, —(CH$_2$)$_r$C$_{4-7}$cycloalkenyl, —(CH$_2$)$_r$C$_{3-7}$cycloheteroalkyl, —(CH$_2$)$_r$C$_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl. In a class of this embodiment, each R$^f$ and R$^i$ is independently selected from: —C$_{1-6}$alkyl. In a subclass of this class, each R$^f$ and R$^i$ is independently selected from: —CH$_3$ and —CH$_2$CH$_3$.

In another embodiment of the present invention, each R$^f$ is independently selected from: C$_{1-6}$alkyl, —(CH$_2$)$_r$C$_{4-7}$cycloalkyl, —(CH$_2$)$_r$C$_{4-7}$cycloalkenyl, —(CH$_2$)$_r$C$_{3-7}$cycloheteroalkyl, —(CH$_2$)$_r$C$_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl. In a class of this embodiment, each R$^f$ is independently selected from: —C$_{1-6}$alkyl and —C$_{3-7}$cycloheteroalkyl. In a subclass of this class, each R$^f$ is independently selected from: —CH$_3$, —CH$_2$CH$_3$, and piperidine. In another class of this embodiment, each R$^f$ is independently selected from: —C$_{1-6}$alkyl. In a subclass of this class, each R$^f$ is independently selected from: —CH$_3$ and —CH$_2$CH$_3$.

In another class of this embodiment, each R$^f$ is independently selected from: —C$_{1-6}$alkyl. In a subclass of this class, each R$^f$ is independently selected from: —CH$_3$ and —CH$_2$CH$_3$.

In another embodiment of the present invention, each R$^i$ is independently selected from: —C$_{1-6}$alkyl, —(CH$_2$)$_r$C$_{4-7}$cycloalkyl, —(CH$_2$)$_r$C$_{4-7}$cycloalkenyl, —(CH$_2$)$_r$C$_{3-7}$cycloheteroalkyl, —(CH$_2$)$_r$C$_{3-7}$cycloheteroalkenyl, —(CH$_2$)$_r$aryl, and —(CH$_2$)$_r$heteroaryl, wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH(C$_{1-6}$alkyl), —N(C$_{1-6}$alkyl)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, and heteroaryl. In a class of this embodiment, each R$^i$ is independently selected from: —C$_{1-6}$alkyl. In a subclass of this class, each R$^i$ is independently selected from: —CH$_3$ and —CH$_2$CH$_3$.

In another embodiment of the present invention, a is 1 or 2. In a class of this embodiment, a is 1. In another class of this embodiment, a is 2.

In another embodiment of the present invention, b is 1 or 2. In a class of this embodiment, b is 1. In another class of this embodiment, b is 2.

In another embodiment of the present invention, n is 0, 1, 2, 3 or 4. In a class of this embodiment, n is 1, 2 or 3. In another class of this embodiment, n is 0, 1 or 2. In another class of this embodiment, n is 0. In another class of this embodiment, n is 1. In another class of this embodiment, n is 2.

In another embodiment of the present invention, m is 0, 1, 2, 3, or 4. In a class of this embodiment, m is 0, 1, 2 or 3. In another class of this embodiment, m is 1, 2 or 3. In another class of this embodiment, m is 0, 1 or 2. In another class of this embodiment, m is 0 or 1. In another class of this embodiment, m is 0. In another class of this embodiment, m is 1.

In another embodiment of the present invention, p is 0, 1, 2 or 3. In a class of this embodiment, p is 1, 2 or 3. In another class of this embodiment, p is 0, 1 or 2. In another class of this embodiment, p is 0 or 2. In another class of this embodiment, p is 0. In another class of this embodiment, p is 1. In another class of this embodiment, p is 2.

In another embodiment of the present invention, q is 0, 1, 2, 3 or 4. In a class of this embodiment, q is 1, 2 or 3. In another class of this embodiment, q is 0, 1 or 2. In another class of this embodiment, q is 1 or 2. In another class of this embodiment, q is 0. In another class of this embodiment, q is 1. In another class of this embodiment, q is 2.

In another embodiment of the present invention, r is 0, 1 or 2. In a class of this embodiment, r is 0 or 1. In another class of this embodiment, r is 0. In another class of this embodiment, r is 1. In another class of this embodiment, r is 2.

In another embodiment of the present invention, s is 0, 1, 2, 3 or 4. In a class of this embodiment, s is 0, 1, 2 or 3. In a class of this embodiment, s is 0, 1 or 2. In another class of this embodiment, s is 0 or 1. In another class of this embodiment, s is 1 or 2. In another class of this embodiment, s is 0 or 2. In another class of this embodiment, s is 0. In another class of this embodiment, s is 1. In another class of this embodiment, s is 2. In another class of this embodiment, s is 3.

In another embodiment of the present invention, t is 0, 1, 2, 3 or 4. In a class of this embodiment, t is 0, 1, 2 or 3. In a class of this embodiment, t is 0, 1 or 2. In another class of this embodiment, t is 0 or 1. In another class of this embodiment, t is 1 or 2. In another class of this embodiment, t is 0 or 2. In another class of this embodiment, t is 0. In another class of this embodiment, t is 1. In another class of this embodiment, t is 2. In another class of this embodiment, t is 3.

In another embodiment of the present invention, u is 0, 1, 2, 3 or 4. In a class of this embodiment, u is 0, 1, 2 or 3. In a class of this embodiment, u is 0, 1 or 2. In another class of this embodiment, u is 0 or 1. In another class of this embodiment, u is 1 or 2. In another class of this embodiment, u is 0 or 2. In another class of this embodiment, u is 0. In another class of this embodiment, u is 1. In another class of this embodiment, u is 2. In another class of this embodiment, u is 3. In another class of this embodiment, u is 4.

Another embodiment of the present invention relates to compounds of structural formula I wherein:
T is N;
U is —$CR^1$—;
V is —$CR^2$—;
W is —$CR^4$—;
X is selected from:
  (1) —$CH_2$—,
  (2) —S—,
  (3) —O—,
  (4) O—$CH_2CH_2$—, and
  (5) —NH—;
Y is selected from:

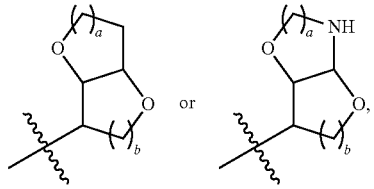

wherein Y is unsubstituted or substituted with 1, 2, 3 or 4 substituents selected from $R^b$;
Z is $NR^5$;
each $R^1$ is independently selected from:
  (1) $C_{2-10}$cycloheteroalkyl,
  (2) aryl-$C_{2-8}$alkynyl-$C_{2-10}$cycloheteroalkyl,
  (3) aryl-$C_{2-10}$cycloheteroalkyl,
  (4) aryl-$C_{2-10}$cycloheteroalkenyl,
  (5) aryl-aryl,
  (6) aryl-heteroaryl,
  (7) heteroaryl,
  (8) heteroaryl-$C_{2-10}$cycloheteroalkyl,
  (9) heteroaryl-aryl, and
  (10) heteroaryl-heteroaryl,
wherein each alkynyl, cycloheteroalkyl, cycloheteroalkenyl, aryl and heteroaryl is unsubstituted or substituted with 1, 2, 3 or 4 substituents independently selected from $R^a$;
$R^2$ is selected from halogen;
$R^4$ is hydrogen; and
$R^5$ is selected from: hydrogen, —$C_{1-6}$alkyl and —$(CH_2)_u$OH;
or a pharmaceutically acceptable salt thereof In a class of this embodiment, Y is:

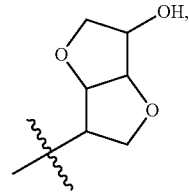

wherein Y is unsubstituted or substituted with 1, 2, 3 or 4 substituents selected from $R^b$. In another class of this embodiment, Y is:

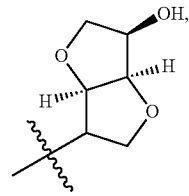

wherein Y is unsubstituted or substituted with 1, 2, 3 or 4 substituents selected from $R^b$.

Another embodiment of the present invention relates to compounds of structural formula I wherein:
T is N;
U is —$CR^1$—;
V is —$CR^2$—;
W is —$CR^4$—;
X is —O—;
Y is selected from:

wherein Y is unsubstituted or substituted with 1, 2, 3 or 4 substituents selected from R$^b$;

Z is NR$^5$;

each R$^1$ is independently selected from:
(1) aryl-C$_2$ alkynyl-C$_{2-10}$ cycloheteroalkyl,
(2) aryl-C$_{2-10}$cycloheteroalkyl, and
(3) aryl-aryl, wherein each alkynyl, cycloheteroalkyl and aryl is unsubstituted or substituted with 1, 2, 3 or 4 substituents independently selected from R$^a$, R$^2$ is halogen;
R$^4$ is hydrogen; and
R$^5$ is hydrogen;
or a pharmaceutically acceptable salt thereof In a class of this embodiment, Y is:

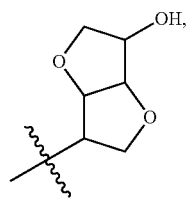

wherein Y is unsubstituted or substituted with 1, 2, 3 or 4 substituents selected from R$^b$. In another class of this embodiment, Y is:

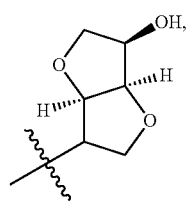

wherein Y is unsubstituted or substituted with 1, 2, 3 or 4 substituents selected from R$^b$.

In another embodiment of the present invention, the invention relates to compounds of structural formula Ia:

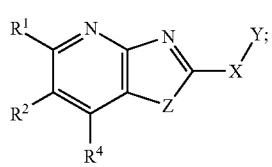

(Ia)

or a pharmaceutically acceptable salt thereof

In another embodiment of the present invention, the invention relates to compounds of structural formula Ib:

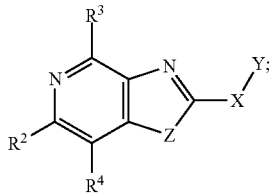

(Ib)

or a pharmaceutically acceptable salt thereof

In another embodiment of the present invention, the invention relates to compounds of structural formula Ic:

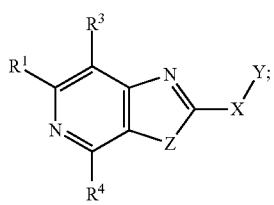

(Ic)

or a pharmaceutically acceptable salt thereof

In another embodiment of the present invention, the invention relates to compounds of structural formula Id:

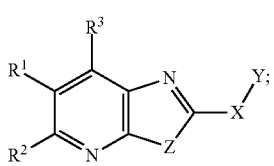

(Id)

or a pharmaceutically acceptable salt thereof.

In another embodiment of the present invention, the invention relates to compounds of structural formula Ie:

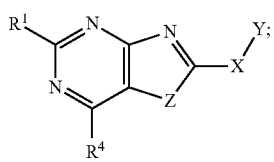

(Ie)

or a pharmaceutically acceptable salt thereof.

In another embodiment of the present invention, the invention relates to compounds of structural formula If:

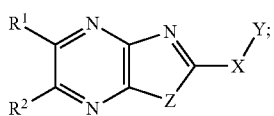

(If)

or a pharmaceutically acceptable salt thereof.

In another embodiment of the present invention, the invention relates to compounds of structural formula Ig:

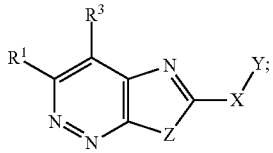

or a pharmaceutically acceptable salt thereof

The compound of structural formula I, includes the compounds of structural formulas Ia, Ib, Ic, Id, Ie, If and Ig and pharmaceutically acceptable salts, hydrates and solvates thereof Illustrative, but non-limiting, examples of the compounds of the present invention that are useful as activators of AMP-protein kinase are the following compounds:

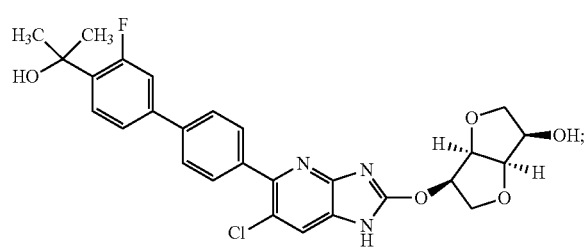

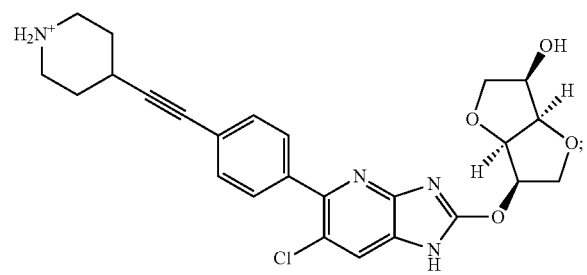

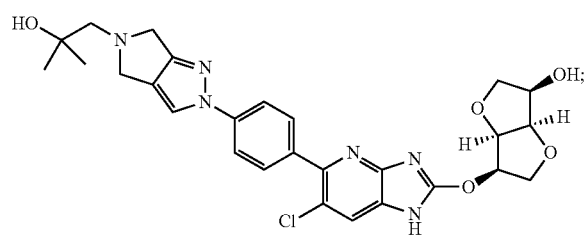

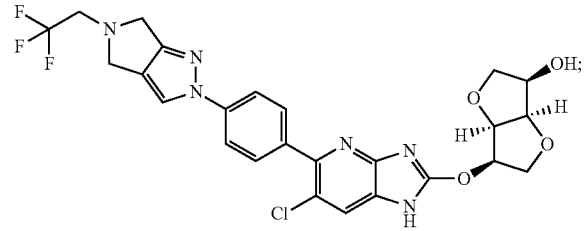

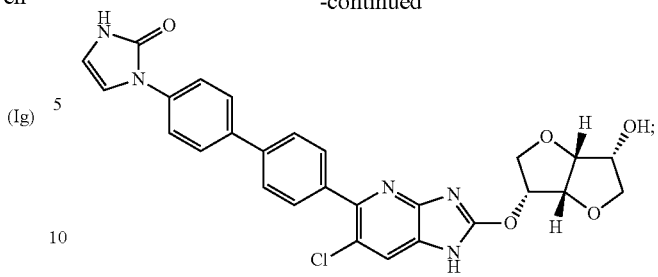

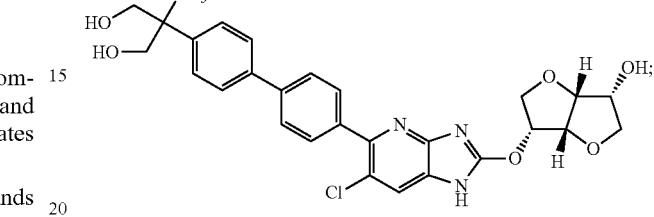

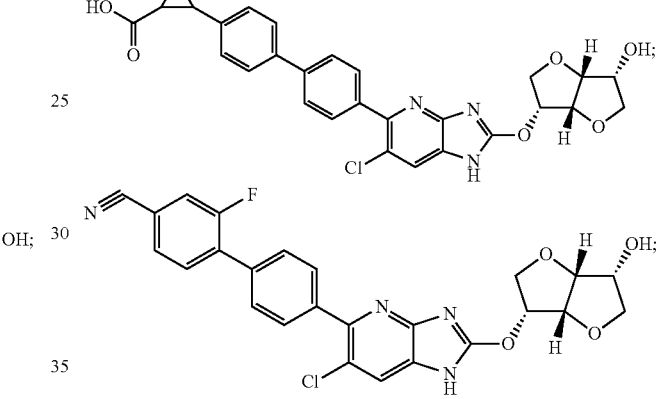

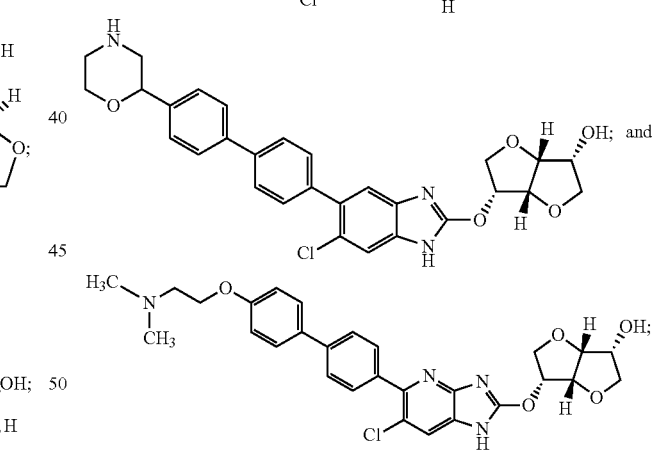

and pharmaceutically acceptable salts thereof

"Alkyl", as well as other groups having the prefix "alk", such as alkoxy, alkanoyl, means carbon chains of up to 10 carbons which may be linear or branched or combinations thereof. Examples of alkyl groups include methyl, ethyl, n-propyl, isopropyl, butyl, isobutyl, sec- and tert-butyl, pentyl, hexyl, heptyl, octyl, nonyl, and the like.

"Alkenyl" means carbon chains up to 10 carbons which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like. In one embodiment of the present invention, alkenyl is vinyl.

"Alkynyl" means carbon chains up to 10 carbons which contain at least one carbon-carbon triple bond, and which may be linear or branched or combinations thereof. In one embodiment, $C_{2-8}$alkynyl means a carbon chain with 2 to 8 carbons that contains one carbon-carbon triple bond. Examples of alkynyl include ethynyl, propargyl, 3-methyl-1-pentynyl, 2-heptynyl and the like. In one embodiment of the present invention, alkynyl is ethynyl. In another embodiment, alkynyl is propargyl.

"Cycloalkyl" means mono- or bicyclic, spiro or bridged saturated carbocyclic rings, each having from 3 to 14 carbon atoms. Examples of cycloalkyl include cyclopropyl, cyclobutyl, cyclopentyl, cyclohexyl, cycloheptyl, cyclooctyl, and decahydronaphthyl, and the like. In one embodiment of the present invention, cycloalkyl is selected from cyclopentyl and cyclohexyl. In another embodiment of the present invention, cycloalkyl is selected from cyclopropyl, cyclopentyl, and cyclohexyl. In another embodiment of the present invention, cycloalkyl is selected from cyclopropyl, cyclobutyl, cyclopentyl, and cyclohexyl.

"Cycloalkenyl" means nonaromatic, mono- or bicyclic, spiro or bridged carbocyclic rings, each having from 3 to 14 carbon atoms and containing at least one double bond. Examples of cycloalkyl include cyclopropenyl, cyclobutenyl, cyclopentenyl, cyclohexenyl, cycloheptenyl, cyclooctenyl, decahydronaphthyl, bicyclo[2.2.1]hept-5-en-2-yl, and the like. In one embodiment of the present invention, cycloalkenyl is selected from: cyclopentene and cyclohexene.

"Cycloheteroalkyl" means nonaromatic, monocyclic, bicyclic, spiro or bridged saturated carbocyclic rings, each having from 2 to 14 carbon atoms and containing 1, 2, 3, 4 or 5 heteroatoms selected from N, NH, O and S. In one embodiment, $C_{2-10}$cycloheteroalkyl means non-aromatic, mono- or bicyclic, spiro or bridged saturated carbocyclic rings, having from 2 to 10 carbon atoms and containing, 1, 2, 3, 4 or 5 heteroatoms selected from N, NH, O and S. In another embodiment, $C_{2-6}$cycloheteroalkyl means non-aromatic, mono- or bicyclic, spiro or bridged saturated carbocyclic rings, having from 2 to 6 carbon atoms and containing, 1, 2, 3, 4 or 5 heteroatoms selected from N, NH, O and S. In another embodiment, $C_{3-7}$cycloheteroalkyl means non-aromatic, mono- or bicyclic, spiro or bridged saturated carbocyclic rings, having from 3 to 7 carbon atoms and containing, 1, 2, 3, 4 or 5 heteroatoms selected from N, NH, O and S. Examples of cycloheteroalkyl include tetrahydrofuranyl, azetidinyl, perhydroazepinyl, dihydrofuranyl, dioxanyl, oxanyl, morpholinyl, 1,4-dithianyl, piperazinyl, piperidinyl, 1,3-dioxolanyl, imidazolidinyl, imidazolinyl, pyrrolinyl, pyrrolidinyl, pyranyl, tetrahydropyranyl, dihydropyranyl, oxathiolanyl, dithiolanyl, 1,3-dithianyl, oxathianyl, thiomorpholinyl, dioxidoisothiazolidinyl, azacycloheptyl, diazobicyclo[3.2.1]-octane, and hexahydroindazolyl. The cycloheteroalkyl ring may be substituted on the ring carbons and/or the ring nitrogens. In one embodiment of the present invention, cycloheteroalkyl is selected from azepane, azetidine, piperazine, piperidine, pyrrolidine, pyrazolidine, oxazolidine, 1,3-oxazolidine-2,4-dione, oxetane, thiamorpholine, thiazolidine, 1,3-thiazolidine-2,4-dione, thietane, cyclobutyldioxolane, tetrahydroisoquinoline, imidazolidine, and hydantoin, and the like. In another embodiment of the present invention cycloheteroalkyl is selected from: morpholine, pyrrolidine, piperazine, and piperidine. In another embodiment of the present invention, cycloheteroalkyl is pyrrolidine.

In another embodiment, $C_{2-10}$cycloheteroalkyl is a non-aromatic monocyclic, bicyclic, spiro or bridged carbocyclic ring having from 2 to 10 carbon atoms, and containing 1 or 2 heteroatoms selected from 0. In another embodiment of the present invention, cycloheteroalkyl is dianhydro-mannitol. In another embodiment of the present invention, cycloheteroalkyl is 1, 4:3, 6-dianhydro-mannitol. In another embodiment of the present invention, cycloheteroalkyl is 1, 4:3, 6-dianhydro-D-mannitol. In another embodiment of the present invention, cycloheteroalkyl is hexahydrofuro[3,2-b]furan. In a class of this embodiment, cycloheteroalkyl is 2,3,3a,5,6,6a-hexahydrofuro[3,2-b]furan.

In another embodiment, $C_{2-10}$cycloheteroalkyl is pyrrolidine or morpholine. In another embodiment, $C_{2-6}$cycloheteroalkyl is 4,6-dihydropyrrolo[3,4-c]pyrazole, piperidine, pyrrolidine, piperazine, morpholine, oxetane, pyrrolidinone, or tetrahydropyran. In another embodiment, $C_{2-10}$cycloheteroalkyl is 4,6-dihydropyrrolo[3,4-c]pyrazole. In another embodiment, $C_{2-10}$cycloheteroalkyl is piperidine. In another embodiment, $C_{2-10}$cycloheteroalkyl is 4,6-dihydropyrrolo[3,4-c]pyrazole, 2,6-diazaspiro[3,3]heptane, 3,9-diazaspiro[5,5]undecane or 2,7-diazaspiro[3,5]nonane.

"Cycloheteroalkenyl" means aromatic monocyclic, bicyclic, spiro or bridged rings each having from 2 to 14 carbon atoms containing at least one double bond and containing 1, 2, 3, 4 or 5 heteroatoms selected from N, NH, O and S. Examples of cycloheteroalkenyl include 1,2,4-oxadiazol-5-one, 1,2,4-thiadiazol-5-one, 1,2,4-triazol-3-one, and 1,2,3,6-tetrahydropyridine, dihydro-1,3,4-oxadiazole, and [1,6]-dihydropyridine and the like. In one embodiment of the present invention, cycloheteroalkenyl is dihydro-1,3,4-oxadiazole. In another embodiment of the present invention, cycloheteroalkenyl is [1,6]-dihydropyridine. In another embodiment of the present invention, cycloheteroalkenyl is [1,6]-dihydropyridine, dihydro-1,3,4-oxadiazole, tetrahydrothiopyran, dihydrothiophene, and dihydroimidazole.

In another embodiment, $C_{2-10}$cycloheteroalkenyl is a non-aromatic, bicyclic carbocyclic ring having from 2 to 10 carbon atoms, and containing 1, 2 or 3 heteroatoms selected from N, and NH. In a class of this embodiment, cycloheteroalkenyl is dihydropyrrolo[3,4-c]pyrazole. In another class of this embodiment, cycloheteroalkenyl is 4,6-dihydropyrrolo[3,4-c]pyrazole.

In another embodiment, $C_{2-6}$cycloheteroalkenyl is a non-aromatic, bicyclic carbocyclic ring having from 2 to 6 carbon atoms, and containing 1 or 2 heteroatoms selected from N, and NH. In a class of this embodiment, cycloheteroalkenyl is dihydroimidazole or tetrahydropyrimidine. In another class of this embodiment, cycloheteroalkenyl is 2,5dihydro-1H-imidazole or 1,4,5,6-tetrahydropyrimidine. In another class of this embodiment, cycloheteroalkenyl is dihydroimidazole. In another class of this embodiment, cycloheteroalkenyl is 2,5dihydro-1H-imidazole. In another class of this embodiment, cycloheteroalkenyl is tetrahydropyrimidine. In another class of this embodiment, cycloheteroalkenyl is 1,4,5,6-tetrahydropyrimidine.

In another embodiment, $C_{2-6}$cycloheteroalkenyl is pyrroline. In another embodiment, $C_{2-10}$cycloheteroalkenyl is dihydroimidazole or phenyl 4,5-dihydro-1H-imidazole.

"Aryl" means a monocyclic, bicyclic or tricyclic ring system containing 5-14 carbon atoms, wherein at least one of the rings is aromatic. Aryl thus includes ring systems in which an aromatic ring is fused to a non-aromatic ring, such as a cycloalkyl or cycloalkenyl ring. Examples of aryl include phenyl, naphthalene, biphenyl, indane and 5,6,7,8-tetrahydronaphthalene, and the like. In one embodiment of the present invention, aryl is phenyl, naphthalene, biphenyl, indane, and 5,6,7,8-tetrahydronaphthalene. In another embodiment of the present invention, aryl is phenyl, naphthalene, indane and 5,6,7,8-tetrahydronaphthalene. In one class of this embodiment, aryl is phenyl and naphthalene. In another class of this embodiment, aryl is phenyl. In another class of this embodiment, aryl is naphthalene.

"Heteroaryl" means a monocyclic, bicyclic or tricyclic ring system containing 5-14 carbon atoms and containing 1, 2, 3, 4 or 5 heteroatoms selected from N, NH, O and S wherein at least one of the heteroatom containing rings is aromatic. Heteroaryl thus includes ring systems in which an aromatic heteroatom containing ring is fused to a non-aromatic ring, such as a cycloalkyl, cycloalkenyl, cycloheteroalkyl or cycloheteroalkenyl ring, and also includes ring systems in which an aryl ring is fused to a non-aromatic heteroatom containing ring, such as a cycloheteroalkyl or cycloheteroalkenyl ring. Examples of heteroaryls include: pyrazole, pyridine, pyrazine, pyrimidine, thiazole, thiophene, benzoimidazole, quinoline, isoquinoline, indole, indazole, carbazole, benzotriazole, benzofuran, benzothiazole, benzothiophene, benzoisooxazole, oxazole, furan, benzoxazole, isoxazole, indoline, isoindoline, tetrazole, imidazole, oxadiazole, thiadiazole, triazole, benzothiazole, benzopyrazole, imidazopyridine, benzodioxole, dihydropyridine, dihydropyrrolopyridine, dihydrobenzooxazine, benzodioxole, benzodioxine, pyrrolopyridine, triazolopyridine, dihydropyridooxazine, dihydrobenzoxazine, dihydroindole, dihydroisoindole, dihydrobenzoimidazole, dihydroquinoline, tetrahydroisoquinoline, tetrahydrocyclopentaindole, tetrahydroquinoxaline, and tetrahydropyridine. In one embodiment of the present invention, heteroaryl is selected from: imidazole, pyrazole, pyridine, pyrazine, pyrimidine, thiazole, thiophene, dihydropyrrolopyrazole, tetrahydropyrazolopyridine, quinazoline, pyridazine, oxazole, tetrazole, oxadiazole, triazole, pyrrole, benzoxazole, thiazolopyridine, benzodioxane, furan, azaindole, benzoimidazole, quinoline, isoquinoline, indole, indazole, carbazole, benzotriazole, benzofuran, benzothiazole, benzo[b]thiophene, benzo[d]isooxazole, 3,4-dihydro-2H-benzo[1,4]oxazine, benzo[1,3]dioxole, benzo[1,4]dioxine, 1H-pyrrolo[2,3-b]pyridine, 1,6-dihydro-pyridine, [1,2,4]triazolo[4,3-a]pyridine, 3,4dihydropyrido[3,2-b][1,4]oxazine, 3,4-dihydro-2H-1,4-benzoxazine, 2,3-dihydro-1H-indole, 2,3-dihydro-1H-isoindole, 2,3-dihydrobenzoimidazole, 1,2-dihydroquinoline, 1,2,3,4-tetrahydroisoquinoline, 1,2,3,4-tetrahydrocyclopenta[b]indole, 1,2,3,4-tetrahydroquinoxaline, and 1,2,3,6-tetrahydropyridine. In another embodiment of the present invention, heteroaryl is tetrazole. In another embodiment, heteroaryl is selected from: pyrazole, pyridine, pyrimidine, isoxazole, imidazole, oxazole, triazole, tetrazole, oxadiazole, thiazole, thiadiazole, and benzoxazole. In another embodiment of this invention, heteroaryl is tetrazole. In another embodiment, heteroaryl is thiazole, pyridine, isoxazole, pyrimidine, furan, or pyrazole. In another embodiment, heteroaryl is pyridine, pyrimidine, imidazole, pyrazole, tetrazole, oxadiazole, triazole, pyridazine, oxazole, 6,7-dihydro-5H-pyrrolo[1,2-α]imidazole, imidazo[1,2-α]pyridine or thiazole. In another embodiment, heteroaryl is isoquinoline. In another embodiment, heteroaryl is pyridine, indole, azaindole, isoxazole, pyrazole, or benzisoxazole.

In another embodiment of the present invention, dihydropyrrolopyrazole is 4,6-dihydropyrrolo[3,4-c]pyrazole, In another embodiment of the present invention, dihydroimidazole is 4,5-dihydro-1H-imidazole.

"Halogen" includes fluorine, chlorine, bromine and iodine. In one embodiment of the present invention, halogen is selected from fluorine, chlorine, and bromine. In another embodiment of the present invention, halogen is selected from fluorine, and chlorine. In another embodiment of the present invention, halogen is fluorine. In another embodiment of the present invention, halogen is chlorine.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$alkylcarbonylamino $C_{1-6}$alkyl substituent is equivalent to:

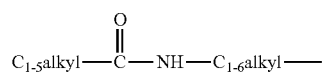

In choosing compounds of the present invention, one of ordinary skill in the art will recognize that the various substituents, i.e. $R^1$, $R^2$, etc., are to be chosen in conformity with well-known principles of chemical structure connectivity and stability.

The term "substituted" shall be deemed to include multiple degrees of substitution by a named substitutent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

Examples of tautomers include, but are not limited to:

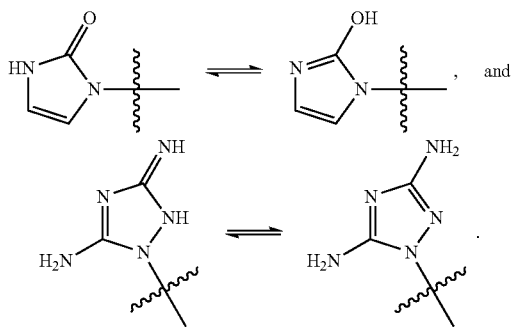

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

Compounds of the Formula I may be separated into diastereoisomeric pairs of enantiomers by, for example, fractional crystallization from a suitable solvent, for example MeOH or ethyl acetate or a mixture thereof. The pair of enantiomers thus obtained may be separated into individual stereoisomers by conventional means, for example by the use of an optically active amine as a resolving agent or on a chiral HPLC column.

Alternatively, any enantiomer of a compound of the general Formula I may be obtained by stereospecific synthesis using optically pure starting materials or reagents of known configuration.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. The term "pharmaceutically acceptable salt" further includes all acceptable salts such as acetate, trifluoroacetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations.

It will be understood that, as used herein, references to the compounds of Formula I are meant to also include the pharmaceutically acceptable salts.

Compounds of the present invention are activators of the AMP-activated protein kinase. The methods of treatment of this invention comprise a method of activating AMPK-activated protein kinase and treating AMPK-activated protein kinase mediated diseases by administering to a patient in need of such treatment a non-toxic therapeutically effective amount of a compound of this invention that activates AMPK-activated protein kinase.

AMP-activated protein kinase (AMPK) is a heterotrimeric enzyme composed of a catalytic α subunit and regulatory β and γ subunits. There are two genes encoding isoforms of both the α and β subunits (α1, α2, β1 and β2) and three genes encoding isoforms of the γ subunit (γ1, γ2 and γ3) leading to 12 possible heterotrimeric combinations. The α2 isoform is predominately found in skeletal and cardiac muscle AMPK; both the α1 and α2 isoforms are found in hepatic AMPK; while in pancreatic islet β-cells the α1 isoform AMPK predominates. In particular, the compounds of structural formula I are activators of at least one heterotrimeric isoform of AMP-activated protein kinase.

An "activator" is a compound that either increases the activity (phosphorylation of downstream substrates) of fully phosphorylated AMPK or that increases the phosphorylation of AMPK.

The compounds of the present invention are efficacious in the treatment and prevention of diseases, disorders and conditions that are responsive to the activation of AMP-activated protein kinase. As AMPK activators, the compounds of the present invention may be useful for the treatment of Type 2 diabetes, insulin resistance, hyperglycemia, obesity, hyperinsulinemia, glucose intolerance, atherosclerosis, Metabolic Syndrome, hypertension, high hepatic glucose output, high blood glucose concentrations, nonalcoholic steatohepatitis, protection against ischemia and reperfusion damage, and lipid disorders, such as dyslipidemia, elevated levels of plasma triglycerides, elevated levels of free fatty acids, elevated levels of cholesterol, high levels of low density lipoprotein (LDL) and low levels of high density lipoprotein (HDL). The compounds of the present invention may also be useful for the treatment of cancer, hypoxia and glucocorticoid-induced apoptosis. The compounds of the present invention may also be useful for the treatment of sarcopenia by treating or preventing the loss of skeletal muscle mass, including but not limited to a loss of skeletal muscle mass due to aging.

One or more of the following diseases may be treated by the administration of a therapeutically effective amount of a compound of Formula I, or a pharmaceutically acceptable salt thereof, to a patient in need of treatment or prevention of: (1) non-insulin dependent diabetes mellitus (Type 2 diabetes);

(2) hyperglycemia; (3) Metabolic Syndrome; (4) obesity; (5) hypercholesterolemia; (6) hypertriglyceridemia (elevated levels of triglyceride-rich-lipoproteins); (7) mixed or diabetic dyslipidemia; (8) low HDL cholesterol; (9) high LDL cholesterol; (10) atherosclerosis; (11) atherosclerosis, (12) hypertension, and (13) sarcopenia.

In one embodiment of the present invention, the compounds of Formula I may be useful for the treatment of one or more of the following diseases by administering a therapeutically effective amount to a patient in need of treatment: (1) Type 2 diabetes; (2) hyperglycemia; (3) Metabolic Syndrome; (4) obesity; (5) hypercholesterolemia; and (6) hypertension.

The compounds of structural Formula I may also be used for manufacturing a medicament for use in the treatment of one or more of the above diseases.

The compounds may also be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds, compositions, methods and medicaments as described herein may also be effective in: a) reducing the risks of adverse sequelae associated with metabolic syndrome, b) reducing the risk of developing atherosclerosis, c) delaying the onset of atherosclerosis, and/or d) reducing the risk of sequelae of atherosclerosis. Sequelae of atherosclerosis include angina, claudication, heart attack, stroke, and others. By keeping hyperglycemia under control, the compounds may also be effective in delaying or preventing vascular restenosis and diabetic retinopathy.

The compounds of this invention may also have utility in improving or restoring β-cell function, and may be useful in treating type 1 diabetes, and in delaying or preventing a patient with Type 2 diabetes from needing insulin therapy.

Other possible outcomes of treatment with the compounds of the present invention may be: 1) a decrease in fatty acid synthesis; 2) an increase in fatty acid oxidation and ketogenesis; 3) a decrease in cholesterol synthesis, lipogenesis, and triglyceride synthesis; 4) a decrease in blood glucose levels and concentration; 5) an improvement in glucose homeostasis; 6) a normalization of glucose metabolism; 7) a decrease in blood pressure; 8) an increase in HDL; 9) a decrease in LDL; 10) a decrease in plasma triglycerides; 11) a decrease in free fatty acids; 12) a decrease in hepatic glucose output; 13) an improvement in insulin action; 14) a decrease in blood pressure; 15) an improvement in insulin sensitivity; 16) a suppression of hepatic glucose output; 17) an inhibition of de novo lipogenesis; 18) stimulation of muscle glucose uptake; 19) modulation of insulin secretion by pancreatic (3 cells; 20) a decrease in body weight; 21) an increase in skeletal muscle mass; and 22) a prevention in the loss of skeletal muscle mass.

The compounds of the present invention may be efficacious in treating one or more of the following diseases: (1) Type 2 diabetes (also known as non-insulin dependent diabetes mellitus, or NIDDM), (2) hyperglycemia, (3) impaired glucose tolerance, (4) insulin resistance, (5) obesity, (6) lipid disorders, (7) dyslipidemia, (8) hyperlipidemia, (9) hypertriglyceridemia, (10) hypercholesterolemia, (11) low HDL levels, (12) high LDL levels, (13) atherosclerosis and its sequelae, (14) vascular restenosis, (15) abdominal obesity, (16) retinopathy, (17) metabolic syndrome, (18) high blood pressure (hypertension), and (19) insulin resistance.

One aspect of the invention provides potential methods for the treatment and control of mixed or diabetic dyslipidemia, hypercholesterolemia, atherosclerosis, low HDL levels, high LDL levels, hyperlipidemia, and/or hypertriglyceridemia, which comprises administering to a patient in need of such treatment a therapeutically effective amount of a compound of formula I alone or with a cholesterol biosynthesis inhibitor, particularly an HMG-CoA reductase inhibitor such as lovastatin, simvastatin, rosuvastatin, pravastatin, fluvastatin, atorvastatin, rivastatin, itavastatin, or ZD-4522. The compound of formula I may also be used advantageously in combination with other lipid lowering drugs such as cholesterol absorption inhibitors (for example stanol esters, sterol glycosides such as tiqueside, and azetidinones such as ezetimibe), ACAT inhibitors (such as avasimibe), CETP inhibitors (for example anacetrapib, torcetrapib, and those described in published applications WO2005/100298, WO2006/014413, and WO2006/014357), niacin and niacin receptor agonists, bile acid sequestrants, microsomal triglyceride transport inhibitors, and bile acid reuptake inhibitors. These combination treatments may be effective for the treatment or control of one or more related conditions selected from the group consisting of hypercholesterolemia, atherosclerosis, hyperlipidemia, hypertriglyceridemia, dyslipidemia, high LDL, and low HDL.

The present invention also provides potential methods and medicaments for the treatment, control, or prevention of Type 2 diabetes by administering the compounds and pharmaceutical compositions of the present invention alone or in combination with a therapeutically effective amount of another agent known to be useful to treat the condition. The present invention also relates to potential methods and medicaments for the treatment, control, or prevention of diabetes related disorders by administering the compounds and pharmaceutical compositions of the present invention alone, or in combination. The present invention also relates to potential methods and medicaments for the treatment and prevention of diabetes in pre-diabetic subject by administering the compounds and pharmaceutical compositions of the present invention alone, or in combination.

The present invention also relates to potential methods and medicaments for the treatment, control, or prevention of obesity by administering the compounds and pharmaceutical compositions of the present invention, alone or in combination with a therapeutically effective amount of another agent known to be useful to treat the condition. The present invention also relates to potential methods and medicaments for the treatment, control, or prevention of obesity related disorders by administering the compounds and pharmaceutical compositions of the present invention alone, or in combination. The present invention also relates to potential methods and medicaments for the treatment and prevention of obesity in overweight subject by administering the compounds and pharmaceutical compositions of the present invention alone, or in combination. The compounds may also be useful for the treatment of obesity related disorders.

The present invention also relates to potential methods and medicaments for the treatment, control, or prevention of hyperglycemia by administering the compounds and pharmaceutical compositions of the present invention, alone or in combination with a therapeutically effective amount of another agent known to be useful to treat the condition.

The present invention also relates to potential methods and medicaments for the treatment, control, or prevention of insulin resistance by administering the compounds and pharmaceutical compositions of the present invention, alone or in combination with a therapeutically effective amount of another agent known to be useful to treat the condition.

The present invention also relates to potential methods and medicaments for the treatment, control, or prevention of lipid disorders by administering the compounds and pharmaceutical compositions of the present invention, alone or in combination with a therapeutically effective amount of another agent known to be useful to treat the condition. The present invention also relates to potential methods and medicaments for the treatment, control, or prevention of dyslipidemia related disorders and lipid disorder-related disorders by administering the compounds and pharmaceutical compositions of the present invention alone, or in combination.

The present invention also relates to potential methods and medicaments for the treatment, control, or prevention of atherosclerosis by administering the compounds and pharmaceutical compositions of the present invention, alone or in combination with a therapeutically effective amount of another agent known to be useful to treat the condition.

The present invention also relates to potential methods and medicaments for the treatment, control, or prevention of hypertension by administering the compounds and pharmaceutical compositions of the present invention, alone or in combination with a therapeutically effective amount of another agent known to be useful to treat the condition. The present invention also relates to potential methods and medicaments for the treatment and prevention of hypertension in pre-hypertensive subject by administering the compounds and pharmaceutical compositions of the present invention alone, or in combination.

The present invention also relates to potential methods and medicaments for the treatment, control, or prevention of Metabolic Syndrome by administering the compounds and pharmaceutical compositions of the present invention, alone or in combination with a therapeutically effective amount of another agent known to be useful to treat the condition. The compounds of the present invention wherein Y is a hexahydrofuro[3,2-b]furan derivative have the unexpected benefit of reduced inhibition of recombinant CYP2C9 or CYP2C8 isozymes, compared to analogous compounds wherein Y is phenyl. In particular, the compounds of the present invention wherein Y is a hexahydrofuro[3,2-b]furan derivative have the unexpected benefit of reduced inhibition of recombinant CYP2C9 or CYP2C8 isozymes, compared to analogous compounds wherein Y is benzoic acid.

Inhibition of a recombinant CYP isozyme is measured by using a probe substrate, which upon oxidation by human liver microsome, is converted to a metabolite which is monitored by LC-MS/MS. NADPH or NADPH regenerating system are used as electron donors for the microsome catalytic cycle. Control incubations containing no inhibitors performed to evaluate the 100% activities. The activity of the enzyme is evaluated in the presence of various concentrations of test compounds. Standard specific enzyme inhibitors are used as positive controls. Inhibition curves are generated and IC50 values are calculated for tested compounds.

Co-administration of CYP inhibitors with pharmaceutical agents that are metabolized by the enzyme can result in elevated circulating concentrations of the pharmaceutical agents. This can lead to adverse events.

Additionally, the compounds of the present invention wherein at least one of T, U, V and W is N or N-oxide have the unexpected benefit of reduced binding to human plasma proteins compared to compounds wherein T is $CR^3$, U is $CR^1$—, V is $CR^2$ and W is $CR^4$. Pharmacological activity in vivo is associated with the concentration of drug unbound to plasma proteins. Plasma proteins, by virtue of their high concentration, control the concentration of drug unbound to plasma proteins in plasma and in compartments in equilibrium with plasma, thereby, effectively attenuating drug potency in vivo (See Trainor, G. L. (2007), Expert Opin. Drug Discov. 2(1), 51-64). A higher concentration of drug unbound to plasma proteins results in an increase in pharmacological activity in vivo. Due to their increased potency and their higher unbound fraction in plasma, the compounds of the present invention are expected to exhibit glucose lowering efficacy at reduced plasma exposures.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity. The compositions may be especially effective for treating Type 2 diabetes. The compositions of the present invention may also be useful for treating and/or preventing gestational diabetes mellitus.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists. The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (>140 mmHg/>90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. An overweight subject is a subject at risk of obesity. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus-type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer.

The compounds of formula I may also be useful for treating or preventing obesity and obesity-related disorders in cats and dogs. As such, the term "mammal" includes companion animals such as cats and dogs.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to the individual or mammal in need of treatment.

The administration of the compound of structural formula I in order to practice the present methods of therapy is carried out by administering an effective amount of the compound of structural formula I to the mammal in need of such treatment or prophylaxis. The need for a prophylactic administration according to the methods of the present invention is determined via the use of well known risk factors. The effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

The magnitude of prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it may be necessary to use dosages outside these limits in some cases.

For use where a composition for intravenous administration is employed, a suitable dosage range is from about 0.001 mg to about 100 mg in one embodiment from about 0.01 mg to about 50 mg, and in another embodiment from 0.1 mg to 10 mg of a compound of Formula I per kg of body weight per day.

In the case where an oral composition is employed, a suitable dosage range is, e.g. from about 0.01 mg to about 1000 mg of a compound of Formula I per day. In one embodiment, the range is from about 0.1 mg to about 10 mg per day. For oral administration, the compositions are preferably provided in the form of tablets containing from 0.01 to 1,000 mg, preferably 0.01, 0.05, 0.1, 0.5, 1, 2, 2.5, 3, 4, 5, 6, 7, 8, 9, 10, 12, 12.5, 15, 20, 25, 30, 40, 50, 100, 250, 500, 750 or 1000 milligrams of the active ingredient for the symptomatic adjustment of the dosage to the patient to be treated.

Another aspect of the present invention provides pharmaceutical compositions which comprises a compound of Formula I and a pharmaceutically acceptable carrier. The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula I, additional active ingredient(s), and pharmaceutically acceptable excipients.

Any suitable route of administration may be employed for providing a mammal, particularly a human or a companion animal such as a dog or cat, with an effective dosage of a compound of the present invention. For example, oral, rectal, topical, parenteral, ocular, pulmonary, and nasal routes of administration, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. By "pharmaceutically acceptable" it is meant the carrier, diluent or excipient must be compatible with the other ingredients of the formulation and not deleterious to the recipient thereof. The compositions include compositions suitable for oral, rectal, topical, parenteral (including subcutaneous, intramuscular, and intravenous), ocular (ophthalmic), pulmonary (aerosol inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For administration by inhalation, the compounds of the present invention are conveniently delivered in the form of an aerosol spray presentation from pressurized packs or nebulizers, or as powders which may be formulated and the powder composition may be inhaled with the aid of an insufflation powder inhaler device. The preferred delivery systems for inhalation are metered dose inhalation (MDI) aerosol, which may be formulated as a suspension or solution of a compound of Formula I in suitable propellants, such as fluorocarbons or hydrocarbons and dry powder inhalation (DPI) aerosol, which may be formulated as a dry powder of a compound of Formula I with or without additional excipients.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to 5% by weight of the active compound in admixture with a pharmaceutically acceptable vehicle. Transdermal skin patches useful for administering the compounds of the present invention include those known to those of ordinary skill in that art.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719.

Pharmaceutical compositions of the present invention suitable for oral administration may be presented as discrete units such as capsules (including timed release and sustained release formulations), pills, cachets, powders, granules or tablets each containing a predetermined amount of the active ingredient, as a powder or granules or as a solution or a suspension in an aqueous liquid, a non-aqueous liquid, an oil-in-water emulsion or a water-in-oil liquid emulsion, including elixirs, tinctures, solutions, suspensions, syrups and emulsions. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet cachet or capsule contains from about 0.01 to 1,000 mg, particularly 0.01, 0.05, 0.1, 0.5, 1.0, 2, 2.5, 3, 4, 5, 6, 7, 8, 9, 10, 12, 15, 25, 30, 40, 50, 75, 100, 125, 150, 175, 180, 200, 225, 250, 500, 750 and 1,000 milligrams of the active ingredient for the symptomatic adjustment of the dosage to the patient to be treated.

Additional suitable means of administration of the compounds of the present invention include injection, intravenous bolus or infusion, intraperitoneal, subcutaneous, intramuscular, intranasal, and topical, with or without occlusion.

Exemplifying the invention is a pharmaceutical composition comprising any of the compounds described above and a pharmaceutically acceptable carrier. Also exemplifying the invention is a pharmaceutical composition made by combining any of the compounds described above and a pharmaceutically acceptable carrier. An illustration of the invention is a process for making a pharmaceutical composition comprising combining any of the compounds described above and a pharmaceutically acceptable carrier.

The dose may be administered in a single daily dose or the total daily dosage may be administered in divided doses of two, three or four times daily. Furthermore, based on the properties of the individual compound selected for administration, the dose may be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through a continual intravenous solution, the dosage administration will, of course, be continuous rather than intermittent throughout the dosage regimen.

The following are examples of representative pharmaceutical dosage forms for the compounds of Formula I:

| Injectable Suspension (I.M.) | mg/mL |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 mL | |

| Tablet | mg/tablet |
|---|---|
| Compound of Formula I | 25 |
| Microcrystalline Cellulose | 415 |
| Povidone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

| Aerosol | Per canister |
|---|---|
| Compound of Formula I | 24 mg |
| Lecithin, NF Liq. Conc. | 1.2 mg |

| Aerosol | Per canister |
|---|---|
| Trichlorofluoromethane, NF | 4.025 g |
| Dichlorodifluoromethane, NF | 12.15 g |

Compounds of Formula I may be used in combination with other drugs that are used in the treatment/prevention/suppression or amelioration of the diseases, disorders or conditions for which compounds of Formula I may be useful. Such other drugs may be administered, by a route and in an amount commonly used therefor, contemporaneously or sequentially with a compound of Formula I. When a compound of Formula I is used contemporaneously with one or more other drugs, a pharmaceutical composition containing such other drugs in addition to the compound of Formula I is preferred. Accordingly, the pharmaceutical compositions of the present invention include those that also contain one or more other active ingredients, in addition to a compound of Formula I. Examples of other active ingredients that may be combined with a compound of Formula I include, but are not limited to: other anti-diabetic agents, anti-dylipidemic agents, and anti-hypertensive agents, anti-obesity agents, and anorectic agents, which may be administered separately or in the same pharmaceutical compositions.

The present invention also provides a method for the treatment or prevention of an AMPK-activated protein kinase (AMPK) mediated disease, which method comprises administration to a patient in need of such treatment or at risk of developing an AMPK mediated disease of an amount of an AMPK activator and an amount of one or more active ingredients, such that together they give effective relief In a further aspect of the present invention, there is provided a pharmaceutical composition comprising an AMPK activator and one or more active ingredients, together with at least one pharmaceutically acceptable carrier or excipient.

Thus, according to a further aspect of the present invention there is provided the use of an AMPK activator and one or more active ingredients for the manufacture of a medicament for the treatment or prevention of an AMPK mediated disease. In a further or alternative aspect of the present invention, there is provided a product comprising an AMPK activator and one or more active ingredients as a combined preparation for simultaneous, separate or sequential use in the treatment or prevention of an AMPK mediated disease. Such a combined preparation may be, for example, in the form of a twin pack.

It will be appreciated that for the potential treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent effective to threat that disorder, such that together they give effective relief The present invention also provides a potential method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief Examples of other active ingredients that may be administered separately or in the same pharmaceutical composition in combination with a compound of the formulas described herein include, but are not limited to:

(1) dipeptidyl peptidase-IV (DPP-4) inhibitors (e.g., sitagliptin, alogliptin, linagliptin, vildagliptin, saxagliptin, teneligliptin, omarigliptin);

(2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814);

(3) insulin or insulin analogs (e.g., insulin detemir, insulin glulisine, insulin degludec, insulin glargine, insulin lispro, SBS1000 and oral and inhalable formulations of insulin and insulin analogs);

(4) leptin and leptin derivatives and agonists;

(5) amylin and amylin analogs (e.g., pramlintide);

(6) sulfonylurea and non-sulfonylurea insulin secretagogues (e.g., tolbutamide, glyburide, glipizide, glimepiride, mitiglinide, meglitinides, nateglinide and repaglinide);

(7) α-glucosidase inhibitors (e.g., acarbose, voglibose and miglitol);

(8) glucagon receptor antagonists (e.g., NOXG15, LY2409021);

(9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, GSK2374697, ADX72231, RG7685, NN9924, ZYOG1, CJC-1131, and BIM-51077, including intranasal, transdermal, and once-weekly formulations thereof), and oxyntomodulin and oxyntomodulin analogs and derivatives;

(10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA:cholesterol acyltransferase inhibitors, (e.g., avasimibe);

(11) HDL-raising drugs, (e.g., niacin and nicotinic acid receptor agonists, and extended-release versions thereof; MK-524A, which is a combination of niacin extended-release and the DP-1 antagonist MK-524);

(12) antiobesity compounds;

(13) agents intended for use in inflammatory conditions, such as aspirin, non-steroidal anti-inflammatory drugs or NSAIDs, glucocorticoids, and selective cyclooxygenase-2 or COX-2 inhibitors;

(14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers, and calcium channel blockers;

(15) glucokinase activators (GKAs) (e.g., AZD6370);

(16) inhibitors of 11β-hydroxysteroid dehydrogenase type 1, (e.g., such as those disclosed in U.S. Pat. No. 6,730,690, and LY-2523199);

(17) CETP inhibitors (e.g., anacetrapib, evacetrapib and torcetrapib);

(18) inhibitors of fructose 1,6-bisphosphatase, (e.g., such as those disclosed in U.S. Pat. Nos. 6,054,587; 6,110,903; 6,284,748; 6,399,782; and 6,489,476);

(19) inhibitors of acetyl CoA carboxylase-1 or 2 (ACC1 or ACC2);

(20) AMP-activated Protein Kinase (AMPK) activators, such as MB 1055, ETC 1002;

(21) other agonists of the G-protein-coupled receptors: (i) GPR-109, (ii) GPR-119 (e.g., MBX2982, APD597, GSK1292263, HM47000, and PSN821), and (iii) GPR-40 (e.g., TAK875, MR 1704, TUG 469, TUG499, ASP 4178);

(22) SSTR3 antagonists (e.g., such as those disclosed in WO 2009/001836);

(23) neuromedin U receptor agonists (e.g., such as those disclosed in WO 2009/042053, including, but not limited to, neuromedin S (NMS));

(24) SCD inhibitors;

(25) GPR-105 antagonists (e.g., such as those disclosed in WO 2009/000087);

(26) SGLT inhibitors (e.g., ASP1941, SGLT-3, empagliflozin, dapagliflozin, canagliflozin, BI-10773, PF-04971729, remogliflozin, TS-071, tofogliflozin, ipragliflozin, and LX-4211);

(27) inhibitors of acyl coenzyme A:diacylglycerol acyltransferase 1 and 2 (DGAT-1 and DGAT-2);

(28) inhibitors of fatty acid synthase;

(29) inhibitors of acyl coenzyme A:monoacylglycerol acyltransferase 1 and 2 (MGAT-1 and MGAT-2);

(30) agonists of the TGR5 receptor (also known as GPBAR1, BG37, GPCR19, GPR131, and M-BAR);

(31) ileal bile acid transporter inhibitors;

(32) PACAP, PACAP mimetics, and PACAP receptor 3 agonists;

(33) PPAR agonists;

(34) protein tyrosine phosphatase-1B (PTP-1B) inhibitors;

(35) IL-1b antibodies, (e.g., XOMA052 and canakinumab);

(36) bromocriptine mesylate and rapid-release formulations thereof;

(37) GPR 120 agonists (such as KDT501.

Other suitable pharmaceutical agents of use in combination with a compound of the present invention, include, but are not limited to:

(a) anti-diabetic agents such as (1) PPARγ agonists such as glitazones (e.g. ciglitazone; darglitazone; englitazone; isaglitazone (MCC-555); pioglitazone (ACTOS); rosiglitazone (AVANDIA); troglitazone; rivoglitazone, BRL49653; CLX-0921; 5-BTZD, GW-0207, LG-100641, R483, and LY-300512, and the like and compounds disclosed in WO97/10813, 97/27857, 97/28115, 97/28137, 97/27847, 03/000,685, and 03/027,112 and SPPARMS (selective PPAR gamma modulators) such as T131 (Amgen), FK614 (Fujisawa), netoglitazone, and metaglidasen; (2) biguanides such as buformin; metformin; and phenformin, and the like; (3) protein tyrosine phosphatase-1B (PTP-1B) inhibitors such as ISIS 113715, A-401674, A-364504, IDD-3, IDD 2846, KP-40046, KR61639, MC52445, MC52453, C7, OC-060062, OC-86839, OC29796, TTP-277BC1, and those agents disclosed in WO 04/041799, 04/050646, 02/26707, 02/26743, 04/092146, 03/048140, 04/089918, 03/002569, 04/065387, 04/127570, and US 2004/167183; (4) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (5) meglitinides such as repaglinide, metiglinide (GLUFAST) and nateglinide, and the like; (6) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (7) alpha-amylase inhibitors such as tendamistat, trestatin, and A1-3688, and the like; (8) insulin secreatagogues such as linogliride nateglinide, mitiglinide (GLUFAST), ID1101 A-4166, and the like; (9) fatty acid oxidation inhibitors, such as clomoxir, and etomoxir, and the like; (10) A2 antagonists, such as midaglizole; isaglidole; deriglidole; idazoxan; earoxan; and fluparoxan, and the like; (11) insulin or insulin mimetics, such as biota, LP-100, novarapid, insulin detemir, insulin lispro, insulin glargine, insulin zinc suspension (lente and ultralente); Lys-Pro insulin, GLP-1 (17-36), GLP-1 (73-7) (insulintropin); GLP-1 (7-36)-NH$_2$) exenatide/Exendin-4, Exenatide LAR, Linaglutide, AVE0010, CJC 1131, BIM51077, CS 872, TH0318, BAY-694326, GP010, ALBUGON (GLP-1 fused to albumin), HGX-007 (Epac agonist), S-23521, and compounds disclosed in WO 04/022004, WO 04/37859, and the like; (12) non-thiazolidinediones such as JT-501, and farglitazar (GW-2570/GI-262579), and the like; (13) PPARα/γ dual agonists such as AVE 0847, CLX-0940, GW-1536, GW1929, GW-2433, KRP-297, L-796449, LBM 642, LR-90, LY510919, MK-0767, ONO 5129, SB 219994, TAK-559, TAK-654, 677954 (GlaxoSmithkline), E-3030 (Eisai), LY510929 (Lilly), AK109 (Asahi), DRF2655 (Dr. Reddy), DRF8351 (Dr. Reddy), MC3002 (Maxocore), TY51501 (ToaEiyo), farglitazar, naveglitazar, muraglitazar, peliglitazar, tesaglitazar (GALIDA), reglitazar (JT-501), chiglitazar, and those disclosed in WO 99/16758, WO 99/19313, WO 99/20614, WO 99/38850, WO 00/23415, WO 00/23417, WO 00/23445, WO 00/50414, WO 01/00579, WO 01/79150, WO 02/062799, WO 03/033481, WO 03/033450, WO 03/033453; and (14), insulin, insulin mimetics and other insulin sensitizing drugs; (15) VPAC2 receptor agonists; (16) GLK modulators, such as PSN105, RO 281675, RO 274375 and those disclosed in WO 03/015774, WO 03/000262, WO 03/055482, WO 04/046139, WO 04/045614, WO 04/063179, WO 04/063194, WO 04/050645, and the like; (17) retinoid modulators such as those disclosed in WO 03/000249; (18) GSK 3beta/GSK 3 inhibitors such as 4-[2-(2-bromophenyl)-4-(4-fluorophenyl-1H-imidazol-5-yl]pyridine, CT21022, CT20026, CT-98023, SB-216763, SB410111, SB-675236, CP-70949, XD4241 and those compounds disclosed in WO 03/037869, 03/03877, 03/037891, 03/024447, 05/000192, 05/019218 and the like; (19) glycogen phosphorylase (HGLPa) inhibitors, such as AVE 5688, PSN 357, GPi-879, those disclosed in WO 03/037864, WO 03/091213, WO 04/092158, WO 05/013975, WO 05/013981, US 2004/0220229, and JP 2004-196702, and the like; (20) ATP consumption promotors such as those disclosed in WO 03/007990; (21) fixed combinations of PPAR γ agonists and metformin such as AVANDAMET; (22) PPAR pan agonists such as GSK 677954; (23) GPR40 (G-protein coupled receptor 40) also called SNORF 55 such as BG 700, and those disclosed in WO 04/041266, 04/022551, 03/099793; (24) GPR119 (G-protein coupled receptor 119, also called RUP3; SNORF 25) such as RUP3, HGPRBMY26, PFI 007, SNORF 25; (25) adenosine receptor 2B antagonists such as ATL-618, AT1-802, E3080, and the like; (26) carnitine palmitoyl transferase inhibitors such as ST 1327, and ST 1326, and the like; (27) Fructose 1,6-bisphospohatase inhibitors such as CS-917, MB7803, and the like; (28) glucagon antagonists such as AT77077, BAY 694326, GW 4123X, NN2501, and those disclosed in WO 03/064404, WO 05/00781, US 2004/0209928, US 2004/029943, and the like; (30) glucose-6-phosphase inhibitors; (31) phosphoenolpyruvate carboxykinase (PEPCK) inhibitors; (32) pyruvate dehydrogenase kinase (PDK) activators; (33) RXR agonists such as MC1036, CS00018, JNJ 10166806, and those disclosed in WO 04/089916, U.S. Pat. No. 6,759,546, and the like; (34) SGLT inhibitors such as AVE 2268, KGT 1251, T1095/RWJ 394718; (35) BLX-1002; (36) alpha glucosidase inhibitors; (37) glucagon receptor agonists; (38) glucokinase activators; 39) GIP-1; 40) insulin secretagogues; 41) GPR-40 agonists, such as TAK-875, 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy) phenyl)phenyl)methoxy)-phenyl)iso, 5-(4-((3-(2-methyl-6-(3-hydroxypropoxyl)pyridine-3-yl)-2-methylphenyl)methoxy)-phenyl)isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and those disclosed in WO 11/078371.

(b) anti-dyslipidemic agents such as (1) bile acid sequestrants such as, cholestyramine, colesevelem, colestipol, dialkylaminoalkyl derivatives of a cross-linked dextran; Colestid®; LoCholest®; and Questran®, and the like; (2) HMG-CoA reductase inhibitors such as atorvastatin, itavastatin, pitavastatin, fluvastatin, lovastatin, pravastatin, rivastatin, simvastatin, rosuvastatin (ZD-4522), and other statins, particularly simvastatin; (3) HMG-CoA synthase inhibitors; (4) cholesterol absorption inhibitors such as FMVP4 (Forbes Medi-Tech), KT6-971 (Kotobuki Pharmaceutical), FM-VAl2 (Forbes Medi-Tech), FM-VP-24 (Forbes Medi-Tech), stanol esters, beta-sitosterol, sterol glycosides such as tiqueside; and azetidinones such as ezetimibe, and those disclosed in WO 04/005247 and the like; (5) acyl coenzyme A-cholesterol acyl transferase (ACAT) inhibitors such as avasimibe, eflucimibe, pactimibe (KY505), SMP 797 (Sumitomo), SM32504 (Sumitomo), and those disclosed in WO 03/091216, and the like; (6) CETP inhibitors such as anacetrapib, JTT 705 (Japan Tobacco), torcetrapib, CP 532,632, BAY63-2149 (Bayer), SC 591, SC 795, and the like; (7) squalene synthetase inhibitors; (8) anti-oxidants such as probucol, and the like; (9) PPARα agonists such as beclofibrate, bezafibrate, ciprofibrate, clofibrate, etofibrate, fenofibrate, gemcabene, and gemfibrozil, GW 7647, BM 170744 (Kowa), LY518674 (Lilly), GW590735 (GlaxoSmithkline), KRP-101 (Kyorin), DRF10945 (Dr. Reddy), NS-220/R1593 (Nippon Shinyaku/Roche, ST1929 (Sigma Tau) MC3001/MC3004 (MaxoCore Pharmaceuticals, gemcabene calcium, other fibric acid derivatives, such as Atromid®, Lopid® and Tricor®, and those disclosed in U.S. Pat. No. 6,548,538, and the like; (10) FXR receptor modulators such as GW 4064 (GlaxoSmithkline), SR 103912, QRX401, LN-6691 (Lion Bioscience), and those disclosed in WO 02/064125, WO 04/045511, and the like; (11) LXR receptor modulators such as GW 3965 (GlaxoSmithkline), T9013137, and XTC0179628 (X-Ceptor Therapeutics/Sanyo), and those disclosed in WO 03/031408, WO 03/063796, WO 04/072041, and the like; (12) lipoprotein synthesis inhibitors such as niacin; (13) renin angiotensin system inhibitors; (14) PPAR δ partial agonists, such as those disclosed in WO 03/024395; (15) bile acid reabsorption inhibitors, such as BARI 1453, SC435, PHA384640, S8921, AZD7706, and the like; and bile acid sequesterants such as colesevelam (WELCHOL/CHOLESTAGEL), colestipol, cholestyramine, and dialkylaminoalkyl derivatives of a cross-linked dextran, (16) PPAR6 agonists such as GW 501516 (Ligand, GSK), GW 590735, GW-0742 (GlaxoSmithkline), T659 (Amgen/Tularik), LY934 (Lilly), NNC610050 (Novo Nordisk) and those disclosed in WO97/28149, WO 01/79197, WO 02/14291, WO 02/46154, WO 02/46176, WO 02/076957, WO 03/016291, WO 03/033493, WO 03/035603, WO 03/072100, WO 03/097607, WO 04/005253, WO 04/007439, and JP10237049, and the like; (17) triglyceride synthesis inhibitors; (18) microsomal triglyceride transport (MTTP) inhibitors, such as implitapide, LAB687, JTT130 (Japan Tobacco), CP346086, and those disclosed in WO 03/072532, and the like; (19) transcription modulators; (20) squalene epoxidase inhibitors; (21) low density lipoprotein (LDL) receptor inducers; (22) platelet aggregation inhibitors; (23) 5-LO or FLAP inhibitors; and (24) niacin receptor agonists including HM74A receptor agonists; (25) PPAR modulators such as those disclosed in WO 01/25181, WO 01/79150, WO 02/79162, WO 02/081428, WO 03/016265, WO 03/033453; (26) niacin-bound chromium, as disclosed in WO 03/039535; (27) substituted acid derivatives disclosed in WO 03/040114; (28) infused HDL such as LUV/ETC-588 (Pfizer), APO-A1 Milano/ETC216 (Pfizer), ETC-642 (Pfizer), ISIS301012, D4F (Bruin Pharma), synthetic trimeric ApoA1, Bioral Apo A1 targeted to foam cells, and the like; (29) IBAT inhibitors such as BARI143/HMR145A/HMR1453 (Sanofi-Aventis, PHA384640E (Pfizer), 58921 (Shionogi) AZD7806 (AstrZeneca), AK105 (Asah Kasei), and the like; (30) Lp-PLA2 inhibitors such as SB480848 (GlaxoSmithkline), 659032 (GlaxoSmithkline), 677116 (GlaxoSmithkline), and the like; (31) other agents which affect lipic composition including ETC1001/ESP31015 (Pfizer), ESP-55016 (Pfizer), AGI1067 (AtheroGenics), AC3056 (Amylin), AZD4619 (AstrZeneca); and (c) anti-hypertensive agents such as (1) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (2) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (4) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (5) neutral endopeptidase inhibitors such as omapatrilat, cadoxatril and ecadotril, fosidotril, sampatrilat, AVE7688, ER4030, and the like; (6) endothelin antagonists such as tezosentan, A308165, and YM62899, and the like; (7) vasodilators such as hydralazine, clonidine, minoxidil, and nicotinyl alcohol, nicotinic acid or salt thereof, and the like; (8) angiotensin II receptor antagonists such as candesartan, eprosartan, irbesartan, losartan, pratosartan, tasosartan, telmisartan, valsartan, and EXP-3137, FI6828K, and RNH6270, and the like; (9) α/β adrenergic blockers as nipradilol, arotinolol and amosulalol, and the like; (10) alpha 1 blockers, such as terazosin, urapidil, prazosin, bunazosin, trimazosin, doxazosin, naftopidil, indoramin, WHIP 164, and XEN010, and the like; (11) alpha 2 agonists such as lofexidine, tiamenidine, moxonidine, rilmenidine and guanobenz, and the like; (12) aldosterone inhibitors, and the like; (13) angiopoietin-2-binding agents such as those disclosed in WO 03/030833; and (d) anti-obesity agents, such as (1) 5HT (serotonin) transporter inhibitors, such as paroxetine, fluoxetine, fenfluramine, fluvoxamine, sertraline, and imipramine, and those disclosed in WO 03/00663, as well as serotonin/noradrenaline re uptake inhibitors such as sibutramine (MERIDIA/REDUCTIL) and dopamine uptake inhibitor/Norepenephrine uptake inhibitors such as radafaxine hydrochloride, 353162 (GlaxoSmithkline), and the like; (2) NE (norepinephrine) transporter inhibitors, such as GW 320659, despiramine, talsupram, and nomifensine; (3) CB1 (cannabinoid-1 receptor) antagonist/inverse agonists, such as taranabant, rimonabant (ACCOMPLIA Sanofi Synthelabo), SR-147778 (Sanofi Synthelabo), AVE1625 (Sanofi-Aventis), BAY 65-2520 (Bayer), SLV 319 (Solvay), SLV326 (Solvay), CP945598 (Pfizer), E-6776 (Esteve), 01691 (Organix), ORG14481 (Organon), VER24343 (Vernalis), NESS0327 (Univ of Sassari/Univ of Cagliari), and those disclosed in U.S. Pat. Nos. 4,973,587, 5,013,837, 5,081, 122, 5,112,820, 5,292,736, 5,532,237, 5,624,941, 6,028, 084, and 6,509367; and WO 96/33159, WO97/29079, WO98/31227, WO 98/33765, WO98/37061, WO98/41519, WO98/43635, WO98/43636, WO99/02499, WO00/10967, WO00/10968, WO 01/09120, WO 01/58869, WO 01/64632, WO 01/64633, WO 01/64634, WO 01/70700, WO 01/96330, WO 02/076949, WO 03/006007, WO 03/007887, WO 03/020217, WO 03/026647, WO 03/026648, WO 03/027069, WO 03/027076, WO 03/027114, WO 03/037332, WO 03/040107, WO 04/096763, WO 04/111039, WO 04/111033, WO 04/111034, WO 04/111038, WO 04/013120, WO 05/000301, WO 05/016286, WO 05/066126 and EP-658546 and the like; (4) ghrelin agonists/antagonists, such as BVT81-97 (BioVitrum), RC1291 (Rejuvenon), SRD-04677 (Sumitomo), unacylated ghrelin (TheraTechnologies), and those disclosed in WO 01/87335, WO 02/08250, WO 05/012331, and the like; (5) H3 (histamine H3) antagonist/inverse agonists, such as thioperamide, 3-(1H-imidazol-4-yl)propyl N-(4-pentenyl)carbamate), clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)) and histamine H3 receptor modulators such as those disclosed in WO 03/024928 and WO 03/024929; (6) melanin-concentrating hormone 1 receptor (MCH1R) antagonists, such as T-226296 (Takeda), T71 (Takeda/Amgen), AMGN-608450, AMGN-503796 (Amgen), 856464 (GlaxoSmithkline), A224940 (Abbott), A798 (Abbott), ATC0175/AR224349 (Arena Pharmaceuticals), GW803430 (GlaxoSmithkine), NBI-1A (Neurocrine Biosciences), NGX-1 (Neurogen), SNP-7941 (Synaptic), SNAP9847 (Synaptic), T-226293 (Schering Plough), TPI-1361-17 (Saitama Medical School/University of California Irvine), and those disclosed WO 01/21169, WO 01/82925, WO 01/87834, WO 02/051809, WO 02/06245, WO 02/076929, WO 02/076947, WO 02/04433, WO 02/51809, WO 02/083134, WO 02/094799, WO 03/004027, WO 03/13574, WO 03/15769, WO 03/028641, WO 03/035624, WO 03/033476, WO 03/033480, WO 04/004611, WO 04/004726, WO 04/011438, WO 04/028459, WO 04/034702, WO 04/039764, WO 04/052848, WO 04/087680; and Japanese Patent Application Nos. JP 13226269, JP 1437059, JP2004315511, and the like; (7) MCH2R (melanin concentrating hormone 2R) agonist/antagonists; (8) NPY1 (neuropeptide Y Y1) antagonists, such as BMS205749, BIBP3226, J-115814, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (9) NPY5 (neuropeptide Y Y5) antagonists, such as 152,804, S2367 (Shionogi), E-6999 (Esteve), GW-569180A, GW-594884A (GlaxoSmithkline), GW-587081X, GW-548118X; FR 235,208; FR226928, FR240662, FR252384; 1229U91, GI-264879A, CGP71683A, C-75 (Fasgen) LY-377897, LY366377, PD-160170, SR-120562A, SR-120819A,S2367 (Shionogi), JCF-104, and H409/22; and those compounds disclosed in U.S. Pat. Nos. 6,140,354, 6,191,160, 6,258,837, 6,313,298, 6,326,375, 6,329,395, 6,335,345, 6,337,332, 6,329,395, and 6,340,683; and EP-01010691, EP-01044970, and FR252384; and PCT Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648, WO 02/051806, WO 02/094789, WO 03/009845, WO 03/014083, WO 03/022849, WO 03/028726, WO 05/014592, WO 05/01493; and Norman et al., J. Med. Chem. 43:4288-4312 (2000); (10) leptin, such as recombinant human leptin (PEG-OB, Hoffman La Roche) and recombinant methionyl human leptin (Amgen); (11) leptin derivatives, such as those disclosed in U.S. Pat. Nos. 5,552,524; 5,552,523; 5,552,522; 5,521,283; and WO 96/23513; WO 96/23514; WO 96/23515; WO 96/23516; WO 96/23517; WO 96/23518; WO 96/23519; and WO 96/23520; (12) opioid antagonists, such as nalmefene (Revex®), 3-methoxynaltrexone, naloxone, and naltrexone; and those disclosed in WO 00/21509; (13) orexin antagonists, such as SB-334867-A (GlaxoSmithkline); and those disclosed in WO 01/96302, 01/68609, 02/44172, 02/51232, 02/51838, 02/089800, 02/090355, 03/023561, 03/032991, 03/037847, 04/004733, 04/026866, 04/041791, 04/085403, and the like; (14) BRS3 (bombesin receptor subtype 3) agonists; (15) CCK-A (cholecystokinin-A) agonists, such as AR-R 15849, GI 181771, JMV-180, A-71378, A-71623, PD170292, PD 149164, SR146131, SR125180, butabindide, and those disclosed in U.S. Pat. No. 5,739,106; (16) CNTF (ciliary neurotrophic factors), such as GI-181771 (Glaxo-SmithKline); SR146131 (Sanofi Synthelabo); butabindide; and PD170,292, PD 149164 (Pfizer); (17) CNTF derivatives, such as axokine (Regeneron); and those disclosed in WO 94/09134, WO 98/22128, and WO 99/43813; (18) GHS (growth hormone secretagogue receptor) agonists, such as NN703, hexarelin, MK-0677, SM-130686, CP-424,391, L-692,429 and L-163,255, and those disclosed in U.S. Pat. No. 6,358,951, U.S. Patent Application Nos. 2002/049196 and 2002/022637; and WO 01/56592, and WO 02/32888; (19) 5HT2c (serotonin receptor 2c) agonists, such as APD3546/AR10A (Arena Pharmaceuticals), ATH88651 (Athersys), ATH88740 (Athersys), BVT933 (Biovitrum/GSK), DPCA37215 (BMS), IK264; LY448100 (Lilly), PNU 22394; WAY 470 (Wyeth), WAY629 (Wyeth), WAY161503 (Biovitrum), R-1065, VR1065 (Vernalis/Roche) YM 348; and those disclosed in U.S. Pat. No. 3,914,250; and PCT Publications 01/66548, 02/36596, 02/48124, 02/10169, 02/44152; 02/51844, 02/40456, 02/40457, 03/057698, 05/000849, and the like; (20) Mc3r (melanocortin 3 receptor) agonists; (21) Mc4r (melanocortin 4 receptor) agonists, such as CHIR86036 (Chiron), CHIR915 (Chiron); ME-10142 (Melacure), ME-10145 (Melacure), HS-131 (Melacure), NBI72432 (Neurocrine Biosciences), NNC 70-619 (Novo Nordisk), TTP2435 (Transtech) and those disclosed in PCT Publications WO 99/64002, 00/74679, 01/991752, 01/0125192, 01/52880, 01/74844, 01/70708, 01/70337, 01/91752, 01/010842, 02/059095, 02/059107, 02/059108, 02/059117, 02/062766, 02/069095, 02/12166, 02/11715, 02/12178, 02/15909, 02/38544, 02/068387, 02/068388, 02/067869, 02/081430, 03/06604, 03/007949, 03/009847, 03/009850, 03/013509, 03/031410, 03/094918, 04/028453, 04/048345, 04/050610, 04/075823, 04/083208, 04/089951, 05/000339, and EP 1460069, and US 2005049269, and JP2005042839, and the like; (22) monoamine reuptake inhibitors, such as sibutratmine (Meridia®/Reductil®) and salts thereof, and those compounds disclosed in U.S. Pat. Nos. 4,746,680, 4,806,570, and 5,436,272, and U.S. Patent Publication No. 2002/0006964, and WO 01/27068, and WO 01/62341; (23) serotonin reuptake inhibitors, such as dexfenfluramine, fluoxetine, and those in U.S. Pat. No. 6,365,633, and WO 01/27060, and WO 01/162341; (24) GLP-1 (glucagon-like peptide 1) agonists; (25) Topiramate (Topimax®); (26) phytopharm compound 57 (CP 644,673); (27) ACC2 (acetyl-CoA carboxylase-2) inhibitors; (28) P3 (beta adrenergic receptor 3) agonists, such as rafebergron/AD9677/TAK677 (Dainippon/Takeda), CL-316,243, SB 418790, BRL-37344, L-796568, BMS-196085, BRL-35135A, CGP12177A, BTA-243, GRC1087 (Glenmark Pharmaceuticals) GW 427353 (solabegron hydrochloride), Trecadrine, Zeneca D7114, N-5984 (Nisshin Kyorin), LY-377604 (Lilly), KT07924 (Kissei), SR 59119A, and those disclosed in U.S. Pat. No. 5,705,515, U.S. Pat. No. 5,451,677; and WO94/18161, WO95/29159, WO97/46556, WO98/04526 WO98/32753, WO 01/74782, WO 02/32897, WO 03/014113, WO 03/016276, WO 03/016307, WO 03/024948, WO 03/024953, WO 03/037881, WO 04/108674, and the like; (29) DGAT1 (diacylglycerol acyltransferase 1) inhibitors; (30) DGAT2 (diacylglycerol acyltransferase 2) inhibitors; (31) FAS (fatty acid synthase) inhibitors, such as Cerulenin and C75; (32) PDE (phosphodiesterase) inhibitors, such as theophylline, pentoxifylline, zaprinast, sildenafil, amrinone, milrinone, cilostamide, rolipram, and cilomilast, as well as those described in WO 03/037432, WO 03/037899; (33) thyroid hormone 13 agonists, such as KB-2611 (KaroBioBMS), and those disclosed in WO 02/15845; and Japanese Patent Application No. JP 2000256190; (34) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TT-NPB), and retinoic acid; and those disclosed in WO 99/00123; (35) acyl-estrogens, such as oleoyl-estrone, disclosed in del Mar-Grasa, M. et al., Obesity Research, 9:202-9 (2001); (36) glucocorticoid receptor antagonists, such as CP472555 (Pfizer), KB 3305, and those disclosed in WO 04/000869, WO 04/075864, and the like; (37) 1113 HSD-1 (11-beta hydroxy steroid dehydrogenase type 1) inhibitors, such as BVT 3498 (AMG 331), BVT 2733, 3-(1-adamantyl)-4-ethyl-5-(ethylthio)-4H-1,2,4-triazole, 3-(1-adamantyl)-5-(3,4,5-trimethoxyphenyl)-4-methyl-4H-1,2,4-triazole, 3-adamantanyl-4,5,6,7,8,9,10,11,12,3a-decahydro-1,2,4-triazolo[4,3-a][11]annulene, and those compounds disclosed in WO 01/90091, 01/90090, 01/90092, 02/072084, 04/011410, 04/033427, 04/041264, 04/027047, 04/056744, 04/065351, 04/089415, 04/037251, and the like; (38) SCD-1 (stearoyl-CoA desaturase-1) inhibitors; (39) dipeptidyl peptidase IV (DPP-4) inhibitors, such as isoleucine thiazolidide, valine pyrrolidide, sitagliptin (Januvia), saxagliptin, alogliptin, NVP-DPP728, LAF237 (vildagliptin), P93/01, TSL 225, TMC-2A/2B/2C, FE 999011, P9310/K364, VIP 0177, SDZ 274-444, GSK 823093, E 3024, SYR 322, TS021, SSR 162369, GRC 8200, K579, NN7201, CR 14023, PHX 1004, PHX 1149, PT-630, SK-0403; and the compounds disclosed in WO 02/083128, WO 02/062764, WO 02/14271, WO 03/000180, WO 03/000181, WO 03/000250, WO 03/002530, WO 03/002531, WO 03/002553, WO 03/002593, WO 03/004498, WO 03/004496, WO 03/005766, WO 03/017936, WO 03/024942, WO 03/024965, WO 03/033524, WO 03/055881, WO 03/057144, WO 03/037327, WO 04/041795, WO 04/071454, WO 04/0214870, WO 04/041273, WO 04/041820, WO 04/050658, WO 04/046106, WO 04/067509, WO 04/048532, WO 04/099185, WO 04/108730, WO 05/009956, WO 04/09806, WO 05/023762, US 2005/043292, and EP 1 258 476; (40) lipase inhibitors, such as tetrahydrolipstatin (orlistat/XENICAL), ATL962 (Alizyme/Takeda), GT389255 (Genzyme/Peptimmune) Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, WO 04/111004, and U.S. Pat. Nos. 4,598,089, 4,452,813, 5,512,565, 5,391,571, 5,602,151, 4,405,644, 4,189,438, and 4,242,453, and the like; (41) fatty acid transporter inhibitors; (42) dicarboxylate transporter inhibitors; (43) glucose transporter inhibitors; and (44) phosphate transporter inhibitors; (45) anorectic bicyclic compounds such as 1426 (Aventis) and 1954 (Aventis), and the compounds disclosed in WO 00/18749, WO 01/32638, WO 01/62746, WO 01/62747, and WO 03/015769; (46) peptide YY and PYY agonists such as PYY336 (Nastech/Merck), AC162352 (IC Innovations/Curis/Amylin), TM30335/TM30338 (7TM Pharma), PYY336 (Emisphere Tehcnologies), pegylated peptide YY3-36, those disclosed in WO 03/026591, 04/089279, and the like; (47) lipid metabolism modulators such as maslinic acid, erythrodiol, ursolic acid uvaol, betulinic acid, betulin, and the like and compounds disclosed in WO 03/011267; (48) transcription factor modulators such as those disclosed in WO 03/026576; (49) Mc5r (melanocortin 5 receptor) modulators, such as those disclosed in WO 97/19952, WO 00/15826, WO 00/15790, US 20030092041, and the like; (50) Brain derived neutotropic factor (BDNF), (51) Mc1r (melanocortin 1 receptor modulators such as LK-184 (Proctor & Gamble), and the like; (52) 5HT6 antagonists such as BVT74316 (BioVitrum), BVT5182c (BioVitrum), E-6795 (Esteve), E-6814 (Esteve), SB399885 (GlaxoSmithkline), SB271046 (GlaxoSmithkline), RO-046790 (Roche), and the like; (53) fatty acid transport protein 4 (FATP4); (54) acetyl-CoA carboxylase (ACC) inhibitors such as CP640186, CP610431, CP640188 (Pfizer); (55) C-terminal growth hormone fragments such as AOD9604 (Monash Univ/Metabolic Pharmaceuticals), and the like; (56) oxyntomodulin; (57) neuropeptide FF receptor antagonists such as those disclosed in WO 04/083218, and the like; (58) amylin agonists such as Symlin/pramlintide/AC137 (Amylin); (59) Hoodia and trichocaulon extracts; (60) BVT74713 and other gut lipid appetite suppressants; (61) dopamine agonists such as bupropion (WELLBUTRIN/GlaxoSmithkline); (62) zonisamide (ZONEGRAN/Dainippon/Elan), and the like; and (e) anorectic agents suitable for use in combination with a compound of the present invention include, but are not limited to, aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; and pharmaceutically acceptable salts thereof. A particularly suitable class of anorectic agent are the halogenated amphetamine derivatives, including chlorphentermine, cloforex, clortermine, dexfenfluramine, fenfluramine, picilorex and sibutramine; and pharmaceutically acceptable salts thereof. Particular halogenated amphetamine derivatives of use in combination with a compound of the present invention include: fenfluramine and dexfenfluramine, and pharmaceutically acceptable salts thereof Specific compounds of use in combination with a compound of the present invention include: simvastatin, mevastatin, ezetimibe, atorvastatin, sitagliptin, metformin, sibutramine, orlistat, Qnexa, topiramate, naltrexone, bupriopion, phentermine, and losartan, losartan with hydrochlorothiazide. Specific CB1 antagonists/inverse agonists of use in combination with a compound of the present invention include: those described in WO03/077847, including: N-[3-(4-chlorophenyl)-2(S)-phenyl-1(S)-methylpropyl]-2-(4-trifluoromethyl-2-pyrimidyloxy)-2-methylpropanamide, N-[3-(4-chlorophenyl)-2-(3-cyanophenyl)-1-methylpropyl]-2-(5-trifluoromethyl-2-pyridyloxy)-2-methylpropanamide, N-[3-(4-chlorophenyl)-2-(5-chloro-3-pyridyl)-1-methylpropyl]-2-(5-trifluoromethyl-2-pyridyloxy)-2-methylpropanamide, and pharmaceutically acceptable salts thereof; as well as those in WO05/000809, which includes the following: 3-{1-[bis(4-chlorophenyl)methyl]azetidin-3-ylidene}-3-(3,5-difluorophenyl)-2,2-dimethylpropanenitrile, 1-{1-[1-(4-chlorophenyl)pentyl]azetidin-3-yl}-1-(3,5-difluorophenyl)-2-methylpropan-2-ol. 3-((S)-(4-chlorophenyl){3-[(1S)-1-(3,5-difluorophenyl)-2-hydroxy-2-methylpropyl]azetidin-1-yl}methyl)benzonitrile, 3-((S)-(4-chlorophenyl){3-[(1S)-1-(3,5-difluorophenyl)-2-fluoro-2-methylpropyl]azetidin-1-yl}methyl)benzonitrile, 3-((4-chlorophenyl){3-[1-(3,5-difluorophenyl)-2,2-dimethylpropyl]azetidin-1-yl}methyl)benzonitrile, 3-((1S)-1-{1-[(S)-(3-cyanophenyl)(4-cyanophenyl)methyl]azetidin-3-yl}-2-fluoro-2-methylpropyl)-5-fluorobenzonitrile, 3-[(S)-(4-chlorophenyl)(3-{(1S)-2-fluoro-1-[3-fluoro-5-(4H-1,2,4-triazol-4-yl)phenyl]-2-methylpropyl}azetidin-1-yl)methyl]benzonitrile, and 5-((4-chlorophenyl){3-[(1S)-1-(3,5-difluorophenyl)-2-fluoro-2-methylpropyl]azetidin-1-yl}methyl)thiophene-3-carbonitrile, and pharmaceutically acceptable salts thereof; as well as: 3-[(S)-(4-chlorophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-chlorophenyl)methyl]benzonitrile, 3-[(S)-(4-cyanophenyl)(3-{(1S)-2-fluoro-1-[3-fluoro-5-(5-oxo-4,5-dihydro-1,3,4-oxadiazol-2-yl)phenyl]-2-methylpropyl}azetidin-1-yl)methyl]benzonitrile, 3-[(S)-(3-{(1S)-1-[3-(5-amino-1,3,4-oxadiazol-2-yl)-5-fluorophenyl]-2-fluoro-2-methylpropyl}azetidin-1-yl)(4-cyanophenyl)methyl]-benzonitrile, 3-[(S)-(4-cyanophenyl)(3-{(1S)-2-fluoro-1-[3-fluoro-5-(1,3,4-oxadiazol-2-yl)phenyl]-2-methylpropyl}azetidin-1-yl)methyl]benzonitrile, 3-[(S)-(4-chlorophenyl)(3-{(1S)-2-fluoro-1-[3-fluoro-5-(1,2,4-oxadiazol-3-yl)phenyl]-2-methylpropyl}azetidin-1-yl)methyl]benzonitrile, 3-[(1S)-1-(1-{(S)-(4-cyanophenyl)[3-(1,2,4-oxadiazol-3-yl)phenyl]-methyl}azetidin-3-yl)-2-fluoro-2-methylpropyl]-5-fluorobenzonitrile, 5-(3-{1-[1-(diphenylmethyl)azetidin-3-yl]-2-fluoro-2-methylpropyl}-5-fluorophenyl)-1H-tetrazole, 5-(3-{1-[1-(diphenylmethyl)azetidin-3-yl]-2-fluoro-2-methylpropyl}-5-fluorophenyl)-1-methyl-1H-tetrazole, 5-(3-{1-[1-(diphenylmethyl)azetidin-3-yl]-2-fluoro-2-methylpropyl}-5-fluorophenyl)-2-methyl-2H-tetrazole, 3-[(4-chlorophenyl)(3-{2-fluoro-1-[3-fluoro-5-(2-methyl-2H-tetrazol-5-yl)phenyl]-2-methylpropyl}azetidin-1-yl)methyl]benzonitrile, 3-[(4-chlorophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(1-methyl-1H-tetrazol-5-yl)phenyl]-2-methylpropyl}azetidin-1-yl)methyl]benzonitrile, 3-[(4-cyanophenyl)(3-{2-fluoro-1-[3-fluoro-5-(2-methyl-2H-tetrazol-5-yl)phenyl]-2-methylpropyl}azetidin-1-yl)methyl]benzonitrile, 5-{3-[(S)-{3-[(1S)-1-(3-bromo-5-fluorophenyl)-2-fluoro-2-methylpropyl]azetidin-1-yl}(4-chlorophenyl)methyl]phenyl}-1,3,4-oxadiazol-2(3H)-one, 3-[(1S)-1-(1-{(S)-(4-chlorophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(5-oxo-4,5-dihydro-1,3,4-oxadiazol-2-yl)phenyl]methyl}azetidin-3-yl)-2-fluoro-2-methylpropyl]-5-fluorobenzonitrile, 3-[(1S)-1-(1-{(S)-(4-cyanophenyl)[3-(1,3,4-oxadiazol-2-yl)phenyl]methyl}-azetidin-3-yl)-2-fluoro-2-methylpropyl]-5-fluorobenzonitrile, 3-[(1S)-1-(1-{(S)-(4-chlorophenyl)[3-(1,3,4-oxadiazol-2-yl)phenyl]methyl}azetidin-3-yl)-2-fluoro-2-methylpropyl]-5-fluorobenzonitrile, 3-((1S)-1-{1-[(S)-[3-(5-amino-1,3,4-oxadiazol-2-yl)phenyl](4-chlorophenyl)methyl]azetidin-3-yl}-2-fluoro-2-methylpropyl)-5-fluorobenzonitrile, 3-((1S)-1-{1-[(S)-[3-(5-amino-1,3,4-oxadiazol-2-yl)phenyl](4-cyanophenyl)methyl]azetidin-3-yl}-2-fluoro-2-methylpropyl)-5-fluorobenzonitrile, 3-[(1S)-1-(1-{(S)-(4-cyanophenyl)[3-(1,2,4-oxadiazol-3-yl)phenyl]methyl}azetidin-3-yl)-2-fluoro-2-methylpropyl]-5-fluorobenzonitrile, 3-[(1S)-1-(1-{(S)-(4-chlorophenyl)[3-(1,2,4-oxadiazol-3-yl)phenyl]methyl}azetidin-3-yl)-2-fluoro-2-methylpropyl]-5-fluorobenzonitrile, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 5-[3-((S)-(4-chlorophenyl){3-[(1S)-1-(3,5-difluorophenyl)-2-fluoro-2-methylpropyl]azetidin-1-yl}methyl)phenyl]-1,3,4-oxadiazol-2(3H)-one, 4-{(S)-{3-[(1S)-1-(3,5-difluorophenyl)-2-fluoro-2-methylpropyl]azetidin-1-yl}[3-(5-oxo-4,5-dihydro-1,3,4-oxadiazol-2-yl)phenyl]methyl}-benzonitrile, and pharmaceutically acceptable salts thereof Specific NPY5 antagonists of use in combination with a compound of the present invention include: 3-oxo-N-(5-phenyl-2-pyrazinyl)-spiro[isobenzofuran-1(3H),4'-piperidine]-1'-carboxamide, 3-oxo-N-(7-trifluoromethylpyrido[3,2-b]pyridin-2-yl)spiro-[isobenzofuran-1(3H),4'-piperidine]-1'-carboxamide, N-[5-(3-fluorophenyl)-2-pyrimidinyl]-3-oxospiro-[isobenzofuran-1(3H),4'-piperidine]-1'-carboxamide, trans-3'-oxo-N-(5-phenyl-2-pyrimidinyl)spiro[cyclohexane-1,1'(3'H)-isobenzofuran]-4-carboxamide, trans-3'-oxo-N-[1-(3-quinolyl)-4-imidazolyl]spiro[cyclohexane-1,1'(3'H)-isobenzofuran]-4-carboxamide, trans-3-oxo-N-(5-phenyl-2-pyrazinyl)spiro[4-azaiso-benzofuran-1(3H),1'-cyclohexane]-4'-carboxamide, trans-N-[5-(3-fluorophenyl)-2-pyrimidinyl]-3-oxospiro[5-azaisobenzofuran-1(3H),1'-cyclohexane]-4'-carboxamide, trans-N-[5-(2-fluorophenyl)-2-pyrimidinyl]-3-oxospiro[5-azaisobenzofuran-1(3H),1'-cyclohexane]-4'-carboxamide, trans-N-[1-(3,5-difluorophenyl)-4-imidazolyl]-3-oxospiro[7-azaisobenzofuran-1(3H),1'-cyclohexane]-4'-carboxamide, trans-3-oxo-N-(1-phenyl-4-pyrazolyl)spiro[4-azaisobenzofuran-1(3H),1'-cyclohexane]-4'-carboxamide, trans-N-[1-(2-fluorophenyl)-3-pyrazolyl]-3-oxospiro[6- azaisobenzofuran-1(3H),1'-cyclohexane]-4'-carboxamide, trans-3-oxo-N-(1-phenyl-3-pyrazolyl)spiro[6-azaisobenzofuran-1(3H),1'-cyclohexane]-4'-carboxamide, trans-3-oxo-N-(2-phenyl-1,2,3-triazol-4-yl)spiro[6-azaisobenzofuran-1(3H),1'-cyclohexane]-4'-carboxamide, and pharmaceutically acceptable salts and esters thereof.

Specific ACC-1/2 inhibitors of use in combination with a compound of the present invention include: 1'-[(4,8-dimethoxyquinolin-2-yl)carbonyl]-6-(1H-tetrazol-5-yl) spiro[chroman-2,4'-piperidin]-4-one; (5-{1'-[(4,8-dimethoxyquinolin-2-yl)carbonyl]-4-oxospiro[chroman-2,4'-piperidin]-6-yl}-2H-tetrazol-2-yl)methyl pivalate; 5-{1'-[(8-cyclopropyl-4-methoxyquinolin-2-yl)carbonyl]-4-oxospiro[chroman-2,4'-piperidin]-6-yl}nicotinic acid; 1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof. Specific MCH1R antagonist compounds of use in combination with a compound of the present invention include: 1-{4-[(1-ethylazetidin-3-yl)oxy]phenyl}-4-[(4-fluorobenzyl)oxy]pyridin-2(1H)-one, 4-[(4-fluorobenzyl)oxy]-1-{4-[(1-isopropylazetidin-3-yl)oxy]phenyl}pyridin-2(1H)-one, 1-[4-(azetidin-3-yloxy)phenyl]-4-[(5-chloropyridin-2-yl)methoxy]pyridin-2(1H)-one, 4-[(5-chloropyridin-2-yl)methoxy]-1-{4-[(1-ethylazetidin-3-yl)oxy]phenyl}pyridin-2(1H)-one, 4-[(5-chloropyridin-2-yl)methoxy]-1-{4-[(1-propylazetidin-3-yl)oxy]phenyl}pyridin-2(1H)-one, and 4-[(5-chloropyridin-2-yl)methoxy]-1-(4-{[(2S)-1-ethylazetidin-2-yl]methoxy}phenyl)pyridin-2(1H)-one, or a pharmaceutically acceptable salt thereof.

Specific DP-IV inhibitors of use in combination with a compound of the present invention are selected from Januvia, 7-[(3R)-3-amino-4-(2,4,5-trifluorophenyl)butanoyl]-3-(trifluoromethyl)-5,6,7,8-tetrahydro-1,2,4-triazolo[4,3-a]pyrazine. In particular, the compound of formula I is favorably combined with 7-[(3R)-3-amino-4-(2,4,5-trifluorophenyl)butanoyl]-3-(trifluoromethyl)-5,6,7,8-tetrahydro-1,2,4-triazolo[4,3-a]pyrazine, and pharmaceutically acceptable salts thereof Specific H3 (histamine H3) antagonists/inverse agonists of use in combination with a compound of the present invention include: those described in WO05/077905, including:3-{4-[(1-cyclobutyl-4-piperidinyl)oxy]phenyl}-2-ethylpyrido[2,3-d]-pyrimidin-4(3H)-one, 3-{4-[(1-cyclobutyl-4-piperidinyl)oxy]phenyl}-2-methylpyrido[4,3-d]pyrimidin-4(3H)-one, 2-ethyl-3-(4-{3-[(3S)-3-methylpiperidin-1-yl]propoxy}phenyl)pyrido[2,3-d]pyrimidin-4(3H)-one 2-methyl-3-(4-{3-[(3S)-3-methylpiperidin-1-yl]propoxy}phenyl)pyrido[4,3-d]pyrimidin-4 (3H)-one, 3-{4-[(1-cyclobutyl-4-piperidinyl)oxy]phenyl}-2,5-dimethyl-4(3H)-quinazolinone, 3-{4-[(1-cyclobutyl-4-piperidinyl)oxy]phenyl}-2-methyl-5-trifluoromethyl-4(3H)-quinazolinone, 3-{4-[(1-cyclobutyl-4-piperidinyl)oxy]phenyl}-5-methoxy-2-methyl-4(3H)-quinazolinone, 3-{4-[(1-cyclobutylpiperidin-4-yl)oxy]phenyl}-5-fluoro-2-methyl-4(3H)-quinazolinone, 3-{4-[(1-cyclobutylpiperidin-4-yl)oxy]phenyl}-7-fluoro-2-methyl-4(3H)-quinazolinone, 3-{4-[(1-cyclobutylpiperidin-4-yl)oxy]phenyl}-6-methoxy-2-methyl-4(3H)-quinazolinone, 3-{4-[(1-cyclobutylpiperidin-4-yl)oxy]phenyl}-6-fluoro-2-methyl-4(3H)-quinazolinone, 3-{4-[(1-cyclobutylpiperidin-4-yl)oxy]phenyl}-8-fluoro-2-methyl-4(3H)-quinazolinone, 3-{4-[(1-cyclopentyl-4-piperidinyl)oxy]phenyl}-2-methylpyrido[4,3-d]pyrimidin-4 (3H)-one, 3-{4-[(1-cyclobutylpiperidin-4-yl)oxy]phenyl}-6-fluoro-2-methylpyrido[3,4-d]pyrimidin-4 (3H)-one, 3-{4-[(1-cyclobutyl-4-piperidinyl)oxy]phenyl}-2-ethylpyrido[4,3-d]pyrimidin-4(3H)-one, 6-methoxy-2-methyl-3-{4-[3-(1-piperidinyl)propoxy]phenyl}pyrido[3,4-d]pyrimidin-4(3H)-one, 6-methoxy-2-methyl-3-{4-[3-(1-pyrrolidinyl)propoxy]phenyl}pyrido[3,4-d]pyrimidin-4 (3H)-one, 2,5-dimethyl-3-{4-[3-(1-pyrrolidinyl)propoxy]phenyl}-4(3H)-quinazolinone, 2-methyl-3-{4-[3-(1-pyrrolidinyl)propoxy]phenyl}-5-trifluoromethyl-4(3H)-quinazolinone, 5-fluoro-2-methyl-3-{4-[3-(1-piperidinyl)propoxy]phenyl}-4(3H)-quinazolinone, 6-methoxy-2-methyl-3-{4-[3-(1-piperidinyl)propoxy]phenyl}-4(3H)-quinazolinone, 5-methoxy-2-methyl-3-(4-{3-[(3S)-3-methylpiperidin-1-yl]propoxy}phenyl)-4(3H)-quinazolinone, 7-methoxy-2-methyl-3-(4-{3-[(3S)-3-methylpiperidin-1-yl]propoxy}phenyl)-4(3H)-quinazolinone, 2-methyl-3-(4-{3-[(3S)-3-methylpiperidin-1-yl]propoxy}phenyl)pyrido[2,3-d]pyrimidin-4(3H)-one, 5-fluoro-2-methyl-3-(4-{3-[(2R)-2-methylpyrrolidin-1-yl]propoxy}phenyl)-4(3H)-quinazolinone, 2-methyl-3-(4-{3-[(2R)-2-methylpyrrolidin-1-yl]propoxy}phenyl)pyrido[4,3-d]pyrimidin-4(3H)-one, 6-methoxy-2-methyl-3-(4-{3-[(2R)-2-methylpyrrolidin-1-yl]propoxy}phenyl)-4(3H)-quinazolinone, 6-methoxy-2-methyl-3-(4-{3-[(2S)-2-methylpyrrolidin-1-yl]propoxy}phenyl)-4(3H)-quinazolinone, and pharmaceutically acceptable salts thereof.

Specific CCK1R agonists of use in combination with a compound of the present invention include: 3-(4-{[1-(3-ethoxyphenyl)-2-(4-methylphenyl)-1H-imidazol-4-yl]carbonyl}-1-piperazinyl)-1-naphthoic acid; 3-(4-{[1-(3-ethoxyphenyl)-2-(2-fluoro-4-methylphenyl)-1H-imidazol-4-yl]carbonyl}-1-piperazinyl)-1-naphthoic acid; 3-(4-{[1-(3-ethoxyphenyl)-2-(4-fluorophenyl)-1H-imidazol-4-yl]carbonyl}-1-piperazinyl)-1-naphthoic acid; 3-(4-{[1-(3-ethoxyphenyl)-2-(2,4-difluorophenyl)-1H-imidazol-4-yl]carbonyl}-1-piperazinyl)-1-naphthoic acid; and 3-(4-{[1-(2,3-dihydro-1,4-benzodioxin-6-yl)-2-(4-fluorophenyl)-1H-imidazol-4-yl]carbonyl}-1-piperazinyl)-1-naphthoic acid; and pharmaceutically acceptable salts thereof.

Specific MC4R agonists of use in combination with a compound of the present invention include: 1) (5S)-1'-{[(3R,4R)-1-tert-butyl-3-(2,3,4-trifluorophenyl)piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 2) (5R)-1'-{[(3R,4R)-1-tert-butyl-3-(2,3,4-trifluorophenyl)-piperidin-4-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 3) 2-(1'-{[(3S,4R)-1-tert-butyl-4-(2,4-difluorophenyl)pyrrolidin-3-yl]carbonyl}-3-chloro-2-methyl-5H-spiro[furo[3,4-b]pyridine-7,4'-piperidin]-5-yl)-2-methylpropanenitrile; 4) 1'-{[(3S,4R)-1-tert-butyl-4-(2,4-difluorophenyl)pyrrolidin-3-yl]carbonyl}-3-chloro-2-methyl-5-[1-methyl-1-(1-methyl-1H-1,2,4-triazol-5-yl)ethyl]-5H-spiro[furo[3,4-b]pyridine-7,4'-piperidine]; 5) N-[(3R,4R)-3-({3-chloro-2-methyl-5-[1-methyl-1-(1-methyl-1H-1,2,4-triazol-5-yl)ethyl]-1'H,5H-spiro[furo-[3,4-b]pyridine-7,4'-piperidin]-1'-yl}carbonyl)-4-(2,4-difluorophenyl)-cyclopentyl]-N-methyltetrahydro-2H-pyran-4-amine; 6) 2-[3-chloro-1'-({(1R,2R)-2-(2,4-difluorophenyl)-4-[methyl(tetrahydro-2H-pyran-4-yl)amino]-cyclopentyl}-carbonyl)-2-methyl-5H-spiro[furo[3,4-b]pyridine-7,4'-piperidin]-5-yl]-2-methyl-propane-nitrile; and pharmaceutically acceptable salts thereof.

Suitable neurokinin-1 (NK-1) receptor antagonists may be favorably employed with the AMP-kinase activators of the present invention. NK-1 receptor antagonists of use in the present invention are fully described in the art. Specific neurokinin-1 receptor antagonists of use in the present invention include: (±)-(2R3R,2S3S)—N-{[2-cyclopropoxy-5-(trifluoromethoxy)-phenyl]methyl}-2-phenylpiperidin-3-amine; 2-(R)-(1-(R)-(3,5-bis(trifluoromethyl)-phenyl)ethoxy)-3-(S)-(4-fluorophenyl)-4-(3-(5-oxo-1H,4H-1,2,4-triazolo)methyl)morpholine; aperpitant; CJ17493; GW597599; GW679769; R673; RO67319; R1124; R1204; SSR146977; SSR240600; T-2328; and T2763; or a pharmaceutically acceptable salts thereof.

The term "therapeutically effective amount" means the amount the compound of structural formula I that will elicit the biological or medical response of a tissue, system, animal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes humans, and companion animals such as dogs and cats.

The weight ratio of the compound of the Formula I to the second active ingredient may be varied and will depend upon the effective dose of each ingredient. Generally, an effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

The compounds of structural formula I of the present invention can be prepared according to the procedures of the following Schemes, Intermediates and Examples, using appropriate materials and are further exemplified by the following specific examples. Moreover, by utilizing the procedures described in the disclosure contained herein, one of ordinary skill in the art can readily prepare additional compounds of the present invention claimed herein. The compounds illustrated in the examples are not, however, to be construed as forming the only genus that is considered as the invention. The Examples further illustrate details for the preparation of the compounds of the present invention. Those skilled in the art will readily understand that known variations of the conditions and processes of the following preparative procedures can be used to prepare these compounds. The instant compounds are generally isolated in the form of their pharmaceutically acceptable salts, such as those previously described herein. The use of protecting groups for the amine and carboxylic acid functionalities to facilitate the desired reaction and minimize undesired reactions is well documented. Conditions required to remove protecting groups are found in standard textbooks such as Greene, T, and Wuts, P. G. M., Protective Groups in Organic Synthesis, John Wiley & Sons, Inc., New York, N.Y., 1991. CBZ and BOC are commonly used protecting groups in organic synthesis, and their removal conditions are known to those skilled in the art. All temperatures are degrees Celsius unless otherwise noted. Mass spectra (MS) were measured by electron-spray ion-mass spectroscopy.

Abbreviations used in the description of the preparation of the compounds of the present invention: ACN is acetonitrile; AcOH is acetic acid; aq or aq. is aqueous; Boc$_2$O is t-butoxycarbonyl anhydride; n-BuLi is n-butyllithium; C is carbon; CPME is cyclopentyl methyl ether; CV is column volume(s); DAST is (diethylamino)sulfur trifluoride; DBU is 1,8-diazabicyclo[5.4.0]-undec-7-ene; DIBAL-H is di-isobutyl aluminum hydride; DCE is dichloroethane; DCM is dichloromethane; DEAD is diethyl azodicarboxylate; DIAD is diisopropyl azodicarboxylate; DIEA and DIPEA is diisopropylethyl amine; DMA is dimethyl acetal; DMAc is dimethyl acetamide; DMAP is 4-(Dimethylamino)pyridine; DME is 1,2-dimethoxyethane; DMF is dimethyl formamide; DMSO is dimethyl sulfoxide; dppf DCM complex is 1,1'-bis(diphenyl-phosphino)ferrocene dichloromethane complex; DPPP is diphenyl phosphinopropane; EDC is N-(3-Dimethylaminopropyl)-N'-ethylcarbodiimide; Et$_2$O is diethyl ether; EtOAc is ethyl acetate; dppf is 1,1'-Bis(diphenyl-phosphino)ferrocene; EtOH is ethanol; Et$_3$N is triethyl amine; h is hour(s); HATU is O-(7-Azabenzotriazol-1-yl)-N,N,N',N'-tetramethyluronium hexafluoro-phosphate; Hex or hex is hexanes; HOBT is 1-Hydroxybenzotriazole; HPLC is high pressure liquid chromatography; ISCO R$_f$ is the Rf determined via medium pressure liquid chromato-graphy using a Teledyne ISCO RediSep® column; isomannide is 1,4:3,6-Di-anhydromannitol; KOAc is potassium acetate; L is liter; LC/MS and LC-MS is liquid chromatography/mass spectroscopy; KOTMS is potassium trimethylsilanolate; LAH is lithium aluminum hydride; M is molar; ml and mL is milliliter; Me is methyl, MeCN is acetonitrile; MeI is methyl iodide; MeMgBr is methyl magnesium bromide; MeOH is methanol; MgBr is magnesium bromide; min is minutes; mmol is millimole(s); m-CPBA is meta chloro per benzoic acid; MPLC is medium pressure liquid chromatography; MS is molecular sieves; MTBE is tert-butyl methyl ether; N is normal; NaOAc is sodium acetate; NBS is N-bromo succinamide; NIS is N-iodo succinamide; Pd$_2$(dba)$_3$ is tris(dibenzylideneacetone)-dipalladium(0); [PdCl$_2$(dppf)]CH$_2$Cl$_2$ or PdCl$_2$(dppf)-DCM is 1,1'-Bis(diphenylphosphino)-ferrocene-palladium(II) dichloride dichloromethane complex; PPh3 is triphenyl phosphine; PhSiH is phenyl silane; wt % is weight percent; psi is pounds per square inch; RT, r.t. and rt is room temperature; Rt is retention time; Rochelles' Salt is potassium sodium tartrate; RuPhos is 2-Dicyclohexyl-phosphino-2',6'-diisopropoxybiphenyl; sat, sat'd or sat. is saturated; SEM is 2-(trimethylsilyl)ethoxymethyl; SEM-C$_1$ and SEMC1 is 2-(trimethylsilyl)-ethoxymethyl chloride; TBABr is tetrabutyl ammonium bromide; TBAF is tetrabutyl ammonium fluoride; TBSC1 and TBDMSC1 is tert-butyldimethylsilyl chloride; TEA is triethylamine; TESC1 is chlorotriethylsilane; TFA is trifluoro acetic acid; THF is tetrahydrofuran; TMS is trimethylsilyl; Tosyl-C$_1$ is p-toluene-sulfonyl chloride; and XPhos is 2-Dicyclohexylphosphino-2',4',6'-triisopropylbiphenyl.

Microwave (MW) reactions were performed with a single mode operating Biotage Emrys Optimizer in sealed reaction vials at the indicated fixed temperature held constant for the designated reaction time. The medium pressure liquid chromatography (MPLC) purifications were performed with Teledyne ISCO RediSep® normal-phase columns pre-packed with 35-60 micron silica gel. The LC-MS system contained an Applied Biosystems API150EX MS operating in a positive ion mode receiving 0.1 mL/min flowrate with a Shimadzu UV detector receiving 0.1 mL/min flowrate. Unless specified, the LC conditions were solvent A=0.05% TFA in acetonitrile; solvent B=0.05% TFA in water; flowrate=10 mL/min; column: Chromolith Performance RP-18e, 100×4.6 mm. Unless specified, the $^1$H NMRs were obtained in CD$_3$OD at 500 MHz and spectra were recorded in units 6. C, H, N microanalyses were performed by Robertson Microlit Laboratories, Inc., Madison, N.J.

The following reaction schemes illustrate methods which may be employed for the synthesis of the compounds of structural formula I described in this invention. All substituents are as defined above unless indicated otherwise. Several strategies based upon synthetic transformations known in the literature of organic synthesis may be employed for the preparation of the compounds of general formula I.
GENERAL SCHEME
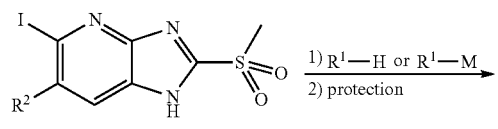
Intermediate
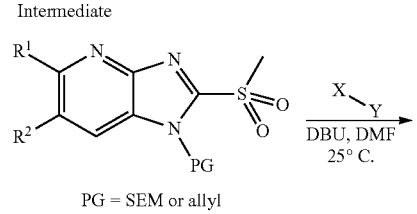
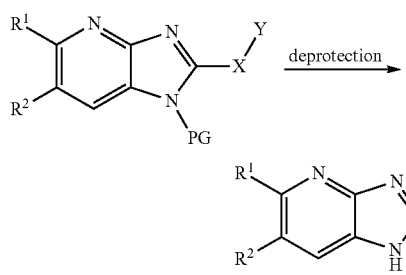
PG = SEM or allyl
SCHEME 1
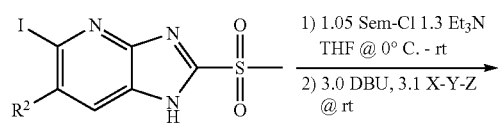
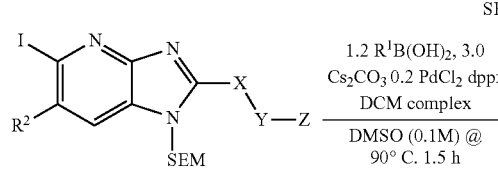
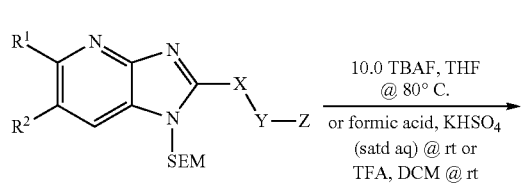
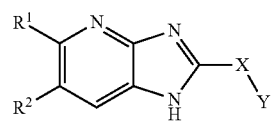
SCHEME 2
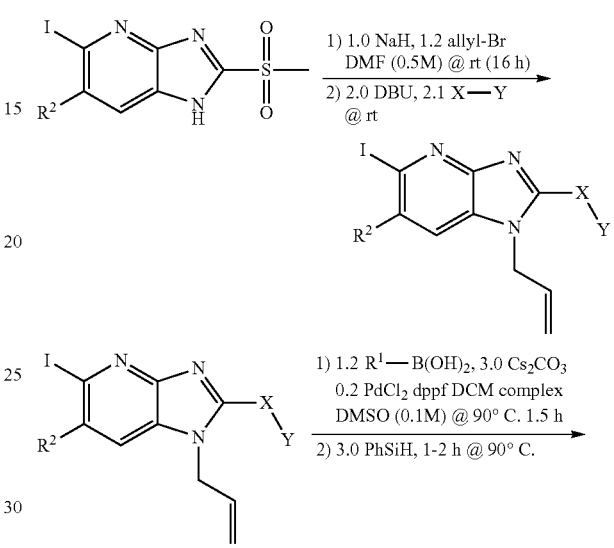
SCHEME 3
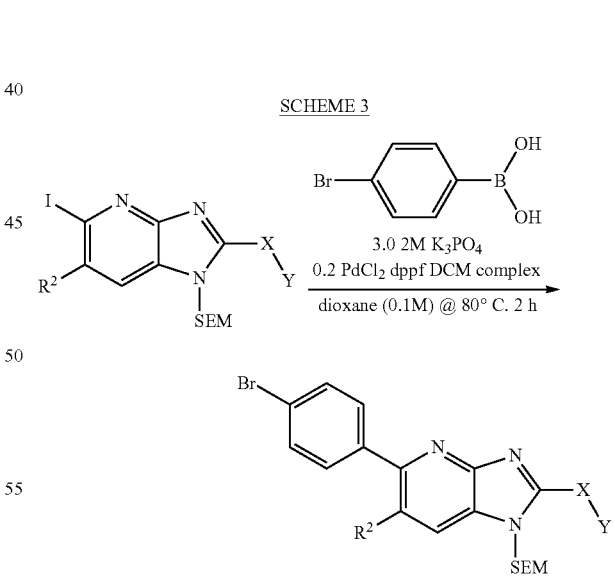

81

-continued

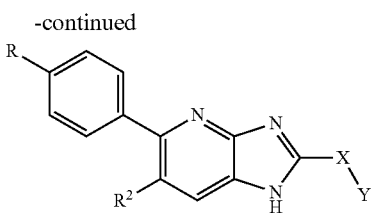

SCHEME 4

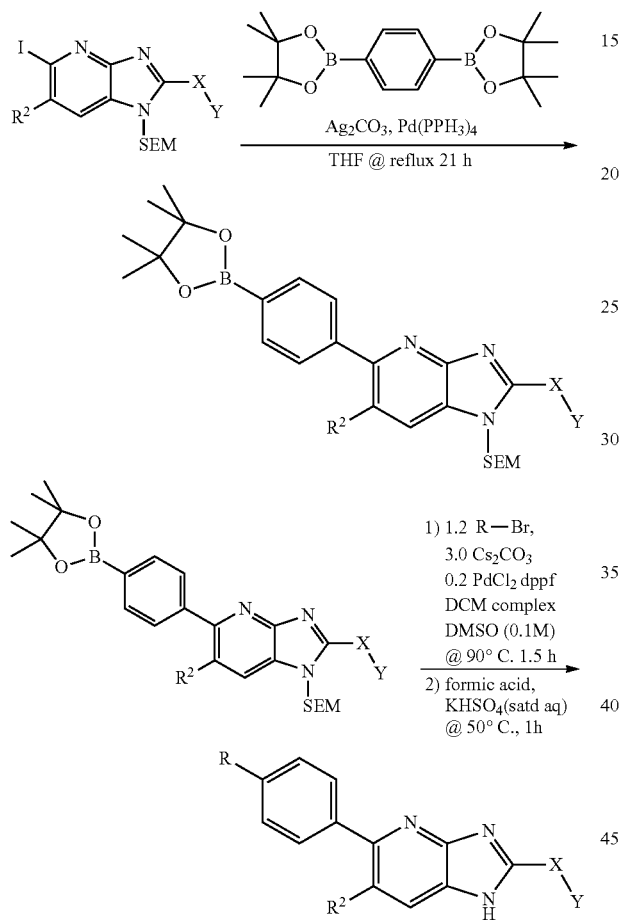

INTERMEDIATE 1

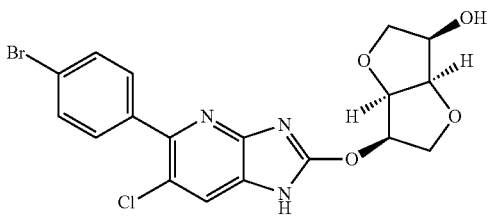 [SMILES: O[C@@H]1CO[C@H]2[C@@H]1OC[C@H]2Oc1nc2nc(-c3ccc(Br)cc3)c(Cl)cc2[nH]1]

82

(3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol A flask was charged with (3R,3aR,6R,6aR)-6-[5-(4-bromophenyl)-6-chloro-1-(2-trimethylsilylethoxy-methyl)imidazo[4,5-b]pyridin-2-yl]oxy-2,3,3a,5,6,6a-hexahydrofuro[3,2-b]furan-3-ol (270.1 mg, 0.463 mmol), formic acid (1.5 ml, 39.1 mmol), and saturated aqueous $KHSO_4$ (0.15 ml). The reaction mixture was stirred at room temperature for 16 h, then at 40° C. for 23 h. The reaction mixture was cooled in an ice bath. The pH of the reaction mixture was adjusted to 14 through the addition of 5 N aqueous NaOH (8.0 ml, 40 mmol). The reaction mixture was allowed to warm to room temperature. After 10 min, the pH of the reaction mixture was adjusted to 8 through the addition of 2N aqueous HCl. The reaction mixture was partitioned between EtOAc and water. The aqueous layer was extracted with EtOAc. The organic layers were combined, washed with brine, dried over $Na_2SO_4$, filtered, evaporated under reduced pressure, and lyophilized from ethanol and benzene to give the title compound as a yellow solid, which was used without further purification. LC-MS: calculated for $C_{18}H_{15}BrClN_3O_4$ 450.99, 452.99 observed m/e: 452.05, 454.02 $(M+H)^+$ (Rt 1.15/2 min).

INTERMEDIATE 2

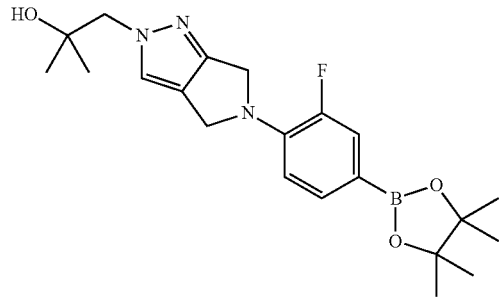 [SMILES: CC(C)(O)Cn1cc2c(n1)CN(c1ccc(B3OC(C)(C)C(C)(C)O3)cc1F)C2]

1-[5-[2-fluoro-4-(4,4,5,5-tetramethyl-1,3,2-dioxaborolan-2-yl)phenyl]-4,6-dihydropyrrolo[3,4-c]pyrazol-2-yl]-2-methyl-propan-2-ol Step A 1-[5-(4-chloro-2-fluoro-phenyl)-4,6-dihydropyrrolo[3,4-c]pyrazol-2-yl]-2-methyl-propan-2-ol 1-bromo-4-chloro-2-fluorobenzen (0.28 ml, 2.243 mmol) and chloro(2-dicyclohexyl-phosphino-2',6'-di-i-propoxy-1,1'-biphenyl)[2-(2-aminoethylphenyl)]Pd(II), and Chloro(2-dicyclohexylphosphino-2',6'-di-i-propoxy-1,1'-biphenyl)[2-(2-aminoethylphenyl)]-Pd(II), methyl-t-butylether adduct (68.2 mg, 0.094 mmol, Strem) were added to a stirred suspension of 1-(5,6-dihydro-4H-pyrrolo[3,4-c]pyrazol-5-ium-2-yl)-2-methyl-propan-2-ol; 2,2,2-trifluoroacetate (314.1 mg, 1.064 mmol) and sodium tert-butoxide (411.9 mg, 4.29 mmol) in THF (10.0 ml). The reaction mixture was degassed and placed under nitrogen before being heated to 80° C. After 17 h, the reaction mixture was cooled to room temperature before being partitioned between EtOAc and water. The aqueous layer was extracted with EtOAc. The organic layers were combined, washed with brine, dried over $MgSO_4$, filtered, and evaporated under reduced pressure to give a dark residue.

Flash chromatography of the residue utilizing a 24 g silica RediSep R_f® column and employing a 0-70% EtOAc/hexane gradient afforded the desired product as an amber residue. LC-MS: calculated for $C_{15}H_{17}ClFN_3O$ 309.1 observed m/e: 310.13 $(M+H)^+$ (Rt 1.20/2 min)

Step B 1-[5-[2-fluoro-4-(4,4,5,5-tetramethyl-1,3,2-dioxaborolan-2-yl)phenyl]-4,6-dihydropyrrolo[3,4-c]pyrazol-2-yl]-2-methyl-propan-2-ol Pd(II)(OAc)$_2$ (7.7 mg, 0.034 mmol) was added to a stirred suspension of 1-(5-(4-chloro-2-fluorophenyl)-5,6-dihydropyrrolo[3,4-c]pyrazol-2(4H)-yl)-2-methylpropan-2-ol (35.7 mg, 0.115 mmol), bis(pinacolato)diboron (53.2 mg, 0.209 mmol), potassium acetate (50.0 mg, 0.509 mmol), and 2-(dicyclohexylphosphino)-2',4',6'-triisopropylbiphenyl (9.7 mg, 0.020 mmol) in dioxane (1.2 ml). The reaction mixture was degassed and placed under nitrogen before being heated to 80° C. After 2 hours, the reaction mixture was cooled to room temperature before being partitioned between EtOAc and water (30 ml). The aqueous layer was extracted with EtOAc (2×20 ml). The organic layers were combined, washed with brine (1×20 ml), dried over MgSO$_4$, filtered, and evaporated under reduced pressure to give a dark amber residue. This material was dissolved in EtOAc and loaded onto a 500 micron 20 cm×20 cm silica gel plate, which was developed using 60% EtOAc/hexane. The silica containing the product band (R$_f$=0.5) was collected and extracted with EtOAc (80 ml). The solvent was evaporated under reduced pressure to give the title compound as an amber oil. LC-MS: calculated for $C_{21}H_{29}BFN_3O_3$ 401.23 observed m/e: 402.17 $(M+H)^+$ (Rt 1.25/2 min)

INTERMEDIATE 3

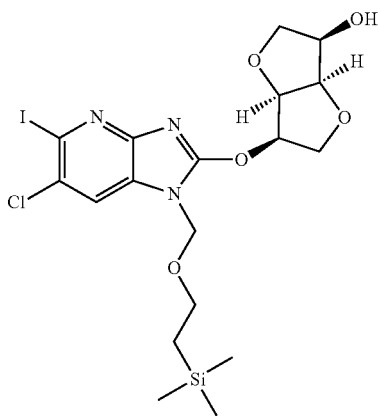 [SMILES: C[Si](C)(C)CCOCn1c(O[C@@H]2CO[C@H]3[C@@H]2OC[C@H]3O)nc2nc(I)c(Cl)cc21]

(3R,3aR,6R,6aR)-6-[6-chloro-5-iodo-1-(2-trimethylsilylethoxymethyl)imidazol[4,5-b]pyridin-2-yl]oxy-2,3,3a,5,6,6a-hexahydrofuro[3,2-b]furan-3-ol SEMC1 (3.42 ml, 19.30 mmol) was added to a stirred solution of 6-chloro-5-iodo-2-methylsulfonyl-1H-imidazo[4,5-b]pyridine (6 g, 16.78 mmol) and DBU (7.59 ml, 50.3 mmol) in DMF (100 ml). The reaction mixture was stirred at room temperature. After 1 h, 1,4:3,6-dianhydro-D-mannitaol (7.36 g, 50.3 mmol) was added to the reaction mixture, and stirring continued at room temperature overnight. The reaction mixture was diluted with EtOAc (200 ml) and washed with water (2×100 ml). The organic layer was dried over Na$_2$SO$_4$, filtered, and evaporated under reduced pressure. The resulting residue was purified on a 65i column eluting with a 20-50% EtOAc/heptane. The product fractions were evaporated under reduced pressure to give the title compound as a colorless syrup. LC-MS: calculated for $C_{18}H_{25}ClIN_3O_5Si$ 553.03 observed m/e: 554.27 $(M+H)^+$ (Rt 2.29/4 min).

INTERMEDIATE 4

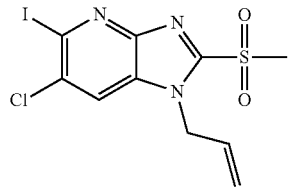 [SMILES: C=CCn1c(S(C)(=O)=O)nc2nc(I)c(Cl)cc21]

1-allyl-6-chloro-5-iodo-2-methylsulfonyl-imidazo[4,5-b]pyridine

N,N-diisopropylethylamine (0.69 ml, 3.95 mmol) and allyl bromide (0.32 ml, 3.70 mmol) were added to a stirred suspension of 6-chloro-5-iodo-2-methylsulfonyl-1H-imidazo[4,5-b]pyridine (1.0824 g, 3.03 mmol) in THF (12.0 ml). The reaction mixture was heated to 60° C. for 18 h, then cooled to room temperature. The reaction mixture was partitioned between EtOAc (50 ml) and brine (50 ml). The organic layer was washed with brine (1×50 ml). The combined aqueous layers were extracted with EtOAc (1×50 ml). The organic layers were combined, dried over Na$_2$SO$_4$, filtered, and evaporated under reduced pressure to give the title compound as a yellow foam. This material was a mixture of the allyl regioisomers and was used without further purification. LC-MS: calculated for $C_{10}H_9ClIN_3O_2S$ 396.91 observed m/e: 397.89 $(M+H)^+$ (Rt 1.12 and 1.17/2 min).

INTERMEDIATE 5

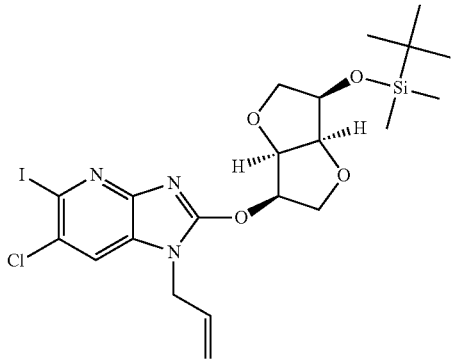 [SMILES: C=CCn1c(O[C@@H]2CO[C@H]3[C@@H]2OC[C@H]3O[Si](C)(C)C(C)(C)C)nc2nc(I)c(Cl)cc21]

[(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethylsilane A 250-mL, three-necked, round-bottomed flask was charged with the 1,4:3,6-dianhydro-D-mannitaol (12.45 g, 92 mmol), DBU (2.77 ml, 18.41 mmol), and DMF (90 ml). A solution of 1-allyl-6-chloro-5-iodo-2-methylsulfonyl-imidazo[4,5-b]pyridine in DMF (30 ml) was added dropwise to the reaction mixture over 2.25 h while stirring at room temperature. The reaction mixture was diluted with EtOAc and water. The organic layer was separated, washed with water and brine, dried over MgSO$_4$, filtered, and concentrated. The crude reaction mixture was dissolved in DMF (75 ml) and charged with imidazole (2.089 g, 30.7 mmol) and TBS-Cl (3.47 g, 23.01 mmol). The reaction mixture was stirred at room for 12 h before being diluted with EtOAc and water. The organic layer was separated, washed with water and brine, dried over MgSO$_4$, filtered, and concentrated. Flash chromatography of the residue utilizing a 220 g silica RediSep R$_f$® column and employing a 10-30% EtOAc/hexane gradient afforded the desired product as a white solid. LC-MS: calculated for $C_{21}H_{29}ClIN_3O_4Si$ 577.07 observed m/e: 578.21 (M+H)$^+$ (Rt 1.38/2 min)

INTERMEDIATE 6

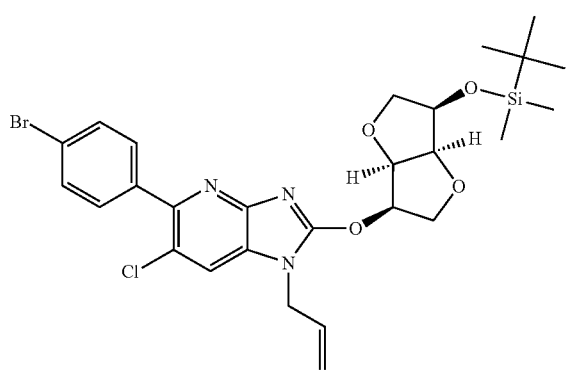 [SMILES: C=CCn1c(O[C@@H]2CO[C@H]3[C@@H]2OC[C@H]3O[Si](C)(C)C(C)(C)C)nc2nc(-c3ccc(Br)cc3)c(Cl)cc21]

[(3R,3aR,6R,6aS)-3-[1-allyl-5-(4-bromophenyl)-6-chloro-imidazo[4,5-b]pyridin-2-yl]oxy-2,3,3a,5,6,6a-hexahydrofuro[3,2-b]furan-6-yl]oxy-tert-butyl-dimethyl-silane Palladium tetrakistriphenylphosphine (204.6 mg, 0.177 mmol) was added to a stirred suspension of [(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethyl-silane (1.0083 g, 1.745 mmol), 4-bromophenylboronic acid (385.9 mg, 1.922 mmol), and tripotassium phosphate (1.1412 g, 5.38 mmol) in dioxane (14.0 ml) and water (3.5 ml). The reaction mixture was degassed (3×) and placed under nitrogen before being heated to 100° C. for 16 h. The reaction mixture was cooled to room temperature and partitioned between EtOAc (150 ml) and water (150 ml). The aqueous layer was extracted with EtOAc (2×75 ml). The organic layers were combined, washed with brine (1×75 ml), dried over MgSO$_4$, filtered, and evaporated under reduced pressure to give a yellow foam. Flash chromatography of the foam utilizing a 80 g silica RediSep R$_f$® column and employing a 0-30% EtOAc/hexane gradient followed by 30% EtOAc/hexane afforded the title compound as a yellow foam. LC-MS: calculated for $C_{27}H_{33}BrClN_3O_4Si$ 605.11, 607.11 observed m/e: 606.20, 608.16 (M+H)$^+$ (Rt 1.47/2 min)

INTERMEDIATE 7

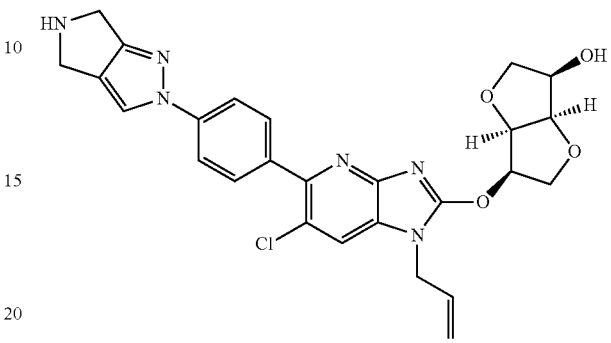

(3R,3aR,6R,6aR)-6-[1-allyl-6-chloro-5-[4-(5,6-dihydro-4H-pyrrolo[3,4-c]pyrazol-2-yl)phenyl]imidazo[4,5-b]pyridin-2-yl]oxy-2,3,3a,5,6,6a-hexahydrofuro[3,2-b]furan-3-ol Step A: tert-butyl 2-[4-[2-[[(3R,3aR,6R,6aS)-6-[tert-butyl(dimethyl)silyl]oxy-2,3,3a,5,6,6a-hexahydrofuro[3,2-b]furan-3-yl]oxy]-1-allyl-6-chloro-imidazo[4,5-b]pyridin-5-yl]phenyl]-4,6-dihydropyrrolo[3,4-c]pyrazole-5-carboxylate A vial was charged with [(3R,3aR,6R,6aS)-3-[1-allyl-5-(4-bromophenyl)-6-chloro-imidazo[4,5-b]pyridin-2-yl]oxy-2,3,3a,5,6,6a-hexahydrofuro[3,2-b]furan-6-yl]oxy-tert-butyl-dimethyl-silane (508.1 mg, 0.837 mmol), tert-butyl 4,6-dihydro-2H-pyrrolo[3,4-c]pyrazole-5-carboxylate (213.1 mg, 1.018 mmol), tripotassium phosphate (603.1 mg, 2.84 mmol), and copper(I) iodide (33.2 mg, 0.174 mmol). The vial was evacuated and backfilled with nitrogen (3×). Trans-N,N'-dimethylcyclohexane-1,2-diamine (53 µl, 0.335 mmol) and dioxane (1.6 ml) were added to the vial to give a pale blue suspension that was heated at 100° C. with stirring for 24 h. The reaction mixture was cooled to room temperature and partitioned between EtOAc (100 ml) and water (100 ml). The aqueous layer was extracted with EtOAc (2×50 ml). The organic layers were combined, washed with brine (1×30 ml), dried over MgSO$_4$, filtered, and evaporated under reduced pressure to give a light green residue. Flash chromatography of the residue utilizing an 40 g silica RediSep R$_f$® column and employing a 0-40% EtOAc/hexane gradient followed by 40% EtOAc/hexane afforded the desired product as a white foam. LC-MS: calculated for $C_{37}H_{47}ClN_6O_6Si$ 734.3 observed m/e: 735.34 (M+H)$^+$ (Rt 1.47/2 min)

Step B: (3R,3aR,6R,6aR)-6-[1-allyl-6-chloro-5-[4-(5,6-dihydro-4H-pyrrolo[3,4-c]pyrazol-2-yl)phenyl]imidazo[4,5-b]pyridin-2-yl]oxy-2,3,3a,5,6,6a-hexahydrofuro[3,2-b]furan-3-ol TFA (3.2 ml, 41.5 mmol) was added to a stirred solution of tert-butyl 2-[4-[2-[[(3R,3aR,6R,6aS)-6-[tert-butyl(dimethyl)silyl]oxy-2,3,3a,5,6,6a-hexahydrofuro[3,2-b]furan-3-yl]oxy]-1-allyl-6-chloro-imidazo[4,5-b]pyridin-5-yl]phenyl]-4,6-dihydropyrrolo[3,4-c]pyrazole-5-carboxylate (477.4 mg, 0.649 mmol) in DCM (3.2 ml). The reaction mixture was a pale yellow solution that was stirred at room temperature for 3 days. The reaction mixture was evaporated under reduced pressure to give a light yellow oil. Flash chromatography of the oil utilizing a 40 g silica RediSep R$_f$® column and employing a 0-10% (10% NH$_4$OH/MeOH)/DCM gradient followed by 10% (10% NH$_4$OH/MeOH)/DCM afforded the title compound as an off-white solid following lyophilization from ethanol and benzene. LC-MS: calculated for C$_{26}$H$_{25}$ClN$_6$O$_4$ 520.16 observed m/e: 521.15 (M+H)$^+$ (Rt 1.00/2 min)

INTERMEDIATE 8

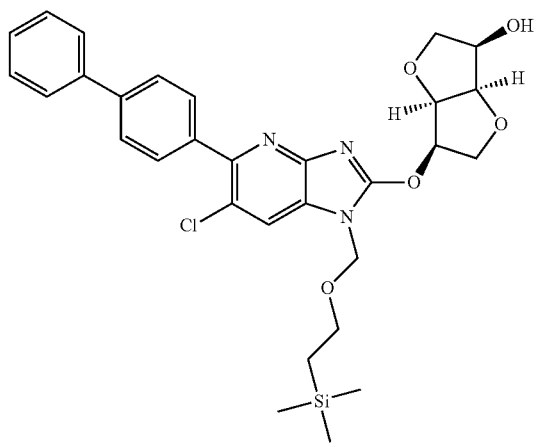 [SMILES: C[Si](C)(C)CCOCn1c(O[C@@H]2CO[C@H]3[C@@H]2OC[C@H]3O)nc2nc(-c3ccc(-c4ccccc4)cc3)c(Cl)cc21]

(3R,3aR,6R,6aR)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-ol LiOH (1.3 ml, 3.90 mmol) and 1,1'-bis(diphenylphosphino)ferrocene-palladium(II)dichloride dichloromethane complex (107.7 mg, 0.132 mmol) were added to a stirred solution of (3R,3aR,6R,6aR)-6-[5-(4-bromophenyl)-6-chloro-1-(2-trimethylsilylethoxymethyl)-imidazo[4,5-b]pyridin-2-yl]oxy-2,3,3a,5,6,6a-hexahydrofuro[3,2-b]furan-3-ol (776.2 mg, 1.332 mmol) and phenylboronic acid (201.9 mg, 1.656 mmol) in dioxane (10.5 ml) and water (1.3 ml). The reaction mixture was degassed (3×) and placed under nitrogen before being heated to 80° C. for 20 h. The reaction mixture was cooled to room temperature and partitioned between EtOAc (100 ml) and water (100 ml). The aqueous layer was extracted with EtOAc (2×50 ml). The organic layers were combined, washed with brine (1×30 ml), dried over MgSO$_4$, filtered, and evaporated under reduced pressure to give an amber residue. This material was purified by flash chromatography, utilizing a 40 g silica RediSep R$_f$® column and employing a 0-70% EtOAc/hexane gradient followed by 70% EtOAc/hexane. The product fractions were combined, evaporated under reduced pressure, and lyophilized from ethanol and benzene to give the title compound as a yellow solid. LC-MS: calculated for C$_{30}$H$_{34}$ClN$_3$O$_5$Si 579.2 observed m/e: 580.24 (M+H)$^+$ (Rt 1.36/2 min).

INTERMEDIATE 9

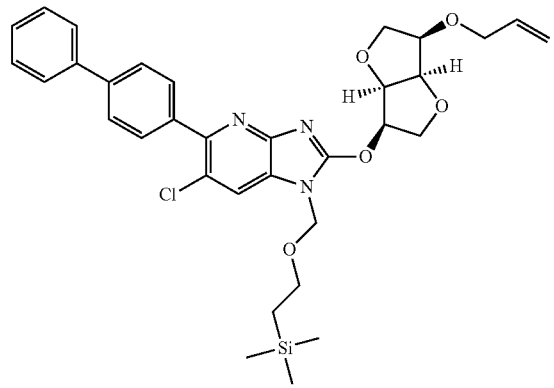 [SMILES: C=CCO[C@@H]1CO[C@H]2[C@@H]1OC[C@H]2Oc1nc2nc(-c3ccc(-c4ccccc4)cc3)c(Cl)cc2n1COCC[Si](C)(C)C]

2-[[2-[[(3R,3aR,6R,6aR)-3-allyloxy-2,3,3a,5,6,6a-hexahydrofuro[3,2-b]furan-6-yl]oxy]-6-chloro-5-(4-phenylphenyl)imidazo[4,5-b]pyridin-1-yl]methoxy]ethyl-trimethyl-silane Allyl iodide (130 µl, 1.422 mmol) and sodium hydride (16.0 mg, 0.400 mmol) were added to a stirred solution of (3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydro-furo[3,2-b]furan-3-ol (82.8 mg, 0.143 mmol) in DMF (1.4 ml). The reaction mixture was stirred at room temperature for 3 h. The reaction mixture was partitioned between EtOAc (75 ml), water (20 ml), and 2 N HCl (10 ml). The organic layer was washed with water (2×30 ml, brine was added to each wash to break an emulsion) and brine (1×20 ml), dried over MgSO$_4$, filtered, and evaporated under reduced pressure to give an amber residue. Flash chromatography of the residue utilizing a 4 g silica RediSep R$_f$® column and employing a 0-40% EtOAc/hexane gradient followed by 40% EtOAc/hexane afforded the title compound as a pale yellow solid. LC-MS: calculated for C$_{33}$H$_{38}$ClN$_3$O$_5$Si 619.23 observed m/e: 620.32 (M+H)$^+$ (Rt 1.43/2 min).

INTERMEDIATE 10

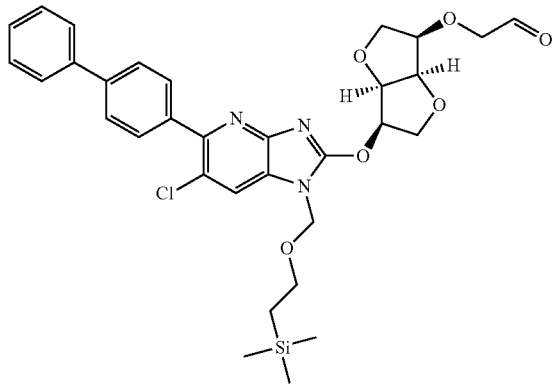 [SMILES: C[Si](C)(C)CCOCn1c(O[C@@H]2CO[C@H]3[C@@H]2OC[C@H]3OCC=O)nc2nc(-c3ccc(-c4ccccc4)cc3)c(Cl)cc21]

2-[[(3R,3aR,6R,6aR)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]oxy]acetaldehyde Sodium periodate (53.4 mg, 0.250 mmol) was added to a stirred suspension of 2-[[2-[[(3R,3aR,6R,6aR)-3-allyloxy-2,3,3a,5,6,6a-hexahydrofuro[3,2-b]furan-6-yl]oxy]-6-chloro-5-(4-phenylphenyl)imidazo[4,5-b]pyridin-1-yl]methoxy]ethyl-trimethyl-silane (68.9 mg, 0.111 mmol) and ruthenium (III) chloride hydrate (1.9 mg, 8.43 μmol) in acetonitrile (0.95 ml) and water (0.16 ml). The reaction mixture was stirred at room temperature for 4 h. Additional sodium periodate (31.8 mg, 0.149 mmol) was added and the reaction mixture was stirred for 2 h at room temperature, then in the refrigerator overnight. The reaction mixture was allowed to warm to room temperature before being partitioned between EtOAc (40 ml) and saturated aqueous sodium thiosulfate (30 ml). An inseparable emulsion formed, which was filtered through a pad of Celite™. The biphasic filtrate was re-partitioned and the aqueous layer was extracted with EtOAc (2×20 ml). The organic layers were combined, washed with brine (1×15 ml), dried over MgSO$_4$, filtered, and evaporated under reduced pressure to give a colorless residue. The residue was dissolved in EtOAc and loaded onto two 500 micron 20 cm×20 cm silica gel plates, which were developed using 10% MeOH/DCM. The silica containing the desired product band was collected and eluted with 10% MeOH/DCM (80 ml). The solvent was evaporated under reduced pressure and the resulting residue was lyophilized from ethanol and benzene to give the title compound as a white solid. LC-MS: calculated for C$_{32}$H$_{36}$ClN$_3$O$_6$Si 621.21 observed m/e: 622.31 (M+H)$^+$ (Rt 1.34/2 min)

INTERMEDIATE 11

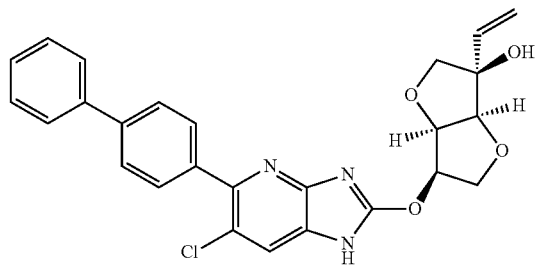 [SMILES: C=C[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-3-[[6-chloro-5-(4-phenylphenyl)-1H-imidazo[4,5-b]pyridin-2-yl]oxy]-6-vinyl-3,3a,5,6a-tetrahydro-2H-furo[3,2-b]furan-6-ol A stirred suspension of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (75.4 mg, 0.168 mmol) in THF (1.6 ml) was degassed (3×) and placed under nitrogen after being cooled to 0° C. in an ice bath. Vinylmagnesium bromide (1.6 ml, 1.600 mmol) was added to the reaction mixture slowly. The reaction mixture was stirred at 0° C. for 20 min, then at room temperature for 1.5 h. The reaction mixture was added via pipette to saturated aqueous NaHCO$_3$ (20 ml) before being partitioned between EtOAc (40 ml) and water (20 ml). The aqueous layer was extracted with EtOAc (2×20 ml). The organic layers were combined, washed with brine (1×20 ml), dried over MgSO$_4$, filtered, and evaporated under reduced pressure to give a yellow residue. This material was purified by preparative HPLC reverse phase (C-18), using a 30×150 mm Sunfire™ column and eluting with a 20%-100% acetonitrile/water+0.05% TFA gradient, followed by a 100% acetonitrile+0.05% TFA. The product fractions were combined, evaporated under reduced pressure, and lyophilized from ethanol and benzene to give the title compound as a white solid. LC-MS: calculated for C$_{26}$H$_{22}$ClN$_3$O$_4$ 475.13 observed m/e: 476.18 (M+H)$^+$ (Rt 1.21/2 min).

INTERMEDIATE 12

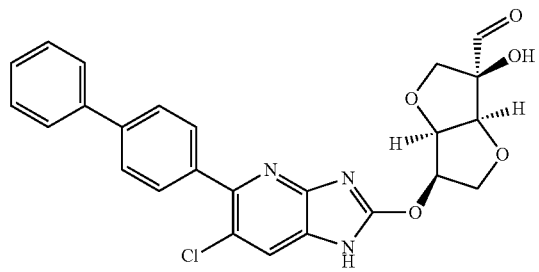 [SMILES: O=C[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-carbaldehyde Sodium periodate (21.9 mg, 0.102 mmol) was added to a stirred suspension of (3R,3aR,6R,6aS)-3-[[6-chloro-5-(4-phenylphenyl)-1H-imidazo[4,5-b]pyridin-2-yl]oxy]-6-vinyl-3,3a,5,6a-tetrahydro-2H-furo[3,2-b]furan-6-ol (23.4 mg, 0.049 mmol) and ruthenium(III) chloride hydrate (1.0 mg, 4.44 μmol) in acetonitrile (0.42 ml) and water (0.07 ml). The reaction mixture was stirred at room temperature for 4 h, then partitioned between EtOAc (20 ml) and saturated aqueous sodium thiosulfate (20 ml). The aqueous layer was extracted with EtOAc (2×20 ml). The organic layers were combined, washed with brine (1×10 ml), dried over MgSO$_4$, filtered, and evaporated under reduced pressure to give a colorless residue. The residue was dissolved in EtOAc/MeOH and loaded onto a 500 micron 20 cm×20 cm silica gel plate, which was developed twice using 5% MeOH/DCM. The silica containing the product band was collected and eluted with 10% MeOH/DCM (80 ml). The solvent was evaporated under reduced pressure to give the title compound as a colorless residue. LC-MS: calculated for C$_{25}$H$_{20}$ClN$_3$O$_5$ 477.11 observed m/e: 478.05 (M+H)$^+$ (Rt 1.15/2 min)

INTERMEDIATE 13

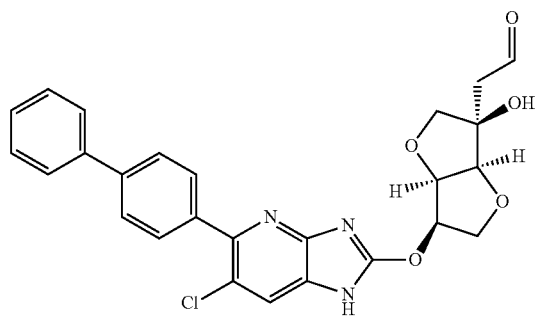 [SMILES: O=CC[C@@]1(O)CO[C@@H]2[C@H](Oc3nc4nc(-c5ccc(-c6ccccc6)cc5)c(Cl)cc4[nH]3)CO[C@@H]21]

2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetaldehyde Ruthenium(III) chloride hydrate (3.7 mg, 0.016 mmol) and sodium periodate (121.7 mg, 0.569 mmol) were added to a stirred solution of (3R,3aR,6R,6aS)-6-allyl-3-[[6-chloro-5-(4-phenylphenyl)-1H-imidazo[4,5-b]pyridin-2-yl]oxy]-3,3a,5,6a-tetrahydro-2H-furo[3,2-b]furan-6-ol (122.5 mg, 0.250 mmol) in acetonitrile (2.14 ml) and water (0.36 ml). The reaction mixture was stirred at room temperature for 3 h, then partitioned between EtOAc (75 ml) and saturated aqueous sodium thiosulfate (40 ml). The aqueous layer was extracted with EtOAc (2×50 ml). The organic layers were combined, washed with brine (1×30 ml), dried over MgSO$_4$, filtered, and evaporated under reduced pressure to give a colorless residue. This material was dissolved in EtOAc and loaded onto three 500 micron 20 cm×20 cm silica gel plates, which were developed using 10% MeOH/DCM. The silica containing the product band was collected and eluted with 10% MeOH/DCM (80 ml). The solvent was evaporated under reduced pressure and the resulting residue was lyophilized from ethanol and benzene to give the title compound as a white solid. LC-MS: calculated for C$_{26}$H$_{22}$ClN$_3$O$_5$ 491.12 observed m/e: 492.18 (M+H)$^+$ (Rt 1.18/2 min).

INTERMEDIATE 14

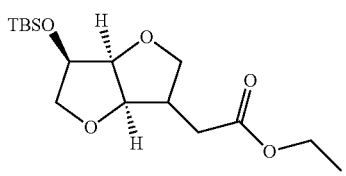 [SMILES: CCOC(=O)CC1CO[C@H]2[C@@H]1OC[C@H]2O[Si](C)(C)C(C)(C)C]

Ethyl 2-((3aR,6R,6aS)-6-((tert-butyldimethylsilyl)oxy)hexahydrofuro[3,2-b]furan-3-yl)acetate Et$_3$N (0.677 ml, 4.86 mmol) and tert-butyldimethylsilyl trifluoro-methanesulfonate (0.967 ml, 4.21 mmol) were added to a stirred, cooled (0° C.) mixture of ethyl 243aR,6R,6aR)-6-hydroxyhexahydrofuro[3,2-b]furan-3-yl)acetate (700 mg, 3.24 mmol) in DCM (5 ml), and the reaction was stirred at 0° C. to room temperature overnight. Water (50 mL) was added and the mixture was extracted with ethyl acetate (2×100 mL). The combined organic fractions were washed with aqueous sodium hydrogen carbonate (saturated, 50 mL), dried (Na$_2$SO$_4$), filtered and the solvent was evaporated under reduced pressure. The residue was purified by column chromatography on silica gel Biotage™ 40S, eluting with 0-15% EtOAc/hexane to give the title compound. $^1$H NMR δ (ppm) (CDCl$_3$): 4.56 (t, 1H), 4.45 (t, 1H), 4.34 (m, 1H), 4.18 (dd, 2H), 4.12 (t, 1H), 4.38 (dd, 1H), 3.56-3.51 (m, 2H), 2.69 (dd, 1H), 2.61 (m, 1H), 2.45 (dd, 1H), 1.28 (t, 3H), 0.93 (s, 9H), 0.13 (d, 6H).

INTERMEDIATE 15

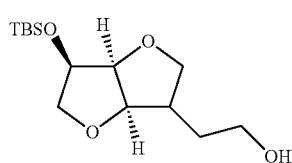 [SMILES: CC(C)(C)[Si](C)(C)O[C@@H]1CO[C@@H]2C(CCO)CO[C@@H]21]

2-((3aR,6R,6aS)-6-((tert-butyldimethylsilyl)oxy)hexahydrofuro[3,2-b]furan-3-yl)ethanol LiAlH$_4$ (1.077 ml, 1.077 mmol) was added to a stirred, cooled (0° C.) mixture of ethyl 2-((3aR,6R,6aS)-6-((tert-butyldimethylsilyl)oxy)hexahydrofuro[3,2-b]furan-3-yl)acetate (178 mg, 0.539 mmol) in THF (5 ml) and the mixture was stirred at room temperature for 2 h. The reaction mixture was quenched with 1N NaOH (1 mL), stirred for 10 minutes, filtered through Celite™ and washed with EtOAc (50 mL). The solution was washed with brine (20 mL), dried (Na$_2$SO$_4$) and concentrated to dryness to give title compound. LC-MS: calculated for C14H28O4Si 288.18 observed m/e: 289.21 (M+H)$^+$ (Rt 1.16/2 min)

INTERMEDIATE 16

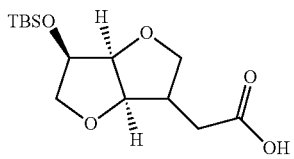 [SMILES: CC(C)(C)[Si](C)(C)O[C@@H]1CO[C@@H]2C(CC(=O)O)CO[C@@H]21]

2-((3aR,6R,6aS)-6-((tert-butyldimethylsilyl)oxy)hexahydrofuro[3,2-b]furan-3-yl)acetic acid LiOH (0.652 g, 27.2 mmol) was added to a stirred mixture of ethyl 243aR,6R,6aS)-6-((tert-butyldimethylsilyl)oxy)hexahydrofuro[3,2-b]furan-3-yl)acetate (1.5 g, 4.54 mmol) in THF (5 ml)/water (5 ml), and the mixture was stirred at room temperature overnight. Aqueous hydrochloric acid (1M, 80 mL) was added and the mixture was extracted with ethyl acetate (3×100 mL). The combined organic fractions were washed with brine (saturated, 50 mL), dried (Na$_2$SO$_4$), filtered and the solvent was evaporated under reduced pressure. The resulting residue was purified by column chromatography on silica gel Biotage™ 40S, eluting with 0-65% EtOAc/hexane to give title compound. LC-MS: calculated for C14H26O5Si 302.15 observed m/e: 325.17 (M+Na)$^+$ (Rt 1.16/2 min)

INTERMEDIATE 17

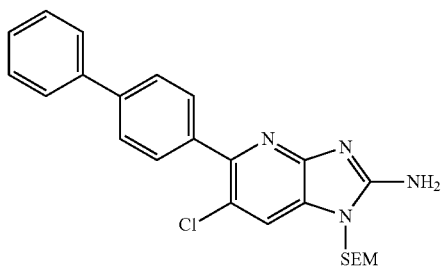 [SMILES: C[Si](C)(C)CCOCn1c(N)nc2nc(-c3ccc(-c4ccccc4)cc3)c(Cl)cc21]

5-([1,1'-biphenyl]-4-yl)-6-chloro-1-((2-(trimethylsilyl)ethoxy)methyl)-1H-imidazo[4,5-b]pyridin-2-amine DBU (0.204 ml, 1.354 mmol) was added to a stirred mixture of 5-([1,1'-biphenyl]-4-yl)-6-chloro-2-(methylsulfonyl)-

1-((2-(trimethylsilyl)ethoxy)methyl)-1H-imidazo[4,5-b]pyridine (232 mg, 0.451 mmol) and ammonium acetate (348 mg, 4.51 mmol) in DMF (2 ml), and the mixture was stirred at room temperature overnight. Water (30 mL) was added and the mixture was extracted with ethyl acetate (2×30 mL). The combined organic fractions were washed with brine (saturated, 20 mL), dried (Na$_2$SO$_4$), filtered and the solvent was evaporated under reduced pressure. The resulting residue was purified by preparative HPLC Reverse phase (C-18), eluting with acetonitrile/water+0.1% TFA. The combined fractions was concentrated, dissolved in MeOH, neutralized with NH$_4$OH, concentrated, redissolved in MeOH, filtered through silica gel pad, washed with DCM:MeOH:NH$_4$OH (10:1:0.1) and dried to give title compound. LC-MS: calculated for C24H$_{27}$ClN4OSi 450.16 observed m/e: 451.13 (M+H)$^+$ (Rt 1.25/2 min).

INTERMEDIATE 18

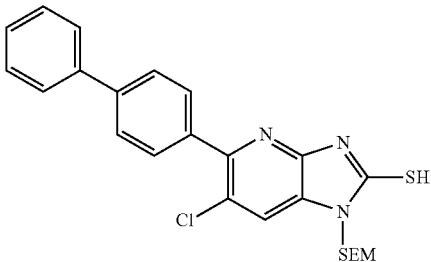 [SMILES: C[Si](C)(C)CCOCn1c(S)nc2nc(-c3ccc(-c4ccccc4)cc3)c(Cl)cc21]

5-([1,1'-biphenyl]-4-yl)-6-chloro-1-((2-(trimethylsilyl)ethoxy)methyl)-1H-imidazo[4,5-b]pyridine-2-thiol Sodium sulfide (65.6 mg, 0.840 mmol) was added to a stirred mixture of 5-([1,1'-biphenyl]-4-yl)-6-chloro-2-(methylsulfonyl)-1-((2-(trimethylsilyl)ethoxy)-methyl)-1H-imidazo[4,5-b]pyridine (144 mg, 0.280 mmol) in DMF (2 ml) and the mixture was stirred at room temperature for 3 h. Water (30 mL) was added and the mixture was extracted with ethyl acetate (3×30 mL). The combined organic fractions were washed with brine (saturated, 30 mL), dried (Na$_2$SO$_4$), filtered and the solvent was evaporated under reduced pressure. The resulting residue was purified by column chromatography on silica gel Biotage™ 25S, eluting with 0-30% EtOAc/hexane to give title compound. LC-MS: calculated for C24H26ClN3OSSi 467.13 observed m/e: 468.12 (M+H)$^+$ (Rt 1.38/2 min).

INTERMEDIATE 19

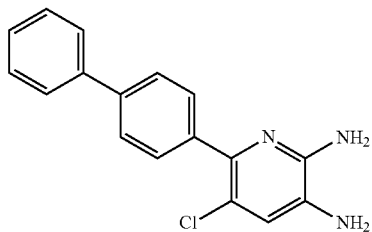 [SMILES: Nc1cc(Cl)c(-c2ccc(-c3ccccc3)cc2)nc1N]

6-([1,1'-biphenyl]-4-yl)-5-chloropyridine-2,3-diamine

Step A: 6-([1,1'-biphenyl]-4-yl)-5-chloro-2-nitropyridin-3-amine

LiOH (5.73 ml, 17.19 mmol) was added to a stirred mixture of 4-biphenylboronic acid (1.498 g, 7.57 mmol), 5-chloro-6-iodo-2-nitropyridin-3-amine (2.0595 g, 6.88 mmol) and 1,1'-bis(diphenylphosphino)ferrocene-palladium(II)dichloride dichloromethane complex (0.562 g, 0.688 mmol) in dioxane (15 ml)/water (4 ml) and the mixture was stirred under N$_2$ at 80° C. for 2 h. The mixture was cooled, then aqueous ammonium chloride (saturated, 100 mL) was added and the mixture was extracted with ethyl acetate (2×100 mL). The combined organic fractions were washed with brine (saturated, 80 mL), dried (Na$_2$SO$_4$), filtered and the solvent was evaporated under reduced pressure. The resulting residue was purified by column chromatography on silica gel Biotage™40M, eluting with 0-20% EtOAc/hexane to give the title compound. LC-MS: calculated for C17H12ClN3O2 325.06 observed m/e: 326.09 (M+H)$^+$ (Rt 1.28/2 min).

Step B: 6-([1,1'-biphenyl]-4-yl)-5-chloropyridine-2, 3-diamine

Ammonium chloride (632 mg, 11.82 mmol) and iron (1320 mg, 23.64 mmol) were added to a stirred mixture of 6-([1,1'-biphenyl]-4-yl)-5-chloro-3-nitropyridin-2-amine (550 mg, 1.688 mmol) in water (2 ml)/Ethanol (2 mL) and the mixture was stirred at 60° C. for 3 h. The mixture was filtered through Celite™, rinsing with ethyl acetate (100 mL). Water (80 mL) was added and the mixture was extracted with ethyl acetate (2×100 mL). The combined organic fractions were washed with brine (saturated, 80 mL), dried (Na$_2$SO$_4$), filtered and the solvent was evaporated under reduced pressure. The resulting residue was purified by column chromatography on silica gel Biotage™ 40S, eluting with 0-60% EtOAc/hexane to give title compound. LC-MS: calculated for C17H14ClN3 295.09 observed m/e: 296.12 (M+H)$^+$ (Rt 1.09/2 min).

INTERMEDIATE 20

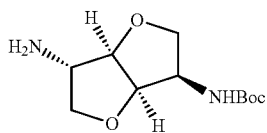

tert-butylN-[(3S,3aR,6R,6aR)-3-amino-2,3,3a,5,6, 6a-hexahydrofuro[3,2-b]furan-6-yl]carbamate Step A: (3R,3aS,6S,6aS)-hexahydrofuro[3,2-b]furan-3,6-diyl bis(4-methylbenzenesulfonate)

p-Toluenesulfonyl chloride (2722 g, 14.28 mol) was added to a solution of isosorbide (869 g, 5.95 mol) in pyridine (5000 mL) in portions with stirring at 0° C. After the reaction mixture was stirred at ambient temperature overnight, the mixture was poured into ice-water (5000 mL) with stirring, and extracted with DCM (4000 mL×3). The combined organic layers were washed successively with water (3000 mL×3), 1 N aqueous HCl (3000 mL×3, pH=6), and saturated aqueous NaHCO₃ (3000 mL×2), and dried over anhydrous Na₂SO₄. After removal of the solvent via vacuum, ethanol (1000 mL) was added. The resulting precipitate was filtered, and washed with ethanol to give the desired product as a white solid.

Step B: (3R,3aR,6S,6aR)-3,6-diazidohexahydrofuro[3,2-b]furan

A mixture of (3R,3aS,6S,6aS)-hexahydrofuro[3,2-b]furan-3,6-diylbis(4-methylbenzenesulfonate) (19.5 g, 42.90 mmol) and sodium azide (16.9 g, 0.26 mol) in DMF (150 mL) was heated at 130° C. overnight. The mixture was allowed to cool to room temperature, diluted with water (100 mL), and extracted with DCM (300 mL×3). The combined organic layers were dried over anhydrous Na₂SO₄, and evaporated via vacuum. The resulting residue was purified by column chromatography (petroleum ether:EtOAc=10:1) to give the desired compound as a yellow oil.

Step C: (3R,3aR,6S,6aR)-hexahydrofuro[3,2-b]furan-3,6-diamine

A mixture of (3R,3aR,6S,6aR)-3,6-diazidohexahydrofuro[3,2-b]furan (2.5 g, 12.74 mmol) and 5% palladium on active carbon (0.25 g) in methanol (300 mL) was hydrogenated under 40 psi in an autoclave overnight. The catalyst was removed by filtration and the solvent was evaporated to give the desired product, which was used in the next step without further purification.

Step D: tert-butylN-[(3S,3aR,6R,6aR)-3-amino-2,3,3a,5,6,6a-hexahydrofuro[3,2-b]furan-6-yl]carbamate A solution of Boc₂O (116.6 g, 0.54 mol) in DCM (500 mL) was added dropwise to a solution of (3R,3aR,6S,6aR)-hexahydrofuro[3,2-b]furan-3,6-diamine (115 g, 0.54 mol) and triethylamine (108 g, 1.07 mol) in DCM (1500 mL) with stirring at 0° C. After the addition, the reaction mixture was stirred at ambient temperature overnight. Water (2000 mL) was added into the reaction mixture, and the mixture was extracted with DCM (2000 mL×3). The combined organic layers were dried over anhydrous Na₂SO₄, and concentrated under reduced pressure. The residue was purified by column chromatography (DCM:MeOH=20:1) to give a light yellow solid, which was re-crystallized from EtOAc/hexane (1:3) to afford the title compound as a white solid.

INTERMEDIATE 21

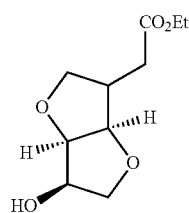 [SMILES: CCOC(=O)CC1CO[C@@H]2[C@H](O)CO[C@H]12]

Ethyl 2-[(3aR,6R,6aR)-6-hydroxy-2,3,3a,5,6,6a-hexahydrofuro[3,2-b]furan-3-yl]acetate

Step A: Ethyl(2E)-2-[(3R,3aS,6aR)-3-[tert-butyl(dimethyl)silyl]oxy-2,3,3a,6a-tetrahydrofuro[3,2-b]furan-6-ylidene]acetate A 20 mL sample vial was charged (3R,3aS,6aS)-3-[tert-butyl(dimethyl)silyl]oxy-2,3,3a,6a-tetrahydrofuro[3,2-b]furan-6-one (400 mg, 1.548 mmol), ethyl 2-(diethoxyphosphoryl)acetate (521 mg, 2.322 mmol) and THF (5 ml). The vial was flushed with nitrogen and cooled in an ice bath. To the mixture was then added slowly 60% sodium hydride (93 mg, 2.3 mmol) and the resulting reaction mixture was stirred at room temperature for 6 h. The reaction was partitioned between water (10 mL) and ethyl acetate (20 mL). The aqueous layer was extracted with ethyl acetate (3×10 mL). The combined organic phases were dried over MgSO₄, filtered and concentrated. The resulting residue was then purified by MPLC (40 g silica gel, 0 to 20% ethyl acetate in hexanes) to afford the desired product as a mixture of E/Z isomers. LC-MS: calculated for C16H28O5Si, [M+H]+Calc: 328.17. Found: 329.2, Rt=2.24 and 2.31 min (E and Z mix, 4 min run).

Step B: ethyl 2-[(3aR,6R,6aR)-6-hydroxy-2,3,3a,5,6,6a-hexahydrofuro[3,2-b]furan-3-yl]acetate A 20 mL vessel was charged ethyl(2E)-2-[(3R,3aS,6aR)-3-[tert-butyl(dimethyl)silyl]oxy-2,3,3a,6a-tetrahydrofuro[3,2-b]furan-6-ylidene]acetate (45 mg, 0.137 mmol), nickel chloride hexahydrate (32.6 mg, 0.137 mmol) and ethanol (1 mL). Sodium borohydride (51.8 mg, 1.37 mmol) was added slowly and the mixture was stirred at room temperature for 1 h. The reaction was quenched with water (0.5 mL) and partitioned between water (4 mL) and ethyl acetate (10 mL). The aqueous layer was extracted with ethyl acetate (3×5 mL). The combined organic phases were dried over MgSO₄, filtered and concentrated to afford the title compound. LC-MS: calculated for C10H16O5, [M+Na]+Calc: 239.1. Found: 239.1, Rt=0.22 min (4 min run).

INTERMEDIATE 22

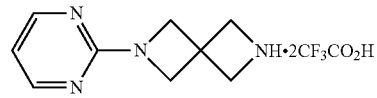

6-Pyrimidin-2-yl-6-azaspiro[3,3]heptane TFA salt

Step A: tert-butyl 2-pyrimidin-2-yl-2,6-diazaspiro[3.3]heptane-6-carboxylate A 2 L round-bottom flask was charged with tert-butyl 2,6-diazaspiro[3,3]heptane-6-carboxylate (64.3 g, 0.32 mol), cesium carbonate (317.0 g, 0.97 mol), 2-chloropyrimidine (45.5 g, 0.4 mol), and DMF (759.0 mL). The reaction mixture was heated to 100-105° C. for 20 min. The reaction mixture was cooled to ambient temperature, diluted with water (759.0 mL) and EtOAc (759.0 mL). The organic layer was washed with water (2×500.0 mL) and brine (500.0 mL). The organic layer was dried over sodium sulfate and filtered through Celite™. The filtrate was concentrated under reduced pressure. Column chromatography of the resulting crude product on silica gel, eluting with EtOAc and heptane (50-100%) afforded the desired product.

Step B: 6-pyrimidin-2-yl-6-azaspiro[3,3]heptane TFA salt

A 1 L round-bottom flask was charged with trifluoroacetic acid (153.0 mL) and the mixture cooled to 0-5° C. Tert-butyl 2-pyrimidin-2-yl-2,6-diazaspiro[3,3]heptane-6-carboxylate (51.0 g, 0.19 mol) was added and the reaction mixture was stirred at 0-5° C. until dissolution occurred. Then the reaction mixture warmed to 20-25° C. and stirred for 60 min. The reaction mixture was concentrated, azeotroped with DCM (2×50.0 mL), and diluted with DCM (150.0 mL). This solution was slowly added to a well-stirred solution of MTBE (600.0 mL). The resultant slurry was heated to 35-40° C. to give a free-flowing off-white solid. The slurry was cooled to <15° C. and filtered to afford the title compound. $^1$H NMR (300 MHz, CD$_3$OD) δ: 8.39 (d, J=5.03 Hz, 2H), 6.77 (t, J=5.03 Hz, 1H), 4.35 (s, 4H), 4.32 (s, 4H); $^{13}$C NMR (75 MHz, DMSO-d$_6$) δ: 162.5, 158.2, 111.2, 60.0, 55.3, 36.0; LC/MS: m/z=177 [M]$^+$.

INTERMEDIATE 23

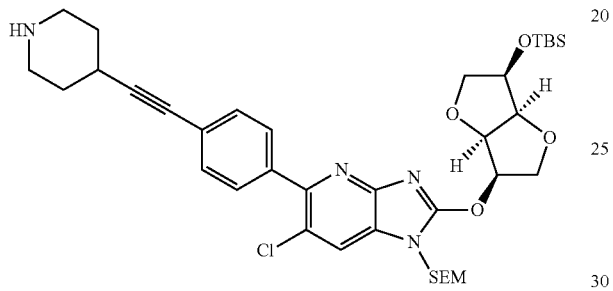

2-(((3R,3aR,6R,6aS)-6-((tert-butyldimethylsilyl)oxy) hexahydrofuro[3,2-b]furan-3-yl)oxy)-6-chloro-5-(4-(piperidin-4-ylethynyl)phenyl)-1-((2-(trimethylsilyl) ethoxy)-methyl)-1H-imidazo[4,5-b]pyridine Step A: tert-butyl 4-((4-(2-(((3R,3aR,6R,6aS)-6-((tert-butyldimethylsilyl)oxy)-hexahydrofuro[3,2-b] furan-3-yl)oxy)-6-chloro-1-((2-(trimethylsilyl) ethoxy)methyl)-1H-imidazo[4,5-b]pyridin-5-yl) phenyl)ethynyl)piperidine-1-carboxylate To a round bottom flask fitted with a reflux condenser under a nitrogen atmosphere was added 5-(4-bromophenyl)-2-(((3R,3aR,6R,6aS)-6-((tert-butyldimethylsilyl)oxy)hexahydrofuro[3,2-b]furan-3-yl)oxy)-6-chloro-1-((2-(trimethylsilyl)ethoxy)methyl)-1H-imidazo[4,5-b]pyridine (436 mg, 0.625 mmol), tert-butyl 4-ethynylpiperidine-1-carboxylate (157 mg, 0.750 mmol), CuI (9.5 mg, 0.049 mmol), and Pd(PPh$_3$)$_2$Cl$_2$ (70 mg, 0.100 mmol). Then triethylamine (4.0 mL) was added. The reaction mixture was cooled to −78°, evacuated and placed under an inert nitrogen atmosphere. Then the mixture was warmed to room temperature, and heated to 50° C. for 17 h. The mixture was allowed to cool to room temperature, and then filtered through Celite™ and rinsed with ethyl acetate until the filtrate was colorless. The filtrate was concentrated under reduced pressure. Flash silica gel chromatography of the resulting residue utilizing a Biotage™ 50 G SNAP cartridge and employing a linear gradient: 0-30% EtOAc in 1:1 Hexane/DCM over 20 column volumes afforded the desired product as a clear, colorless oil following concentration under reduced pressure. LC-MS: calculated for C$_{42}$H$_{61}$ClN$_4$O$_7$Si$_2$ 824.38, observed m/e: 825.60 (M+H)$^+$ (Rt 3.32/4 min)

Step B: 2-(((3R,3aR,6R,6aS)-6-((tert-butyldimethyl-silyl)oxy)hexahydrofuro[3,2-b]furan-3-yl)oxy)-6-chloro-5-(4-(piperidin-4-ylethynyl)phenyl)-1-((2-(trimethylsilyl)ethoxy)-methyl)-1H-imidazo[4,5-b] pyridine To a stirred solution of tert-butyl 4-((4-(2-(((3R,3aR,6R, 6aS)-6-((tert-butyldimethylsilyl)oxy)hexahydrofuro[3,2-b] furan-3-yl)oxy)-6-chloro-1-((2-(trimethylsilyl)ethoxy)methyl)-1H-imidazo[4,5-b]pyridin-5-yl)phenyl)ethynyl) piperidine-1-carboxylate (147 mg, 0.178 mmol) in anhydrous DCM (2.0 mL) at room temperature was added trifluoroacetic acid (0.2 mL). The reaction was stirred for 2 h at room temperature, and then poured into saturated aqueous sodium bicarbonate (40 mL). The aqueous layer was extracted with ethyl acetate (2×50 mL). The combined organic layers were dried over sodium sulfate, and then concentrated under reduced pressure to afford the title compound as a colorless oil. LC-MS: calculated for C$_{37}$H$_{53}$ClN$_4$O$_5$Si$_2$ 724.32 observed m/e: 725.32 (M+H)$^+$ (Rt 2.56/4 min).

INTERMEDIATE 24

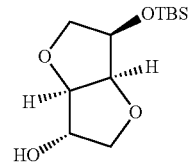 [SMILES: CC(C)(C)[Si](C)(C)O[C@@H]1CO[C@H]2[C@@H]1OC[C@@H]2O]

(3S,3aR,6R,6aS)-6-((tert-butyldimethylsilyl)oxy) hexahydrofuro[3,2-b]furan-3-ol

To a stirred solution of triphenylphosphine (542 mg, 2.066 mmol), benzoic acid (252 mg, 2.066 mmol), and (3R,3aR,6R, 6aS)-6-((tert-butyldimethylsilyl)oxy)hexahydrofuro[3,2-b] furan-3-ol (538 mg, 2.066 mmol) in anhydrous THF (8.0 mL) under nitrogen at room temperature was added DIAD (0.40 mL, 418 mg, 2.066 mmol), dropwise, over 10 min. After stirring for 16 h at room temperature, the mixture was concentrated under reduced pressure. The resultant residue was chromatographed using a Biotage™ 50 g (2×25 g in series) silica gel cartridge eluting with 0-50% EtOAc in 1:1 Hexane/ DCM over 20 column volumes. The fractions containing desired product were combined and concentrated under reduced pressure. The resultant colorless oil was dissolved in MeOH (10 mL), and 5N aqueous NaOH (2.0 mL, 10.0 mmol) was added. After stirring for 20 h at room temperature, the mixture was poured into saturated aqueous sodium bicarbonate (100 mL) and extracted with ethyl acetate (2×100 mL). The combined organic layers were dried over sodium sulfate, and then concentrated under reduced pressure to afford the title compound as a white solid. LC-MS: calculated for C$_{12}$H$_{24}$O$_4$Si 260.14, observed m/e: 261.17 (M+H)$^+$ (Rt 0.42/4 min) $^1$H NMR (500 MHz, CDCl$_3$): δ 4.49 (t, J=4.5 Hz, 1H), 4.34 (d, J=4.3 Hz, 1H), 4.25 (m, 2H), 3.92 (dd, J=10.0, 3.5 Hz, 1H), 3.84 (d, J=10.0 Hz, 1H), 3.73 (dd, J=8.5, 6.0 Hz, 1H), 3.50 (t, J=8.0 Hz, 1H), 2.84 (s, 1H), 0.88 (s, 9H), 0.09 (s, 3H), 0.08 (s, 3H).

INTERMEDIATE 25

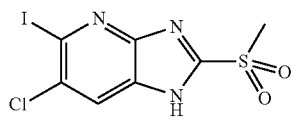

6-chloro-5-iodo-2-(methylsulfonyl)-1H-imidazo[4,5-b]pyridine

Step A 5,6-dichloro-3-nitropyridin-2-amine

To a solution of 5-chloro-3-nitropyridin-2-amine (16 g, 92 mmol) in AcOH (70 mL) was added N-chlorosuccinimide (14.8 g 111 mmol). The mixture was stirred overnight at 80° C. for 3 h, cooled to rt, diluted with MeOH (30 mL) and filtered. The solid residue was washed with AcOH, water, and then dried to afford the desired product as a white solid, which was used in the next step without further purification. LC-MS: calculated for $C_5H_3Cl_2N_3O_2$ 208.0, observed m/e: 208.07 (M+H)$^+$ (Rt 1.48/5 min)

Step B 5-chloro-6-iodo-3-nitropyridin-2-amine

To a solution of 5,6-dichloro-3-nitropyridin-2-amine (15 g, 72.1 mmol) in AcOH (70 mL) was added sodium iodide (43.2 g 149.9 mmol). The mixture was stirred at 90° C. for 2 h, cooled to rt, diluted with water (70 mL) and filtered. The solid residue was washed with water, and then dried under vacuum to afford the desired product as a pale yellow solid, which was used in the next step without further purification. LC-MS: calculated for $C_5H_3ClIN_3O_2$ 299.45, observed m/e: 299.94 (M+H)$^+$ (Rt 2.18/5 min).

Step C 5-chloro-6-iodopyridine-2,3-diamine

To a suspension of 5-chloro-6-iodo-3-nitropyridin-2-amine (18.9 g, 63.1 mmol) in EtOH (100 mL) was added tin (II) chloride dihydrate (57 g, 252 mmol). The mixture was heated at 70° C. for 0.5 h. The rxn was warmed to rt and treated with a slurry of 150 mL water and 60 g KF and stirred for 0.5 h. The mixture was then partitioned between ethyl acetate (300 mL) and water (300 mL). The ethyl acetate layer was washed with brine, dried over magnesium sulfate and filtered through a 100 g pad of silica gel. The filtrate was concentrated and dried under vacuum to give an off-white solid, which was used in next step without further purification. LC-MS: calculated for $C_5H_5ClIN_3$ 269.47, observed m/e: 269.99 (M+H)$^+$ (Rt 1.35/5 min)

Step D 6-chloro-5-iodo-1,3-dihydro-2H-imidazo[4,5-b]pyridine-2-thione

DMAP (15.4 g, 126 mmol) was added to a THF (200 mL) solution of 5-chloro-6-iodopyridine-2,3-diamine (17 g, 63.1 mmol). Thiophosgene (4.9 mL, 63.1 mmol) was then added drop-wise via addition funnel under nitrogen and allowed to stir at rt for 1 h. The mixture was then partitioned between ethyl acetate (500 mL) and 2N HCl (100 mL). The ethyl acetate layer was washed with brine, dried over magnesium sulfate and concentrated to give the desired product as a white powder, which was used in the next step without further purification. LC-MS: calculated for $C_6H_3ClIN_3S$ 311.5, observed m/e: 311.91 (M+H)$^+$ (Rt 1.69/5 min)

Step E 6-chloro-5-iodo-2-(methylsulfanyl)-1H-imidazo[4,5-b]pyridine

A suspension of 6-chloro-5-iodo-1,3-dihydro-2H-imidazo[4,5-b]pyridine-2-thione (11.0 g, 35.3 mmol) and KOH (2.38 g, 42.4 mmol) in ethanol (200 mL) was stirred at rt for 0.5 h. Iodomethane (2.2 mL, 35.3 mmol) was then added and the reaction was allowed to stir for 1 h at rt. The ethanol was removed in vacuo and the resulting residue was partitioned between ethyl acetate (250 mL) and 2N HCl (50 mL). The ethyl acetate layer was washed with brine, dried over magnesium sulfate, filtered through a 100 g pad of silica gel and concentrated to give the desired product as a white solid. LC-MS: calculated for $C_7H_5ClIN_3S$ 325.56, observed m/e: 325.88 (M+H)$^+$ (Rt 2.05/5 min).

Step F 6-chloro-5-iodo-2-(methylsulfonyl)-1H-imidazo[4,5-b]pyridine

Oxone (20.8 g, 33.8 mmol) was added to an acetonitrile (100 mL)/water (100 mL) suspension of 6-chloro-5-iodo-2-(methylsulfanyl)-1H-imidazo[4,5-b]pyridine (5.0 g, 15.4 mmol) and the reaction was allowed to stir for 18 h at rt. The suspension was filtered through a sintered glass funnel and the filtrate was partitioned between ethyl acetate and saturated sodium bisulfate. The ethyl acetate layer was washed with brine, dried over magnesium sulfate and concentrated to afford the title compound as a white solid that was used in subsequent steps without further purification. LC-MS: calculated for $C_7H_5ClIN_3O_2S$ 357.56, observed m/e: 357.07 (M+H)$^+$ (Rt 1.36/4 min) 1H NMR δ (ppm)(DMSO-d$_6$): 8.44 (1H, s), 3.53 (3H, s).

INTERMEDIATE 26

6-chloro-5-iodo-2-(methylsulfonyl)-1-{[2-(trimethylsilyl)ethoxy]methyl}-imidazo[4,5-b]pyridine SEM-C$_1$ (2.48 mL, 14 mmol) was added to a THF (100 mL) solution of Intermediate 25 (5.0 g, 14 mmol) and triethylamine (2.92 mL, 21 mmol) at 0° C. under nitrogen atmosphere. The reaction was warmed to rt over 30 min. The reaction was partitioned between ethyl acetate and saturated aqueous ammonium chloride. The organic layer was washed with water, brine, dried over magnesium sulfate and concentrated. Flash chromatography of the resulting residue utilizing a Biotage™ 100 G SNAP cartridge and employing a linear gradient: 0-20% EtOAc/hexane and then 20-100% EtOAc/hexane; afforded the title compound as a clear oil. LC-MS: calculated for $C_{13}H_{19}ClN_3O_3SSi$ 487.8, observed m/e: 428.9 (M+H)$^+$ (Rt 2.54/4 min).

INTERMEDIATE 27

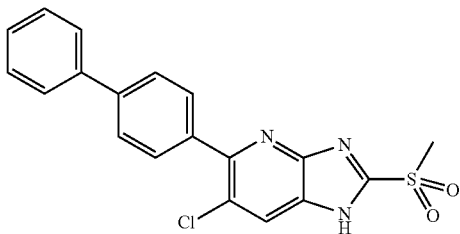 [SMILES: CS(=O)(=O)c1nc2nc(-c3ccc(-c4ccccc4)cc3)c(Cl)cc2[nH]1]

5-(biphenyl-4-yl)-6-chloro-2-(methylsulfonyl)-1H-imidazo[4,5-b]pyridine

Intermediate 25 (50 g, 140 mmol), 4-Biphenylboronic acid (33.2 g, 168 mmol) and tripotassium phosphate (89 g, 212.3 mmol) were dissolved in THF (500 mL) and water (50 mL), then sparged with $N_2$ for 20 min. A solution of palladium acetate (3.14 g, 14.0 mmol) and n-butyldiadamantylphosphine (Catacxium A, 10 g, 28 mmol) in THF (30 mL) was sparged with $N_2$ for 20 minutes, and then added to the mixture of Intermediate 25, biphenylboronic acid and base. The reaction was heated to 45° C. for 18 h. An additional aliquot of palladium acetate (3.14 g, 14.0 mmol) and n-butyldiadamantylphosphine (Catacxium A, 10 g, 28 mmol) in THF (30 mL) was sparged with $N_2$ for 20 minutes and added to the reaction mixture. After 24 h at 45° C., the reaction was cooled to rt and diluted with EtOAc and brine. The organic layer was concentrated and triturated with THF/MTBE to provide the title compound as a tan solid. LC-MS: calculated for $C_{19}H_{14}ClN_3O_2S$ 383.05; observed m/e: 383.9 (M+H)$^+$ (Rt 2.01/4 min).

INTERMEDIATE 28

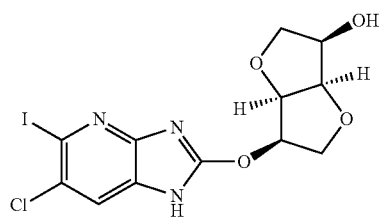 [SMILES: O[C@@H]1CO[C@H]2[C@@H]1OC[C@H]2Oc1nc2nc(I)c(Cl)cc2[nH]1]

(3R,3aR,6R,6aR)-6-[(6-chloro-5-iodo-1H-imidazo[4,5-b]pyridin-2-yl)oxy]-2,3,3a,5,6,6a-hexahydrofuro[3,2-b]furan-3-ol Trifluoroacetic acid (70.0 ml, 909 mmol) was added to a stirred solution of (3R,3aR,6R,6aR)-6-[6-chloro-5-iodo-1-(2-trimethylsilylethoxymethyl)imidazo[4,5-b]pyridin-2-yl]oxy-2,3,3a,5,6,6a-hexahydrofuro[3,2-b]furan-3-ol (14.99 g, 27.1 mmol) in dichloromethane (70 ml). The reaction mixture was an amber solution that was stirred at room temperature. After 3 hours, the reaction mixture was concentrated under reduced pressure to give an amber oil. Methanol (50 ml) was added and the resulting solution was stirred at room temperature. After about 5 minutes, the product crystallized and precipitated to give a white suspension. Dichloromethane (50 ml) was added to the reaction mixture. The crystalline product was collected from the reaction mixture by vacuum filtration and was dried overnight under vacuum to give the title compound as a crystalline white solid. LC-MS: calculated for $C_{12}H_{11}ClIN_3O_4$ 422.95 observed m/e: 424.0 (M+H)$^+$ (Rt 0.92/2 min).

INTERMEDIATE 29

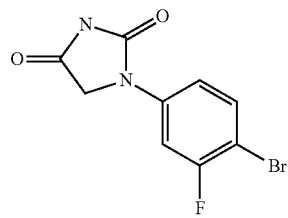 [SMILES: O=C1CN(c2ccc(Br)c(F)c2)C(=O)N1]

1-(4-bromo-3-fluoro-phenyl)imidazolidine-2,4-dione

Step A: ethyl 2-(4-bromo-3-fluoro-anilino)acetate

A stirred solution of 4-bromo-3-fluoro-aniline (120 g, 0.63 mol) and diisopropylethylamine (162 g, 1.26 mol) in acetonitrile (1.0 L) was heated to 60° C. and ethyl bromoacetate (105 g, 0.63 mol) was added dropwise within 2 h. The reaction mixture was stirred at this temperature for 12 h and was then evaporated to dryness. Water was added to the residue and the solid was filtered. Crystallization from petroleum ether and ethyl acetate (5:1) provided the desired product as a white solid.

Step B: 1-(4-bromo-3-fluoro-phenyl)imidazolidine-2,4-dione

To a solution of ethyl 2-(4-bromo-3-fluoro-anilino)acetate (86 g, 0.31 mol) in acetic acid (1.5 L) and water (100 mL) was added a solution of potassium cyanate (50 g, 0.6 mol) in water (200 mL). The reaction mixture was stirred at room temperature for 12 h and then evaporated to dryness. Then 1.5 L of 25% HCl was added to the residue and the mixture was heated to reflux for 3 h. After cooling to room temperature, the solid was filtered and dried to give the title compound. LC-MS: calculated for $C_9H_6BrFN_2O_2$ 271.96 observed m/e: 273.35 (M+H)$^+$ (Rt 3.44/6.5 min).

INTERMEDIATE 30

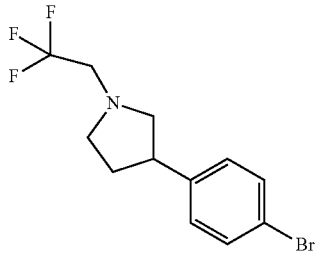 [SMILES: FC(F)(F)CN1CCC(c2ccc(Br)cc2)C1]

3-(4-bromophenyl)-1-(2,2,2-trifluoroethyl)pyrrolidine

Diisopropylethylamine (0.26 ml, 1.489 mmol) and 2,2,2-trifluoroethyl trifluoromethanesulfonate (0.13 ml, 0.902 mmol) were added to a stirred solution of 3-(4-bromophenyl)pyrrolidine 2,2,2-trifluoroacetate (254.5 mg, 0.748 mmol) in dioxane (3.0 ml). The reaction mixture was heated to 80° C. After 17 hours, the reaction mixture was cooled to room temperature and evaporated under reduced pressure to give a yellow residue. The residue was dissolved in dichloromethane and loaded onto a 5 g silica solid load cartridge. The residue was purified using an ISCO R$_f$ and a 12 g silica column (CV=16.8 ml). The column was eluted as follows: 100% dichloromethane (3 CV), 0-3% MeOH/dichloromethane gradient (17 CV), 3% MeOH/dichloromethane (10 CV), 3-5% MeOH/dichloromethane gradient (15 CV), 5% MeOH/dichloromethane (5 CV) at 30 ml/min. The product fractions were combined and evaporated under reduced pressure to give the title compound as a yellow oil. LC-MS: calculated for $C_{12}H_{13}BrF_3N$ 307.02, 309.02 observed m/e: 308.05, 310.05 (M+H)$^+$ (Rt 1.02/2 min).

INTERMEDIATE 31

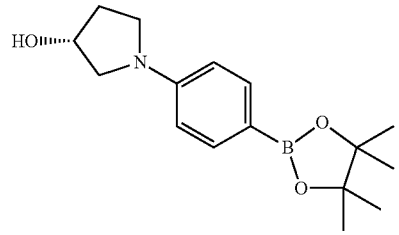 [SMILES: CC1(C)OB(c2ccc(N3CC[C@@H](O)C3)cc2)OC1(C)C]

(3R)-1-[4-(4,4,5,5-tetramethyl-1,3,2-dioxaborolan-2-yl)phenyl]pyrrolidin-3-ol

Palladium(II) acetate (31.1 mg, 0.139 mmol) was added to a stirred suspension of (3R)-1-(4-bromophenyl)pyrrolidin-3-ol (211.5 mg, 1.070 mmol), bis(pinacolato)diboron (438.1 mg, 1.725 mmol), potassium acetate (326.8 mg, 3.33 mmol), and dicyclohexyl(2',4',6'-triisopropyl-[1,1'-biphenyl]-2-yl)phosphine (113.1 mg, 0.237 mmol) in dioxane (10.5 ml). The reaction mixture was degassed (3×) and placed under nitrogen before being heated to 100° C. After 4 hours the reaction mixture was allowed to cool to room temperature. The reaction mixture was partitioned between EtOAc (75 ml) and water (50 ml). The aqueous layer was extracted with EtOAc (2×50 ml). The organic layers were combined, washed with brine (1×30 ml), dried over MgSO$_4$, filtered, and evaporated under reduced pressure to give a dark residue. This material was dissolved in DCM and loaded onto a 5 g silica solid load cartridge. The residue was purified using an ISCO R$_f$ and a 24 g silica gold column (CV=35.9 ml). The column was eluted as follows: 100% Hex (1 CV), 0-40% EtOAc/Hex gradient (20 CV), 40% EtOAc/Hex (5 CV) at 35 ml/min. The product fractions were combined and evaporated under reduced pressure to give the title compound as a white residue. LC-MS: calculated for $C_{16}H_{24}BNO_3$ 289.18 observed m/e: 290.22 (M+H)$^+$ (Rt 1.15/2 min).

TABLE 18

Intermediates prepared according to the methods in intermediate 31. Minor variations in conditions are noted.

| Intermediate Number | Structure | HPLC-mass spectrum m/e | Notes | Conditions |
|---|---|---|---|---|
| 32 | 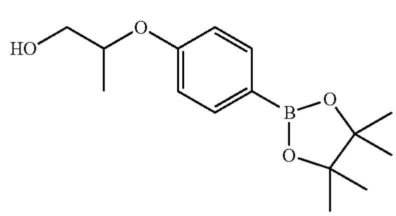 [SMILES: CC(CO)Oc1ccc(B2OC(C)(C)C(C)(C)O2)cc1] | 279.32 | Derived from faster eluting isomer off of chiral AS—H column.* | (Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst) 110° C. Cyclopentylmethyl ether |

TABLE 18-continued

Intermediates prepared according to the methods in intermediate 31. Minor variations in conditions are noted.

| Intermediate Number | Structure | HPLC-mass spectrum m/e | Notes | Conditions |
|---|---|---|---|---|
| 33 | (structure) | 279.16 | Derived from slower eluting isomer off of chiral AS—H column.* | (Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst) |
| 34 | (structure) | 265.21 | | (Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalyst) |
| 35 | (structure) | 287.22 | | (Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalsyt) 80° C. |
| 36 | (structure) | 321.27 | | (Chloro(2-dicyclohexylphosphino-2',4',6'-triisopropyl-1,1'-biphenyl)[2-(2'-amino-1,1'-biphenyl)]palladium(II), X-Phos aminobiphenyl palladium chloride precatalsyt) |
| 37 | (structure) | 356.19 | | |

*The chiral separation was performed on the bromo-phenyl starting material.

INTERMEDIATE 38

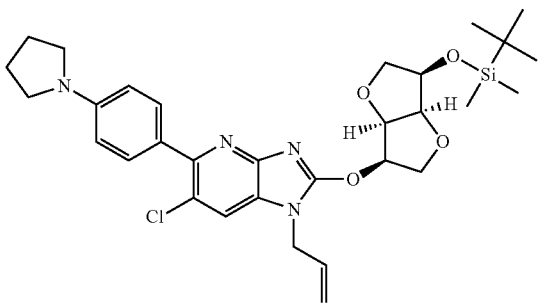 [SMILES: C=CCn1c(O[C@@H]2CO[C@H]3[C@@H]2OC[C@H]3O[Si](C)(C)C(C)(C)C)nc2nc(-c3ccc(N4CCCC4)cc3)c(Cl)cc21]

[(3R,3aR,6R,6aS)-3-[1-allyl-6-chloro-5-(4-pyrrolidin-1-ylphenyl)imidazo[4,5-b]pyridin-2-yl]oxy-2,3,3a,5,6,6a-hexahydrofuro[3,2-b]furan-6-yl]oxy-tert-butyl-dimethyl-silane 1,1'-bis(diphenylphosphino)ferrocene-palladium(II) dichloride dichlormethane complex (17.1 mg, 0.021 mmol) was added to a stirred suspension of [(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethyl-silane (99.8 mg, 0.173 mmol), 1-(4-(4,4,5,5-tetramethyl-1,3,2-dioxaborolan-2-yl)phenyl)pyrrolidine (59.6 mg, 0.218 mmol), and tripotassium phosphate (225.0 mg, 1.060 mmol) in dioxane (1.38 ml) and water (0.35 ml). The reaction mixture was degassed (3×) and placed under nitrogen before being heated to 80° C. After 15 hours, the reaction mixture was cooled to room temperature. The reaction mixture was partitioned between EtOAc (40 ml) and water (40 ml). The aqueous layer was extracted with EtOAc (2×20 ml). The organic layers were combined, washed with brine, dried over $MgSO_4$, filtered, and evaporated under reduced pressure to give an amber residue. This residue was dissolved in DCM, loaded onto a 5 g silica solid load cartridge and purified using an ISCO $R_f$ and a 4 g silica column (CV=4.8 ml). The column was eluted as follows: 100% hexane (5 CV), 0-30% EtOAc/hexane gradient (70 CV), 30% EtOAc/hexane (21 CV) at 18 ml/min. The product fractions were combined and evaporated under reduced pressure to give the title compound as a yellow residue. LC-MS: calculated for $C_{31}H_{41}ClN4O_4Si$ 596.26 observed m/e: 597.39 $(M+H)^+$ (Rt 1.34/2 min).

TABLE 19

| | Intermediates prepared according to the methods in intermediate 38. | |
|---|---|---|
| Intermediate Number | Structure | HPLC-mass spectrum m/e |
| 39 | 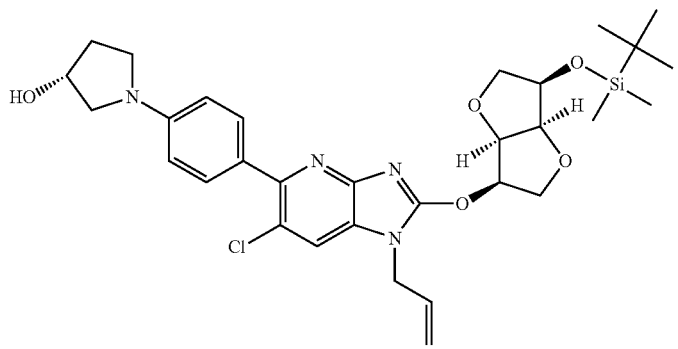 [SMILES: C=CCn1c(O[C@@H]2CO[C@H]3[C@@H]2OC[C@H]3O[Si](C)(C)C(C)(C)C)nc2nc(-c3ccc(N4CC[C@@H](O)C4)cc3)c(Cl)cc21] | 613.50 |

109
INTERMEDIATE 40

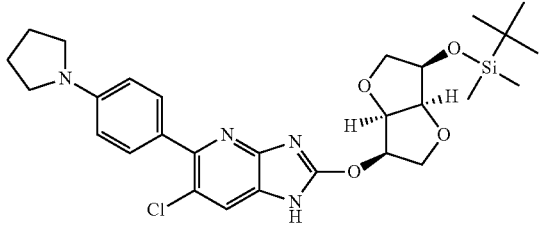 [SMILES: CC(C)(C)[Si](C)(C)O[C@@H]1CO[C@H]2[C@@H]1OC[C@H]2Oc1nc2nc(-c3ccc(N4CCCC4)cc3)c(Cl)cc2[nH]1]

[(3R,3aR,6R,6aS)-3-[[6-chloro-5-(4-pyrrolidin-1-ylphenyl)-1H-imidazo[4,5-b]pyridin-2-yl]oxy]-2,3,3a,5,6,6a-hexahydrofuro[3,2-b]furan-6-yl]oxy-tert-butyl-dimethyl-silane 1,4-bis(diphenylphosphino)butane (5.9 mg, 0.014 mmol), palladium(II) acetate (4.0 mg, 0.018 mmol), and ethanol (0.17 ml) were combined in a 4 ml vial. The catalyst mixture was degassed (3×) and placed under nitrogen. The catalyst mixture was an amber suspension that was stirred at room temperature. Sodium borohydride (19.0 mg, 0.502 mmol) was added to a stirred solution of [(3R,3aR,6R,6aS)-3-[1-allyl-6-chloro-5-(4-pyrrolidin-1-ylphenyl)imidazo[4,5-b]pyridin-2-yl]oxy-2,3,3a,5,6,6a-hexahydrofuro[3,2-b]furan-6-yl]oxy-tert-butyl-dimethyl-silane (50.3 mg, 0.084 mmol) in ethanol (0.67 ml). The reaction mixture was a yellow suspension that was degassed (3×) and placed under nitrogen. After being stirred at room temperature for 40 minutes, the catalyst mixture was transferred to the reaction mixture via syringe. The reaction mixture was degassed (2×) and placed under nitrogen. After 3.5 hours, the reaction mixture was filtered and evaporated under reduced pressure. The resulting residue was purified by preparative HPLC reverse phase (C-18), using a 30×150 mm Sunfire™ column and eluting (20 ml/min) with a 14 minute 20%-100% acetonitrile/water+ 0.05% TFA gradient followed by a 5 minute 100% acetonitrile+0.05% TFA flush. The product fractions were combined, frozen, and lyophilized to give the title compound as a yellow solid. LC-MS: calculated for $C_{28}H_{37}ClN_4O_4Si$ 556.23 observed m/e: 557.29 (M+H)$^+$ (Rt 1.24/2 min).

110
INTERMEDIATE 42

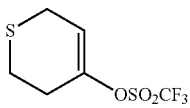

3,6-dihydro-2H-thiopyran-4-yl trifluoromethanesulfonate

To a stirred solution of diisopropylamine (4.86 ml, 3.45 g, 34.1 mmol) in anhydrous THF (48.0 ml) at 0° C. under nitrogen was added a solution of 2.5M n-butyllithium in hexanes (13.63 ml, 34.1 mmol), dropwise, over 5 minutes. The mixture was cooled to −78° and a solution of dihydro-2H-thiopyran-4(3H)-one (3.77 g, 32.4 mmol) in anhydrous THF (36.0 ml) was added dropwise over 10 minutes. After stirring at −78° C. for 15 minutes, 1,1,1-trifluoro-N-phenyl-N-((trifluoromethyl)sulfonyl)methanesulfonamide (12.75 g, 35.7 mmol) was added as a solid in 5 portions over 10 minutes. The dry-ice bath was removed and the mixture was allowed to stir at room temperature for 18 hours. The mixture was diluted with diethyl ether (200 ml), washed with aqueous 1N NaOH (150 ml), washed with brine (100 ml), then dried over sodium sulfate. The organic layer was concentrated under reduced pressure and dried under high vacuum for 18 hours to provide the title compound as a red oil. $^1$H NMR (400 MHz, CDCl$_3$) δ: 5.95 (d, J=8.0 Hz, 1H), 3.26 (m, 2H), 2.82 (m, 2H), 2.57 (m, 2H).

INTERMEDIATE 43

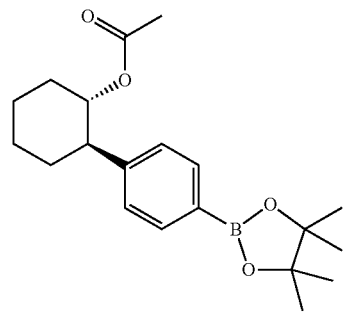 [SMILES: CC(=O)O[C@H]1CCCC[C@@H]1c1ccc(B2OC(C)(C)C(C)(C)O2)cc1]

TABLE 20

Intermediates prepared according to the methods in intermediate 40.

| Intermediate Number | Structure | HPLC-mass spectrum m/e |
|---|---|---|
| 41 | | 573.32 | trans-racemic-2-(4-(4,4,5,5-tetramethyl-1,3,2-dioxaborolan-2-yl)phenyl)cyclohexyl acetate

Step A: trans-racemic-2-phenylcyclohexyl acetate

To a stirred solution of trans-racemic-2-phenylcyclohexanol (4.63 g, 26.3 mmol) and tin(II)trifluoromethanesulfonate (219 mg, 0.525 mmol) under nitrogen in anhydrous DCM (100 ml) at room temperature was added acetic anhydride (3.72 ml, 4.02 g, 39.4 mmol) in one portion. The mixture was stirred for 18 hours at room temperature. The mixture was poured into saturated aqueous sodium bicarbonate (200 ml). The mixture was extracted with DCM (2×200 ml). The combined organic layers were washed with brine (70 ml), dried over sodium sulfate, and concentrated under reduced pressure to provide the desired product as a light yellow oil. LC-MS: calculated for $C_{14}H_{18}O_2$ 218.29 observed m/e: 219.33 (M+H)$^+$ (Rt 0.93/2 min)

Step B: trans-racemic-2-(4-iodophenyl)cyclohexyl acetate

To a stirred solution of trans-racemic-2-phenylcyclohexyl acetate (5.60 g, 25.7 mmol) under nitrogen in TFA (50 ml) at 0° C. was added N-iodosuccinimide (5.77 g, 25.7 mmol) portionwise over 5 minutes. The mixture was allowed to warm and stir at room temperature for 3 hours. The mixture was concentrated under reduced pressure. The resultant oil was chromatographed using an 80 g silica gel cartridge eluted with 0-20% ethyl acetate in hexanes over 15 column volumes. The desired product fractions were combined and concentrated under reduced pressure to provide the desired product as a yellow oil. LC-MS: calculated for $C_{14}H_{17}IO_2$ 344.19 observed m/e: 345.33 (M+H)$^+$ (Rt 2.60/4 min).

Step C: trans-racemic-2-(4-(4,4,5,5-tetramethyl-1,3,2-dioxaborolan-2-yl)phenyl)cyclohexyl acetate Placed trans-racemic-2-(4-iodophenyl)cyclohexyl acetate (8.14 g, 23.65 mmol), potassium acetate (6.96 g, 70.9 mmol), and bis(pinacolato)diboron (6.31 g, 24.83 mmol) under nitrogen in anhydrous DMSO (30.0 ml). The reaction flask was evacuated, then filled with nitrogen (3×), followed by the addition of [1,1'-bis(diphyenylphosphino)ferrocene]-dichloropalladium (II) (0.865 g, 1.182 mmol). The reaction flask was evacuated, then filled with nitrogen (3×) again, then the mixture was stirred at 80° C. for 4.5 hours. The mixture was allowed to cool to room temperature, and poured into water (200 ml), followed by extraction with diethyl ether (2×200 ml). The combined organic layers were washed with brine (80 ml), dried over sodium sulfate, and concentrated under reduced pressure. The resulting dark oil was chromatographed using an 80 g silica gel cartridge eluted with 5-10% ethyl acetate in hexanes over 15 column volumes. The desired product fractions were concentrated under reduced pressure to provide the desired product as a white solid. LC-MS: calculated for $C_{20}H_{29}BO_4$ 344.25 observed m/e: 344.00 (M+H)$^+$ (Rt 2.87/4 min)

INTERMEDIATE 44

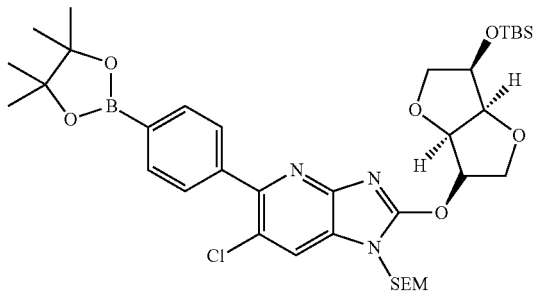

2-(((3R,3aR,6R,6aS)-6-((tert-butyldimethylsilyl)oxy)hexahydrofuro[3,2-b]furan-3-yl)oxy)-6-chloro-5-(4-(4,4,5,5-tetramethyl-1,3,2-dioxaborolan-2-yl)phenyl)-1-((2-(trimethylsilyl)ethoxy)-methyl)-1H-imidazo[4,5-b]pyridine To a stirred solution of (3R,3aR,6R,6aR)-6-((6-chloro-5-(4-(4,4,5,5-tetramethyl-1,3,2-dioxaborolan-2-yl)phenyl)-1-((2-(trimethylsilyl)ethoxy)methyl)-1H-imidazo[4,5-b]pyridin-2-yl)oxy)hexahydrofuro[3,2-b]furan-3-ol (1.059 g, 1.681 mmol) under nitrogen in anhydrous DMF (12.0 ml) at room temperature was added triethylamine (0.35 ml. 0.255 g, 2.52 mmol) and DMAP (0.021 g, 0.168 mmol). The mixture was cooled to 0° C. and TBSCl (0.304 g, 2.017 mmol) was added in one portion. The mixture was stirred at room temperature for 18 hours, then stirred at 50° C. for 4 hours. The mixture was poured into saturated aqueous sodium bicarbonate (50 ml) and extracted with ethyl acetate (2×75 ml). The combined organic layers were washed with brine (50 ml), dried over sodium sulfate, and concentrated under reduced pressure. The resultant dark oil was chromatographed using a 40 g silica gel cartridge eluted with 0-100% ethyl acetate in hexanes over 20 column volumes. The desired product fractions were combined and concentrated under reduced pressure to provide the desired product as a clear, colorless oil. LC-MS: calculated for $C_{36}H_{55}BClN_3O_7Si_2$ 744.27 observed m/e: 745.48 (M+H)$^+$ (Rt 2.00/2 min)

INTERMEDIATE 45

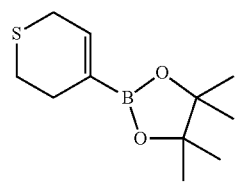

2-(3,6-dihdro-2H-thioran-4-yl)-4,4,5,5-tetramethyl-1,3,2-dioxaborolane 1,1'-Bis(diphenyl-phosphino)ferrocene-palladium(II) dichloride dichoromethane complex (219.0 mg, 0.268 mmol)

was added to a suspension of 3,6-dihydro-2H-thiopyran-4-yl trifluoromethanesulfonate (Intermediate 42, 666.1 mg, 2.68 mmol), bis(pinacolato)diboron (1.022 g, 40.02 mmol), and potassium acetate (790.0 mg, 8.05 mmol) in degassed 10% water in dioxane (3.3 mL). The mixture was stirred at 100° C. for 20 h, then cooled to RT and added to stirring EtOAc (70 mL)/water (25 mL). The organic layer was separated and dried over $Na_2SO_4$, filtered, and evaporated under reduced pressure. Flash chromatography of the resulting residue utilizing a 40 g silica RediSep $R_f$® Gold column and employing a 0-100% EtOAc/hexane gradient afforded the title compound. LC-MS: calculated for C11H19BO2S 226.12 observed m/e: 227.10 $(M+H)^+$ (Rt 1.47/2.0 min)

INTERMEDIATE 46

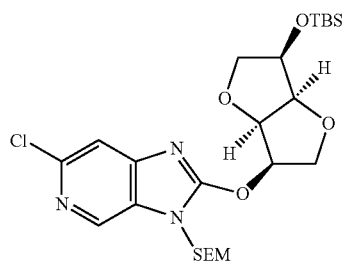 [SMILES: CC(C)(C)[Si](C)(C)O[C@@H]1CO[C@H]2[C@@H]1OC[C@H]2Oc1nc2cc(Cl)ncc2n1COCC[Si](C)(C)C]

2-(((3R,3aR,6R,6aS)-6-((tert-butyldimethylsilyl)oxy)hexahydrofuro[3,2-b]furan-3-yl)oxy)-6-chloro-3-((2-(trimethylsilyl)ethoxy)methyl)-3H-imidazo[4,5-c]pyridine Step A:
6-chloro-1H-imidazo[4,5-c]pyridine-2(3H)-thione A stirred mixture of 6-chloropyridine-3,4-diamine (500 mg, 3.48 mmol), 1,1'-thiocarbonyldiimidazole (1.24 g, 6.97 mmol), and triethylamine (0.49 mL, 3.48 mmol) in anhydrous DMF (15.0 mL) was microwaved in a Biotage Initiator at 100° C. at normal power for 1 h. Then the reaction mixture was evaporated at reduced pressure, and the resulting residue extracted with DCM (200 mL) and allowed to stand at 10° C. overnight. The mixture filtered and the solids washed with cold DCM (2×20 mL), and air dried to afford the title compound as a solid. LC-MS: calculated for C6H4ClN3S 184.98 observed m/e: 186.07 $(M+H)^+$ (Rt 0.62/2.0 min)

Step B:
6-chloro-2-(methylthio)-3H-imidazo[4,5-c]pyridine

To a stirring solution of 6-chloro-1H-imidazo[4,5-c]pyridine-2(3H)-thione (1.49 g, 8.03 mmol) and potassium hydroxide (540 mg, 9.63 mmol) in anhydrous EtOH (49.7 mL) was added iodomethane (0.50 mL, 8.03 mmol). The reaction solution was stirred at RT for 3.5 h, and then partitioned between EtOAc (64 mL) and 2N HCl (11.3 mL). The aqueous layer was separated, and the pH was adjusted to a slightly basic pH with the addition of saturated $NaHCO_3$, followed by extraction with EtOAc (100 mL). The combined organic layers were concentrated, and dried under vacuum to afford the title compound as a solid. LC-MS: calculated for C7H6ClN3S 199.00 observed m/e: 200.04 $(M+H)^+$ (Rt 1.12/2.0 min).

Step C: 6-chloro-2-(methylsulfonyl)-3H-imidazo[4,5-c]pyridine

To a stirring solution of 6-chloro-2-(methylthio)-3H-imidazo[4,5-c]pyridine (954.0 mg, 4.78 mmol) in 50% $CH_3CN$/water (61.4 mL) was added potassium peroxymonosulfate (oxone, 6.46 g, 10.51 mmol). The reaction was stirred under $N_2$ at RT for 15 h, then filtered and the filtrate added to a stirring mixture of EtOAc (1.27 L)/water (0.70 L). The aqueous layer was separated and back-extracted with EtOAc (0.25 L). The combined organic layers were evaporated under reduced pressure to afford the title compound. LC-MS: calculated for C7H6ClN3O2S 230.99 observed m/e: 231.98 $(M+H)^+$ (Rt 1.72/2.0 min)

Step D: 6-chloro-2-(methylsulfonyl)-3-((2-(trimethylsilyl)ethoxy)methyl)-3H-imidazo[4,5-c]pyridine To a stirring solution of 6-chloro-2-(methylsulfonyl)-3H-imidazo[4,5-c]pyridine (847 mg, 3.66 mmol) and N,N-diisopropylethylamine (5.11 mL, 29.20 mmol) in anhydrous DMF (25.0 mL) was added 2-(trimethylsilyl)ethoxymethyl chloride (3.24 mL, 18.28 mmol). The reaction was stirred under $N_2$ at RT for 18 h, then added to EtOAc (1.4 L) and washed with saturated $NH_4Cl$ (0.3 L). The aqueous layer was separated and back-extracted with EtOAc (0.3 L). The combined organic layers were evaporated under reduced pressure. Flash chromatography of the resulting residue utilizing a 40 g silica RediSep $R_f$® Gold column and employing a 0-30% EtOAc/hexane gradient afforded the title compound. LC-MS: calculated for C13H20ClN3O3SSi 361.07 observed m/e: 362.31 $(M+H)^+$ (Rt 1.32/2.0 min)

Step E: 2-(((3R,3aR,6R,6aS)-6-((tert-butyldimethylsilyl)oxy)hexahydrofuro[3,2-b]furan-3-yl)oxy)-6-chloro-3-((2-(trimethylsilyl)ethoxy)methyl)-3H-imidazo[4,5-c]pyridine To a stirring solution of 6-chloro-2-(methylsulfonyl)-3-((2-(trimethylsilyl)ethoxy)methyl)-3H-imidazo[4,5-c]pyridine (100 mgs, 0.276 mmol) and (3R,3aR,6R,6aS)-6-((tert-butyldimethylsilyl)oxy)hexahydrofuro[3,2-b]furan-3-ol (72.0 mg, 0.276 mmol) in anhydrous DMF (2.3 mL) was added diazabicyclo[5.4.0]undec-7-ene (DBU, 0.06 mL, 0.42 mmol). The reaction was stirred under $N_2$ at RT for 20 h, then evaporated under reduced pressure. Flash chromatography of the resulting residue utilizing a 24 g silica RediSep $R_f$® Gold column and employing a 0-90% EtOAc/hexane gradient afforded the title compound. LC-MS: calculated for C24H40ClN3O5Si2 541.22 observed m/e: 542.08 $(M+H)^+$ (Rt 1.74/2.0 min)

INTERMEDIATE 47

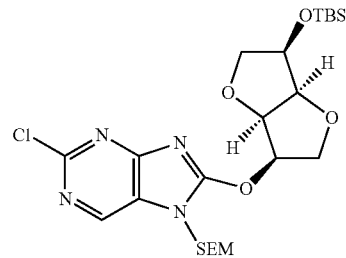 [SMILES: CC(C)(C)[Si](C)(C)O[C@@H]1CO[C@H]2[C@@H]1OC[C@H]2Oc1nc2nc(Cl)ncc2n1COCC[Si](C)(C)C]

8-(((3R,3aR,6R,6aS)-6-((tert-butyldimethylsilyl)oxy) hexahydrofuro[3,2-b]furan-3-yl)oxy)-2-chloro-7-((2-(trimethylsilyl) ethoxy)methyl)-7H-purine Step A: 2-chloro-8-(methylthio)-7H-purine To a stirring solution of 2-chloro-7H-purine-8(9H)-thione (2.00 g, 10.72 mmol) and potassium hydroxide (722 mg, 12.86 mmol) in anhydrous EtOH (66.4 mL) was added iodomethane (0.67 mL, 10.72 mmol). The reaction solution was stirred under $N_2$ at RT for 4 h, then partitioned between EtOAc (85 mL) and 2N HCl (15 mL) and allowed to settle overnight. To the aqueous layer, which contained solid material, was added more water (60 mL). The mixture was filtered, and dried under vacuum to afford the title compound as a solid. LC-MS: calculated for C6H5ClN4S 199.99 observed m/e: 200.99 (M+H)+ (Rt 0.99/1.8 min).

Step B: 2-chloro-8-(methylsulfonyl)-7H-purine

To a stirring solution of 2-chloro-8-(methylthio)-7H-purine (700.0 mg, 3.49 mmol) in 50% $CH_3CN$/water (44.8 mL) was added potassium peroxymonosulfate (oxone, 4.72 g, 7.68 mmol). The reaction was stirred under $N_2$ at RT for 17 h, then filtered and the filtrate was added to a stirring EtOAc (1 L)/water (0.56 L) mixture. The aqueous layer was separated and back-extracted with EtOAc (0.2 L). The combined organic layers were evaporated under reduced pressure to afford the title compound. LC-MS: calculated for C6H5ClN4O2S 231.98 observed m/e: 233.11 (M+H)+ (Rt 0.58/2.0 min).

Step C: 2-chloro-8-(methylsulfonyl)-7-((2-(trimethylsilyl)ethoxy)methyl)-7H-purine To a stirring solution of 2-chloro-8-(methylsulfonyl)-7H-purine (570 mg, 2.45 mmol) and N,N-diisopropylethylamine (3.42 mL, 19.60 mmol) in anhydrous DMF (16.7 mL) was added 2-(trimethylsilyl)ethoxymethyl chloride (2.17 mL, 12.25 mmol). The reaction was stirred under $N_2$ at RT for 20 h, then added to EtOAc (1.0 L) and washed with saturated $NH_4Cl$ (0.2 L). The aqueous layer was separated and back-extracted with EtOAc (0.2 L). The organic layers combined and evaporated under reduced pressure. Flash chromatography of the resulting residue utilizing a 24 g silica RediSep $R_f$® Gold column and employing a 0-40% EtOAc/hexane gradient afforded the title compound. LC-MS: calculated for C12H19ClN4O3SSi 362.06 observed m/e: 385.30 (M+23)' (Rt 1.33/2.0 min)

Step D: 8-(((3R,3aR,6R,6aS)-6-((tert-butyldimethylsilyl)oxy)hexahydrofuro[3,2-b]furan-3-yl)oxy)-2-chloro-7-((2-(trimethylsilyl)ethoxy)methyl)-7H-purine To a stirring solution of 2-chloro-8-(methylsulfonyl)-7-((2-(trimethylsilyl)ethoxy)methyl)-7H-purine (182 mgs, 0.50 mmol) and (3R,3aR,6R,6aS)-6-((tert-butyldimethylsilyl)oxy)hexahydrofuro[3,2-b]furan-3-ol (131.0 mg, 0.50 mmol) in anhydrous DMF (4.1 mL) was added diazabicyclo [5.4.0]undec-7-ene (DBU, 0.11 mL, 0.75 mmol). The reaction was stirred under $N_2$ at RT for 16 h and then evaporated under reduced pressure. Flash chromatography of the resulting residue utilizing a 24 g silica RediSep $R_f$® Gold column and employing a 0-75% EtOAc/hexane gradient afforded the title compound. LC-MS: calculated for C23H39ClN4O5Si2 542.21 observed m/e: 543.53 (M+H)+ (Rt 1.54/2.0 min)

EXAMPLE 1

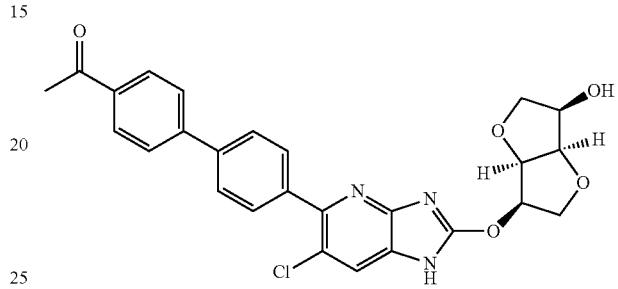

1-[4-[4-[2-[[(3R,3aR,6R,6aR)-3-hydroxy-2,3,3a,5,6, 6a-hexahydrofuro[3,2-b]furan-6-yl]oxy]-6-chloro-1H-imidazo[4,5-b]pyridin-5-yl]phenyl]phenyl]ethanone LiOH (0.41 ml, 1.230 mmol) and 1,1'-bis(diphenylphosphino)ferrocene-palladium(II)dichloride dichloromethane complex (41.8 mg, 0.051 mmol) were added to a stirred solution of (3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol (225.2 mg, 0.497 mmol) and 4-acetylphenylboronic acid (100.3 mg, 0.612 mmol) in dioxane (4.0 ml) and water (0.59 ml). The reaction mixture was degassed (3×) and placed under nitrogen before being heated to 80° C. for 18 h. The reaction mixture was then partitioned between EtOAc (50 ml) and water (50 ml). The aqueous layer was extracted with EtOAc (2×50 ml). The organic layers were combined, washed with brine (1×50 ml), dried over $Na_2SO_4$, filtered, and evaporated under reduced pressure to give a yellow solid. The solid was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The desired fractions were combined, evaporated under reduced pressure, and lyophilized from ethanol and benzene to give the title compound as a light yellow solid. LC-MS: calculated for $C_{26}H_{22}ClN_3O_5$ 491.12 observed m/e: 492.10 (M+H)+ (Rt 1.14/2 min); $^1H$ NMR δ (ppm) (CD$_3$OD): 8.11 (d, J=8.5 Hz, 2H), 7.85 (d, J=8.5 Hz, 2H), 7.83 (s, 1H), 7.77-7.82 (m, 4H), 5.55 (qt, J=5 Hz, 1H), 4.97 (t, J=5.3 Hz, 1H), 4.47 (t, J=4.8, 1H), 4.27-4.30 (m, 1H), 4.17 (dd, J=5.8, J=10.3, 1H), 4.11 (dd, J=4.8 Hz, J=10.3, 1H), 3.90 (t, J=7.5 Hz, 1H), 3.60 (t, J=8.8 Hz, 1H) 2.65 (s, 3H).

TABLE 1

Compounds prepared according to the methods in Example 1.

| Example Number | Structure | HPLC-mass spectrum m/e |
|---|---|---|
| 2 | 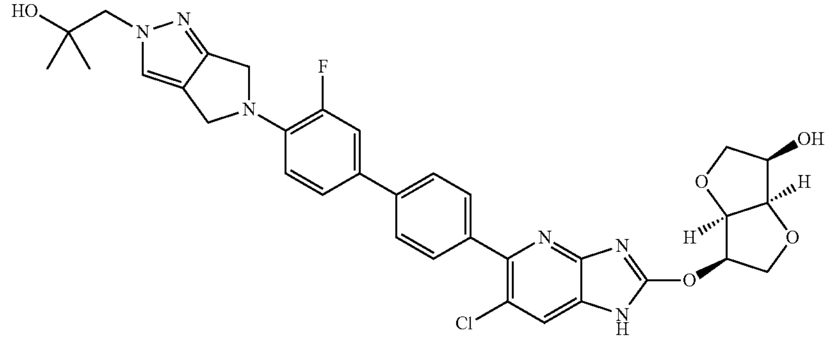 [SMILES: CC(C)(O)Cn1cc2c(n1)CN(c1ccc(-c3ccc(-c4nc5nc(O[C@@H]6CO[C@H]7[C@@H]6OC[C@H]7O)[nH]c5cc4Cl)cc3)cc1F)C2] | 647.26 |
| 3 | Chiral | 508.00 |
| 4 | Chiral | 525.88 |

EXAMPLES 5 and 6

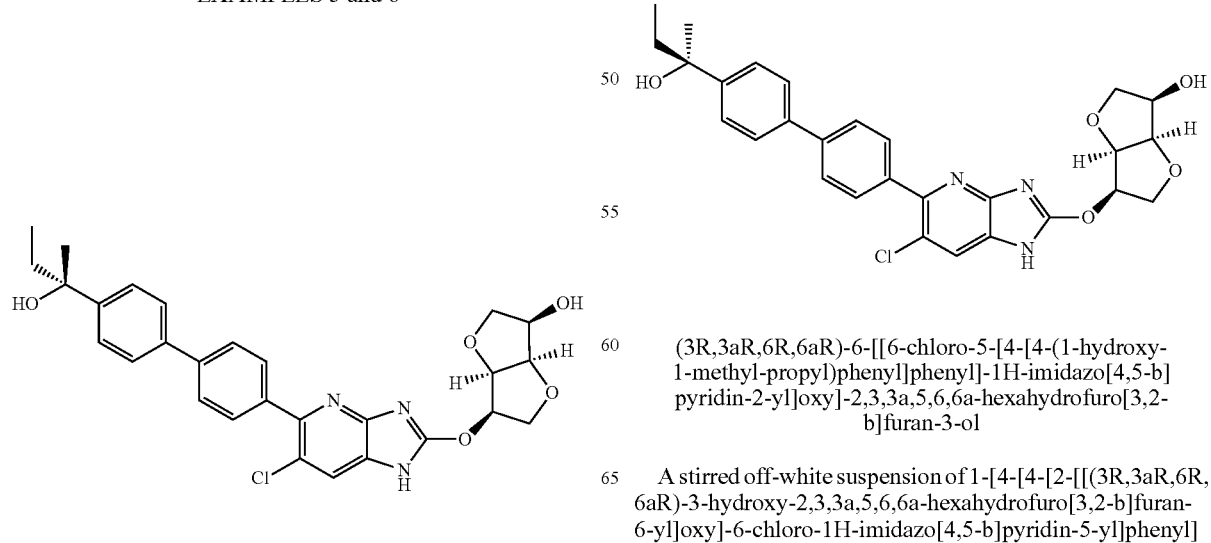

(3R,3aR,6R,6aR)-6-[[6-chloro-5-[4-[4-(1-hydroxy-1-methyl-propyl)phenyl]phenyl]-1H-imidazo[4,5-b]pyridin-2-yl]oxy]-2,3,3a,5,6,6a-hexahydrofuro[3,2-b]furan-3-ol A stirred off-white suspension of 1-[4-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]

phenyl]ethanone (55.6 mg, 0.113 mmol) in THF (2.3 ml) was degassed (3×) and placed under nitrogen before being cooled to 0° C. in an ice bath. Ethylmagnesium bromide 3.0 M in diethyl ether (0.38 ml, 1.140 mmol) was added to the reaction mixture dropwise, to give a green suspension. After a few minutes, the reaction mixture was removed from the ice bath and allowed to warm to room temperature. After 2 hours, the reaction mixture was pipetted into saturated aqueous NaHCO$_3$ (30 ml). The resulting biphasic suspension was partitioned between EtOAc (30 ml) and water (10 ml). The aqueous layer was extracted with EtOAc (2×20 ml). The organic layers were combined, washed with brine (1×20 ml), dried over Na$_2$SO$_4$, filtered, and evaporated under reduced pressure to give a green residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined and evaporated under reduced pressure to give the racemic product as a colorless residue, which was separated by preparative HPLC Chiralpak AD™, eluting with 30% isopropanol/heptane at 9 mL/minute. The fractions from the faster eluting peak were collected, evaporated under reduced pressure, and lyophilized from ethanol and benzene to give isomer A of the title compound as a white solid. LC-MS: calculated for C$_{28}$H$_{28}$ClN$_3$O$_5$ 521.17 observed m/e: 522.23 (M+H)$^+$ (Rt 1.16/2 min); $^1$H NMR δ (ppm) (CD$_3$OD): 7.82 (s, 1H), 7.73 (s, 4H), 7.66 (d, J=8.5 Hz, 2H), 7.54 (d, J=8.5 hz, 2H), 5.54 (qt, Hz=5.4 Hz, 1H), 4.96 (t, J=5.2 Hz, 1H), 4.47 (t, J=5.0 Hz, 1H), 4.26-4.30 (m, 1H), 4.17 (dd, J=5.8 Hz, J=10.2 Hz, 1H), 4.10 (dd, J=4.9 Hz, 10.2 Hz, 1H), 3.90 (dd, J=6.9 Hz, J=8.1 Hz, 1H), 3.60 (t, J=8.6 Hz, 1H), 1.83-1.88 (m, 2H), 1.55 (s, 3H), 0.82 (t, J=7.4 Hz, 3H).

The fractions from the slower eluting peak were collected, evaporated under reduced pressure, and lyophilized from ethanol and benzene to give isomer B of the title compound as a white solid. LC-MS: calculated for C$_{28}$H$_{28}$ClN$_3$O$_5$ 521.17 observed m/e: 522.22 (M+H)$^+$ (Rt 1.16/2 min); $^1$H NMR δ (ppm) (CD$_3$OD): 7.81 (s, 1H), 7.73 (s, 4H), 7.66 (d, J=8.4 Hz, 2H), 7.54 (d, J=8.4, 2H), 5.54 (qt, J=5.4 Hz, 1H), 4.97 (t, J=5.2 Hz, 1H), 4.47 (t, J=5.0 Hz, 1H), 4.26-4.30 (m, 1H), 4.17 (dd, J=5.7 Hz, J=10.1 Hz, 1H), 4.10 (dd, J=4.9, J=10.1 Hz, 1H), 3.90 (dd, J=6.9 Hz, J=8.1 Hz, 1H), 3.60 (t, J=8.6 Hz, 1H), 1.83-1.88 (m, 2H), 1.55 (s, 3H), 0.82 (t, J=7.4 Hz, 3H).

EXAMPLE 7

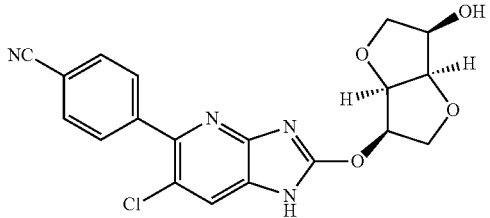 [SMILES: N#Cc1ccc(-c2nc3nc(O[C@@H]4CO[C@H]5[C@@H]4OC[C@H]5O)[nH]c3cc2Cl)cc1]

4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]benzonitrile Step A: 4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]-benzonitrile LiOH (0.43 ml, 1.290 mmol) and 1,1'-bis(diphenylphosphino)ferrocene-palladium(II)dichloride dichloromethane complex (43.2 mg, 0.053 mmol) were added to a stirred solution of (3R,3aR,6R,6aR)-6-[6-chloro-5-iodo-1-(2-trimethylsilylethoxy-methyl)imidazo[4,5-b]pyridin-2-yl]oxy-2,3,3a,5,6,6a-hexahydrofuro[3,2-b]furan-3-ol (284.9 mg, 0.514 mmol) and 4-(4,4,5,5-tetramethyl-1,3,2-dioxaborolan-2-yl)benzonitrile (143.1 mg, 0.625 mmol) in dioxane (4.2 ml) and water (0.60 ml). The reaction mixture was degassed (3×) and placed under nitrogen before being heated to 80° C. for 1.5 hours. Then the reaction mixture was cooled and partitioned between EtOAc (50 ml) and water (50 mL). The aqueous layer was extracted with EtOAc (2×50 ml). The organic layers were combined, washed with brine (1×50 ml), dried over Na$_2$SO$_4$, filtered, and evaporated under reduced pressure to give an amber residue. Flash chromatography of the residue utilizing a 12 g silica RediSep R$_f$® column and employing a 0-60% EtOAc/hexane gradient followed by 60% EtOAc/hexane afforded the title compound as a yellow residue. LC-MS: calculated for C$_{25}$H$_{29}$ClN$_4$O$_5$Si 528.16 observed m/e: 529.22 (M+H)$^+$ (Rt 2.34/4 min).

Step B: 4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]benzonitrile A flask was charged with 4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)-imidazo[4,5-b]pyridin-5-yl]benzonitrile (209.8 mg, 0.397 mmol), formic acid (3.6 ml, 94 mmol), and saturated aqueous KHSO$_4$ (0.4 ml). The reaction mixture was heated to 40° C. for 16 h. Then the reaction mixture was cooled to room temperature before being cooled to 0° C. in an ice bath. A 50% weight solution of aqueous NaOH (5.3 ml, 200.7 mmol) was added to the reaction mixture, which solidified after being removed from the ice bath and was allowed to warm to room temperature. The reaction mixture was diluted with THF (2.0 ml) and water (10.0 ml) to give a hazy biphasic mixture with a pH of 14 that was stirred at room temperature for 30 min. The pH was adjusted to 5 by the addition of 2 N aqueous HCl. The reaction mixture was partitioned between EtOAc (50 ml) and water (20 ml). The aqueous layer was extracted with EtOAc (2×50 ml). The organic layers were combined, washed with brine (1×30 ml), dried over Na$_2$SO$_4$, filtered, and evaporated under reduced pressure to give a light pink residue. This material was purified by preparative HPLC reverse phase (C-18), using a 30×150 mm Sunfire™ column and eluting with a 20%-100% acetonitrile/water+0.05% TFA gradient, followed by a 100% acetonitrile+0.05% TFA flush. The product fractions were combined, evaporated under reduced pressure, and lyophilized from ethanol and benzene to give the title compound as a white solid. LC-MS: calculated for C$_{19}$H$_{15}$ClN$_4$O$_4$ 398.08 observed m/e: 399.09 (M+H)$^+$ (Rt 1.07/2 min); $^1$H NMR δ (ppm) (CD$_3$OD): 7.84 (s, 1H), 7.84 (qt, J=8.3 Hz, 4H), 5.54 (qt, J=5.3 Hz, 1H), 4.96 (t, J=5.2 Hz, 1H), 4.46 (t, J=5.0 Hz, 1H), 4.25-4.30 (m, 1H), 4.16 (dd, J=5.6 Hz, J=10.2, 1H), 4.11 (dd, J=4.7 Hz, J=10.2 Hz, 1H), 3.89 (dd, J=7.0 Hz, J=8.1 Hz, 1H), 3.59 (t, J=8.6 Hz, 1H).

TABLE 2

Compounds prepared according to the methods in Example 7.

| Example Number | Structure | | HPLC-mass spectum m/e |
|---|---|---|---|
| 8 | 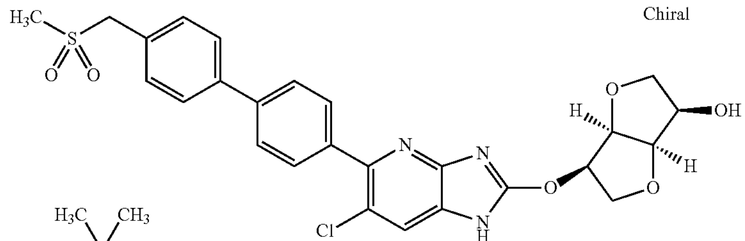 [SMILES: CS(=O)(=O)Cc1ccc(-c2ccc(-c3nc4nc(O[C@@H]5CO[C@H]6[C@@H]5OC[C@H]6O)[nH]c4cc3Cl)cc2)cc1] | Chiral | 541.81 |
| 9 | 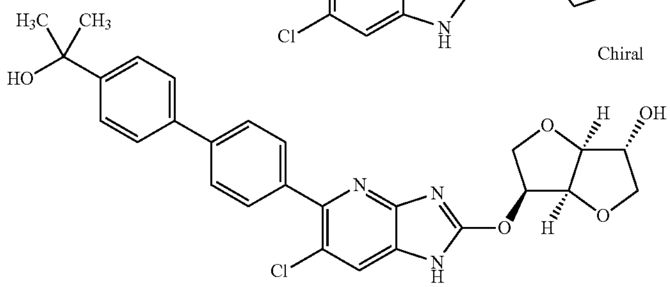 | Chiral | 508.13 |

EXAMPLE 10

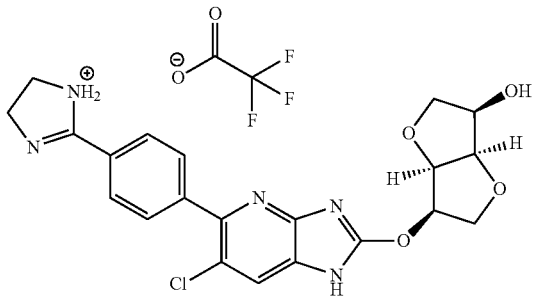 [SMILES: O[C@@H]1CO[C@H]2[C@@H]1OC[C@H]2Oc1nc2nc(-c3ccc(C4=NCC[NH2+]4)cc3)c(Cl)cc2[nH]1 ; O=C([O-])C(F)(F)F]

(3R,3aR,6R,6aR)-6-[[6-chloro-5-[4-(4,5-dihydro-1H-imidazol-2-yl)phenyl]-1H-imidazo[4,5-b]pyridin-2-yl]oxy]-2,3,3a,5,6,6a-hexahydrofuro[3,2-b]furan-3-ol A vial was charged with 4-[2-[[(3R,3aR,6R,6aR)-3-hydroxy-2,3,3a,5,6,6a-hexahydro-furo[3,2-b]furan-6-yl]oxy]-6-chloro-1H-imidazo[4,5-b]pyridin-5-yl]benzonitrile (24.8 mg, 0.062 mmol), ethylenediamine (0.5 ml, 7.46 mmol), and carbon disulfide (5 µl, 0.083 mmol). The reaction mixture was heated to 50° C. for 19 h. The reaction mixture was cooled to room temperature before being concentrated under reduced pressure to 0.1 mL. The concentrated reaction mixture was purified by preparative HPLC reverse phase (C-18), using a 30×150 mm Sunfire™ column and eluting with a 0%-30% acetonitrile/water+0.05% TFA gradient, followed by a 30% acetonitrile/water+0.05% TFA flush. The product fractions were combined, evaporated under reduced pressure, and lyophilized from ethanol and benzene to give the title compound as a white solid. LC-MS: calculated for $C_{21}H_{20}ClN_5O_4$ 441.12 observed m/e: 442.19 (M+H)$^+$ (Rt 0.25/2 min); $^1$H NMR δ (ppm) (CD$_3$OD): 7.95 (s, 4H), 7.85 (s, 1H), 5.54 (qt, J=5.3 Hz, 1H), 4.96 (t, J=5.2 Hz, 1H), 4.46 (t, J=5.0 Hz, 1H), 4.26-4.30 (m, 1H), 4.16 (dd, J=5.7 Hz, J=10.3 Hz, 1H), 4.14 (s, 4H), 4.11 (dd, J=4.7 Hz, J=10.2 Hz, 1H), 3.89 (dd, J=6.8 Hz, J=8.1 Hz, 1H), 3.59 (t, J=8.6 Hz, 1H).

TABLE 3

Compounds prepared according to the methods in Example 10.

| Example Number | Structure | HPLC-mass spectum m/e |
|---|---|---|
| 11 | 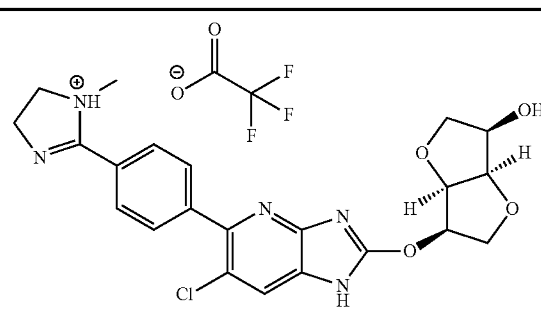 | 456.19 |

EXAMPLE 12

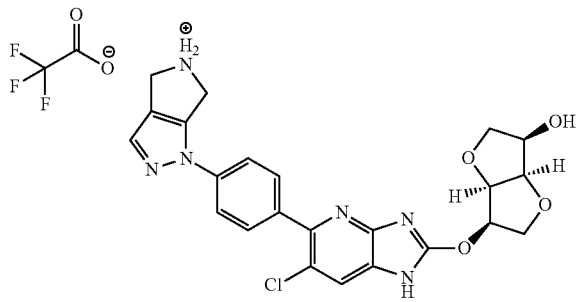

(3R,3aR,6R,6aR)-6-((6-chloro-5-(4-(5,6-dihydropyr-rolo[3,4-c]pyrazol-1(4H)-yl)phenyl)-1H-imidazo[4,5-b]pyridin-2-yl)oxy)hexahydrofuro[3,2-b]furan-3-ol 2,2,2-trifluoroacetate Step A tert-butyl 1-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-4,6-dihydropyrrolo[3,4-c]pyrazole-5-carboxylate A vial was charged with (3R,3aR,6R,6aR)-6-[5-(4-bromophenyl)-6-chloro-1-(2-trimethylsilylethoxymethyl)-imidazo[4,5-b]pyridin-2-yl]oxy-2,3,3a,5,6,6a-hexahydrofuro[3,2-b]furan-3-ol (501.8 mg, 0.861 mmol), tert-butyl 4,6-dihydro-2H-pyrrolo[3,4-c]pyrazole-5-carboxylate (240.3 mg, 1.148 mmol), tripotassium phosphate (581.6 mg, 2.74 mmol), and copper(I) iodide (37.2 mg, 0.195 mmol). The reaction was evacuated (3×) and backfilled with nitrogen. Trans-N,N'-dimethylcyclohexane-1,2-diamine (55 µl, 0.348 mmol) and dioxane (1.7 ml) were added to the vial to give a hazy suspension, which was heated to 100° C. for 24 h. The reaction mixture was then cooled to room temperature and partitioned between EtOAc (100 ml) and water (100 ml). The aqueous layer was extracted with EtOAc (2×50 ml). The organic layers were combined, washed with brine (1×30 ml), dried over MgSO$_4$, filtered, and evaporated under reduced pressure to give a pale green residue. Flash chromatography of the residue utilizing a 40 g silica RediSep R$_f$® column and employing a 0-100% EtOAc/hexane gradient afforded a mixture of the two pyrazole linked regioisomers as a pale amber foam. LC-MS: calculated for C$_{34}$H$_{43}$ClN$_6$O$_7$Si 710.27 observed m/e: 711.29 (M+H)$^+$ (Rt 1.30/2 min)

Step B: (3R,3aR,6R,6aR)-6-((6-chloro-5-(4-(5,6-dihydropyrrolo[3,4-c]pyrazol-1(4H)-yl)phenyl)-1H-imidazo[4,5-b]pyridin-2-yl)oxy)hexahydrofuro[3,2-b]furan-3-ol 2,2,2-trifluoroacetate TFA (2.5 ml, 32.4 mmol) was added to a stirred solution of (3R,3aR,6R,6aR)-6-((6-chloro-5-(4-(5,6-dihydropyrrolo[3,4-c]pyrazol-1(4H)-yl)phenyl)-1H-imidazo[4,5-b]pyridin-2-yl)oxy)hexahydrofuro[3,2-b]furan-3-ol 2,2,2-trifluoroacetate (358.9 mg, 0.505 mmol) in DCM (2.5 ml). The reaction mixture was stirred at room temperature for 1.5 h. The reaction mixture was then evaporated under reduced pressure and the resulting residue was dissolved in DCM/MeOH and evaporated several times to give a yellow solid. The solid was purified by thin layer chromatography using two 500 micron 20 cm×20 cm silica gel plates, which were developed using 15% (10% NH$_4$OH/MeOH)/DCM. The silica containing the faster eluting isomer was collected and eluted with 15% (10% NH$_4$OH/MeOH)/DCM (80 ml). The solvent was evaporated under reduced pressure to give an off white solid. This material was further purified by preparative HPLC reverse phase (C-18), using a 30×150 mm Sunfire™ column and eluting with a 10%-50% acetonitrile/water+0.05% TFA gradient, followed by a 50% acetonitrile/water+0.05% TFA flush. The product fractions were combined, evaporated under reduced pressure, and lyophilized from ethanol and benzene to give the title compound as a white solid. LC-MS: calculated for C$_{23}$H$_{21}$ClN$_6$O$_4$ 480.13 observed m/e: 481.13 (M+H)$^+$ (Rt 0.94/2 min); $^1$H NMR δ (ppm) (CD$_3$OD): 7.87 (s, 1H), 7.85 (d, J=8.4 Hz, 2H), 7.72 (d, J=8.6 Hz, 2H), 7.65 (s, 1H), 5.56 (qt, J=5.3 Hz, 1H), 4.98 (t, J=5.2 Hz, 1H), 4.87 (s, 2H), 4.51 (s, 2H), 4.48 (t, J=5.0 Hz, 1H), 4.28-4.32 (m, 1H), 4.18 (dd, J=5.7 Hz, J=10.2 Hz, 1H), 4.13 (dd, J=4.8 Hz, J=10.2 Hz, 1H), 3.91 (t, J=7.6 Hz, 1H), 3.61 (t, J=8.6 Hz, 1H).

EXAMPLE 13

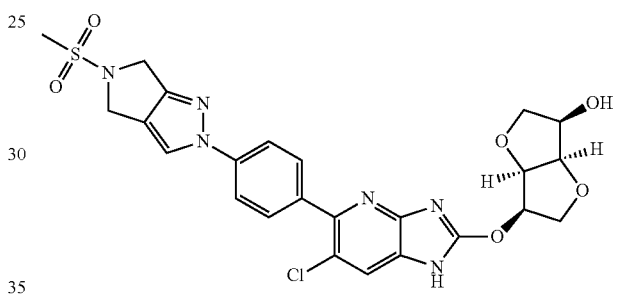

(3R,3aR,6R,6aR)-6-[[6-chloro-5-[4-(5-methylsulfonyl-4,6-dihydropyrrolo[3,4-c]pyrazol-2-yl)phenyl]-1H-imidazo[4,5-b]pyridin-2-yl]oxy]-2,3,3a,5,6,6a-hexahydrofuro[3,2-b]furan-3-ol Step A: tert-butyl 2-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)-imidazo[4,5-b]pyridin-5-yl]phenyl]-4,6-dihydropyrrolo[3,4-c]pyrazole-5-carboxylate A vial was charged with (3R,3aR,6R,6aR)-6-[5-(4-bromophenyl)-6-chloro-1-(2-trimethylsilylethoxymethyl)imidazo[4,5-b]pyridin-2-yl]oxy-2,3,3a,5,6,6a-hexahydrofuro[3,2-b]furan-3-ol (501.8 mg, 0.861 mmol), tert-butyl 4,6-dihydro-2H-pyrrolo[3,4-c]pyrazole-5-carboxylate (240.3 mg, 1.148 mmol), tripotassium phosphate (581.6 mg, 2.74 mmol), and copper (I) iodide (37.2 mg, 0.195 mmol). The vial was evacuated (3×) and backfilled with nitrogen. Trans-N,N'-dimethylcyclohexane-1,2-diamine (55 µl, 0.348 mmol) and dioxane (1.7 ml) were added to the vial to give a hazy suspension that was heated to 100° C. for 24 h. The reaction mixture was cooled to room temperature and partitioned between EtOAc (100 ml) and water (100 ml). The aqueous layer was extracted with EtOAc (2×50 ml). The organic layers were combined, washed with brine (1×30 ml), dried over MgSO$_4$, filtered, and evaporated under reduced pressure to give a pale green residue. Flash chromatography of the residue utilizing a 40 g silica RediSep R$_f$® column and employing a 0-100% EtOAc/hexane gradient afforded a mixture of the two pyrazole linked regioisomers as a pale amber foam. LC-MS: calculated for $C_{34}H_{43}ClN_6O_7Si$ 710.27 observed m/e: 711.29 $(M+H)^+$ (Rt 1.30/2 min)

Step B: (3R,3aR,6R,6aR)-6-[[6-chloro-5-[4-(5,6-dihydro-4H-pyrrolo[3,4-c]pyrazol-2-yl)phenyl]-1H-imidazo[4,5-b]pyridin-2-yl]oxy]-2,3,3a,5,6,6a-hexahydrofuro[3,2-b]furan-3-ol; 2,2,2-trifluoroacetate TFA (2.5 ml, 32.4 mmol) was added to a stirred solution of tert-butyl 2-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]-4,6-dihydropyrrolo[3,4-c]pyrazole-5-carboxylate (358.9 mg, 0.505 mmol) in DCM (2.5 ml). The reaction mixture was stirred at room temperature for 1.5 h. The reaction mixture was then evaporated under reduced pressure. The resulting residue was dissolved in DCM/MeOH and evaporated under reduced pressure several times to give a yellow solid. The solid was used in the next step without further purification. LC-MS: calculated for $C_{23}H_{21}ClN_6O_4$ 480.13 observed m/e: 481.16 $(M+H)^+$ (Rt 0.95/2 min)

Step C: (3R,3aR,6R,6aR)-6-[[6-chloro-5-[4-(5-methylsulfonyl-4,6-dihydropyrrolo[3,4-c]pyrazol-2-yl)phenyl]-1H-imidazo[4,5-b]pyridin-2-yl]oxy]-2,3,3a,5,6,6a-hexahydrofuro[3,2-b]furan-3-ol Triethylamine (30 μl, 0.215 mmol) and methanesulfonyl chloride (4.5 μl, 0.058 mmol) were added to a stirred suspension of (3R,3aR,6R,6aR)-6-[[6-chloro-5-[4-(5,6-dihydro-4H-pyrrolo[3,4-c]pyrazol-2-yl)phenyl]-1H-imidazo[4,5-b]pyridin-2-yl]oxy]-2,3,3a,5,6,6a-hexahydrofuro[3,2-b]furan-3-ol; 2,2,2-trifluoroacetate (29.1 mg, 0.049 mmol) in DCM (0.5 ml). After 10 min, 1,4-dioxane (0.5 ml) was added to the reaction mixture. Following sonication, the reaction mixture was a yellow suspension. After stirring for an additional 10 min, the reaction mixture was evaporated under reduced pressure. DMF (0.5 ml), triethylamine (30 μl, 0.215 mmol), and methanesulfonyl chloride (4.5 μl, 0.058 mmol) were added to the resulting residue to give a fine yellow suspension that was stirred at room temperature. After 30 min, EtOAc (2 ml) was added to the reaction mixture, causing a white precipitate to form. The reaction mixture was filtered and the filtrate was partitioned between EtOAc (30 ml) and water (30 ml). The organic filtrate was washed with water (2×10 ml) and brine (1×10 ml), dried over $MgSO_4$, filtered, and evaporated under reduced pressure to give a white residue. THF (1.0 ml) was added followed by potassium trimethylsilanolate (41.6 mg, 0.324 mmol). The reaction mixture was a pale yellow suspension that was stirred at room temperature. After 20 hours, the reaction mixture was evaporated under reduced pressure to give a yellow/white solid. This material was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{24}H_{23}ClN_6O_6S$ 558.11 observed m/e: 559.18 $(M+H)^+$ (Rt 1.06/2 min); $^1H$ NMR δ (ppm) $((CD_3)_2SO)$: 8.43 (s, 1H), 7.98 (broad s, 1H), 7.90 (d, J=8.5 Hz, 2H), 7.77 (d, J=8.6 Hz, 1H), 5.48 (qt, J=5.7 Hz, 1H), 4.99 (d, J=6.5 Hz, 1H), 4.84 (t, J=5.1 Hz, 1H), 4.54 (s, 2H), 4.51 (s, 2H), 4.36 (t, J=4.8 Hz, 1H), 4.10-4.17 (m, 2H), 3.91 (dd, J=5.9 Hz, J=9.5 Hz, 1H), 3.78 (t, J=7.4 Hz, 1H), 3.43 (t, J=8.5 Hz, 1H), 3.05 (s, 3H).

EXAMPLE 14

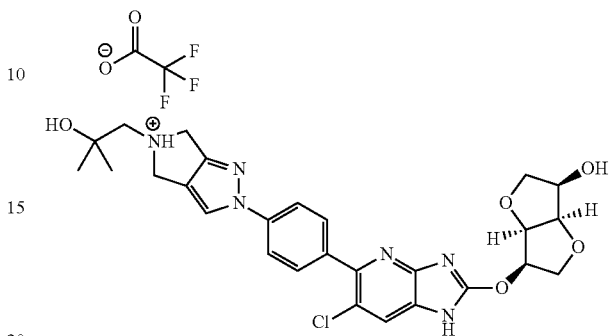

(3R,3aR,6R,6aR)-6-[[6-chloro-5-[4-[5-(2-hydroxy-2-methyl-propyl)-5,6-dihydro-4H-pyrrolo[3,4-c]pyrazol-5-ium-2-yl]phenyl]-1H-imidazo[4,5-b]pyridin-2-yl]oxy]-2,3,3a,5,6,6a-hexahydrofuro[3,2-b]furan-3-ol; 2,2,2-trifluoroacetate Step A: (3R,3aR,6R,6aR)-6-[1-allyl-6-chloro-5-[4-[5-(2-hydroxy-2-methyl-propyl)-4,6-dihydropyrrolo[3,4-c]pyrazol-2-yl]phenyl]imidazo[4,5-b]pyridin-2-yl]oxy-2,3,3a,5,6,6a-hexahydrofuro[3,2-b]furan-3-ol Isobutylene oxide (17 μl, 0.191 mmol) was added to a stirred solution of (3R,3aR,6R,6aR)-6-[1-allyl-6-chloro-5-[4-(5,6-dihydro-4H-pyrrolo[3,4-c]pyrazol-2-yl)phenyl]imidazo[4,5-b]pyridin-2-yl]oxy-2,3,3a,5,6,6a-hexahydrofuro[3,2-b]furan-3-ol (83.4 mg, 0.160 mmol) in dioxane (0.64 ml). The reaction mixture was a pale yellow solution that was heated to 80° C. After 3 days, additional isobutylene oxide (8 μl, 0.090 mmol) was added. After stirring an additional 16 h, the reaction mixture was cooled to room temperature. The reaction mixture was then diluted with MeOH/DCM and loaded onto two 500 micron 20 cm×20 cm silica gel plates, which were developed twice using 10% (10% $NH_4OH$/MeOH)/DCM. The silica containing the product band was collected and eluted with 10% (10% $NH_4OH$/MeOH)/DCM (80 ml). The solvent was evaporated under reduced pressure to give the desired product as a yellow residue. LC-MS: calculated for $C_{30}H_{33}ClN_6O_5$ 592.22 observed m/e: 593.25 $(M+H)^+$ (Rt 1.00/2 min)

Step B: (3R,3aR,6R,6aR)-6-[[6-chloro-5-[4-[5-(2-hydroxy-2-methyl-propyl)-5,6-dihydro-4H-pyrrolo[3,4-c]pyrazol-5-ium-2-yl]phenyl]-1H-imidazo[4,5-b]pyridin-2-yl]oxy]-2,3,3a,5,6,6a-hexahydrofuro[3,2-b]furan-3-ol; 2,2,2-trifluoroacetate A vial was charged with palladium (II) acetate (0.8 mg, 3.56 μmol), 1,4-bis(diphenylphosphino)butane (2.4 mg, 5.63 μmol), and ethanol (0.1 ml). This catalyst mixture was degassed (3×) and placed under nitrogen. The mixture was an amber suspension that was stirred at room temperature for 15 min. Sodium borohydride (6.8 mg, 0.180 mmol) was added to a stirred solution of (3R,3aR,6R,6aR)-6-[1-allyl-6-chloro-5-[4-[5-(2-hydroxy-2-methyl-propyl)-4,6-dihydropyrrolo[3,4-c]pyrazol-2-yl]phenyl]imidazo[4,5-b]pyridin-2-yl]oxy-2,3, 3a,5,6,6a-hexahydrofuro[3,2-b]furan-3-ol (15.3 mg, 0.026 mmol) in ethanol (0.2 ml) and DCM (0.05 ml). The reaction mixture was degassed (3×) and placed under nitrogen. The catalyst mixture was transferred via syringe to the sodium borohydride mixture. After stirring at room temperature for 3 h, the reaction mixture was filtered and evaporated under reduced pressure to give an amber residue. This material was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{27}H_{29}ClN_6O_5$ 552.19 observed m/e: 553.22 $(M+H)^+$ (Rt 0.96/2 min); $^1H$ NMR δ (ppm) ($CD_3OD$): 8.26 (s, 1H), 7.87 (d, J=8.6 Hz, 2H), 7.85 (s, 1H), 7.82 (d, J=8.7 Hz, 2H), 5.56 (qt, J=5.3 Hz, 1H), 4.98 (t, J=5.2 Hz, 1H), 4.92 (broad s, 2H), 4.62 (broad s, 2H), 4.48 (t, J=5.0 Hz, 1H), 4.28-4.32 (m, 1H), 4.18 (dd, J=5.7 Hz, J=10.2 Hz, 1H), 4.12 (dd, J=4.9 Hz, J=10.2 Hz, 1H), 3.91 (t, J=7.6 Hz, 1H), 3.61 (t, J=8.5 Hz, 1H), 3.61 (s, 2H), 1.42 (s, 6H).

EXAMPLE 15

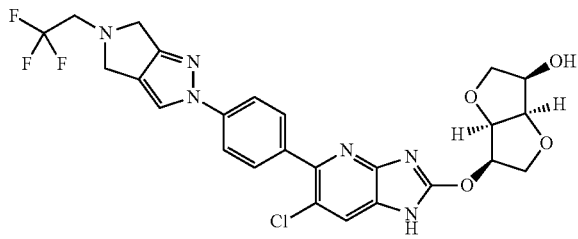 [SMILES: O[C@@H]1CO[C@H]2[C@@H]1OC[C@H]2Oc1nc2nc(-c3ccc(-n4cc5c(n4)CN(CC(F)(F)F)C5)cc3)c(Cl)cc2[nH]1]

(3R,3aR,6R,6aR)-6-[[6-chloro-5-[4-[5-(2,2,2-trifluoroethyl)-4,6-dihydropyrrolo[3,4-c]pyrazol-2-yl]phenyl]-1H-imidazo[4,5-b]pyridin-2-yl]oxy]-2,3,3a,5,6,6a-hexahydrofuro[3,2-b]furan-3-ol Step A: (3R,3aR,6R,6aR)-6-[1-allyl-6-chloro-5-[4-[5-(2,2,2-trifluoroethyl)-4,6-dihydropyrrolo[3,4-c]pyrazol-2-yl]phenyl]imidazo[4,5-b]pyridin-2-yl]oxy-2,3,3a,5,6,6a-hexahydrofuro[3,2-b]furan-3-ol 2-iodo-1,1,1-trifluoroethane (12.5 µl, 0.127 mmol) was added to a stirred solution of (3R,3aR,6R,6aR)-6-[1-allyl-6-chloro-5-[4-(5,6-dihydro-4H-pyrrolo[3,4-c]pyrazol-2-yl)phenyl]imidazo[4,5-b]pyridin-2-yl]oxy-2,3,3a,5,6,6a-hexahydrofuro[3,2-b]furan-3-ol (59.9 mg, 0.115 mmol) in dioxane (0.46 ml). The reaction mixture was a pale yellow solution that was heated to 80° C. After 2 days, N,N-diisopropylethylamine (40 µl, 0.229 mmol), 2,2,2-trifluoroethyl trifluoromethane-sulfonate (34 µl, 0.236 mmol), and additional dioxane (0.2 ml) were added to the reaction mixture. After stirring an additional 18 hours, the reaction mixture was cooled to room temperature. The reaction mixture was evaporated under reduced pressure to give a dark amber residue. The residue was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined and evaporated under reduced pressure to give the desired product as an amber residue. LC-MS: calculated for $C_{28}H_{26}ClF_3N_6O_4$ 602.17 observed m/e: 603.19 $(M+H)^+$ (Rt 1.20/2 min)

Step B: (3R,3aR,6R,6aR)-6-[[6-chloro-5-[4-[5-(2,2,2-trifluoroethyl)-4,6-dihydropyrrolo[3,4-c]pyrazol-2-yl]phenyl]-1H-imidazo[4,5-b]pyridin-2-yl]oxy]-2,3,3a,5,6,6a-hexahydrofuro[3,2-b]furan-3-ol A 4 mL vial was charged with palladium(II) acetate (2.6 mg, 0.012 mmol), 1,4-bis(diphenylphosphino)butane (3.0 mg, 7.03 µmol), and ethanol (0.1 ml). This catalyst mixture was degassed (3×) and stirred under nitrogen for 15 min. Sodium borohydride (3.5 mg, 0.093 mmol) was added to a stirred solution of (3R,3aR,6R,6aR)-6-[1-allyl-6-chloro-5-[4-[5-(2,2,2-trifluoroethyl)-4,6-dihydropyrrolo[3,4-c]pyrazol-2-yl]phenyl]imidazo[4,5-b]pyridin-2-yl]oxy-2,3,3a,5,6,6a-hexahydrofuro[3,2-b]furan-3-ol (9.5 mg, 0.016 mmol) in ethanol (0.15 ml) and DCM (0.05 ml). The sodium borohydride mixture was degassed (3×) and placed under nitrogen. The catalyst mixture was transferred via syringe to the sodium borohydride reaction mixture.

The resulting reaction mixture was a dark suspension that was stirred at room temperature. After 3 hours, the reaction mixture was evaporated under reduced pressure to give a black residue. The residue was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{25}H_{22}ClF_3N_6O_4$ 562.13 observed m/e: 563.14 $(M+H)^+$ (Rt 1.12/2 min); $^1H$ NMR δ (ppm) ($CD_3OD$): 8.10 (s, 1H), 7.91 (s, 1H), 7.85 (d, J=8.6 Hz, 2H), 7.79 (d, J=8.7 Hz, 2H), 5.57 (qt, J=5.3 Hz, 1H), 4.98 (t, J=5.3 Hz, 1H), 4.48 (t, J=5.0 Hz, 1H), 4.26-4.32 (m, 1H) 4.26 (s, 4H), 4.18 (dd, J=5.6 Hz, J=10.3 Hz, 1H), 4.14 (dd, J=4.7 Hz, J=10.2 Hz, 1H), 3.91 (t, J=7.6 Hz, 1H), 3.81 (qt, J=9.5 Hz, 2H), 3.61 (t, J=8.7 Hz, 1H).

EXAMPLE 16

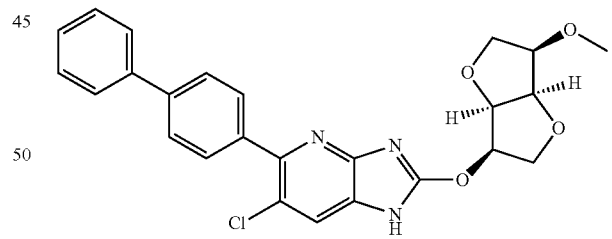

2-[[(3R,3aR,6R,6aR)-3-methoxy-2,3,3a,5,6,6a-hexahydrofuro[3,2-b]furan-6-yl]oxy]-6-chloro-5-(4-phenylphenyl)-1H-imidazo[4,5-b]pyridine Step A: 2-[[2-[[(3R,3aR,6R,6aR)-3-methoxy-2,3,3a,5,6,6a-hexahydrofuro[3,2-b]furan-6-yl]oxy]-6-chloro-5-(4-phenylphenyl)imidazo[4,5-b]pyridin-1-yl]methoxy]ethyl-trimethyl-silane Iodomethane (40 µl, 0.640 mmol) and sodium hydride (7.7 mg, 0.193 mmol) were added to a stirred solution of (3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-ol (35.6 mg, 0.061 mmol) in DMF (0.2 ml). The reaction mixture was stirred at room temperature for 4 hours. The reaction mixture was then partitioned between EtOAc (40 ml), water (10 ml), and 2 N HCl (10 ml). The organic layer was washed with water (2×20 ml) and brine (1×10 ml), dried over MgSO4, filtered, and evaporated under reduced pressure to give a pale amber residue. The residue was dissolved in EtOAc and loaded onto a 500 micron 20 cm×20 cm silica gel plate, which was developed using 70% EtOAc/hexane. The silica containing the product bands was collected and eluted with EtOAc (80 ml). The solvent was evaporated under reduced pressure to give the desired product as a colorless residue. LC-MS: calculated for $C_{31}H_{36}ClN_3O_5Si$ 593.21 observed m/e: 594.24 (M+H)+ (Rt 1.40/2 min)

Step B: 2-[[(3R,3aR,6R,6aR)-3-methoxy-2,3,3a,5,6,6a-hexahydrofuro[3,2-b]furan-6-yl]oxy]-6-chloro-5-(4-phenylphenyl)-1H-imidazo[4,5-b]pyridine TFA (0.7 ml, 9.09 mmol) was added to a stirred solution of 2-[[2-[[(3R,3aR,6R,6aR)-3-methoxy-2,3,3a,5,6,6a-hexahydrofuro[3,2-b]furan-6-yl]oxy]-6-chloro-5-(4-phenylphenyl)-imidazo[4,5-b]pyridin-1-yl]methoxy]ethyl-trimethyl-silane in DCM (0.7 ml). The reaction mixture was stirred at room temperature. After 1.5 hours, the reaction mixture was evaporated under reduced pressure to give a colorless residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{25}H_{22}ClN_3O_4$ 463.13 observed m/e: 464.16 (M+H)+ (Rt 1.21/2 min); 1H NMR δ (ppm) (CD3OD): 8.10 (s, 1H), 7.78 (ab qt, J=8.2 Hz, J=11.5 Hz, 4H), 7.72 (d, J=8.0 Hz, 2H), 7.50 (t, J=7.8 Hz, 2H), 7.40 (t, J=7.5 Hz, 1H), 5.62 (qt, J=5.0 Hz, 1H), 5.02 (t, J=5.3 Hz, 1H), 4.65 (t, J=4.8 Hz, 1H), 4.18 (dd, J=4.4 Hz, J=10.6 Hz, 1H), 4.14 (dd, J=5.4 Hz, 10.6 Hz, 1H), 3.99-4.03 (m, 1H), 3.98 (t, J=7.2 Hz, 1H), 3.64 (t, J=8.3 Hz, 1H), 3.49 (s, 3H).

TABLE 4

Compounds prepared according to the methods in Example 16.

| Example Number | Structure | HPLC-mass spectrum m/e |
|---|---|---|
| 17 | 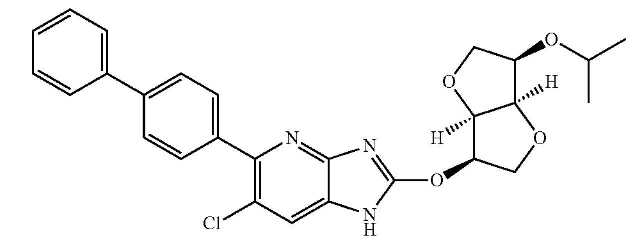 [SMILES: CC(C)O[C@@H]1CO[C@H]2[C@@H]1OC[C@H]2Oc1nc2nc(-c3ccc(-c4ccccc4)cc3)c(Cl)cc2[nH]1] | 492.22 |
| 18 | 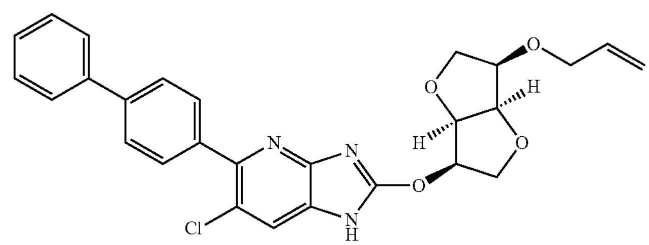 [SMILES: C=CCO[C@@H]1CO[C@H]2[C@@H]1OC[C@H]2Oc1nc2nc(-c3ccc(-c4ccccc4)cc3)c(Cl)cc2[nH]1] | 490.19 |

EXAMPLE 19

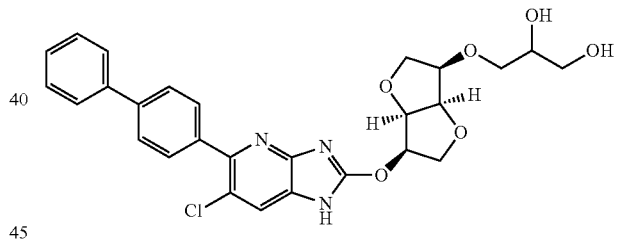

3-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]propane-1,2-diol Step A: 3-[[(3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]oxy]propane-1,2-diol Sodium periodate (53.4 mg, 0.250 mmol) was added to a stirred suspension of 2-[[2-[[(3R,3aR,6R,6aR)-3-allyloxy-2,3,3a,5,6,6a-hexahydrofuro[3,2-b]furan-6-yl]oxy]-6-chloro-5-(4-phenylphenyl)imidazo[4,5-b]pyridin-1-yl]methoxy]ethyl-trimethyl-silane (68.9 mg, 0.111 mmol) and ruthenium (III) chloride hydrate (1.9 mg, 8.43 μmol) in acetonitrile (0.95 ml) and water (0.16 ml). The reaction mixture was stirred at room temperature. After 4 hours, additional sodium periodate (31.8 mg, 0.149 mmol) was added to the reaction mixture. After 2 more hours, the reaction mixture was placed in the refrigerator overnight. The reaction mixture was removed from the refrigerator and allowed to warm to room temperature before being partitioned between EtOAc (40 ml) and saturated aqueous sodium thiosulfate (30 ml). An inseparable emulsion formed, which was filtered through a pad of Celite™. The biphasic filtrate was re-partitioned and the aqueous layer was extracted with EtOAc (2×20 ml). The organic layers were combined, washed with brine (1×15 ml), dried over MgSO$_4$, filtered, and evaporated under reduced pressure to give a colorless residue. The residue was dissolved in EtOAc and loaded onto two 500 micron 20 cm×20 cm silica gel plates, which were developed using 10% MeOH/DCM. The silica containing the product band was collected and eluted with 10% MeOH/DCM (80 ml). The solvent was evaporated under reduced pressure to give the desired product as a colorless residue. LC-MS: calculated for C$_{33}$H$_{40}$ClN$_3$O$_7$Si 653.23 observed m/e: 654.36 (M+H)$^+$ (Rt 1.33/2 min)

Step B: 3-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]propane-1,2-diol TFA (0.25 ml, 3.24 mmol) was added to a stirred solution of 3-[[(3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]oxy]propane-1,2-diol (6.1 mg, 9.32 μmol) in DCM (0.25 ml). The reaction mixture was stirred at room temperature. After 2.5 hours, the reaction mixture was evaporated under reduced pressure. Potassium trimethylsilanolate (9.2 mg, 0.072 mmol) was added to a stirred solution of the residue in THF (0.5 ml). The reaction mixture was stirred at room temperature. After 1.5 hours, additional potassium trimethylsilanolate (18.2 mg, 0.142 mmol) was added to the reaction mixture. After an additional 1.5 hours, the reaction mixture was evaporated under reduced pressure to give a pale amber residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for C$_{27}$H$_{26}$ClN$_3$O$_6$ 523.15 observed m/e: 524.22 (M+H)$^+$ (Rt 1.16/2 min); $^1$H NMR δ (ppm) (CD$_3$OD): 7.98 (s, 1H), 7.74-7.78 (m, 4H), 7.71 (d, J=7.4 Hz, 2H), 7.48 (t, J=7.7 Hz, 2H), 7.39 (t, J=7.4 Hz, 1H), 5.59 (qt, J=5.1 Hz, 1H), 5.01 (t, J=5.3 Hz, 1H), 4.65 (t, J=5.0 Hz, 1H), 4.13-4.17 (m, 3H), 3.98-4.01 (m, 1H), 3.54-3.81 (m, 6H).

EXAMPLE 20

2-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]ethanol Step A: 2-[[(3R,3aR,6R,6aR)-6-[6-chloro-5-(4-phenylphenyl)-1-(2-trimethylsilylethoxy-methyl)imidazo[4,5-b]pyridin-2-yl]oxy-2,3,3a,5,6,6a-hexahydrofuro[3,2-b]furan-3-yl]oxy]ethanol Sodium borohydride (3.1 mg, 0.082 mmol) was added to a stirred solution of 2-[[(3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]oxy]acetaldehyde (11.1 mg, 0.018 mmol) in MeOH (0.3 ml) that had been cooled to 0° C. in an ice bath. After 1.5 hours, the reaction mixture was removed from the ice bath and allowed to warm to room temperature. The reaction mixture was evaporated under reduced pressure to give the desired product as a white residue. LC-MS: calculated for C$_{32}$H$_{38}$ClN$_3$O$_6$Si 623.22 observed m/e: 624.37 (M+H)$^+$ (Rt 1.35/2 min)

Step B: 2-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]ethanol TFA (0.25 ml, 3.24 mmol) was added to a stirred solution of the residue from the previous step in DCM (0.25 ml). The reaction mixture was stirred at room temperature. After 2 hours, the reaction mixture was evaporated under reduced pressure to give a colorless residue. Potassium trimethylsilanolate (30.6 mg, 0.239 mmol) was added to a stirred solution of the residue in THF (0.5 ml). The reaction mixture was stirred at room temperature. After 1.5 hours, the reaction mixture was evaporated under reduced pressure to give a white residue. This material was purified by preparative HPLC reverse phase (C-18), using a 30×150 mm Sunfire™ column and eluting with a 20%-100% acetonitrile/water+0.05% TFA gradient, followed by a 100% acetonitrile+0.05% TFA flush. The product fractions were combined, evaporated under reduced pressure, and lyophilized from ethanol and benzene to give the title compound as a white solid. LC-MS: calculated for C$_{26}$H$_{24}$ClN$_3$O$_5$ 493.14 observed m/e: 494.18 (M+H)$^+$ (Rt 1.18/2 min); $^1$H NMR δ (ppm) (CD$_3$OD): 7.95 (s, 1H), 7.73-7.77 (m, 4H), 7.70 (d, J=7.8 Hz, 2H), 7.48 (t, J=7.6 Hz, 2H), 7.38 (t, J=7.4 Hz, 1H), 5.58 (qt, J=5.1 Hz, J=10.4 Hz, 1H), 5.01 (t, J=5.3 Hz, 1H), 4.64 (t, J=4.9 Hz, 1H), 4.13-4.16 (m, 3H), 4.00 (t, J=7.5 Hz, 1H), 3.76-3.80 (m, 1H), 3.61-3.72 (m, 4H).

EXAMPLE 21

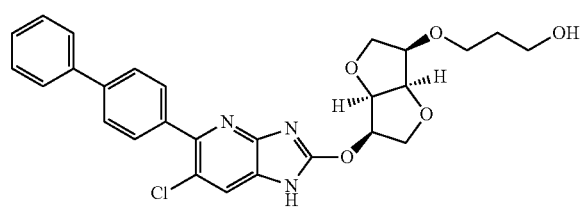 [SMILES: OCCCO[C@@H]1CO[C@H]2[C@@H]1OC[C@H]2Oc1nc2nc(-c3ccc(-c4ccccc4)cc3)c(Cl)cc2[nH]1]

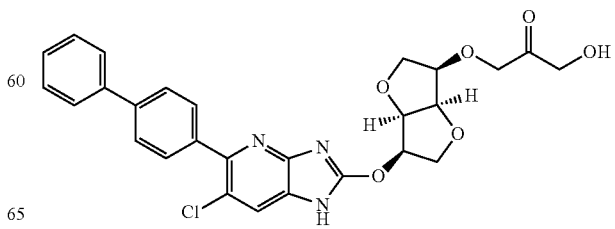

2-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]acetic acid Step A: 2-[[(3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]oxy]acetic acid Sodium periodate (19.4 mg, 0.091 mmol) and ruthenium (III) chloride hydrate (1.3 mg, 5.77 μmol) were added to a stirred biphasic mixture of 2-[[(3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]oxy]acetaldehyde (13.8 mg, 0.022 mmol) in carbon tetrachloride (0.12 ml), acetonitrile (0.09 ml), and water (0.15 ml). The reaction mixture was stirred at room temperature. After 3 hours, the reaction mixture was partitioned between EtOAc (30 ml) and water (30 ml). The aqueous layer was extracted with EtOAc (2×20 ml). The organic layers were combined, washed with brine (1×20 ml), dried over $MgSO_4$, filtered, and evaporated under reduced pressure to give a colorless residue. The residue was dissolved in EtOAc and loaded onto a 500 micron 20 cm×20 cm silica gel plate, which was developed twice using a 94:5:1 DCM/MeOH/AcOH solvent mixture (fresh solvent was used for each development). The silica containing the product band was collected and eluted with a 90:9:1 DCM/MeOH/AcOH solvent mixture (80 ml). The solvent was evaporated under reduced pressure to give the desired product as a colorless residue. LC-MS: calculated for $C_{32}H_{36}ClN_3O_7Si$ 637.2 observed m/e: 638.33 (M+H)$^+$ (Rt 1.35/2 min)

Step B: 2-[[(3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]oxy]acetic acid TFA (0.5 ml, 6.49 mmol) was added to a stirred solution of the residue from the previous step in DCM (0.5 ml). The reaction mixture was stirred at room temperature. After 3.5 hours, the reaction mixture was evaporated under reduced pressure to give a yellow residue. The residue was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{26}H_{22}ClN_3O_6$ 507.12 observed m/e: 508.17 (M+H)$^+$ (Rt 1.18/2 min); $^1$H NMR δ (ppm) (CD$_3$OD): 7.96 (s, 1H), 7.74-7.77 (m, 4H), 7.71 (d, J=7.9 Hz, 2H), 7.48 (t, J=7.7 Hz, 2H), 7.39 (t, J=7.4 Hz, 1H), 5.57 (qt, J=5.3 Hz, 1H), 4.99 (t, J=5.4 Hz, 1H), 4.67 (t, J=5.1 Hz, 1H), 4.26 (ab qt, J=16.7 Hz, J=50.4 Hz, 2H), 4.13-4.25 (m, 3H), 4.01 (dd, J=6.9 Hz, J=8.5 hz, 1H), 3.76 (t, J=8.5 Hz, 1H).

EXAMPLE 22

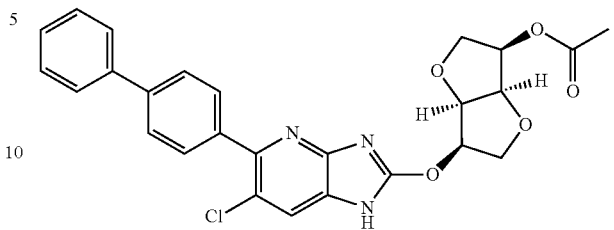

[(3R,3aR,6R,6aR)-3-[[6-chloro-5-(4-phenylphenyl)-1H-imidazo[4,5-b]pyridin-2-yl]oxy]-2,3,3a,5,6,6a-hexahydrofuro[3,2-b]furan-6-yl]acetate Step A: [(3R,3aR,6R,6aR)-3-[6-chloro-5-(4-phenylphenyl)-1-(2-trimethylsilylethoxy-methyl)imidazo[4,5-b]pyridin-2-yl]oxy-2,3,3a,5,6,6a-hexahydrofuro[3,2-b]furan-6-yl]acetate Triethylamine (22 μl, 0.158 mmol) and acetyl chloride (10 μl, 0.141 mmol) were added to a stirred solution of (3R,3aR,6R,6aR)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-ol (44.5 mg, 0.077 mmol) in DCM (0.77 ml). The reaction mixture was stirred at room temperature. After 3.5 hours, additional triethylamine (22 μl, 0.158 mmol) and acetyl chloride (10 μl, 0.141 mmol) were added to the reaction mixture. After an additional 18.5 hours, the reaction mixture was evaporated under reduced pressure to give the desired product as an amber residue. LC-MS: calculated for $C_{32}H_{36}ClN_3O_6Si$ 621.21 observed m/e: 622.30 (M+H)$^+$ (Rt 1.40/2 min)

Step B: [(3R,3aR,6R,6aR)-3-[[6-chloro-5-(4-phenylphenyl)-1H-imidazo[4,5-b]pyridin-2-yl]oxy]-2,3,3a,5,6,6a-hexahydrofuro[3,2-b]furan-6-yl]acetate TFA (0.5 ml, 6.49 mmol) was added to a stirred solution of the residue from the previous step in DCM (0.5 ml). The reaction mixture was stirred at room temperature. After 1 hour, the reaction mixture was evaporated under reduced pressure to give an amber residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{26}H_{22}ClN_3O_5$ 491.12 observed m/e: 492.20 (M+H)$^+$ (Rt 1.22/2 min); $^1$H NMR δ (ppm) (CD$_3$OD): 7.97 (s, 1H), 7.75 (s, 4H), 7.70 (d, J=7.5 Hz, 2H), 7.48 (t, J=7.7 Hz, 2H), 7.38 (t, J=7.4 Hz, 1H), 5.55 (qt, J=5.6 Hz, 1H), 5.10 (qt, J=6.4 Hz, 1H), 4.98 (t, J=5.3 Hz, 1H), 4.79 (t, J=5.4 Hz, 1H), 4.20 (dd, J=5.9 Hz, J=9.8 Hz, 1H), 4.03-4.07 (m, 2H), 3.85 (dd, J=7.2 Hz, J=9.1 Hz, 1H), 2.12 (s, 3H).

EXAMPLE 23

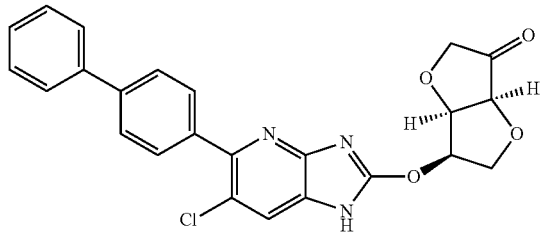 [SMILES: O=C1CO[C@H]2[C@@H]1OC[C@H]2Oc1nc2nc(-c3ccc(-c4ccccc4)cc3)c(Cl)cc2[nH]1]

(3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one Combined (3R,3aR,6R,6aR)-6-[[6-chloro-5-(4-phenylphenyl)-1H-imidazo[4,5-b]pyridin-2-yl]oxy]-2,3,3a,5,6,6a-hexahydrofuro[3,2-b]furan-3-ol (5.00 g, 11.11 mmol) and Dess-Martin Periodinane 0.3 M in DCM (49.0 ml, 14.70 mmol) in a 250 ml flask. The reaction mixture was stirred at room temperature. After 5.5 hours, additional Dess-Martin Periodinane (2.3407 g, 5.52 mmol) in DCM (18.0 ml) was added to the reaction mixture. After an additional 20 hours, additional Dess-Martin Periodinane (1.01 g, 2.38 mmol) in DCM (9.0 ml) was added to the reaction mixture. After an additional 5 hours, additional Dess-Martin Periodinane (566.7 mg, 1.34 mmol) was added to the reaction mixture. After an additional 16 hours, the reaction mixture was partitioned between EtOAc (400 ml) and water (200 ml). A white solid precipitated to give a thick white suspension, which was filtered through a pad of Celite™. The biphasic filtrate was separated. The filtered solid was washed with EtOAc (2×50 ml). The aqueous layer was extracted with each of the EtOAc washes after additional EtOAc (50 ml) had been added to each wash. The organic layers were combined, washed with brine (1×50 ml), dried over MgSO$_4$, filtered, and evaporated under reduced pressure to give a yellow residue. The filtered solid was suspended in DCM/MeOH (~300 ml). Sodium thiosulfate (4.72 g, 29.85 mmol) in water (100 ml) was added to the suspension, which was stirred in a 1 L Erlemeyer flask. 5 N NaOH (10.0 ml, 50.0 mmol) was added to the suspension, which quickly caused the solid to dissolve. The biphasic mixture was separated. The aqueous layer was acidified to pH 5 with concentrated aqueous HCl, resulting in a white precipitate. Saturated aqueous NaHCO$_3$ was added to the aqueous layer to dissolve the precipitate before the aqueous layer was extracted with DCM (3×100 ml). The organic layers were combined, washed with saturated aqueous NaHCO$_3$ (2×50 ml) and brine (1×50 ml), dried over MgSO$_4$, filtered, combined with the material from the first workup, and evaporated under reduced pressure to give a yellow foam. The foam was purified by flash chromatography utilizing a 220 g silica RediSep R$_f$® column and employing a 0-90% EtOAc/hexane gradient. The product fractions were combined, evaporated under reduced pressure, and lyophilized from ethanol and benzene to give the title compound as a white solid. LC-MS: calculated for $C_{24}H_{18}ClN_3O_4$ 447.1 observed m/e: 448.15 (M+H)$^+$ (Rt 1.16/2 min); $^1$H NMR δ (ppm) (CD$_3$OD): 7.95 (s, 1H), 7.75 (s, 4H), 7.71 (d, J=7.8 Hz, 2H), 7.48 (t, J=7.6 Hz, 2H), 7.38 (t, J=7.4 Hz, 1H), 5.55 (qt, J=5.4 Hz, 1H), 5.02 (t, J=5.4 Hz, 1H), 4.25 (d, J=5.1 Hz, 1H), 4.18 (dd, J=5.7 Hz, J=10.0 Hz, 1H), 4.11 (dd, J=5.1 Hz, J=10.1 Hz, 1H), 3.89 (d, J=9.5 Hz, 1H), 3.64 (d, J=9.4 Hz, 1H).

EXAMPLE 24

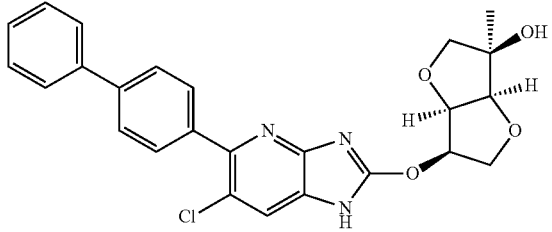 [SMILES: C[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-3-[[6-chloro-5-(4-phenylphenyl)-1H-imidazo[4,5-b]pyridin-2-yl]oxy]-6-methyl-3,3a,5,6a-tetrahydro-2H-furo[3,2-b]furan-6-ol A stirred solution of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (21.4 mg, 0.048 mmol) in THF (0.5 ml) was degassed (3×) and placed under nitrogen after being cooled to 0° C. in an ice bath. Methylmagnesium bromide 3.0 M in diethyl ether (0.16 ml, 0.480 mmol) was added to the reaction mixture. After 20 minutes, the reaction mixture was removed from the bath and allowed to warm to room temperature. After 1 hour, the reaction mixture was transferred via pipette into saturated aqueous NaHCO$_3$ (15 ml) before being partitioned between EtOAc (30 ml) and water (15 ml). The aqueous layer was extracted with EtOAc (2×20 ml). The organic layers were combined, washed with brine (1×15 ml), dried over MgSO$_4$, filtered, and evaporated under reduced pressure to give a colorless residue. This material was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{25}H_{22}ClN_3O_4$ 463.13 observed m/e: 464.12 (M+H)$^+$ (Rt 1.19/2 min); $^1$H NMR δ (ppm) (CD$_3$OD): 8.00 (s, 1H), 7.74-7.78 (m, 4H), 7.71 (d, J=7.4 Hz, 2H), 7.49 (t, J=7.7 Hz, 2H), 7.39 (t, J=7.4 Hz, 1H), 5.60 (qt, J=5.1 Hz, 1H), 5.00 (t, J=5.2 Hz, 1H), 4.13-4.19 (m, 2H), 4.07 (d, J=4.8 Hz, 1H), 3.70 (d, J=8.1 Hz, 1H), 3.54 (d, J=8.1 Hz, 1H), 1.32 (s, 3H).

TABLE 5

Compounds prepared according to the methods in Example 24.

| Example Number | Structure | HPLC-mass spectrum m/e |
|---|---|---|
| 25 | 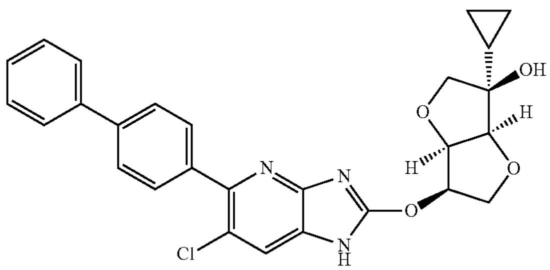 [SMILES: O[C@]1(C2CC2)CO[C@@H]2[C@H](Oc3nc4nc(-c5ccc(-c6ccccc6)cc5)c(Cl)cc4[nH]3)CO[C@@H]21] | 490.17 |
| 26 | 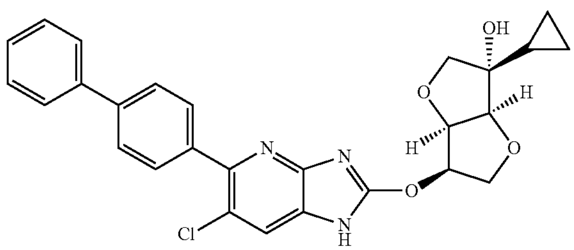 [SMILES: O[C@@]1(C2CC2)CO[C@@H]2[C@H](Oc3nc4nc(-c5ccc(-c6ccccc6)cc5)c(Cl)cc4[nH]3)CO[C@@H]21] | 490.16 |
| 27 | 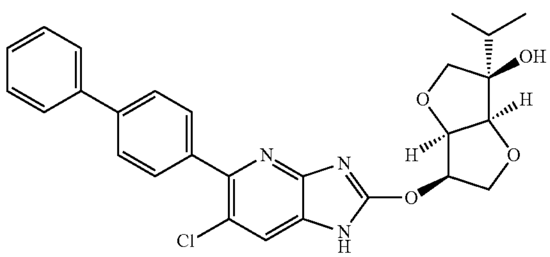 [SMILES: CC(C)[C@@]1(O)CO[C@@H]2[C@H](Oc3nc4nc(-c5ccc(-c6ccccc6)cc5)c(Cl)cc4[nH]3)CO[C@@H]21] | 492.22 |
| 28 | 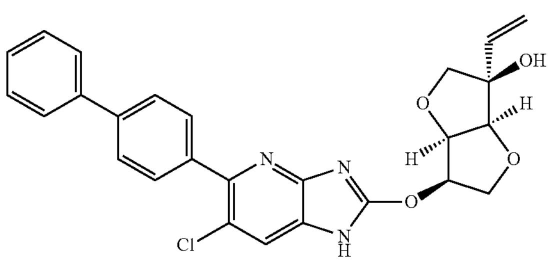 [SMILES: C=C[C@@]1(O)CO[C@@H]2[C@H](Oc3nc4nc(-c5ccc(-c6ccccc6)cc5)c(Cl)cc4[nH]3)CO[C@@H]21] | 476.18 |
| 29 | 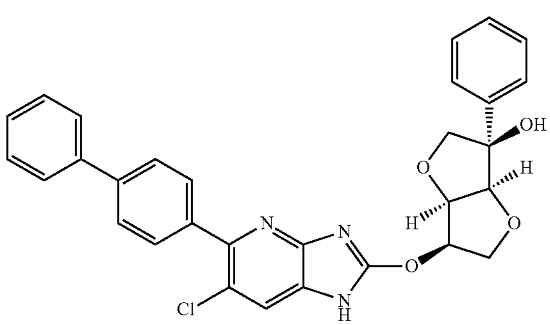 [SMILES: O[C@]1(c2ccccc2)CO[C@@H]2[C@H](Oc3nc4nc(-c5ccc(-c6ccccc6)cc5)c(Cl)cc4[nH]3)CO[C@@H]21] | 526.22 |

EXAMPLE 30

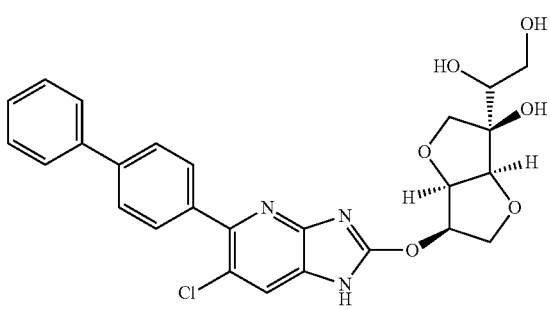 [SMILES: OCC(O)[C@@]1(O)CO[C@@H]2[C@H](Oc3nc4nc(-c5ccc(-c6ccccc6)cc5)c(Cl)cc4[nH]3)CO[C@@H]21]

1-[(3R,3aR,6S,6aS)-3-[[6-chloro-5-(4-phenylphe-
nyl)-1H-imidazo[4,5-b]pyridin-2-yl]oxy]-6-hydroxy-
3,3a,5,6a-tetrahydro-2H-furo[3,2-b]furan-6-yl]
ethane-1,2-diol Sodium periodate (21.9 mg, 0.102 mmol) was added to a stirred suspension of (3R,3aR,6R,6aS)-3-[[6-chloro-5-(4-phenylphenyl)-1H-imidazo[4,5-b]pyridin-2-yl]oxy]-6-vinyl-3,3a,5,6a-tetrahydro-2H-furo[3,2-b]furan-6-ol (23.4 mg, 0.049 mmol) and ruthenium (III) chloride hydrate (1.0 mg, 4.44 µmol) in acetonitrile (0.42 ml) and water (0.07 ml). The reaction mixture was stirred at room temperature. After 4 hours, the reaction mixture was partitioned between EtOAc (20 ml) and saturated aqueous sodium thiosulfate (20 ml). The aqueous layer was extracted with EtOAc (2×20 ml). The organic layers were combined, washed with brine (1×10 ml), dried over $MgSO_4$, filtered, and evaporated under reduced pressure to give a colorless residue. The residue was dissolved in EtOAc/MeOH and loaded onto a 500 micron 20 cm×20 cm silica gel plate, which was developed twice using fresh 5% MeOH/DCM each time. The silica containing the product band was collected and eluted with 10% MeOH/DCM (80 ml). The solvent was evaporated under reduced pressure and the resulting residue was lyophilized from ethanol and benzene to give the title compound as a white solid. LC-MS: calculated for $C_{26}H_{24}ClN_3O_6$ 509.14 observed m/e: 510.12 $(M+H)^+$ (Rt 1.15/2 min); $^1H$ NMR δ (ppm) ($CD_3OD$): 7.84 (broad s, 1H), 7.72-7.76 (m, 4H), 7.70 (d, J=7.9 Hz, 2H), 7.48 (t, J=7.7 Hz, 2H), 7.37 (t, J=7.4 Hz, 1H), 5.50-5.51 (m, 1H), 4.93 (t, J=5.4 Hz, 1H, minor isomer) 4.91 (t, J=5.5 Hz, 1H, major isomer), 4.66 (d, J=5.4 Hz, 1H, minor isomer) 4.59 (d, J=5.2 Hz, 1H, major isomer), 4.26 (dd, J=6.5 Hz, J=9.2 Hz, 1H), 4.12 (dd, J=6.7 Hz, J=9.1 Hz, 1H), 3.99 (d, J=9.5 Hz, 1H, major isomer), 3.91 (d, J=9.6 Hz, 1H, minor isomer), 3.80-3.84 (m, 1H, major isomer), 3.75 (d, J=9.4 Hz, 1H, major isomer), 3.71-3.76 (m, 2H, minor isomer), 3.60-3.65 (m, 2H).

EXAMPLE 31

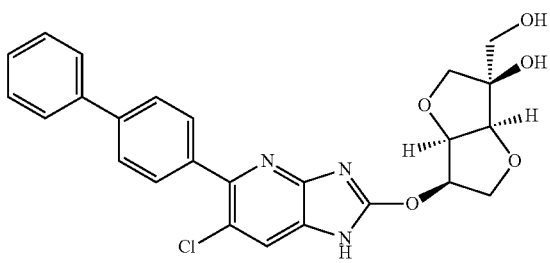 [SMILES: OC[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-3-[[6-chloro-5-(4-phenylphenyl)-
1H-imidazo[4,5-b]pyridin-2-yl]oxy]-6-(hydroxym-
ethyl)-3,3a,5,6a-tetrahydro-2H-furo[3,2-b]furan-6-ol Sodium borohydride (1.3 mg, 0.034 mmol) was added to a stirred solution of (3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-carbaldehyde (5.4 mg, 0.011 mmol) in methanol (0.5 ml) that had been cooled to 0° C. in an ice bath. After 1.5 hours, additional sodium borohydride (3.0 mg, 0.079 mmol) was added to the reaction mixture. After an additional 1.5 hours, additional sodium borohydride (2.8 mg, 0.074 mmol) was added to the reaction mixture. After another hour, the reaction mixture was placed in the refrigerator overnight. In the morning, the reaction mixture was removed from the refrigerator and placed in an ice bath. Additional sodium borohydride (3.2 mg, 0.085 mmol) was added to the reaction mixture. After 1.5 hours, the reaction mixture was removed from the ice bath and allowed to warm to room temperature. The reaction mixture was directly purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{25}H_{22}ClN_3O_5$ 479.12 observed m/e: 480.18 $(M+H)^+$ (Rt 1.16/2 min); $^1H$ NMR δ (ppm) ($CD_3OD$): 7.86 (s, 1H), 7.73-7.77 (m, 4H), 7.71 (d, J=7.8 Hz, 2H), 7.48 (t, J=7.6 Hz, 2H), 7.38 (t, J=6.8 Hz, 1H), 5.56 (qt, J=5.4 Hz, 1H), 4.98 (t, J=5.3 Hz, 1H), 4.30 (d, J=5.0 Hz, 1H), 4.20 (dd, J=5.6 Hz, J=10.3 Hz, 1H), 4.15 (dd, J=5.1 Hz, J=10.0 Hz, 1H), 3.80 (d, J=8.7 Hz, 1H), 3.67 (d, J=8.8 Hz, 1H), 3.52-3.58 (m, 2H).

EXAMPLE 32

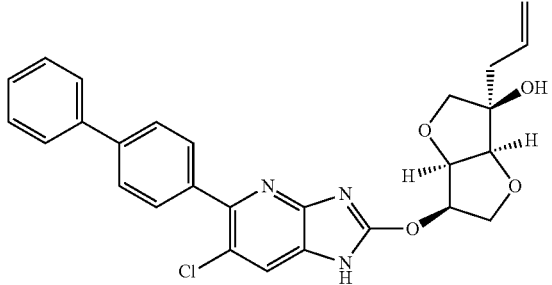 [SMILES: C=CC[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-6-allyl-3-[[6-chloro-5-(4-phe-
nylphenyl)-1H-imidazo[4,5-b]pyridin-2-yl]oxy]-3,
3a,5,6a-tetrahydro-2H-furo[3,2-b]furan-6-ol A stirred suspension of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (314.3 mg, 0.702 mmol) in THF (7.0 ml) was degassed (3×) and placed under nitrogen after being cooled to 0° C. in an ice bath. Allylmagnesium bromide 1.0 M in ether (1.4 ml, 1.400 mmol) was added to the reaction mixture dropwise over 6 minutes. After 1 hour, the reaction mixture was removed from the ice bath and allowed to warm to room temperature. The reaction mixture was transferred via pipette into saturated aqueous $NaHCO_3$ (50 ml) before being partitioned between EtOAc (100 ml) and water (50 ml). The aqueous layer was extracted with EtOAc (2×50 ml). The organic layers were combined, washed with brine (1×30 ml), dried over MgSO$_4$, filtered, and evaporated under reduced pressure to give a pale yellow residue. The residue was purified by flash chromatography utilizing a 40 g silica RediSep R$_f$® column and employing a 0-80% EtOAc/hexane gradient. The product fractions were combined and evaporated under reduced pressure to give the title compound as a colorless residue. LC-MS: calculated for C$_{27}$H$_{24}$ClN$_3$O$_4$ 489.15 observed m/e: 490.19 (M+H)$^+$ (Rt 1.23/2 min); $^1$H NMR δ (ppm) (CD$_3$OD): 7.81 (s, 1H), 7.70-7.75 (m, 4H), 7.69 (d, J=7.9 Hz, 2H), 7.47 (t, J=7.7 Hz, 2H), 7.36 (t, J=7.4 Hz, 1H), 5.90-5.99 (m, 1H), 5.53 (qt, J=5.5 Hz, J=10.8 Hz, 1H), 5.14 (broad d, J=12.9 Hz, 2H), 4.96 (t, J=5.3 Hz, 1H), 4.10-4.18 (m, 3H), 3.67 (abqt, J=8.5 Hz, J=24.6 Hz, 2H), 2.30-2.38 (m, 2H).

EXAMPLE 33

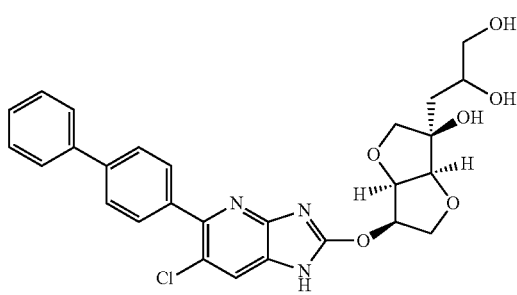 [SMILES: OCC(O)C[C@@]1(O)CO[C@@H]2[C@H](Oc3nc4nc(-c5ccc(-c6ccccc6)cc5)c(Cl)cc4[nH]3)CO[C@@H]21]

3-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]propane-1,2-diol Ruthenium(III) chloride hydrate (3.7 mg, 0.016 mmol) and sodium periodate (121.7 mg, 0.569 mmol) were added to a stirred solution of (3R,3aR,6R,6aS)-6-allyl-3-[[6-chloro-5-(4-phenylphenyl)-1H-imidazo[4,5-b]pyridin-2-yl]oxy]-3,3a,5,6a-tetrahydro-2H-furo[3,2-b]furan-6-ol (122.5 mg, 0.250 mmol) in acetonitrile (2.14 ml) and water (0.36 ml). The reaction mixture was stirred at room temperature. After 3 hours, the reaction mixture was partitioned between EtOAc (75 ml) and saturated aqueous sodium thiosulfate (40 ml). The aqueous layer was extracted with EtOAc (2×50 ml). The organic layers were combined, washed with brine (1×30 ml), dried over MgSO$_4$, filtered, and evaporated under reduced pressure to give a colorless residue. This material was dissolved in EtOAc and loaded onto three 500 micron 20 cm×20 cm silica gel plates, which were developed using 10% MeOH/DCM. The silica containing the product band was collected and eluted with 10% MeOH/DCM (80 ml). The solvent was evaporated under reduced pressure and the resulting residue was lyophilized from ethanol and benzene to give the title compound as a white solid. LC-MS: calculated for C$_{27}$H$_{26}$ClN$_3$O$_6$ 523.15 observed m/e: 524.24 (M+H)$^+$ (Rt 1.16/2 min); $^1$H NMR δ (ppm) (CD$_3$OD): 7.83 (s, 1H), 7.11-7.76 (m, 4H), 7.70 (d, J=7.8 Hz, 2H), 7.48 (t, J=7.7 Hz, 2H), 7.37 (t, J=7.4 Hz, 1H), 5.53-5.58 (m, 1H major and minor isomers), 4.97-5.00 (m, 1H major and minor isomers), 4.47 (d, J=4.7 Hz, 1H minor isomer), 4.28 (d, J=4.9 Hz, 1H major isomer), 4.12-4.22 (m, 2H major and minor isomers), 3.99-4.02 (m, 1H major and minor isomers), 3.86 (d, J=8.8 Hz, 1H major isomer), 3.69-3.74 (m, 1H major isomer, 2H minor isomer), 3.45-3.49 (m, 2H, major and minor isomers), 1.77-1.83 (m, 1H, major and minor isomers) 1.67-1.73 (m, 1H, major and minor isomers).

EXAMPLE 34

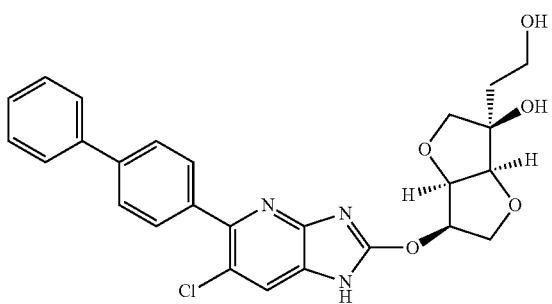 [SMILES: OCC[C@@]1(O)CO[C@@H]2[C@H](Oc3nc4nc(-c5ccc(-c6ccccc6)cc5)c(Cl)cc4[nH]3)CO[C@@H]21]

(3R,3aR,6R,6aS)-3-[[6-chloro-5-(4-phenylphenyl)-1H-imidazo[4,5-b]pyridin-2-yl]oxy]-6-(2-hydroxy-ethyl)-3,3a,5,6a-tetrahydro-2H-furo[3,2-b]furan-6-ol A stirred suspension of 2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetaldehyde (12.9 mg, 0.026 mmol) in methanol (0.5 ml) was cooled to 0° C. in an ice bath. Sodium boro-hydride (3.5 mg, 0.093 mmol) was added to the reaction mixture, resulting in gas evolution. The reaction mixture was allowed to warm to room temperature overnight. The next day, the reaction mixture was directly purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for C$_{26}$H$_{24}$ClN$_3$O$_5$ 493.14 observed m/e: 494.24 (M+H)$^+$ (Rt 1.17/2 min); $^1$H NMR δ (ppm) (CD$_3$OD): 7.97 (s, 1H), 7.74-7.77 (m, 4H), 7.71 (d, J=7.7 Hz, 2H), 7.48 (t, J=7.6 Hz, 2H), 7.38 (t, J=7.4 Hz, 1H), 5.58 (qt, J=5.3 Hz, J=10.6 Hz, 1H), 4.98 (t, J=5.3 Hz, 1H), 4.29 (d, J=4.9 Hz, 1H), 4.15-4.20 (m, 2H), 3.77-3.84 (m, 2H), 3.71 (abqt, J=8.7 Hz, J=21.2 Hz, 2H), 1.85 (t, J=6.6 Hz, 2H).

EXAMPLE 35

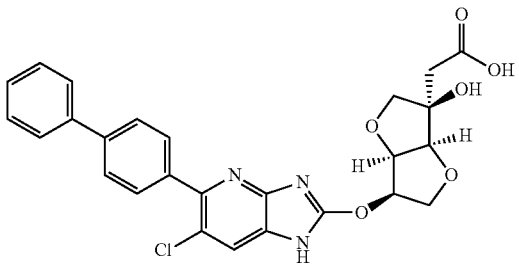 [SMILES: O=C(O)C[C@@]1(O)CO[C@@H]2[C@H](Oc3nc4nc(-c5ccc(-c6ccccc6)cc5)c(Cl)cc4[nH]3)CO[C@@H]21]

2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetic acid Sodium periodate (41.5 mg, 0.194 mmol) and ruthenium (III) chloride hydrate (1.5 mg, 6.65 μmol) were added to a stirred solution of 2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetaldehyde (32.4 mg, 0.066 mmol) in carbon tetrachloride (0.2 ml), acetonitrile (0.2 ml), and water (0.26 ml). The reaction mixture was stirred at room temperature. After 6 hours, the reaction mixture was placed in the refrigerator overnight. In the morning, the reaction mixture was removed from the refrigerator and allowed to warm to room temperature. After 4 hours, the reaction mixture was partitioned between EtOAc (40 ml) and water (40 ml). The aqueous layer was extracted with EtOAc (2×20 ml). The organic layers were combined, dried over $MgSO_4$, filtered, and evaporated under reduced pressure to give an off-white residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give the title compound as a white solid. LC-MS: calculated for $C_{26}H_{22}ClN_3O_6$ 507.12 observed m/e: 508.21 (M+H)$^+$ (Rt 1.17/2 min); $^1$H NMR δ (ppm) (CD$_3$OD): 7.97 (s, 1H), 7.74-7.77 (m, 4H), 7.70 (d, J=7.8 Hz, 2H), 7.48 (t, J=7.7 Hz, 2H), 7.38 (t, J=7.3 Hz, 1H), 5.58 (qt, J=5.4 Hz, J=10.8 Hz, 1H), 4.99 (t, J=5.4 Hz, 1H), 4.41 (d, J=4.9 Hz, 1H), 4.15-4.21 (m, 2H), 3.83 (abqt, J=8.9 Hz, J=69.3 Hz, 2H), 2.58-2.65 (m, 2H).

EXAMPLE 36

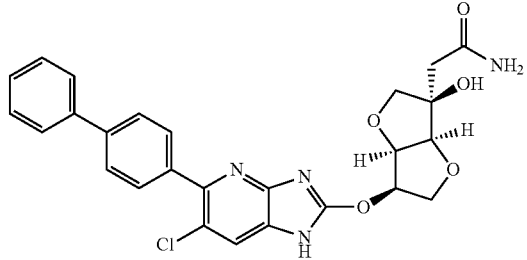 [SMILES: NC(=O)C[C@@]1(O)CO[C@@H]2[C@H](Oc3nc4nc(-c5ccc(-c6ccccc6)cc5)c(Cl)cc4[nH]3)CO[C@@H]21]

2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetamide Triethylamine (7 μl, 0.050 mmol) was added to a stirred solution of 2-[(3R,3aR,6R,6aS)-3-[[6-chloro-5-(4-phenylphenyl)-1H-imidazo[4,5-b]pyridin-2-yl]oxy]-6-hydroxy-3,3a,5,6a-tetrahydro-2H-furo[3,2-b]furan-6-yl]acetic acid (7.7 mg, 0.015 mmol) in 1,2-dimethoxyethane (0.3 ml). The reaction mixture was cooled to 0° C. in an ice bath prior to the addition of ethyl chloroformate (4.5 μl, 0.047 mmol). After an hour, ammonia was blown into the reaction for 5 minutes. The reaction mixture was removed from the ice bath and allowed to warm to room temperature. After 40 minutes, the reaction mixture was evaporated under reduced pressure to give a white residue. 1,2-Dimethoxyethane (0.4 ml) and triethylamine (0.14 ml, 1.00 mmol) were combined with the residue and the resulting suspension was cooled to 0° C. in an ice bath. Ethyl chloroformate (0.09 ml, 0.937 mmol) was added to the reaction mixture dropwise. After half an hour, ammonia was blown into the reaction for five minutes. The reaction mixture was removed from the ice bath and allowed to warm to room temperature. After 20 minutes, potassium trimethylsilanolate (23.2 mg, 0.181 mmol) was added to the reaction mixture. After 40 minutes, additional potassium trimethylsilanolate (50.8 mg, 0.396 mmol) was added to the reaction mixture. After an additional 1 hour, 5N NaOH (0.2 ml, 1.000 mmol) was added to the reaction mixture. After 1.5 hours, MeOH (0.5 ml) was added to the reaction mixture. After 16 hours, the reaction mixture was evaporated under reduced pressure to give a white solid. The solid was purified by preparative HPLC reverse phase (C-18), using a 30×150 mm Sunfire™ column and eluting with a 20%-80% acetonitrile/water+0.05% TFA gradient followed by a 80% acetonitrile/water+0.05% TFA flush. The product fractions were combined, evaporated under reduced pressure, and lyophilized from ethanol and benzene to give the title compound as a white solid. LC-MS: calculated for $C_{26}H_{23}ClN_4O_5$ 506.14 observed m/e: 507.21 (M+H)$^+$ (Rt 1.16/2 min); $^1$H NMR δ (ppm) (CD$_3$OD): 7.87 (s, 1H), 7.73-7.76 (m, 4H), 7.71 (d, J=7.9 Hz, 2H), 7.48 (t, J=7.7 Hz, 2H), 7.37 (t, J=7.4 Hz, 1H), 5.57 (qt, J=5.3 Hz, J=10.7 Hz, 1H), 5.01 (t, J=5.4 Hz, 1H), 4.31 (d, J=4.9 Hz, 1H), 4.14-4.20 (m, 2H), 3.76 (abqt, J=8.7 Hz, J=22.4 Hz, 2H), 2.48-2.55 (m, 2H).

EXAMPLE 37

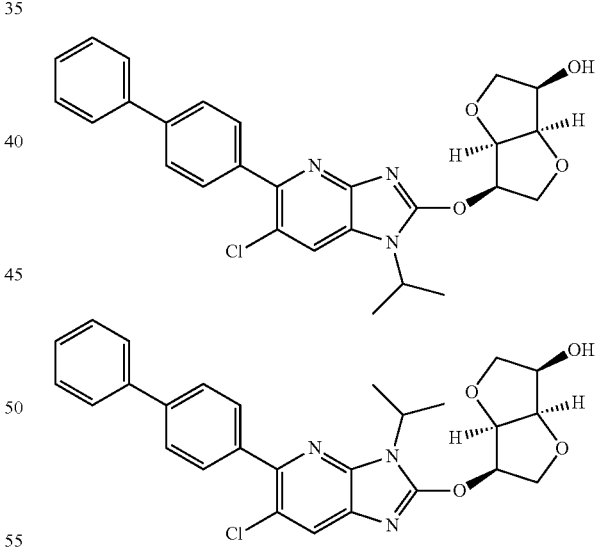

(3R,3aR,6R,6aR)-6-[6-chloro-1-isopropyl-5-(4-phenylphenyl)imidazo[4,5-b]pyridin-2-yl]oxy-2,3,3a,5,6,6a-hexahydrofuro[3,2-b]furan-3-ol and (3R,3aR,6R,6aR)-6-[6-chloro-3-isopropyl-5-(4-phenylphenyl)imidazo[4,5-b]pyridin-2-yl]oxy-2,3,3a,5,6,6a-hexahydrofuro[3,2-b]furan-3-ol A stirred solution of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (27.8 mg, 0.062 mmol) in THF (0.6 ml) was degassed (3×) and placed under nitrogen after being cooled to 0° C. in an ice bath. Isopropylmagnesium bromide 2.9 M in 2-methyltetrahydrofuran (0.22 ml, 0.638 mmol) was added slowly to the reaction mixture. After 10 minutes, the reaction mixture was removed from the ice bath and allowed to warm to room temperature. After 1.5 hours, the reaction mixture was transferred via pipette into saturated aqueous NaHCO$_3$ (15 ml) and the resulting mixture was partitioned between EtOAc (30 ml) and water (15 ml). The aqueous layer was extracted with EtOAc (2×20 ml). The organic layers were combined, washed with brine (1×15 ml), dried over MgSO$_4$, filtered, and evaporated under reduced pressure to give a pale yellow residue. This material was purified by preparative HPLC reverse phase (C-18), using a 30×150 mm Sunfire™ column and eluting with a 20%-100% acetonitrile/water+0.05% TFA gradient followed by a 100% acetonitrile+0.05% TFA flush. The product fractions were combined, evaporated under reduced pressure, and lyophilized from ethanol and benzene to give a mixture of the title compounds as a white solid. LC-MS: calculated for C$_{22}$H$_{26}$ClN$_3$O$_4$ 491.16 observed m/e: 492.19 (M+H)$^+$ (Rt 1.25/2 min); $^1$H NMR δ (ppm) (CD$_3$OD): 7.86 (s, 1H minor isomer), 7.66-7.75 (m, 7H major isomer, 6H minor isomer), 7.48 (t, J=7.6 Hz, 2H minor and major isomers), 7.38 (t, J=7.4 Hz, 1H minor and major isomers), 5.60 (qt, J=5.8 Hz, J=11.4 Hz, 1H major isomer), 5.52-5.57 (m, 1H minor isomer), 5.07-5.10 (m, 1H minor isomer), 4.99 (t, J=5.1 Hz, 1H major isomer), 4.51 (t, J=4.9 Hz, 1H major isomer), 4.35-4.40 (m, 1H minor isomer), 4.30-4.34 (m, 1H major isomer), 4.25 (dd, J=6.1 Hz, J=9.7 Hz, 1H major and minor isomers), 4.14-4.21 (m, 1H minor isomer), 4.09 (dd, J=5.7 Hz, J=9.8 Hz, 1H major and minor isomers), 3.94 (t, J=7.6 Hz, 1H major and minor isomers), 3.83-3.89 (m, 1H, major and minor isomers), 3.63 (t, J=8.5 Hz, 1H major isomer), 3.56-3.59 (m, 1H minor isomer), 1.54 (d, J=7.1 Hz, 6H major isomer), 1.31 (d, J=4.0 Hz, 6H minor isomer).

EXAMPLE 38

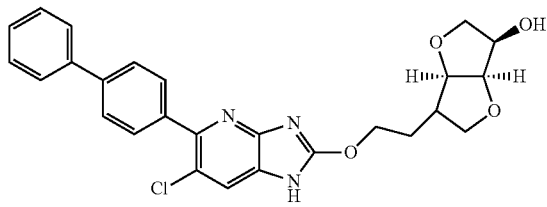 [SMILES: O[C@@H]1CO[C@@H]2C(CCOc3nc4nc(-c5ccc(-c6ccccc6)cc5)c(Cl)cc4[nH]3)CO[C@H]12]

(3R,3aR,6aR)-6-(2-((5-([1,1'-biphenyl]-4-yl)-6-chloro-1H-imidazo[4,5-b]pyridin-2-yl)oxy)ethyl)hexahydrofuro[3,2-b]furan-3-ol Step A: 5-([1,1'-biphenyl]-4-yl)-2-(2-((3aR,6R,6aS)-6-((tert-butyldimethylsilyloxy)hexa-hydrofuro[3,2-b]furan-3-yl)ethoxy)-6-chloro-1-((2-(trimethylsilyl)ethoxy)methyl)-1H-imidazo[4,5-b]pyridine 2,3,4,6,7,8,9,10-octahydropyrimido[1,2-a]azepine (0.019 ml, 0.128 mmol) was added to a stirred mixture of 5-([1,1'-biphenyl]-4-yl)-6-chloro-2-(methylsulfonyl)-1-((2-(trimethylsilyl)ethoxy)methyl)-1H-imidazo[4,5-b]pyridine (52.6 mg, 0.102 mmol) and 2-((3aR,6R,6aS)-6-((tert-butyldimethylsilyl)-oxy)hexahydro-furo[3,2-b]furan-3-yl)ethanol (38.4 mg, 0.133 mmol) in DMF (1 ml) and the mixture was stirred at room temperature overnight. Water (20 mL) was added and the mixture was extracted with ethyl acetate (2×30 mL). The combined organic fractions were washed with brine (saturated, 20 mL), dried (Na$_2$SO$_4$), filtered and the solvent was evaporated under reduced pressure. The resulting residue was purified by preparative TLC, eluting with EtOAc/isohexane (1:1) to give the title compound. LC-MS: calculated for C38H52ClN3O5Si2 721.31 observed m/e: 722.39 (M+H)$^+$ (Rt 1.58/2 min)

Step B: 3R,3aR,6aR)-6-(2-((5-([1,1'-biphenyl]-4-yl)-6-chloro-1H-imidazo[4,5-b]pyridin-2-yl)oxy)ethyl)hexahydrofuro[3,2-b]furan-3-ol TFA (0.746 μl, 9.69 μmol) was added to a stirred mixture of 5-([1,1'-biphenyl]-4-yl)-2-(243aR,6R,6aS)-6-((tert-butyldimethylsilyl)oxy)hexahydrofuro[3,2-b]furan-3-yl)ethoxy)-6-chloro-1-((2-(trimethylsilyl)ethoxy)methyl)-1H-imidazo[4,5-b]pyridine (7 mg, 9.69 μmol) in DCM (0.5 ml) and the mixture was stirred at room temperature for overnight. The reaction mixture was concentrated and the resulting residue was purified by preparative HPLC Reverse phase (C-18), eluting with acetonitrile/water+0.1% TFA, to give the title compound. LC-MS: calculated for C26H$_{24}$ClN3O4 477.15 observed m/e: 500.26 (M+Na)$^+$ (Rt 1.19/2 min); $^1$H NMR δ (ppm) (CD$_3$OD): 7.79-7.69 (m, 7H), 7.48 (m, 2H), 7.38 (m, 1H), 4.64 (m, 2H), 4.58 (m, 1H), 4.51 (m, 1H), 4.27 (dd, 1H), 4.16 (t, 1H), 3.83 (dd, 1H), 3.52 (m, 2H), 2.43 (m, 1H), 2.19 (m, 1H), 2.02 (m, 1H).

EXAMPLE 39A AND 39B

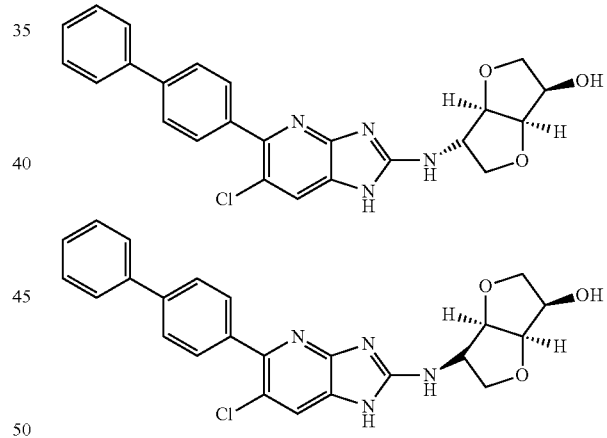

(3R,3aR,6aR)-6-((5-([1,1'-biphenyl]-4-yl)-6-chloro-1H-imidazo[4,5-b]pyridin-2-yl)amino)hexahydrofuro[3,2-b]furan-3-ol Step A: 5-([1,1'-biphenyl]-4-yl)-N-((3aR,6R,6aS)-6-((tert-butyldimethylsilyl)-oxy)hexahydrofuro[3,2-b]furan-3-yl)-6-chloro-1-((2-(trimethylsilyl)ethoxy)methyl)-1H-imidazo[4,5-b]pyridin-2-amine(minor) and 5-([1,1'-biphenyl]-4-yl)-N-((3aR,6R,6aS)-6-((tert-butyldimethylsilyl)oxy)hexahydrofuro[3,2-b]furan-3-yl)-6-chloro-1-((2-(trimethylsilyl)ethoxy)methyl)-1H-imidazo[4,5-b]pyridin-2-amine Titanium (IV) isopropoxide (0.039 ml, 0.133 mmol) was added to a stirred mixture of 5-([1,1'-biphenyl]-4-yl)-6- chloro-1-((2-(trimethylsilyl)ethoxy)methyl)-1H-imidazo[4,5-b]pyridin-2-amine (30 mg, 0.067 mmol) and (3aS,6R,6aS)-6-((tert-butyldimethylsilyl)oxy)-tetrahydrofuro[3,2-b]furan-3(2H)-one (25.8 mg, 0.100 mmol) in DCE (1 ml) and the mixture was stirred at 60° C. for 15 min. Then NaCNBH₄ (16.72 mg, 0.266 mmol) was added and the reaction mixture was stirred at 60° C. for 30 min. The mixture was cooled, diluted with ethyl acetate (40 mL)/brine (saturated, 30 mL), stirred at room temperature for 5 min. The reaction mixture was filtered through Celite™. The organic phase was dried (Na₂SO₄), filtered and the solvent was evaporated under reduced pressure. The resulting residue was purified by preparative TLC, eluting with EtOAc/isohexane (1:2) to give 2 title isomers. Minor:LC-MS: calculated for C36H49ClN4O4Si2 692.30 observed m/e: 693.45 (M+H)⁺ (Rt 1.40/2 min); and Major: LC-MS: calculated for C36H49ClN4O4Si2 692.30 observed m/e: 693.41 (M+H)⁺ (Rt 1.45/2 min);

Step B(a): (3R,3aR,6aR)-6-((5-([1,1'-biphenyl]-4-yl)-6-chloro-1H-imidazo[4,5-b]pyridin-2-yl)amino)hexahydrofuro[3,2-b]furan-3-ol (minor isomer)

TFA (0.1 mL) was added to a stirred mixture of 5-([1,1'-biphenyl]-4-yl)-N-((3aR,6R,6aS)-6-((tert-butyldimethylsilyl)-oxy)hexahydrofuro[3,2-b]furan-3-yl)-6-chloro-1-((2-(trimethylsilyl)ethoxy)methyl)-1H-imidazo[4,5-b]pyridin-2-amine (minor isomer) (3.2 mg, 4.61 μmol) in DCM (0.5 ml) and the mixture was stirred at room temperature overnight. The reaction mixture was concentrated under reduced pressure. The resulting residue was purified by preparative HPLC Reverse phase (C-18), eluting with acetonitrile/water+0.1% TFA, to give title compound. LC-MS: calculated for C24H21ClN4O3 448.13 observed m/e: 449.16 (M+H)⁺ (Rt 1.10/2 min); ¹H NMR δ (ppm) (CD₃OD): 7.72 (m, 5H), 7.61 (m, 1H), 7.49 (m, 3H), 7.54 (m, 1H), 4.61 (m, 3H), 4.31 (m, 1H), 4.14 (m, 1H), 4.03 (d, 1H), 3.91 (dd, 1H), 3.62 (dd, 1H).

(3R,3aR,6aR)-6-((5-([1,1'-biphenyl]-4-yl)-6-chloro-1H-imidazo[4,5-b]pyridin-2-yl)amino)hexahydrofuro[3,2-b]furan-3-ol (major isomer)

Step B(b): TFA (0.1 mL) was added to a stirred mixture of 5-([1,1'-biphenyl]-4-yl)-N-((3aR,6R,6aS)-6-((tert-butyldimethylsilyl)oxy)hexahydrofuro[3,2-b]furan-3-yl)-6-chloro-1-((2-(trimethylsilyl)ethoxy)methyl)-1H-imidazo[4,5-b]pyridin-2-amine (major isomer) (20 mg, 0.029 mmol) in DCM (0.5 ml) and the mixture was stirred at room temperature overnight. The reaction mixture was concentrated under reduced pressure. The residue was purified by preparative HPLC Reverse phase (C-18), eluting with acetonitrile/water+0.1% TFA to give the title compound. LC-MS: calculated for C24H21ClN4O3 448.13 observed m/e: 449.15 (M+H)⁺ (Rt 1.18/2 min); ¹H NMR δ (ppm) (CD₃OD): 7.88-7.34 (m, 10H), 4.75 (m, 1H), 4.62 (m, 1H), 4.46 (m 1H), 4.37 (m, 1H), 4.28 (dd, 1H), 4.00 (dd, 1H), 3.81 (dd, 1H), 3.68 (dd, 1H).

EXAMPLE 40

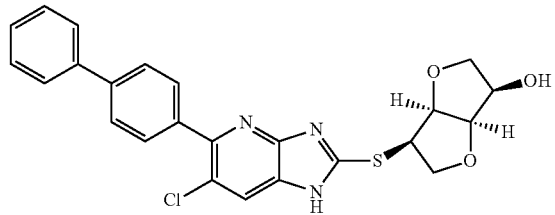 [SMILES: O[C@@H]1CO[C@H]2[C@@H]1OC[C@H]2Sc1nc2nc(-c3ccc(-c4ccccc4)cc3)c(Cl)cc2[nH]1]

(3R,3aR,6R,6aS)-6-((5-([1,1'-biphenyl]-4-yl)-6-chloro-1H-imidazo[4,5-b]pyridin-2-yl)thio)hexahydrofuro[3,2-b]furan-3-ol Step A: 5-([1,1'-biphenyl]-4-yl)-2-4(3R,3aS,6R,6aS)-6-((tert-butyldimethylsilyl)-oxy)hexahydrofuro[3,2-b]furan-3-yl)thio)-6-chloro-1-((2-(trimethylsilyl)ethoxy)methyl)-1H-imidazo[4,5-b]pyridine Triphenylphosphine (34.1 mg, 0.130 mmol) and DEAD (0.021 ml, 0.130 mmol) were added to a stirred mixture of 5-([1,1'-biphenyl]-4-yl)-6-chloro-1-((2-(trimethylsilyl)ethoxy)methyl)-1H-imidazo[4,5-b]pyridine-2-thiol (30.4 mg, 0.065 mmol) and (3S,3aR,6R,6aS)-6-((tert-butyldimethylsilyl)oxy)hexahydrofuro[3,2-b]furan-3-ol (25.4 mg, 0.097 mmol) in THF (1 ml) and the mixture was stirred at room temperature overnight. The reaction mixture was concentrated under reduced pressure and the resulting residue was purified by preparative TLC, eluting with EtOAc/isohexane (2:8) to give the title compound. LC-MS: calculated for C36H48ClN3O4SSi2 709.26 observed m/e: 710.42 (M+H)⁺ (Rt 1.59/2 min);

Step B: (3R,3aR,6R,6aS)-6-((5-([1,1'-biphenyl]-4-yl)-6-chloro-1H-imidazo[4,5-b]pyridin-2-yl)thio)hexahydrofuro[3,2-b]furan-3-ol TFA (0.5 mL, 6.49 mmol) was added to a stirred mixture of 5-([1,1'-biphenyl]-4-yl)-2-((3R,3aS,6R,6aS)-6-((tert-butyldimethylsilyl)oxy)hexahydrofuro[3,2-b]furan-3-yl)thio)-6-chloro-1-((2-(trimethylsilyl)ethoxy)methyl)-1H-imidazo[4,5-b]pyridine (5.2 mg, 7.32 μmol) in DCM (0.5 ml) and the mixture was stirred at room temperature for 6 h. Then the reaction mixture was concentrated under reduced pressure. The resulting residue was purified by preparative HPLC Reverse phase (C-18), eluting with Acetonitrile/Water+0.1% TFA, to give the title compound. LC-MS: calculated for C24H20ClN3O3S 465.09 observed m/e: 466.14 (M+H)⁺ (Rt 1.20/2 min); ¹H NMR δ (ppm) (CD₃OD): 7.99 (s, 1H), 7.77-7.70 (m, 6H), 7.48 (m, 2H), 7.38 (m, 1H), 4.62-4.54 (m, 4H), 4.36 (m, 1H), 3.95 (m, 1H), 3.85 (m, 1H), 3.61 (m, 1H).

TABLE 6

Compounds prepared according to the methods in Example 40.

| Example Number | Structure | HPLC-mass spectrum m/e |
|---|---|---|
| 41 | 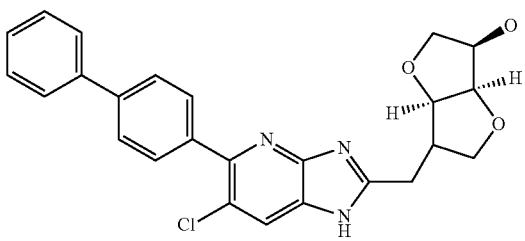 [SMILES: O[C@@H]1CO[C@@H]2C(Cc3nc4nc(-c5ccc(-c6ccccc6)cc5)c(Cl)cc4[nH]3)CO[C@H]12] | 466.07 |

EXAMPLE 42

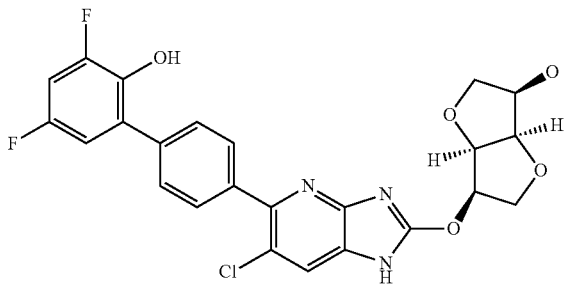 [SMILES: Oc1c(F)cc(F)cc1-c1ccc(-c2nc3nc(O[C@@H]4CO[C@H]5[C@@H]4OC[C@H]5O)[nH]c3cc2Cl)cc1]

(3R,3aR,6aR)-6-((5-([1,1'-biphenyl]-4-yl)-6-chloro-1H-imidazo[4,5-b]pyridin-2-yl)methyl)hexahydro-furo[3,2-b]furan-3-ol Triphenyl phosphite (0.034 ml, 0.129 mmol) was added to a mixture of 6-([1,1'-biphenyl]-4-yl)-5-chloropyridine-2,3-diamine (31.9 mg, 0.108 mmol) and (3R,3aR,6aR)-6-((5-([1,1'-biphenyl]-4-yl)-6-chloro-1H-imidazo[4,5-b]pyridin-2-yl)methyl)hexahydro-furo[3,2-b]furan-3-ol (6 mg, 0.013 mmol) in pyridine (0.5 ml) and the mixture was placed in a microwave reactor at 200° C. for 15 min. The reaction mixture was concentrated under reduced pressure. The resulting residue was purified by preparative TLC, eluting with DCM/MeOH (20:1), and then purified by preparative HPLC Reverse phase (C-18), eluting with acetonitrile/water+0.1% TFA, to give the title compound. LC-MS: calculated for C25H22ClN3O3 447.13 observed m/e: 448.15 (M+H)+ (Rt 1.13/2 min); $^1$H NMR δ (ppm) (CD$_3$OD): 8.23 (s, 1H), 7.80-7.70 (m, 6H), 7.48 (m, 2H), 7.39 (m, 1H), 4.53 (m, 2H), 4.29 (m, 1H), 4.15 (dd, 1H), 3.89 (dd, 1H), 3.68-3.61 (m, 2H), 3.37 (dd, 1H), 3.22 (dd, 1H), 2.90 (m, 1H).

EXAMPLE 44

(3S)-6-[[6-chloro-5-[4-(3,5-difluoro-2-hydroxy-phenyl)phenyl]-1H-imidazo[4,5-b]pyridin-2-yl]oxy]-2,3,3a,5,6,6a-hexahydrofuro[3,2-b]furan-3-ol Step A: (3S)-6-[[6-chloro-5-[4-(3,5-difluoro-2-methoxy-phenyl)phenyl]-1-(2-trimethylsilylethoxymethyl)imidazo[4,5-b]pyridin-2-yl]oxy]-2,3,3a,5,6,6a-hexahydrofuro[3,2-b]furan-3-ol LiOH (0.15 ml of a 3M aqueous solution, 0.45 mmol) and 1,1'-bis(diphenylphosphino)ferrocene-palladium(II)dichloride dichloromethane complex (16.3 mg, 0.020 mmol) were added to a stirred solution of (3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol (105.6 mg, 0.181 mmol) and (3,5-difluoro-2-methoxy-phenyl)boronic acid (52.5 mg, 0.279 mmol) in dioxane (1.45 ml) and water (0.21 ml). The reaction mixture was degassed (3×) and placed under nitrogen before being heated to 80° C. After 18 hours, the reaction mixture was diluted with EtOAc (40 ml), washed with water (3×20 ml), brine (15 mL) and dried over MgSO$_4$, filtered, and evaporated under reduced pressure to give an oil. The oil was purified on preparative silica plates (2×1000 u 65% EtOAc/hexanes) and eluted with EtOAc to give the title compound as an oil. LC-MS: calculated for C31H34ClF2N3O6Si 645.19 observed m/e: 646.16 (M+H)+ (Rt 1.38/2 min)

Step B: (3S)-6-[[6-chloro-5-[4-(3,5-difluoro-2-methoxy-phenyl)phenyl]-1H-imidazo[4,5-b]pyridin-2-yl]oxy]-2,3,3a,5,6,6a-hexahydrofuro[3,2-b]furan-3-ol Combined (3S)-6-[6-chloro-5-[4-(3,5-difluoro-2-methoxy-phenyl)phenyl]-1-(2-trimethylsilylethoxymethyl)imidazo[4,5-b]pyridin-2-yl]oxy-2,3,3a,5,6,6a-hexa-hydrofuro [3,2-b]furan-3-ol (36.8 mg, 0.057 mmol), formic acid (0.6 ml, 15.6 mmol), and saturated aqueous KHSO$_4$ (0.05 ml) in a flask. The yellow solution was heated to 40° C. with stirring. After 22 hours, the reaction mixture was cooled to room temperature before being cooled to 0° C. in an ice bath. Then 5N NaOH (3 ml) was added to the reaction mixture and the mixture was allowed to warm to room temperature. The reaction mixture was diluted with THF (2.0 ml) to give a hazy mixture. After 20 minutes, 2 N aqueous HCl (1.1 mL) was added. The reaction mixture was partitioned between EtOAc (35 ml) and water (20 ml), then the organic phase was washed with brine (1×10 ml), dried over MgSO$_4$, filtered, and evaporated under reduced pressure to a give the product as a solid.

LC-MS: calculated for C25H20ClF2N3O5 515.11 observed m/e: 516.10 (M+H)⁺ (Rt 1.22/2 min)

Step C: (3S)-6-[[6-chloro-5-[4-(3,5-difluoro-2-hydroxy-phenyl)phenyl]-1H-imidazo[4,5-b]pyridin-2-yl]oxy]-2,3,3a,5,6,6a-hexahydrofuro[3,2-b]furan-3-ol A mixture of (3S)-6-[[6-chloro-5-[4-(3,5-difluoro-2-methoxy-phenyl)phenyl]-1H-imidazo[4,5-b]pyridin-2-yl]oxy]-2,3,3a,5,6,6a-hexahydrofuro[3,2-b]furan-3-ol (5.2 mg, 0.01 mmol), and lithium chloride (45.0 mg, 1.06 mmol) in DMF (0.5 mL) was heated in a 140° C. oil bath for 20 hours and then 3.5 additional hours at 150° C. The reaction mixture was cooled to room temperature and purified by preparative HPLC reverse phase (C-18), using a 30×150 mm Sunfire™ column eluting with a 20%-100% acetonitrile/water+0.05% TFA gradient followed by a 100% acetonitrile/water+0.05% TFA flush. The desired fractions were combined, evaporated under reduced pressure, and lyophilized from ethanol and benzene to give the title compound as a light yellow solid. LC-MS: calculated for C24H18ClF2N3O5 501.09 observed m/e: 502.13 (M+H)⁺ (Rt 1.16/2 min); ¹H NMR δ (ppm) (CD₃OD): 7.83 (s, 1H), 7.66-7.74 (m, 4H), 6.93-6.98 (m, 2H), 5.55 (qt, 1H), 4.97 (t, 1H), 4.47 (t, 1H), 4.26-4.30 (m, 1H), 4.17 (dd, 1H), 4.11 (dd, 1H), 3.90 (t, 1H), 3.60 (t, 1H).

TABLE 7

Compounds prepared according to the methods in Example 44.

| Example Number | Structure | HPLC-mass spectrum m/e |
|---|---|---|
| 45 | 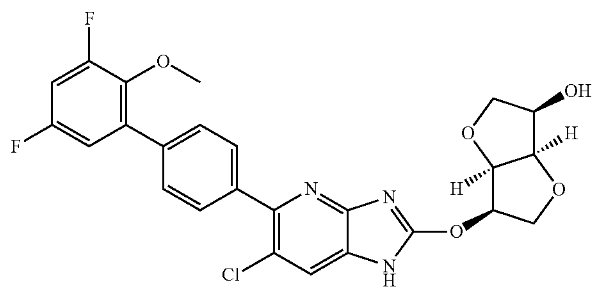 [SMILES: COc1c(F)cc(F)cc1-c1ccc(-c2nc3nc(O[C@@H]4CO[C@H]5[C@@H]4OC[C@H]5O)[nH]c3cc2Cl)cc1] | 515.11 |
| 46 | 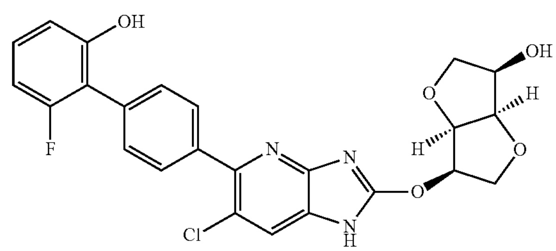 [SMILES: Oc1cccc(F)c1-c1ccc(-c2nc3nc(O[C@@H]4CO[C@H]5[C@@H]4OC[C@H]5O)[nH]c3cc2Cl)cc1] | 484.19 |
| 47 | 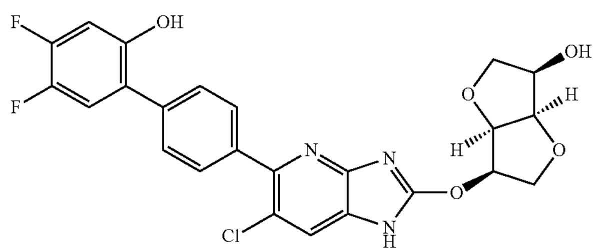 [SMILES: Oc1cc(F)c(F)cc1-c1ccc(-c2nc3nc(O[C@@H]4CO[C@H]5[C@@H]4OC[C@H]5O)[nH]c3cc2Cl)cc1] | 502.04 |
| 48 | 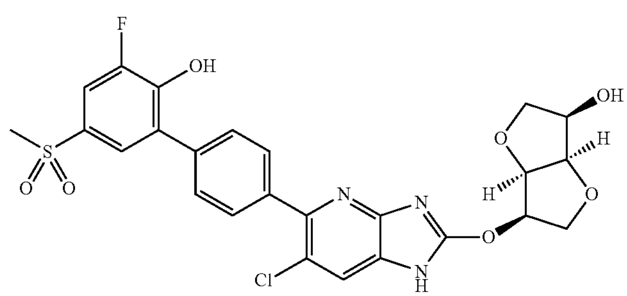 [SMILES: CS(=O)(=O)c1cc(F)c(O)c(-c2ccc(-c3nc4nc(O[C@@H]5CO[C@H]6[C@@H]5OC[C@H]6O)[nH]c4cc3Cl)cc2)c1] | 562.23 |

EXAMPLE 49

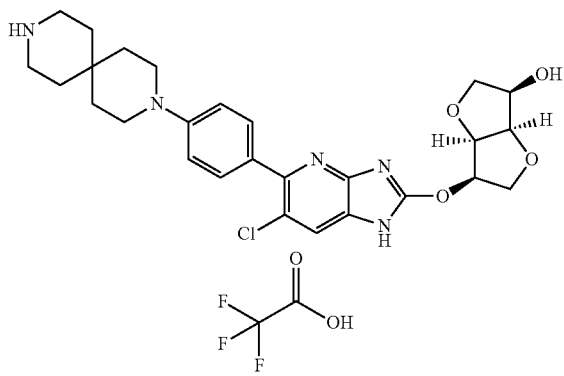

(3S)-6-[[6-chloro-5-[4-(3,9-diazaspiro[5,5]undecan-9-yl)phenyl]-1H-imidazo[4,5-b]pyridin-2-yl]oxy]-2,3,3a,5,6,6a-hexahydrofuro[3,2-b]furan-3-ol; 2,2,2-trifluoroacetic acid Step A: tert-butyl 3-[4-[2-[[(3R,3aR,6R,6aR)-3-hydroxy-2,3,3a,5,6,6a-hexahydrofuro-[3,2-b]furan-6-yl]oxy]-6-chloro-1-(2-trimethylsilylethoxymethyl)imidazo[4,5-b]pyridin-5-yl]phenyl]-3,9-diazaspiro[5,5]undecane-9-carboxylate A mixture of Pd$_2$dba$_3$ (3.4 mg, 0.0037 mmol) and catacxium (3.4 mg, 0.012 mmol, Aldrich) was combined in dioxane (0.25 mL) under nitrogen, and stirred at room temperature for 35 minutes. Then a solution of (3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol (67 mg, 0.115 mmol) and tert-butyl 3,9-diazaspiro[5.5]undecane-9-carboxylate 2,2,2-trifluoroacetic acid (52.7 mg, 0.143 mmol) in dioxane (1.5 ml) was added, followed by a 2M aqueous solution of potassium phosphate tribasic (0.5 mL, 1.0 mmol). The reaction mixture was degassed (3×) and placed under nitrogen before being heated to 105° C. After 17 hours, the reaction mixture was diluted with EtOAc (30 ml), washed with water (20 ml), brine (10 mL), dried over MgSO$_4$, filtered, and evaporated under reduced pressure to give the product as an oil. The oil was purified on preparative silica plates (2×1000 u prep tlc, developed and eluted with EtOAc) to give the title compound as a solid. C38H54ClN5O7Si 755.35 observed m/e: 756.16 (M+H)$^+$ (Rt 1.22/2 min)

Step B: (3R,3aR,6R,6aR)-6-[[6-chloro-5-[4-(3,9-diazaspiro[5,5]undecan-9-yl)phenyl]-1H-imidazo[4,5-b]pyridin-2-yl]oxy]-2,3,3a,5,6,6a-hexahydrofuro[3,2-b]furan-3-ol 2,2,2-trifluoroacetic acid Combined tert-butyl 3-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilyl-ethoxymethyl)imidazo[4,5-b]pyridin-5-yl]phenyl]-3,9-diazaspiro[5.5]undecane-9-carboxylate (43.9 mg, 0.058 mmol), formic acid (1.5 ml), and saturated aqueous KHSO$_4$ (0.2 ml) in a flask. The yellow solution was stirred at room temperature. After 18 hours, the reaction mixture was partitioned between EtOAc (35 ml) and saturated aqueous sodium bicarbonate (20 ml), and the aqueous phase was extracted with additional EtOAc (20 mL). The combined organic phases were washed with brine (1×10 ml), dried over MgSO$_4$, filtered, and evaporated under reduced pressure to a yellow oil. The oil was dissolved in MeOH (1 mL), and 3N aqueous NaOH (6 drops) was added. After 5 minutes, the reaction mixture was concentrated under reduced pressure and purified by preparative HPLC reverse phase (C-18), using a 30×150 mm Sunfire™ column and eluting with a 20%-100% acetonitrile/water+0.05% TFA gradient, followed by a 100% acetonitrile/water+0.05% TFA flush. The desired fractions were combined, evaporated under reduced pressure, and lyophilized from ethanol and benzene to give the title compound as a light yellow solid. LC-MS: calculated for C27H32ClN5O4 525.21 observed m/e: 526.02 (M+H)$^+$ (Rt 0.88/2 min); $^1$H NMR δ (ppm) (CD$_3$OD): 7.83 (s, 1H), 7.66 (d, 2H), 7.26 (d, 2H), 5.55 (qt, 1H), 4.97 (t, 1H), 4.47 (t, 1H), 4.26-4.31 (m, 1H), 4.17 (dd, 1H), 4.12 (dd, 1H), 3.90 (t, 1H), 3.60 (t, 1H), 3.44 (m, 2H), 3.25 (m, 2H) and 1.85 (m, 4H).

TABLE 8

Compounds prepared according to the methods in Example 49.

| Example Number | Structure | HPLC-mass spectum m/e |
|---|---|---|
| 50 | 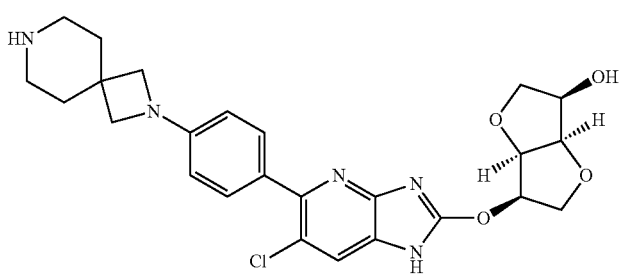 [SMILES: O[C@@H]1CO[C@H]2[C@@H]1OC[C@H]2Oc1nc2nc(-c3ccc(N4CC5(CCNCC5)C4)cc3)c(Cl)cc2[nH]1] | 498.17 |

EXAMPLE 51

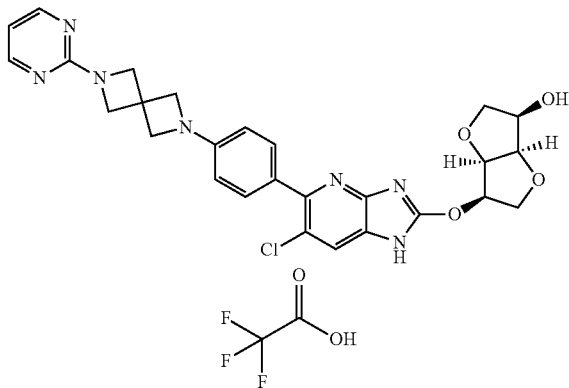

(3R,3aR,6R,6aR)-6-[[6-chloro-5-[4-(6-pyrimidin-2-yl-2,6-diazaspiro[3.3]heptan-2-yl)phenyl]-1H-imidazo[4,5-b]pyridin-2-yl]oxy]-2,3,3a,5,6,6a-hexahydrofuro[3,2-b]furan-3-ol 2,2,2-trifluoroacetic acid Step A: (3R,3aR,6R,6aR)-6-[6-chloro-5-[4-(6-pyrimidin-2-yl-2,6-diazaspiro[3.3]heptan-2-yl)phenyl]-1-(2-trimethylsilylethoxymethyl)imidazo[4,5-b]pyridin-2-yl]oxy-2,3,3a,5,6,6a-hexahydrofuro[3,2-b]furan-3-ol A mixture of RuPHOS indoline precatalyst (9.4 mg, 0.013 mmol, Strem), 6-pyrimidin-2-yl-2,6-diazaspiro[3.3]heptane 2,2,2-trifluoroacetic acid (58 mg, 0.20 mmol), potassium phosphate tribasic (129 mg, 0.608 mmol) and (3R,3aR,6R,6aR)-6-[[5-(4-bromophenyl)-6-chloro-1H-imidazo[4,5-b]pyridin-2-yl]oxy]-2,3,3a,5,6,6a-hexahydrofuro[3,2-b]furan-3-ol (80 mg, 0.137 mmol) in dioxane (1.0 ml) was degassed (3×) and placed under nitrogen before being heated to 80° C. After 22 hours, the reaction mixture was diluted with EtOAc (20 ml), washed with water (20 ml), brine (10 mL), dried over MgSO$_4$, filtered, and evaporated under reduced pressure to give an oil. The oil was purified on preparative silica plates (1×1000 u developed and eluted with 5% MeOH/DCM) to give the title compound as a mixture of regioisomers. C33H40ClN7O5Si 677.25 observed m/e: 678.30 (M+H)$^+$ (Rt 1.07/2 min).

Step B: (3R,3aR,6R,6aR)-6-[[6-chloro-5-[4-(6-pyrimidin-2-yl-2,6-diazaspiro[3.3]heptan-2-yl)phenyl]-1H-imidazo[4,5-b]pyridin-2-yl]oxy]-2,3,3a,5,6,6a-hexahydrofuro[3,2-b]furan-3-ol 2,2,2-trifluoroacetic acid A mixture of (3R,3aR,6R,6aR)-6-[6-chloro-5-[4-(6-pyrimidin-2-yl-2,6-diazaspiro[3.3]heptan-2-yl)phenyl]-1-(2-trimethylsilylethoxy-methyl)imidazo[4,5-b]pyridin-2-yl]oxy-2,3,3a,5,6,6a-hexahydrofuro[3,2-b]furan-3-ol (54.3 mg, 0.08 mmol) in TFA (0.5 mL) and DCM (0.5 mL) was stirred at room temperature. After 2 hours, the reaction mixture was evaporated to give an oil. The oil was dissolved in MeOH (1 mL) and purified by preparative HPLC reverse phase (C-18), using a 30×150 mm Sunfire™ column and eluting with a 20%-100% acetonitrile/water+0.05% TFA gradient followed by a 100% acetonitrile/water+0.05% TFA flush. The desired fractions were combined, evaporated under reduced pressure, and lyophilized from ethanol and benzene to give the title compound as a solid. LC-MS: calculated for C27H$_{26}$ClN7O4 547.17 observed m/e: 548.35 (M+H)$^+$ (Rt 0.70/2 min); $^1$H NMR δ (ppm) (CD$_3$OD): 8.44 (d, 2H), 7.96 (s, 1H), 7.56 (d, 2H), 6.81 (m, 1H), 6.65 (d, 2H), 5.58 (qt, 1H), 4.96 (t, 1H), 4.48 (t, 1H), 4.43 (s, 4H), 4.26-4.31 (m, 1H), 4.18 (s, 4H), 4.16 (dd, 1H), 4.12 (dd, 1H), 3.90 (t, 1H), 3.60 (t, 1H).

TABLE 9

Compounds prepared according to the methods in Example 51.

| Example Number | Structure | HPLC-mass spectrum m/e |
|---|---|---|
| 52 | 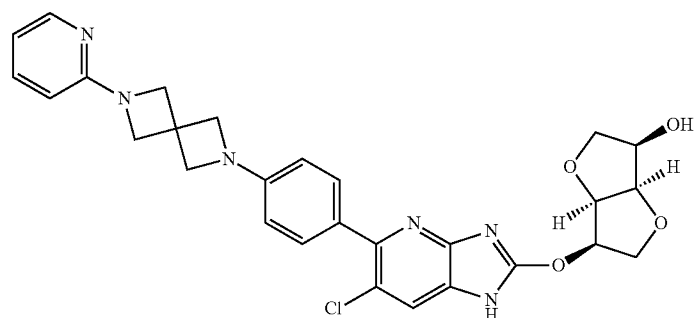 [SMILES: O[C@@H]1CO[C@H]2[C@@H]1OC[C@H]2Oc1nc2nc(-c3ccc(N4CC5(C4)CN(c4ccccn4)C5)cc3)c(Cl)cc2[nH]1] | 547.34 |
| 53 | 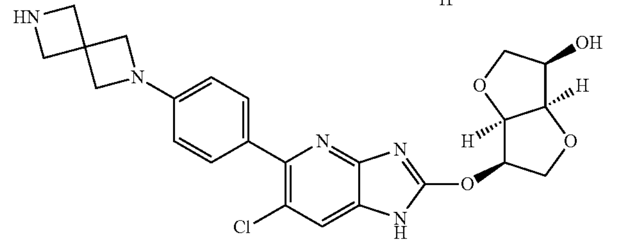 | 470.29 |

EXAMPLE 54

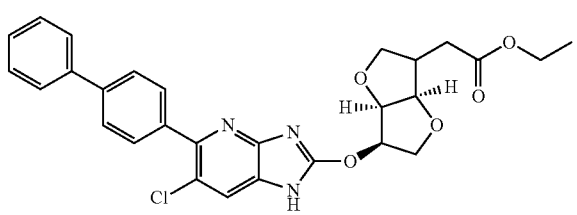 [SMILES: CCOC(=O)CC1CO[C@H]2[C@@H]1OC[C@H]2Oc1nc2nc(-c3ccc(-c4ccccc4)cc3)c(Cl)cc2[nH]1]

Ethyl 2-[(3R,3aR,6R,6 aS)-6-[[6-chloro-5-(4-phenylphenyl)-1H-imidazo[4,5-b]pyridin-2-yl]oxy]-2,3,3a,5,6,6a-hexahydro furo[3,2-b]furan-3-yl]acetate Step A: Ethyl 2-[(3R,3aR,6R,6aS)-6-[6-chloro-5-(4-phenylphenyl)-1-(2-trimethylsilyl-ethoxy-methyl)imidazo[4,5-b]pyridin-2-yl]oxy-2,3,3a,5,6,6a-hexahydrofuro[3,2-b]furan-3-yl]acetate A mixture of 2-[[6-chloro-2-methylsulfonyl-5-(4-phenylphenyl)imidazo-[4,5-b]pyridin-1-yl]-methoxy]ethyl-trimethyl-silane (357 mg, 0.694 mmol), ethyl 2-[(3aR,6R,6aR)-6-hydroxy-2,3,3a,5,6,6a-hexahydrofuro[3,2-b]furan-3-yl]acetate (180 mg, 0.832 mmol), and DBU (150 uL, 0.995 mmol) in DMF (1.0 ml) was stirred at room temperature for 1 hour. The reaction mixture was diluted with EtOAc (200 ml), washed with water (5×30 ml), brine (1×10 mL), dried over MgSO$_4$, filtered, and evaporated under reduced pressure to give the title compound as a mixture of isomers. C34H40ClN3O6Si 649.24 observed m/e: 650.28 (M+H)$^+$ (Rt 1.09 and 1.17/2 min)

Step B: Ethyl 2-[(3R,3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]acetate A mixture of ethyl 2-[(3R,3aR,6R,6aS)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]acetate (34 mg, 0.052 mmol) in TFA (0.5 mL) and DCM (0.5 mL) was stirred at room temperature. After 1 hour, the reaction mixture was evaporated to an oil, dissolved in EtOH (1 mL) and purified by preparative HPLC reverse phase (C-18), using a 30×150 mm Sunfire™ column and eluting with a 20%-100% acetonitrile/water+0.05% TFA gradient followed by a 100% acetonitrile/water+0.05% TFA flush. The desired fractions were lyophilized to give the title compound as a solid. LC-MS: calculated for C28H26ClN3O5 519.16 observed m/e: 520.22 (M+H)$^+$ (Rt 0.74/2 min); $^1$H NMR δ (ppm) (CD$_3$OD): 7.87 (s, 1H), 7.75 (ABq, 4H), 7.71 (d, 2H), 7.48 (dd, 2H), 7.38 (dd, 1H), 5.57 (qt, 1H), 5.01 (t, 1H), 4.60 (t, 1H), 4.16 (q, 2H), 4.10 (dd, 1H), 4.00-4.06 (m, 2H), 3.53 (dd, 1H), 2.71 (dd, 1H), 2.59 (m, 1H), 2.51 (dd, 1H) and 1.27 (t, 3H).

EXAMPLE 55

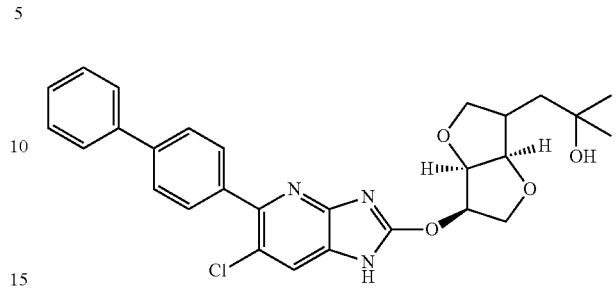

1-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]-2-methyl-propan-2-ol Step A: 1-[(3aR,6R,6aS)-6-[6-chloro-5-(4-phenylphenyl)-1-(2-trimethylsilylethoxy-methyl)imidazo[4,5-b]pyridin-2-yl]oxy-2,3,3a,5,6,6a-hexahydrofuro[3,2-b]furan-3-yl]-2-methyl-propan-2-ol Methyl magnesium bromide (3M in ether) (0.308 mL, 0.923 mmol) was added rapidly to an ice cold mixture of ethyl 2-[(3aR,6R,6aS)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]acetate (100 mg, 0.154 mmol) in THF (0.5 mL). The yellow solution was stirred for 1 hour in an ice bath, then EtOAc (30 mL) and saturated aqueous NaHCO$_3$ (10 mL) were added, and the organic phase was separated, washed with brine (1×10 mL), dried (MgSO4), filtered and concentrated under reduced pressure to furnish a yellow oil. The oil was purified by preparative silica plates (1×1000 u prep tlc, developed with EtOAc. eluted with 10% MeOH/CH2Cl2) to give the title compound. C34H42ClN3O5Si 635.26 observed m/e: 636.31 (M+H)$^+$ (Rt 1.04 and minor 1.11/2 min).

Step B: 1-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]-2-methyl-propan-2-ol A mixture of 1-[(3aR,6R,6aS)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]-2-methyl-propan-2-ol (66 mg, 0.104 mmol) in TFA (0.5 mL) and DCM (1.0 mL) was stirred at room temperature. After 1.5 hours, the reaction mixture was concentrated under reduced pressure to give an oil. The oil was dissolved in EtOH (1 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. Major isomer LC-MS: calculated for C28H28ClN3O4 505.18 observed m/e: 506.23 (M+H)$^+$ (Rt 1.16/2 min); $^1$H NMR δ (ppm) (CD$_3$OD): 7.87 (s, 1H), 7.75 (ABq, 4H), 7.71 (d, 2H), 7.48 (dd, 2H), 7.38 (dd, 1H), 5.56

(qt, 1H), 4.96 (t, 1H), 4.54 (t, 1H), 4.10-4.00 (m, 3H), 3.51 (dd, 1H), 2.63 (m, 1H), 2.59 (m, 1H), 1.95 (dd, 1H), 1.58 (dd, 1H) and 1.25 (s, 3H).

Examples 56 and 57

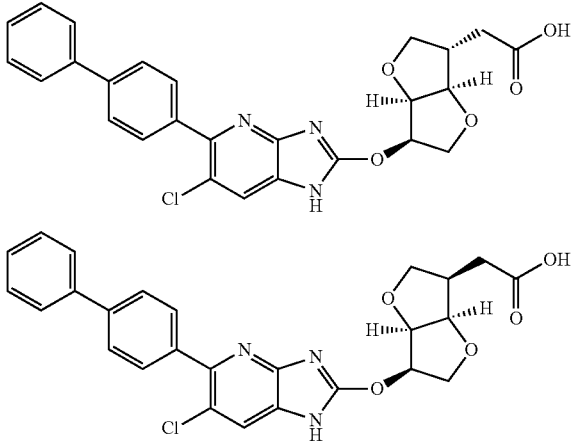

2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]acetic acid A mixture ethyl 2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]acetate (4.4 mg, 0.0085 mmol) and 3M sodium hydroxide (2.8 uL, 0.085 mmol) in ethanol (0.5 ml) was stirred at room temperature for 20 minutes. The reaction mixture was then purified by preparative HPLC reverse phase (C-18), using a 30×150 mm Sunfire™ column and eluting with a 20%-80% acetonitrile/water to give a major and minor isomers which were lyophilized to give the title compounds. Minor isomer: LC-MS: calculated for C26H22ClN3O5 491.12 observed m/e: 492.22 (M+H)$^+$ (Rt 1.11/2 min); $^1$H NMR δ (ppm) (CD$_3$OD): 7.88 (s, 1H), 7.75 (ABq, 4H), 7.71 (d, 2H), 7.48 (dd, 2H), 7.38 (dd, 1H), 5.56 (qt, 1H), 4.98 (t, 1H), 4.42 (d, 1H), 4.13 (dd, 2H), 4.05-3.98 (m, 3H), 3.72 (dd, 1H), 2.71 (m, 1H) and 2.44-2.33 (m, 2H). Major isomer: LC-MS: calculated for C26H22ClN3O5 491.12 observed m/e: 492.20 (M+H)$^+$ (Rt 1.12/2 min); $^1$H NMR δ (ppm) (CD$_3$OD): 7.94 (s, 1H), 7.76 (ABq, 4H), 7.72 (d, 2H), 7.49 (dd, 2H), 7.39 (dd, 1H), 5.59 (m, 1H), 5.01 (t, 1H), 4.61 (t, 1H), 4.12 (dd, 2H), 4.08-4.00 (m, 3H), 3.53 (dd, 1H), 2.70 (dd, 1H), 2.59 (m, 1H) and 2.49 (dd, 1H).

EXAMPLE 58

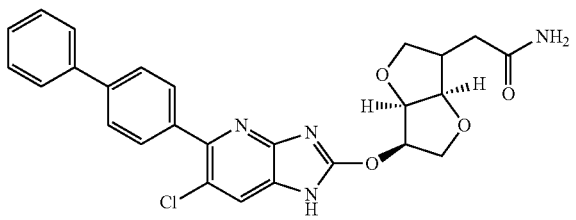 [SMILES: NC(=O)CC1CO[C@H]2[C@@H]1OC[C@H]2Oc1nc2nc(-c3ccc(-c4ccccc4)cc3)c(Cl)cc2[nH]1]

2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]acetamide Step A: 2-[(3aR,6R,6aS)-6-[6-chloro-5-(4-phenylphenyl)-1-(2-trimethylsilylethoxy-methyl)-imidazo[4,5-b]pyridin-2-yl]oxy-2,3,3a,5,6,6a-hexahydrofuro[3,2-b]furan-3-yl]acetamide Concentrated ammonium hydroxide (0.15 mL) was added to a solution of ethyl 2-[(3aR,6R,6aS)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]acetate (41.1 mg, 0.063 mmol) in ethanol (0.5 mL). The solution was stirred for 29 hours in a 50 degree oil bath. After cooling to room temperature, additional concentrated ammonium hydroxide (0.3 mL) was added and the mixture was heated for an additional 24 hours in a 50 degree oil bath. The solvents were removed under vacuum to give the title compound. C32H37ClN4O5Si 620.22 observed m/e: 621.38 (M+H)$^+$ (Rt 0.98/2 min)

Step B: 2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]acetamide 2-[(3aR,6R,6aS)-6-[6-chloro-5-(4-phenylphenyl)-1-(2-trimethylsilylethoxymethyl)-imidazo[4,5-b]pyridin-2-yl]oxy-2,3,3a,5,6,6a-hexahydrofuro[3,2-b]furan-3-yl]acetamide was dissolved in TFA (0.5 mL) and DCM (0.5 mL) and stirred at room temperature for 2 hours. The reaction mixture was evaporated to give an oil. The oil was dissolved in methanol (0.5 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. Major isomer LC-MS: calculated for C26H23ClN4O4 490.14 observed m/e: 491.23 (M+H)$^+$ (Rt 0.53/2 min); $^1$H NMR δ (ppm) (CD$_3$OD): 7.94 (s, 1H), 7.76 (ABq, 4H), 7.71 (d, 2H), 7.48 (dd, 2H), 7.38 (dd, 1H), 5.58 (qt, 1H), 5.00 (t, 1H), 4.56 (t, 1H), 4.12 (dd, 1H), 4.02 (m, 2H), 3.54 (dd, 1H), 2.64 (dd, 1H), 2.58 (m, 1H) and 2.38 (dd, 1H).

EXAMPLE 59

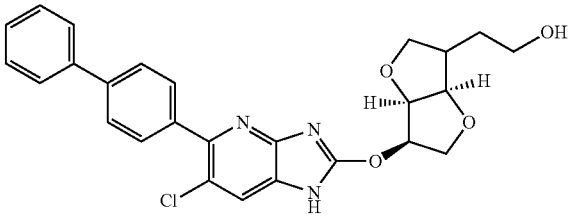 [SMILES: OCCC1CO[C@H]2[C@@H]1OC[C@H]2Oc1nc2nc(-c3ccc(-c4ccccc4)cc3)c(Cl)cc2[nH]1]

2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]ethanol Step A: 2-[(3aR,6R,6aS)-6-[6-chloro-5-(4-phenylphenyl)-1-(2-trimethylsilylethoxy-methyl)-imidazo[4,5-b]pyridin-2-yl]oxy-2,3,3a,5,6,6a-hexahydrofuro[3,2-b]furan-3-yl]ethanol Lithium chloride (2 mg, 0.047 mmol) and sodium borohydride (90 mg, 2.38 mmol) were added to a solution of ethyl 2-[(3aR,6R,6aS)-6-[6-chloro-5-(4-phenylphenyl)-1-(2-trimethylsilylethoxy-methyl)imidazo[4,5-b]pyridin-2-yl]oxy-2,3,3a,5,6,6a-hexahydrofuro[3,2-b]furan-3-yl]acetate (133 mg, 0.205 mmol) in ethanol (2.0 mL). After 2.5 hours, additional sodium borohydride (34 mg, 0.9 mmol) was added and the mixture was stirred for an additional 20 hours. The mixture was partitioned between ethyl acetate (20 mL)/1N aqueous HCl (4.5 mL) and water (5 mL). The organic layer was washed with brine (1×5 mL), dried with MgSO$_4$, filtered and the solvents were removed under vacuum. The crude residue was purified on preparative silica gel plates (1×1000 u prep tlc—developed with 5% methanol/DCM and eluted with 10% methanol/DCM) to give the title compound. C32H38ClN3O5Si 607.23 observed m/e: minor isomer 608.23 (M+H)$^+$ (Rt 0.98/2 min) and major isomer 608.23 (M+H)$^+$ (Rt 1.04/2 min)

Step B: 2-[(3aR,6R,6aS)-6-[[6-chloro-5-(4-phenylphenyl)-1H-imidazo[4,5-b]pyridin-2-yl]oxy]-2,3,3a,5,6,6a-hexahydrofuro[3,2-b]furan-3-yl]ethanol 2-[(3aR,6R,6aS)-6-[6-chloro-5-(4-phenylphenyl)-1-(2-trimethylsilylethoxymethyl)imidazo[4,5-b]pyridin-2-yl]oxy-2,3,3a,5,6,6a-hexahydrofuro[3,2-b]furan-3-yl]acetamide (84.6 mg, 0.139 mmol) was dissolved in TFA (0.5 mL) and DCM (1.0 mL) and the reaction was stirred at room temperature for 1 hour. The reaction mixture was then evaporated to an oil, dissolved in methanol (0.5 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. Major isomer LC-MS: calculated for C26H24ClN3O4 477.15 observed m/e: 478.26 (M+H)$^+$ (Rt 1.10/2 min); $^1$H NMR δ (ppm) (CD$_3$OD): 7.87 (s, 1H), 7.75 (ABq, 4H), 7.71 (d, 2H), 7.48 (dd, 2H), 7.38 (dd, 1H), 5.56 (qt, 1H), 4.98 (t, 1H), 4.53 (t, 1H), 4.10 (dd, 1H), 4.04-3.96 (m, 3H), 3.63 (t, 2H), 3.54 (dd, 1H), 2.34 (m, 2H), 1.95 (m, 2H) and 1.77 (m, 2H).

EXAMPLE 60

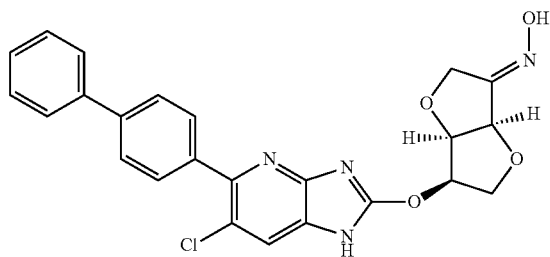 [SMILES: O/N=C1\CO[C@H]2[C@@H]1OC[C@H]2Oc1nc2nc(-c3ccc(-c4ccccc4)cc3)c(Cl)cc2[nH]1]

(3R,3aS,6aR)-3-[[6-chloro-5-(4-phenylphenyl)-1H-imidazo[4,5-b]pyridin-2-yl]oxy]-2,3,3a,6a-tetrahydrofuro[3,2-b]furan-6-one oxime A mixture of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (88 mg, 0.196 mmol) and hydroxylamine hydrochloride (39.5 mg, 0.568 mmol) in pyridine (0.5 ml) was stirred at room temperature for 2 hours. Then the reaction mixture was evaporated to give a foam, which was dissolved in methanol (2 mL) and purified by preparative HPLC reverse phase (C-18), using a 30×150 mm Sunfire™ column and eluting with a 20%-80% acetonitrile/water to give the title compound. Major Oxime stereoisomer LC-MS: calculated for C24H19ClN4O4 462.11 observed m/e: 463.18 (M+H)$^+$ (Rt 1.20/2 min); $^1$H NMR δ (ppm) (CD$_3$OD): 7.94 (s, 1H), 7.76 (ABq, 4H), 7.71 (d, 2H), 7.49 (dd, 2H), 7.39 (dd, 1H), 5.62 (m, 1H), 5.14 (t, 1H), 5.00 (d, 1H), 4.63 (s, 2H), 4.27 (dd, 2H) and 4.08 (dd, 1H). (Contains a small amount of minor oxime stereoisomer).

EXAMPLE 61

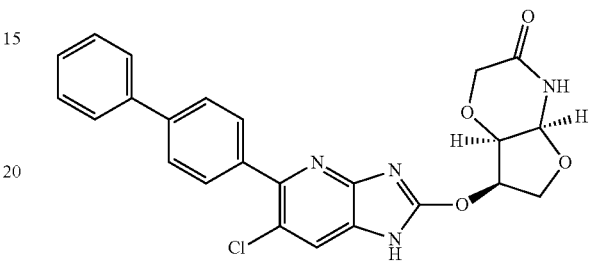

(4aS,7R,7aR)-7-[[6-chloro-5-(4-phenylphenyl)-1H-imidazo[4,5-b]pyridin-2-yl]oxy]-4a,6,7,7a-tetrahydro-4H-furo[3,2-b][1,4]oxazin-3-one (3R,3aS,6aR)-3-[[6-chloro-5-(4-phenylphenyl)-1H-imidazo[4,5-b]pyridin-2-yl]oxy]-2,3,3a,6a-tetrahydrofuro[3,2-b]furan-6-one oxime (20 mg, 0.043 mmol) was dissolved in pyridine and was cooled in an ice bath. Toluene sulfonyl chloride (21.2 mg, 0.11 mmol) was added in one portion and the mixture was stirred in an ice bath for 1 hour. The mixture was warmed to room temperature and additional toluene sulfonyl chloride (17 mg, 0.09 mmol) was added. After 2 hours, the solution was placed in a 60 degree oil bath for 1.5 hours and then cooled to room temperature. The reaction mixture was evaporated to give a foam, which was dissolved in methanol (2 mL) and purified by preparative HPLC reverse phase (C-18), using a 30×150 mm Sunfire™ column and eluting with a 20%-80% acetonitrile/water to give the title compound. LC-MS: calculated for C24H19ClN4O4 462.11 observed m/e: 463.95 (M+14)$^+$ (Rt 1.25/2 min); $^1$H NMR δ (ppm) (CD$_3$OD): 7.93 (s, 1H), 7.78 and 7.73 (ABq, 4H), 7.70 (d, 2H), 7.48 (dd, 2H), 7.38 (dd, 1H), 6.44 (d, 1H), 5.48 (t, 1H), 4.83 (t, 1H), 4.63 (ABq, 2H), 4.50 (dd, 2H) and 4.45 (dd, 1H).

EXAMPLE 62

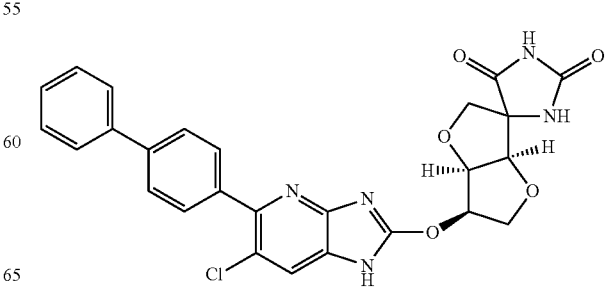

163

(3R,3aS,6aR)-3-[[6-chloro-5-(4-phenylphenyl)-1H-imidazo[4,5-b]pyridin-2-yl]oxy]spiro[3,3a,5,6a-tetrahydro-2H-furo[3,2-b]furan-6,5'-imidazolidine]-2',4'-dione A mixture of (3R,3aR,6aS)-3-[[6-chloro-5-(4-phenylphenyl)-1H-imidazo[4,5-b]pyridin-2-yl]oxy]-2,3,3a,6a-tetrahydrofuro[3,2-b]furan-6-one (91 mg, 0.203 mmol), ammonium carbonate (39.0 mg, 0.406 mmol) and potassium cyanide (14.6 mg, 0.224 mmol) in methanol (0.4 ml) was stirred at room temperature for 22 hours. The mixture was placed in a 40 degree oil bath for an additional 23 hours. Then the reaction mixture was partitioned between ethyl acetate (30 mL) and water (20 mL), washed with brine (1×5 mL), MgSO4, filtered and evaporated to give a residue. The residue was dissolved in dimethylsulfoxide and purified by preparative HPLC reverse phase (C-18), using a 30×150 mm Sunfire™ column and eluting with a 20%-80% acetonitrile/water to give the title compound. LC-MS: calculated for C26H20ClN5O5 517.12 observed m/e: 518.19 (M+H)+ (Rt 1.17/2 min); $^1$H NMR δ (ppm) (CD$_3$OD): 7.94 (s, 1H), 7.76 (ABq, 4H), 7.71 (d, 2H), 7.48 (dd, 2H), 7.39 (dd, 1H), 5.64 (m, 1H), 5.18 (t, 1H), 4.58 (d, 1H), 4.26 (dd, 2H), 4.19 (dd, 1H), 4.11 (d, 1H) and 3.95 (d, 1H).

EXAMPLE 63

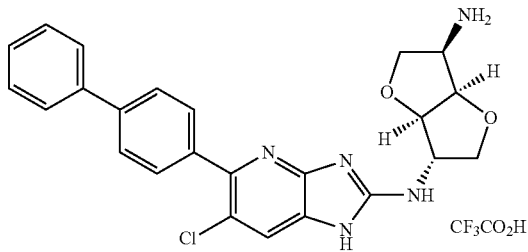 [SMILES: N[C@@H]1CO[C@H]2[C@@H]1OC[C@@H]2Nc1nc2nc(-c3ccc(-c4ccccc4)cc3)c(Cl)cc2[nH]1 ; "CF3CO2H"]

(3R,3aR,6S,6aR)—N6-[6-chloro-5-(4-phenylphenyl)-1H-imidazo[4,5-b]pyridin-2-yl]-2,3,3a,5,6,6a-hexahydrofuro[3,2-b]furan-3,6-diamine 2,2,2-trifluoroacetic acid Step A: tert-butyl N-[(3S,3aR,6R,6aR)-3-[[6-chloro-5-(4-phenylphenyl)-1-(2-trimethylsilylethoxymethyl)imidazo[4,5-b]pyridin-2-yl]amino]-2,3,3a,5,6,6a-hexahydrofuro[3,2-b]furan-6-yl]carbamate DBU (18.3 uL, 0.122 mmol) was added to a mixture of 2-[[6-chloro-2-methylsulfonyl-5-(4-phenylphenyl)imidazo[4,5-b]pyridin-1-yl]methoxy]ethyl-trimethyl-silane (50 mg, 0.097 mmol) and tert-butyl N-[(3S,3aR,6R,6aR)-3-amino-2,3,3a,5,6,6a-hexahydrofuro-[3,2-b]furan-6-yl]carbamate (72.6 mg, 0.297 mmol) in DMF (0.39 mL). After 18 hours, the mixture was diluted with ethyl acetate (20 mL) and washed with water (5×20 mL). The organic layer was separate, washed with brine (1×10 mL), dried with MgSO$_4$, filtered and the solvent was removed under vacuum. The crude reaction mixture was then purified on preparative silica gel plates (1×1000 u—developed with 30% EtOAc/hexanes and eluted with EtOAc) to give the title compound. LC-MS: calculated for C35H44ClN5O5Si 677.28 observed m/e minor isomer 678.31 (M+H)+ (Rt 1.34/2 min) and major isomer 608.23 (M+H)+ (Rt 1.04/2 min)

164

Step B: (3R,3aR,6S,6aR)—N6-[6-chloro-5-(4-phenylphenyl)-1H-imidazo[4,5-b]pyridin-2-yl]-2,3,3a,5,6,6a-hexahydrofuro[3,2-b]furan-3,6-diamine 2,2,2-trifluoroacetic acid Tert-butyl N-[(3S,3aR,6R,6aR)-3-[[6-chloro-5-(4-phenylphenyl)-1-(2-trimethylsilylethoxy-methyl)imidazo[4,5-b]pyridin-2-yl]amino]-2,3,3a,5,6,6a-hexahydrofuro[3,2-b]furan-6-yl]carbamate (1.1 mg, 0.0016 mmol) was dissolved in TFA (0.2 mL) and DCM (0.5 mL) and stirred at room temperature for 1 hour. Then the reaction mixture was evaporated to give an oil, which was dissolved in methanol (0.5 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. Major isomer LC-MS: calculated for C24H$_{22}$ClN5O2 447.15 observed m/e: 448.24 (M+H)+ (Rt 0.96/2 min); $^1$H NMR δ (ppm) (CD$_3$OD): 7.82 (s, 1H), 7.76 (ABq, 4H), 7.71 (d, 2H), 7.49 (dd, 2H), 7.39 (dd, 1H), 4.90 (m, 1H), 4.79 (d, 1H), 4.52 (br d, 1H), 4.28 (dd, 1H), 4.20-4.12 (m, 2H), 3.96 (m, 1H) and 3.82 (dd, 1H).

EXAMPLE 64

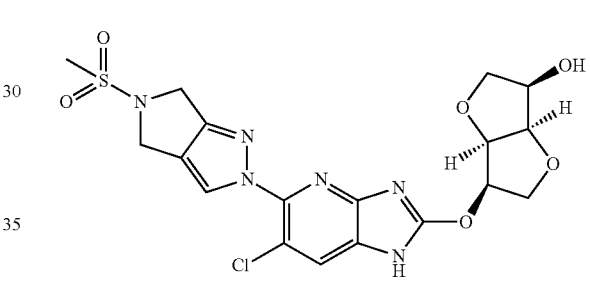

(3R,3aR,6R,6aR)-6-[[6-chloro-5-(5-methylsulfonyl-4,6-dihydropyrrolo[3,4-c]pyrazol-2-yl)-1H-imidazo[4,5-b]pyridin-2-yl]oxy]-2,3,3a,5,6,6a-hexahydrofuro[3,2-b]furan-3-ol Step A: [(3R,3aR,6R,6aS)-3-[1-allyl-6-chloro-5-(5,6-dihydro-4H-pyrrolo[3,4-c]pyrazol-2-yl)imidazo[4,5-b]pyridin-2-yl]oxy-2,3,3a,5,6,6a-hexahydrofuro[3,2-b]furan-6-yl]oxy-tert-butyl-dimethyl-silane 2,2,2-trifluoroacetic acid A mixture of (1R,2R)—N1,N2-dimethylcyclohexane-1,2-diamine (25 uL, 0.158 mmol), copper (I) iodide (4.0 mg, 0.021 mmol), potassium phosphate tribasic (69.7 mg, 0.328 mmol), tert-butyl 4,6-dihydro-2H-pyrrolo[3,4-c]pyrazole-5-carboxylate (42.7 mg, 0.204 mmol) and [(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethyl-silane (84 mg, 0.145 mmol) in dioxane (1.0 ml) was degassed (3×) and placed under nitrogen before being heated to 100° C. After 6 hours, the reaction mixture was diluted with EtOAc (30 ml), washed with water (20 ml), brine (10 mL), dried over MgSO$_4$, filtered, and evaporated under reduced pressure to give an oil. The oil was purified on preparative silica plates (1×1000 u developed with 1:1 EtOAc/hexanes). The resulting solid (86.4 mg, 0.131 mmol) was dissolved in TFA (1.0 mL) and DCM (1.0 mL) and was stirred at room temperature. After 1 hour, the reaction mixture was evaporated to give an oil, and which was lyophilized from ethanol and benzene to give the title compound as a solid. LC-MS: calculated for C26H35ClN6O4Si 558.22 observed m/e: 559.27 (M+H)+ (Rt 1.15/2 min).

Step B: [(3R,3aR,6R,6aS)-3-[1-allyl-6-chloro-5-(5-methylsulfonyl-4,6-dihydropyrrolo-[3,4-c]pyrazol-2-yl)imidazo[4,5-b]pyridin-2-yl]oxy-2,3,3a,5,6,6a-hexahydrofuro[3,2-b]furan-6-yl]oxy-tert-butyl-dimethyl-silane Triethylamine (91 uL, 0.653 mmol) was added to a ice cold mixture of [(3R,3aR,6R,6aS)-3-[1-allyl-6-chloro-5-(5,6-dihydro-4H-pyrrolo[3,4-c]pyrazol-2-yl)imidazo[4,5-b]pyridin-2-yl]oxy-2,3,3a,5,6,6a-hexahydrofuro-[3,2-b]furan-6-yl]oxy-tert-butyl-dimethyl-silane 2,2,2-trifluoroacetic acid (86.4 mg, 0.128 mmol) and methane sulfonyl chloride (16 uL, 0.205 mmol) in DCM (1.0 ml). After 20 minutes, the reaction mixture was diluted with EtOAc (30 ml), water (20 ml) and 2N HCl (2 mL). The EtOAc layer was washed with brine (10 mL), dried over MgSO4, filtered, and evaporated under reduced pressure to give an oil. The oil was purified on preparative silica plates (2×1000 u developed with 1:1 EtOAc/hexanes) to give the title compound. LC-MS: calculated for C27H37ClN6O6SSi 636.20 observed m/e: 637.13 (M+H)+ (Rt 1.35/2 min)

Step C: (3R,3aR,6R,6aR)-6-[[6-chloro-5-(5-methyl-sulfonyl-4,6-dihydropyrrolo[3,4-c]pyrazol-2-yl)-1H-imidazo[4,5-b]pyridin-2-yl]oxy]-2,3,3a,5,6,6a-hexahydrofuro[3,2-b]furan-3-ol A mixture of palladium acetate (2.5 mg, 0.011 mmol) and DPPP (1.6 mg, 0.0039 mmol) in ethanol (0.1 mL) was stirred for 20 minutes under nitrogen. The resulting dark suspension was added to a mixture of sodium borohydride (18 mg, 0.476 mmol) and [(3R,3aR,6R,6aS)-3-[1-allyl-6-chloro-5-(5-methylsulfonyl-4,6-dihydropyrrolo[3,4-c]pyrazol-2-yl)imidazo[4,5-b]pyridin-2-yl]oxy-2,3,3a,5,6,6a-hexahydrofuro[3,2-b]furan-6-yl]oxy-tert-butyl-dimethyl-silane (50.6 mg, 0.079 mmol) in ethanol (0.9 ml). The reaction was stirred at room temperature under a nitrogen atmosphere for 2.5 hours. The reaction mixture was then purified directly on preparative silica plates (1×1000 u developed with 5% MeOH/DCM). The resulting solid was dissolved in 1M TBAF in THF (0.1 mL, 0.1 mmol) and stirred at room temperature for 1 hour. The mixture was diluted with ethyl acetate (20 mL) and washed with water (10 mL). The organic layer was washed with brine (1×5 mL), dried with MgSO4, filtered and the solvent was removed under vacuum. The resulting solid was dissolved in methanol (1.0 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. LC-MS: calculated for C18H19ClN6O6S 482.08 observed m/e: 483.12 (M+H)+ (Rt 0.97/2 min); 1H NMR δ (ppm) (CD3OD): 7.92 (s, 1H), 7.86 (s, 1H), 5.56 (m, 1H), 4.61 (s, 4H), 4.47 (dd, 1H), 4.29 (m, 1H), 4.18-4.10 (m, 2H), 3.90 (dd, 1H), 3.60 (dd, 1H) and 3.02 (s, 3H).

TABLE 10

Compounds prepared according to the methods in Example 64.

| Example Number | Structure | HPLC-mass spectrum m/e |
|---|---|---|
| 65 | 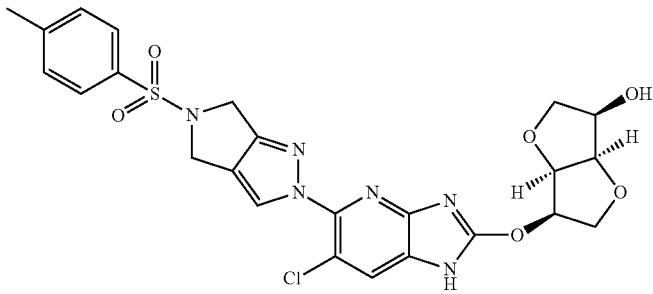 [SMILES: Cc1ccc(S(=O)(=O)N2Cc3cn(-c4nc5nc(O[C@@H]6CO[C@H]7[C@@H]6OC[C@H]7O)[nH]c5cc4Cl)nc3C2)cc1] | 559.18 |

EXAMPLE 66

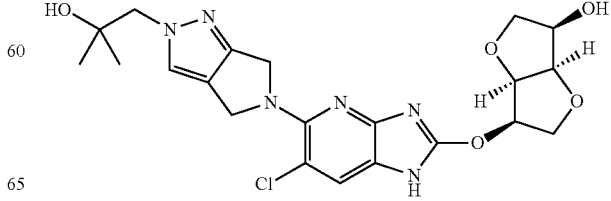

(3R,3aR,6R,6aR)-6-[[6-chloro-5-[2-(2-hydroxy-2-methyl-propyl)-4,6-dihydropyrrolo[3,4-c]-pyrazol-5-yl]-1H-imidazo[4,5-b]pyridin-2-yl]oxy]-2,3,3a,5,6,6a-hexahydrofuro[3,2-b]furan-3-ol Step A: 1-[5-[2-[[(3R,3aR,6R,6aS)-6-[tert-butyl(dimethyl)silyl]oxy-2,3,3a,5,6,6a-hexahydrofuro[3,2-b]furan-3-yl]oxy]-1-allyl-6-chloro-imidazo[4,5-b]pyridin-5-yl]-4,6-dihydropyrrolo[3,4-c]pyrazol-2-yl]-2-methyl-propan-2-ol A mixture of Ruphos indoline precatalyst (12.6 mg, 0.017 mmol, Strem), 1-(5,6-dihydro-4H-pyrrolo[3,4-c]pyrazol-2-yl)-2-methyl-propan-2-ol 2,2,2-trifluoroacetic acid (102 mg, 0.346 mmol), potassium phosphate tribasic (184 mg, 0.865 mmol) and [(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethyl-silane (100 mg, 0.173 mmol) in dioxane (1.0 ml) was degassed (3×) and placed under nitrogen before being heated to 110° C. After 18 hours, the reaction mixture was cooled to room temperature, diluted with EtOAc (30 ml), washed with water (20 ml), brine (10 mL), dried over MgSO₄, filtered, and evaporated under reduced pressure to give an oil. The oil was purified on preparative silica plates (1×1000 u developed and eluted with EtOAc) to give the title compound. LC-MS: calculated for C30H43ClN6O5Si 630.28 observed m/e: 631.27 (M+H)⁺ (Rt 1.36/2 min)

Step B: (3R,3aR,6R,6aR-6-[[6-chloro-5-[2-(2-hydroxy-2-methyl-propyl)-4,6-dihydropyrrolo[3,4-c]pyrazol-5-yl]-1H-imidazo[4,5-b]pyridin-2-yl]oxy]-2,3,3a,5,6,6a-hexahydrofuro[3,2-b]furan-3-ol A mixture of tetrakis(triphenylphosphine)palladium(0) (3.7 mg, 0.003 mmol), 1,3-dimethylbarbaturic acid (10.2 mg, 0.066 mmol) and 1-[5-[2-[[(3R,3aR,6R,6aS)-6-[tert-butyl(dimethyl)silyl]oxy-2,3,3a,5,6,6a-hexahydrofuro[3,2-b]furan-3-yl]oxy]-1-allyl-6-chloro-imidazo[4,5-b]pyridin-5-yl]-4,6-dihydropyrrolo[3,4-c]pyrazol-2-yl]-2-methyl-propan-2-ol (20.6 mg, 0.033 mmol) in ethanol (0.5 ml) was heated in a 50 degree oil bath under a nitrogen atmosphere for 18 hours. The reaction mixture was cooled to room temperature and purified directly on preparative silica plates (1×1000 u developed with 5% MeOH/DCM). The resulting solid (18 mg, 0.030 mmol) was dissolved in 1M TBAF in THF (0.1 mL, 0.1 mmol) and stirred at room temperature for 3 hours. The mixture was diluted with ethyl acetate (20 mL) and washed with water (10 mL). The organic layer was washed with brine (1×5 mL), dried with MgSO4, filtered and the solvents were removed under vacuum. The resulting solid was dissolved in methanol (1.0 mL) and purified by preparative HPLC reverse phase (C-18), using a 30×150 mm Sunfire™ column and eluting with a 20%-80% acetonitrile/water+0.05% TFA gradient. The desired fractions were lyophilized to give the title compound as a solid. LC-MS: calculated for C21H25ClN6O5 476.16 observed m/e: 477.23 (M+H)⁺ (Rt 1.01/2 min) ¹H NMR δ (ppm) (CD₃OD): 7.66 (s, 1H), 7.45 (s, 1H), 5.42 (m, 1H), 4.95 (m, 1H), 4.48 (dd, 1H), 4.28 (m, 1H), 4.16-4.08 (m, 6H), 3.90 (dd, 1H), 3.58 (dd, 1H) and 1.20 (s, 6H).

EXAMPLE 67

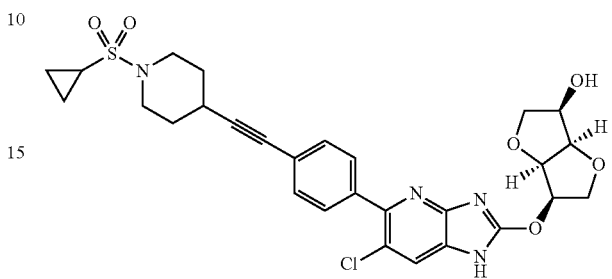

(3R,3aR,6R,6aR)-6-((6-chloro-5-(4-((1-(cyclopropylsulfonyl)piperidin-4-yl)ethynyl)phenyl)-1H-imidazo[4,5-b]pyridin-2-yl)oxy)hexahydrofuro[3,2-b]furan-3-ol To a stirred solution of 2-(((3R,3aR,6R,6aS)-6-((tertbutyldimethylsilyl)oxy)hexa-hydrofuro[3,2-b]furan-3-yl)oxy)-6-chloro-5-(4-(piperidin-4-ylethynyl)phenyl)-1-((2-(trimethylsilyl)ethoxy)-methyl)-1H-imidazo[4,5-b]pyridine (33 mg, 0.045 mmol) in anhydrous dichloromethane (1.00 mL) was added DIEA (0.016 mL, 0.091 mmol) and cyclopropylsulfonyl chloride (14.6 mg, 0.113 mmol). After 2 hours, the mixture was directly loaded onto a Biotage™ 10 G silica gel SNAP cartridge and employing a linear gradient: 0-50% EtOAc in 1:1 Hex/DCM over 25 column volumes. The desired product fractions were combined and concentrated under reduced pressure to afford a colorless oil. The resultant colorless oil was dissolved in formic acid (1.0 mL), then saturated aqueous KHSO₄ (0.25 mL) was added and the mixture was stirred at 50° C. After 2 hours, the reaction mixture was poured into saturated aqueous sodium bicarbonate (120 mL) and extracted with ethyl acetate (2×100 mL). The combined organic layers were concentrated under reduced pressure to afford a white solid which was dissolved in methanol (5 mL) and then treated with aqueous sodium hydroxide (3N, 1.0 mL). After stirring for 10 minutes, the mixture was neutralized with 1N aqueous HCl (3.0 mL), and poured into saturated aqueous sodium bicarbonate (40 mL). The aqueous mixture was extracted with ethyl acetate (2×60 mL). The combined organic layers were dried over sodium sulfate and concentrated under reduced pressure. The resultant white solid was dissolved in acetonitrile/water mixture, cooled to −78° C., and then lyophilized to dryness to afford the title compound as a white solid. LC-MS: calculated for C28H29ClN4O6S 584.15, observed m/e: 585.14 (M+H)⁺ (Rt 1.95/4 min); ¹H NMR δ (ppm) (CD₃OD): 7.78 (s, 1H), 7.60 (d, J=4.3 Hz, 2H), 7.45 (d, J=4.3 Hz, 2H), 5.52 (q, J=5.5 Hz, 1H), 4.95 (t, J=5.5 Hz, 1H), 4.45 (t, J=5.0 Hz), 4.27 (m, 1H), 4.15 (dd, J=10.0, 6.0 Hz, 1H), 4.09 (dd, J=10.0, 6.0 Hz, 1H), 3.88 (dd, J=8.0, 7.0 Hz, 1H), 3.59 (m, 4H), 3.21 (m, 2H), 2.88 (m, 1H), 2.49 (m, 1H), 2.03 (m, 2H), 1.80 (m, 2H), 1.03 (m, 4H).

TABLE 11
Compounds prepared according to the methods in Example 67.
| Example Number | Structure | HPLC-mass spectrum m/e |
|---|---|---|
| 68 | 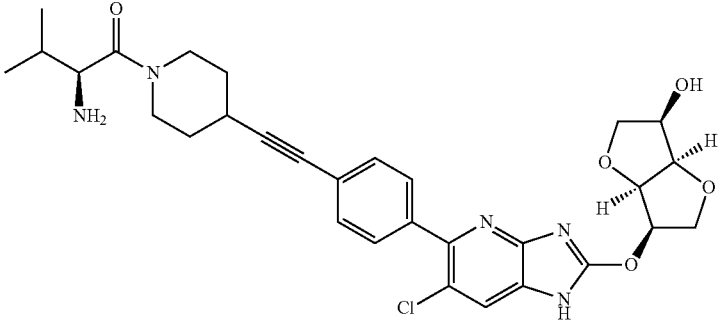 [SMILES: CC(C)[C@H](N)C(=O)N1CCC(C#Cc2ccc(-c3nc4nc(O[C@@H]5CO[C@H]6[C@@H]5OC[C@H]6O)[nH]c4cc3Cl)cc2)CC1] | 580.19 |
| 69 | 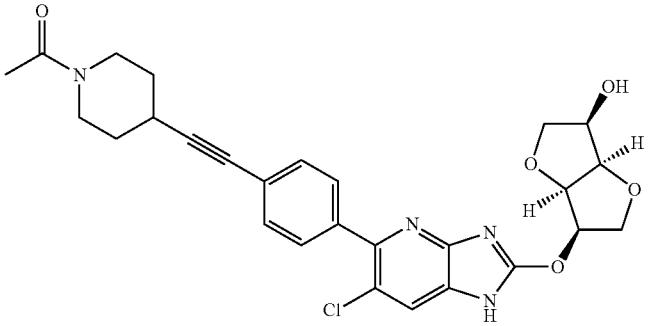 [SMILES: CC(=O)N1CCC(C#Cc2ccc(-c3nc4nc(O[C@@H]5CO[C@H]6[C@@H]5OC[C@H]6O)[nH]c4cc3Cl)cc2)CC1] | 523.14 |
| 70 | 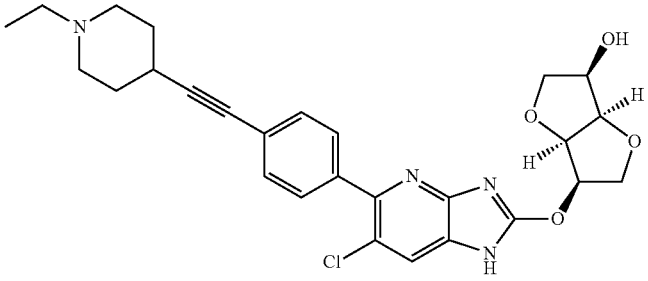 [SMILES: CCN1CCC(C#Cc2ccc(-c3nc4nc(O[C@@H]5CO[C@H]6[C@@H]5OC[C@H]6O)[nH]c4cc3Cl)cc2)CC1] | 509.22 |
| 71 | 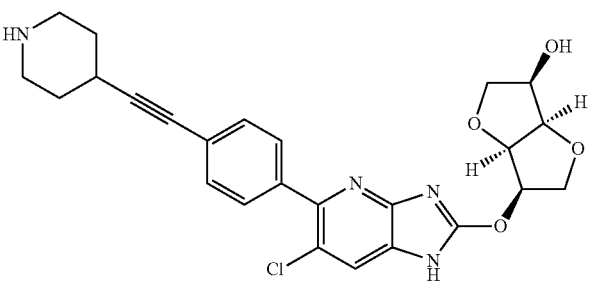 [SMILES: O[C@@H]1CO[C@H]2[C@@H]1OC[C@H]2Oc1nc2nc(-c3ccc(C#CC4CCNCC4)cc3)c(Cl)cc2[nH]1] | 481.12 |

EXAMPLE 72

(3R,3aR,6R,6aR)-6-((5-(3',4'-difluoro-[1,1'-biphenyl]-4-yl)-4,6-difluoro-1H-benzo[d]imidazol-2-yl)oxy)hexahydrofuro[3,2-b]furan-3-ol

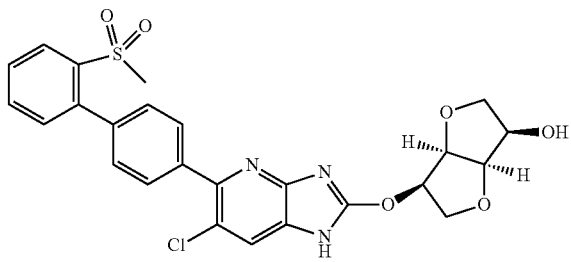 [SMILES: CS(=O)(=O)c1ccccc1-c1ccc(-c2nc3nc(O[C@@H]4CO[C@H]5[C@@H]4OC[C@H]5O)[nH]c3cc2Cl)cc1]

(3R,3aR,6R,6aR)-6-((6-chloro-5-(4-(4,4,5,5-tetramethyl-1,3,2-dioxaborolan-2-yl)phenyl)-1H-imidazo[4,5-b]pyridin-2-yl)oxy)hexahydrofuro-[3,2-b]furan-3-ol (15.0 mg, 0.030 mmol) and 1-bromo-2-(methylsulfonyl)-benzene (8.47 mg, 0.036 mmol) in anhydrous dimethylacetamide (0.4 ml) was purged with $N_2$ and then chloro[(tri-tert-butylphosphine)-2-(2-aminobiphenyl)]palladium(II) (3.08 mg, 0.006 mmol) and tripotassium phosphate (0.09 ml, 0.09 mmol) were added under $N_2$ flow. The mixture was heated to 80° C. overnight. The resulting residue was diluted with 0.5 ml DMA, filtered and purified by mass-directed reverse phase eluting with acetonitrile/water+0.1% TFA to give the title product. LC-MS: calculated for $C25H_{22}ClN3O6S$, 527.09, observed m/e: 528.09 $(M+H)^+$ (Rt 0.62/2.00 min)

TABLE 12

Compounds prepared according to the methods in Example 72.

| Example | Structure | Exact Mass [M + H]+ |
|---|---|---|
| 73 | 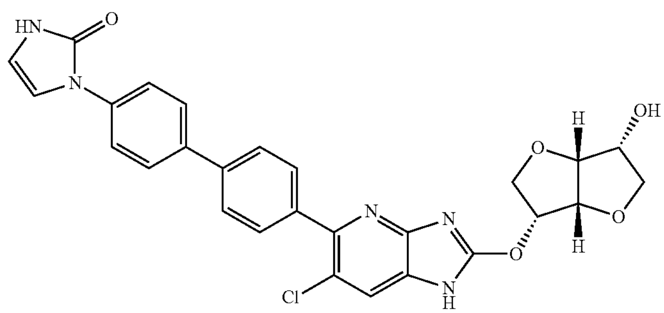 [SMILES: O=c1[nH]ccn1-c1ccc(-c2ccc(-c3nc4nc(O[C@@H]5CO[C@H]6[C@@H]5OC[C@H]6O)[nH]c4cc3Cl)cc2)cc1] | 532.13 |
| 74 | 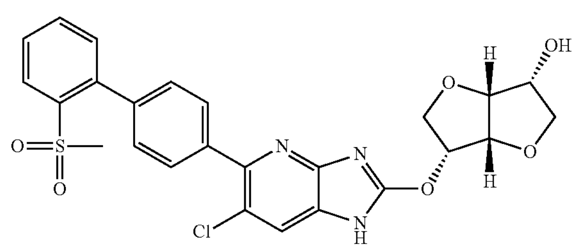 [SMILES: CS(=O)(=O)c1ccccc1-c1ccc(-c2nc3nc(O[C@@H]4CO[C@H]5[C@@H]4OC[C@H]5O)[nH]c3cc2Cl)cc1] | 528.09 |
| 75 | 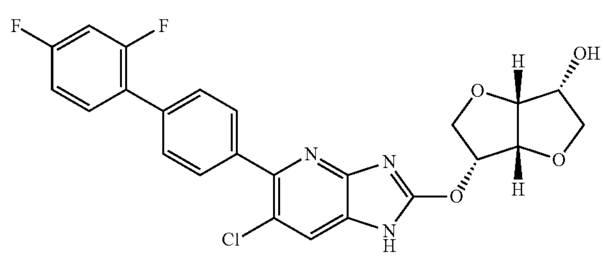 [SMILES: O[C@@H]1CO[C@H]2[C@@H]1OC[C@H]2Oc1nc2nc(-c3ccc(-c4ccc(F)cc4F)cc3)c(Cl)cc2[nH]1] | 486.1 |

TABLE 12-continued

Compounds prepared according to the methods in Example 72.

| Example | Structure | Exact Mass [M + H]+ |
|---|---|---|
| 76 | 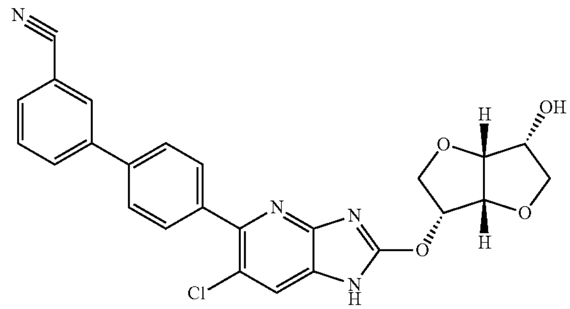 [SMILES: N#Cc1cccc(-c2ccc(-c3nc4nc(O[C@@H]5CO[C@H]6[C@@H]5OC[C@H]6O)[nH]c4cc3Cl)cc2)c1] | 475.11 |
| 77 | 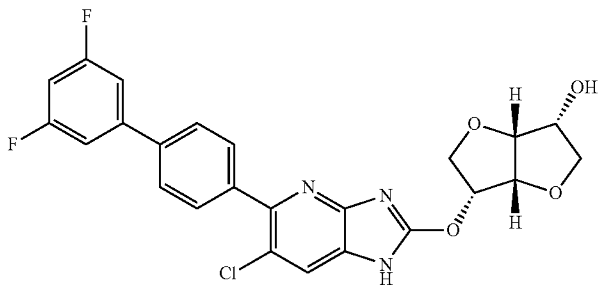 [SMILES: O[C@@H]1CO[C@H]2[C@@H]1OC[C@H]2Oc1nc2nc(-c3ccc(-c4cc(F)cc(F)c4)cc3)c(Cl)cc2[nH]1] | 486.1 |
| 78 | 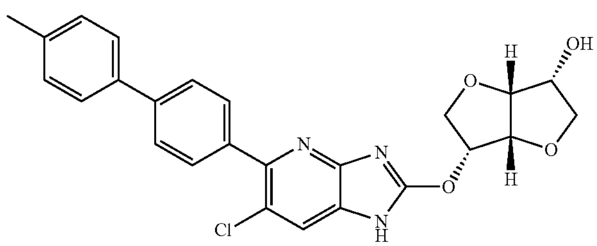 [SMILES: Cc1ccc(-c2ccc(-c3nc4nc(O[C@@H]5CO[C@H]6[C@@H]5OC[C@H]6O)[nH]c4cc3Cl)cc2)cc1] | 464.13 |
| 79 | 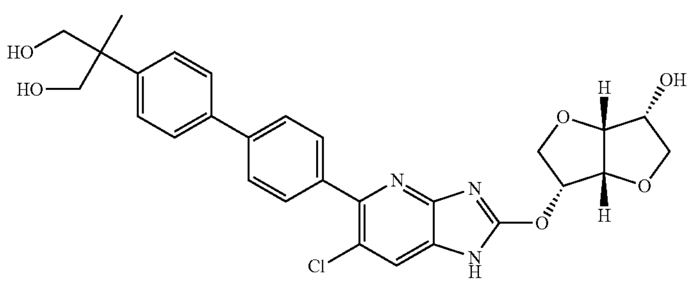 [SMILES: CC(CO)(CO)c1ccc(-c2ccc(-c3nc4nc(O[C@@H]5CO[C@H]6[C@@H]5OC[C@H]6O)[nH]c4cc3Cl)cc2)cc1] | 538.17 |
| 80 | 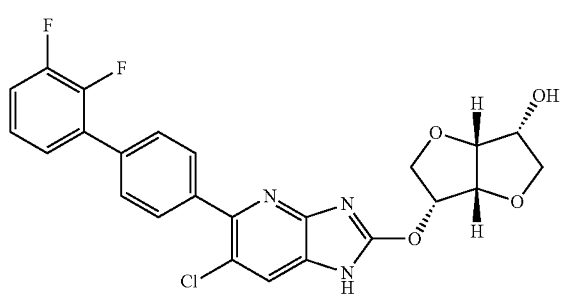 [SMILES: O[C@@H]1CO[C@H]2[C@@H]1OC[C@H]2Oc1nc2nc(-c3ccc(-c4cccc(F)c4F)cc3)c(Cl)cc2[nH]1] | 486.1 |

TABLE 12-continued

Compounds prepared according to the methods in Example 72.

| Example | Structure | Exact Mass [M + H]+ |
|---|---|---|
| 81 | 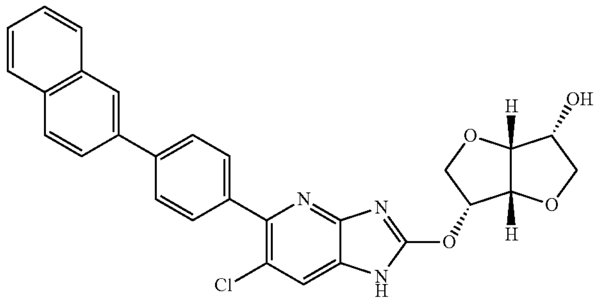 [SMILES: O[C@@H]1CO[C@H]2[C@@H]1OC[C@H]2Oc1nc2nc(-c3ccc(-c4ccc5ccccc5c4)cc3)c(Cl)cc2[nH]1] | 500.13 |
| 82 | 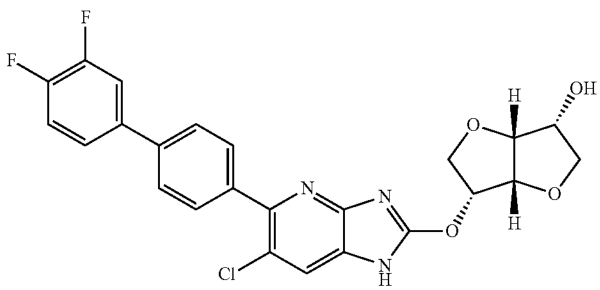 [SMILES: O[C@@H]1CO[C@H]2[C@@H]1OC[C@H]2Oc1nc2nc(-c3ccc(-c4ccc(F)c(F)c4)cc3)c(Cl)cc2[nH]1] | 486.1 |
| 83 | 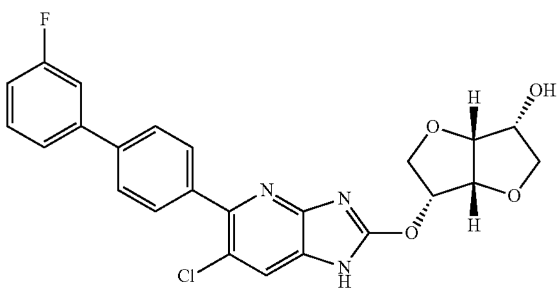 [SMILES: O[C@@H]1CO[C@H]2[C@@H]1OC[C@H]2Oc1nc2nc(-c3ccc(-c4cccc(F)c4)cc3)c(Cl)cc2[nH]1] | 468.11 |
| 84 | 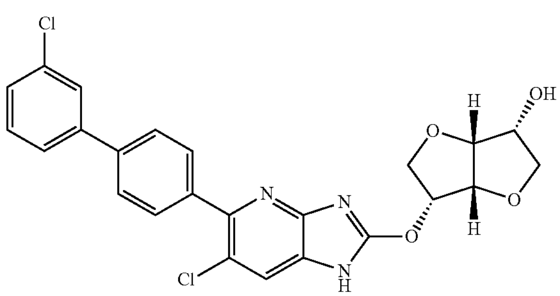 | 484.08 |
| 85 | 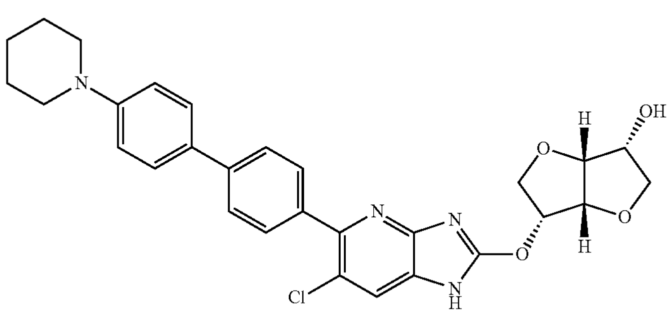 [SMILES: O[C@@H]1CO[C@H]2[C@@H]1OC[C@H]2Oc1nc2nc(-c3ccc(-c4ccc(N5CCCCC5)cc4)cc3)c(Cl)cc2[nH]1] | 533.19 |

TABLE 12-continued

Compounds prepared according to the methods in Example 72.

| Example | Structure | Exact Mass [M + H]+ |
|---------|-----------|---------------------|
| 86 | 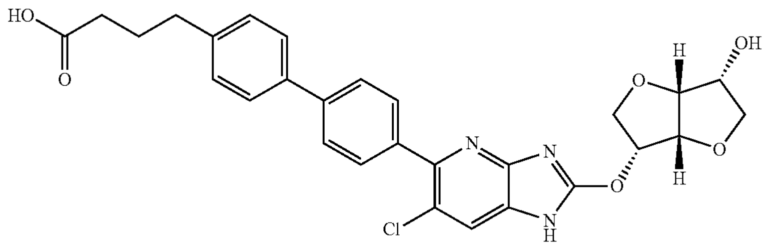 [SMILES: O=C(O)CCCc1ccc(-c2ccc(-c3nc4nc(O[C@@H]5CO[C@H]6[C@@H]5OC[C@H]6O)[nH]c4cc3Cl)cc2)cc1] | 536.15 |
| 87 | 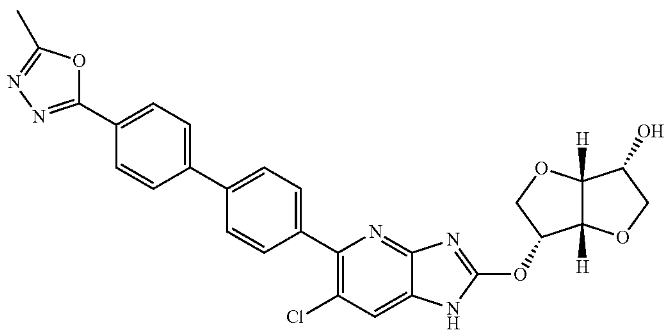 [SMILES: Cc1nnc(-c2ccc(-c3ccc(-c4nc5nc(O[C@@H]6CO[C@H]7[C@@H]6OC[C@H]7O)[nH]c5cc4Cl)cc3)cc2)o1] | 532.13 |
| 88 | 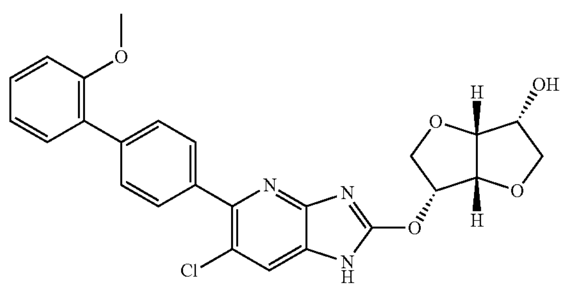 [SMILES: COc1ccccc1-c1ccc(-c2nc3nc(O[C@@H]4CO[C@H]5[C@@H]4OC[C@H]5O)[nH]c3cc2Cl)cc1] | 480.13 |
| 89 | 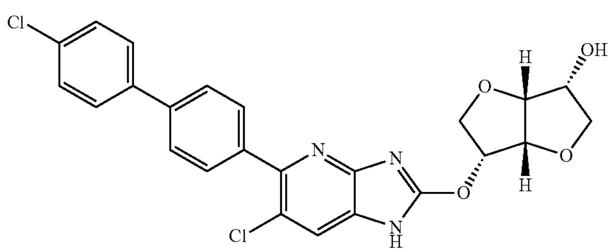 [SMILES: O[C@@H]1CO[C@H]2[C@@H]1OC[C@H]2Oc1nc2nc(-c3ccc(-c4ccc(Cl)cc4)cc3)c(Cl)cc2[nH]1] | 484.08 |
| 90 | 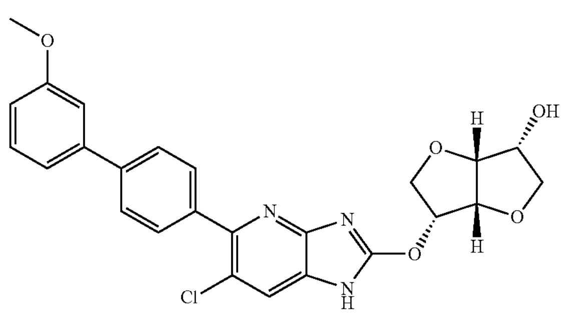 [SMILES: COc1cccc(-c2ccc(-c3nc4nc(O[C@@H]5CO[C@H]6[C@@H]5OC[C@H]6O)[nH]c4cc3Cl)cc2)c1] | 480.13 |

TABLE 12-continued

Compounds prepared according to the methods in Example 72.

| Example | Structure | Exact Mass [M + H]+ |
|---------|-----------|---------------------|
| 91 | 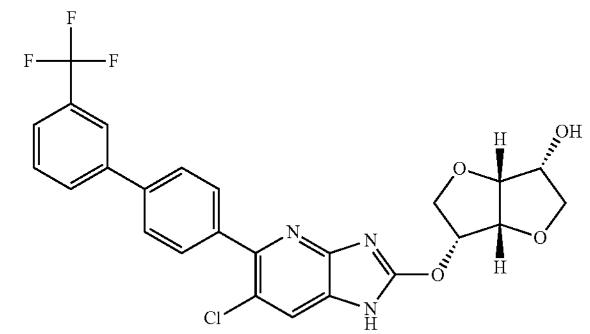 [SMILES: O[C@@H]1CO[C@H]2[C@@H]1OC[C@H]2Oc1nc2nc(-c3ccc(-c4cccc(C(F)(F)F)c4)cc3)c(Cl)cc2[nH]1] | 518.1 |
| 92 | 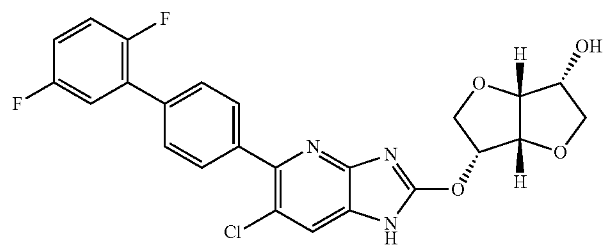 [SMILES: O[C@@H]1CO[C@H]2[C@@H]1OC[C@H]2Oc1nc2nc(-c3ccc(-c4cc(F)ccc4F)cc3)c(Cl)cc2[nH]1] | 486.1 |
| 93 | 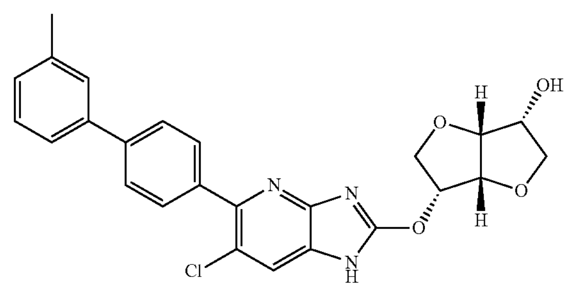 [SMILES: Cc1cccc(-c2ccc(-c3nc4nc(O[C@@H]5CO[C@H]6[C@@H]5OC[C@H]6O)[nH]c4cc3Cl)cc2)c1] | 464.13 |
| 94 | 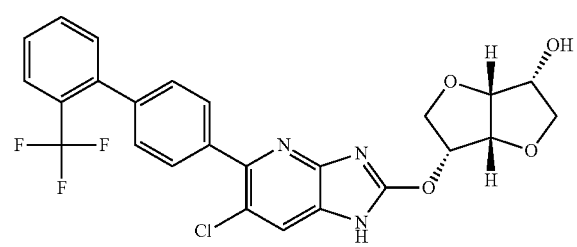 [SMILES: O[C@@H]1CO[C@H]2[C@@H]1OC[C@H]2Oc1nc2nc(-c3ccc(-c4ccccc4C(F)(F)F)cc3)c(Cl)cc2[nH]1] | 518.1 |
| 95 | 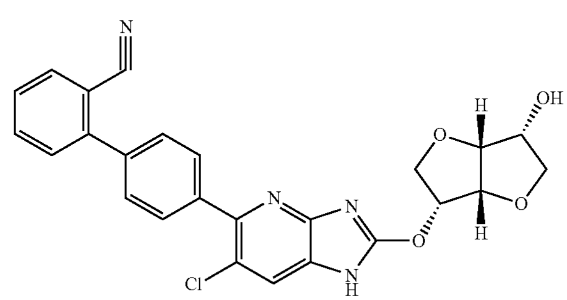 [SMILES: N#Cc1ccccc1-c1ccc(-c2nc3nc(O[C@@H]4CO[C@H]5[C@@H]4OC[C@H]5O)[nH]c3cc2Cl)cc1] | 475.11 |

TABLE 12-continued

Compounds prepared according to the methods in Example 72.

| Example | Structure | Exact Mass [M + H]+ |
|---|---|---|
| 96 | 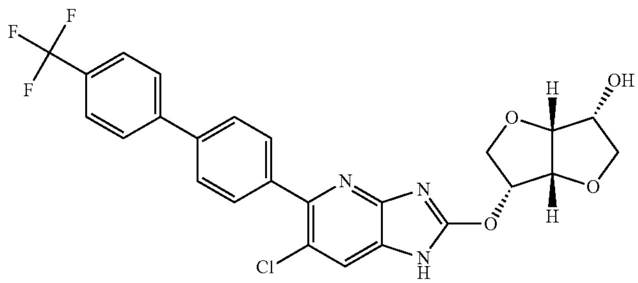 [SMILES: O[C@@H]1CO[C@H]2[C@@H]1OC[C@H]2Oc1nc2nc(-c3ccc(-c4ccc(C(F)(F)F)cc4)cc3)c(Cl)cc2[nH]1] | 518.1 |
| 97 | 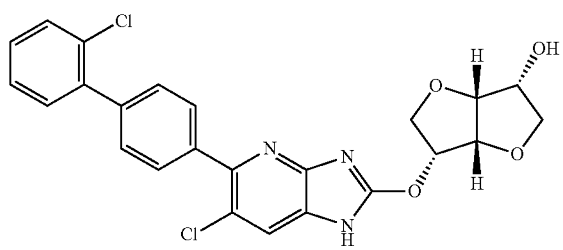 [SMILES: O[C@@H]1CO[C@H]2[C@@H]1OC[C@H]2Oc1nc2nc(-c3ccc(-c4ccccc4Cl)cc3)c(Cl)cc2[nH]1] | 484.08 |
| 98 | 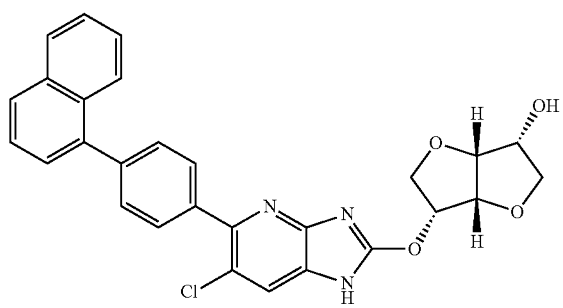 [SMILES: O[C@@H]1CO[C@H]2[C@@H]1OC[C@H]2Oc1nc2nc(-c3ccc(-c4cccc5ccccc45)cc3)c(Cl)cc2[nH]1] | 500.13 |
| 99 | 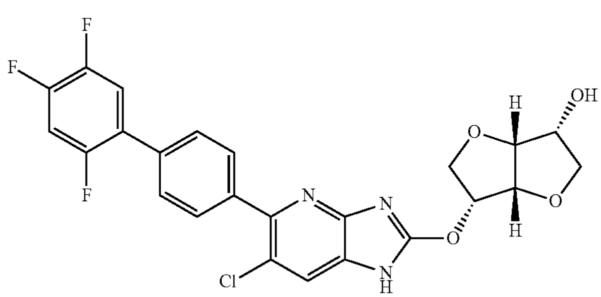 [SMILES: O[C@@H]1CO[C@H]2[C@@H]1OC[C@H]2Oc1nc2nc(-c3ccc(-c4cc(F)c(F)cc4F)cc3)c(Cl)cc2[nH]1] | 504.09 |
| 100 | 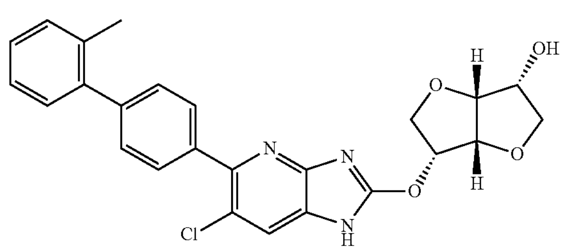 [SMILES: Cc1ccccc1-c1ccc(-c2nc3nc(O[C@@H]4CO[C@H]5[C@@H]4OC[C@H]5O)[nH]c3cc2Cl)cc1] | 464.13 |

TABLE 12-continued

Compounds prepared according to the methods in Example 72.

| Example | Structure | Exact Mass [M + H]+ |
|---------|-----------|---------------------|
| 101 | 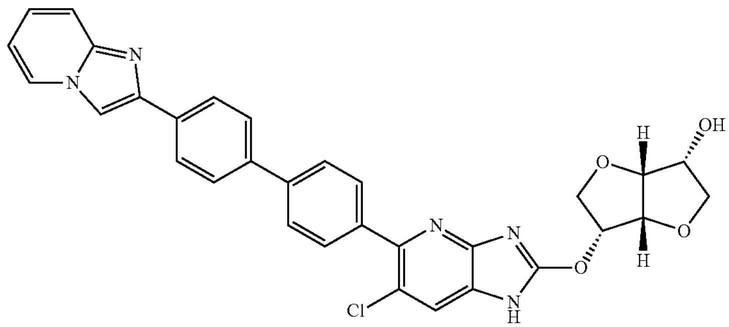 [SMILES: O[C@@H]1CO[C@H]2[C@@H]1OC[C@H]2Oc1nc2nc(-c3ccc(-c4ccc(-c5cn6ccccc6n5)cc4)cc3)c(Cl)cc2[nH]1] | 566.15 |
| 102 | 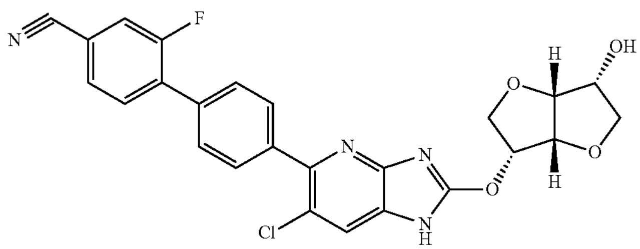 [SMILES: N#Cc1ccc(-c2ccc(-c3nc4nc(O[C@@H]5CO[C@H]6[C@@H]5OC[C@H]6O)[nH]c4cc3Cl)cc2)c(F)c1] | 493.1 |
| 103 | 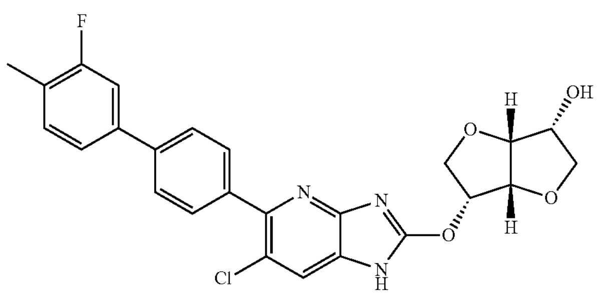 [SMILES: Cc1ccc(-c2ccc(-c3nc4nc(O[C@@H]5CO[C@H]6[C@@H]5OC[C@H]6O)[nH]c4cc3Cl)cc2)cc1F] | 482.12 |
| 104 | 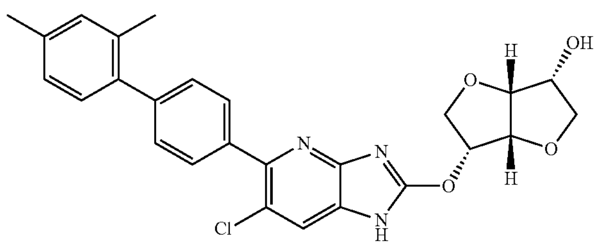 [SMILES: Cc1ccc(-c2ccc(-c3nc4nc(O[C@@H]5CO[C@H]6[C@@H]5OC[C@H]6O)[nH]c4cc3Cl)cc2)c(C)c1] | 478.15 |
| 105 | 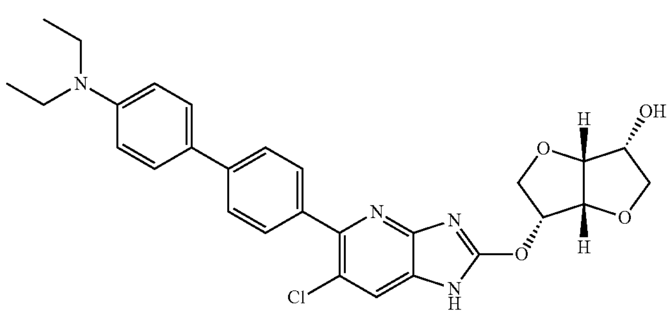 [SMILES: CCN(CC)c1ccc(-c2ccc(-c3nc4nc(O[C@@H]5CO[C@H]6[C@@H]5OC[C@H]6O)[nH]c4cc3Cl)cc2)cc1] | 521.19 |

EXAMPLE 106

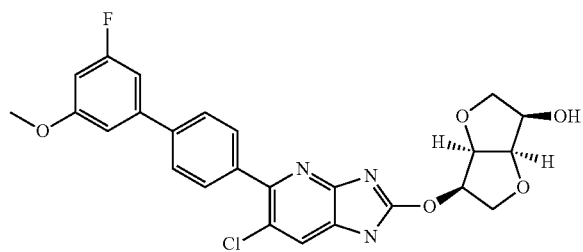 [SMILES: COc1cc(F)cc(-c2ccc(-c3nc4nc(O[C@@H]5CO[C@H]6[C@@H]5OC[C@H]6O)[nH]c4cc3Cl)cc2)c1]

(3R,3aR,6R,6aR)-6-((6-chloro-5-(3'-fluoro-5'-methoxy-[1,1'-biphenyl]-4-yl)-1H-imidazo[4,5-b]pyridin-2-yl)oxy)hexahydrofuro[3,2-b]furan-3-ol (3R,3aR,6R,6aR)-6-((6-chloro-5-(4-(4,4,5,5-tetramethyl-1,3,2-dioxaborolan-2-yl)phenyl)-1-((2-(trimethyl-silyl)ethoxy)methyl)-1H-imidazo[4,5-b]pyridin-2-yl)oxy)hexahydrofuro[3,2-b]furan-3-ol (40 mg, 0.063 mmol) and 1-bromo-3-fluoro-5-methoxybenzene (15.62 mg, 0.076 mmol) in anhydrous dioxane (0.4 ml) was purged with $N_2$ and then chloro[tri-tert-butylphosphine)-2-(2-aminobiphenyl)]palladium(II) (6.5 mg, 0.013 mmol) and tripotassium phosphate (0.191 ml, 0.191 mmol) were added under $N_2$ flow. The mixture was heated to 60° C. overnight. Then the crude mixture was extracted with DCM. The combined organic extracts were washed with water and evaporated under reduced pressure. 1 mL of 1:1 $CH_2Cl_2$ and TFA was added to the resulting residue and the solution was stirred for 2 h. Then the solvent was evaporated under reduced pressure to give an amber residue. The residue was diluted with 1.5 ml DMSO, filtered and purified by mass directed reverse phase column chromatography eluting with acetonitrile/water+0.1% TFA to give the title product. LC-MS: calculated for $C25H_{21}ClFN3O5$, 497.12, observed m/e: 498.11 $(M+H)^+$ (RT 1.03/2.00 min)

TABLE 13

Compounds prepared according to the methods in Example 106.

| Example | Structure | Exact Mass [M + H]+ |
|---|---|---|
| 107 | 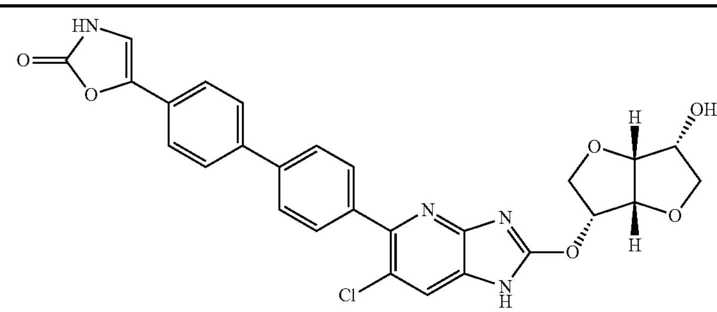 | 533.11 |
| 108 | 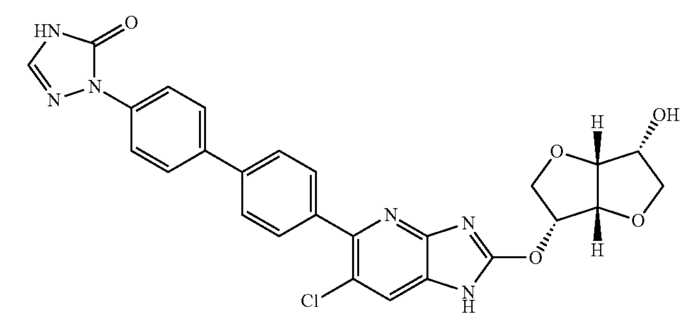 [SMILES: O=c1[nH]cnn1-c1ccc(-c2ccc(-c3nc4nc(O[C@@H]5CO[C@H]6[C@@H]5OC[C@H]6O)[nH]c4cc3Cl)cc2)cc1] | 533.13 |
| 109 | 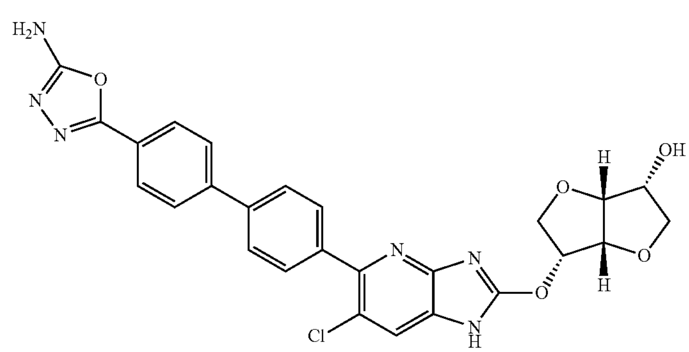 [SMILES: Nc1nnc(-c2ccc(-c3ccc(-c4nc5nc(O[C@@H]6CO[C@H]7[C@@H]6OC[C@H]7O)[nH]c5cc4Cl)cc3)cc2)o1] | 533.13 |

TABLE 13-continued

Compounds prepared according to the methods in Example 106.

| Example | Structure | Exact Mass [M + H]+ |
|---|---|---|
| 110 | 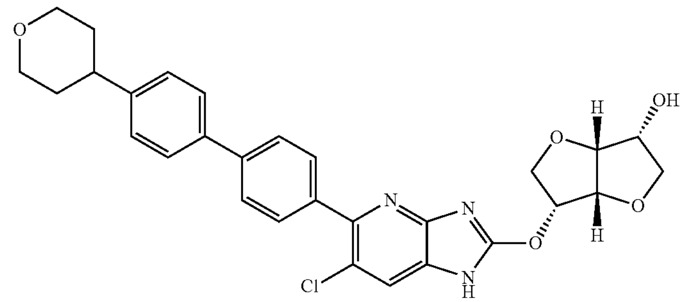 [SMILES: O[C@@H]1CO[C@H]2[C@@H]1OC[C@H]2Oc1nc2nc(-c3ccc(-c4ccc(C5CCOCC5)cc4)cc3)c(Cl)cc2[nH]1] | 534.17 |
| 111 | 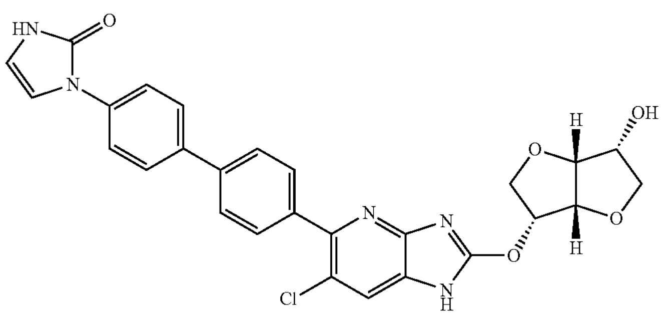 [SMILES: O=c1[nH]ccn1-c1ccc(-c2ccc(-c3nc4nc(O[C@@H]5CO[C@H]6[C@@H]5OC[C@H]6O)[nH]c4cc3Cl)cc2)cc1] | 532.13 |
| 112 | 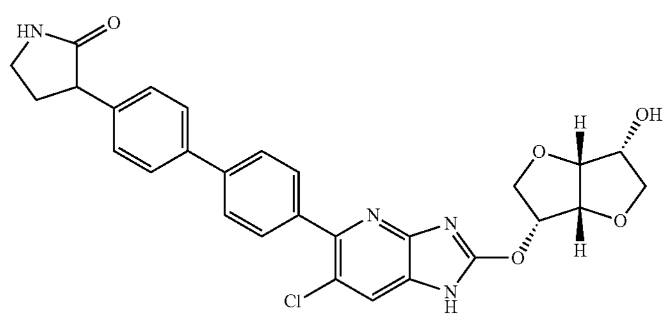 [SMILES: O=C1NCCC1c1ccc(-c2ccc(-c3nc4nc(O[C@@H]5CO[C@H]6[C@@H]5OC[C@H]6O)[nH]c4cc3Cl)cc2)cc1] | 533.15 |
| 113 | 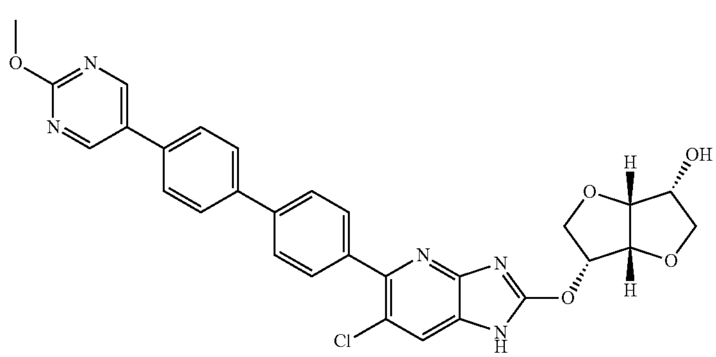 [SMILES: COc1ncc(-c2ccc(-c3ccc(-c4nc5nc(O[C@@H]6CO[C@H]7[C@@H]6OC[C@H]7O)[nH]c5cc4Cl)cc3)cc2)cn1] | 558.15 |

TABLE 13-continued

Compounds prepared according to the methods in Example 106.

| Example | Structure | Exact Mass [M + H]+ |
|---------|-----------|---------------------|
| 114 | 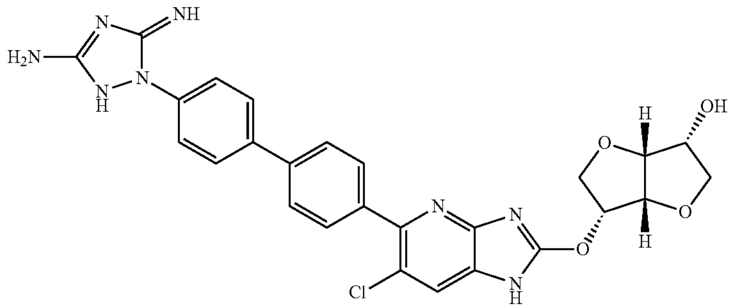 [SMILES: N=c1nc(N)[nH]n1-c1ccc(-c2ccc(-c3nc4nc(O[C@@H]5CO[C@H]6[C@@H]5OC[C@H]6O)[nH]c4cc3Cl)cc2)cc1] | 547.15 |
| 115 | 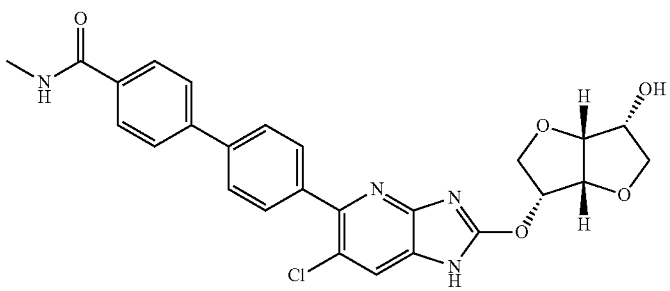 [SMILES: CNC(=O)c1ccc(-c2ccc(-c3nc4nc(O[C@@H]5CO[C@H]6[C@@H]5OC[C@H]6O)[nH]c4cc3Cl)cc2)cc1] | 507.14 |
| 116 | 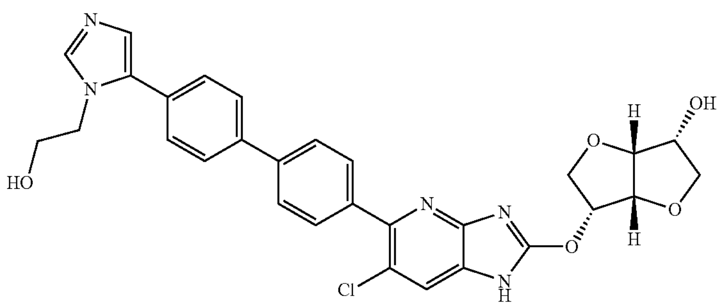 [SMILES: OCCn1cncc1-c1ccc(-c2ccc(-c3nc4nc(O[C@@H]5CO[C@H]6[C@@H]5OC[C@H]6O)[nH]c4cc3Cl)cc2)cc1] | 560.16 |
| 117 | 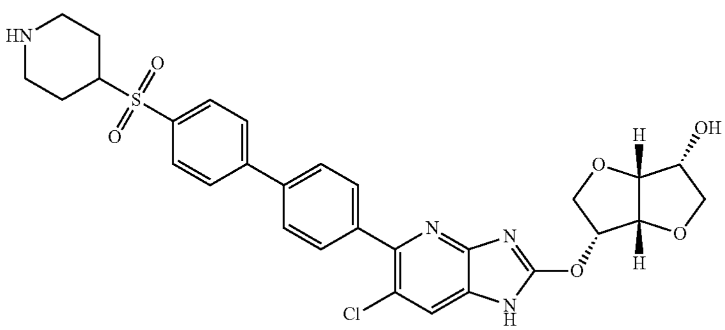 [SMILES: O=S(=O)(c1ccc(-c2ccc(-c3nc4nc(O[C@@H]5CO[C@H]6[C@@H]5OC[C@H]6O)[nH]c4cc3Cl)cc2)cc1)C1CCNCC1] | 597.15 |
| 118 | 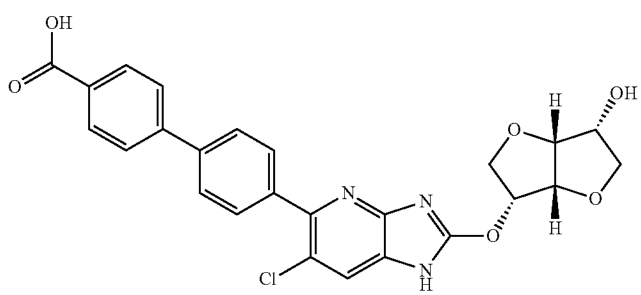 [SMILES: O=C(O)c1ccc(-c2ccc(-c3nc4nc(O[C@@H]5CO[C@H]6[C@@H]5OC[C@H]6O)[nH]c4cc3Cl)cc2)cc1] | 494.1 |

TABLE 13-continued

Compounds prepared according to the methods in Example 106.

| Example | Structure | Exact Mass [M + H]+ |
|---|---|---|
| 119 | 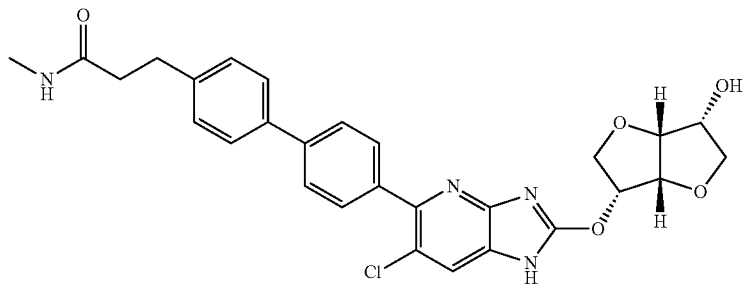 [SMILES: CNC(=O)CCc1ccc(-c2ccc(-c3nc4nc(O[C@@H]5CO[C@H]6[C@@H]5OC[C@H]6O)[nH]c4cc3Cl)cc2)cc1] | 535.17 |
| 120 | 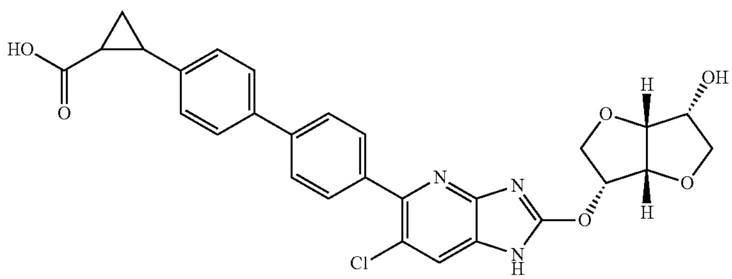 [SMILES: O=C(O)C1CC1c1ccc(-c2ccc(-c3nc4nc(O[C@@H]5CO[C@H]6[C@@H]5OC[C@H]6O)[nH]c4cc3Cl)cc2)cc1] | 534.14 |
| 121 | 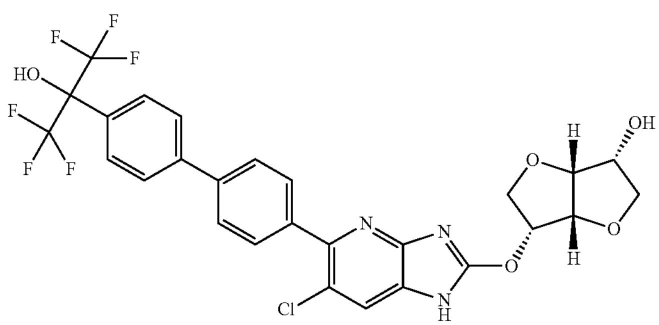 [SMILES: O[C@@H]1CO[C@H]2[C@@H]1OC[C@H]2Oc1nc2nc(-c3ccc(-c4ccc(C(O)(C(F)(F)F)C(F)(F)F)cc4)cc3)c(Cl)cc2[nH]1] | 616.1 |
| 122 | 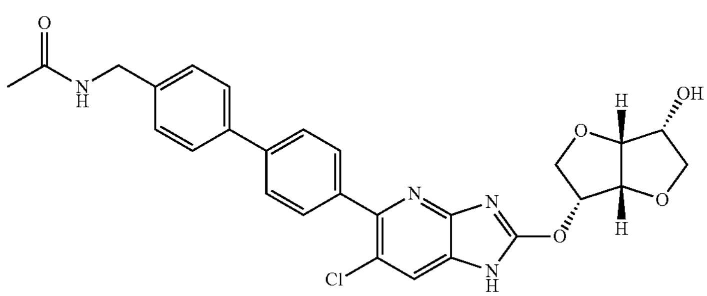 [SMILES: CC(=O)NCc1ccc(-c2ccc(-c3nc4nc(O[C@@H]5CO[C@H]6[C@@H]5OC[C@H]6O)[nH]c4cc3Cl)cc2)cc1] | 521.15 |
| 123 | 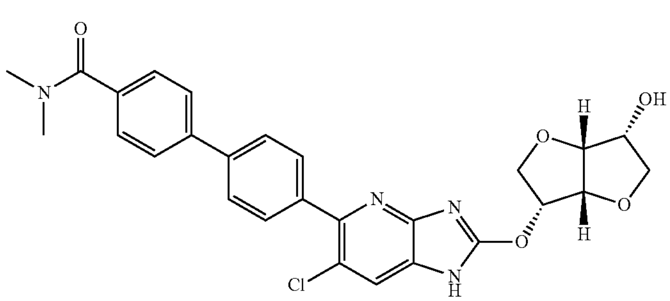 [SMILES: CN(C)C(=O)c1ccc(-c2ccc(-c3nc4nc(O[C@@H]5CO[C@H]6[C@@H]5OC[C@H]6O)[nH]c4cc3Cl)cc2)cc1] | 521.15 |

TABLE 13-continued

Compounds prepared according to the methods in Example 106.

| Example | Structure | Exact Mass [M + H]+ |
|---------|-----------|---------------------|
| 124 | 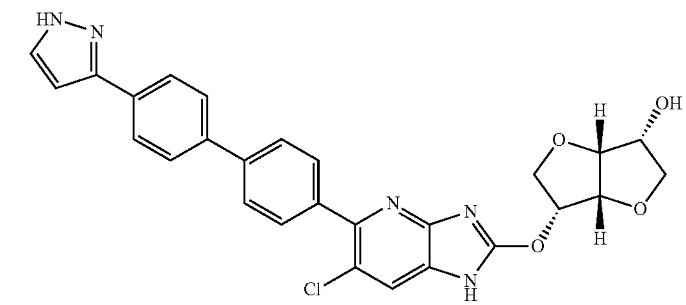 [SMILES: O[C@@H]1CO[C@H]2[C@@H]1OC[C@H]2Oc1nc2nc(-c3ccc(-c4ccc(-c5cc[nH]n5)cc4)cc3)c(Cl)cc2[nH]1] | 516.14 |
| 125 | 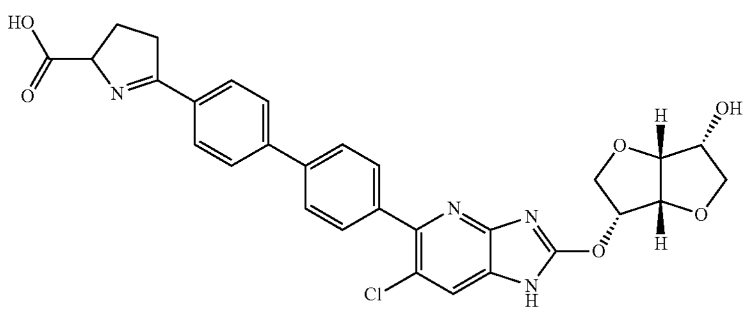 [SMILES: O=C(O)C1CCC(c2ccc(-c3ccc(-c4nc5nc(O[C@@H]6CO[C@H]7[C@@H]6OC[C@H]7O)[nH]c5cc4Cl)cc3)cc2)=N1] | 561.15 |
| 126 | 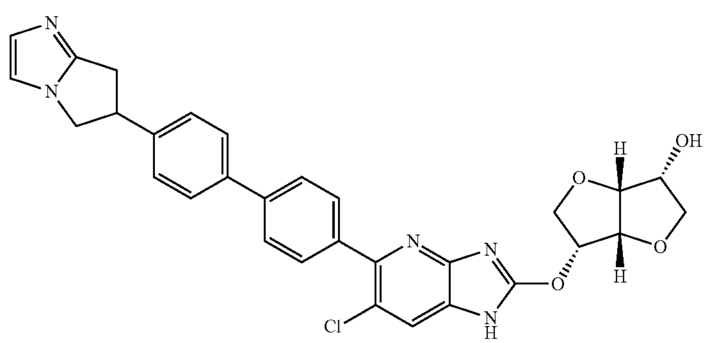 [SMILES: O[C@@H]1CO[C@H]2[C@@H]1OC[C@H]2Oc1nc2nc(-c3ccc(-c4ccc(C5Cc6nccn6C5)cc4)cc3)c(Cl)cc2[nH]1] | 556.17 |
| 127 | 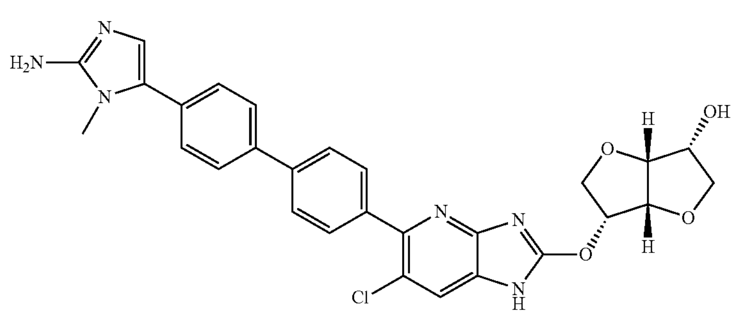 [SMILES: Cn1c(-c2ccc(-c3ccc(-c4nc5nc(O[C@@H]6CO[C@H]7[C@@H]6OC[C@H]7O)[nH]c5cc4Cl)cc3)cc2)cnc1N] | 545.16 |

TABLE 13-continued

Compounds prepared according to the methods in Example 106.

| Example | Structure | Exact Mass [M + H]+ |
|---|---|---|
| 128 | 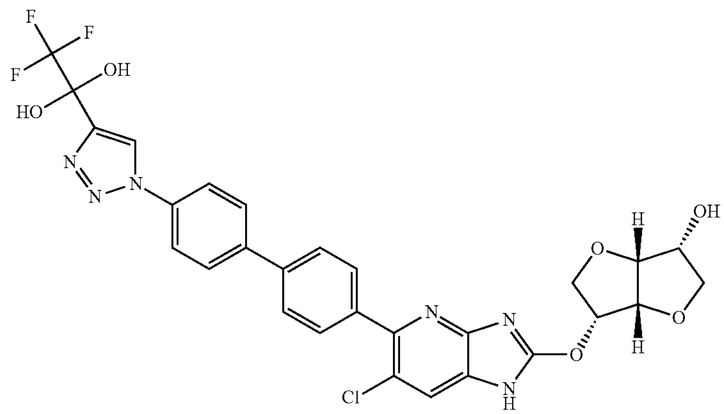 [SMILES: O[C@@H]1CO[C@H]2[C@@H]1OC[C@H]2Oc1nc2nc(-c3ccc(-c4ccc(-n5cc(C(O)(O)C(F)(F)F)nn5)cc4)cc3)c(Cl)cc2[nH]1] | 631.12 |
| 129 | 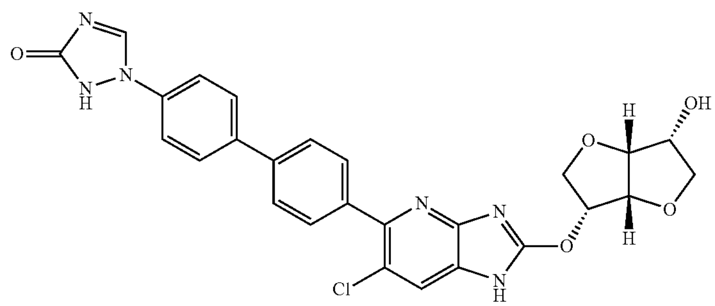 [SMILES: O=c1ncn(-c2ccc(-c3ccc(-c4nc5nc(O[C@@H]6CO[C@H]7[C@@H]6OC[C@H]7O)[nH]c5cc4Cl)cc3)cc2)[nH]1] | 533.13 |
| 130 | 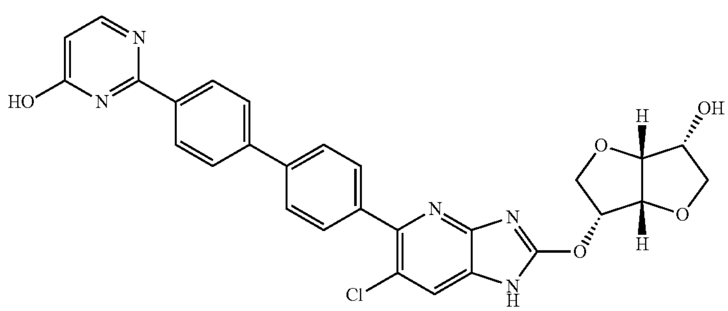 [SMILES: Oc1ccnc(-c2ccc(-c3ccc(-c4nc5nc(O[C@@H]6CO[C@H]7[C@@H]6OC[C@H]7O)[nH]c5cc4Cl)cc3)cc2)n1] | 544.13 |
| 131 | 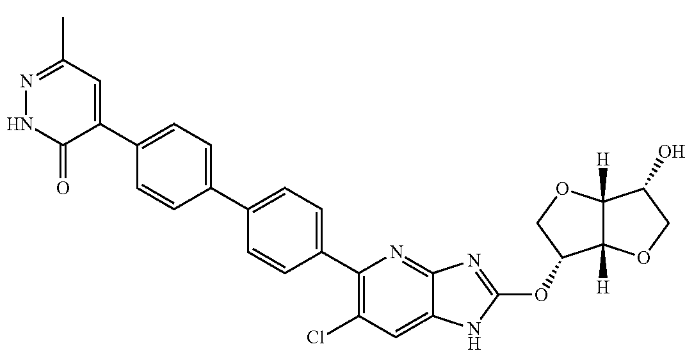 [SMILES: Cc1cc(-c2ccc(-c3ccc(-c4nc5nc(O[C@@H]6CO[C@H]7[C@@H]6OC[C@H]7O)[nH]c5cc4Cl)cc3)cc2)c(=O)[nH]n1] | 558.15 |

TABLE 13-continued

Compounds prepared according to the methods in Example 106.

| Example | Structure | Exact Mass [M + H]+ |
|---------|-----------|---------------------|
| 132 | 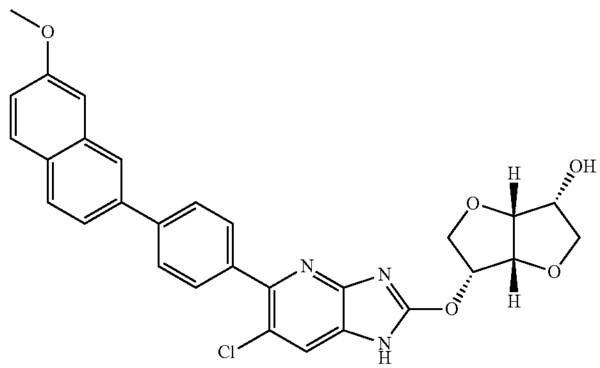 [SMILES: COc1ccc2ccc(-c3ccc(-c4nc5nc(O[C@@H]6CO[C@H]7[C@@H]6OC[C@H]7O)[nH]c5cc4Cl)cc3)cc2c1] | 530.14 |
| 133 | 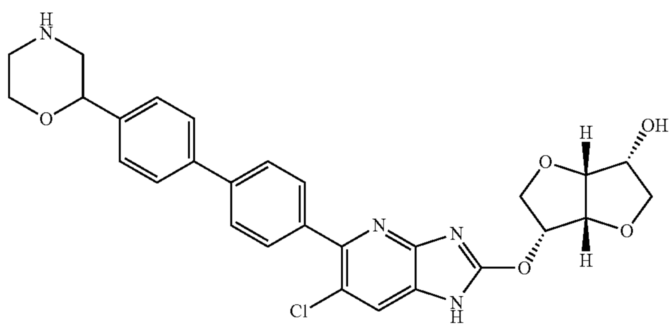 [SMILES: O[C@@H]1CO[C@H]2[C@@H]1OC[C@H]2Oc1nc2nc(-c3ccc(-c4ccc(C5CNCCO5)cc4)cc3)c(Cl)cc2[nH]1] | 535.17 |
| 134 | 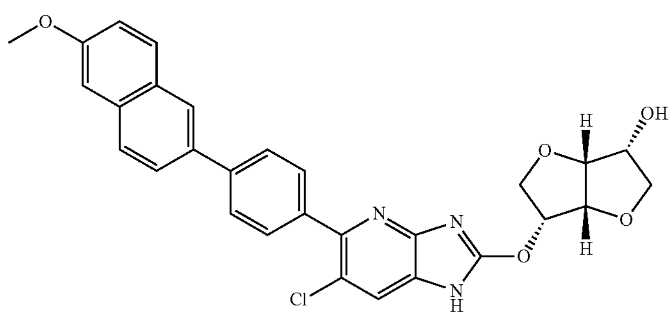 [SMILES: COc1ccc2cc(-c3ccc(-c4nc5nc(O[C@@H]6CO[C@H]7[C@@H]6OC[C@H]7O)[nH]c5cc4Cl)cc3)ccc2c1] | 530.14 |
| 135 | 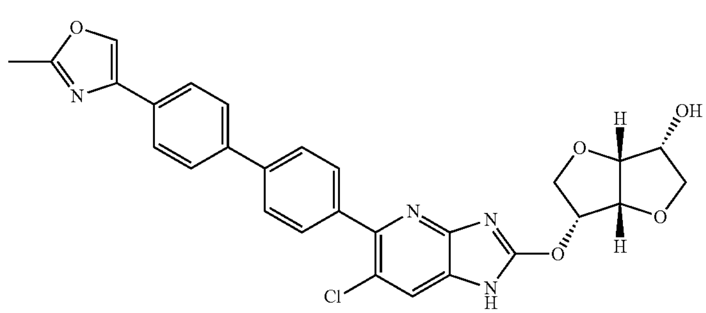 [SMILES: Cc1nc(-c2ccc(-c3ccc(-c4nc5nc(O[C@@H]6CO[C@H]7[C@@H]6OC[C@H]7O)[nH]c5cc4Cl)cc3)cc2)co1] | 531.14 |

TABLE 13-continued

Compounds prepared according to the methods in Example 106.

| Example | Structure | Exact Mass [M + H]+ |
|---|---|---|
| 136 | 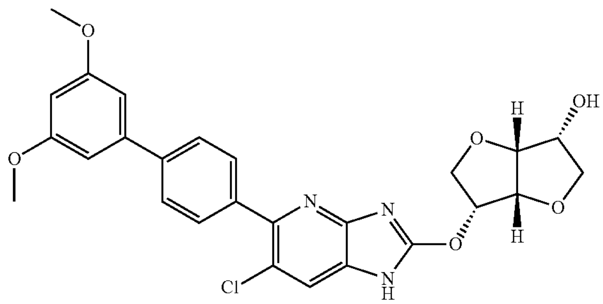 [SMILES: COc1cc(F)cc(-c2ccc(-c3nc4nc(O[C@@H]5CO[C@H]6[C@@H]5OC[C@H]6O)[nH]c4cc3Cl)cc2)c1] | 510.14 |
| 137 | 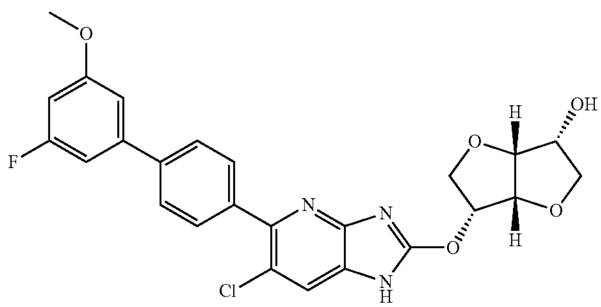 | 498.11 |
| 138 | 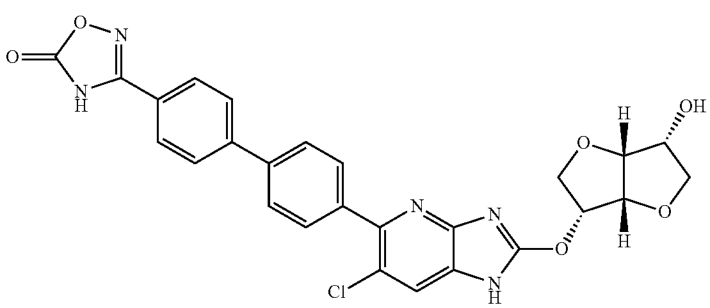 [SMILES: O=c1[nH]c(-c2ccc(-c3ccc(-c4nc5nc(O[C@@H]6CO[C@H]7[C@@H]6OC[C@H]7O)[nH]c5cc4Cl)cc3)cc2)no1] | 534.11 |
| 139 | 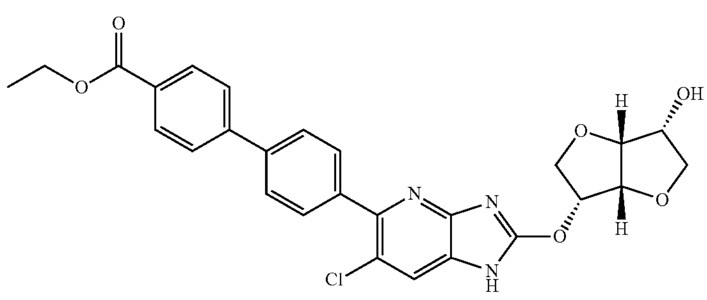 [SMILES: CCOC(=O)c1ccc(-c2ccc(-c3nc4nc(O[C@@H]5CO[C@H]6[C@@H]5OC[C@H]6O)[nH]c4cc3Cl)cc2)cc1] | 522.14 |
| 140 | 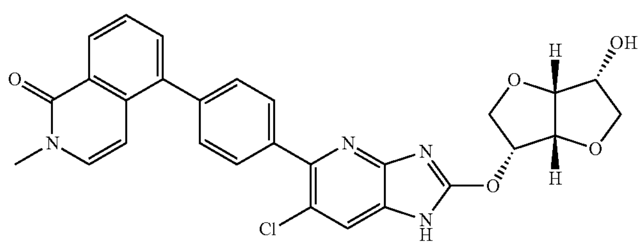 [SMILES: Cn1ccc2c(-c3ccc(-c4nc5nc(O[C@@H]6CO[C@H]7[C@@H]6OC[C@H]7O)[nH]c5cc4Cl)cc3)cccc2c1=O] | 531.14 |

TABLE 13-continued

Compounds prepared according to the methods in Example 106.

| Example | Structure | Exact Mass [M + H]+ |
|---|---|---|
| 141 | 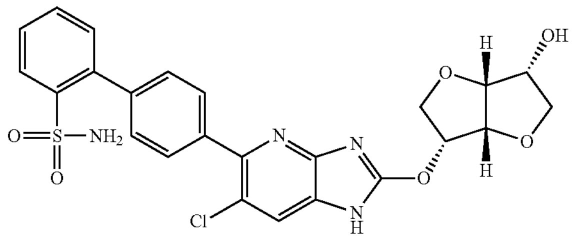 [SMILES: NS(=O)(=O)c1ccccc1-c1ccc(-c2nc3nc(O[C@@H]4CO[C@H]5[C@@H]4OC[C@H]5O)[nH]c3cc2Cl)cc1] | 529.09 |
| 142 | 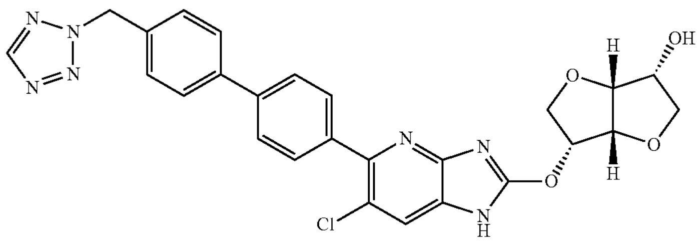 [SMILES: O[C@@H]1CO[C@H]2[C@@H]1OC[C@H]2Oc1nc2nc(-c3ccc(-c4ccc(Cn5ncnn5)cc4)cc3)c(Cl)cc2[nH]1] | 532.14 |
| 143 | 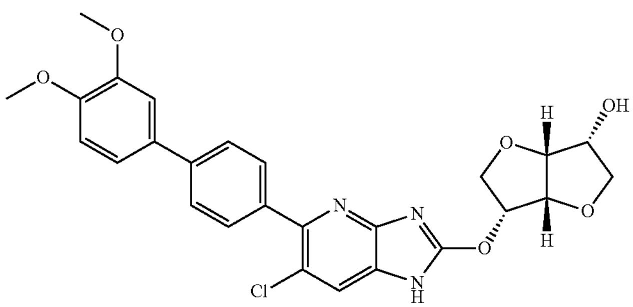 [SMILES: COc1ccc(-c2ccc(-c3nc4nc(O[C@@H]5CO[C@H]6[C@@H]5OC[C@H]6O)[nH]c4cc3Cl)cc2)cc1OC] | 510.14 |
| 144 | 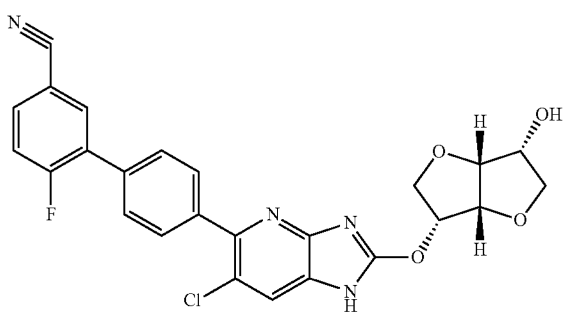 [SMILES: N#Cc1ccc(F)c(-c2ccc(-c3nc4nc(O[C@@H]5CO[C@H]6[C@@H]5OC[C@H]6O)[nH]c4cc3Cl)cc2)c1] | 493.1 |
| 145 | 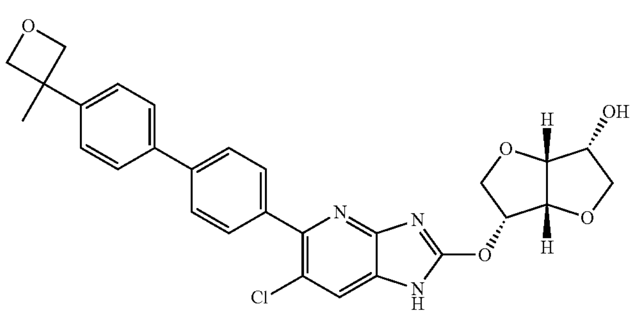 [SMILES: CC1(c2ccc(-c3ccc(-c4nc5nc(O[C@@H]6CO[C@H]7[C@@H]6OC[C@H]7O)[nH]c5cc4Cl)cc3)cc2)COC1] | 520.16 |

TABLE 13-continued

Compounds prepared according to the methods in Example 106.

| Example | Structure | Exact Mass [M + H]+ |
|---|---|---|
| 146 | 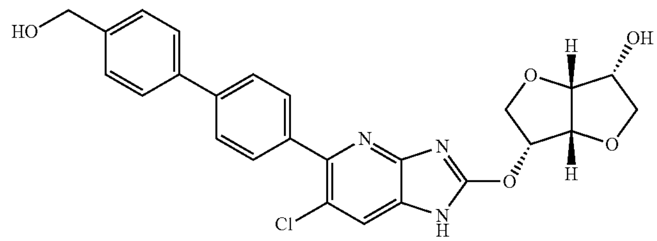 [SMILES: OCc1ccc(-c2ccc(-c3nc4nc(O[C@@H]5CO[C@H]6[C@@H]5OC[C@H]6O)[nH]c4cc3Cl)cc2)cc1] | 480.13 |
| 147 | 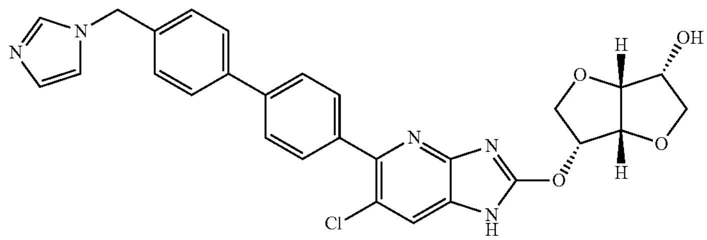 [SMILES: O[C@@H]1CO[C@H]2[C@@H]1OC[C@H]2Oc1nc2nc(-c3ccc(-c4ccc(Cn5ccnc5)cc4)cc3)c(Cl)cc2[nH]1] | 530.15 |
| 148 | 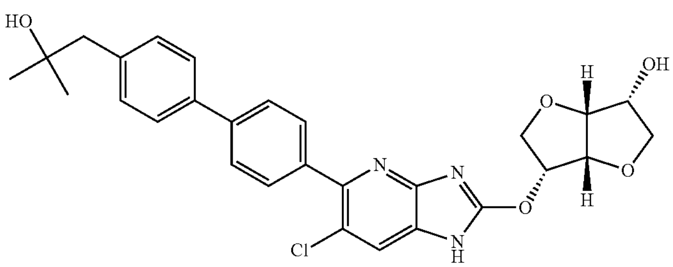 [SMILES: CC(C)(O)Cc1ccc(-c2ccc(-c3nc4nc(O[C@@H]5CO[C@H]6[C@@H]5OC[C@H]6O)[nH]c4cc3Cl)cc2)cc1] | 522.17 |
| 149 | 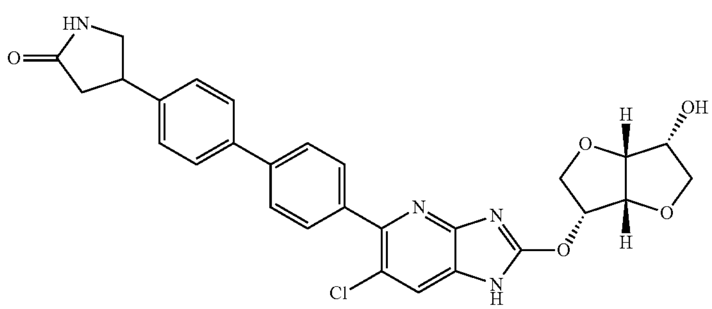 [SMILES: O=C1CC(c2ccc(-c3ccc(-c4nc5nc(O[C@@H]6CO[C@H]7[C@@H]6OC[C@H]7O)[nH]c5cc4Cl)cc3)cc2)CN1] | 533.15 |
| 150 | 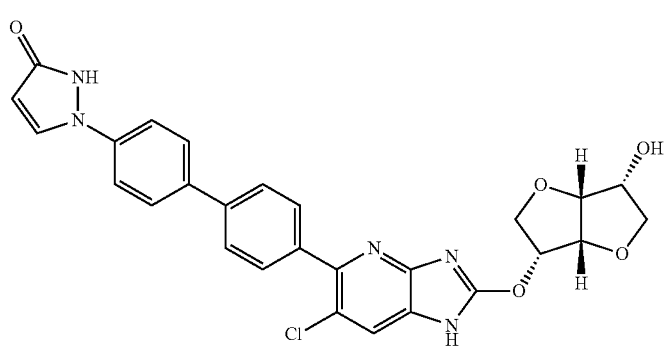 [SMILES: O=c1ccn(-c2ccc(-c3ccc(-c4nc5nc(O[C@@H]6CO[C@H]7[C@@H]6OC[C@H]7O)[nH]c5cc4Cl)cc3)cc2)[nH]1] | 532.13 |

TABLE 13-continued

Compounds prepared according to the methods in Example 106.

| Example | Structure | Exact Mass [M + H]+ |
|---|---|---|
| 151 | 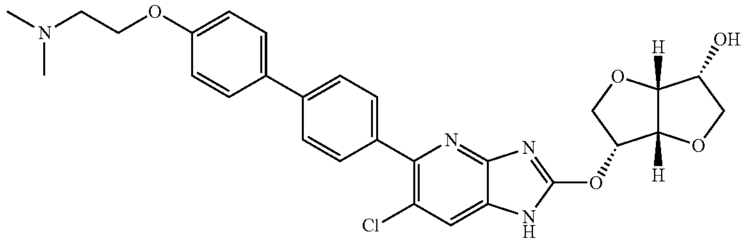 [SMILES: CN(C)CCOc1ccc(-c2ccc(-c3nc4nc(O[C@@H]5CO[C@H]6[C@@H]5OC[C@H]6O)[nH]c4cc3Cl)cc2)cc1] | 537.18 |
| 152 | 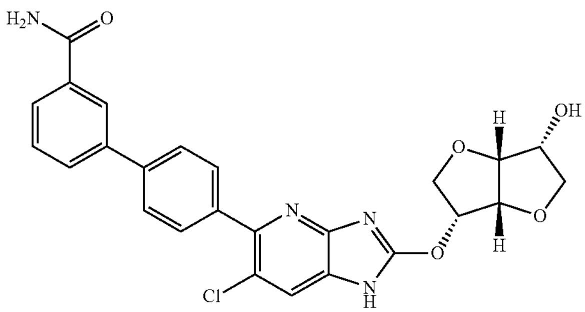 [SMILES: NC(=O)c1cccc(-c2ccc(-c3nc4nc(O[C@@H]5CO[C@H]6[C@@H]5OC[C@H]6O)[nH]c4cc3Cl)cc2)c1] | 493.12 |

EXAMPLE 153

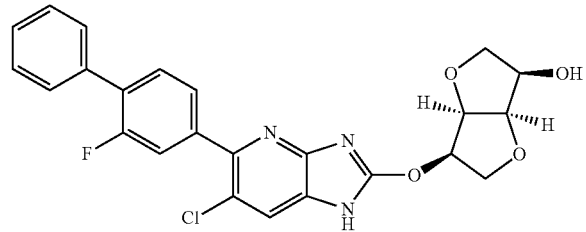 [SMILES: O[C@@H]1CO[C@H]2[C@@H]1OC[C@H]2Oc1nc2nc(-c3ccc(-c4ccccc4)c(F)c3)c(Cl)cc2[nH]1]

(3R,3aR,6R,6aR)-6-((6-chloro-5-(2-fluoro-[1,1'-biphenyl]-4-yl)-1H-imidazo[4,5-b]pyridin-2-yl)oxy)hexahydrofuro[3,2-b]furan-3-ol A mixture of (3R,3aR,6R,6aR)-6-((6-chloro-5-iodo-1-((2-(trimethylsilyl)ethoxy)methyl)-1H-imidazo[4,5-b]pyridin-2-yl)oxy)hexahydrofuro[3,2-b]furan-3-ol (40 mg, 0.072 mmol) and (2-fluoro-[1,1'-biphenyl]-4-yl)boronic acid (18.72 mg, 0.087 mmol) in anhydrous dioxane (0.4 ml) was purged with $N_2$ and then chloro[(tri-tert-butylphosphine)-2-(2-aminobiphenyl)]palladium(II) (7.4 mg, 0.014 mmol) and tripotassium phosphate (0.217 ml, 0.217 mmol) were added under $N_2$ flow. The mixture was stirred at 25° C. overnight. The crude mixture was extracted with DCM and the combined organic extracts were washed with water and evaporated under reduced pressure. 1 ml of 1:1 $CH_2Cl_2$ and TFA was added to the resulting residue and the reaction mixture was stirred for 2 hours. Then the solvent was evaporated under reduced pressure to give an amber residue. The residue was diluted with 1.5 ml DMSO, filtered and purified by mass directed reverse phase column chromatography eluting with acetonitrile/water+0.1% TFA to give the title product. LC-MS: calculated for C24H19ClFN3O4, 467.10, observed m/e: 468.11 (M+H)+ (RT 0.76/2.00 min).

TABLE 14

Compounds prepared according to the methods in Example 153.

| Example | Structure | Exact Mass [M + H]+ |
|---|---|---|
| 154 | 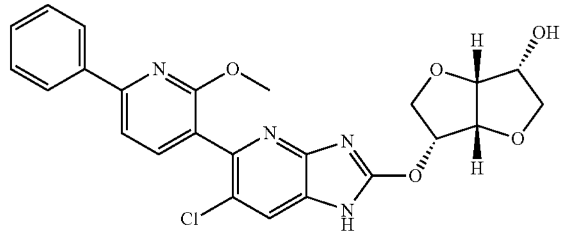 [SMILES: COc1nc(-c2ccccc2)ccc1-c1nc2nc(O[C@@H]3CO[C@H]4[C@@H]3OC[C@H]4O)[nH]c2cc1Cl] | 481.12 |

TABLE 14-continued

Compounds prepared according to the methods in Example 153.

| Example | Structure | Exact Mass [M + H]+ |
|---|---|---|
| 155 | 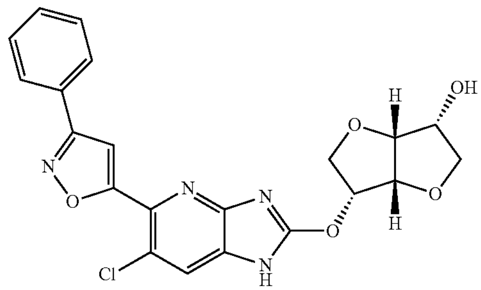 | 441.09 |
| 156 | 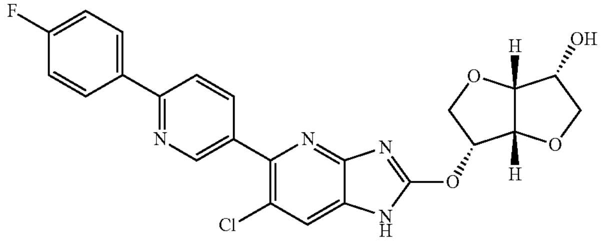 [SMILES: O[C@@H]1CO[C@H]2[C@@H]1OC[C@H]2Oc1nc2nc(-c3ccc(-c4ccc(F)cc4)nc3)c(Cl)cc2[nH]1] | 469.1 |
| 157 | 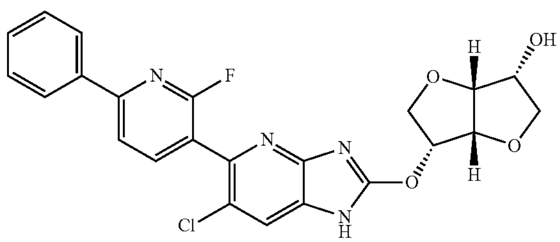 [SMILES: O[C@@H]1CO[C@H]2[C@@H]1OC[C@H]2Oc1nc2nc(-c3ccc(-c4ccccc4)nc3F)c(Cl)cc2[nH]1] | 469.1 |
| 158 | 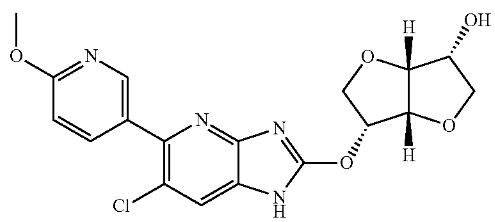 [SMILES: COc1ccc(-c2nc3nc(O[C@@H]4CO[C@H]5[C@@H]4OC[C@H]5O)[nH]c3cc2Cl)cn1] | 405.09 |
| 159 | 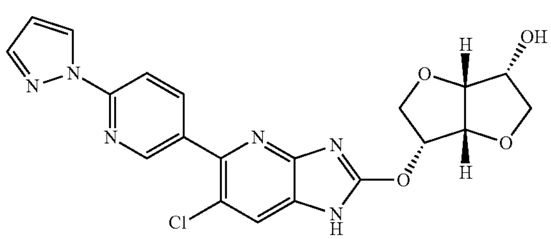 [SMILES: O[C@@H]1CO[C@H]2[C@@H]1OC[C@H]2Oc1nc2nc(-c3ccc(-n4cccn4)nc3)c(Cl)cc2[nH]1] | 441.1 |
| 160 | 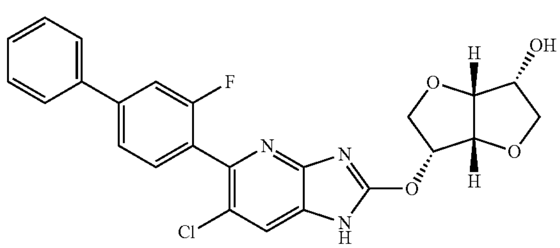 [SMILES: O[C@@H]1CO[C@H]2[C@@H]1OC[C@H]2Oc1nc2nc(-c3ccc(-c4ccccc4)cc3F)c(Cl)cc2[nH]1] | 468.11 |

TABLE 14-continued

Compounds prepared according to the methods in Example 153.

| Example | Structure | Exact Mass [M + H]+ |
|---|---|---|
| 161 | 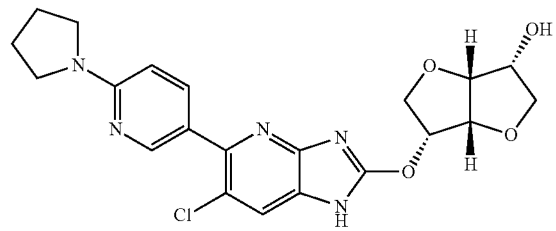 [SMILES: O[C@@H]1CO[C@H]2[C@@H]1OC[C@H]2Oc1nc2nc(-c3ccc(N4CCCC4)nc3)c(Cl)cc2[nH]1] | 444.14 |
| 162 | 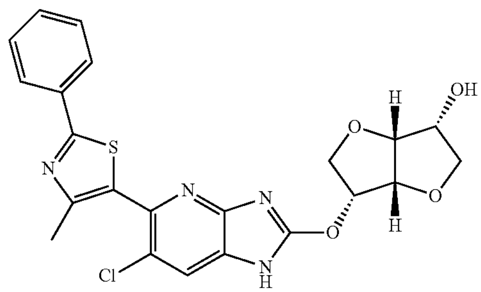 [SMILES: Cc1nc(-c2ccccc2)sc1-c1nc2nc(O[C@@H]3CO[C@H]4[C@@H]3OC[C@H]4O)[nH]c2cc1Cl] | 471.08 |
| 163 | 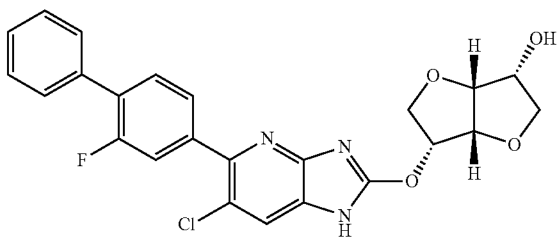 [SMILES: O[C@@H]1CO[C@H]2[C@@H]1OC[C@H]2Oc1nc2nc(-c3ccc(-c4ccccc4)c(F)c3)c(Cl)cc2[nH]1] | 468.11 |
| 164 | 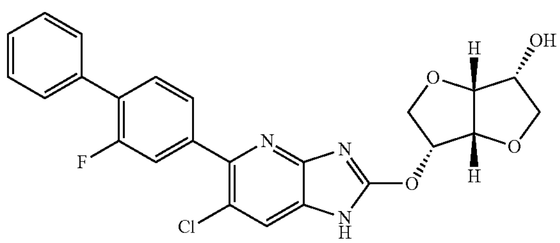 [SMILES: O[C@@H]1CO[C@H]2[C@@H]1OC[C@H]2Oc1nc2nc(-c3ccc(-c4ccccc4)c(F)c3)c(Cl)cc2[nH]1] | 468.11 |
| 165 | 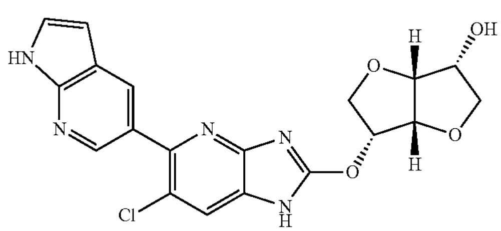 [SMILES: O[C@@H]1CO[C@H]2[C@@H]1OC[C@H]2Oc1nc2nc(-c3cnc4[nH]ccc4c3)c(Cl)cc2[nH]1] | 414.09 |
| 166 | 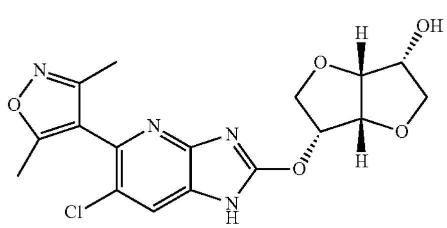 [SMILES: Cc1noc(C)c1-c1nc2nc(O[C@@H]3CO[C@H]4[C@@H]3OC[C@H]4O)[nH]c2cc1Cl] | 393.09 |

TABLE 14-continued
Compounds prepared according to the methods in Example 153.
| Example | Structure | Exact Mass [M + H]+ |
|---|---|---|
| 167 | 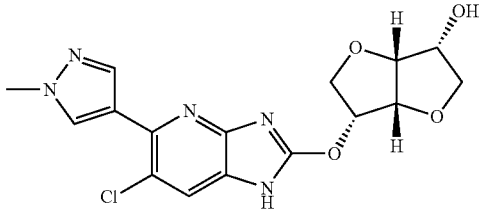 [SMILES: Cn1cc(-c2nc3nc(O[C@@H]4CO[C@H]5[C@@H]4OC[C@H]5O)[nH]c3cc2Cl)cn1] | 378.09 |
| 168 | 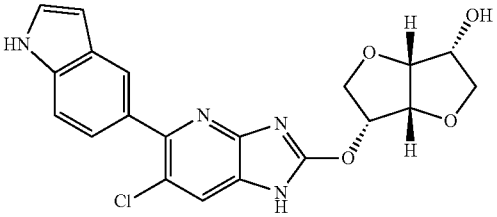 | 413.09 |
| 169 | 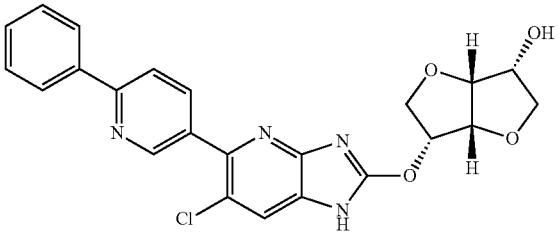 [SMILES: O[C@@H]1CO[C@H]2[C@@H]1OC[C@H]2Oc1nc2nc(-c3ccc(-c4ccccc4)nc3)c(Cl)cc2[nH]1] | 451.11 |
| 170 | 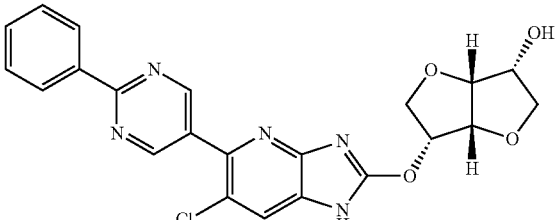 | 452.11 |
| 171 | 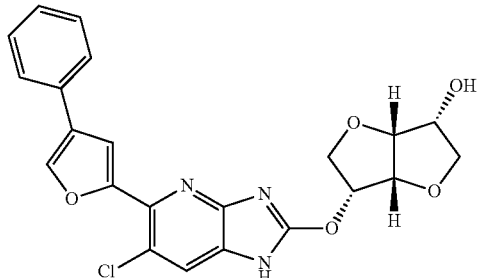 | 440.09 |
| 172 | 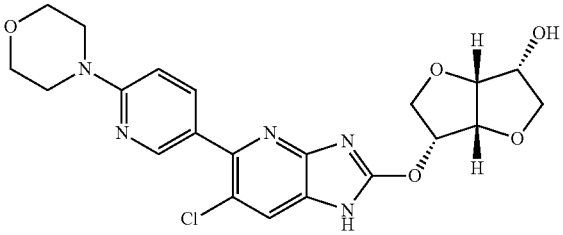 [SMILES: O[C@@H]1CO[C@H]2[C@@H]1OC[C@H]2Oc1nc2nc(-c3ccc(N4CCOCC4)nc3)c(Cl)cc2[nH]1] | 460.13 |

TABLE 14-continued

Compounds prepared according to the methods in Example 153.

| Example | Structure | Exact Mass [M + H]+ |
|---|---|---|
| 173 | 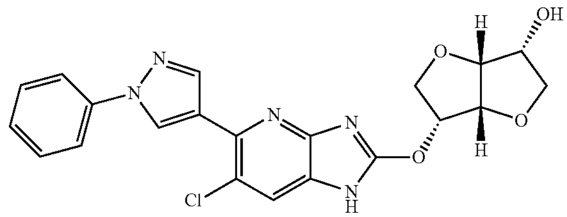 [SMILES: O[C@@H]1CO[C@H]2[C@@H]1OC[C@H]2Oc1nc2nc(-c3cnn(-c4ccccc4)c3)c(Cl)cc2[nH]1] | 440.11 |
| 174 | 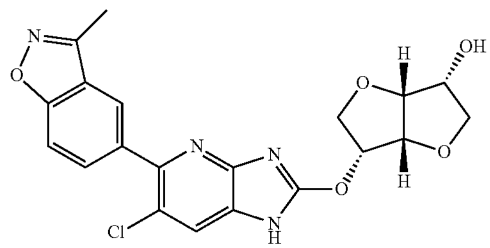 [SMILES: Cc1noc2ccc(-c3nc4nc(O[C@@H]5CO[C@H]6[C@@H]5OC[C@H]6O)[nH]c4cc3Cl)cc12] | 429.09 |

EXAMPLE 175

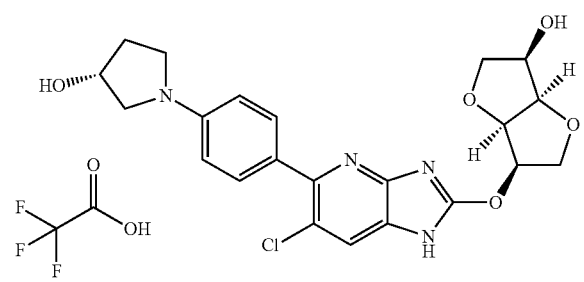 [SMILES: O=C(O)C(F)(F)F ; O[C@@H]1CCN(c2ccc(-c3nc4nc(O[C@@H]5CO[C@H]6[C@@H]5OC[C@H]6O)[nH]c4cc3Cl)cc2)C1]

(3R)-1-[4-[2-[[3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]pyrrolidin-3-ol; 2,2,2-trifluoroacetic acid Lithium hydroxide (9.0 ml, 27.0 mmol) and 1,1'-bis(diphenylphosphino)ferrocene-palladium(II)dichloride dichloromethane complex (798.5 mg, 0.978 mmol) were added to a stirred suspension of (3R)-1-[4-(4,4,5,5-tetramethyl-1,3,2-dioxaborolan-2-yl)phenyl]pyrrolidin-3-ol (3.3251 g, 11.50 mmol) and (3R,3aR,6R,6aR)-6-[(6-chloro-5-iodo-1H-imidazo[4,5-b]pyridin-2-yl)oxy]-2,3,3a,5,6,6a-hexahydrofuro[3,2-b]furan-3-ol (4.10 g, 9.68 mmol) in dioxane (78.0 ml) and water (10.0 ml). The reaction mixture was degassed (3×) and placed under nitrogen before being heated to 80° C. After 3 hours, the reaction mixture was cooled to room temperature. Additional lithium hydroxide (0.7 ml, 2.1 mmol) and 1,1'-bis(diphenylphosphino)ferrocene-palladium(II)dichloride dichloromethane complex (10.2 mg, 0.012 mmol) were added to the reaction mixture, which was degassed (3×) and placed under nitrogen before being heated to 80° C. After 2.5 hr, the reaction mixture was cooled to room temperature. The reaction mixture was partitioned between EtOAc (600 ml) and water (300 ml). Solids precipitated after the reaction mixture was partitioned and were removed through vacuum filtration. The aqueous and organic layers were refiltered as needed when further solids precipitate from both layers during the course of the workup. The aqueous layer was extracted with EtOAc until product no longer remained in the aqueous layer. The organic layers were combined, washed with brine, dried over MgSO$_4$, filtered, and evaporated under reduced pressure to give a dark green residue. This material (loaded in DMSO) was purified by preparative HPLC reverse phase (C-18), using a 30×150 mm Sunfire™ column and eluting (20 ml/min) with a 17 minute 10%-60% acetonitrile/water+ 0.05% TFA gradient followed by a 2 minute 60% acetonitrile/water+0.05% TFA flush. The product fractions were combined, frozen, and lyophilized to give the title compound as a yellow solid. LC-MS: calculated for $C_{22}H_{23}ClN_4O_5$ 458.14 observed m/e: 459.1 (M+H)$^+$ (Rt 1.14/4 min); $^1$H NMR δ (ppm) (500 MHz CD$_3$OD): 7.96 (s, 1H), 7.53-7.56 (m, 2H), 6.67-6.70 (m, 2H), 5.58 (q, J=5.3 Hz, 1H), 4.97 (t, J=5.2 Hz, 1H), 4.58 (tt, J=4.7, 2.5 Hz, 1H), 4.47 (t, J=5.0 Hz, 1H), 4.29 (ddd, J=8.9, 6.8, 5.1 Hz, 1H), 4.17 (dd, J=10.3, 5.5 Hz, 1H), 4.14 (dd, J=10.2, 4.7 Hz, 1H), 3.90 (dd, J=8.3, 6.8 Hz, 1H), 3.52-3.62 (m, 3H), 3.45 (td, J=8.7, 3.5 Hz, 1H), 3.29-3.35 (broad m, 1H) 2.17-2.24 (m, 1H), 2.05-2.10 (m, 1H).

TABLE 21

Compounds prepared according to the methods in Example 175.

| Example Number | Structure | HPLC-mass spectum m/e | Conditions |
|---|---|---|---|
| 176 | 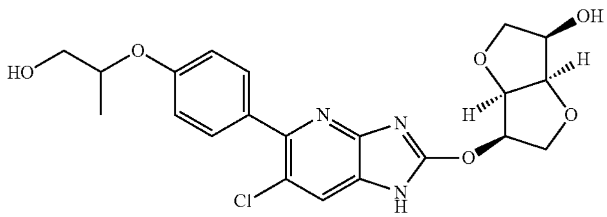 [SMILES: CC(CO)Oc1ccc(-c2nc3nc(O[C@@H]4CO[C@H]5[C@@H]4OC[C@H]5O)[nH]c3cc2Cl)cc1] | 448.20 | Derived from faster eluting isomer Pd(dppf)Cl$_2$K$_3$PO$_4$ |
| 177 | 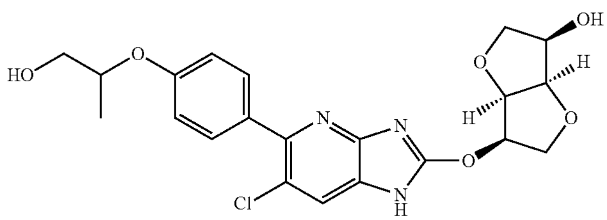 [SMILES: CC(CO)Oc1ccc(-c2nc3nc(O[C@@H]4CO[C@H]5[C@@H]4OC[C@H]5O)[nH]c3cc2Cl)cc1] | 448.1 | Derived from slower eluting isomer |
| 178 | 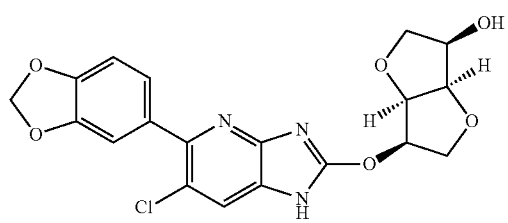 [SMILES: O[C@@H]1CO[C@H]2[C@@H]1OC[C@H]2Oc1nc2nc(-c3ccc4c(c3)OCO4)c(Cl)cc2[nH]1] | 418.00 | |
| 179 | 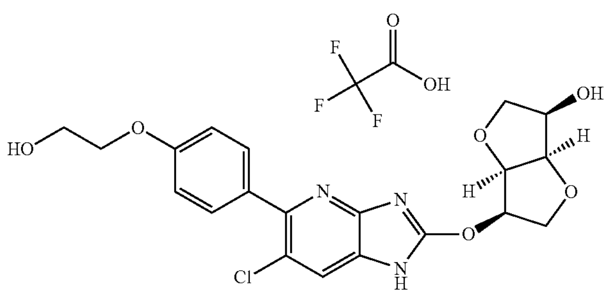 [SMILES: OCCOc1ccc(-c2nc3nc(O[C@@H]4CO[C@H]5[C@@H]4OC[C@H]5O)[nH]c3cc2Cl)cc1 ; O=C(O)C(F)(F)F] | 434.08 | |
| 180 | 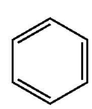 | 455.98 | |
| 181 | 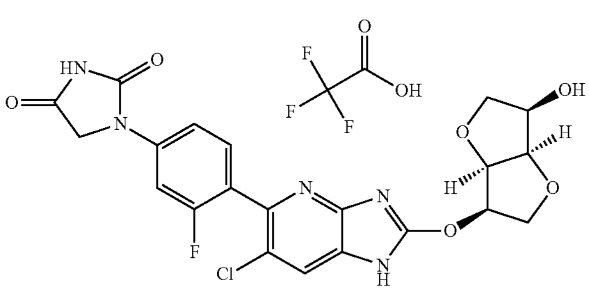 [SMILES: O=C1CN(c2ccc(-c3nc4nc(O[C@@H]5CO[C@H]6[C@@H]5OC[C@H]6O)[nH]c4cc3Cl)c(F)c2)C(=O)N1 ; O=C(O)C(F)(F)F] | 490.00 | |

TABLE 21-continued

Compounds prepared according to the methods in Example 175.

| Example Number | Structure | HPLC-mass spectrum m/e | Conditions |
|---|---|---|---|
| 182 | 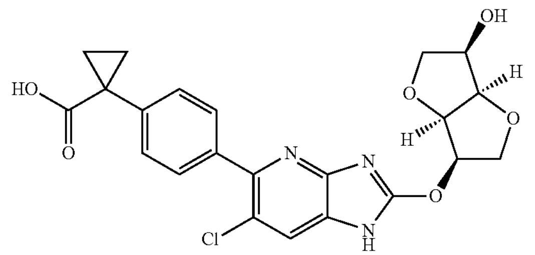 [SMILES: O=C(O)C1(c2ccc(-c3nc4nc(O[C@@H]5CO[C@H]6[C@@H]5OC[C@H]6O)[nH]c4cc3Cl)cc2)CC1] | 458.09 | |
| 183 | 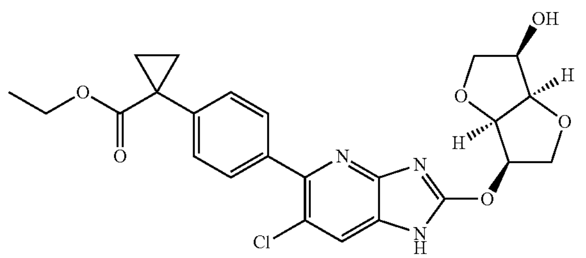 [SMILES: CCOC(=O)C1(c2ccc(-c3nc4nc(O[C@@H]5CO[C@H]6[C@@H]5OC[C@H]6O)[nH]c4cc3Cl)cc2)CC1] | 488.00 | |
| 184 | 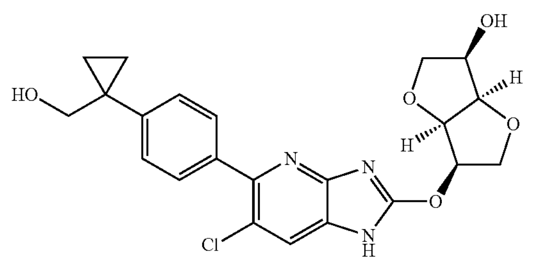 [SMILES: OCC1(c2ccc(-c3nc4nc(O[C@@H]5CO[C@H]6[C@@H]5OC[C@H]6O)[nH]c4cc3Cl)cc2)CC1] | 444.17 | |

EXAMPLE 185

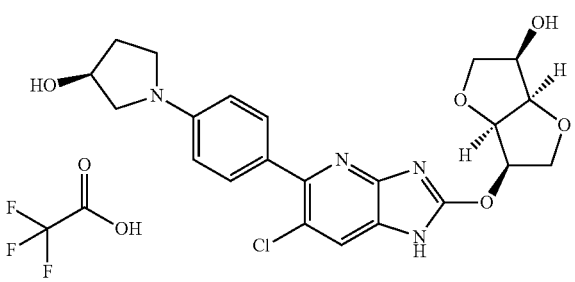 [SMILES: O=C(O)C(F)(F)F ; O[C@H]1CCN(c2ccc(-c3nc4nc(O[C@@H]5CO[C@H]6[C@@H]5OC[C@H]6O)[nH]c4cc3Cl)cc2)C1]

(3S)-1-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]pyrrolidin-3-ol; 2,2,2-trifluoroacetic acid Step A: (3S)-1-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]pyrrolidin-3-ol 2-(di-tert-butyl-phosphino)-1-phenyl-1H-pyrrole (21.2 mg, 0.074 mmol) and Pd$_2$(dba)$_3$ (62.3 mg, 0.068 mmol) were combined in a 40 ml vial, which was evacuated (3×) and placed under nitrogen. Dioxane (1.0 ml) was added to the vial to give a dark solution that was stirred at room temperature. Tripotassium phosphate (1.1 ml, 2.200 mmol) was added to a solution of (3R,3aR,6R,6aR)-6-[5-(4-bromophenyl)-6-chloro-1-(2-trimethylsilylethoxymethyl)imidazo[4,5-b]pyridin-2-yl]oxy-2,3,3a,5,6,6a-hexahydrofuro[3,2-b]furan-3-ol and (S)-3-hydroxypyrrolidine (101.2 mg, 1.162 mmol) in dioxane (3.0 ml). This biphasic mixture was transferred to the catalyst solution via syringe after the catalyst solution had been stirred for 40 minutes. The reaction mixture was degassed (3×) and placed under nitrogen before being heated to 110° C. After 17 hours, the reaction mixture was cooled to room temperature. The reaction mixture was partitioned between EtOAc (100 ml) and water (100 ml). The aqueous layer was extracted with EtOAc (2×50 ml). The organic layers were combined, washed with brine (1×30 ml), dried over MgSO$_4$, filtered, and evaporated under reduced pressure to give an amber residue. The residue was dissolved in EtOAc and loaded onto three 1000 micron 20 cm×20 cm silica gel plates, which were developed using 80% EtOAc/Hex. The silica containing the product band was collected and eluted with EtOAc (125 ml). The solvent was evaporated under reduced pressure to give the desired product as an amber residue. LC-MS: calculated for C$_{28}$H$_{37}$ClN$_4$O$_6$Si 588.22 observed m/e: 589.14 (M+H)$^+$ (Rt 1.42/2 min).

Step B: (3S)-1-[4-[2-[[(3R,3aR,6R,6aR)-3-hydroxy-2,3,3a,5,6,6a-hexahydrofuro[3,2-b]furan-6-yl]oxy]-6-chloro-1H-imidazo[4,5-b]pyridin-5-yl]phenyl]pyrrolidin-3-ol; 2,2,2-trifluoroacetic acid Trifluoroacetic acid (1.2 ml, 15.58 mmol) was added to a stirred solution of (3S)-1-[4-[2-[[(3R,3aR,6R,6aR)-3-hydroxy-2,3,3a,5,6,6a-hexahydrofuro[3,2-b]furan-6-yl]oxy]-6-chloro-1-(2-trimethylsilylethoxymethyl)imidazo[4,5-b]pyridin-5-yl]phenyl]pyrrolidin-3-ol (114.8 mg, 0.195 mmol) in dichloromethane (1.2 ml). The reaction mixture was an amber solution that was stirred at room temperature. After 1.25 hours, the reaction mixture was evaporated under reduced pressure to give an amber residue. The residue (loaded in MeOH) was purified by preparative HPLC reverse phase (C-18), using a 30×150 mm Sunfire™ column and eluting (20 ml/min) with a 17 minute 10%-60% acetonitrile/water+0.05% TFA gradient followed by a 2 minute 60% acetonitrile/water+0.05% TFA flush. The product fractions were combined, frozen, and lyophilized to give the title compound as a yellow solid. LC-MS: calculated for $C_{22}H_{23}ClN_4O_5$ 458.14 observed m/e: 459.1 (M+H)$^+$ (Rt 0.88/2 min); $^1$H NMR δ (ppm) (500 MHz CD$_3$OD): 8.04 (s, 1H), 7.55 (d, J=8.3 Hz, 2H), 6.71 (d, J=8.3 Hz, 2H), 5.60 (q, J=5.3 Hz, 1H), 4.97 (t, J=5.3 Hz, 1H), 4.56-4.59 (m, 1H), 4.47 (t, J=5.0 Hz, 1H), 4.29 (ddd, J=8.9, 6.8, 5.1 Hz, 1H), 4.13-4.19 (m, 2H), 3.90 (dd, J=8.3, 6.7 Hz, 1H), 3.52-3.61 (m, 3H), 3.45 (td, J=8.2, 3.3 Hz, 1H), 3.29-3.35 (broad m, 1H), 2.16-2.23 (m, 1H), 2.05-2.10 (m, 1H).

TABLE 22

Compounds prepared according to the methods in Example 185.

| Example Number | Structure | HPLC-mass spectrum m/e |
|---|---|---|
| 186 | 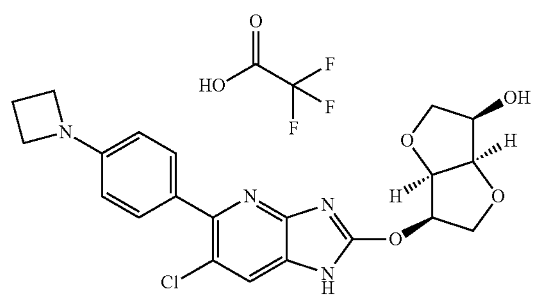 [SMILES: O[C@@H]1CO[C@H]2[C@@H]1OC[C@H]2Oc1nc2nc(-c3ccc(N4CCC4)cc3)c(Cl)cc2[nH]1 ; O=C(O)C(F)(F)F] | 429.1 |
| 187 | 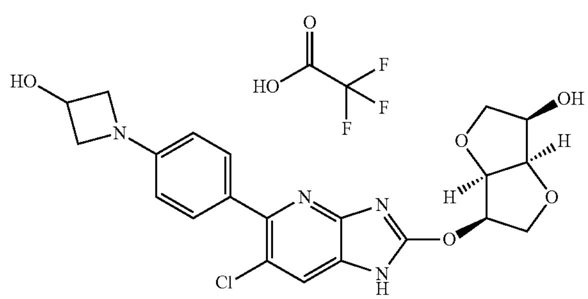 [SMILES: OC1CN(c2ccc(-c3nc4nc(O[C@@H]5CO[C@H]6[C@@H]5OC[C@H]6O)[nH]c4cc3Cl)cc2)C1 ; O=C(O)C(F)(F)F] | 445.1 |
| 188 | 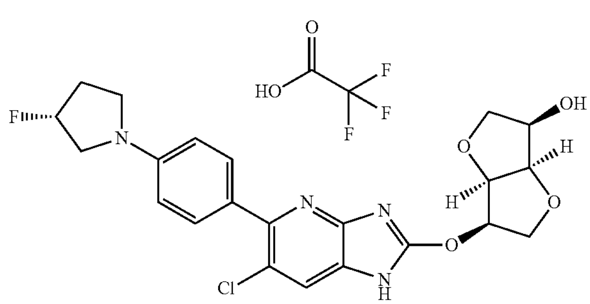 [SMILES: O[C@@H]1CO[C@H]2[C@@H]1OC[C@H]2Oc1nc2nc(-c3ccc(N4CC[C@@H](F)C4)cc3)c(Cl)cc2[nH]1 ; O=C(O)C(F)(F)F] | 461.16 |

TABLE 22-continued

Compounds prepared according to the methods in Example 185.

| Example Number | Structure | HPLC-mass spectum m/e |
|---|---|---|
| 189 | 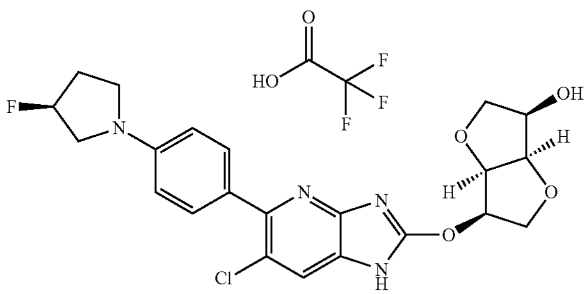 [SMILES: O[C@@H]1CO[C@H]2[C@@H]1OC[C@H]2Oc1nc2nc(-c3ccc(N4CC[C@H](F)C4)cc3)c(Cl)cc2[nH]1 ; O=C(O)C(F)(F)F] | 460.19 |
| 190 | 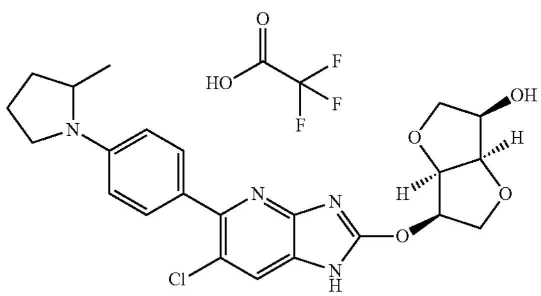 [SMILES: CC1CCCN1c1ccc(-c2nc3nc(O[C@@H]4CO[C@H]5[C@@H]4OC[C@H]5O)[nH]c3cc2Cl)cc1 ; O=C(O)C(F)(F)F] | 456.89 |
| 191 | 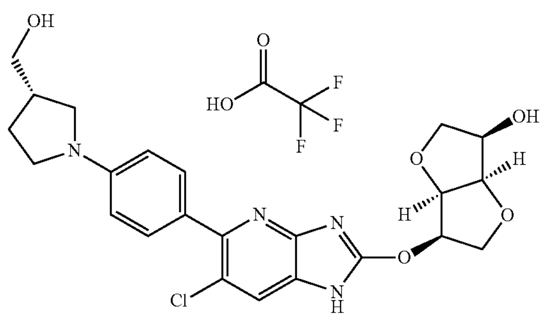 [SMILES: OC[C@H]1CCN(c2ccc(-c3nc4nc(O[C@@H]5CO[C@H]6[C@@H]5OC[C@H]6O)[nH]c4cc3Cl)cc2)C1 ; O=C(O)C(F)(F)F] | 473.12 |
| 192 | 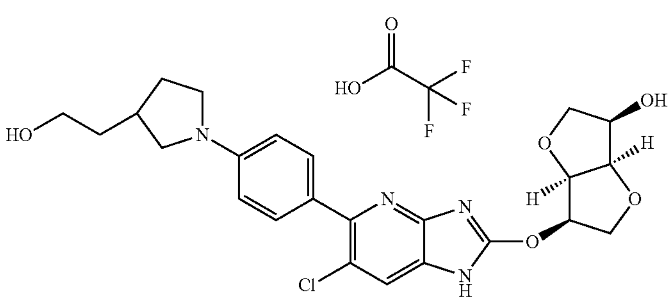 [SMILES: OCCC1CCN(c2ccc(-c3nc4nc(O[C@@H]5CO[C@H]6[C@@H]5OC[C@H]6O)[nH]c4cc3Cl)cc2)C1 ; O=C(O)C(F)(F)F] | 487.2 |
| 193 | 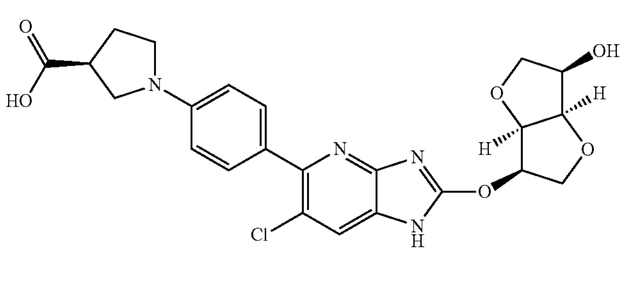 [SMILES: O=C(O)[C@H]1CCN(c2ccc(-c3nc4nc(O[C@@H]5CO[C@H]6[C@@H]5OC[C@H]6O)[nH]c4cc3Cl)cc2)C1] | 487.2 |

TABLE 22-continued

Compounds prepared according to the methods in Example 185.

| Example Number | Structure | HPLC-mass spectrum m/e |
|---|---|---|
| 194 | 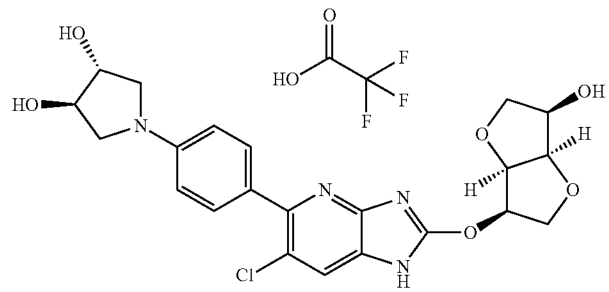 [SMILES: O[C@@H]1CO[C@H]2[C@@H]1OC[C@H]2Oc1nc2nc(-c3ccc(N4C[C@@H](O)[C@H](O)C4)cc3)c(Cl)cc2[nH]1 ; O=C(O)C(F)(F)F] | 475.16 |
| 195 | 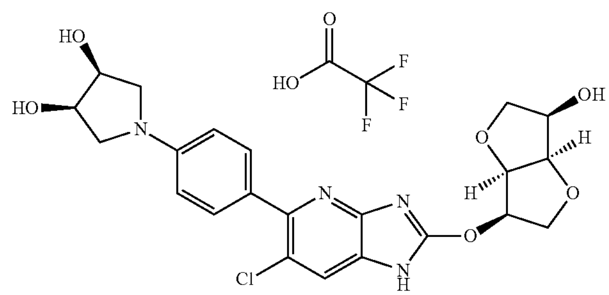 [SMILES: O[C@@H]1CO[C@H]2[C@@H]1OC[C@H]2Oc1nc2nc(-c3ccc(N4C[C@@H](O)[C@@H](O)C4)cc3)c(Cl)cc2[nH]1 ; O=C(O)C(F)(F)F] | 475.08 |
| 196 | 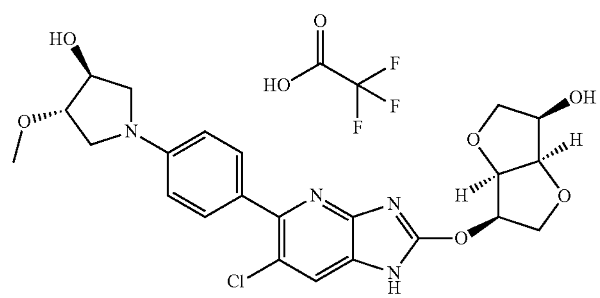 [SMILES: CO[C@H]1CN(c2ccc(-c3nc4nc(O[C@@H]5CO[C@H]6[C@@H]5OC[C@H]6O)[nH]c4cc3Cl)cc2)C[C@@H]1O ; O=C(O)C(F)(F)F] | 489.13 |
| 197 | 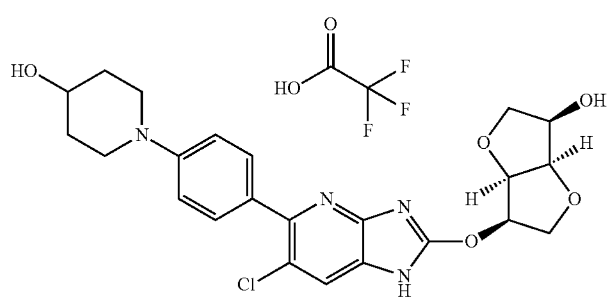 [SMILES: OC1CCN(c2ccc(-c3nc4nc(O[C@@H]5CO[C@H]6[C@@H]5OC[C@H]6O)[nH]c4cc3Cl)cc2)CC1 ; O=C(O)C(F)(F)F] | 473.01 |
| 198 | 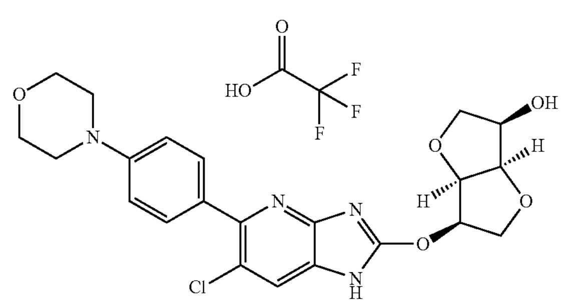 [SMILES: O[C@@H]1CO[C@H]2[C@@H]1OC[C@H]2Oc1nc2nc(-c3ccc(N4CCOCC4)cc3)c(Cl)cc2[nH]1 ; O=C(O)C(F)(F)F] | 459.1 |

| Example Number | Structure | HPLC-mass spectrum m/e |
|---|---|---|
| 199 | 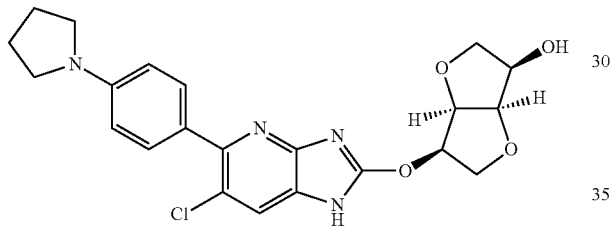 | 487.2 |

EXAMPLE 200

(3R,3aR,6R,6aR)-6-[[6-chloro-5-(4-pyrrolidin-1-ylphenyl)-1H-imidazo[4,5-b]pyridin-2-yl]oxy]-2,3,3a,5,6,6a-hexahydrofuro[3,2-b]furan-3-ol

[(3R,3aR,6R,6aS)-3-[[6-chloro-5-(4-pyrrolidin-1-ylphenyl)-1H-imidazo[4,5-b]pyridin-2-yl]oxy]-2,3,3a,5,6,6a-hexahydrofuro[3,2-b]furan-6-yl]oxy-tert-butyl-dimethyl-silane (31.8 mg, 0.057 mmol) and tetrabutylammonium fluoride 1.0 M in THF (0.6 ml, 0.600 mmol) were combined in a vial. The reaction mixture was a light amber solution that was stirred at room temperature. After 3.5 hours, the reaction mixture was partitioned between EtOAc (40 ml) and water (40 ml). The aqueous layer was extracted with EtOAc (2×20 ml) and a few milliliters of brine. The organic layers were combined, washed with brine (1×20 ml), dried over MgSO$_4$, filtered, and evaporated under reduced pressure to give a pale yellow residue. The residue (loaded in DMSO/MeOH) was purified by preparative HPLC reverse phase (C-18), using a 30×150 mm Sunfire™ column and eluting (20 ml/min) with a 17 minute 20%-80% acetonitrile/water+0.05% TFA gradient followed by a 2 minute 80% acetonitrile/water+0.05% TFA flush. The product fractions were combined, frozen, and lyophilized to give the title compound as a yellow solid. LC-MS: calculated for C$_{22}$H$_{23}$ClN$_4$O$_4$ 442.14 observed m/e: 443.19 (M+H)$^+$ (Rt 1.09/2 min); $^1$H NMR δ (ppm) (500 MHz CD$_3$OD): 8.01 (s, 1H), 7.54-7.56 (m, 2H), 6.72-6.74 (m, 2H), 5.59 (q, J=5.4 Hz, 1H), 4.97 (t, J=5.3 Hz, 1H), 4.48 (t, J=5.0 Hz, 1H), 4.27-4.31 (m, 1H), 4.13-4.19 (m, 2H), 3.88-3.91 (m, 1H), 3.60 (dd, J=9.1, 7.6 Hz, 1H), 3.37-3.40 (m, 4H), 2.08-2.10 (m, 4H).

EXAMPLE 201

(3R,3aR,6R,6aR)-6-[[6-chloro-5-(4-pyrrol-1-ylphenyl)-1H-imidazo[4,5-b]pyridin-2-yl]oxy]-2,3,3a,5,6,6a-hexahydrofuro[3,2-b]furan-3-ol (3R)-1-[4-[2-[[(3R,3aR,6R,6aS)-6-[tert-butyl(dimethyl)silyl]oxy-2,3,3a,5,6,6a-hexahydrofuro[3,2-b]furan-3-yl]oxy]-6-chloro-1H-imidazo[4,5-b]pyridin-5-yl]phenyl]pyrrolidin-3-ol (229.7 mg, 0.401 mmol) and tetrabutylammonium fluoride 1.0 M in THF (4.2 ml, 4.20 mmol) were combined in a 40 ml vial. The reaction mixture was an amber solution that was stirred at room temperature. After 1.25 hours, the reaction mixture was partitioned between EtOAc (100 ml) and water (50 ml). The aqueous layer was separated, and extracted with EtOAc (2×50 ml). The organic layers were combined, washed with brine (1×30 ml), dried over MgSO$_4$, filtered, and evaporated under reduced pressure to give a yellow residue. This material (loaded in DMSO/MeOH) was purified by preparative HPLC reverse phase (C-18), using a 30×150 mm Sunfire™ column and eluting (20 ml/min) with a 17 minute 10%-60% acetonitrile/water+0.05% TFA gradient followed by a 2 minute 60% acetonitrile/water+0.05% TFA flush. The product fractions were combined, frozen, and lyophilized to give the title compound as a light yellow solid. LC-MS: calculated for $C_{22}H_{19}ClN_4O_4$ 438.11 observed m/e: 439.18 (M+H)+ (Rt 1.14/2 min); $^1$H NMR δ (ppm) (500 MHz CD$_3$OD): 7.87 (s, 1H), 7.77 (d, J=8.3 Hz, 2H), 7.60 (d, J=8.3 Hz, 2H), 7.28 (d, J=2.5 Hz, 2H), 6.33 (d, J=2.5 Hz, 2H), 5.57 (q, J=5.6 Hz, 1H), 4.98 (t, J=5.3 Hz, 1H), 4.48 (t, J=5.1 Hz, 1H), 4.28-4.32 (m, 1H), 4.18 (dd, J=10.3, 5.8 Hz, 1H), 4.13 (dd, J=10.6, 4.7 Hz, 1H), 3.91 (dd, J=8.3, 6.7 Hz, 1H), 3.61 (dd, J=9.0, 7.6 Hz, 1H).

EXAMPLE 202

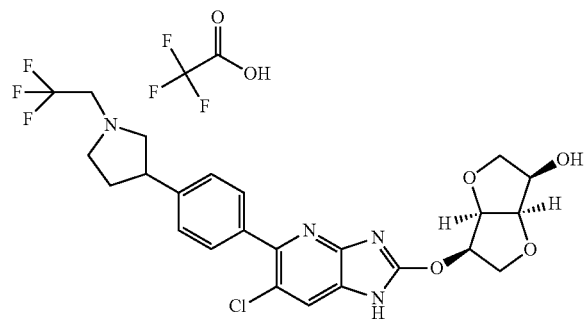

(3R,3aR,6R,6aR)-6-[[6-chloro-5-[4-[1-(2,2,2-trifluoroethyl)pyrrolidin-3-yl]phenyl]-1H-imidazo[4,5-b]pyridin-2-yl]oxy]-2,3,3a,5,6,6a-hexahydrofuro[3,2-b]furan-3-ol; 2,2,2-trifluroacetic acid (faster eluting isomer)

Step A: (3R,3aR,6R,6aR)-6-[6-chloro-5-[4-[1-(2,2,2-trifluoroethyl)pyrrolidin-3-yl]phenyl]-1-(2-trimethylsilylethoxymethyl)imidazo[4,5-b]pyridin-2-yl]oxy-2,3,3a,5,6,6a-hexahydrofuro[3,2-b]furan-3-ol Tripotassium phosphate 2.0 M aqueous solution (0.6 ml, 1.200 mmol) and 1,1'-bis(diphenylphosphino)ferrocene-palladium(II)dichloride dichloromethane complex (25.2 mg, 0.031 mmol) were added to a stirred solution of (3R,3aR,6R,6aR)-6-[6-chloro-5-iodo-1-(2-trimethylsilylethoxymethyl)imidazo[4,5-b]pyridin-2-yl]oxy-2,3,3a,5,6,6a-hexahydrofuro[3,2-b]furan-3-ol (147.1 mg, 0.266 mmol) and 3-[4-(4,4,5,5-tetramethyl-1,3,2-dioxaborolan-2-yl)phenyl]-1-(2,2,2-trifluoroethyl)pyrrolidine (94.6 mg, 0.266 mmol) in dioxane (2.1 ml). The reaction mixture was degassed (3×) and placed under nitrogen before being heated to 80° C. After 18 hours, the reaction mixture was cooled to room temperature before being partitioned between EtOAc (50 ml) and water (50 ml). The aqueous layer was separated and extracted with EtOAc (2×50 ml). The organic layers were combined, washed with brine (1×30 ml), dried over MgSO$_4$, filtered, and evaporated under reduced pressure to give a yellow residue. The residue was dissolved in DCM, loaded onto a 5 g silica solid load cartridge, and purified using an ISCO R$_f$ and a 12 g silica column (CV=16.8 ml) by eluting as follows: 100% Hex (5 CV), 0-70% EtOAc/Hex gradient (50 CV), 70% EtOAc/Hex (35 CV) at 30 ml/min. The product fractions were combined and evaporated under reduced pressure to give the desired product as a yellow residue. LC-MS: calculated for $C_{30}H_{38}ClF_3N_4O_5Si$ 654.23 observed m/e: 655.32 (M+H)+ (Rt 1.37/2 min)

Step B: (3R,3aR,6R,6aR)-6-[[6-chloro-5-[4-[1-(2,2,2-trifluoroethyl)pyrrolidin-3-yl]phenyl]-1H-imidazo[4,5-b]pyridin-2-yl]oxy]-2,3,3a,5,6,6a-hexahydrofuro[3,2-b]furan-3-ol; 2,2,2-trifluroacetic acid (faster eluting isomer)

The racemic product material from the previous step was separated using the following method: AD 20×250 mm column, 15% MeOH (0.05% NH$_4$OH)/CO$_2$, 70 ml/min, 100 bar, 210 nm, 35° C., sample loaded in MeOH. The fractions containing the faster eluting isomer were combined and evaporated to give the faster eluting isomer of (3R,3aR,6R,6aR)-6-[6-chloro-5-[4-[1-(2,2,2-trifluoroethyl)pyrrolidin-3-yl]phenyl]-1-(2-trimethylsilylethoxymethyl)imidazo[4,5-b]pyridin-2-yl]oxy-2,3,3a,5,6,6a-hexahydrofuro[3,2-b]furan-3-ol as a colorless residue. Trifluoroacetic acid (0.5 ml, 6.49 mmol) was added to a stirred solution of (3R,3aR,6R,6aR)-6-[6-chloro-5-[4-[1-(2,2,2-trifluoroethyl)pyrrolidin-3-yl]phenyl]-1-(2-trimethylsilylethoxymethyl)imidazo[4,5-b]pyridin-2-yl]oxy-2,3,3a,5,6,6a-hexahydrofuro[3,2-b]furan-3-ol (the faster eluting isomer, 8.8 mg, 0.013 mmol) in DCM (0.5 ml). The reaction mixture was stirred at room temperature. After 1.5 hours, the reaction mixture was evaporated under reduced pressure to give a purple residue. The residue (loaded in MeOH) was purified by preparative HPLC reverse phase (C-18), using a 30×100 mm Sunfire™ column and eluting (20 ml/min) with a 10 minute 10%-90% acetonitrile/water+0.05% TFA gradient. The product fractions were combined, frozen, and lyophilized to give the title compound as a white solid. LC-MS: calculated for $C_{24}H_{24}ClF_3N_4O_4$ 524.14 observed m/e: 525.31 (M+H)+ (Rt 0.69/2 min); $^1$H NMR δ (ppm) (400 MHz CD$_3$OD): 7.72 (s, 1H), 7.53-7.56 (m, 2H), 7.33-7.36 (m, 2H), 5.44 (q, J=5.3 Hz, 1H), 4.86 (t, J=5.2 Hz, 1H), 4.37 (t, J=5.0 Hz, 1H), 4.18 (ddd, J=8.9, 6.8, 5.1 Hz, 1H), 4.06 (dd, J=10.1, 5.6 Hz, 1H), 4.01 (dd, J=10.3, 4.8 Hz, 1H), 3.89-4.02 (broad m, 2H), 3.80 (dd, J=8.3, 6.8 Hz, 1H), 3.65-3.75 (broad m, 1H), 3.53-3.62 (m, 1H), 3.49 (t, J=8.7 Hz, 1H), 3.41-3.51 (broad m, 2H), 3.21-3.31 (broad m, 1H), 2.42-2.50 (m, 1H), 2.08-2.18 (m, 1H).

TABLE 23

Compounds prepared according to the methods in Example 202.

| Example Number | Structure | HPLC-mass spectum m/e | Notes |
|---|---|---|---|
| 203 | 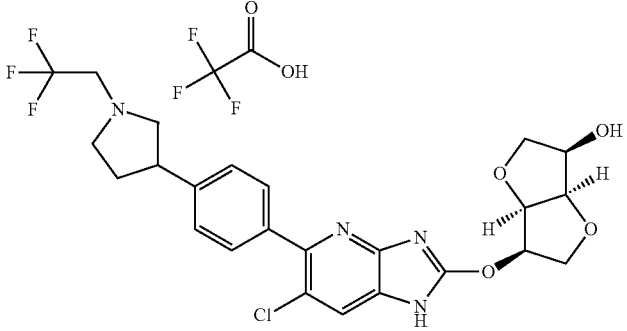 | 525.33 | Derived from slower eluting isomer |

EXAMPLE 204

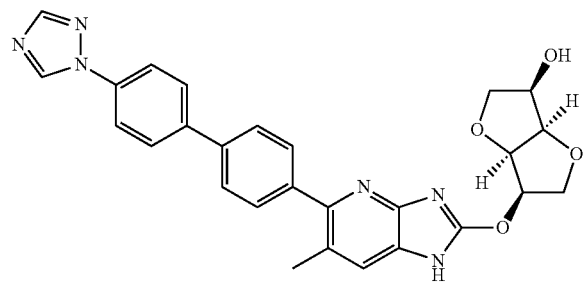 [SMILES: Cc1cc2[nH]c(O[C@@H]3CO[C@H]4[C@@H]3OC[C@H]4O)nc2nc1-c1ccc(-c2ccc(-n3cncn3)cc2)cc1]

(3R,3aR,6R,6aR)-6-((5-(4'-(1H-1,2,4-triazol-1-yl)-[1,1'-biphenyl]-4-yl)-6-methyl-1H-imidazo[4,5-b]pyridin-2-yl)oxy)hexahydrofuro[3,2-b]furan-3-ol Methyl boronic acid (174 mg, 2.90 mmol), (3R,3aR,6R,6aR)-6-((5-(4'-(1H-1,2,4-triazol-1-yl)-[1,1'-biphenyl]-4-yl)-6-chloro-1H-imidazo[4,5-b]pyridin-2-yl)oxy)hexahydrofuro[3,2-b]furan-3-ol (150 mg, 0.290 mmol) and chloro(2-dicyclohexylphosphino-2',4',6'-triisopropyl-1,1'-biphenyl)[2-(2-aminoethyl)phenyl)]palladium(II) (86 mg, 0.116 mmol) were added as solids to a microwave tube, followed by degassed 1,4-dioxane (2 mL) and 2 M aqueous potassium carbonate (1741 uL, 3.48 mmol). The tube was sealed and heated to 140° C. in a microwave for 30 minutes. The organic phase of the reaction was removed and evaporated under reduced pressure. The crude mixture was diluted in DMSO (2 mL) and purified by preparative HPLC reverse phase (C-18), using a 30×150 mm Sunfire™ column and eluting with a 5%-100% acetonitrile/water+0.05% TFA gradient followed by a 100% acetonitrile+0.05% TFA flush. The desired fractions were combined, evaporated under reduced pressure, and lyophilized from water/acetonitrile to give the title compound as white solid. LC-MS: calculated for $C_{22}H_{24}N_6O_4$ 496.19 observed m/e: 497.24 $(M+H)^+$ (Rt 0.79/2.5 min); $^1H$ NMR δ (ppm) $((CD_3)_2SO)$:

TABLE 24

Compounds prepared according to the methods in Example 204.

| Example Number | Structure | HPLC-mass spectum m/e |
|---|---|---|
| 205 | 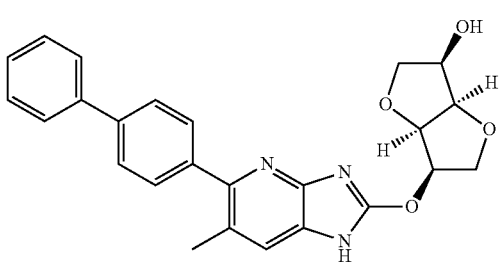 [SMILES: Cc1cc2[nH]c(O[C@@H]3CO[C@H]4[C@@H]3OC[C@H]4O)nc2nc1-c1ccc(-c2ccccc2)cc1] | 430.22 |

TABLE 24-continued

Compounds prepared according to the methods in Example 204.

| Example Number | Structure | HPLC-mass spectum m/e |
|---|---|---|
| 206 | 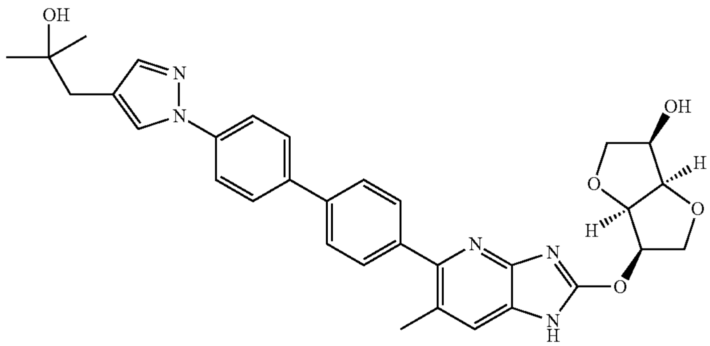 [SMILES: Cc1cc2[nH]c(O[C@@H]3CO[C@H]4[C@@H]3OC[C@H]4O)nc2nc1-c1ccc(-c2ccc(-n3cc(CC(C)(C)O)cn3)cc2)cc1] | 568.24 |
| 207 | 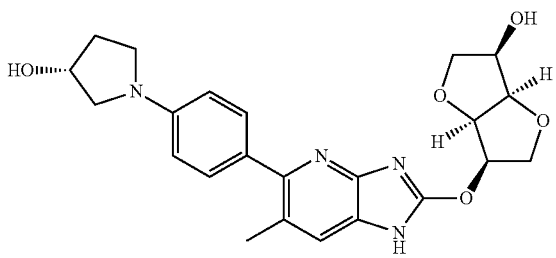 [SMILES: Cc1cc2[nH]c(O[C@@H]3CO[C@H]4[C@@H]3OC[C@H]4O)nc2nc1-c1ccc(N2CC[C@@H](O)C2)cc1] | 439.51 |
| 208 | 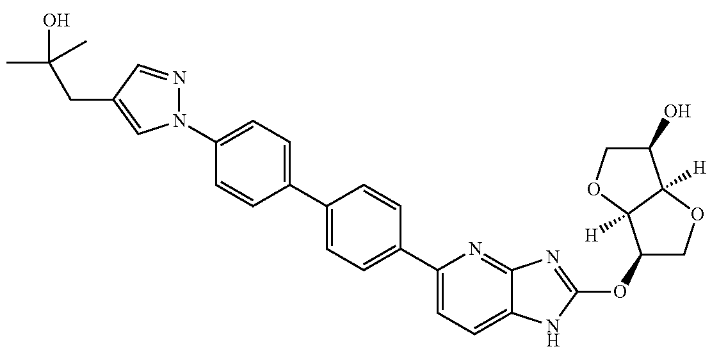 [SMILES: CC(C)(O)Cc1cnn(-c2ccc(-c3ccc(-c4ccc5[nH]c(O[C@@H]6CO[C@H]7[C@@H]6OC[C@H]7O)nc5n4)cc3)cc2)c1] | 554.29 |
| 209 | 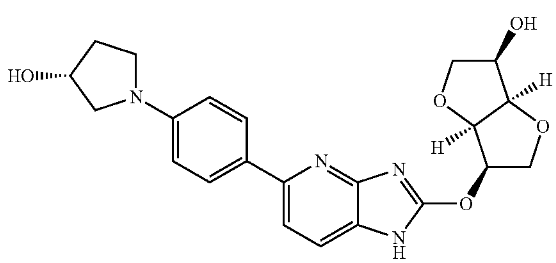 [SMILES: O[C@@H]1CCN(c2ccc(-c3ccc4[nH]c(O[C@@H]5CO[C@H]6[C@@H]5OC[C@H]6O)nc4n3)cc2)C1] | 425.49 |
| 210 | 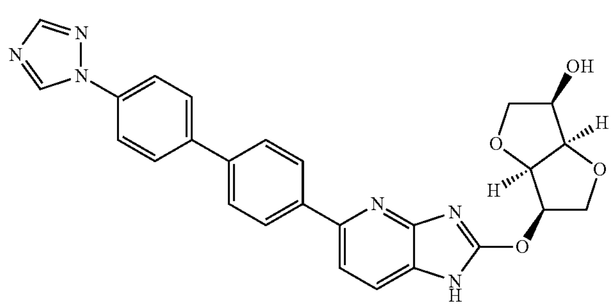 [SMILES: O[C@@H]1CO[C@H]2[C@@H]1OC[C@H]2Oc1nc2nc(-c3ccc(-c4ccc(-n5cncn5)cc4)cc3)ccc2[nH]1] | 483.18 |

TABLE 24-continued

Compounds prepared according to the methods in Example 204.

| Example Number | Structure | HPLC-mass spectum m/e |
|---|---|---|
| 211 | 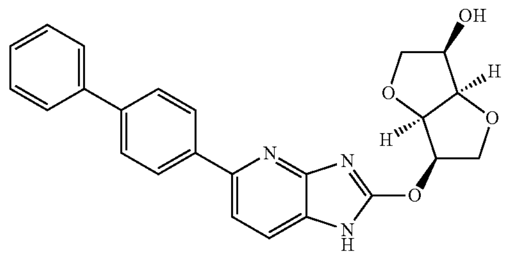 [SMILES: O[C@@H]1CO[C@H]2[C@@H]1OC[C@H]2Oc1nc2nc(-c3ccc(-c4ccccc4)cc3)ccc2[nH]1] | 416.22 |

EXAMPLE 212

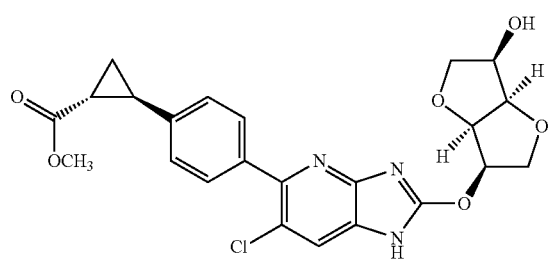 [SMILES: COC(=O)[C@@H]1C[C@H]1c1ccc(-c2nc3nc(O[C@@H]4CO[C@H]5[C@@H]4OC[C@H]5O)[nH]c3cc2Cl)cc1]

(1R,2R)-methyl 2-(4-(6-chloro-2-(((3R,3aR,6R,6aR)-6-hydroxyhexahydrofuro[3,2-b]furan-3-yl)oxy)-1H-imidazo[4,5-b]pyridin-5-yl)phenyl)cyclopropanecarboxylate Placed (3R,3aR,6R,6aR)-6-((5-(4-bromophenyl)-6-chloro-1-((2-(trimethylsilyl)ethoxy)methyl)-1H-imidazo[4,5-b]pyridin-2-yl)oxy)hexahydrofuro[3,2-b]furan-3-ol (60 mg, 0.103 mmol), potassium trifluoro((1R,2R)-2-(methoxycarbonyl)cyclopropyl)borate (30 mg, 0.146 mmol), and cesium carbonate (101 mg, 0.309 mmol) under nitrogen in dioxane (1.0 ml) and water (0.1 ml). Cooled in a dry-ice/acetone bath. Then chloro-(2-dicyclohexylphosphino-2',6'-diisopropoxy-1,1'-biphenyl)[2-(2-aminoethyl)phenyl]palladium(II) (16 mg, 0.022 mmol) was added to the frozen mixture. The ice bath was removed and the mixture was stirred at 90° C. for 4.5 hours. Then the mixture was allowed to cool to room temperature, poured into water (25 ml) and extracted with ethyl acetate (2×50 ml). The combined organic layers were dried over sodium sulfate and concentrated under reduced pressure. The resultant yellow oil was chromatographed using a 12 g silica gel cartridge eluted with 0-100% ethyl acetate in 1:1 hexanes/DCM over 15 column volumes. The fractions containing the desired product were combined and concentrated under reduced pressure. The resultant yellow oil was dissolved in DCM (1.0 ml) and TFA (1.0 ml). The mixture was stirred at room temperature for 2 hours. The mixture was poured into saturated aqueous sodium bicarbonate (70 ml) and extracted with ethyl acetate (2×70 ml). The combined organic layers were dried over sodium sulfate and concentrated under reduced pressure. The resultant yellow oil was chromatographed using a 12 g silica gel cartridge eluted with 0-10% methanol in DCM over 15 column volumes. The desired product fractions were combined and concentrated under reduced pressure. The resultant oily film was dissolved in acetonitrile/water, frozen at −78° C., and lyophilized to dryness to provide the title compound as a white solid. LC-MS: calculated for $C_{23}H_{22}ClN_3O_6$ 471.12 observed m/e: 471.98 (M+H)⁺ (Rt 1.12 and 3.04/4 min).

TABLE 25

Compounds prepared according to the methods in Example 212.

| Example | Structure | Exact Mass [M + H]+ |
|---|---|---|
| 213 | 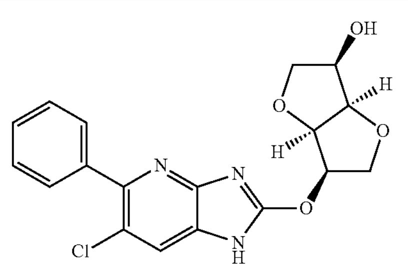 [SMILES: O[C@@H]1CO[C@H]2[C@@H]1OC[C@H]2Oc1nc2nc(-c3ccccc3)c(Cl)cc2[nH]1] | 374.01 |

TABLE 25-continued

Compounds prepared according to the methods in Example 212.

| Example | Structure | Exact Mass [M + H]+ |
|---------|-----------|---------------------|
| 214 | 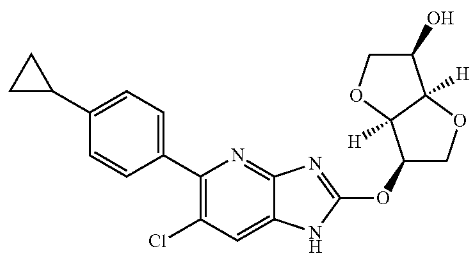 [SMILES: O[C@@H]1CO[C@H]2[C@@H]1OC[C@H]2Oc1nc2nc(-c3ccc(C4CC4)cc3)c(Cl)cc2[nH]1] | 413.99 |
| 215 | 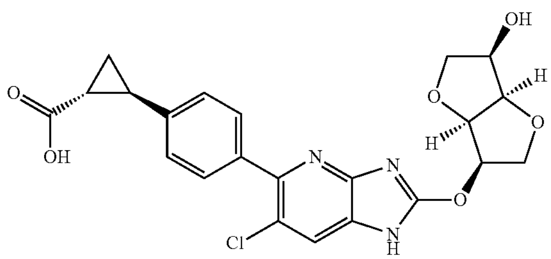 [SMILES: O=C(O)[C@@H]1C[C@H]1c1ccc(-c2nc3nc(O[C@@H]4CO[C@H]5[C@@H]4OC[C@H]5O)[nH]c3cc2Cl)cc1] | 457.97 |
| 216 | 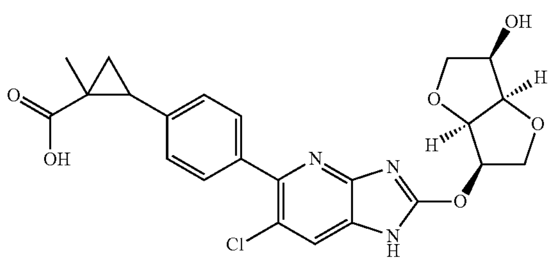 [SMILES: CC1(C(=O)O)CC1c1ccc(-c2nc3nc(O[C@@H]4CO[C@H]5[C@@H]4OC[C@H]5O)[nH]c3cc2Cl)cc1] | 471.97 |
| 217 | 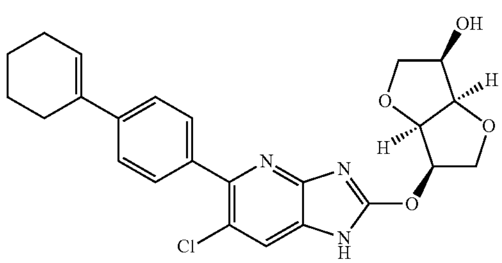 [SMILES: O[C@@H]1CO[C@H]2[C@@H]1OC[C@H]2Oc1nc2nc(-c3ccc(C4=CCCCC4)cc3)c(Cl)cc2[nH]1] | 454.03 |
| 218 | 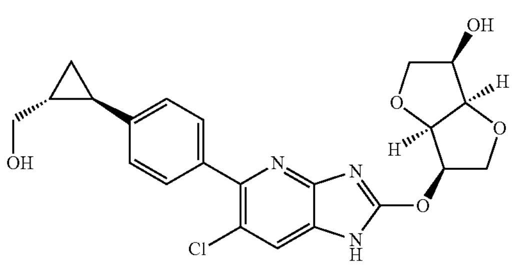 [SMILES: OC[C@@H]1C[C@H]1c1ccc(-c2nc3nc(O[C@@H]4CO[C@H]5[C@@H]4OC[C@H]5O)[nH]c3cc2Cl)cc1] | 444.01 |

EXAMPLE 219

4-(4-(6-chloro-2-(((3R,3aR,6R,6aR)-6-hydroxy-hexahydrofuro[3,2-b]furan-3-yl)oxy)-1H-imidazo[4,5-b]pyridin-5-yl)phenyl)-3,6-dihydro-2H-thiopyran 1,1-dioxide To a stirred solution of (3R,3aR,6R,6aR)-6-((6-chloro-5-(4-(3,6-dihydro-2H-thiopyran-4-yl)phenyl)-1H-imidazo[4,5-b]pyridin-2-yl)oxy)hexahydrofuro[3,2-b]furan-3-ol (98 mg, 0.166 mmol) in DCM (5.0 ml) under nitrogen at room temperature was added m-CPBA (77% w/w, 37 mg, 0.166 mmol). After 1 hour, added more m-CPBA (98 mg, 0.166 mmol). After 30 minutes, the mixture was poured into saturated aqueous sodium bicarbonate (25 ml) and extracted with ethyl acetate (2×40 ml). The combined organic layers were dried over sodium sulfate and concentrated under reduced pressure. The resultant oil was chromatographed using a 24 g silica gel cartridge eluted with 0-10% methanol in DCM over 20 column volumes. The desired product fractions were combined and concentrated under reduced pressure. The resultant residue was dissolved in acetonitrile/water, frozen at −78° C., and lyophilized to dryness to provide the title compound as a white solid. LC-MS: calculated for $C_{23}H_{22}ClN_3O_6S$ 503.09 observed m/e: 503.95 (M+H)$^+$ (Rt 2.58/4 min).

EXAMPLE 221

4-(4-(6-chloro-2-(((3R,3aR,6R,6aR)-6-hydroxy-hexahydrofuro[3,2-b]furan-3-yl)oxy)-1H-imidazol[4,5-b]pyridin-5-yl)phenyl)tetrahydro-2H-thiopyran 1,1-dioxide Placed 4-(4-(6-chloro-2-(((3R,3aR,6R,6aR)-6-hydroxy-hexahydrofuro[3,2-b]furan-3-yl)oxy)-1H-imidazo[4,5-b]pyridin-5-yl)phenyl)-3,6-dihydro-2H-thiopyran 1,1-dioxide (5 mg, 0.010 mmol) under nitrogen in methanol (1.0 ml). A few drops of DCM were added to dissolve the solid. Then 10% Pd(C) (10 mg, 9.92 μmol) was added and a slight vacuum was pulled followed by the introduction of hydrogen gas (3×). The reaction mixture was stirred under 1 atmosphere of hydrogen gas at room temperature for 1.5 hours, then filtered and concentrated under reduced pressure. The resulting residue was chromatographed using a 20 g silica gel cartridge eluted with 0-10% methanol in DCM over 10 column volumes. The desired product fractions were combined and concentrated under reduced pressure to provide the title compound as a white solid. LC-MS: calculated for $C_{23}H_{24}ClN_3O_6S$ 505.09 observed m/e: 505.98 (M+H)$^+$ (Rt 2.58/4 min).

TABLE 26

Compounds prepared according to the methods in Example 219.

| Example | Structure | Exact Mass [M + H]+ |
|---|---|---|
| 220 | 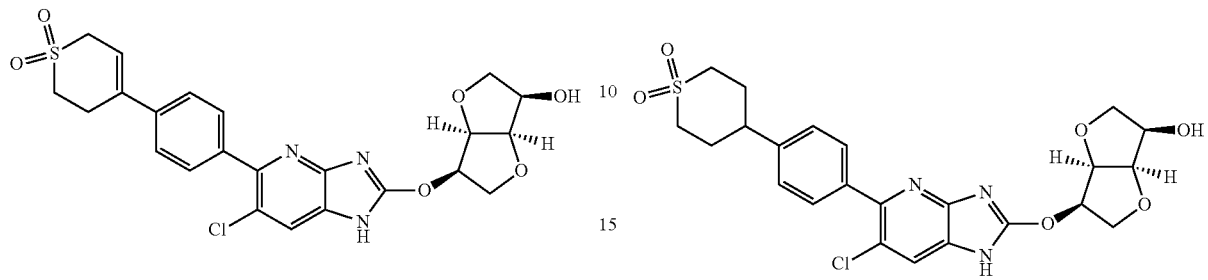 | 487.95 (intermediate formed during reaction) |

SCHEME 5

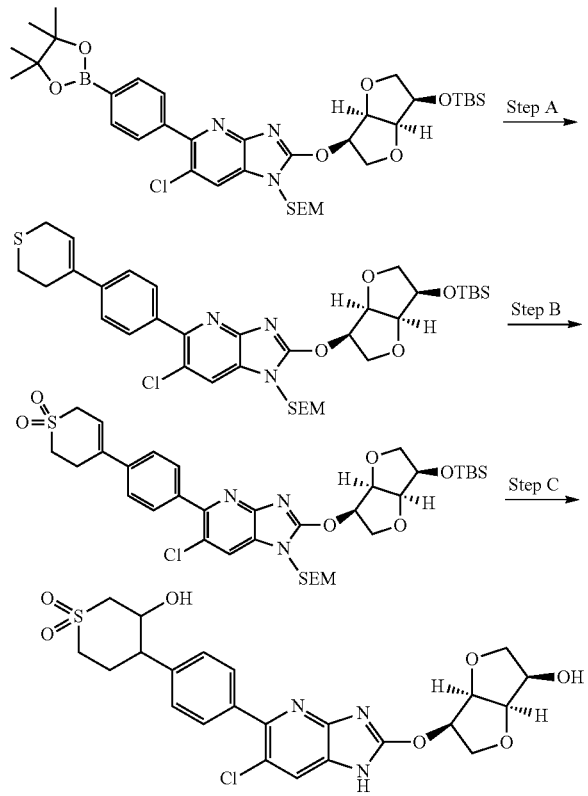

EXAMPLE 222

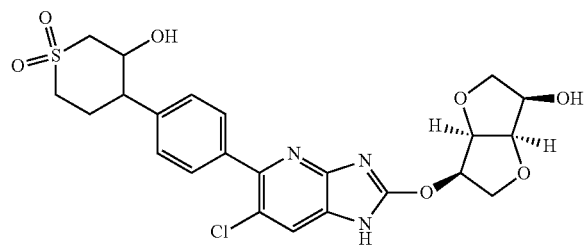 [SMILES: O=S1(=O)CCC(c2ccc(-c3nc4nc(O[C@@H]5CO[C@H]6[C@@H]5OC[C@H]6O)[nH]c4cc3Cl)cc2)C(O)C1]

4-(4-(6-chloro-2-(((3R,3aR,6R,6aR)-6-hydroxy-hexahydrofuro[3,2-b]furan-3-yl)oxy)-1H-imidazo[4,5-b]pyridin-5-yl)phenyl)-3-hydroxytetrahydro-2H-thiopyran 1,1-dioxide Step A: 2-(((3R,3aR,6R,6aS)-6-((tert-butyldimethylsilyl)oxy)hexahydrofuro[3,2-b]furan-3-yl)oxy)-6-chloro-5-(4-(3,6-dihydro-2H-thiopyran-4-yl)phenyl)-1-((2-(trimethylsilyl)ethoxy)-methyl)-1H-imidazo[4,5-b]pyridine Placed 2-(((3R,3aR,6R,6aS)-6-((tert-butyldimethylsilyl)-oxy)hexahydrofuro[3,2-b]furan-3-yl)oxy)-6-chloro-5-(4-(4,4,5,5-tetramethyl-1,3,2-dioxaborolan-2-yl)phenyl)-1-((2-(trimethylsilyl)ethoxy)methyl)-1H-imidazo[4,5-b]pyridine (500 mg, 0.672 mmol), 3,6-dihydro-2H-thiopyran-4-yl trifluoromethanesulfonate (250 mg, 10.8 mmol), and 1M aqueous potassium phosphate tribasic (2.02 ml, 2.02 mmol) under nitrogen in dioxane (7.0 ml). Cooled in dry-ice/acetone bath, pulled a hard vacuum, then introduced nitrogen (3×). Added [1,1'-bis(diphyenylphosphino)ferrocene]dichloropalladium (II) (55 mg, 0.067 mmol) to the frozen mixture, pulled a hard vacuum, then introduced nitrogen (3×). Removed ice bath and stirred mixture at 80° C. for 6 hours. The mixture was cooled to room temperature and poured into saturated aqueous sodium bicarbonate (50 ml). The mixture was extracted with ethyl acetate (2×100 ml), dried over sodium sulfate, and concentrated under reduced pressure. The resultant dark oil was chromatographed using a 40 g silica gel cartridge eluted with 0-40% EtOAc in hexanes over 20 column volumes. The desired product fractions were combined and concentrated under reduced pressure to provide the desired product as a white solid.

Step B: 4-(4-(2-(((3R,3aR,6R,6aS)-6-((tert-butyldimethylsilyl)oxy)hexahydrofuro[3,2-b]furan-3-yl)oxy)-6-chloro-1-((2-(trimethylsilyl)ethoxy)methyl)-1H-imidazo[4,5-b]pyridin-5-yl)phenyl)-3,6-dihydro-2H-thiopyran 1,1-dioxide To a stirred solution of 2-(((3R,3aR,6R,6aS)-6-((tert-butyldimethylsilyl)oxy)hexahydrofuro[3,2-b]furan-3-yl)oxy)-6-chloro-5-(4-(3,6-dihydro-2H-thiopyran-4-yl)phenyl)-1-((2-(trimethylsilyl)ethoxy)methyl)-1H-imidazo[4,5-b]pyridine (389 mg, 0.543 mmol) in DCM (5.00 ml) under nitrogen at room temperature was added m-CPBA (77% w/w, 282 mg, 1.629 mmol) portionwise over 1.5 hours. After 2 hours, the mixture was poured into saturated aqueous sodium bicarbonate (50 ml) and extracted with ethyl acetate (2×100 ml). The combined organic layers were dried over sodium sulfate and concentrated under reduced pressure. The resultant oil was chromatographed using a 40 g silica gel cartridge eluted with 0-100% EtOAc in hexanes over 20 column volumes. The fractions containing desired product were combined and concentrated under reduced pressure. The resultant oil was dissolved in acetonitrile/water, frozen at −78° C., and lyophilized to dryness to provide the desired product as a white solid. LC-MS: calculated for $C_{35}H_{50}ClN_3O_7SSi_2$ 747.26 observed m/e: 748.32 (M+H)$^+$ (Rt 1.58/2 min)

Step C: 4-(4-(6-chloro-2-(((3R,3aR,6R,6aR)-6-hydroxyhexahydrofuro[3,2-b]furan-3-yl)oxy)-1H-imidazo[4,5-b]pyridin-5-yl)phenyl)-3-hydroxytetrahydro-2H-thiopyran 1,1-dioxide To a stirred solution of 4-(4-(2-(((3R,3aR,6R,6aS)-6-((tert-butyldimethylsilyl)oxy)hexahydrofuro[3,2-b]furan-3-yl)oxy)-6-chloro-1-((2-(trimethylsilyl)ethoxy)methyl)-1H-imidazo[4,5-b]pyridin-5-yl)phenyl)-3,6-dihydro-2H-thiopyran 1,1-dioxide (50 mg, 0.067 mmol) under nitrogen in anhydrous THF (0.7 ml) at room temperature was added 1M diborane in THF (0.08 ml, 0.08 mmol). The mixture was stirred at room temperature for 3 hours, then an additional aliquot of 1M diborane in THF (0.16 ml, 0.16 mmol) was added. The mixture was stirred for 17 hours, then a premixed solution of aqueous 5M NaOH (20 µl, 0.100 mmol) and 30% aqueous hydrogen peroxide (10 µl, 11 mg, 0.100 mmol) was added. After 20 hours, the mixture was poured into saturated aqueous sodium thiosulfite (20 ml) and extracted with ethyl acetate (2×50 ml). The combined organic layers were dried over sodium sulfate and concentrated under reduced pressure. The resultant oil was chromatographed using a 12 g silica gel cartridge eluted with 0-100% ethyl acetate in hexanes over 20 column volumes. The desired product fractions were combined and concentrated under reduced pressure. The resulant oily film was dissolved in DCM (1.0 ml) and TFA (1.0 ml). The mixture was stirred for 17 hours, then concentrated under reduced pressure. The resultant film was chromatographed using a Gilson reverse phase prep HPLC eluted with 10-90% acetonitrile in water (with 0.05% TFA). The desired product fractions were combined, frozen at −78° C., and lyophilized to dryness to provide the title compound as a white solid. LC-MS: calculated for $C_{23}H_{24}ClN_3O_7S$ 521.10 observed m/e: 522.28 (M+H)$^+$ (Rt 1.58/2 min).

TABLE 27

Compounds prepared according to the methods in Example 222.

| Example | Structure | Exact Mass [M + H]+ |
|---|---|---|
| 223 | 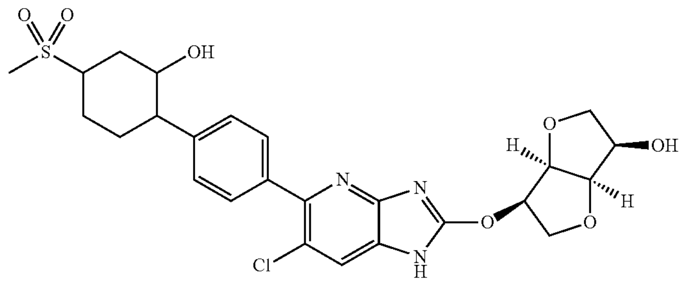 [SMILES: CS(=O)(=O)C1CCC(c2ccc(-c3nc4nc(O[C@@H]5CO[C@H]6[C@@H]5OC[C@H]6O)[nH]c4cc3Cl)cc2)C(O)C1] | 550.47 |

EXAMPLE 224

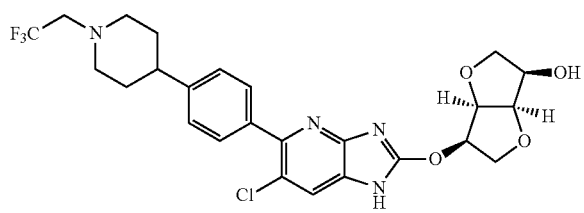 [SMILES: O[C@@H]1CO[C@H]2[C@@H]1OC[C@H]2Oc1nc2nc(-c3ccc(C4CCN(CC(F)(F)F)CC4)cc3)c(Cl)cc2[nH]1]

(3R,3aR,6R,6aR)-6-(((6-chloro-5-(4-(1-(2,2,2-trifluoroethyl)piperidin-4-yl)phenyl-1H-imidazo[4,5-b]pyridin-2-yl)oxy)hexahydrofuro[3,2-b]furan-3-ol A mixture of (3R,3aR,6R,6aR)-6-(((6-chloro-5-iodo-1H-imidazo[4,5-b]pyridin-2-yl)oxy)hexahydrofuro[3,2-b]furan-3-ol (30 mg, 0.071 mmol) and (4-(1-(2,2,2-trifluoroethyl)piperidin-4-yl)phenyl)boronic acid (24.4 mg, 0.085 mmol) in DMF (0.4 ml) was purged with $N_2$ and then chloro[(tri-tert-butylphosphine)-2-(2-aminobiphenyl)]palladium(II) (7.4 mg, 0.014 mmol) and tripotassium phosphate (0.212 ml, 0.212 mmol) were added under $N_2$ flow. The mixture was stirred at 60° C. overnight. The residue was diluted with 1.5 ml DMSO, filtered and purified by mass directed reverse phase column chromatography eluting with acetonitrile/water+0.1% TFA to give the title product. LC-MS: calculated for $C25H_{26}ClF3N4O4$, 538.16, observed m/e: 539.16 (M+H)$^+$ (RT 0.82/2.00 min)

TABLE 28

Compounds prepared according to the methods in Example 224.

| Example | Structure | Exact Mass |
|---|---|---|
| 225 | | 539.16 |
| 226 | | 543.19 |

TABLE 28-continued
Compounds prepared according to the methods in Example 224.
| 227 | 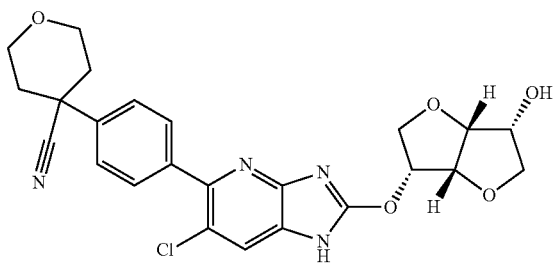 [SMILES: N#CC1(c2ccc(-c3nc4nc(O[C@@H]5CO[C@H]6[C@@H]5OC[C@H]6O)[nH]c4cc3Cl)cc2)CCOCC1] | 483.14 |
| 228 | 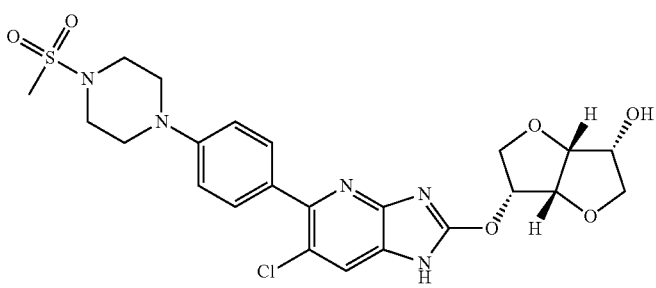 [SMILES: CS(=O)(=O)N1CCN(c2ccc(-c3nc4nc(O[C@@H]5CO[C@H]6[C@@H]5OC[C@H]6O)[nH]c4cc3Cl)cc2)CC1] | 536.13 |
| 229 | 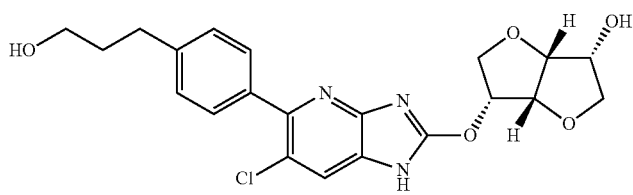 [SMILES: OCCCc1ccc(-c2nc3nc(O[C@@H]4CO[C@H]5[C@@H]4OC[C@H]5O)[nH]c3cc2Cl)cc1] | 432.13 |
| 230 | 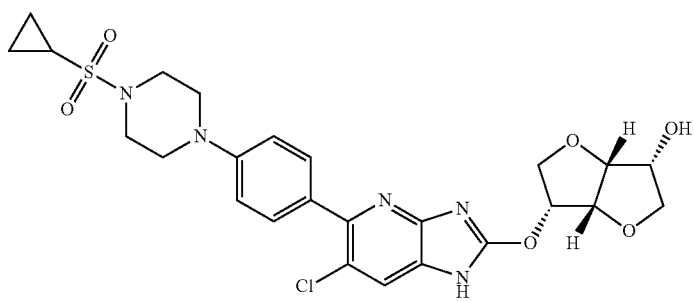 [SMILES: O=S(=O)(C1CC1)N1CCN(c2ccc(-c3nc4nc(O[C@@H]5CO[C@H]6[C@@H]5OC[C@H]6O)[nH]c4cc3Cl)cc2)CC1] | 562.15 |
| 231 | 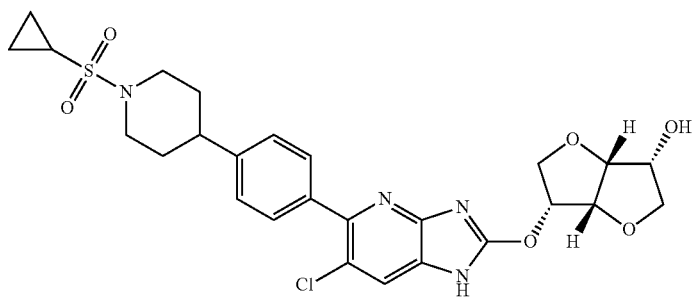 [SMILES: O=S(=O)(C1CC1)N1CCC(c2ccc(-c3nc4nc(O[C@@H]5CO[C@H]6[C@@H]5OC[C@H]6O)[nH]c4cc3Cl)cc2)CC1] | 561.15 |
| 232 | 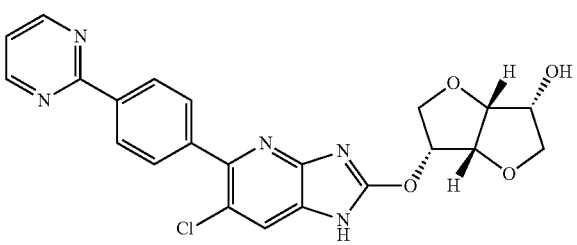 [SMILES: O[C@@H]1CO[C@H]2[C@@H]1OC[C@H]2Oc1nc2nc(-c3ccc(-c4ncccn4)cc3)c(Cl)cc2[nH]1] | 452.11 |

TABLE 28-continued
Compounds prepared according to the methods in Example 224.
| 233 | 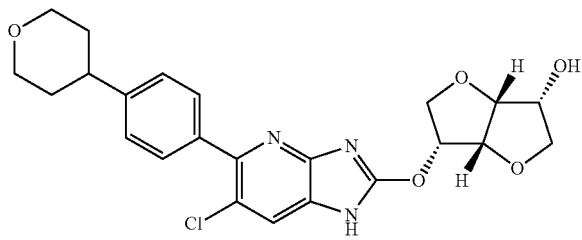 [SMILES: O[C@@H]1CO[C@H]2[C@@H]1OC[C@H]2Oc1nc2nc(-c3ccc(C4CCOCC4)cc3)c(Cl)cc2[nH]1] | 458.14 |
| 234 | 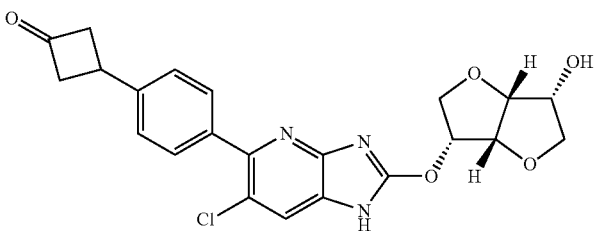 [SMILES: O=C1CC(c2ccc(-c3nc4nc(O[C@@H]5CO[C@H]6[C@@H]5OC[C@H]6O)[nH]c4cc3Cl)cc2)C1] | 442.11 |
| 235 | 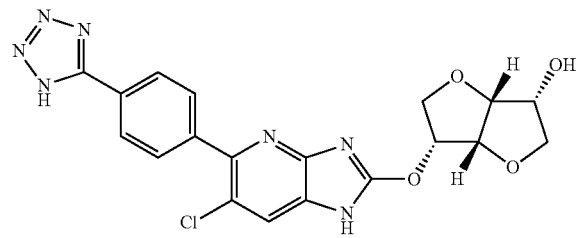 [SMILES: O[C@@H]1CO[C@H]2[C@@H]1OC[C@H]2Oc1nc2nc(-c3ccc(-c4nnn[nH]4)cc3)c(Cl)cc2[nH]1] | 442.1 |
| 236 | 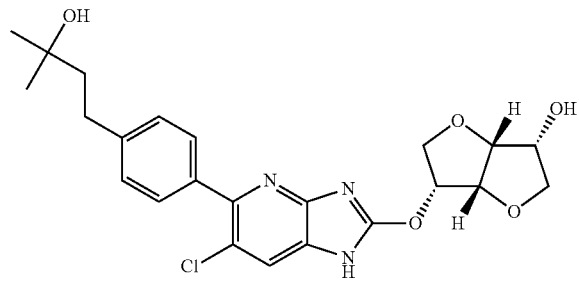 [SMILES: CC(C)(O)CCc1ccc(-c2nc3nc(O[C@@H]4CO[C@H]5[C@@H]4OC[C@H]5O)[nH]c3cc2Cl)cc1] | 460.16 |
| 237 | 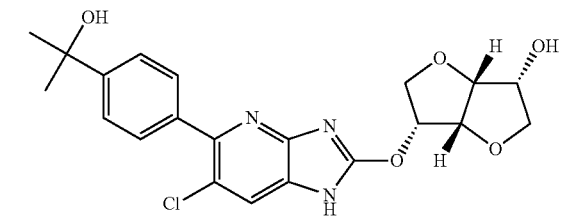 [SMILES: CC(C)(O)c1ccc(-c2nc3nc(O[C@@H]4CO[C@H]5[C@@H]4OC[C@H]5O)[nH]c3cc2Cl)cc1] | 432.13 |
| 238 | 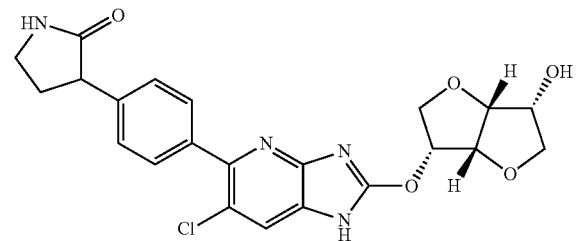 [SMILES: O=C1NCCC1c1ccc(-c2nc3nc(O[C@@H]4CO[C@H]5[C@@H]4OC[C@H]5O)[nH]c3cc2Cl)cc1] | 457.12 |

TABLE 28-continued

Compounds prepared according to the methods in Example 224.

| # | Structure | Mass |
|---|---|---|
| 239 | [structure] | 508.09 |
| 240 | [structure] | 488.15 |
| 241 | [structure] | 444.13 |
| 242 | [structure] | 404.09 |
| 243 | [structure] | 472.08 |
| 244 | [structure] | 507.1 |

TABLE 28-continued
Compounds prepared according to the methods in Example 224.
| | | |
|---|---|---|
| 245 | 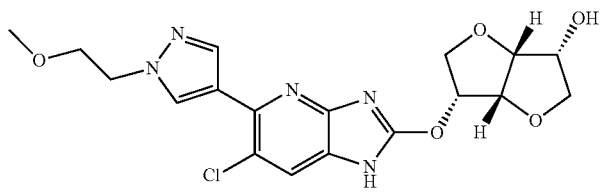 [SMILES: COCCn1cc(-c2nc3nc(O[C@@H]4CO[C@H]5[C@@H]4OC[C@H]5O)[nH]c3cc2Cl)cn1] | 422.11 |
| 246 | 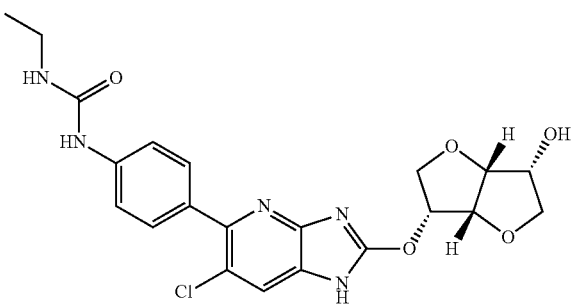 [SMILES: CCNC(=O)Nc1ccc(-c2nc3nc(O[C@@H]4CO[C@H]5[C@@H]4OC[C@H]5O)[nH]c3cc2Cl)cc1] | 460.13 |
| 247 | 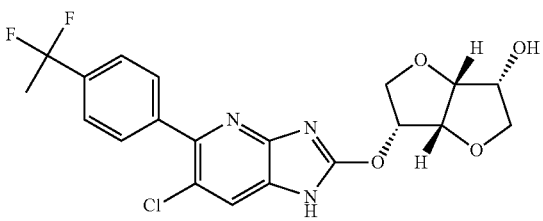 [SMILES: CC(F)(F)c1ccc(-c2nc3nc(O[C@@H]4CO[C@H]5[C@@H]4OC[C@H]5O)[nH]c3cc2Cl)cc1] | 438.1 |
| 248 | 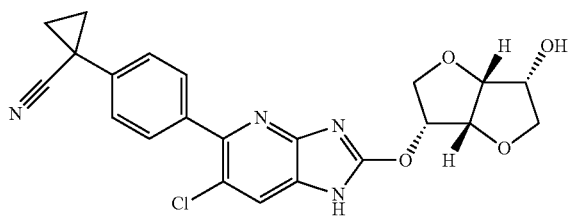 [SMILES: N#CC1(c2ccc(-c3nc4nc(O[C@@H]5CO[C@H]6[C@@H]5OC[C@H]6O)[nH]c4cc3Cl)cc2)CC1] | 439.11 |
| 249 | 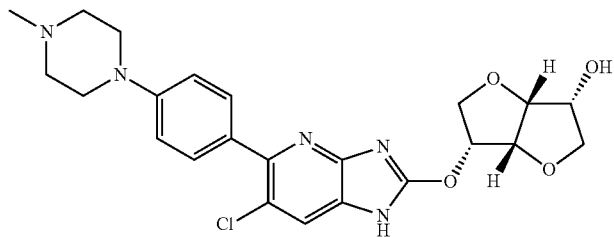 [SMILES: CN1CCN(c2ccc(-c3nc4nc(O[C@@H]5CO[C@H]6[C@@H]5OC[C@H]6O)[nH]c4cc3Cl)cc2)CC1] | 472.17 |
| 250 | 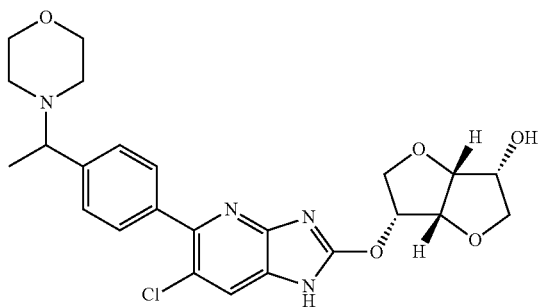 [SMILES: CC(c1ccc(-c2nc3nc(O[C@@H]4CO[C@H]5[C@@H]4OC[C@H]5O)[nH]c3cc2Cl)cc1)N1CCOCC1] | 487.17 |

TABLE 28-continued
Compounds prepared according to the methods in Example 224.
| | | |
|---|---|---|
| 251 | 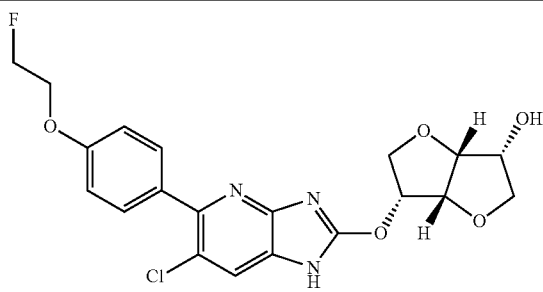 | 436.1 |
| 252 | 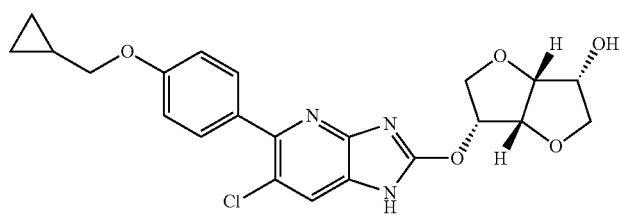 [SMILES: O[C@@H]1CO[C@H]2[C@@H]1OC[C@H]2Oc1nc2nc(-c3ccc(OCC4CC4)cc3)c(Cl)cc2[nH]1] | 444.13 |
| 253 | 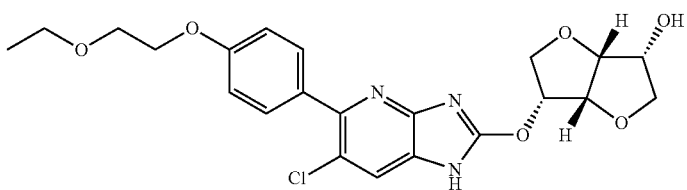 [SMILES: CCOCCOc1ccc(-c2nc3nc(O[C@@H]4CO[C@H]5[C@@H]4OC[C@H]5O)[nH]c3cc2Cl)cc1] | 462.14 |
| 254 | 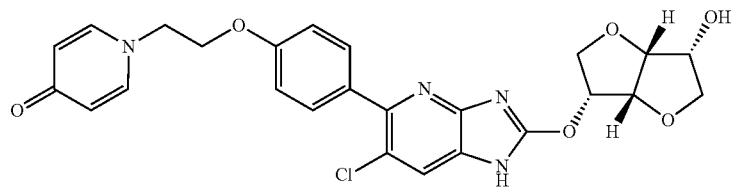 [SMILES: O=c1ccn(CCOc2ccc(-c3nc4nc(O[C@@H]5CO[C@H]6[C@@H]5OC[C@H]6O)[nH]c4cc3Cl)cc2)cc1] | 511.13 |
| 255 | 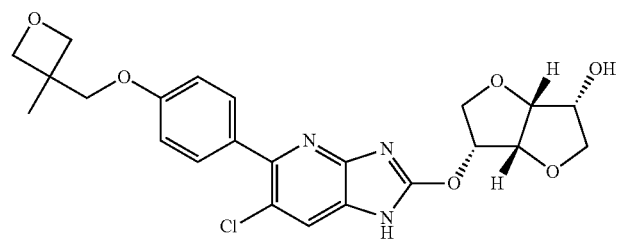 [SMILES: CC1(COc2ccc(-c3nc4nc(O[C@@H]5CO[C@H]6[C@@H]5OC[C@H]6O)[nH]c4cc3Cl)cc2)COC1] | 474.14 |
| 256 | 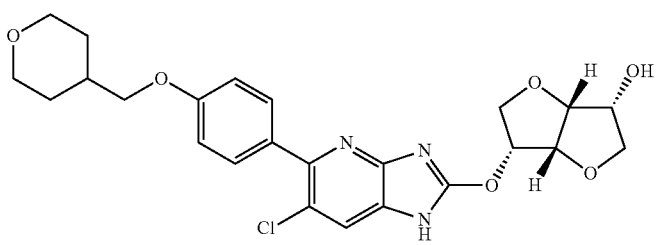 [SMILES: O[C@@H]1CO[C@H]2[C@@H]1OC[C@H]2Oc1nc2nc(-c3ccc(OCC4CCOCC4)cc3)c(Cl)cc2[nH]1] | 488.15 |
| 257 | 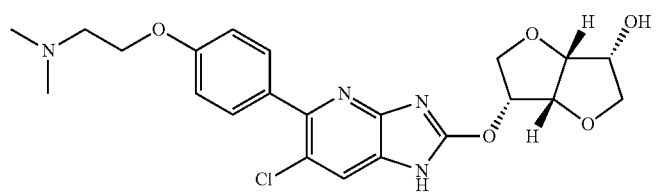 [SMILES: CN(C)CCOc1ccc(-c2nc3nc(O[C@@H]4CO[C@H]5[C@@H]4OC[C@H]5O)[nH]c3cc2Cl)cc1] | 461.15 |

TABLE 28-continued
Compounds prepared according to the methods in Example 224.
| 258 | 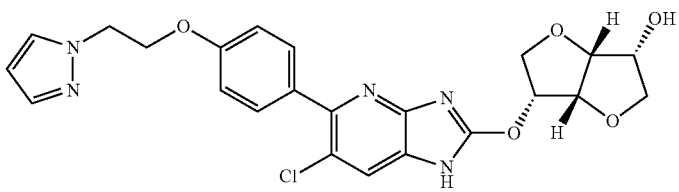 [SMILES: O[C@@H]1CO[C@H]2[C@@H]1OC[C@H]2Oc1nc2nc(-c3ccc(OCCn4cccn4)cc3)c(Cl)cc2[nH]1] | 484.13 |
| --- | --- | --- |
| 259 | 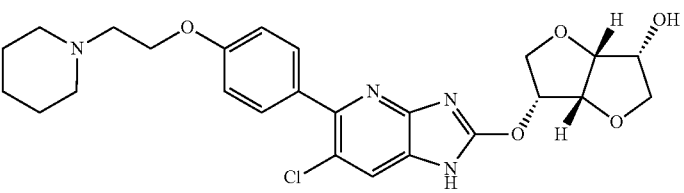 [SMILES: O[C@@H]1CO[C@H]2[C@@H]1OC[C@H]2Oc1nc2nc(-c3ccc(OCCN4CCCCC4)cc3)c(Cl)cc2[nH]1] | 501.18 |
| 260 | 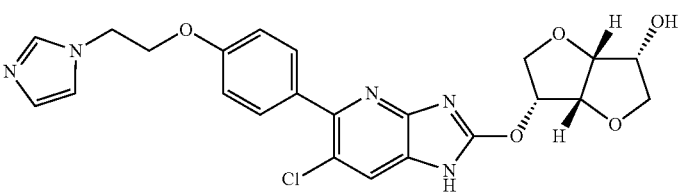 [SMILES: O[C@@H]1CO[C@H]2[C@@H]1OC[C@H]2Oc1nc2nc(-c3ccc(OCCn4ccnc4)cc3)c(Cl)cc2[nH]1] | 484.13 |
| 261 | 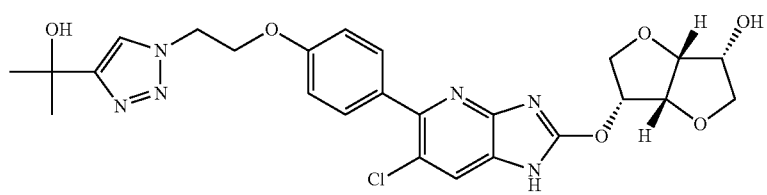 [SMILES: CC(C)(O)c1cn(CCOc2ccc(-c3nc4nc(O[C@@H]5CO[C@H]6[C@@H]5OC[C@H]6O)[nH]c4cc3Cl)cc2)nn1] | 543.17 |
| 262 | 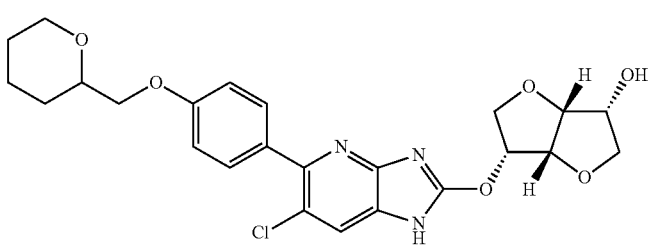 [SMILES: O[C@@H]1CO[C@H]2[C@@H]1OC[C@H]2Oc1nc2nc(-c3ccc(OCC4CCCCO4)cc3)c(Cl)cc2[nH]1] | 488.15 |
| 263 | 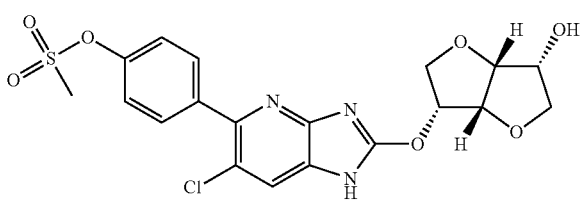 [SMILES: CS(=O)(=O)Oc1ccc(-c2nc3nc(O[C@@H]4CO[C@H]5[C@@H]4OC[C@H]5O)[nH]c3cc2Cl)cc1] | 468.05 |
| 264 | 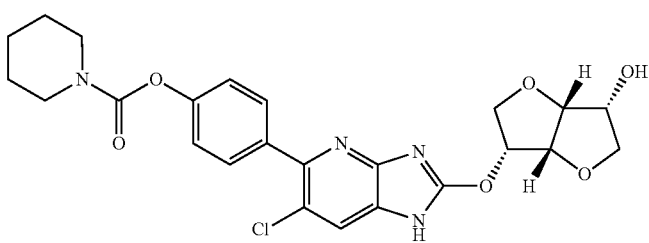 [SMILES: O=C(Oc1ccc(-c2nc3nc(O[C@@H]4CO[C@H]5[C@@H]4OC[C@H]5O)[nH]c3cc2Cl)cc1)N1CCCCC1] | 501.15 |

TABLE 28-continued

Compounds prepared according to the methods in Example 224.

| | | |
|---|---|---|
| 265 | | 517.18 |
| 266 | | 533.17 |
| 267 | | 466.11 |
| 268 | | 444.13 |
| 269 | | 503.16 |
| 270 | | 510.14 |
| 271 | | 448.12 |

TABLE 28-continued
Compounds prepared according to the methods in Example 224.
| 272 | 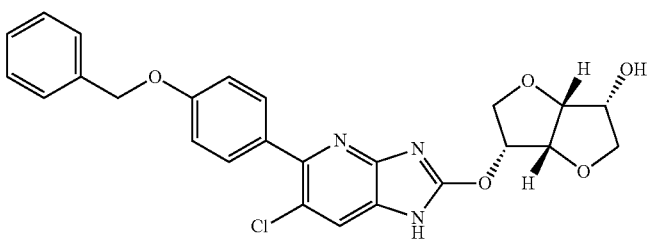 [SMILES: O[C@@H]1CO[C@H]2[C@@H]1OC[C@H]2Oc1nc2nc(-c3ccc(OCc4ccccc4)cc3)c(Cl)cc2[nH]1] | 480.13 |
| --- | --- | --- |
| 273 | 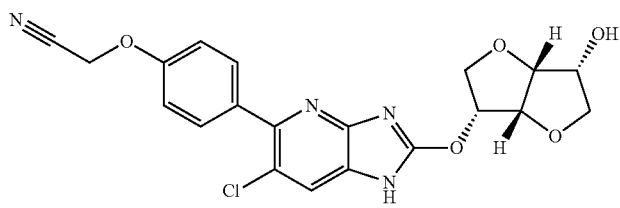 [SMILES: N#CCOc1ccc(-c2nc3nc(O[C@@H]4CO[C@H]5[C@@H]4OC[C@H]5O)[nH]c3cc2Cl)cc1] | 429.09 |
| 274 | 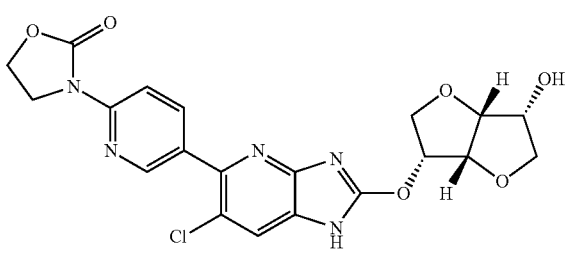 [SMILES: O=C1OCCN1c1ccc(-c2nc3nc(O[C@@H]4CO[C@H]5[C@@H]4OC[C@H]5O)[nH]c3cc2Cl)cn1] | 460.1 |
| 275 | 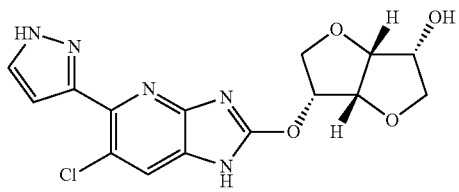 [SMILES: O[C@@H]1CO[C@H]2[C@@H]1OC[C@H]2Oc1nc2nc(-c3cc[nH]n3)c(Cl)cc2[nH]1] | 364.07 |
| 276 | 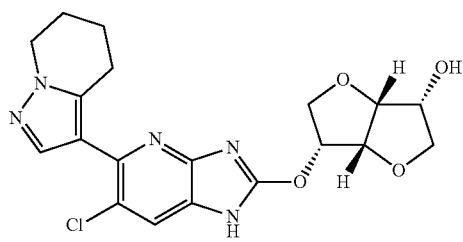 [SMILES: O[C@@H]1CO[C@H]2[C@@H]1OC[C@H]2Oc1nc2nc(-c3cnn4c3CCCC4)c(Cl)cc2[nH]1] | 418.12 |
| 277 | 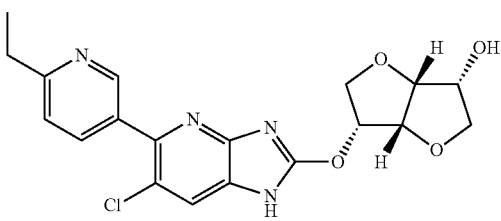 [SMILES: CCc1ccc(-c2nc3nc(O[C@@H]4CO[C@H]5[C@@H]4OC[C@H]5O)[nH]c3cc2Cl)cn1] | 403.11 |
| 278 | 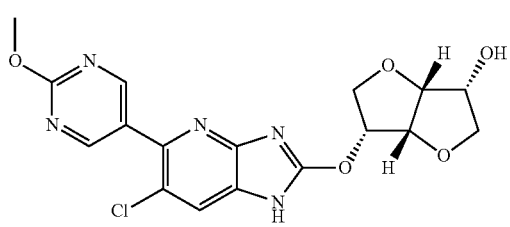 [SMILES: COc1ncc(-c2nc3nc(O[C@@H]4CO[C@H]5[C@@H]4OC[C@H]5O)[nH]c3cc2Cl)cn1] | 406.08 |

TABLE 28-continued
Compounds prepared according to the methods in Example 224.
| | | |
|---|---|---|
| 279 | 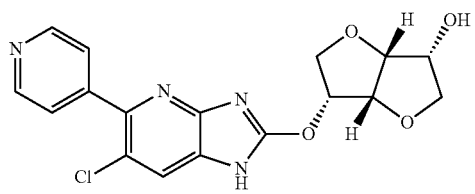 [SMILES: O[C@@H]1CO[C@H]2[C@@H]1OC[C@H]2Oc1nc2nc(-c3ccncc3)c(Cl)cc2[nH]1] | 375.08 |
| 280 | 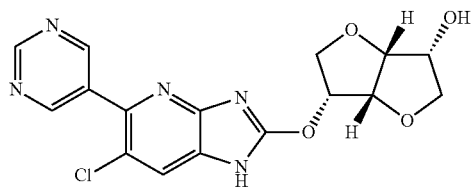 [SMILES: O[C@@H]1CO[C@H]2[C@@H]1OC[C@H]2Oc1nc2nc(-c3cncnc3)c(Cl)cc2[nH]1] | 376.07 |
| 281 | 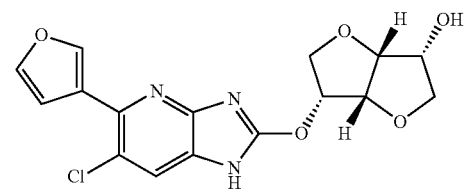 [SMILES: O[C@@H]1CO[C@H]2[C@@H]1OC[C@H]2Oc1nc2nc(-c3ccoc3)c(Cl)cc2[nH]1] | 364.06 |
| 282 | 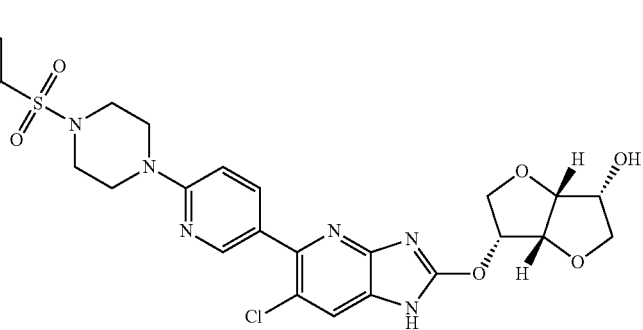 | 633.1 |
| 283 | 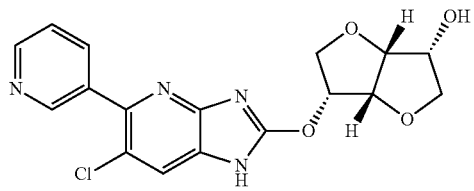 [SMILES: O[C@@H]1CO[C@H]2[C@@H]1OC[C@H]2Oc1nc2nc(-c3cccnc3)c(Cl)cc2[nH]1] | 375.08 |
| 284 | 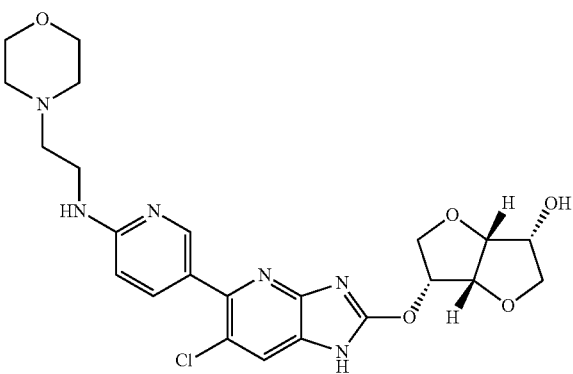 [SMILES: O[C@@H]1CO[C@H]2[C@@H]1OC[C@H]2Oc1nc2nc(-c3ccc(NCCN4CCOCC4)nc3)c(Cl)cc2[nH]1] | 503.17 |

TABLE 28-continued

Compounds prepared according to the methods in Example 224.

| # | Structure | Mass |
|---|-----------|------|
| 285 | | 380.04 |
| 286 | | 458.15 |
| 287 | | 454.05 |
| 288 | | 363.08 |
| 289 | | 473.16 |
| 290 | | 405.09 |
| 291 | | 364.07 |

TABLE 28-continued

Compounds prepared according to the methods in Example 224.

| 292 | | 481.09 |
| --- | --- | --- |
| 293 | | 457.16 |
| 294 | | 487.08 |
| 295 | | 458.11 |
| 296 | | 457.12 |
| 297 | | 443.1 |

TABLE 28-continued
Compounds prepared according to the methods in Example 224.
| | | |
|---|---|---|
| 298 | 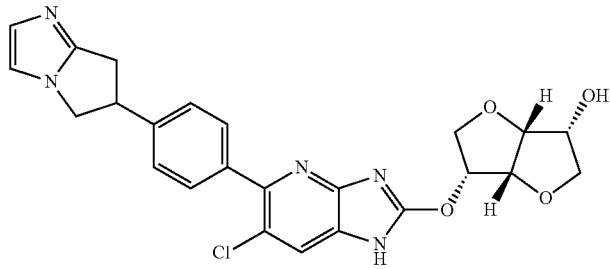 [SMILES: O[C@@H]1CO[C@H]2[C@@H]1OC[C@H]2Oc1nc2nc(-c3ccc(C4Cc5nccn5C4)cc3)c(Cl)cc2[nH]1] | 480.14 |
| 299 | 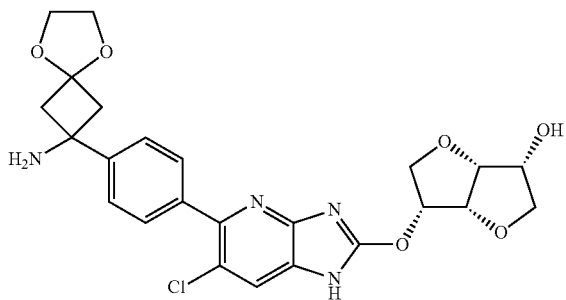 [SMILES: NC1(c2ccc(-c3nc4nc(O[C@@H]5CO[C@H]6[C@@H]5OC[C@H]6O)[nH]c4cc3Cl)cc2)CC2(C1)OCCO2] | 501.15 |
| 300 | 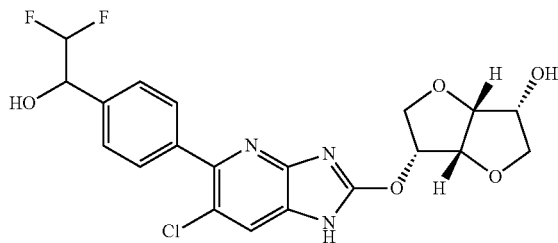 [SMILES: OC(c1ccc(-c2nc3nc(O[C@@H]4CO[C@H]5[C@@H]4OC[C@H]5O)[nH]c3cc2Cl)cc1)C(F)F] | 454.09 |
| 301 | 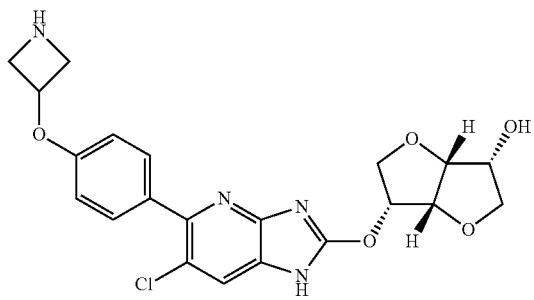 [SMILES: O[C@@H]1CO[C@H]2[C@@H]1OC[C@H]2Oc1nc2nc(-c3ccc(OC4CNC4)cc3)c(Cl)cc2[nH]1] | 445.12 |
| 302 | 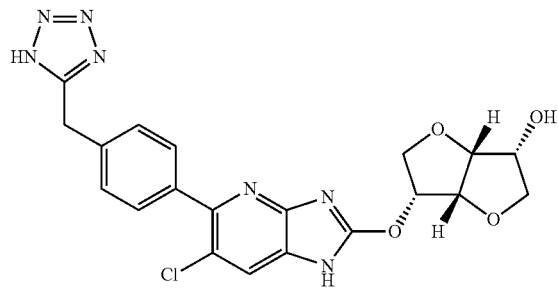 [SMILES: O[C@@H]1CO[C@H]2[C@@H]1OC[C@H]2Oc1nc2nc(-c3ccc(Cc4nnn[nH]4)cc3)c(Cl)cc2[nH]1] | 456.11 |

EXAMPLE 305

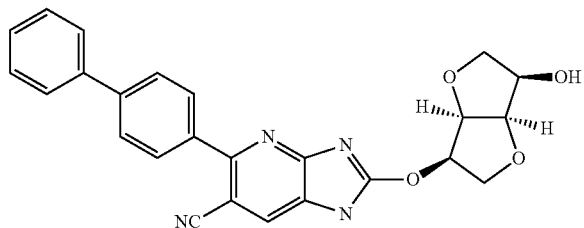 [SMILES: N#Cc1cc2[nH]c(O[C@@H]3CO[C@H]4[C@@H]3OC[C@H]4O)nc2nc1-c1ccc(-c2ccccc2)cc1]

5-([1,1'-biphenyl]-4-yl)-2-(((3R,3aR,6R,6aR)-6-hydroxyhexahydrofuro[3,2-b]furan-3-yl)oxy)-1H-imidazo[4,5-b]pyridine-6-carbonitrile A mixture of PdOAc$_2$ (15.48 mg, 0.069 mmol) and 1,1'-bis(di-tert-butylphoshino)ferrocene (32.7 mg, 0.069 mmol) in DMAc (0.25 ml) was treated with sulfuric acid (6.76 mg, 0.069 mmol) and stirred at 80° C. for 30 min. Then a solution of (3R,3aR,6R,6aR)-6-((5-([1,1'-biphenyl]-4-yl)-6-chloro-1-((2-(trimethylsilyl)ethoxy)methyl)-1H-imidazo[4,5-b]pyridin-2-yl)oxy)hexahydrofuro[3,2-b]furan-3-ol (Intermediate 8, 40 mg, 0.069 mmol) and dicyanozinc (9.71 mg, 0.083 mmol) in DMAc (0.25 ml) was added to the reaction and the reaction was heated to 120 degrees for 16 h. The residue was diluted with 0.7 ml DMF, filtered and purified by mass directed reverse phase column chromatography eluting with acetonitrile/water+0.1% TFA to give the title compound. LC-MS: calculated for C25H20N4O4, 440.15, observed m/e: 441.15 (M+H)$^+$ (RT 0.58/2.00 min).

EXAMPLE 306

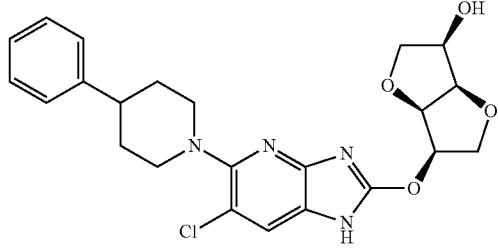

(3R,3aR,6R,6aR)-6-((6-chloro-5-(4-phenylpiperidin-1-yl)-1H-imidazo[4,5-b]pyridin-2-yl)oxy)hexahydrofuro[3,2-b]furan-3-ol Step A: (3R,3aR,6R,6aR)-6-[6-chloro-5-(4-phenylpiperidin-1-yl)-1-((2-(trimethylsilyl]ethoxy)methyl)-1H-imidazo[4,5-b]pyridin-2-yl)oxy)hexahydrofuro[3,2-b]furan-3-ol A 2 dram vial was charged with (3R,3aR,6R,6aR)-6-((6-chloro-5-iodo-1-((2-(trimethylsilyl)-ethoxy)methyl)-1H-imidazo[4,5-b]pyridin-2-yl)oxy)hexahydrofuro[3,2-b]furan-3-ol (Intermediate 3, 300 mg, 0.542 mmol), 4-phenylpiperidine (96 mg, 0.596 mmol), L-proline (12.47 mg, 0.108 mmol), cuprous iodide (10.32 mg, 0.054 mmol), potassium carbonate (150 mg, 1.083 mmol), and DMSO (1354 μl). The reaction vial under nitrogen was placed in a heating block set to 70° C. and then heated to 90° C. for 16 hours. The reaction was cooled to r.t. and diluted with ethyl acetate. The organic layer was washed with brine, dried over Na$_2$SO$_4$, and concentrated. The resulting residue was purified via silica gel chromatography using methanol/dichloromethane to afford the title compound as an orange waxy solid. LC-MS: calculated for C$_{29}$H$_{39}$ClN$_4$O$_5$Si 586.24 observed m/e: 587.44 (M+H)$^+$ (Rt 1.41/2 min).

Step B: (3R,3aR,6R,6aR)-6-((6-chloro-5-(4-phenylpiperidin-1-yl)-1H-imidazo[4,5-b]pyridin-2-yl)oxy)hexahydrofuro[3,2-b]furan-3-ol To a r.t. solution of (3R,3aR,6R,6aR)-6-((6-chloro-5-(4-phenylpiperidin-1-yl)-1-((2-(trimethylsilyl)ethoxy)methyl)-1H-imidazo[4,5-b]pyridin-2-yl)oxy)hexahydrofuro[3,2-b]furan-3-ol (77 mg, 0.131 mmol) in dichloromethane (2 mL) was added trifluoroacetic acid (2 mL). The reaction was concentrated after 4 hours and diluted with ethyl acetate and saturated aqueous NaHCO$_3$. This mixture was then extracted with ethyl acetate, and the combined the organic layers were washed with brine, dried over Na$_2$SO$_4$, and concentrated. This material was then purified via reverse phase HPLC on a 19×50 mm Waters Sunfire C18 column (5μ particle size) using a linear gradient with acetonitrile/water and buffering with 0.16% TFA at a flow rate 25 mL/min. The desired fractions were concentrated to obtain the title compound as a white sticky solid. LC-MS: calculated for C$_{23}$H$_{25}$ClN$_4$O$_4$ 456.16 observed m/e: 457.33 (M+H)$^+$ (Rt 1.08/2 min). $^1$H NMR δ (ppm) (DMSO): 7.76 (s, 1H), 7.30-7.28 (m, 4H), 7.19 (m, 1H), 5.38 (q, 1H), 4.80 (t, 1H), 4.33 (t, 1H), 4.14-4.09 (m, 2H), 3.85 (m, 1H), 3.74 (m, 1H), 3.59 (d, 2H), 3.40 (t, 1H), 2.85 (t, 2H), 2.68 (m, 1H), 1.85 (m, 4H).

TABLE 29

Compounds prepared according to the methods in Example 306.

| Example Number | Structure | HPLC-mass spectrum m/e |
|---|---|---|
| 307 | 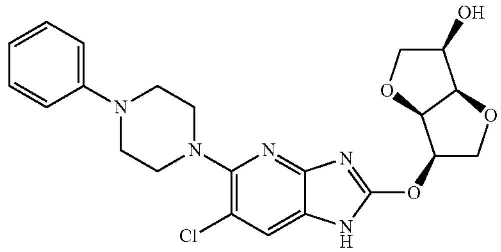 [SMILES: O[C@@H]1CO[C@H]2[C@@H]1OC[C@H]2Oc1nc2nc(N3CCN(c4ccccc4)CC3)c(Cl)cc2[nH]1] | 458.32 |
| 308 | 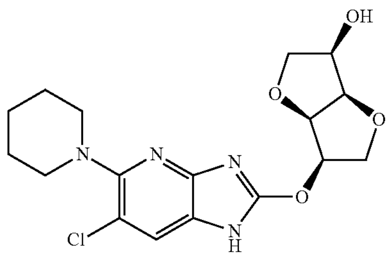 [SMILES: O[C@@H]1CO[C@H]2[C@@H]1OC[C@H]2Oc1nc2nc(N3CCCCC3)c(Cl)cc2[nH]1] | 380.93 |
| 309 | 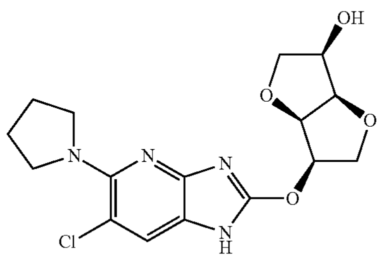 [SMILES: O[C@@H]1CO[C@H]2[C@@H]1OC[C@H]2Oc1nc2nc(N3CCCC3)c(Cl)cc2[nH]1] | 367.03 |
| 310 | racemic | 442.95 |

EXAMPLE 311

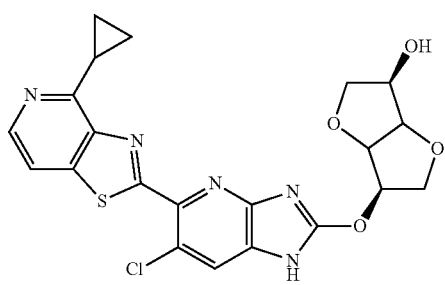 [SMILES: O[C@@H]1COC2C1OC[C@H]2Oc1nc2nc(-c3nc4c(C5CC5)nccc4s3)c(Cl)cc2[nH]1]

(3R,3aR,6R,6aR)-6-((6-chloro-5-(4-cyclopropylthiazolo[4,5-c]pyridin-2-yl)-1H-imidazo[4,5-b]pyridin-2-yl)oxy)hexahydrofuro[3,2-b]furan-3-ol Step A: 2-(2-(((3R,6R)-6-((tert-butyldimethylsilyl)oxy)hexahydrofuro[3,2-b]furan-3-yl)oxy)-6-chloro-1H-imidazo[4,5-b]pyridin-5-yl)-4-cyclopropylthiazolo[4,5-c]pyridine Palladium tetrakistriphenylphosphine (200.0 mg, 0.173 mmol) was added to a stirred suspension of [(3R,3aR,6R,6aS)-3-(1-allyl-6-chloro-5-iodo-imidazo[4,5-b]pyridin-2-yl)oxy-2,3,3a,5,6,6a-hexahydrofuro[3,2-b]furan-6-yl]oxy-tert-butyl-dimethyl-silane (500.0 mg, 0.865 mmol, Intermediate 5), 4-cyclopropylthiazolo[4,5-c]pyridine (183.0 mg, 1.038 mmol), cesium carbonate (1.409 g, 4.33 mmol), and copper (I) iodide (99.0 mg, 0.519 mmol) in degassed DMF (3.2 mL). The reaction mixture placed under nitrogen before being heated to 100° C. for 3 h. The reaction mixture was cooled to room temperature and added to EtOAc (80 ml). The mixture filtered and the solids washed with EtOAc (2×30 mL). The filtrate was evaporated under reduced pressure. Flash chromatography of the resulting residue utilizing a 40 g silica RediSep R$_f$® Gold column and employing a 0-100% EtOAc/hexane gradient afforded the title compound. LC-MS: calculated for $C_{27}H_{32}ClN_5O_4SSi$ 585.16 observed m/e: 586.17 (M+H)$^+$ (Rt 1.18/1.8 min)

Step B: (3R,3aR,6R,6aR)-6-((6-chloro-5-(4-cyclopropylthiazolo[4,5-c]pyridin-2-yl)-1H-imidazo[4,5-b]pyridin-2-yl)oxy)hexahydrofuro[3,2-b]furan-3-ol To a solution of 2-(2-(((3R,6R)-6-((tert-butyldimethylsilyl)-oxy)hexahydrofuro[3,2-b]furan-3-yl)oxy)-6-chloro-1H-imidazo[4,5-b]pyridin-5-yl)-4-cyclopropyl-thiazolo[4,5-c]pyridine (20.0 mg, 0.034 mmol) dissolved in anhydrous THF (0.3 mL) was added 1M TBAF in THF (0.07 mL, 0.070 mmol) and stirred at RT for 19 h. The reaction solution evaporated down under reduced pressure. Flash chromatography of the resulting residue utilizing a 4 g silica RediSep R$_f$® Gold column and employing a 0-15% MeOH/DCM gradient afforded the title compound. LC-MS: calculated for C21H18ClN5O4S 471.08 observed m/e: 472.01 (M+H)$^+$ (Rt 1.02/1.8 min)

TABLE 30

Compounds prepared according to the methods in Example 311.

| Example Number | Structure | HPLC-mass spectrum m/e |
|---|---|---|
| 312 | 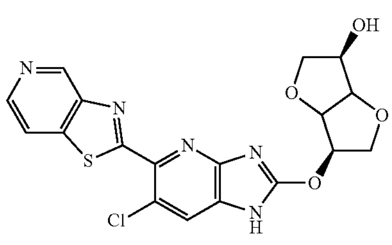 [SMILES: O[C@@H]1COC2C1OC[C@H]2Oc1nc2nc(-c3nc4cnccc4s3)c(Cl)cc2[nH]1] | 431.88 |
| 313 | 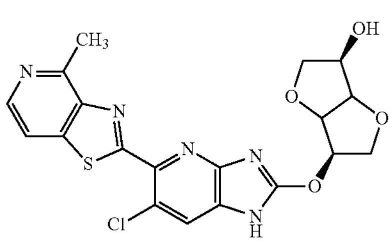 [SMILES: Cc1nccc2sc(-c3nc4nc(O[C@@H]5COC6C5OC[C@H]6O)[nH]c4cc3Cl)nc12] | 445.91 |

EXAMPLE 314

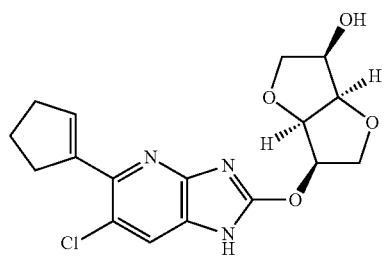 [SMILES: O[C@@H]1CO[C@H]2[C@@H]1OC[C@H]2Oc1nc2nc(C3=CCCC3)c(Cl)cc2[nH]1]

(3R,3aR,6R,6aR)-6-((6-chloro-5-(cyclopent-1-en-1-yl)-1H-imidazo[4,5-b]pyridin-2-yl)oxy)hexahydrofuro[3,2-b]furan-3-ol Step A: (3R,3aR,6R,6aR)-6-((6-chloro-5-(cyclopent-1-en-1-yl)-1-((2-(trimethylsilyl)ethoxy)methyl)-1H-imidazo[4,5-b]pyridin-2-yl)oxy)hexahydrofuro[3,2-b]furan-3-ol Palladium tetrakistriphenylphosphine (41.7 mg, 0.036 mmol) was added to a stirred suspension of (3R,3aR,6R,6aR)-6-((6-chloro-5-iodo-1-((2-(trimethylsilyl)ethoxy)methyl)-1H-imidazo[4,5-b]pyridin-2-yl)oxy)hexahydro furo[3,2-b]furan-3-ol (Intermediate 3, 100.0 mg, 0.181 mmol), cyclopent-1-en-1-ylboronic acid (30.3 mg, 0.270 mmol), and potassium phosphate tribasic (115.0 mg, 0.542 mmol) in degassed 20% water in dioxane (1.85 mL). The reaction mixture placed under N$_2$ before being heated to 85° C. for 10 h. The reaction mixture was cooled to room temperature. The lower aqueous layer drawn off and discarded. The remaining reaction mixture was evaporated under reduced pressure. Flash chromatography utilizing a 12 g silica RediSep R$_f$® Gold column and employing a 0-100% EtOAc/hexane gradient afforded the title compound. LC-MS: calculated for C23H32ClN3O5Si 493.18 observed m/e: 494.23 (M+H)$^+$ (Rt 1.67/2.0 min)

Step B: (3R,3aR,6R,6aR)-6-((6-chloro-5-(cyclopent-1-en-1-yl)-1H-imidazo[4,5-b]pyridin-2-yl)oxy) hexahydrofuro[3,2-b]furan-3-ol To (3R,3aR,6R,6aR)-6-((6-chloro-5-(cyclopent-1-en-1-yl)-1-((2-(trimethylsilyl)ethoxy)methyl)-1H-imidazo[4,5-b]pyridin-2-yl)oxy)hexahydrofuro[3,2-b]furan-3-ol (15 mg, 0.030 mmol) in anhydrous DCM (0.55 mL) was added TFA (0.55 mL, 7.13 mmol). The solution stirred at RT for 54 h. The reaction solution was evaporated under reduced pressure. Flash chromatography utilizing a 4 g silica RediSep R$_f$® Gold column and employing a 0-20% (1% NH$_4$OH in MeOH)/DCM gradient afforded the title compound. LC-MS: calculated for C17H18ClN3O4 363.10 observed m/e: 364.11 (M+H)$^+$ (Rt 1.20/2.0 min).

TABLE 31

Compounds prepared according to the methods in Example 314.

| Example Number | Structure | HPLC-mass spectrum m/e |
|---|---|---|
| 315 | 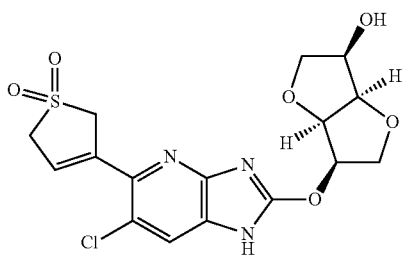 [SMILES: O=S1(=O)CC=C(c2nc3nc(O[C@@H]4CO[C@H]5[C@@H]4OC[C@H]5O)[nH]c3cc2Cl)C1] | 378.13 |

EXAMPLE 316

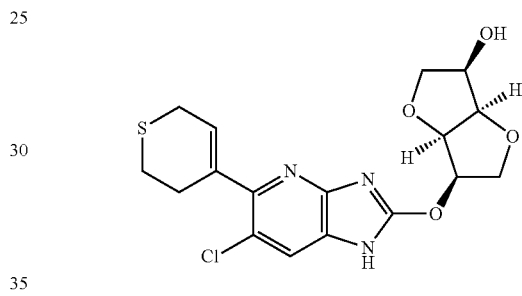

3-(6-chloro-2-(((3R,3aR,6R,6aR)-6-hydroxyhexahydrofuro[3,2-b]furan-3-yl)oxy)-1H-imidazo[4,5-b]pyridin-5-yl)-2,5-dihydrothiophene 1,1-dioxide Step A: 3-(6-chloro-2-(((3R,3aR,6R,6aR)-6-hydroxyhexahydrofuro[3,2-b]furan-3-yl)oxy)-1-((2-(trimethylsilyl)ethoxymethyl)-1H-imidazo[4,5-b]pyridin-5-yl-2,5-dihydrothiophene 1,1-dioxide To a suspension of (3R,3aR,6R,6aR)-6-((6-chloro-5-iodo-1-((2-(trimethylsilyl)ethoxy)methyl)-1H-imidazo[4,5-b]pyridin-2-yl)oxy)hexahydrofuro[3,2-b]furan-3-ol (Intermediate 3, 100.0 mg, 0.181 mmol), 2,5-dihydrothiophene 1,1-dioxide (sulfolene, 22.4 mg, 0.190 mmol), palladium (II) acetate (2.0 mg, 9.0 µmol), and triethylamine (0.03 mL, 0.226 mmol) in anhydrous toluene (0.3 mL) was added TBABr (58.2 mg, 0.181 mmol). The mixture allowed to stir under N$_2$ at RT for 12 days. The mixture added to EtOAc (50 mL), filtered, and the filtrate evaporated under reduced pressure. Flash chromatography utilizing a 12 g silica RediSep R$_f$® Gold column and employing a 0-100% EtOAc/hexane gradient afforded the title compound. LC-MS: calculated for C22H30ClN3O7SSi 543.13 observed m/e: 544.16 (M+H)$^+$ (Rt 1.30/2.0 min)

Step B: 3-(6-chloro-2-(03R,3aR,6R,6aR)-6-hydroxyhexahydrofuro[3,2-b]furan-3-yl)oxy)-1H-imidazo[4,5-b]pyridin-5—O—2,5-dihydrothiophene 1,1-dioxide To 3-(6-chloro-2-(((3R,3aR,6R,6aR)-6-hydroxyhexahydrofuro[3,2-b]furan-3-yl)oxy)-1-((2-(trimethylsilyl)ethoxy)methyl)-1H-imidazo[4,5-b]pyridin-5-yl)-2,5-dihydrothiophene 1,1-dioxide (24 mg, 0.044 mmol) in anhydrous DCM (0.2 mL) was added TFA (0.2 mL, 2.60 mmol). The solution stirred at RT for 18 h. The reaction solution was added to saturated NaHCO$_3$ (11 mL) and extracted with EtOAc (2×14 mL). The organic layers combined, dried over Na$_2$SO$_4$, filtered, and the filtrate evaporated under reduced pressure. Flash chromatography utilizing a 4 g silica RediSep R$_f$® Gold column and employing a 0-15% MeOH/DCM gradient afforded the title compound. LC-MS: calculated for C16H16ClN3O6S 413.04 observed m/e: 413.95 (M+H)$^+$ (Rt 0.61/2.0 min)

EXAMPLE 317

(3R,3aR,6R,6aR)-6-((6-chloro-5-(3,6-dihydro-2H-thiopyran-4-yl)-1H-imidazo[4,5-b]pyridin-2-yl)oxy)hexahydrofuro[3,2-b]furan-3-ol Step A: (3R,3aR,6R,6aR)-6-((6-chloro-5-(3,6-dihydro-2H-thiopyran-4-yl)-1-((2-(trimethylsilyl)ethoxy)methyl)-1H-imidazo[4,5-b]pyridin-2-yl)oxy)hexahydrofuro[3,2-b]furan-3-ol Palladium tetrakistriphenylphosphine (41.7 mg, 0.036 mmol) was added to a stirred suspension of (3R,3aR,6R,6aR)-6-((6-chloro-5-iodo-1-((2-(trimethylsilyl)ethoxy)methyl)-1H-imidazo[4,5-b]pyridin-2-yl)oxy)-hexahydrofuro[3,2-b]furan-3-ol (Intermediate 3, 100.0 mg, 0.181 mmol), 2-(3,6-dihydro-2H-thiopyran-4-yl)-4,4,5,5-tetramethyl-1,3,2-dioxaborolane (Intermediate 45, 61.2 mg, 0.270 mmol), and potassium phosphate tribasic (115.0 mg, 0.542 mmol) in degassed 20% water in dioxane (1.85 mL). The reaction mixture placed under N$_2$ and heated at 85° C. for 10 h. The reaction mixture was cooled to room temperature. The lower aqueous layer drawn off and discarded. The remaining reaction mixture was evaporated under reduced pressure. Flash chromatography of the resulting residue utilizing a 12 g silica RediSep R$_f$® Gold column and employing a 0-100% EtOAc/hexane gradient afforded the title compound. LC-MS: calculated for C23H32ClN3O5SSi 525.15 observed m/e: 526.17 (M+H)$^+$ (Rt 1.64/2.0 min)

Step B: (3R,3aR,6R,6aR)-6-((6-chloro-5-(3,6-dihy-dro-2H-thiopyran-4-yl)-1H-imidazo[4,5-b]pyridin-2-yl)oxy)hexahydrofuro[3,2-b]furan-3-ol To (3R,3aR,6R,6aR)-6-((6-chloro-5-(3,6-dihydro-2H-thiopyran-4-yl)-1-((2-(trimethylsilyl)ethoxy)methyl)-1H-imidazo[4,5-b]pyridin-2-yl)oxy)hexahydrofuro[3,2-b]furan-3-ol (74 mg, 0.141 mmol) in anhydrous DCM (0.45 mL) was added TFA (0.45 mL, 5.84 mmol). The solution stirred at RT for 18 h. The reaction solution was added to saturated NaHCO$_3$ (35 mL) and extracted with EtOAc (2×45 mL). The organic layers combined, dried over Na$_2$SO$_4$, filtered, and the filtrate evaporated under reduced pressure. Flash chromatography utilizing a 12 g silica RediSep R$_f$® Gold column and employing a 0-10% MeOH/DCM gradient afforded the title compound. LC-MS: calculated for C17H18ClN3O4S 395.07 observed m/e: 395.90 (M+H)$^+$ (Rt 0.84/2.0 min)

EXAMPLE 318

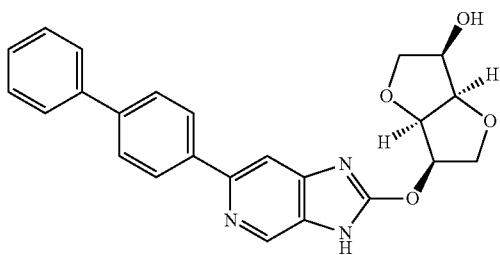 [SMILES: O[C@@H]1CO[C@H]2[C@@H]1OC[C@H]2Oc1nc2cc(-c3ccc(-c4ccccc4)cc3)ncc2[nH]1]

(3R,3aR,6R,6aR)-6-((6-([1,1'-biphenyl]-4-yl)-3H-imidazo[4,5-c]pyridin-2-yl)oxy)hexahydrofuro[3,2-b]furan-3-ol Step A: 6-([1,1'-biphenyl]-4-yl)-2-(((3R,3aR,6R,6aS)-6-((tert-butyldimethylsilyl)oxy)hexahydrofuro[3,2-b]furan-3-yl)oxy)-3-((2-(trimethylsilyl)ethoxy)methyl)-3H-imidazo[4,5-c]pyridine Palladium tetrakistriphenylphosphine (42.6 mg, 0.037 mmol) was added to a stirred suspension of 2-(((3R,3aR,6R, 6aS)-6-((tert-butyldimethylsilyl)oxy)hexahydrofuro[3,2-b]furan-3-yl)oxy)-6-chloro-3-((2-(trimethylsilyl)ethoxy)methyl)-3H-imidazo[4,5-c]pyridine (Intermediate 46, 100.0 mg, 0.184 mmol), 4-biphenylboronic acid (54.8 mg, 0.277 mmol), and potassium phosphate tribasic (117.0 mg, 0.553 mmol) in degassed 20% water in dioxane (1.44 mL). The reaction mixture stirred under N$_2$ at 85° C. After 2 h, more palladium tetrakistriphenylphosphine (42.6 mg, 0.037 mmol) was added. The reaction mixture heated under N$_2$ at 85° C. for another 7 h, then cooled to room temperature and the lower aqueous layer was drawn off and discarded. The remaining reaction mixture was added to EtOAc (50 mL), filtered, and the resulting solids were washed with EtOAc (2×15 mL). The filtrate was evaporated under reduced pressure. Flash chromatography of the resulting residue utilizing a 24 g silica RediSep R$_f$® Gold column and employing a 0-100% EtOAc/hexane gradient afforded the title compound. LC-MS: calculated for C36H49N3O5Si2 659.32 observed m/e: 660.13 (M+H)$^+$ (Rt 1.58/2.0 min).

Step B: (3R,3aR,6R,6aR)-6-((6-([1,1'-biphenyl]-4-yl)-3H-imidazo[4,5-c]pyridin-2-yl)oxy)hexahydrofuro[3,2-b]furan-3-ol To 6-([1,1'-biphenyl]-4-yl)-2-(((3R,3aR,6R,6aS)-6-((tert-butyldimethylsilyl)oxy)hexahydrofuro[3,2-b]furan-3-yl)oxy)-3-((2-(trimethylsilyl)ethoxy)methyl)-3H-imidazo[4,5-c]pyridine (26.0 mg, 0.039 mmol) in anhydrous DCM (1.23 mL) was added TFA (0.91 mL, 11.82 mmol). The solution stirred at RT for 52 h. The reaction solution was evaporated under reduced pressure. The residue extracted into EtOAc (35 mL) and washed with 1N NaOH (6.0 mL, 6 mmol) and water (10 mL), dried over Na$_2$SO$_4$, filtered, and evaporated under reduced pressure to afford the title compound. LC-MS: calculated for C24H21N3O4 415.15 observed m/e: 416.16 (M+H)$^+$ (Rt 1.34/2.0 min).

TABLE 32

Compounds prepared according to the methods in Example 318.

| Example Number | Structure | HPLC-mass spectrum m/e |
|---|---|---|
| 319 | 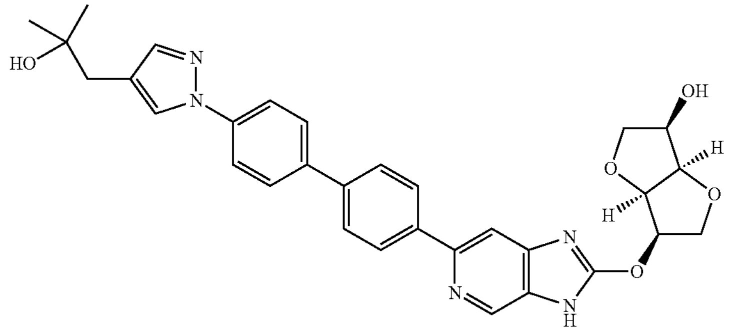 [SMILES: CC(C)(O)Cc1cnn(-c2ccc(-c3ccc(-c4cc5nc(O[C@@H]6CO[C@H]7[C@@H]6OC[C@H]7O)[nH]c5cn4)cc3)cc2)c1] | 554.09 |

EXAMPLE 320

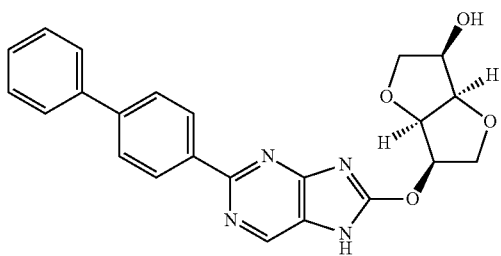 [SMILES: O[C@@H]1CO[C@H]2[C@@H]1OC[C@H]2Oc1nc2nc(-c3ccc(-c4ccccc4)cc3)ncc2[nH]1]

(3R,3aR,6R,6aR)-6-((2-([1,1'-biphenyl]-4-yl)-7H-purin-8-yl)oxy)hexahydrofuro[3,2-b]furan-3-ol Step A: 2-([1,1'-biphenyl]-4-yl)-8-(((3R,3aR,6R,6aS)-6-((tert-butyldimethylsilyl)oxy)hexahydrofuro[3,2-b]furan-3-yl)oxy)-7-((2-(trimethylsilyl)ethoxy)methyl)-7H-purine Palladium tetrakistriphenylphosphine (21.3 mg, 0.018 mmol) was added to a stirred suspension of 8-(((3R,3aR,6R,6aS)-6-((tert-butyldimethyl-silyl)oxy)hexahydrofuro[3,2-b]furan-3-yl)oxy)-2-chloro-7-((2-(trimethylsilyl)ethoxy)methyl)-7H-purine (Intermediate 47, 50.0 mg, 0.092 mmol), 4-biphenylboronic acid (27.3 mg, 0.138 mmol), and potassium phosphate tribasic (58.6 mg, 0.276 mmol) in degassed 20% water in dioxane (0.72 mL). The reaction mixture stirred under $N_2$ at 85° C. for 2.5 h, then additional more palladium tetrakistriphenylphosphine (21.3 mg, 0.018 mmol) was added. The reaction mixture heated under $N_2$ at 85° C. for another 3.5 h and then cooled to room temperature. The lower aqueous layer was drawn off and discarded. The remaining reaction mixture was added to EtOAc (25 mL), and filtered. The resulting solids were washed with EtOAc (2×10 mL). The filtrate was evaporated under reduced pressure to give a residue. Flash chromatography of the resulting residue utilizing a 12 g silica RediSep $R_f$® Gold column and employing a 0-80% EtOAc/hexane gradient afforded the title compound. LC-MS: calculated for C35H48N4O5Si2 660.32 observed m/e: 661.61 (M+H)+ (Rt 1.85/2.0 min).

Step B: (3R,3aR,6R,6aR)-6-((2-([1,1'-biphenyl]-4-yl)-7H-purin-8-yl)oxy)hexahydrofuro[3,2-b]furan-3-ol To 2-([1,1'-biphenyl]-4-yl)-8-(((3R,3aR,6R,6aS)-6-((tert-butyldimethylsilyl)oxy)hexahydrofuro[3,2-b]furan-3-yl)oxy)-7-((2-(trimethylsilyl)ethoxy)methyl)-7H-purine (38.0 mg, 0.057 mmol) in anhydrous DCM (1.8 mL) was added TFA (1.33 mL, 17.25 mmol). The solution stirred at RT for 22 h. The reaction solution cooled to 0° C. and 1N NaOH (18.2 mL, 18.2 mmol) and EtOAc (60 mL) added. The organic layer washed with brine (20 mL), dried over $Na_2SO_4$, filtered, and evaporated under reduced pressure. Flash chromatography utilizing a 12 g silica RediSep $R_f$® Gold column and employing a 0-15% MeOH/DCM gradient afforded the title compound. LC-MS: calculated for C23H20N4O4 416.15 observed m/e: 417.36 (M+H)+ (Rt 0.93/2.0 min).

TABLE 33

Compounds prepared according to the methods in Example 320.

| Example Number | Structure | HPLC-mass spectrum m/e |
|---|---|---|
| 321 | 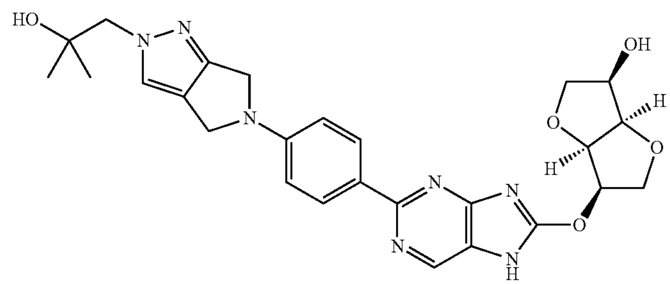 [SMILES: CC(C)(O)Cn1cc2c(n1)CN(c1ccc(-c3ncc4[nH]c(O[C@@H]5CO[C@H]6[C@@H]5OC[C@H]6O)nc4n3)cc1)C2] | 520.15 |

TABLE 34

Compounds prepared according to the methods in Example 1.

| | | |
|---|---|---|
| 322 | | 522.19 |

TABLE 34-continued

Compounds prepared according to the methods in Example 1.

| Example | Structure | Exact Mass [M + H]+ |
|---|---|---|
| 323 | (structure) | 536.24 |
| 324 | (structure) | 550.02 |
| 325 | (structure) | 516.15 |

TABLE 35

Compounds prepared according to the methods in Example 106.

| Example | Structure | Exact Mass [M + H]+ |
|---|---|---|
| 326 | (structure) | 479.15 |
| 327 | (structure) | 471.8 |

TABLE 35-continued

Compounds prepared according to the methods in Example 106.

| Example | Structure | Exact Mass [M + H]+ |
|---|---|---|
| 328 | 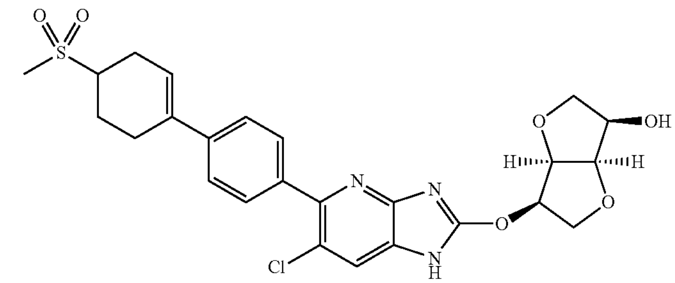 [SMILES: CS(=O)(=O)C1CC=C(c2ccc(-c3nc4nc(O[C@@H]5CO[C@H]6[C@@H]5OC[C@H]6O)[nH]c4cc3Cl)cc2)CC1] | 532.02 |
| 329 | 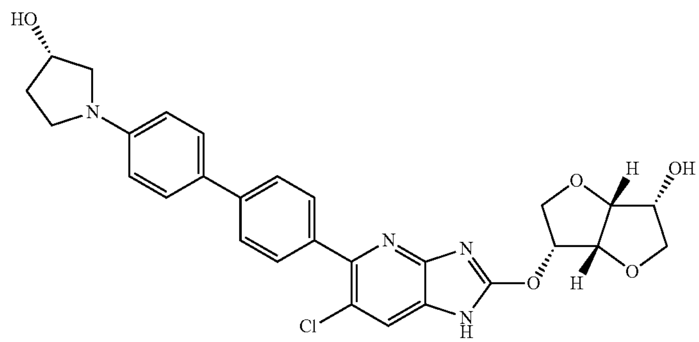 [SMILES: O[C@H]1CCN(c2ccc(-c3ccc(-c4nc5nc(O[C@@H]6CO[C@H]7[C@@H]6OC[C@H]7O)[nH]c5cc4Cl)cc3)cc2)C1] | 535.17 |
| 330 | 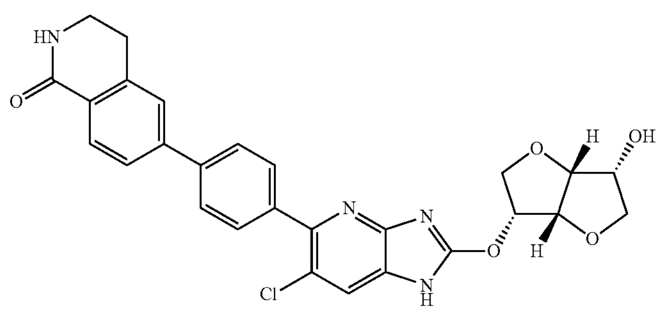 [SMILES: O=C1NCCc2cc(-c3ccc(-c4nc5nc(O[C@@H]6CO[C@H]7[C@@H]6OC[C@H]7O)[nH]c5cc4Cl)cc3)ccc21] | 519.14 |
| 331 | 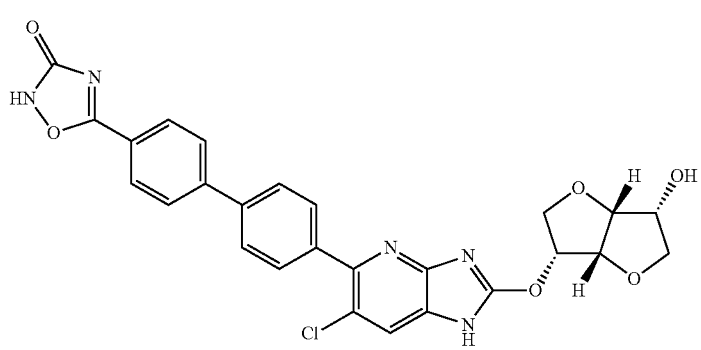 [SMILES: O=c1nc(-c2ccc(-c3ccc(-c4nc5nc(O[C@@H]6CO[C@H]7[C@@H]6OC[C@H]7O)[nH]c5cc4Cl)cc3)cc2)o[nH]1] | 534.27 |

TABLE 35-continued

Compounds prepared according to the methods in Example 106.

| Example | Structure | Exact Mass [M + H]+ |
|---------|-----------|---------------------|
| 332 | 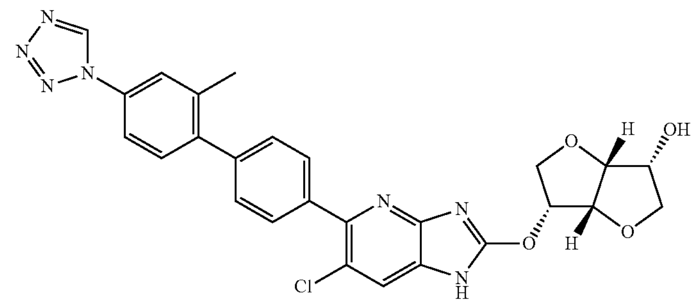 [SMILES: Cc1cc(-n2cnnn2)ccc1-c1ccc(-c2nc3nc(O[C@@H]4CO[C@H]5[C@@H]4OC[C@H]5O)[nH]c3cc2Cl)cc1] | 532.14 |
| 333 | 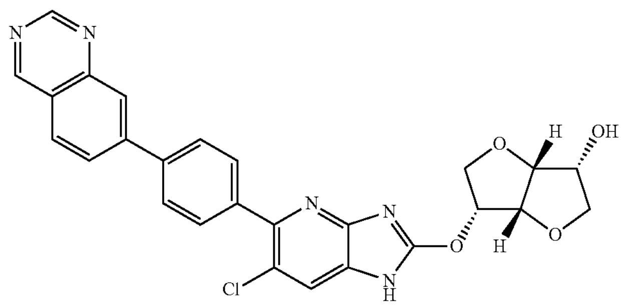 [SMILES: O[C@@H]1CO[C@H]2[C@@H]1OC[C@H]2Oc1nc2nc(-c3ccc(-c4ccc5cncnc5c4)cc3)c(Cl)cc2[nH]1] | 502.12 |
| 334 | 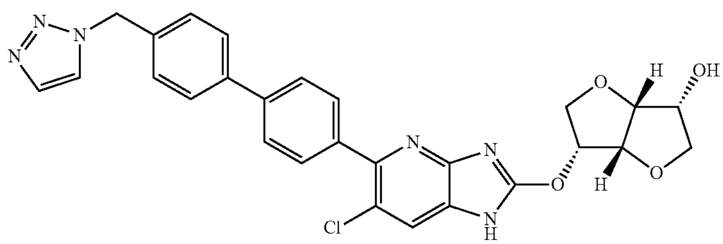 [SMILES: O[C@@H]1CO[C@H]2[C@@H]1OC[C@H]2Oc1nc2nc(-c3ccc(-c4ccc(Cn5ccnn5)cc4)cc3)c(Cl)cc2[nH]1] | 531.15 |
| 335 | 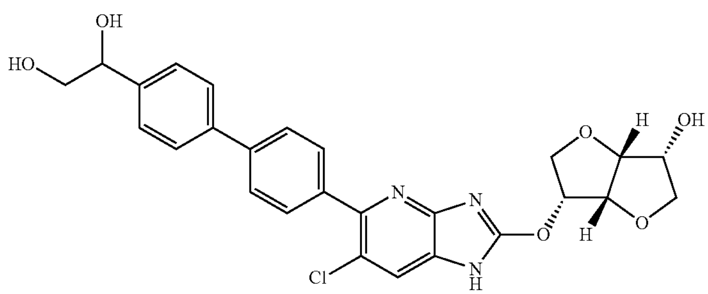 [SMILES: OCC(O)c1ccc(-c2ccc(-c3nc4nc(O[C@@H]5CO[C@H]6[C@@H]5OC[C@H]6O)[nH]c4cc3Cl)cc2)cc1] | 510.14 |
| 336 | 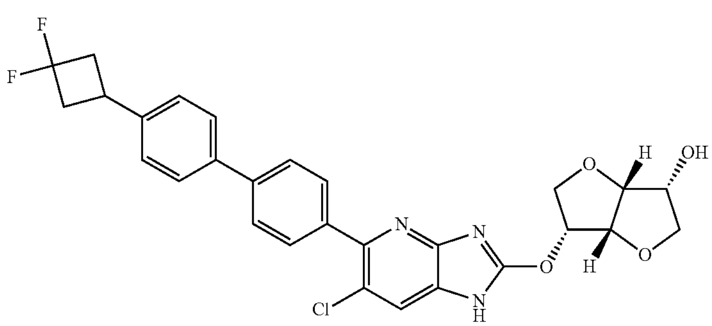 [SMILES: O[C@@H]1CO[C@H]2[C@@H]1OC[C@H]2Oc1nc2nc(-c3ccc(-c4ccc(C5CC(F)(F)C5)cc4)cc3)c(Cl)cc2[nH]1] | 540.14 |

TABLE 35-continued

Compounds prepared according to the methods in Example 106.

| Example | Structure | Exact Mass [M + H]+ |
|---|---|---|
| 337 | 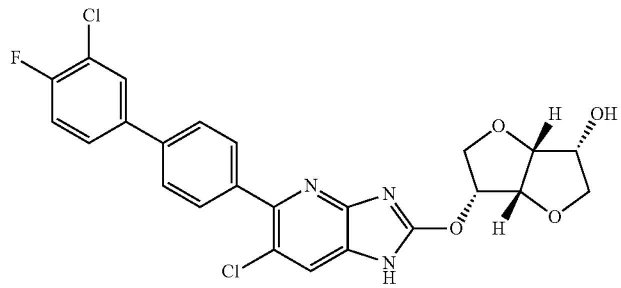 [SMILES: O[C@@H]1CO[C@H]2[C@@H]1OC[C@H]2Oc1nc2nc(-c3ccc(-c4ccc(F)c(Cl)c4)cc3)c(Cl)cc2[nH]1] | 502.07 |
| 338 | 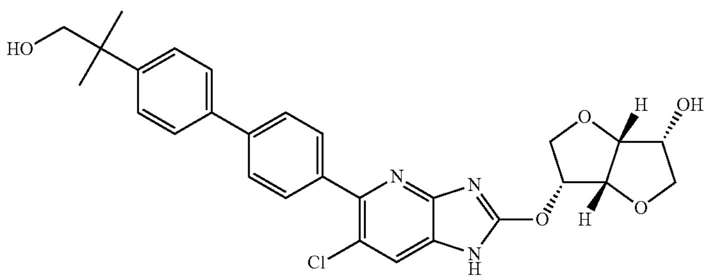 [SMILES: CC(C)(CO)c1ccc(-c2ccc(-c3nc4nc(O[C@@H]5CO[C@H]6[C@@H]5OC[C@H]6O)[nH]c4cc3Cl)cc2)cc1] | 522.17 |
| 339 | 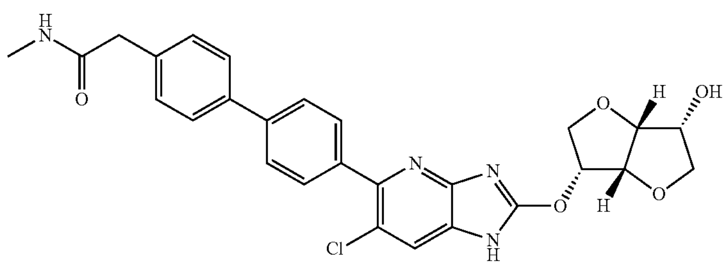 [SMILES: CNC(=O)Cc1ccc(-c2ccc(-c3nc4nc(O[C@@H]5CO[C@H]6[C@@H]5OC[C@H]6O)[nH]c4cc3Cl)cc2)cc1] | 521.15 |

TABLE 36

Compounds prepared according to the methods in Example 153.

| 340 | | 526.96 |
| 341 | | 438.98 |

TABLE 36-continued

Compounds prepared according to the methods in Example 153.

| | | |
|---|---|---|
| 342 | [structure: cyclohexyl-phenyl chloroimidazopyridine with hexahydrofurofuran-OH] | 456.05 |
| 343 | [structure: hydroxycyclohexyl-phenyl chloroimidazopyridine with hexahydrofurofuran-OH] | 472.04 (slower eluting diastereomer) |
| 344 | [structure: hydroxycyclohexyl-phenyl chloroimidazopyridine with hexahydrofurofuran-OH] | 472.05 (slower eluting diastereomer) |

EXAMPLE 345

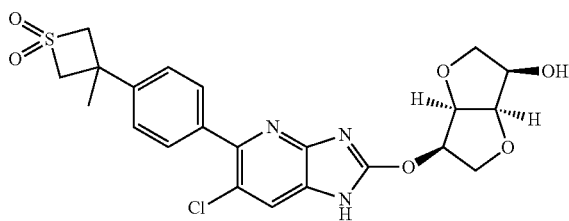 [SMILES: CC1(c2ccc(-c3nc4nc(O[C@@H]5CO[C@H]6[C@@H]5OC[C@H]6O)[nH]c4cc3Cl)cc2)CS(=O)(=O)C1]

3-(4-(6-chloro-2-(((3R,3aR,6R,6aR)-6-hydroxy-hexahydrofuro[3,2-b]furan-3-yl)oxy)-1H-imidazo[4,5-b]pyridin-5-yl)phenyl)-3-methylthietane 1,1-dioxide Step A To 2-(4-bromophenyl)-2-methylpropane-1,3-diol (1226 mg, 5 mmol)) in dichloromethane (25 ml) at 0° C. under $N_2$ atmosphere was added triethylamine (4.18 ml, 30 mmol), p-TsCl (2145 mg, 11.25 mmol) and a few crystals of DMAP. The reaction mixture was warmed to room temperature over 16 hours, and then diluted with EtOAc (150 ml) and saturated aqueous $NH_4Cl$ solution (150 ml). The organic layer was separated, extracted the aqueous layer with EtOAc (100 ml). The combined organic layers were washed with saturated aqueous $NH_4Cl$ solution (250 ml), brine (250 ml), dried ($Na_2SO_4$), filtered and concentrated. The resulting crude material was purified by Isco™ system, 120 g gold cartridge, 85 ml flow rate, 0/100 (2 min) to 30/70 (15 min) to 30/70 (20 min) 100/0 (32 min total run time) of EtOAc/hexanes. The combined product containing fractions were concentrated to obtain 2-(4-bromophenyl)-2-methylpropane-1,3-diylbis(4-methylbenzenesulfonate) as a white solid.

Step B To a solution of 2-(4-bromophenyl)-2-methylpropane-1,3-diyl bis(4-methylbenzenesulfonate) (540 mg, 0.976 mmol, from Step A) in DMF (10 ml) in a thick walled tube, under $N_2$ atmosphere, was added sodium sulfide (90 mg, 1.153 mmol) in one portion. The reaction was heated to 100° C. for 4 hours, then cooled to room temperature, diluted with water (50 ml), and extracted with EtOAc (2×50 ml). The combined organic layers were washed with water (75 ml), brine (75 ml), dried ($Na_2SO_4$), filtered and concentrated. The resulting crude 3-(4-bromophenyl)-3-methylthietane was used in the next step.

Step C. To the crude 3-(4-bromophenyl)-3-methylthietane (200 mg, from Step B) in dichloromethane (10 ml), under $N_2$ atmosphere, at 0° C. was added mCPBA (507 mg, 70%) in one portion with vigorous stirring. The reaction was slowly warmed to room temperature over 5 hrs, then diluted with EtOAc (50 ml) and quenched by the addition of aqueous 10% sodium thiosulfate (25 ml) and saturated sodium bicarbonate solution (25 ml). The aqueous layer was separated, and extracted with EtOAc (50 ml). The combined organic layers were washed with a mixture of aqueous 10% sodium thiosulfate (25 ml)/saturated sodium bicarbonate solution (25 ml), then brine (50 ml), dried ($Na_2SO_4$), filtered and concentrated. The resulting crude 3-(4-bromophenyl)-3-methylthietane 1,1-dioxide, was used in the next step.

Step D To pinacol diboronate (250 mg, 0.986 mmol), potassium acetate (242 mg, 2.466 mmol) and $PdCl_2$(dppf)-

CH$_2$Cl$_2$ adduct (67 mg, 0.082 mmol) in a thick-walled tube was added a solution of 3-(4-bromophenyl)-3-methylthietane 1,1-dioxide (226 mg, from Step C) in DMF (5 ml). The tube was flushed with N$_2$, then capped and heated to 90° C. for 4 hours. Then the reaction was cooled to RT and diluted with EtOAc (30 ml) and water (20 ml). The aqueous layer was separated and extracted with EtOAc (25 ml). The combined organic layers were washed with water (50 ml), dried (Na$_2$SO$_4$), filtered and concentrated. The resulting crude material was purified by Isco™ system, 40 g gold cartridge, 40 ml flow rate, gradient—0/100 (1 min) to 50/50 (19 min) to 50/50 (21 min—total run time) of EtOAc/hexanes. The fractions containing the product were combined and concentrated to provide 3-methyl-3-(4-(4,4,5,5-tetramethyl-1,3,2-dioxaborolan-2-yl)phenyl)thietane 1,1-dioxide as a white solid.

Step E A solution of (3R,3aR,6R,6aR)-6-((6-chloro-5-iodo-1H-imidazo[4,5-b]pyridin-2-yl)oxy)hexahydrofuro[3,2-b]furan-3-ol (100 mg, 0.236 mmol), LiOH (29.7 mg, 0.708 mmol), and PdCl$_2$(dppf)-CH$_2$Cl$_2$ adduct (38.6 mg, 0.047 mmol), in a thick-walled tube, was flushed with N2. Then water (0.5 ml) was added, followed by a solution of 3-methyl-3-(4-(4,4,5,5-tetramethyl-1,3,2-dioxaborolan-2-yl)phenyl) thietane 1,1-dioxide (114 mg, from Step D) in dioxane (3.5 ml). The tube was flushed with N$_2$, and placed in a preheated 72° C. hot oil bath and heated to 80° C. for 3 hours. The reaction mixture was cooled to RT and diluted with EtOAc (30 ml) and water (20 ml). The aqueous layer was separated, and extracted with EtOAc (25 ml). The combined organic layers were dried (Na$_2$SO$_4$), filtered and concentrated. The resulting crude material was purified by Isco™ system, 24 g gold cartridge, 30 ml flow rate, gradient —40/60 (1 min) to 100/0 (15 min) to 100/0 (19 min total run time) of EtOAc/hexanes. The fractions containing product were combined and concentrated to obtain the title compound as an off-white solid. LC-MS: observed m/e: 492.37 (M+H)$^+$ (Rt 0.85/2 min)

BIOLOGICAL EXAMPLE 1

AMPKSAMSF (in vitro AMPK activation assay)

The recombinant human AMPK complex 1 (containing α1β1γ1) or AMPK complex 7 (containing α2β1γ1) was obtained from baculovirus expression system. Recombinant viruses were generated by cotransfection of AMPK/pBac-Pak9 clones with Baculogold baculovirus DNA (Pharmingen) in *spodoptera frugiperda* 21 cells according to the manufacturer's instructions. Each round of virus amplification was performed for 5 days in Grace's medium containing 10% serum. Virus that had been subjected to three rounds of amplification was used for all protein production procedures. To express the AMPK complex, sf21 cells were adapted to serum free medium (SF900II, Invitrogen) by sequential dilution from serum containing stocks into SF900II medium and maintained in shaker flasks at 90 rpm at 27° C. The recombinant AMPK enzyme complex was produced by triple infection, one recombinant virus for each of the subunits, in sf21 cells under serum free conditions. Cells were infected in log phase, 1×10$^6$ cells/ml, at a multiplicity of infection of 5. Cells were harvested by centrifugation at 10,000×g for 15 minutes after 72 hours of infection with viruses. The insect cell pellet from 2 liters of culture was resuspended in 50 ml lysis buffer (20 mM Tris-HCl, 50 mM NaCl, 50 mM NaF, 30 mM Na PPi, 0.25 M sucrose, 10 mM ZnCl$_2$, 2 mM DTT, 0.4 mg/ml digitonin) and subjected to two cycles of freeze-thaw lysis in a dry-ice ethanol bath. Insoluble material was removed by centrifugation at 10,000×g and the supernatant was fractionated with use of polyethylene glycol (PEG). The protein fraction precipitating between 2.5 and 6% PEG was used for further purification using a Blue-Sepharose step (Zhou et al, J. Clin. Invest. 108, 1167-1174, 2001).

The in vitro AMPK activation assay is performed in a volume of 30 μl in a 384-well plate. Enzyme reactions were assembled in the microtiter plate by adding 15 μl of 2× enzyme in assay buffer (20 mM HEPES, pH 7.3, 5 mM MgCl$_2$, 3 mM DTT, 0.01% Brij 35 and CamK Kinase, to activate AMPK) to wells which contained either DMSO or compound. The reaction was initiated with the addition of 15 μl 2× substrate mixture containing 200 μM ATP, and 3.0 μM fluorescently labeled SAMS (5-FAM-HMRSAMS-GLHLVKRR-COOH) in assay buffer. After 45-minute incubation at 25° C., the reaction was stopped by the addition of 70 μl stop buffer (100 mM HEPES, pH 7.3, 40 mM EDTA, 0.015% Brij 35). Phosphorylated 5-FAM SAMS product is assessed using a Caliper EZ Reader LabChip microfluidics reader. Product conversion is determined by calculating the peak heights of the substrate and product and reporting the product/(product+substrate) peak ratio. The 10-point titration data were expressed as % maximum AMP activation. The results were plotted using 4 parameter fit and the inflection point reflecting 50% of the maximum activation was reported as the EC$_{50}$. The % maximum AMP activation for selected compounds is provided in the table below.

The compounds of present invention, including the compounds of Examples 1-174, were tested in the in vitro AMPK activation assay using recombinant human AMPK complex 1 (containing α1β1γ1) or AMPK complex 7 (containing α2β1γ1), and were found to have greater than 50% maximum AMP activation of human AMPK complex 1 (containing α1β1γ1) or AMPK complex 7 (containing α2β1γ1), and EC$_{50}$ values of less than 50 micromolar. Preferred compounds of the present invention were found to have EC$_{50}$ values of less than 0.1 micromolar in the in vitro AMPK activation assay using recombinant human AMPK complex 1 or AMPK complex 7.

Maximum AMP Activation for Selected Compounds

| Example No. | % Maximum AMP Activation of human AMPK Complex 7 | EC$_{50}$ (nM) |
| --- | --- | --- |
| 14 | 276 | 29 |
| 18 | 72 | 6 |
| 71 | 420 | 10 |
| 73 | 357 | 4 |
| 79 | 337 | 2 |
| 86 | 314 | 4 |
| 87 | 285 | 3 |
| 102 | 304 | 5 |
| 105 | 268 | 5 |
| 125 | 350 | 6 |
| 126 | 303 | 3 |
| 127 | 281 | 4 |
| 128 | 286 | 2 |
| 129 | 305 | 1 |
| 130 | 291 | 2 |
| 131 | 289 | 3 |
| 133 | 359 | 1 |
| 138 | 333 | 4 |
| 142 | 337 | 2 |
| 145 | 348 | 8 |
| 146 | 354 | 4 |
| 147 | 348 | 4 |
| 149 | 322 | 2 |
| 150 | 322 | 1 |
| 151 | 323 | 2 |

BIOLOGICAL EXAMPLE 2

Phosphoroylation of Acetyl CoA Carboxylase by AMPK Activators in db/+ Mice

To assess the potential for AMPK activators to increase the phosphorylation of Acetyl COA Carboxylase (ACC) in liver and skeletal muscle, db/+ mice are dosed with AMPK activators at either 2 or 7 h prior to evaluation where phosphorylated ACC (p-ACC)/total ACC levels are compared in the tissues of vehicle and compound treated mice. Briefly, mice are anesthetized using gas anesthesia with 1-4% isoflurane administered to effect via nose cone. Once anesthetized, samples of liver and skeletal muscle (gastrocnemius) are removed, snap frozen in liquid nitrogen, and homogenized. Homogenates are analyzed for protein concentration and equal amounts of protein are assayed for total and phosphorylated ACC (p-ACC) levels using Meso Scale Discovery's Multi-array assay kit. MSD assay plates contain an electrode surface that is coated with streptavidin. Protein sample binds to streptavidin. The primary ACC or p-ACC specific antibody binds to protein and a secondary antibody labeled with MSD SULFO-TAG then binds to the primary antibody. The electrode surface of the MSD plate responds to an electrical stimulus and causes the SULFO-TAG labels bound to ACC and p-ACC to emit a light signal in proportion to the amount of p-ACC or total ACC present. The ratio of p-ACC/total ACC levels are determined for each sample and the ratio of p-ACC/total ACC levels for mice treated with AMPK activators is significantly elevated compared to the ratio of those treated with the vehicle control (significant elevations are described as differences where $p<0.05$).

BIOLOGICAL EXAMPLE 3

Inhibition of Fatty Acid Synthesis (FAS) by AMPK activators in db/+ Mice

To determine the effect of AMPK activators on Fatty Acid Synthesis (FAS) in the liver, the effect of oral pre-dosing of compounds on the amount of $^3$H incorporated into hepatic triglyceride is determined as described by Sakurai T, Miyazawa S, Shindo Y, and T. Hashimoto (Biochim Biophys Acta. 1974 Sep. 19; 360 (3):275-88). Briefly, mice (db/+, Jackson Laboratory, Maine) are orally dosed with AMPK activators at time=−8 h. Then at time=−1 h, mice are injected with 0.5 ml of 0.15 M NaCl containing 0.2 mCi of $^3$H water per 100 g of body weight. At time 0, mice are sacrificed via cervical dislocation and livers are harvested for FAS analysis. To analyze livers for FAS, samples of liver are heated at 90° C. for 5 hours in a 4 M KOH/50% ethanol solution. Then the alkaline hydrolysate of liver is extracted with hexane and acidified to a pH<2 with 10 M $H_2SO_4$. The fatty acids of liver are then extracted from acidified hydrolysate with additional hexane, dried down with a stream of warm air, then re-suspended in scintillation fluid, and counted on a beta counter. The amount of fatty acids synthesized per gram of liver is calculated based on the amount of $^3$H incorporated into hepatic triglyceride. The amount of $^3$H radiolabelled fatty acids synthesized in mice with treated with an AMPK activator is significantly less than the amount of $^3$H radiolabelled fatty acids synthesized in the control mice.

BIOLOGICAL EXAMPLE 4

In Vivo Study for Therapy with an AMPK Activator in Mice (Glucose Tolerance Test)

DIO mice are treated simultaneously with an effective dose of an AMPK-activated protein kinase activator.

Materials and Methods: Male C57BL/6NT mice (Taconic, 16-18 weeks old at the beginning of the drug administration) are used. Mice are given water and high fat diet D12492 (Research Diet Inc.) ad libitum. They are kept in an animal room which is maintained at 23±2 C temperature, 55±15% relative humidity and on a 12-hr light-dark cycle (7:00-19:00) during a quarantine and acclimatization period of 1 week. Animals are then administered vehicle (5 ml/kg of 0.5% methylcellulose in distilled water) by oral gavage twice-daily at 9 AM and 5 PM. After 9 days, stable body weight is observed. The following day (day −1), the mice are fasted for 4 hours and tail bled to determine the glucose and insulin levels. Animals are sorted into groups based on plasma glucose, insulin levels and body weight (n=8). The body weight and food in the hopper are recorded on day 0 before compound dosing is initiated. One of the groups is orally administered vehicle while the second group is administered an AMPK-activated protein kinase activator of the present invention at a dose of 30 mg/kg (5 ml/kg) twice-daily for 12 days by gavage. Body weight and food intake are measured every other day. On day 5, the animals are fasted 4 hours for measuring plasma glucose and insulin levels after morning dosing. At day 12, body weight and food intake are measured and animals receive their last morning dose. Mice again are fasted 4 hours, blood is collected at a set time point (t=0 min), and then challenged with dextrose orally (2 g/kg) Plasma glucose and insulin levels are determined from tail bleeds taken at 20 and 90 minutes after dextrose challenge. The plasma glucose and insulin excursion profile from t=0 to t=90 min is used to integrate an area under the curve (AUC) for each treatment. Percent inhibition values for each treatment are generated from the AUC data normalized to the C57BL/6NT mice feed with D7012. Preferred compounds of the present invention significantly reduce day 12 glucose and/or insulin AUC during the Oral Glucose Tolerance Test after an oral dose in the range of 0.1 to 100 mg/kg.

BIOLOGICAL EXAMPLE 5

Acute Food Intake Studies in Diet Induced Obese (DIO) Mice
General Procedure

Adult DIO mice are used in these studies. After at least 2 days of acclimation to the vivarium conditions (controlled humidity and temperature, lights on for 12 hours out of 24 hours) food (D12492 (Research Diet Inc.) is removed from rodent cages. An AMPK activator of the present invention or the vehicle is administered orally, intraperitoneally, subcutaneously or intravenously before the return of a known amount of food to cage. The optimal interval between dosing and food presentation is based on the half-life of the compound based on when brain concentrations of the compound is the highest. Food remaining is measured at several intervals. Food intake is calculated as grams of food eaten per gram of body weight within each time interval and the appetite-suppressant effect of the AMPK activator is compared to the effect of the vehicle. The food intake of mice treated with an AMPK activator is significantly less than the food intake of control mice.

BIOLOGICAL EXAMPLE 6

Chronic Weight Reduction Studies in Diet Induced Obese (DIO) Mice
General Procedure Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

BIOLOGICAL EXAMPLE 7

Assay for Triglycerides

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

BIOLOGICAL EXAMPLE 8

Assay for Low HDL and/or High LDL

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

BIOLOGICAL EXAMPLE 9

Assay for Sarcopenia

Adult DIO mice are used in these studies. Upon or soon after weaning, rats or mice are made obese due to exclusive access to diets containing fat and sucrose in higher proportions than in the control diet. The diet used to induce obesity is Research Diets D12451 chow (45% fat). The rodents ingest chow until they are significantly heavier and have a higher proportion of body fat than control diet rats, often 9 weeks. The rodents receive injections (1 to 4 per day) or continuous infusions of an AMPK activator of the present invention or the vehicle either orally, intraperitoneally, subcutaneously or intravenously. Food intake and body weights are measured daily or more frequently. Food intake is calculated as grams of food eaten per gram of body weight within each time interval and the appetite-suppressant and weight loss effect of the AMPK activator of the present invention is compared to the effect of the vehicle. The weight loss of mice treated with an AMPK activator is significantly greater than the weight loss of control mice.

The scope of the claims should not be limited by the preferred embodiments set forth in the examples, but should be given the broadest interpretation consistent with the description as a whole.

While the invention has been described and illustrated with reference to certain particular embodiments thereof, those skilled in the art will appreciate that various changes, modifications and substitutions can be made therein without departing from the scope of the invention. For example, effective dosages other than the particular dosages as set forth herein above may be applicable as a consequence of variations in the responsiveness of the mammal being treated for any of the indications for the compounds of the invention indicated above. Likewise, the specific pharmacological responses observed may vary according to and depending upon the particular active compound selected or whether there are present pharmaceutical carriers, as well as the type of formulation and mode of administration employed, and such expected variations or differences in the results are contemplated in accordance with the objects and practices of the present invention.

What is claimed is:
1. A compound of structural formula I:

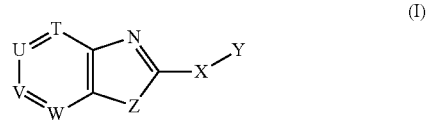

(I)

or a pharmaceutically acceptable salt thereof, wherein:

T is selected from the group consisting of: $CR^3$, N and N-oxide;

U is selected from the group consisting of: $CR^1$, N and N-oxide;

V is selected from the group consisting of: $CR^2$, N and N-oxide;

W is selected from the group consisting of: $CR^4$, N and N-oxide, provided that at least one of T, U, V and W is N or N-oxide;

X is selected from:
    (1) —$CH_2$—,
    (2) —CHF—,
    (3) —$CF_2$—,
    (4) —S—,
    (5) —O—,
    (6) —O—$CH_2$—,
    (7) —O—$CH_2CH_2$—,
    (8) —NH—,
    (9) —C(O)—,
    (10) —NHC(O)—,

(11) —C(O)NH—,
(12) —NHSO$_2$—,
(13) —SO$_2$NH—, and
(14) —CO$_2$—,
wherein each CH$_2$ is unsubstituted or substituted with 1 or 2 substituents selected from: hydroxy, halogen, NH$_2$, C$_{1-6}$alkyl, CO$_2$H, CO$_2$C$_{1-6}$alkyl, COC$_{1-6}$alkyl, phenyl and —CH$_2$phenyl, and wherein each NH is unsubstituted or substituted with 1 substituent selected from: C$_{1-6}$alkyl, CO$_2$H, CO$_2$C$_{1-6}$alkyl, COC$_{1-6}$alkyl, phenyl and —CH$_2$phenyl;
Y is selected from:

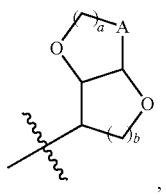

wherein A is selected from: CH$_2$, NH, NC$_{1-6}$alkyl, O and S, and wherein Y is unsubstituted or substituted with 1, 2, 3 or 4 substituents selected from R$^b$;
Z is selected from:
(1) NR$^5$,
(2) —S—, and
(3) —O—;
each R$^1$ and R$^2$ is independently selected from:
(1) hydrogen,
(2) halogen,
(3) CN,
(4) CF$_3$,
(5) —C$_{1-6}$alkyl,
(6) —C$_{2-6}$alkenyl,
(7) —C$_{2-6}$alkynyl,
(8) —(CH$_2$)$_p$C$_{3-10}$cycloalkyl,
(9) —(CH$_2$)$_p$C$_{3-7}$cycloalkyl-aryl,
(10) —(CH$_2$)$_p$C$_{3-7}$cycloalkyl-heteroaryl,
(11) —(CH$_2$)$_p$C$_{4-10}$cycloalkenyl,
(12) —(CH$_2$)$_p$C$_{4-7}$cycloalkenyl-aryl,
(13) —(CH$_2$)$_p$C$_{4-7}$cycloalkenyl-heteroaryl,
(14) —(CH$_2$)$_p$C$_{2-10}$cycloheteroalkyl,
(15) —(CH$_2$)$_p$C$_{2-10}$cycloheteroalkenyl,
(16) —(CH$_2$)$_p$aryl,
(17) —(CH$_2$)$_p$aryl-C$_{1-8}$alkyl,
(18) —(CH$_2$)$_p$aryl-C$_{2-8}$alkenyl,
(19) —(CH$_2$)$_p$aryl-C$_{2-8}$alkynyl-C$_{1-8}$alkyl,
(20) —(CH$_2$)$_p$aryl-C$_{2-8}$alkynyl-C$_{3-7}$cycloalkyl,
(21) —(CH$_2$)$_p$aryl-C$_{2-8}$alkynyl-C$_{3-7}$cycloalkenyl,
(22) —(CH$_2$)$_p$aryl-C$_{2-8}$alkynyl-C$_{2-10}$cycloheteroalkyl,
(23) —(CH$_2$)$_p$aryl-C$_{2-8}$alkynyl-C$_{2-10}$cycloheteroalkenyl,
(24) —(CH$_2$)$_p$aryl-C$_{2-8}$alkynyl-aryl,
(25) —(CH$_2$)$_p$aryl-C$_{2-8}$alkynyl-heteroaryl,
(26) —(CH$_2$)$_p$aryl-C$_{3-7}$cycloalkyl,
(27) —(CH$_2$)$_p$aryl-C$_{3-7}$cycloalkenyl,
(28) —(CH$_2$)$_p$aryl-C$_{2-10}$cycloheteroalkyl,
(29) —(CH$_2$)$_p$aryl-C$_{2-10}$cycloheteroalkenyl,
(30) —(CH$_2$)$_p$aryl-aryl,
(31) —(CH$_2$)$_p$aryl-heteroaryl,
(32) —(CH$_2$)$_p$heteroaryl,
(33) —(CH$_2$)$_p$heteroaryl-C$_{3-7}$cycloalkyl,
(34) —(CH$_2$)$_p$heteroaryl-C$_{2-10}$cycloheteroalkyl,
(35) —(CH$_2$)$_p$heteroaryl-C$_{2-10}$cycloheteroalkenyl,
(36) —(CH$_2$)$_p$heteroaryl-aryl,
(37) —(CH$_2$)$_p$heteroaryl-heteroaryl,
(38) —C$_{2-6}$alkenyl-alkyl,
(39) —C$_{2-6}$alkenyl-aryl,
(40) —C$_{2-6}$alkenyl-heteroaryl,
(41) —C$_{2-6}$alkenyl-C$_{3-7}$cycloalkyl,
(42) —C$_{2-6}$alkenyl-C$_{3-7}$cycloalkenyl,
(43) —C$_{2-6}$alkenyl-C$_{2-7}$cycloheteroalkyl,
(44) —C$_{2-6}$alkenyl-C$_{2-7}$cycloheteroalkenyl,
(45) —C$_2$-6 alkynyl-(CH$_2$)$_{1-3}$—O-aryl,
(46) —C$_{2-6}$alkynyl-alkyl,
(47) —C$_{2-6}$alkynyl-aryl,
(48) —C$_{2-6}$alkynyl-heteroaryl,
(49) —C$_{2-6}$alkynyl-C$_{3-7}$cycloalkyl,
(50) —C$_{2-6}$alkynyl-C$_{3-7}$cycloalkenyl,
(51) —C$_{2-6}$alkynyl-C$_{2-7}$cycloheteroalkyl,
(52) —C$_{2-6}$alkynyl-C$_{2-7}$cycloheteroalkenyl, and
(53) —C(O)NH—(CH$_2$)$_{0-3}$phenyl,
wherein each CH$_2$ is unsubstituted or substituted with 1 or 2 substituents selected from: halogen, CF$_3$, —OH, —NH$_2$, —C$_{1-6}$alkyl, —OC$_{1-6}$alkyl, —NHC$_{1-6}$alkyl, and —N(C$_{1-6}$alkyl)$_2$,
wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from R$^a$,
provided that at least one of and only one of R$^1$ and R$^2$ is selected from the group consisting of: hydrogen, halogen, —CN, —CF$_3$, —C$_{1-6}$alkyl, —C$_{2-6}$alkenyl and —C$_{2-6}$alkynyl;
R$^3$ and R$^4$ are each independently absent or selected from:
(1) hydrogen,
(2) halogen,
(3) —C$_{1-6}$alkyl,
(4) —C$_{2-6}$alkenyl,
(5) —C$_{2-6}$alkynyl,
(6) —C$_{3-10}$cycloalkyl,
(7) —C$_{3-10}$cycloalkenyl,
(8) aryl,
(9) heteroaryl,
(10) —CN,
(11) —CF$_3$,
(12) —OH,
(13) —OC$_{1-6}$alkyl,
(14) —NH$_2$,
(15) —NHC$_{1-6}$alkyl,
(16) —N(C$_{1-6}$alkyl)$_2$,
(17) —SC$_{1-6}$alkyl,
(18) —SOC$_{1-6}$alkyl,
(19) —SO$_2$C$_{1-6}$alkyl,
(20) —NHSO$_2$C$_{1-6}$alkyl,
(21) —NHC(O)C$_{1-6}$alkyl,
(22) —SO$_2$NHC$_{1-6}$alkyl, and
(23) —C(O)NHC$_{1-6}$alkyl;
R$^5$ is selected from:
(1) hydrogen,
(2) —C$_{1-6}$alkyl,
(3) —C$_{1-6}$alkenyl,
(4) —(CH$_2$)$_u$OH,
(5) —CH$_2$CO$_2$H, and
(6) —CH$_2$CO$_2$C$_{1-6}$alkyl;
each R$^a$ is independently selected from the group consisting of:
(1) —(CH$_2$)$_m$-halogen,
(2) oxo,
(3) —(CH$_2$)$_m$OH,
(4) —(CH$_2$)$_m$N(R$^j$)$_2$, (5) —$(CH_2)_mNO_2$,
(6) —$(CH_2)_mCN$,
(7) —$C_{1-6}$alkyl,
(8) —$(CH_2)_mCF_3$,
(9) —$(CH_2)_mOCF_3$,
(10) —O—$(CH_2)_m$—$OC_{1-6}$alkyl,
(11) —$(CH_2)_mN(R^j)C(O)R^f$,
(12) —$(CH_2)_mN(R^j)CO_2R^f$,
(13) —$(CH_2)_mC(=N-OH)N(R^j)_2$,
(14) —$(CH_2)_mOC_{1-6}$alkyl,
(15) —$(CH_2)_mO$—$(CH_2)_m$—$C_{3-7}$cycloalkyl,
(16) —$(CH_2)_mO$—$(CH_2)_m$—$C_{2-7}$cycloheteroalkyl,
(17) —$(CH_2)_mO$—$(CH_2)_m$-aryl,
(18) —$(CH_2)_mO$—$(CH_2)_m$-heteroaryl,
(19) —$(CH_2)_mSC_{1-6}$alkyl,
(20) —$(CH_2)_mS(O)C_{1-6}$alkyl,
(21) —$(CH_2)_mSO_2C_{1-6}$alkyl,
(22) —$(CH_2)_mO$—$SO_2C_{1-6}$alkyl,
(23) —$(CH_2)_mSO_2(CH_2)_m$—$C_{3-7}$cycloalkyl,
(24) —$(CH_2)_mSO_2(CH_2)_m$—$C_{2-7}$cycloheteroalkyl,
(25) —$(CH_2)_mSO_2(CH_2)_m$-aryl,
(26) —$(CH_2)_mSO_2(CH_2)_m$-heteroaryl,
(27) —$(CH_2)_mSO_2NH_2$,
(28) —$(CH_2)_mSO_2NHC_{1-6}$alkyl,
(29) —$(CH_2)_mSO_2NHC_{3-7}$cycloalkyl,
(30) —$(CH_2)_mSO_2NHC_{2-7}$cycloheteroalkyl,
(31) —$(CH_2)_mSO_2NH$-aryl,
(32) —$(CH_2)_mSO_2NH$-heteroaryl,
(33) —$(CH_2)_mNHSO_2$—$C_{1-6}$alkyl,
(34) —$(CH_2)_mNHSO_2$—$C_{3-7}$cycloalkyl,
(35) —$(CH_2)_mNHSO_2$—$C_{2-7}$cycloheteroalkyl,
(36) —$(CH_2)_mNHSO_2$-aryl,
(37) —$(CH_2)_mNHSO_2NH$-heteroaryl,
(38) —$(CH_2)_mN(R^j)$—$C_{1-6}$alkyl,
(39) —$(CH_2)_mN(R^j)$—$C_{3-7}$cycloalkyl,
(40) —$(CH_2)_mN(R^j)$—$(CH_2)_m$—$C_{3-7}$cycloalkyl,
(41) —$(CH_2)_mN(R^j)$—$C_{2-7}$cycloheteroalkyl,
(42) —$(CH_2)_mN(R^j)$—$(CH_2)_m$—$C_{2-7}$cycloheteroalkyl,
(43) —$(CH_2)_mN(R^j)$—$C_{2-7}$cycloheteroalkenyl,
(44) —$(CH_2)_mN(R^j)$—$(CH_2)_m$—$C_{2-7}$cycloheteroalkenyl,
(45) —$(CH_2)_mN(R^j)$-aryl,
(46) —$(CH_2)_mN(R^j)$—$(CH_2)_m$-aryl,
(47) —$(CH_2)_mN(R^j)$-heteroaryl,
(48) —$(CH_2)_mN(R^j)$—$(CH_2)_m$-heteroaryl,
(49) —$(CH_2)_mC(O)R^f$,
(50) —$(CH_2)_mC(O)N(R^j)_2$,
(51) —$(CH_2)_mN(R^j)C(O)N(R^j)_2$,
(52) —$(CH_2)_mCO_2H$,
(53) —$(CH_2)_mOCOH$,
(54) —$(CH_2)_mCO_2R^f$,
(55) —$(CH_2)_mOCOR^f$,
(56) —$(CH_2)_mC_{3-7}$cycloalkyl,
(57) —$(CH_2)_mC_{3-7}$cycloalkenyl,
(58) —$(CH_2)_mC_{2-6}$cycloheteroalkyl,
(59) —$(CH_2)_mC_{2-6}$cycloheteroalkenyl,
(60) —$(CH_2)_m$aryl, and
(61) —$(CH_2)_m$heteroaryl, wherein each $CH_2$ is unsubstituted or substituted with 1 or 2 substituents selected from: oxo, —OH, —$(CH_2)_{1-30}H$, —CN, —$NH_2$, —$NH(C_{1-6}alkyl)$, —$N(C_{1-6}alkyl)_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, phenyl, $CH_2$phenyl, heteroaryl and $CH_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —$(CH_2)_{1-5}OH$, —CN, —$NH_2$, —$NH(C_{1-6}alkyl)$, —$N(C_{1-6}alkyl)_2$, —$C_{1-6}$alkyl, —$C_{1-6}$alkyl substituted with 1-5 OH, —$OC_{1-6}$alkyl, halogen, —$CH_2F$, —$CHF_2$, —$CF_3$, —$(CH_2)_{1-5}CF_3$ optionally substituted with 1, 2 or 3 —OH, —$CO_2H$, —$CO_2C_{1-6}$alkyl, —$SO_2C_{1-6}$alkyl, —$C_{3-7}$cycloalkyl, phenyl, $CH_2$phenyl, heteroaryl and $CH_2$heteroaryl;

each $R^b$ is independently selected from:
(1) hydrogen,
(2) —$C_{1-6}$alkyl,
(3) —$C_{1-6}$alkenyl,
(4) —$(CH_2)_nC_{3-10}$cycloalkyl,
(5) —$(CH_2)_nC_{3-10}$cycloalkenyl,
(6) —$(CH_2)_nC_{2-10}$cycloheteroalkyl,
(7) —$(CH_2)_nC_{2-10}$cycloheteroalkenyl,
(8) —$(CH_2)_n$aryl,
(9) —$(CH_2)_n$heteroaryl,
(10) oxo,
(11) —$(CH_2)_nCF_3$,
(12) —$(CH_2)_nCN$,
(13) —$(CH_2)t$-halogen,
(14) —$(CH_2)s$-OH,
(15) —$(CH_2)_nNO_2$,
(16) —$(CH_2)_nNH_2$,
(17) —$(CH_2)_nNH(C_{1-6}alkyl)$,
(18) —$(CH_2)_nN(C_{1-6}alkyl)_2$,
(19) —$(CH_2)_nNHCO_2H$,
(20) —$(CH_2)_nOC_{1-6}$alkyl,
(21) —$(CH_2)_nOC_{1-6}$alkenyl,
(22) —$(CH_2)_nCOC_{1-6}$alkyl,
(23) —$(CH_2)_nCO_2H$,
(24) —$(CH_2)_nOCOH$,
(25) —$(CH_2)_nCO_2R^i$,
(26) —$(CH_2)_nOC(O)R^i$,
(27) —$(CH_2)_qC(O)N(R^e)_2$,
(28) —$(CH_2)_qCO_2N(R^e)_2$,
(29) —$(CH_2)_nC(O)(CH_2)_nN(R^g)_2$,
(30) —$(CH_2)_nOC(O)(CH_2)_nN(R^g)_2$,
(31) —$(CH_2)_nN(R^e)C(O)C_{1-6}$alkyl,
(32) —$(CH_2)_nN(R^e)SO_2R^i$,
(33) —$(CH_2)_nSO_2C_{1-6}$alkyl,
(34) —$(CH_2)_nSO_2N(R^e)R^g$,
(35) —$(CH_2)_nSO_2N(R^e)C(O)R^i$,
(36) —$(CH_2)_nSO_2N(R^e)CO_2R^i$,
(37) —$(CH_2)_nSO_2N(R^e)CON(R^g)_2$,
(38) —$(CH_2)_nC(O)N(R^e)SO_2R^i$,
(39) —$(CH_2)_nN(R^e)C(O)N(R^g)_2$,
(40) =N(OH), and
(41) =N($OC_{1-6}$alkyl), wherein each $CH_2$ is unsubstituted or substituted with 1 or 2 substituents selected from: —$C_{1-6}$alkyl, —OH, halogen and —$NH_2$ wherein each NH is unsubstituted or substituted with 1 substituent selected from $R^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from $R^c$, or wherein two $R^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from $R^c$;

each $R^c$ is independently selected from:
(1) halogen,
(2) oxo,
(3) —$(CH_2)_rOH$,
(4) —$(CH_2)_rN(R^e)_2$,
(5) —$(CH_2)_rCN$,
(6) —$C_{1-6}$alkyl,
(7) —$CF_3$,
(8) —$C_{1-6}$alkyl-OH,
(9) —$OCH_2OC_{1-6}$alkyl,
(10) —$(CH_2)_rOC_{1-6}$alkyl,
(11) —$OCH_2$aryl,
(12) —$(CH_2)_rSC_{1-6}$alkyl,
(13) —$(CH_2)_rC(O)R^f$,
(14) —$(CH_2)_rC(O)N(R^e)_2$,
(15) —$(CH_2)_rCO_2H$,
(16) —$(CH_2)_rCO_2R^f$,
(17) —$(CH_2)_rC_{3-7}$cycloalkyl,
(18) —$(CH_2)_rC_{2-6}$cycloheteroalkyl,
(19) —$(CH_2)_r$aryl, and
(20) —$(CH_2)_r$heteroaryl,
wherein each $CH_2$ is unsubstituted or substituted with 1 or 2 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —$N(R^h)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl and heteroaryl;
each $R^e$, $R^g$ and $R^h$ is independently selected from:
(1) hydrogen,
(2) —$C_{1-6}$alkyl, and
(3) —O—$C_{1-6}$alkyl,
wherein alkyl is unsubstituted or substituted with 1, 2, 3 or 4 substituents selected from: —OH, oxo, halogen, $C_{1-6}$alkyl, —$OC_{1-6}$alkyl, —$NH_2$, —$NH(C_{1-6}$alkyl), and —$N(C_{1-6}$alkyl$)_2$;
each $R^j$ is independently selected from:
(1) hydrogen,
(2) $C_{1-6}$alkyl,
(3) $C_{3-6}$cycloalkyl,
(4) —$C(O)R^i$,
(5) —$CO_2R^i$, and
(6) —$SO_2R^i$,
wherein alkyl and cycloalkyl are unsubstituted or substituted with 1, 2, 3 or 4 substituents selected from: —OH, oxo, halogen, $C_{1-6}$alkyl, —$OC_{1-6}$alkyl, —$NH_2$, —NH$(C_{1-6}$alkyl), and —$N(C_{1-6}$alkyl$)_2$;
each $R^f$ and $R^i$ is independently selected from:
(1) —$C_{1-6}$alkyl,
(2) —$(CH_2)_sC_{4-7}$cycloalkyl,
(3) —$(CH_2)_sC_{4-7}$cycloalkenyl,
(1) —$(CH_2)_sC_{3-7}$cycloheteroalkyl,
(2) —$(CH_2)_sC_{3-7}$cycloheteroalkenyl,
(3) —$(CH_2)_s$aryl, and
(4) —$(CH_2)_s$heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —$NH_2$, —$NH(C_{1-6}$alkyl), —$N(C_{1-6}$alkyl$)_2$, —$C_{1-6}$alkyl, —$OC_{1-6}$alkyl, halogen, —$CH_2F$, —$CHF_2$, —$CF_3$, —$CO_2H$, —$CO_2C_{1-6}$alkyl, —$C_{3-7}$cycloalkyl, and heteroaryl;

a is 1 or 2;
b is 1 or 2;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4;
t is 0, 1, 2, 3 or 4, and
u is 0, 1, 2, 3 or 4.

2. The compound of claim 1 of structural formula I:

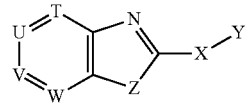

(I)

or a pharmaceutically acceptable salt thereof, wherein:
T is selected from the group consisting of: $CR^3$, N and N-oxide;
U is selected from the group consisting of: $CR^1$, N and N-oxide;
V is selected from the group consisting of: $CR^2$, N and N-oxide;
W is selected from the group consisting of: $CR^4$, N and N-oxide,
provided that at least one of T, U, V and W is N or N-oxide;
X is selected from:
(1) —$CH_2$—,
(2) —CHF—,
(3) —$CF_2$—,
(4) —S—,
(5) —O—,
(6) —O—$CH_2$—,
(7) —O—$CH_2CH_2$—,
(8) —NH—,
(9) —C(O)—,
(10) —NHC(O)—,
(11) —C(O)NH—,
(12) —$NHSO_2$—,
(13) —$SO_2NH$—, and
(14) —$CO_2$—,
wherein each $CH_2$ is unsubstituted or substituted with 1 or 2 substituents selected from: hydroxy, halogen, $NH_2$, $C_{1-6}$alkyl, $CO_2H$, $CO_2C_{1-6}$alkyl, $COC_{1-6}$alkyl, phenyl and —$CH_2$phenyl, and wherein each NH is unsubstituted or substituted with 1 substituent selected from: $C_{1-6}$alkyl, $CO_2H$, $CO_2C_{1-6}$alkyl, $COC_{1-6}$alkyl, phenyl and —$CH_2$phenyl;
Y is selected from:

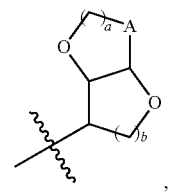

wherein A is selected from: $CH_2$, NH, $NC_{1-6}$alkyl, O and S, and wherein Y is unsubstituted or substituted with 1, 2, 3 or 4 substituents selected from $R^b$;

Z is selected from:
   (1) $NR^5$,
   (2) —S—, and
   (3) —O—;
each $R^1$ and $R^2$ is independently selected from:
   (1) hydrogen,
   (2) halogen,
   (3) CN,
   (4) $CF_3$,
   (5) —$C_{1-6}$alkyl,
   (6) —$C_{2-6}$alkenyl,
   (7) —$C_{2-6}$alkynyl,
   (8) —$(CH_2)_p C_{3-10}$cycloalkyl,
   (9) —$(CH_2)_p C_{3-7}$cycloalkyl-aryl,
   (10) —$(CH_2)_p C_{3-7}$cycloalkyl-heteroaryl,
   (11) —$(CH_2)_p C_{4-10}$cycloalkenyl,
   (12) —$(CH_2)_p C_{4-7}$cycloalkenyl-aryl,
   (13) —$(CH_2)_p C_{4-7}$cycloalkenyl-heteroaryl,
   (14) —$(CH_2)_p C_{2-10}$cycloheteroalkyl,
   (15) —$(CH_2)_p C_{2-10}$cycloheteroalkenyl,
   (16) —$(CH_2)_p$aryl,
   (17) —$(CH_2)_p$aryl-$C_{1-8}$alkyl,
   (18) —$(CH_2)_p$aryl-$C_{2-8}$alkenyl,
   (19) —$(CH_2)_p$aryl-$C_{2-8}$alkynyl-$C_{1-8}$alkyl,
   (20) —$(CH_2)_p$aryl-$C_{2-8}$alkynyl-$C_{3-7}$cycloalkyl,
   (21) —$(CH_2)_p$aryl-$C_{2-8}$alkynyl-$C_{3-7}$cycloalkenyl,
   (22) —$(CH_2)_p$aryl-$C_{2-8}$alkynyl-$C_{2-10}$cycloheteroalkyl,
   (23) —$(CH_2)_p$aryl-$C_{2-8}$alkynyl-$C_{2-10}$cycloheteroalkenyl,
   (24) —$(CH_2)_p$aryl-$C_{2-8}$alkynyl-aryl,
   (25) —$(CH_2)_p$aryl-$C_{2-8}$alkynyl-heteroaryl,
   (26) —$(CH_2)_p$aryl-$C_{3-7}$cycloalkyl,
   (27) —$(CH_2)_p$aryl-$C_{2-10}$cycloheteroalkyl,
   (28) —$(CH_2)_p$aryl-$C_{2-10}$cycloheteroalkenyl,
   (29) —$(CH_2)_p$aryl-aryl,
   (30) —$(CH_2)_p$aryl-heteroaryl,
   (31) —$(CH_2)_p$heteroaryl,
   (32) —$(CH_2)_p$heteroaryl-$C_{3-7}$cycloalkyl,
   (33) —$(CH_2)_p$heteroaryl-$C_{2-10}$cycloheteroalkyl,
   (34) —$(CH_2)_p$heteroaryl-$C_{2-10}$cycloheteroalkenyl,
   (35) —$(CH_2)_p$heteroaryl-aryl,
   (36) —$(CH_2)_p$heteroaryl-heteroaryl,
   (37) —$C_{2-6}$alkenyl-alkyl,
   (38) —$C_{2-6}$alkenyl-aryl,
   (39) —$C_{2-6}$alkenyl-heteroaryl,
   (40) —$C_{2-6}$alkenyl-$C_{3-7}$cycloalkyl,
   (41) —$C_{2-6}$alkenyl-$C_{3-7}$cycloalkenyl,
   (42) —$C_{2-6}$alkenyl-$C_{2-7}$cycloheteroalkyl,
   (43) —$C_{2-6}$alkenyl-$C_{2-7}$cycloheteroalkenyl,
   (44) —$C_2$-6 alkynyl-$(CH_2)_{1-3}$—O-aryl,
   (45) —$C_{2-6}$alkynyl-alkyl,
   (46) —$C_{2-6}$alkynyl-aryl,
   (47) —$C_{2-6}$alkynyl-heteroaryl,
   (48) —$C_{2-6}$alkynyl-$C_{3-7}$cycloalkyl,
   (49) —$C_{2-6}$alkynyl-$C_{3-7}$cycloalkenyl,
   (50) —$C_{2-6}$alkynyl-$C_{2-7}$cycloheteroalkyl,
   (51) —$C_{2-6}$alkynyl-$C_{2-7}$cycloheteroalkenyl, and
   (52) —$C(O)NH$—$(CH_2)_{0-3}$phenyl,
wherein each $CH_2$ is unsubstituted or substituted with 1 or 2 substituents selected from: halogen, $CF_3$, —OH, —$NH_2$, —$C_{1-6}$alkyl, —$OC_{1-6}$alkyl, —$NHC_{1-6}$alkyl, and —$N(C_{1-6}$alkyl$)_2$,
wherein each alkyl, alkenyl, alkynyl, cycloalkyl, cycloalkenyl, cycloheteroalkyl, cycloheteroalkenyl, phenyl, aryl and heteroaryl is unsubstituted or substituted with 1, 2, 3 or 4 substituents independently selected from $R^a$,
provided that at least one of and only one of $R^1$ and $R^2$ is selected from the group consisting of: hydrogen, halogen, —CN, —$CF_3$, —$C_{1-6}$alkyl, —$C_{2-6}$alkenyl and —$C_{2-6}$alkynyl;
$R^3$ and $R^4$ are each independently absent or selected from:
   (1) hydrogen,
   (2) halogen,
   (3) —$C_{1-6}$alkyl,
   (4) —$C_{2-6}$alkenyl,
   (5) —$C_{2-6}$alkynyl,
   (6) —$C_{3-10}$cycloalkyl,
   (7) —$C_{3-10}$cycloalkenyl,
   (8) aryl,
   (9) heteroaryl,
   (10) —CN,
   (11) —$CF_3$,
   (12) —OH,
   (13) —$OC_{1-6}$alkyl,
   (14) —$NH_2$,
   (15) —$NHC_{1-6}$alkyl,
   (16) —$N(C_{1-6}$alkyl$)_2$,
   (17) —$SC_{1-6}$alkyl,
   (18) —$SOC_{1-6}$alkyl,
   (19) —$SO_2 C_{1-6}$alkyl,
   (20) —$NHSO_2 C_{1-6}$alkyl,
   (21) —$NHC(O)C_{1-6}$alkyl,
   (22) —$SO_2 NHC_{1-6}$alkyl, and
   (23) —$C(O)NHC_{1-6}$alkyl;
$R^5$ is selected from:
   (1) hydrogen,
   (2) —$C_{1-6}$alkyl,
   (3) —$C_{1-6}$alkenyl,
   (4) —$(CH_2)_u OH$,
   (5) —$CH_2 CO_2 H$, and
   (6) —$CH_2 CO_2 C_{1-6}$alkyl;
each $R^a$ is independently selected from the group consisting of:
   (1) —$(CH_2)_m$-halogen,
   (2) oxo,
   (3) —$(CH_2)_m OH$,
   (4) —$(CH_2)_m N(R^j)_2$,
   (5) —$(CH_2)_m NO_2$,
   (6) —$(CH_2)_m CN$,
   (7) —$C_{1-6}$alkyl,
   (8) —$(CH_2)_m CF_3$,
   (9) —$(CH_2)_m OCF_3$,
   (10) —O—$(CH_2)_m$—$OC_1$-6 alkyl,
   (11) —$(CH_2)_m N(R^j)C(O)R^f$,
   (12) —$(CH_2)_m N(R^j)CO_2 R^f$,
   (13) —$(CH_2)_m C(=N-OH)N(R^j)_2$,
   (14) —$(CH_2)_m OC_{1-6}$alkyl,
   (15) —$(CH_2)_m O$—$(CH_2)_m$—$C_{3-7}$cycloalkyl,
   (16) —$(CH_2)_m O$—$(CH_2)_m$—$C_{2-7}$cycloheteroalkyl,
   (17) —$(CH_2)_m O$—$(CH_2)_m$-aryl,
   (18) —$(CH_2)_m O$—$(CH_2)_m$-heteroaryl,
   (19) —$(CH_2)_m SC_{1-6}$alkyl,
   (20) —$(CH_2)_m S(O)C_{1-6}$alkyl,
   (21) —$(CH_2)_m SO_2 C_{1-6}$alkyl,
   (22) —$(CH_2)_m SO_2 (CH_2)_m$—$C_{3-7}$cycloalkyl,
   (23) —$(CH_2)_m SO_2 (CH_2)_m$—$C_{2-7}$cycloheteroalkyl,
   (24) —$(CH_2)_m SO_2 (CH_2)_m$-aryl,
   (25) —$(CH_2)_m SO_2 (CH_2)_m$-heteroaryl,
   (26) —$(CH_2)_m SO_2 NH_2$,
   (27) —$(CH_2)_m SO_2 NHC_{1-6}$alkyl,
   (28) —$(CH_2)_m SO_2 NHC_{3-7}$cycloalkyl,
   (29) —$(CH_2)_m SO_2 NHC_{2-7}$cycloheteroalkyl,
   (30) —$(CH_2)_m SO_2 NH$-aryl,

(31) —(CH$_2$)$_m$SO$_2$NH-heteroaryl,
(32) —(CH$_2$)$_m$NHSO$_2$—C$_{1-6}$alkyl,
(33) —(CH$_2$)$_m$NHSO$_2$—C$_{3-7}$cycloalkyl,
(34) —(CH$_2$)$_m$NHSO$_2$—C$_{2-7}$cycloheteroalkyl,
(35) —(CH$_2$)$_m$NHSO$_2$-aryl,
(36) —(CH$_2$)$_m$NHSO$_2$NH-heteroaryl,
(37) —(CH$_2$)$_m$N(R$^j$)—C$_{1-6}$alkyl,
(38) —(CH$_2$)$_m$N(R$^j$)—C$_{3-7}$cycloalkyl,
(39) —(CH$_2$)$_m$N(R$^j$)—C$_{2-7}$cycloheteroalkyl,
(40) —(CH$_2$)$_m$N(R$^j$)—C$_{2-7}$cycloheteroalkenyl,
(41) —(CH$_2$)$_m$N(R$^j$)-aryl,
(42) —(CH$_2$)$_m$N(R$^j$)-heteroaryl,
(43) —(CH$_2$)$_m$C(O)R$^f$,
(44) —(CH$_2$)$_m$C(O)N(R$^j$)$_2$,
(45) —(CH$_2$)$_m$N(R$^j$)C(O)N(R$^j$)$_2$,
(46) —(CH$_2$)$_m$CO$_2$H,
(47) —(CH$_2$)$_m$OCOH,
(48) —(CH$_2$)$_m$CO$_2$R$^f$,
(49) —(CH$_2$)$_m$OCOR$^f$,
(50) —(CH$_2$)$_m$C$_{3-7}$cycloalkyl,
(51) —(CH$_2$)$_m$C$_{3-7}$cycloalkenyl,
(52) —(CH$_2$)$_m$C$_{2-6}$cycloheteroalkyl,
(53) —(CH$_2$)$_m$C$_{2-6}$cycloheteroalkenyl,
(54) —(CH$_2$)$_m$aryl, and
(55) —(CH$_2$)$_m$heteroaryl, wherein each CH$_2$ is unsubstituted or substituted with 1 or 2 substituents selected from: oxo, —OH, —(CH$_2$)$_{1-3}$OH, —CN, —NH$_2$, —NH(C$_{1-6}$alkyl), —N(C$_{1-6}$alkyl)$_2$, oxo, —C$_{1-6}$alkyl, —C$_{1-6}$alkyl substituted with 1-5 OH, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl, phenyl, CH$_2$phenyl, heteroaryl and CH$_2$heteroaryl, and wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —(CH$_2$)$_{1-5}$OH, —CN, —NH$_2$, —NH(C$_{1-6}$alkyl), —N(C$_{1-6}$alkyl)$_2$, —C$_{1-6}$alkyl, —C$_{1-6}$alkyl substituted with 1-5 OH, —OC$_{1-6}$alkyl, halogen, —CH$_2$F, —CHF$_2$, —CF$_3$, —(CH$_2$)$_{1-5}$CF$_3$ optionally substituted with 1, 2 or 3 —OH, —CO$_2$H, —CO$_2$C$_{1-6}$alkyl, —SO$_2$C$_{1-6}$alkyl, —C$_{3-7}$cycloalkyl, phenyl, CH$_2$phenyl, heteroaryl and CH$_2$heteroaryl;

each R$^b$ is independently selected from:
(1) hydrogen,
(2) —C$_{1-6}$alkyl,
(3) —C$_{1-6}$alkenyl,
(4) —(CH$_2$)$_n$C$_{3-10}$cycloalkyl,
(5) —(CH$_2$)$_n$C$_{3-10}$cycloalkenyl,
(6) —(CH$_2$)$_n$C$_{2-10}$cycloheteroalkyl,
(7) —(CH$_2$)$_n$C$_{2-10}$cycloheteroalkenyl,
(8) —(CH$_2$)$_n$aryl,
(9) —(CH$_2$)$_n$heteroaryl,
(10) oxo,
(11) —(CH$_2$)$_n$CF$_3$,
(12) —(CH$_2$)$_n$CN,
(13) —(CH$_2$)t-halogen,
(14) —(CH$_2$)s-OH,
(15) —(CH$_2$)$_n$NO$_2$,
(16) —(CH$_2$)$_n$NH$_2$,
(17) —(CH$_2$)$_n$NH(C$_{1-6}$alkyl),
(18) —(CH$_2$)$_n$N(C$_{1-6}$alkyl)$_2$,
(19) —(CH$_2$)$_n$NHCO$_2$H,
(20) —(CH$_2$)$_n$OC$_{1-6}$alkyl,
(21) —(CH$_2$)$_n$OC$_{1-6}$alkenyl,
(22) —(CH$_2$)$_n$COC$_{1-6}$alkyl,
(23) —(CH$_2$)$_n$CO$_2$H,
(24) —(CH$_2$)$_n$OCOH,
(25) —(CH$_2$)$_n$CO$_2$R$^i$,
(26) —(CH$_2$)$_n$OC(O)R$^i$,
(27) —(CH$_2$)$_q$C(O)N(R$^e$)$_2$,
(28) —(CH$_2$)$_q$CO$_2$N(R$^e$)$_2$,
(29) —(CH$_2$)$_n$C(O)(CH$_2$)$_n$N(R$^g$)$_2$,
(30) —(CH$_2$)$_n$OC(O)(CH$_2$)$_n$N(R$^g$)$_2$,
(31) —(CH$_2$)$_n$N(R$^e$)C(O)C$_{1-6}$alkyl,
(32) —(CH$_2$)$_n$N(R$^e$)SO$_2$R$^i$,
(33) —(CH$_2$)$_n$SO$_2$C$_{1-6}$alkyl,
(34) —(CH$_2$)$_n$SO$_2$N(R$^e$)R$^g$,
(35) —(CH$_2$)$_n$SO$_2$N(R$^e$)C(O)R$^i$,
(36) —(CH$_2$)$_n$SO$_2$N(R$^e$)CO$_2$R$^i$,
(37) —(CH$_2$)$_n$SO$_2$N(R$^e$)CON(R$^g$)$_2$,
(38) —(CH$_2$)$_n$C(O)N(R$^e$)SO$_2$R$^i$,
(39) —(CH$_2$)$_n$N(R$^e$)C(O)N(R$^g$)$_2$,
(40) =N(OH), and
(41) =N(OC$_{1-6}$alkyl), wherein each CH$_2$ is unsubstituted or substituted with 1 or 2 substituents selected from: —C$_{1-6}$alkyl, —OH, halogen and —NH$_2$ wherein each NH is unsubstituted or substituted with 1 substituent selected from R$^c$, and wherein each alkyl, cycloalkyl, cycloalkenyl, cycloheteroalkyl, cycloheteroalkenyl, aryl and heteroaryl is unsubstituted or substituted with 1, 2, 3 or 4 substituents selected from R$^c$, or wherein two R$^b$ substituents and the carbon to which they are attached may form a 3 to 6 membered cycloalkyl ring, a 3-6 membered cycloalkenyl ring, a 3-6 membered cycloheteroalkyl ring or a 3-6 membered cycloheteroalkenyl ring, wherein the ring is unsubstituted or substituted with 1, 2, 3 or 4 substituents selected from R$^c$;

each R$^c$ is independently selected from:
(1) halogen,
(2) oxo,
(3) —(CH$_2$)$_r$OH,
(4) —(CH$_2$)$_r$N(R$^e$)$_2$,
(5) —(CH$_2$)$_r$CN,
(6) —C$_{1-6}$alkyl,
(7) —CF$_3$,
(8) —C$_{1-6}$alkyl-OH,
(9) —OCH$_2$OC$_{1-6}$alkyl,
(10) —(CH$_2$)$_r$OC$_{1-6}$alkyl,
(11) —OCH$_2$aryl,
(12) —(CH$_2$)$_r$SC$_{1-6}$alkyl,
(13) —(CH$_2$)$_r$C(O)R$^f$,
(14) —(CH$_2$)$_r$C(O)N(R$^e$)$_2$,
(15) —(CH$_2$)$_r$CO$_2$H,
(16) —(CH$_2$)$_r$CO$_2$R$^f$,
(17) —(CH$_2$)$_r$C$_{3-7}$cycloalkyl,
(18) —(CH$_2$)$_r$C$_{2-6}$cycloheteroalkyl,
(19) —(CH$_2$)$_r$aryl, and
(20) —(CH$_2$)$_r$heteroaryl, wherein each CH$_2$ is unsubstituted or substituted with 1 or 2 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl, and wherein alkyl, cycloalkyl, cycloheteroalkyl, aryl and heteroaryl are unsubstituted or substituted with 1, 2, 3 or 4 substituents selected from: oxo, —OH, —CN, —N(R$^h$)$_2$, —C$_{1-6}$alkyl, —OC$_{1-6}$alkyl, halogen, —CH$_2$F, —CHF$_2$, —CF$_3$, —CO$_2$H, —CO$_2$C$_{1-6}$alkyl, —C$_{3-7}$cycloalkyl and heteroaryl;

each $R^e$, $R^g$ and $R^h$ is independently selected from:
(1) hydrogen,
(2) —$C_{1-6}$alkyl, and
(3) —O—$C_{1-6}$alkyl,
wherein alkyl is unsubstituted or substituted with 1, 2, 3 or 4 substituents selected from: —OH, oxo, halogen, $C_{1-6}$alkyl, —O$C_{1-6}$alkyl, —NH$_2$, —NH($C_{1-6}$alkyl), and —N($C_{1-6}$alkyl)$_2$;

each $R^j$ is independently selected from:
(1) hydrogen,
(2) $C_{1-6}$alkyl,
(3) $C_3$-6cycloalkyl,
(4) —C(O)$R^i$,
(5) —CO$_2R^i$, and
(6) —SO$_2R^i$,
wherein alkyl and cycloalkyl are unsubstituted or substituted with 1, 2, 3 or 4 substituents selected from: —OH, oxo, halogen, $C_{1-6}$alkyl, —O$C_{1-6}$alkyl, —NH$_2$, —NH($C_{1-6}$alkyl), and —N($C_{1-6}$alkyl)$_2$;

each $R^f$ and $R^i$ is independently selected from:
(1) $C_{1-6}$alkyl,
(2) —(CH$_2$)$_r$$C_{4-7}$cycloalkyl,
(3) —(CH$_2$)$_r$$C_{4-7}$cycloalkenyl,
(4) —(CH$_2$)$_r$$C_{3-7}$cycloheteroalkyl,
(5) —(CH$_2$)$_r$$C_{3-7}$cycloheteroalkenyl,
(6) —(CH$_2$)$_r$aryl, and
(7) —(CH$_2$)$_r$heteroaryl,
wherein alkyl, cycloalkyl, cycloalkenyl, cycloheteroalkyl, cycloheteroalkenyl, aryl and heteroaryl are unsubstituted or substituted with 1, 2, 3 or 4 substituents selected from: oxo, —OH, —CN, —NH$_2$, —NH($C_{1-6}$alkyl), —N($C_{1-6}$alkyl)$_2$, —$C_{1-6}$alkyl, —O$C_{1-6}$alkyl, halogen, —CH$_2$F, —CHF$_2$, —CF$_3$, —CO$_2$H, —CO$_2C_{1-6}$alkyl, —$C_{3-7}$cycloalkyl, and heteroaryl;

a is 1 or 2;
b is 1 or 2;
n is 0, 1, 2, 3 or 4;
m is 0, 1, 2, 3 or 4;
p is 0, 1, 2, or 3;
q is 0, 1, 2, 3 or 4;
r is 0, 1 or 2;
s is 0, 1, 2, 3 or 4;
t is 0, 1, 2, 3 or 4; and
u is 0, 1, 2, 3 or 4.

3. The compound according to claim 1 wherein T is N or N-oxide; U is —$CR^1$—; V is —$CR^2$—; and W is —$CR^4$—; or a pharmaceutically acceptable salt thereof.

4. The compound according to claim 1 wherein T is N; U is —$CR^1$—; V is —$CR^2$—; and W is —$CR^4$—; or a pharmaceutically acceptable salt thereof.

5. The compound according to claim 1, wherein X is selected from:
(1) —CH$_2$—,
(2) —S—,
(3) —O—,
(4) —O—CH$_2$CH$_2$—, and
(5) —NH—;
or a pharmaceutically acceptable salt thereof.

6. The compound according to claim 1, wherein X is —O—; or a pharmaceutically acceptable salt thereof.

7. The compound according to claim 1, wherein Y is selected from:

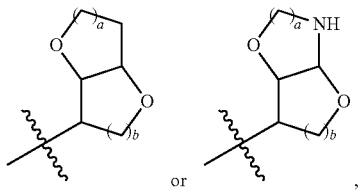

wherein Y is unsubstituted or substituted with 1, 2, 3 or 4 substituents selected from $R^b$; or a pharmaceutically acceptable salt thereof.

8. The compound according to claim 1, wherein Y is selected from:

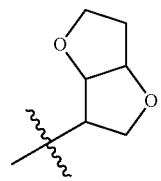

wherein Y is unsubstituted or substituted with 1, 2, 3 or 4 substituents selected from $R^b$; or a pharmaceutically acceptable salt thereof.

9. The compound according to claim 1, wherein Z is $NR^5$; or a pharmaceutically acceptable salt thereof.

10. The compound according to claim 1, each $R^1$ and $R^2$ is independently selected from:
(1) halogen,
(2) —(CH$_2$)$_p$$C_{2-10}$cycloheteroalkyl,
(3) —(CH$_2$)$_p$aryl-$C_{2-8}$alkynyl-$C_{2-10}$cycloheteroalkyl,
(4) —(CH$_2$)$_p$aryl-$C_{2-10}$cycloheteroalkyl,
(5) —(CH$_2$)$_p$aryl-$C_{2-10}$cycloheteroalkenyl,
(6) —(CH$_2$)$_p$aryl-aryl,
(7) —(CH$_2$)$_p$aryl-heteroaryl,
(8) —(CH$_2$)$_p$heteroaryl,
(9) —(CH$_2$)$_p$heteroaryl-$C_{2-10}$cycloheteroalkyl,
(10) —(CH$_2$)$_p$heteroaryl-aryl, and
(11) —(CH$_2$)$_p$heteroaryl-heteroaryl,
wherein each CH$_2$ is unsubstituted or substituted with 1 or 2 substituents selected from: halogen, CF$_3$, —OH, —NH$_2$, —$C_{1-6}$alkyl, —O$C_{1-6}$alkyl, —NH$C_{1-6}$alkyl, and —N($C_{1-6}$alkyl)$_2$, wherein each alkynyl, cycloheteroalkyl, cycloheteroalkenyl, aryl and heteroaryl is unsubstituted or substituted with 1, 2, 3 or 4 substituents independently selected from $R^a$, provided that at least one of and only one of $R^1$ and $R^2$ is selected from halogen; or a pharmaceutically acceptable salt thereof.

11. The compound according to claim 1, wherein each $R^1$ is independently selected from:
(1) $C_{2-10}$cycloheteroalkyl,
(2) aryl-$C_{2-8}$alkynyl-$C_{2-10}$cycloheteroalkyl,
(3) aryl-$C_{2-10}$cycloheteroalkyl,
(4) aryl-$C_{2-10}$cycloheteroalkenyl,
(5) aryl-aryl,
(6) aryl-heteroaryl,
(7) heteroaryl,
(8) heteroaryl-$C_{2-10}$cycloheteroalkyl,
(9) heteroaryl-aryl, and
(10) heteroaryl-heteroaryl,
wherein each alkynyl, cycloheteroalkyl, cycloheteroalkenyl, aryl and heteroaryl is unsubstituted or substituted with 1, 2, 3 or 4 substituents independently selected from $R^a$; and $R^2$ is selected from halogen;
or a pharmaceutically acceptable salt thereof.

12. The compound according to claim 1, wherein each $R^1$ is independently selected from:
   (1) aryl-$C_2$alkynyl-$C_{2-10}$cycloheteroalkyl,
   (2) aryl-$C_{2-10}$cycloheteroalkyl, and
   (3) aryl-aryl,
wherein each alkynyl, cycloheteroalkyl and aryl is unsubstituted or substituted with 1, 2, 3 or 4 substituents independently selected from $R^a$, and
$R^2$ is selected from halogen;
or a pharmaceutically acceptable salt thereof.

13. The compound according to claim 1, wherein $R^3$ is hydrogen or absent; $R^4$ is hydrogen; and $R^5$ is selected from: hydrogen, —$C_{1-6}$alkyl and —$(CH_2)_uOH$; or a pharmaceutically acceptable salt thereof.

14. The compound according to claim 1, wherein $R^3$ is hydrogen or absent; $R^4$ is hydrogen; and $R^5$ is hydrogen; or a pharmaceutically acceptable salt thereof.

15. The compound according to claim 1, wherein $R^3$ is hydrogen or absent; $R^4$ is hydrogen; $R^5$ is hydrogen; and $R^2$ is halogen; or a pharmaceutically acceptable salt thereof.

16. The compound according to claim 1 wherein:
T is N;
U is —$CR^1$—;
V is —$CR^2$—;
W is —$CR^4$—;
X is selected from:
   (1) —$CH_2$—,
   (2) —S—,
   (3) —O—,
   (4) —O—$CH_2CH_2$—, and
   (5) —NH—;
Y is selected from:

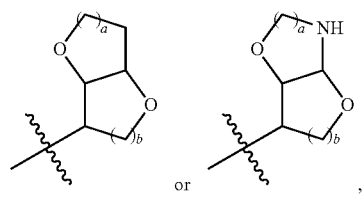

or wherein Y is unsubstituted or substituted with 1, 2, 3 or 4 substituents selected from $R^b$;
Z is $NR^5$;
each $R^1$ is independently selected from:
   (1) $C_{2-10}$cycloheteroalkyl,
   (2) aryl-$C_{2-8}$alkynyl-$C_2$-1 cycloheteroalkyl,
   (3) aryl-$C_{2-10}$cycloheteroalkyl,
   (4) aryl-$C_{2-10}$cycloheteroalkenyl,
   (5) aryl-aryl,
   (6) aryl-heteroaryl,
   (7) heteroaryl,
   (8) heteroaryl-$C_{2-10}$cycloheteroalkyl,
   (9) heteroaryl-aryl, and
   (10) heteroaryl-heteroaryl,
wherein each alkynyl, cycloheteroalkyl, cycloheteroalkenyl, aryl and heteroaryl is unsubstituted or substituted with 1, 2, 3 or 4 substituents independently selected from $R^a$;
$R^2$ is selected from halogen;
$R^4$ is hydrogen; and
$R^5$ is selected from: hydrogen, —$C_{1-6}$alkyl and —$(CH_2)_uOH$;
or a pharmaceutically acceptable salt thereof.

17. The compound according to claim 1 wherein:
T is N;
U is —$CR^1$—;
V is —$CR^2$—;
W is —$CR^4$—;
X is —O—;
Y is selected from:

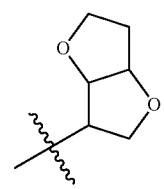

wherein Y is unsubstituted or substituted with 1, 2, 3 or 4 substituents selected from $R^b$;
Z is $NR^5$;
each $R^1$ is independently selected from:
   (1) aryl-$C_2$alkynyl-$C_{2-10}$cycloheteroalkyl,
   (2) aryl-$C_{2-10}$cycloheteroalkyl, and
   (3) aryl-aryl,
wherein each alkynyl, cycloheteroalkyl and aryl is unsubstituted or substituted with 1, 2, 3 or 4 substituents independently selected from $R^a$,
$R^2$ is halogen;
$R^4$ is hydrogen; and
$R^5$ is hydrogen;
or a pharmaceutically acceptable salt thereof.

18. The compound according to claim 1, selected from:

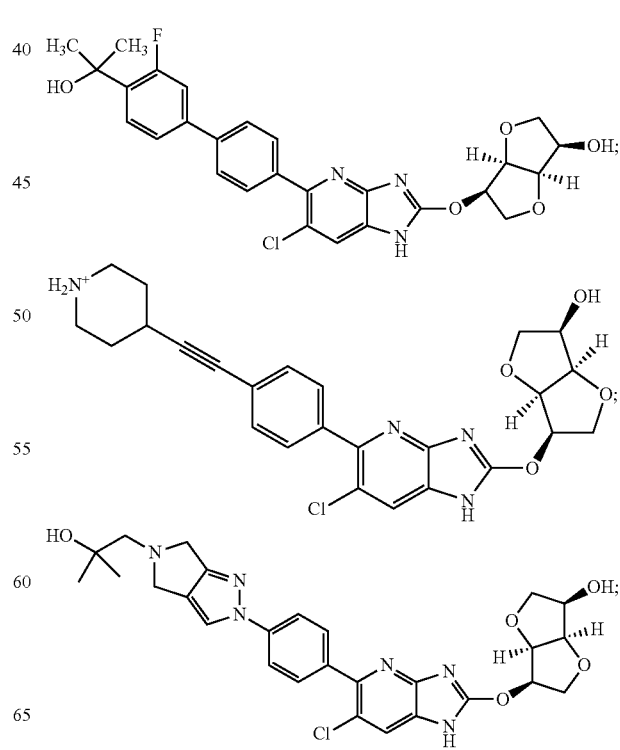

309
-continued

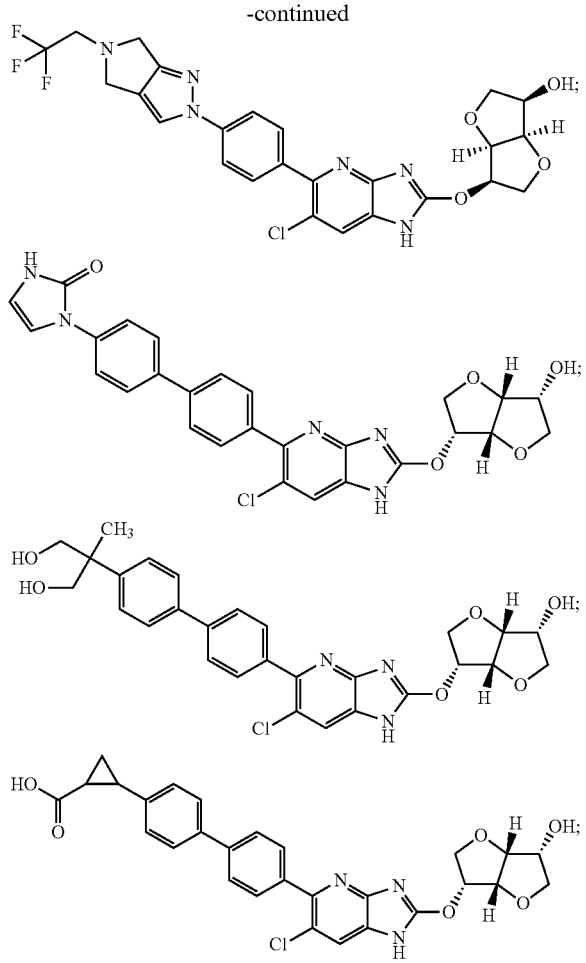

310
-continued

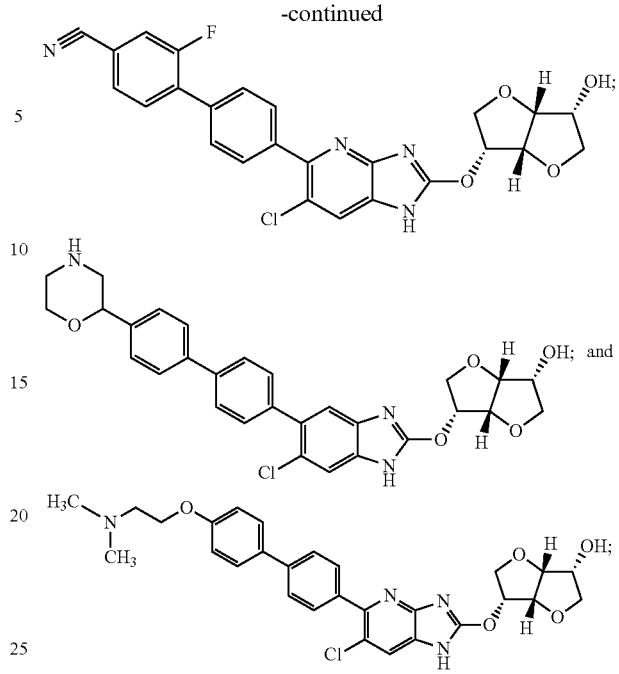

or a pharmaceutically acceptable salt thereof.

19. A composition comprising a compound of claim 1, or a pharmaceutically acceptable salt thereof, and a pharmaceutically acceptable carrier.

20. A composition comprising a compound according to claim 1, or a pharmaceutically acceptable salt thereof, and a compound selected from simvastatin, ezetimibe and sitagliptin; and a pharmaceutically acceptable carrier.

* * * * *